United States Patent
Castanedo et al.

(10) Patent No.: US 9,487,533 B2
(45) Date of Patent: Nov. 8, 2016

(54) PHOSPHOINOSITIDE 3-KINASE INHIBITOR COMPOUNDS AND METHODS OF USE

(75) Inventors: Georgette Castanedo, Redwood City, CA (US); Jennafer Dotson, Belmont, CA (US); Richard Goldsmith, Belmont, CA (US); Janet Gunzner, Berkeley, CA (US); Tim Heffron, San Francisco, CA (US); Simon Mathieu, Burlingame, CA (US); Alan Olivero, Half Moon Bay, CA (US); Daniel P. Sutherlin, South San Francisco, CA (US); Shumei Wang, Foster City, CA (US); Bing-Yan Zhu, Palo Alto, CA (US); Steven Staben, South San Francisco, CA (US); Vickie Tsui, Burlingame, CA (US); Tracy Bayliss, Slough (GB); Irina Chuckowree, Slough (GB); Adrian Folkes, Slough (GB); Nan Chi Wan, Slough (GB)

(73) Assignees: Genentech, Inc., South San Francisco, CA (US); F. Hoffmann-La Roche AG, Basel (CH)

( * ) Notice: Subject to any disclaimer, the term of this patent is extended or adjusted under 35 U.S.C. 154(b) by 1072 days.

(21) Appl. No.: 11/951,189

(22) Filed: Dec. 5, 2007

(65) Prior Publication Data

US 2008/0269210 A1 Oct. 30, 2008

Related U.S. Application Data

(60) Provisional application No. 60/873,422, filed on Dec. 7, 2006.

(51) Int. Cl.
*C07D 491/048* (2006.01)
*C07D 495/04* (2006.01)

(52) U.S. Cl.
CPC ......... *C07D 491/048* (2013.01); *C07D 495/04* (2013.01)

(58) Field of Classification Search
CPC .................. C07D 491/048; C07D 495/04
USPC ....................................... 544/116; 514/234.5
See application file for complete search history.

(56) References Cited

U.S. PATENT DOCUMENTS

| | | |
|---|---|---|
| 3,475,429 A | 10/1969 | Woitun et al. |
| 3,661,908 A | 5/1972 | Woitun et al. |
| 3,763,156 A | 10/1973 | Woitun et al. |
| 3,838,121 A | 9/1974 | Woitun et al. |
| 3,888,851 A | 6/1975 | Narr et al. |
| 4,007,187 A | 2/1977 | Fauran et al. |
| 4,146,716 A | 3/1979 | Cox et al. |
| 4,196,207 A | 4/1980 | Webber |
| 5,075,305 A | 12/1991 | Hobbs et al. |
| 6,187,777 B1 | 2/2001 | Norman et al. |
| 6,608,053 B2 | 8/2003 | Hayakawa et al. |
| 6,838,457 B2 | 1/2005 | Hayakawa et al. |
| 7,037,915 B2 | 5/2006 | Hayakawa et al. |
| 7,173,029 B2 | 2/2007 | Hayakawa et al. |
| 2003/0236271 A1 | 12/2003 | Hayakawa et al. |
| 2006/0229306 A1 | 10/2006 | Belart et al. |
| 2007/0037805 A1 | 2/2007 | Hayakawa et al. |
| 2007/0249587 A1 | 10/2007 | Yonetoku et al. |
| 2008/0039459 A1 | 2/2008 | Folkes et al. |
| 2008/0076758 A1 | 3/2008 | Folkes et al. |

(Continued)

FOREIGN PATENT DOCUMENTS

| | | |
|---|---|---|
| DE | 1959403 A1 | 6/1971 |
| DE | 2050814 A1 | 4/1972 |

(Continued)

OTHER PUBLICATIONS

Cancer and Metastasis Reviews (1998), 17(1), 91-106.*

(Continued)

*Primary Examiner* — Rebecca Anderson
(74) *Attorney, Agent, or Firm* — Viksnins Harris & Padys PLLP

(57) ABSTRACT

Compounds of Formulas Ia-d where X is S or O, mor is a morpholine group, and $R^3$ is a monocyclic heteroaryl group, and including stereoisomers, geometric isomers, tautomers, solvates, metabolites and pharmaceutically acceptable salts thereof, are useful for modulating the activity of lipid kinases including PI3K, and for treating disorders such as cancer mediated by lipid kinases. Methods of using compounds of Formula Ia-d for in vitro, in situ, and in vivo diagnosis, prevention or treatment of such disorders in mammalian cells, or associated pathological conditions, are disclosed.

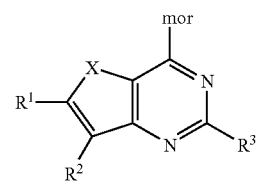

Ic

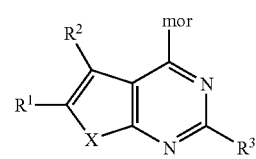

Id

5 Claims, No Drawings

(56) References Cited

U.S. PATENT DOCUMENTS

| | | | |
|---|---|---|---|
| 2008/0076768 A1 | 3/2008 | Chuckowree et al. |
| 2008/0207611 A1 | 8/2008 | Shuttleworth et al. |
| 2008/0242665 A1 | 10/2008 | Bayliss et al. |

FOREIGN PATENT DOCUMENTS

| | | |
|---|---|---|
| EP | 1277738 | 1/2003 |
| GB | 1393161 | 5/1975 |
| WO | WO 2006/046031 | 5/2006 |
| WO | WO 2006/046035 | 5/2006 |
| WO | WO 2006/046040 | 5/2006 |
| WO | WO 2007/122410 | 11/2007 |
| WO | WO 2007/127175 | 11/2007 |
| WO | WO 2007/127183 | 11/2007 |
| WO | WO 2007/132171 | 11/2007 |

OTHER PUBLICATIONS

Science (1999), vol. 286, 531-537.*
Byrn et al., Solid-State Chemistry of Drugs, Second Edition, 1999, pp. 233-247.*
Bourguignon et al., Bulletin De La Societe Chimique De France, 1975; 3-4(pt 2); 815-19.*
International Search Report, PCT/US2007/086533, Jun. 10, 2008.
Written Opinion of the International Searching Authority, PCT/US2007/086533, Jun. 10, 2008.
Bourguignon et al., "No. 152.-Syntheses de thieno[2,3-d]pyrimidines substituees en 2 et 4", *Bull. de la Societe Chimique de France*, 3/4, 815-819, 1975 (English translation provided).
"No. 152.-Synthesis of thieno[2,3-d]pyrimidines substituted at 2 and 4" English translation of: (Bourguignon et al., "No. 152.-Syntheses de thieno[2,3-d]pyrimidines substituees en 2 et 4", *Bull. de la Societe Chimique de France*, 3/4, 815-819, 1975).
Bourguignon et al., "No. 465.-Syntheses de thieno[2,3-d]pyrimidines substituees en 2 et 4 II", *Bull. de la Societe Chimique de France*, 11/12, 2483-2487, 1975 (English translation provided).
"No. 465—Syntheses of 2- and 4-substituted thieno[2,3-d]pyrimidines II" coversheet and pp. 1-14 English translation of: (Bourguignon et al., "No. 465.-Syntheses de thieno[2,3-d]pyrimidines substituees en 2 et 4 II", *Bull. de la Societe Chimique de France*, 11/12, 2483-2487, 1975).
Database Chemcats [online] *Chemical Abstracts Service*, Columbus Ohio, US, XP002481877, Database accession No. 2038647104, Sep. 6, 2007.
Database Chemcats [online] *Chemical Abstracts Service*, Columbus Ohio, US, XP002481878, Database accession No. 2038019439, Sep. 6, 2007.
Database Chemcats [online] *Chemical Abstracts Service*, Columbus Ohio, US, XP002481879, Database accession No. 2038018435, Sep. 6, 2007.
Database Chemcats [online] *Chemical Abstracts Service*, Columbus Ohio, US, XP002481880, Database accession No. 2031400284, Sep. 6, 2007.
Database Chemcats [online] *Chemical Abstracts Service*, Columbus Ohio, US, XP002481881, Database accession No. 2031384736, Sep. 6, 2007.
Database Chemcats [online] *Chemical Abstracts Service*, Columbus Ohio, US, XP002481882, Database accession No. 2026153101, Sep. 6, 2007.
Briel et al., "Selective Nucleophilic Replacement of the Benzylsulfanyl Group in 2,4-Disulfanyl-Substituted Thieno[2,3-D]Pyrimidin-6-Carboxylic Acid Derivatives by Secondary Amines", Journal of Heterocyclic Chemistry (2005), 42(5), 841-846.
Bachman et al., "The *PIK3CA* gene is mutated with high frequency in human breast cancers", *Cancer Biology & Therapy*, 3(8), 772-775, Aug. 2004.
Berge et al., "Pharmaceutical Salts", *Journal of Pharmaceutical Sciences*, 66(1), 1-19, Jan. 1977.
C. Garcia-Echeverria et al., "Drug discovery approaches targeting the PI3/Akt pathway in cancer", *Oncogene*, 27, 5511-5526, 2008.
Kang et al., "Phosphatidylinositol 3-kinase mutations identified in human cancer are oncogenic", *PNAS*, 102(3), 802-807, Jan. 18, 2005.
Raynaud et al., "Biological properties of potent inhibitors of class I phophatidylinositide 3-kinases: from PI-103 through PI-540, PI-620 to the oral agent GDC-0941", *Mol. Cancer Ther.*, 8(7), 1725-1738, Jul. 2009.
Samuels et al., "High frequency of mutations of the *PIK3CA* gene in human cancers", *Science*, 304, 554, Apr. 23, 2004.
Shayesteh et al., "*PIK3CA* is implicated as an oncogene in ovarian cancer", *Nature Genetics*, 21, 99-102, Jan. 1999.
Workman et al., "Drugging the PI3 kinome", *Nature Biotechnology*, 24(7), 794-796, Jul. 2006.
Yap et al., "Targeting the PI3K-AKT-mTOR pathway: progress, pitfalls, and promises", *Current Opinion in Pharmacology*, 8, 393-412, 2008.

* cited by examiner

PHOSPHOINOSITIDE 3-KINASE INHIBITOR COMPOUNDS AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 60/873,422 filed on 7 Dec. 2006, which is incorporated by reference in entirety.

The invention claimed herein was made as a result of activities undertaken within the scope of a joint research agreement between Piramed Limited and Genentech, Inc.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110 α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla.; USA; Ahmadi K and Waterfield M D (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070).

Certain thienopyrimidine compounds have p110 alpha binding, PI3 kinase inhibitory activity and inhibit the growth of cancer cells (WO 2006/046031; WO 2006/046035; WO 2006/046040; WO 2007/122410; WO 2007/127183; WO 2007/127175; U.S. Ser. No. 11/789,423, "PHARMACEUTICAL COMPOUNDS", Chuckowree et al, Filing Date 24 Apr. 2007; U.S. Provisional No. 60/873,448, "PHOSPHOINOSITIDE 3-KINASE INHIBITOR COMPOUNDS AND METHODS OF USE", Bayliss et al, Filing Date 7 Dec. 2006; U.S. Provisional No. 60/977,257, "PHOSPHOINOSITIDE 3-KINASE INHIBITOR COMPOUNDS AND METHODS OF USE", Bayliss et al, Filing Date 3 Oct. 2007).

SUMMARY OF THE INVENTION

The invention relates generally to 2-monocyclic heteroaryl, 4-morpholino substituted thienopyrimidine and furanopyrimidine compounds with anti-cancer activity, and more specifically with PI3 kinase inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the compounds for in vitro, in situ, and in vivo diagnosis or treatment of mammalian cells, organisms, or associated pathological conditions.

More specifically, one aspect of the invention provides 2-monocyclic heteroaryl, 4-morpholino substituted thienopyrimidine (X=S) and furanopyrimidine (X=O) compounds of Formulas Ia and Ib:

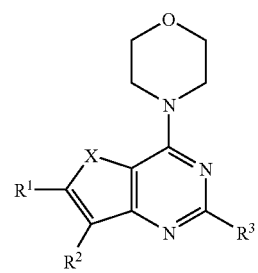

Ia

-continued

Ib

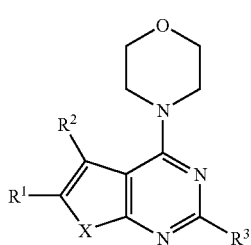

and Formulas Ic and Id:

Ic

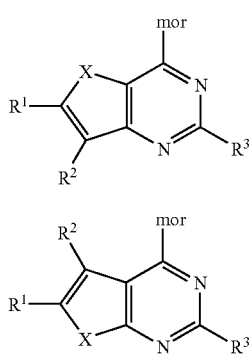

Id and stereoisomers, geometric isomers, tautomers, solvates, metabolites, and pharmaceutically acceptable salts thereof. Groups $R^1$, $R^2$, $R^3$, and mor are as defined herein.

Another aspect of the invention provides a pharmaceutical composition comprising a thienopyrimidine or furanopyrimidine compound of Formula Ia-d and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating cardiovascular disease, agents for treating liver disease, anti-viral agents, agents for treating blood disorders, agents for treating diabetes, and agents for treating immunodeficiency disorders.

Another aspect of the invention provides methods of inhibiting PI3 kinase activity, comprising contacting a PI3 kinase with an effective inhibitory amount of a compound of Formula Ia-d, or a stereoisomer, geometric isomer, tautomer, solvate, metabolite, or pharmaceutically acceptable salt or prodrug thereof.

Another aspect of the invention provides methods of preventing or treating a disease or disorder modulated by PI3 kinases, comprising administering to a mammal in need of such treatment an effective amount of a compound of Formula Ia-d, or a stereoisomer, geometric isomer, tautomer, solvate, metabolite, or pharmaceutically acceptable salt or prodrug thereof. Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, hyperproliferative disorders, infectious diseases, conditions associated with cell death, thrombin-induced platelet aggregation, chronic myelogenous leukemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of Formula Ia-d, or a stereoisomer, geometric isomer, tautomer, solvate, metabolite, or pharmaceutically acceptable salt or prodrug thereof, alone or in combination with one or more additional compounds having anti-hyperproliferative properties.

In a further aspect the present invention provides a method of using a compound of this invention to treat a disease or condition modulated by PI3 kinase in a mammal.

An additional aspect of the invention is the use of a compound of this invention in the preparation of a medicament for the treatment or prevention of a disease or condition modulated by PI3 kinase in a mammal.

Another aspect of the invention includes kits comprising a compound of Formula Ia-d, or a stereoisomer, geometric isomer, tautomer, solvate, metabolite, or pharmaceutically acceptable salt or prodrug thereof, a container, and optionally a package insert or label indicating a treatment.

Another aspect of the invention includes methods of preparing, methods of separating, and methods of purifying compounds of Formula Ia-d.

Another aspect of the invention includes novel intermediates useful for preparing Formula Ia-d compounds.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "monocyclic heteroaryl" refers to a five- or six-membered, unsubstituted or substituted, monocyclic heteroaryl radical which contains 1, 2, 3 or 4 ring heteroatoms independently selected from N, O and S. The monocyclic heteroaryl may be attached to the C-2 position of the pyrimidine ring according to Formulas Ia-d at any carbon (carbon-linked), or nitrogen (nitrogen-linked) atom of the monocyclic heteroaryl $R^3$ group. Monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryls are optionally substituted independently with one or more substituents described herein.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafarnib (SCH 66336), sorafenib (NEXAVAR, Bayer Labs), and gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the PI3 kinase inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula Ia-d" include compounds of Formulas Ia-d and stereoisomers, geometric isomers, tautomers, solvates, metabolites, and pharmaceutically acceptable salts and prodrugs thereof.

The term "mammal" includes, but is not limited to, humans, mice, rats, guinea pigs, monkeys, dogs, cats, horses, cows, pigs, and sheep.

PI3 Kinase Inhibitor Compounds

The present invention provides 4-morpholino thienopyrimidine and furanopyrimidine compounds, and pharmaceutical formulations thereof, which are potentially useful in the treatment of diseases, conditions and/or disorders modulated by PI3 kinases. More specifically, the present invention provides compounds of Formulas Ia and Ib.

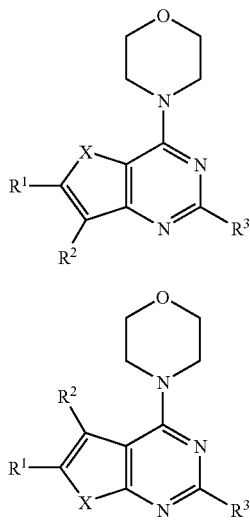

and stereoisomers, geometric isomers, tautomers, solvates, metabolites, and pharmaceutically acceptable salts thereof, wherein:

X is O or S;

$R^1$ is selected from H, F, Cl, Br, I, —C($C_1$-$C_6$ alkyl)$_2$ $NR^{10}R^{11}$, —$(CR^{14}R^{15})_n NR^{10}R^{11}$, —$C(R^{14}R^{15})_n NR^{12}C(=Y)R^{10}$, —$(CR^{14}R^{15})_n NR^{12}S(O)_2 R^{10}$, —$CH(OR^{10})R^{10}$, —$(CR^{14}R^{15})_n OR^{10}$, —$(CR^{14}R^{15})_n S(O)_2 R^{10}$, —$(CR^{14}R^{15})_n S(O)_2 NR^{10}R^{11}$, —$C(=Y)R^{10}$, —$C(=Y)OR^{10}$, —$C(=Y)NR^{10}R^{11}$, —$C(=Y)NR^{12}OR^{10}$, —$C(=O)NR^{12}S(O)_2 R^{10}$, —$C(=O)NR^{12}(CR^{14}R^{15})_m NR^{10}R^{11}$, —$NO_2$, —$NHR^{12}$, —$NR^{12}C(=Y)R^{11}$, —$NR^{12}C(=Y)OR^{11}$, —$NR^{12}C(=Y)NR^{10}R^{11}$, —$NR^{12}S(O)_2 R^{10}$, —$NR^{12}SO_2 NR^{10}R^{11}$, —$S(O)_2 R^{10}$, —$S(O)_2 NR^{10}R^{11}$, —$SC(=Y)R^{10}$, —$SC(=Y)OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^2$ is selected from H, F, Cl, Br, I, $C_6$-$C_{20}$ aryl, $C_1$-$C_{20}$ heteroaryl and $C_1$-$C_6$ alkyl;

$R^3$ is a monocyclic heteroaryl group selected from pyridyl, isoxazolyl, imidazolyl, pyrazolyl, pyrrolyl, thiazolyl, pyridazinyl, pyrimidinyl, pyrazinyl, oxazolyl, furanyl, thienyl, triazolyl, tetrazolyl, where the monocyclic heteroaryl group is optionally substituted with one or more groups selected from F, Cl, Br, I, —CN, —$NR^{10}R^{11}$, —$OR^{10}$, —$C(O)R^{10}$, —$NR^{10}C(O)R^{11}$, —$N(C(O)R^{11})_2$, —$NR^{10}C(O)NR^{10}R^{11}$, —$C(=O)OR^{10}$, —$C(=O)NR^{10}R^{11}$, $C_1$-$C_{12}$ alkyl and ($C_1$-$C_{12}$ alkyl)-$OR^{10}$;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a $C_3$-$C_{20}$ heterocyclic ring optionally containing one or more additional ring atoms selected from N, O or S, wherein said heterocyclic ring is optionally substituted with one or more groups independently selected from oxo, $(CH_2)_n OR^{10}$, $NR^{10}R^{11}$, $CF_3$, F, Cl, Br, I, $SO_2 R^{10}$, $C(=O)R^{10}$, $NR^{12}C(=Y)R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl and heteroaryl are optionally substituted with one or more groups independently selected from F, Cl, Br, I, —CN, $CF_3$, —$NO_2$, oxo, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n NR^{21}SO_2 R^{10}$, —$(CR^{14}R^{15})_n OR^{10}$, —$NR^{10}R^{11}$, —$NR^{12}C(=Y)R^{10}$, —$NR^{12}C(=Y)OR^{11}$, —$NR^{12}C(=Y)NR^{10}R^{11}$, —$NR^{12}SO_2 R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2 R^{10}$, —$S(O)_2 NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

Y is O, S, or $NR^{12}$;

m is 0, 1, 2, 3, 4, 5 or 6;

n is 1, 2, 3, 4, 5 or 6; and t is 2, 3, 4, 5 or 6.

The present invention also provides compounds of Formulas Ic and Id:

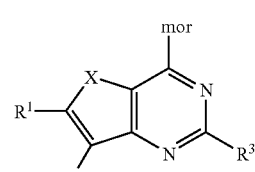

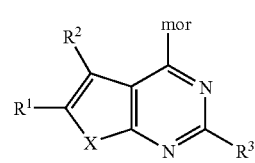

and stereoisomers, geometric isomers, tautomers, solvates, metabolites, and pharmaceutically acceptable salts thereof, wherein:

X is O or S;

R[1] is selected from H, F, Cl, Br, I, —C(C$_1$-C$_6$ alkyl)$_2$NR$^{10}$R$^{11}$, —(CR$^{14}$R$^{15}$)$_t$NR$^{10}$R$^{11}$, —C(R$^{14}$R$^{15}$)$_n$NR$^{12}$C(=Y)R$^{10}$, —(CR$^{14}$R$^{15}$)$_n$NR$^{12}$S(O)$_2$R$^{10}$, —CH(OR$^{10}$)R$^{10}$, —(CR$^{14}$R$^{15}$)$_n$OR$^{10}$, —(CR$^{14}$R$^{15}$)$_n$S(O)$_2$R$^{10}$, —(CR$^{14}$R$^{15}$)$_n$S(O)$_2$NR$^{10}$R$^{10}$, —C(=Y)R$^{10}$, —C(=Y)OR$^{10}$, —C(=Y)NR$^{10}$R$^{11}$, —C(=Y)NR$^{12}$OR$^{10}$, —C(=O)NR$^{12}$S(O)$_2$R$^{10}$, —C(=O)NR$^{12}$(CR$^{14}$R$^{15}$)$_m$NR$^{10}$R$^{11}$, —NO$_2$, —NHR$^{12}$, —NR$^{12}$C(=Y)R$^{11}$—NR$^{12}$C(=Y)OR$^{11}$, —NR$^{12}$C(=Y)NR$^{10}$R$^{11}$, —NR$^{12}$S(O)$_2$R$^{10}$, —NR$^{12}$SO$_2$NR$^{10}$R$^{11}$, —S(O)$_2$R$^{10}$, —S(O)$_2$NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl;

R[2] is selected from H, F, Cl, Br, I, C$_6$-C$_{20}$ aryl, C$_1$-C$_{20}$ heteroaryl, C$_1$-C$_6$ alkyl, C$_2$-C$_8$ alkenyl, and C$_2$-C$_8$ alkynyl;

R[3] is a monocyclic heteroaryl group selected from pyridyl, isoxazolyl, imidazolyl, pyrazolyl, pyrrolyl, thiazolyl, pyridazinyl, pyrimidinyl, pyrazinyl, oxazolyl, furanyl, thienyl, triazolyl, tetrazolyl, where the monocyclic heteroaryl group is optionally substituted with one or more groups selected from F, Cl, Br, I, —CN, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —C(=O)OR$^{10}$, —C(=O)NR$^{10}$R$^{11}$, C$_1$-C$_{12}$ alkyl and (C$_1$-C$_{12}$ alkyl)-OR$^{10}$;

R[10], R[11] and R[12] are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R[10] and R[11] together with the nitrogen to which they are attached optionally form a C$_3$-C$_{20}$ heterocyclic ring optionally containing one or more additional ring atoms selected from N, O or S, wherein said heterocyclic ring is optionally substituted with one or more groups independently selected from oxo, (CH$_2$)$_m$OR$^{10}$, (CH$_2$)$_m$NR$^{10}$R$^{11}$, CF$_3$, F, Cl, Br, I, SO$_2$R$^{10}$, C(=O)R$^{10}$, NR$^{12}$C(=Y)R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R[14] and R[15] are independently selected from H, C$_1$-C$_{12}$ alkyl, or —(CH$_2$)$_n$-aryl, or R[14] and R[15] together with the atoms to which they are attached form a saturated or partially unsaturated C$_3$-C$_{12}$ carbocyclic ring, mor is a morpholine group optionally substituted with one or more groups selected from F, Cl, Br, I, —C(C$_1$-C$_6$ alkyl)$_2$NR$^{10}$R$^{11}$, —(CR$^{14}$R$^{15}$)$_t$NR$^{10}$R$^{11}$, —C(R$^{14}$R$^{15}$)$_n$NR$^{12}$C(=Y)R$^{10}$, —(CR$^{14}$R$^{15}$)$_n$NR$^{12}$S(O)$_2$R$^{10}$, —CH(OR$^{10}$)R$^{10}$, —(CR$^{14}$R$^{15}$)$_n$OR$^{10}$, —(CR$^{14}$R$^{15}$)$_n$S(O)$_2$R$^{10}$, —(CR$^{14}$R$^{15}$)$_n$S(O)$_2$NR$^{10}$R$^{11}$, —C(=Y)R$^{10}$, —C(=Y)OR$^{10}$, —C(=Y)NR$^{10}$R$^{11}$, —C(=Y)NR$^{12}$OR$^{10}$, —C(=O)NR$^{12}$S(O)$_2$R$^{10}$, —C(=O)NR$^{12}$(CR$^{14}$R$^{15}$)$_m$NR$^{10}$R$^{11}$, —NO$_2$, —NHR$^{12}$, —NR$^{12}$C(=Y)R$^{11}$, —NR$^2$C(=Y)OR$^{11}$, —NR$^{12}$C(=Y)NR$^{10}$R$^{11}$, —NR$^{12}$S(O)$_2$R$^{10}$, —NR$^{12}$SO$_2$NR$^{10}$R$^{11}$, —S(O)$_2$R$^{10}$, —S(O)$_2$NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl; or where the C$_3$-C$_{12}$ carbocyclyl, C$_2$-C$_{20}$ heterocyclyl, C$_6$-C$_{20}$ aryl, or C$_1$-C$_{20}$ heteroaryl is substituted at vicinal carbon atoms of the morpholine and forms a fused bicyclic morpholinyl;

where said alkyl, alkenyl, alkynyl, carbocyclyl, heterocyclyl, aryl and heteroaryl are optionally substituted with one or more groups independently selected from F, Cl, Br, I, —CN, CF$_3$, —NO$_2$, oxo, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$C(=Y)NR$^{10}$R$^{11}$, —(CR$^{14}$R$^{15}$)$_n$NR$^{12}$SO$_2$R$^{10}$, —(CR$^{14}$R$^{15}$)$_n$OR$^{10}$, —(CR$^{14}$R$^{15}$)$_n$R$^{10}$, —(CR$^{14}$R$^{15}$)$_n$SO$_2$R$^{10}$, —NR$^{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, optionally substituted C$_1$-C$_{12}$ alkyl, optionally substituted C$_2$-C$_8$ alkenyl, optionally substituted C$_2$-C$_8$ alkynyl, optionally substituted C$_3$-C$_{12}$ carbocyclyl, optionally substituted C$_2$-C$_{20}$ heterocyclyl, optionally substituted C$_6$-C$_{20}$ aryl, and optionally substituted C$_1$-C$_{20}$ heteroaryl;

Y is O, S, or NR[12];

m is 0, 1, 2, 3, 4, 5 or 6;

n is 1, 2, 3, 4, 5 or 6; and t is 2, 3, 4, 5 or 6.

Formula Ia-d compounds are regioisomers, i.e. differ by the placement of atom X in the thienopyrimidine (X=sulfur) or furanopyrimidine (X=oxygen) ring system. Parent molecules of Formula Ia-d compounds are:

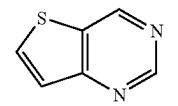

thieno[3,2-d]pyrimidine

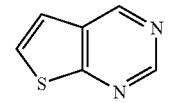

thieno[2,3-d]pyrimidine

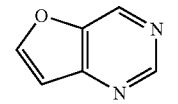

furo[3,2-d]pyrimidine

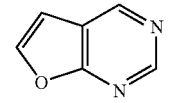

furo[3,2-d]pyrimidine

Compounds of the invention thus include both regioisomers of each of the 4-morpholino thienopyrimidine and 4-morpholino furanopyrimidine compounds, and the substituted forms as described by R[1], R[2], and R[3] herein:

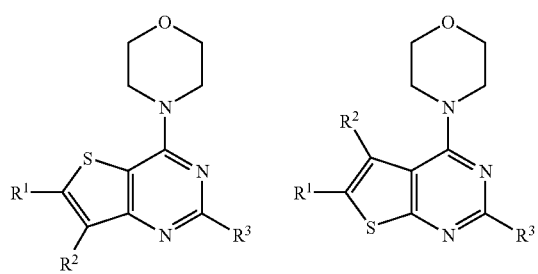

-continued

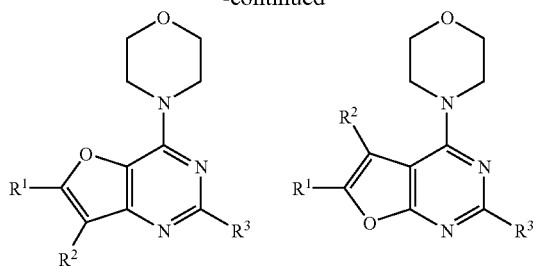

In certain embodiments, mor is selected from the structures:

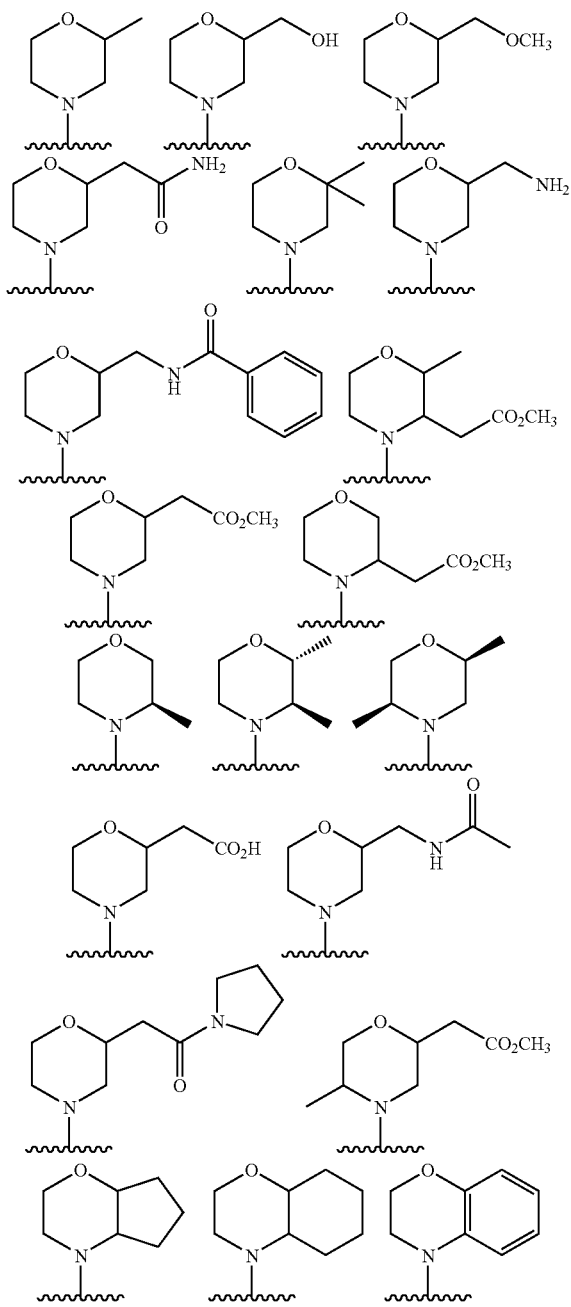

where the wavy line indicates the attachment to the 4-position of the pyrimidine ring.

In certain embodiments, $R^1$ is optionally substituted phenyl, wherein phenyl is substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-9dimethylamino)acetamide, amino, acetylamino, carboxamide, (4-methylsulfonylpiperazino)-1-methyl, (4-methylpiperazino)-1-methyl, hydroxymethyl, and methoxy.

In certain embodiments, $R^1$ is optionally substituted pyridyl, optionally substituted thiazolyl, optionally substituted isoxazolyl, optionally substituted oxadiazolyl, or optionally substituted pyrimidyl.

In certain embodiments, $R^1$ is —CH(CH$_3$)NR$^{10}$R$^{11}$, —C(CH$_3$)$_2$NR$^{10}$R$^{11}$, —C(R$^{14}$R$^{15}$)NR$^{12}$C(=O)R$^{10}$, —C(R$^{14}$R$^{15}$)NR$^{12}$S(O)$_2$R$^{10}$, —C(=O)NR$^{10}$R$^{11}$, or —C(R$^{14}$R$^{15}$)OR$^{10}$.

In certain embodiments, $R^2$ is H or CH$_3$.

In certain embodiments, $R^3$ is selected from the structures:

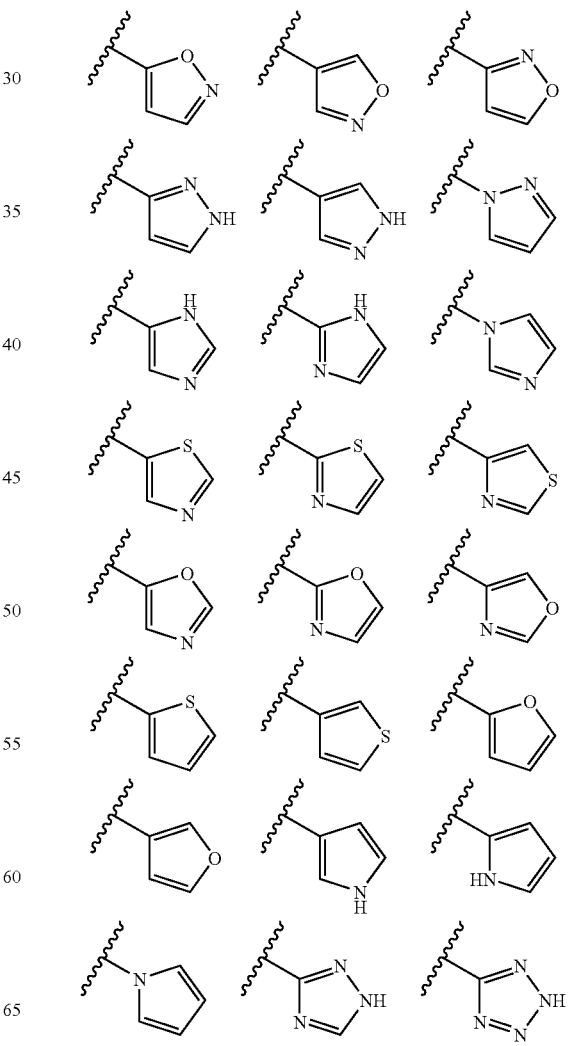

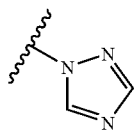

where the monocyclic heteroaryl group is optionally substituted with one or more groups selected from F, Cl, Br, I, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —C(=O)OR$^{10}$, —C(=O)NR$^{10}$R$^{11}$, and C$_1$-C$_{12}$ alkyl.

In certain embodiments, R$^3$ is selected from the structures:

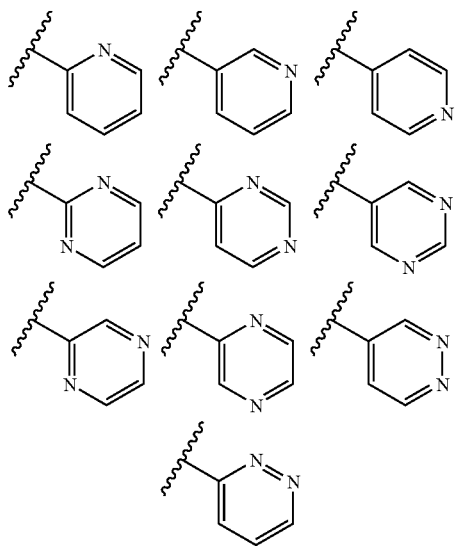

where the monocyclic heteroaryl group is optionally substituted with one or more groups selected from F, Cl, Br, I, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —C(=O)OR$^{10}$, —C(=O)NR$^{10}$R$^{11}$, and C$_1$-C$_{12}$ alkyl.

In certain embodiments, R$^3$ is selected from the structures:

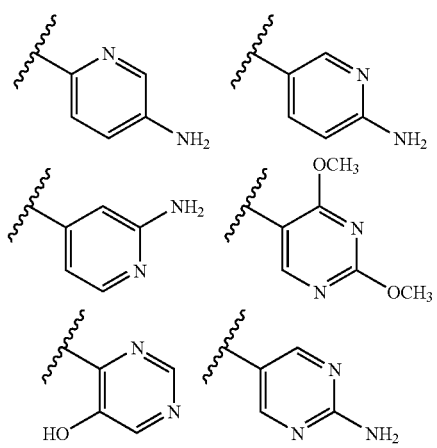

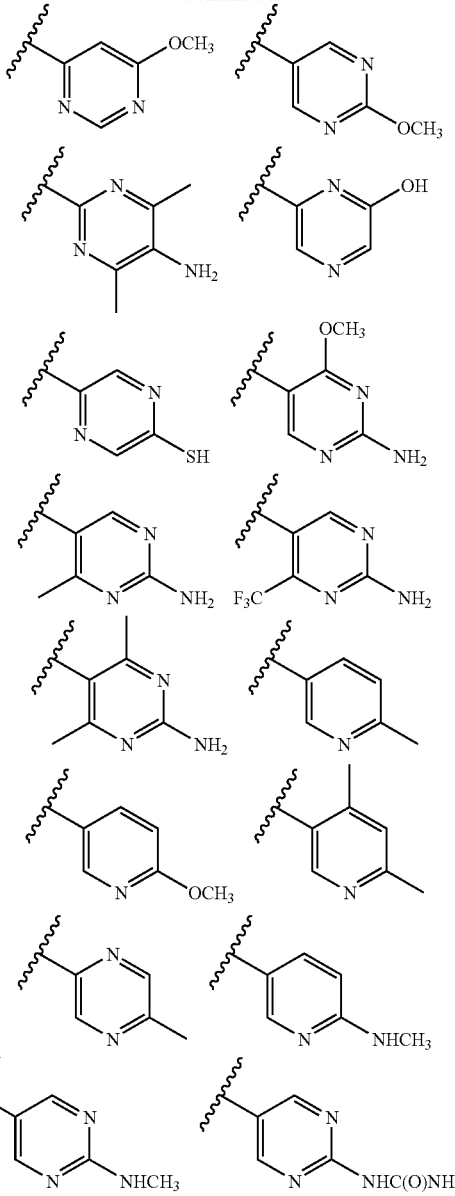

In certain embodiments, the monocyclic heteroaryl group is substituted with one or more groups selected from F, —NH$_2$, —NHCH$_3$, —N(CH$_3$)$_2$, —OH, —OCH$_3$, —C(O)CH$_3$, —NHC(O)CH$_3$, —N(C(O)CH$_3$)$_2$, —NHC(O)NH$_2$, —CO$_2$H, —CHO, —CH$_2$OH, —C(=O)NHCH$_3$, —C(=O)NH$_2$, and —CH$_3$.

The Formula Ia-d compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula Ia-d compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Preparation of Formula Ia-d Compounds

Thienopyrimidine and furanopyrimidine compounds of Formula Ia-d may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

In certain embodiments, compounds of Formula Ia-d may be readily prepared using procedures well-known to prepare thiophenes, furans, pyrimidines (U.S. Pat. No. 6,608,053; U.S. Pat. No. 6,492,383; U.S. Pat. No. 6,232,320; U.S. Pat. No. 6,187,777; U.S. Pat. No. 3,763,156; U.S. Pat. No. 3,661,908; U.S. Pat. No. 3,475,429; U.S. Pat. No. 5,075,305; US 2003/220365; GB 1393161; WO 93/13664;); and other heterocycles, which are described in: Comprehensive Heterocyclic Chemistry, Editors Katritzky and Rees, Pergamon Press, 1984.

Compounds of Formula Ia-d may be prepared singly or as compound libraries comprising at least 2, for example 5 to 1,000 compounds, or 10 to 100 compounds. Libraries of compounds of Formula Ia-d may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-7 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas Ia-d, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

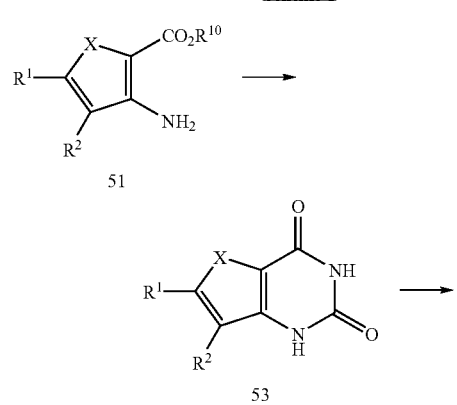

-continued

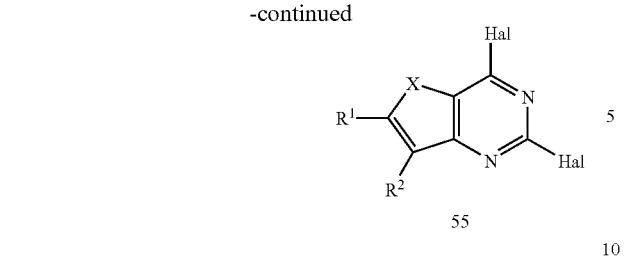

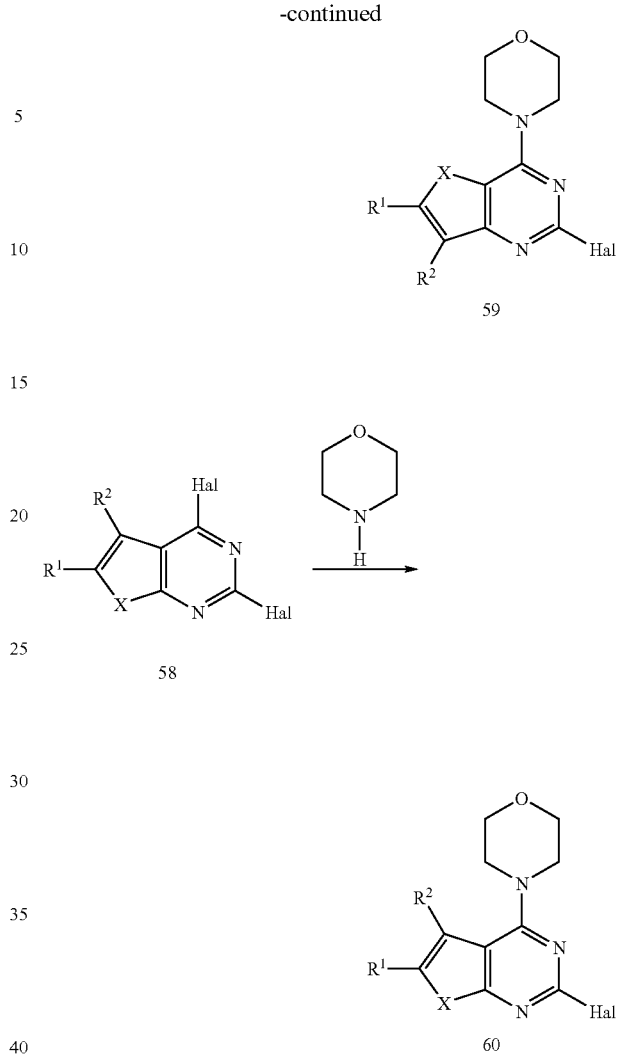

Scheme 1 shows a general method for preparation of the thienopyrimidine and furanopyrimidine intermediates 55 and 56 from 2-carboxyester, 3-amino thiophene (X═S) and furan (X═O), and 2-amino, 3-carboxy ester thiophene (X═S) and furan (X═O) reagents, respectively 51 and 52, wherein X is O or S; Hal is Cl, Br, or I; and $R^1$, $R^2$, and $R^{10}$ are as defined for Formula Ia-d compounds, or precursors or prodrugs thereto.

Scheme 2 shows a general method for selectively displacing a 4-halide from bis-halo thienopyrimidine and 4-morpholino furanopyrimidine intermediates 57 and 58 with morpholine under basic conditions in an organic solvent to prepare 2-halo, 4-morpholino thienopyrimidine and 4-morpholino furanopyrimidine compounds 59 and 60 respectively, wherein X is O or S; Hal is Cl, Br, or I; and $R^1$ and $R^2$ are as defined for Formula Ia-d compounds, or precursors or prodrugs thereto.

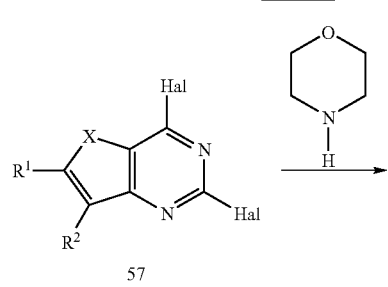

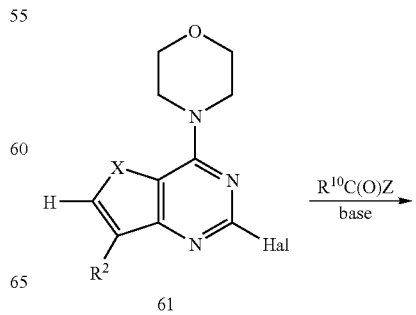

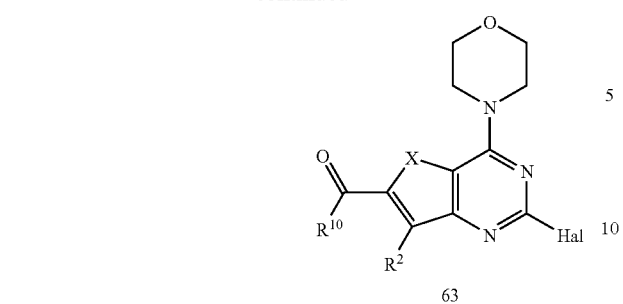

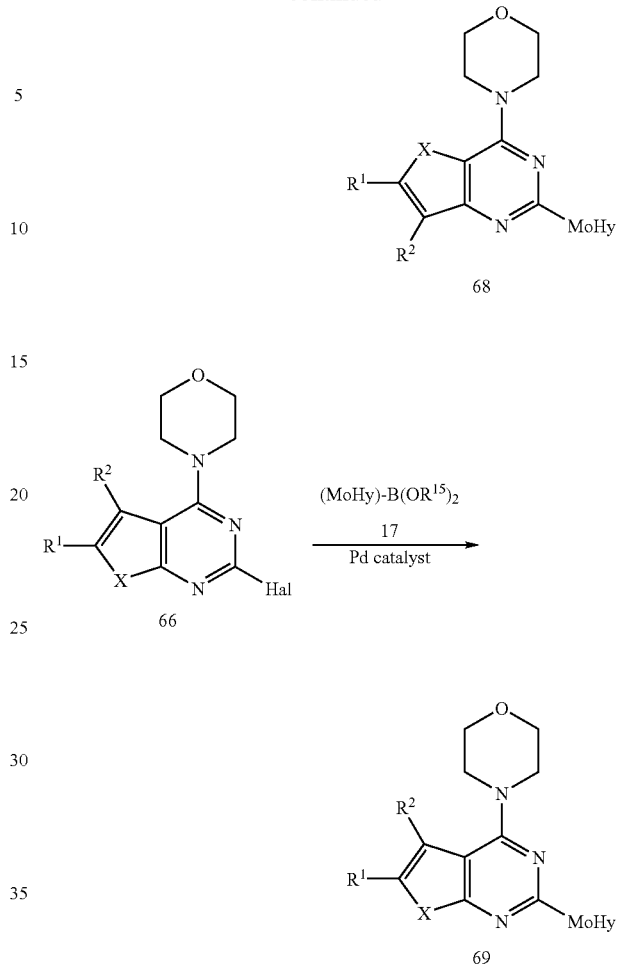

Scheme 3 shows a general method for derivatizing the 6-position of 2-halo, 4-morpholino, 6-hydrogen thienopyrimidine and 4-morpholino furanopyrimidine compounds 61 and 62 where $R^1$ is H. Treating 61 or 62 with a lithiating reagent to remove the 6 position proton, followed by adding an acylating reagent $R^{10}C(O)Z$ where Z is a leaving group, such as halide, NHS ester, carboxylate, or dialkylamino, gives 2-halo, 4-morpholino, 6-acyl thienopyrimidine and 4-morpholino furanopyrimidine compounds 63 and 64, wherein X is O or S; Hal is Cl, Br, or I; and $R^2$ and $R^{10}$ are as defined for Formula Ia-d compounds, or precursors or prodrugs thereto. An example of $R^{10}C(O)Z$ to prepare 6-formyl compounds ($R^{10}$=H) is N,N'-dimethylformamide (DMF).

Scheme 4

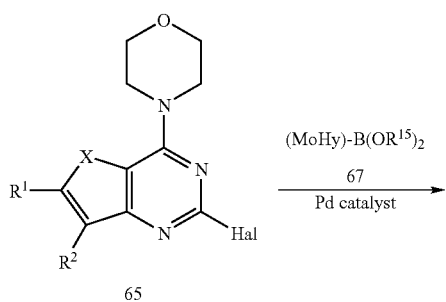

Scheme 4 shows a general method for Suzuki-type coupling of a 2-halo pyrimidine intermediate (65 and 66) with a monocyclic heteroaryl boronate acid ($R^{15}$=H) or ester ($R^{15}$=alkyl) reagent 67 to prepare the 2-monocyclic heteroaryl (MoHy), 4-morpholino thienopyrimidine and 4-morpholino furanopyrimidine compounds (68 and 69) of Formulas Ia-d wherein X is O or S; Hal is Cl, Br, or I; and $R^1$ and $R^2$ are as defined for Formula Ia-d compounds, or precursors or prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt-Bu)$_3$ (Owens et al (2003) Bioorganic & Med. Chem. Letters 13:4143-4145; Molander et al (2002) Organic Letters 4(11):1867-1870; U.S. Pat. No. 6,448,433).

Scheme 5

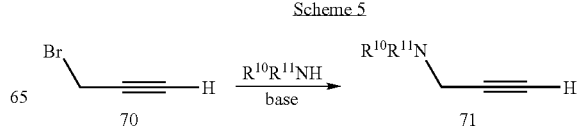

27
-continued

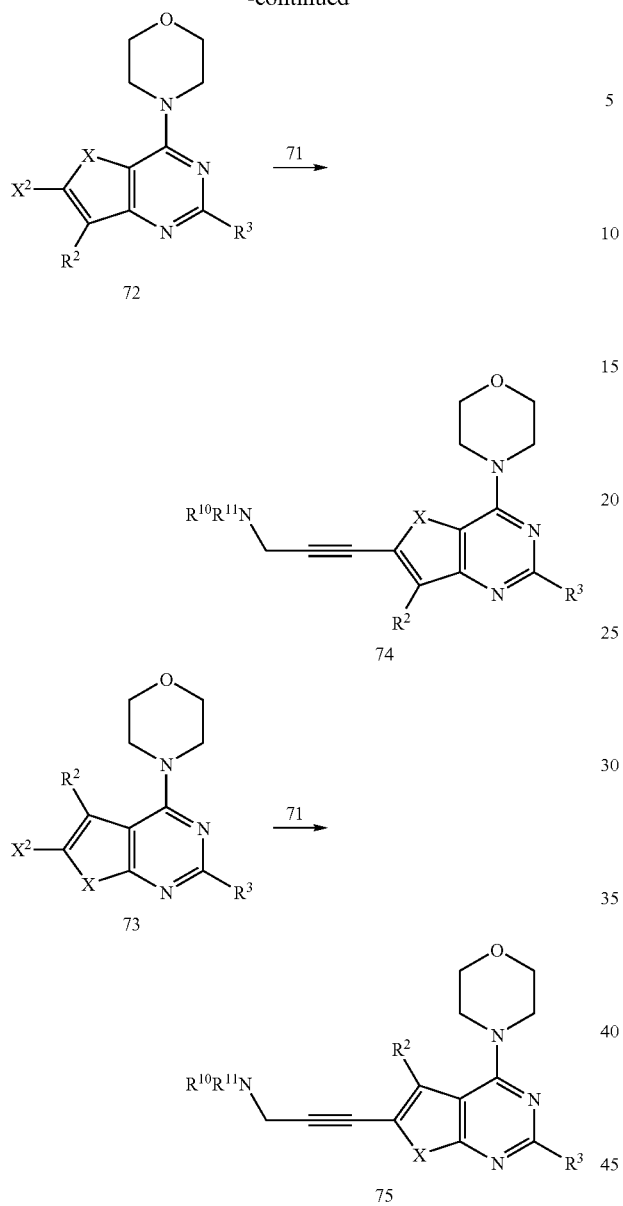

Scheme 5 shows a general method for the synthesis of alkynes 71, which can be used to prepare alkynylated derivatives of compounds 72 and 73. Propargylic amines 71 may be prepared by reaction of propargyl bromide 70 with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* (1995), 2:1039-1074; and Viehe, H. G., (1967) Angew. Chem., Int. Ed. Eng., 6(9):767-778. Alkynes 71 may subsequently be reacted with intermediates 72 ($X^2$=bromo or iodo) or 73 (via Sonogashira coupling), to provide compounds 74 and 75, respectively, wherein X is O or S, and $R^2$ and $R^3$ are as defined for Formula Ia-d compounds, or precursors or prodrugs thereto.

28

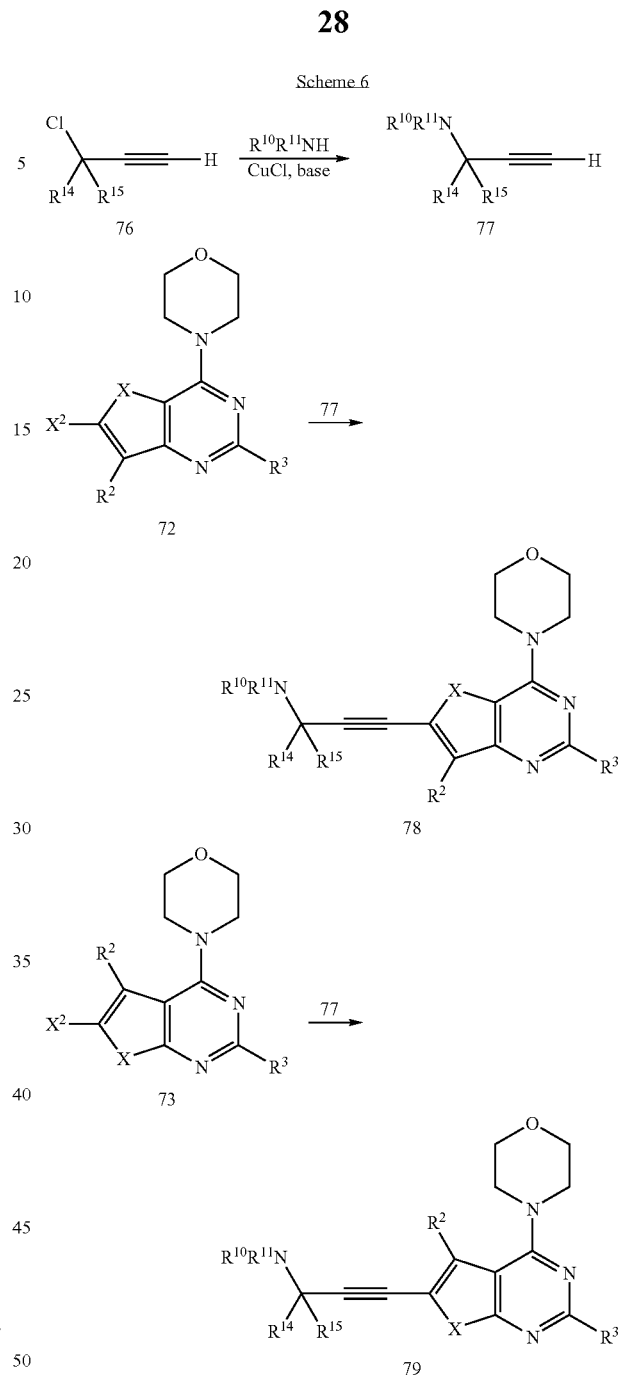

Scheme 6 shows a general method for the synthesis of alkynes 77, which can be used to prepare alkynylated derivatives of compounds 72 and 73. Gem-dialkyl propargylic amines 77 may be prepared using methods described by Zaragoza et al (2004) J. Med. Chem., 47:2833. According to Scheme 6, gem-dialkyl chloride 76 ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the alkyne 77. Alkyne 77 can be reacted with intermediates 72 or 73 (via Sonogashira coupling) to provide compounds 78 and 79, respectively, wherein X is O or S, and $R^2$ and $R^3$ are as defined for Formula Ia-d compounds, or precursors or prodrugs thereto.

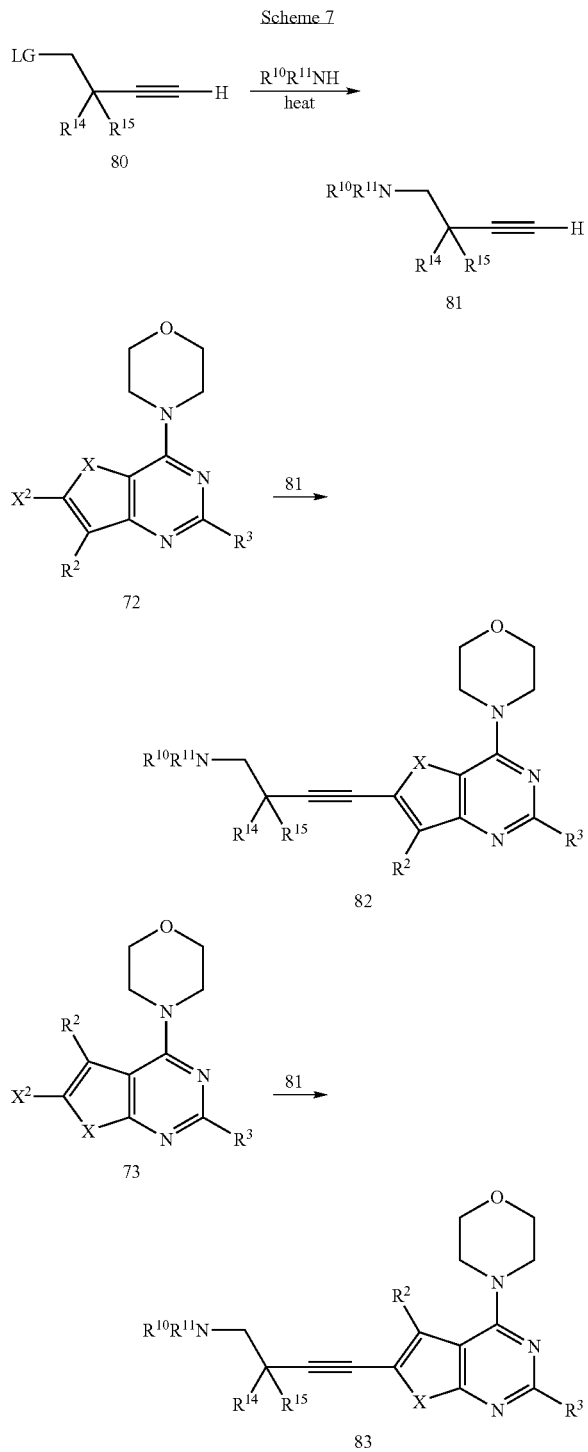

Scheme 7

Scheme 7 shows a general scheme for the synthesis of alkynes 81, which can be used to prepare alkynylated derivatives of compounds 72 and 73. But-3-yn-1-amines 81 (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes 80 (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki M. et al (1960) Ann. Chim. 5:845. Alkynes 81 can subsequently be reacted with intermediates 72 or 73 (via Sonogashira coupling), according to the descriptions provided for Schemes 5 and 6 to provide compounds 82 and 83, respectively, wherein X is O or S, and $R^2$ and $R^3$ are as defined for Formula Ia-d compounds, or precursors or prodrugs thereto.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of PI3 kinase activity of a compound of Formula Ia-d is possible by a number of direct and indirect detection methods. Certain exemplary compounds described herein were assayed for their PI3K binding activity (Example 460) and in vitro activity against tumor cells (Example 461). The range of PI3K binding activities was less than 1 nM (nanomolar) to about 10 μM (micromolar). Certain exemplary compounds of the invention had PI3K binding activity $IC_{50}$ values less than 10 nM. Certain compounds of the invention had tumor cell-based activity $IC_{50}$ values less than 100 nM.

The cytotoxic or cytostatic activity of Formula Ia-d exemplary compounds was measured by: establishing a proliferating mammalian tumor cell line in a cell culture medium, adding a Formula Ia-d compound, culturing the cells for a period from about 6 hours to about 5 days; and measuring cell viability (Example 461). Cell-based in vitro assays were used to measure viability, i.e. proliferation ($IC_{50}$), cytotoxicity ($EC_{50}$), and induction of apoptosis (caspase activation).

The in vitro potency of Formula Ia-d exemplary compounds was measured by the cell proliferation assay, CellTiter-Glo® Luminescent Cell Viability Assay, commercially available from Promega Corp., Madison, Wis. (Example 461). This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay an be used with various multiwell formats, e.g. 96 or 384 well format. Data can be recorded by luminometer or CCD camera imaging device. The luminescence output is presented as relative light units (RLU), measured over time.

The anti-proliferative effects of Formula Ia-d exemplary compounds were measured by the CellTiter-Glo® Assay (Example 461) against several tumor cell lines, including PC3, Detroit 562, and MDAMB361.1. $EC_{50}$ values were established for the tested compounds. The range of in vitro cell potency activities was about 100 nM to about 10 μM.

Certain ADME properties were measured for certain exemplary compounds by assays including: Caco-2 Permeability (Example 462), Hepatocyte Clearance (Example 463), Cytochrome P450 Inhibition (Example 464), Cytochrome P450 Induction (Example 465), Plasma Protein Binding (Example 466), and hERG channel blockage (Example 467).

Exemplary Formula Ia-d compounds No. 101-397 in Table 1 and No. 398-546 in Table 2, which were made according to the methods of this invention, have the following structures and their corresponding names (ChemDraw Ultra, Version 9.0.1, CambridgeSoft Corp., Cambridge Mass.) in Tables 1 and.

TABLE 1

| Compound | Structure | Name |
|---|---|---|
| 101 | 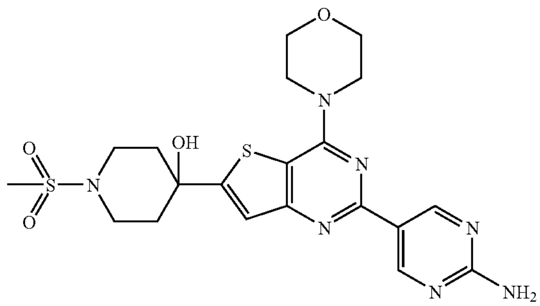 [SMILES: CS(=O)(=O)N1CCC(O)(c2cc3nc(-c4cnc(N)nc4)nc(N4CCOCC4)c3s2)CC1] | 4-(2-(2-aminopyrimidin-5-yl)-4-morpholinothieno[3,2-d]pyrimidin-6-yl)N-methylsulfonylpiperidin-4-ol |
| 102 | 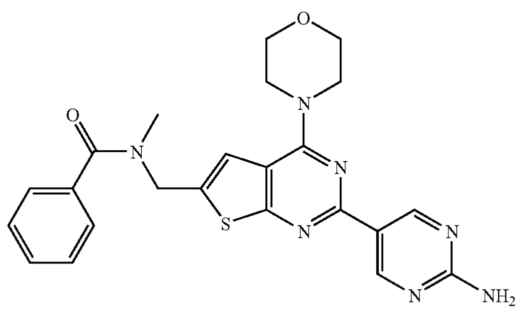 [SMILES: CN(Cc1cc2c(N3CCOCC3)nc(-c3cnc(N)nc3)nc2s1)C(=O)c1ccccc1] | N-((2-(2-aminopyrimidin-5-yl)-4-morpholinothieno[2,3-d]pyrimidin-6-yl)methyl)-N-methylbenzamide |
| 103 | 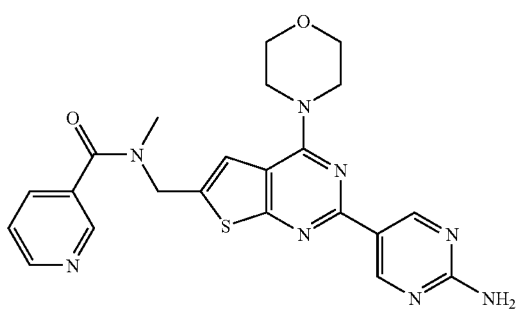 [SMILES: CN(Cc1cc2c(N3CCOCC3)nc(-c3cnc(N)nc3)nc2s1)C(=O)c1cccnc1] | N-((2-(2-aminopyrimidin-5-yl)-4-morpholinothieno[2,3-d]pyrimidin-6-yl)methyl)-N-methylnicotinamide |
| 104 | 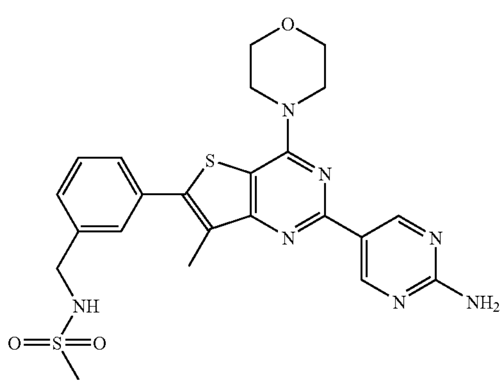 [SMILES: Cc1c(-c2cccc(CNS(C)(=O)=O)c2)sc2c(N3CCOCC3)nc(-c3cnc(N)nc3)nc12] | 5-(6-(3-(N-methylsulfonylaminomethyl)phenyl)-7-methyl-4-morpholinothieno[3,2-d]pyrimidin-2-yl)pyrimidin-2-amine |

TABLE 1-continued

| Compound | Structure | Name |
|---|---|---|
| 105 | 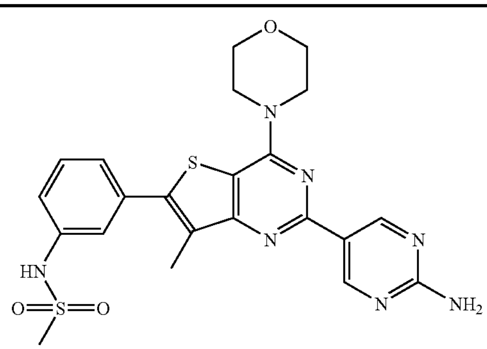 | 5-(6-(3-N-methylsulfonylaminophenyl)-7-methyl-4-morpholinothieno[3,2-d]pyrimidin-2-yl)pyrimidin-2-amine |
| 106 | 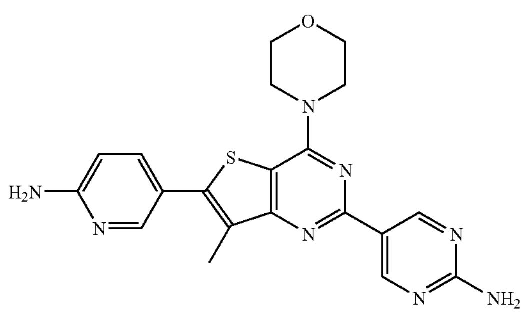 [SMILES: Cc1c(-c2ccc(N)nc2)sc2c(N3CCOCC3)nc(-c3cnc(N)nc3)nc12] | 5-(6-(6-aminopyridin-3-yl)-7-methyl-4-morpholinothieno[3,2-d]pyrimidin-2-yl)pyrimidin-2-amine |
| 107 | 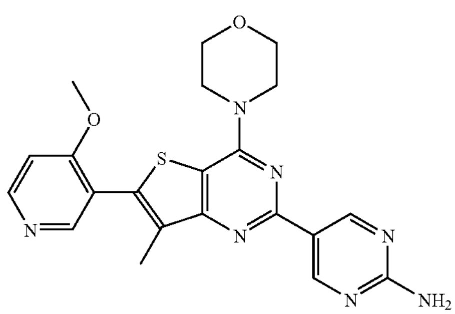 [SMILES: COc1ccncc1-c1sc2c(N3CCOCC3)nc(-c3cnc(N)nc3)nc2c1C] | 5-(6-(4-methoxypyridin-3-yl)-7-methyl-4-morpholinothieno[3,2-d]pyrimidin-2-yl)pyrimidin-2-amine |
| 108 | 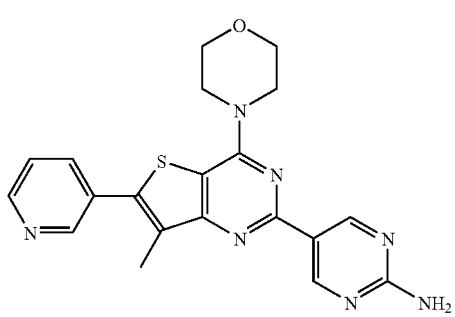 [SMILES: Cc1c(-c2cccnc2)sc2c(N3CCOCC3)nc(-c3cnc(N)nc3)nc12] | 5-(7-methyl-4-morpholino-6-(pyridin-3-yl)thieno[3,2-d]pyrimidin-2-yl)pyrimidin-2-amine |
| 109 | 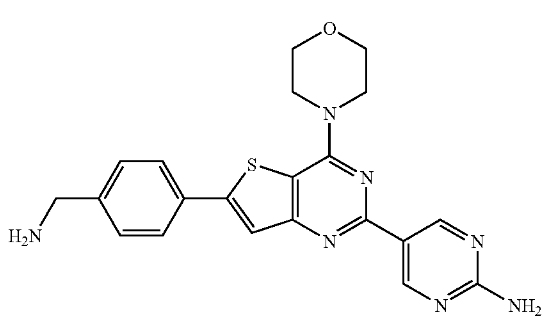 [SMILES: NCc1ccc(-c2cc3nc(-c4cnc(N)nc4)nc(N4CCOCC4)c3s2)cc1] | 5-(6-(4-(aminomethyl)phenyl)-4-morpholinothieno[3,2-d]pyrimidin-2-yl)pyrimidin-2-amine |

TABLE 1-continued

| Compound | Structure | Name |
|---|---|---|
| 110 | 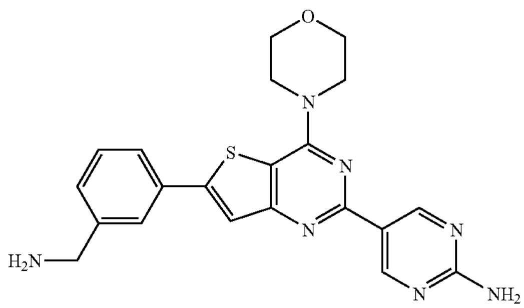 [SMILES: NCc1cccc(-c2cc3nc(-c4cnc(N)nc4)nc(N4CCOCC4)c3s2)c1] | 5-(6-(3-(aminomethyl)phenyl)-4-morpholinothieno[3,2-d]pyrimidin-2-yl)pyrimidin-2-amine |
| 111 | 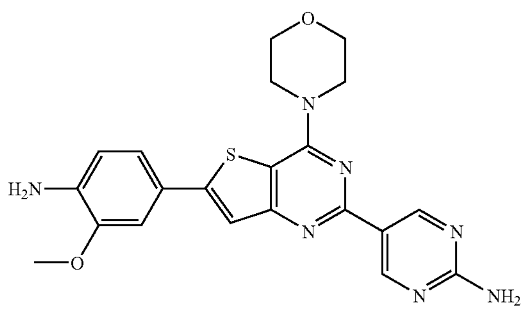 [SMILES: COc1cc(-c2cc3nc(-c4cnc(N)nc4)nc(N4CCOCC4)c3s2)ccc1N] | 5-(6-(4-amino-3-methoxyphenyl)-4-morpholinothieno[3,2-d]pyrimidin-2-yl)pyrimidin-2-amine |
| 112 | 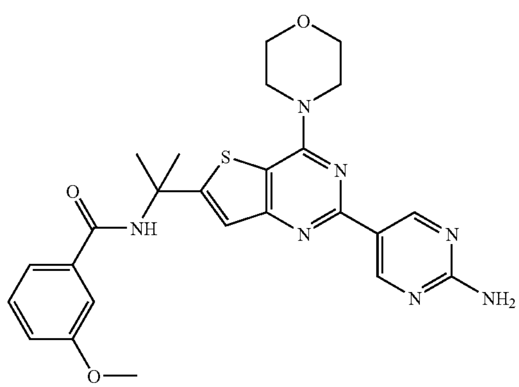 [SMILES: COc1cccc(C(=O)NC(C)(C)c2cc3nc(-c4cnc(N)nc4)nc(N4CCOCC4)c3s2)c1] | N-(2-(2-(2-aminopyrimidin-5-yl)-4-morpholinothieno[3,2-d]pyrimidin-6-yl)propan-2-yl)-3-methoxybenzamide |
| 113 | 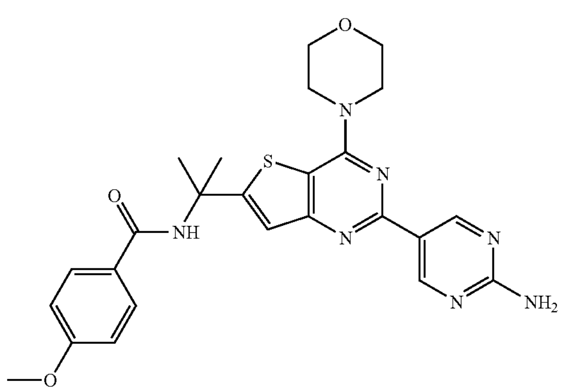 [SMILES: COc1ccc(C(=O)NC(C)(C)c2cc3nc(-c4cnc(N)nc4)nc(N4CCOCC4)c3s2)cc1] | N-(2-(2-(2-aminopyrimidin-5-yl)-4-morpholinothieno[3,2-d]pyrimidin-6-yl)propan-2-yl)-4-methoxybenzamide |

TABLE 1-continued

| Compound | Structure | Name |
|---|---|---|
| 114 | 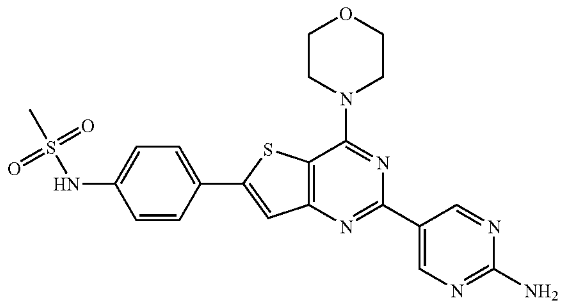 [SMILES: CS(=O)(=O)Nc1ccc(-c2cc3nc(-c4cnc(N)nc4)nc(N4CCOCC4)c3s2)cc1] | 5-(6-(4-N-methylsulfonylaminophenyl)-4-morpholinothieno[3,2-d]pyrimidin-2-yl)pyrimidin-2-amine |
| 115 | 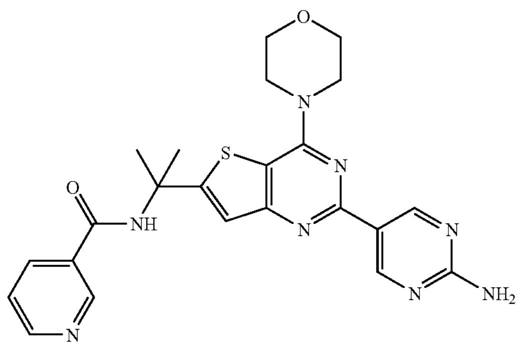 [SMILES: CC(C)(NC(=O)c1cccnc1)c1cc2nc(-c3cnc(N)nc3)nc(N3CCOCC3)c2s1] | N-(2-(2-(2-aminopyrimidin-5-yl)-4-morpholinothieno[3,2-d]pyrimidin-6-yl)propan-2-yl)nicotinamide |
| 116 | 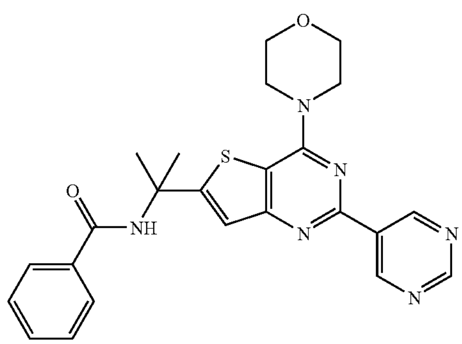 [SMILES: CC(C)(NC(=O)c1ccccc1)c1cc2nc(-c3cncnc3)nc(N3CCOCC3)c2s1] | N-(2-(4-morpholino-2-(pyrimidin-5-yl)thieno[3,2-d]pyrimidin-6-yl)propan-2-yl)benzamide |
| 117 | 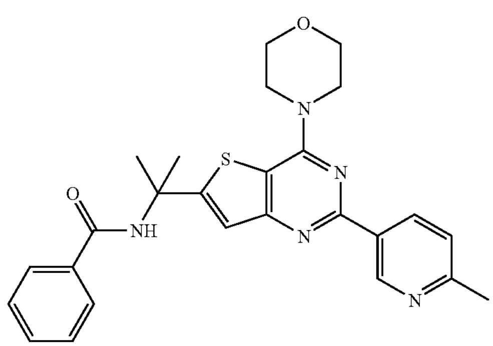 [SMILES: Cc1ccc(-c2nc(N3CCOCC3)c3sc(C(C)(C)NC(=O)c4ccccc4)cc3n2)cn1] | N-(2-(2-(6-methylpyridin-3-yl)-4-morpholinothieno[3,2-d]pyrimidin-6-yl)propan-2-yl)benzamide |

TABLE 1-continued

| Compound | Structure | Name |
|---|---|---|
| 118 | 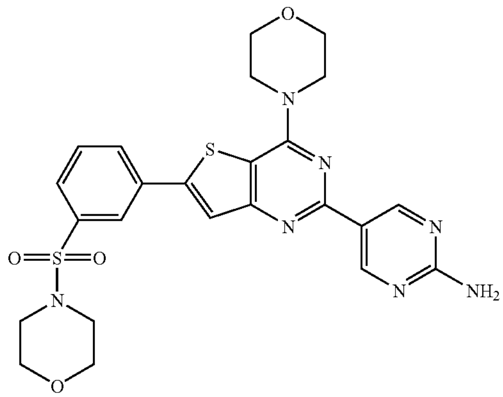 [SMILES: Nc1ncc(-c2nc(N3CCOCC3)c3sc(-c4cccc(S(=O)(=O)N5CCOCC5)c4)cc3n2)cn1] | 5-(4-morpholino-6-(3-morpholinosulfonyl)phenylthieno[3,2-d]pyrimidin-2-yl)pyrimidin-2-amine |
| 119 | 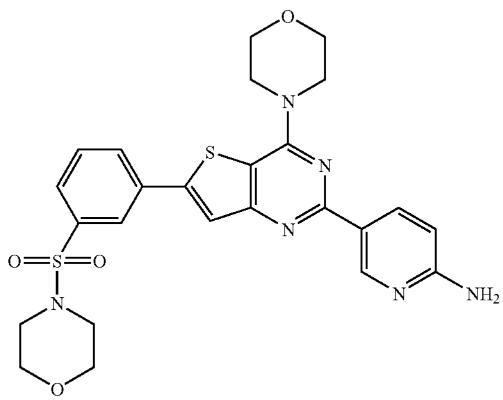 [SMILES: Nc1ccc(-c2nc(N3CCOCC3)c3sc(-c4cccc(S(=O)(=O)N5CCOCC5)c4)cc3n2)cn1] | 5-(4-morpholino-6-(3-morpholinosulfonyl)phenylthieno[3,2-d]pyrimidin-2-yl)pyridin-2-amine |
| 120 | 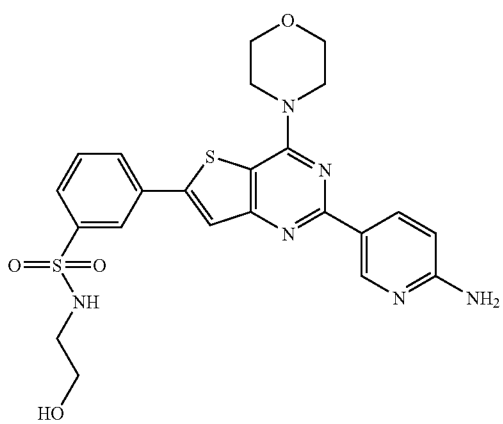 [SMILES: Nc1ccc(-c2nc(N3CCOCC3)c3sc(-c4cccc(S(=O)(=O)NCCO)c4)cc3n2)cn1] | 5-(4-morpholino-6-(3-(2-hydroxyethylamino)sulfonyl)phenyl-thieno[3,2-d]pyrimidin-2-yl)pyridin-2-amine |
| 121 | 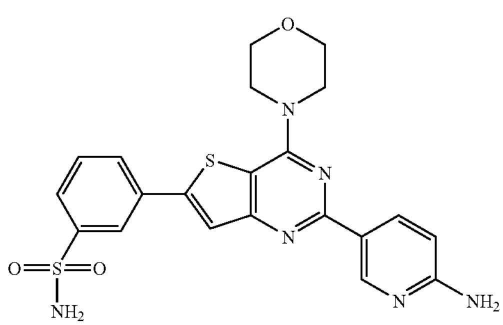 [SMILES: Nc1ccc(-c2nc(N3CCOCC3)c3sc(-c4cccc(S(N)(=O)=O)c4)cc3n2)cn1] | 5-(4-morpholino-6-(3-aminosulfonyl)phenylthieno[3,2-d]pyrimidin-2-yl)pyridin-2-amine |

TABLE 1-continued

| Compound | Structure | Name |
|---|---|---|
| 122 | 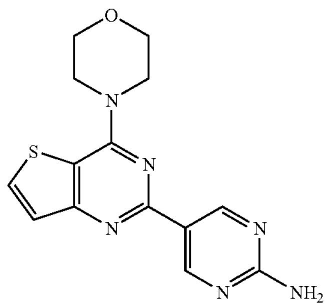 | 5-(4-morpholinothieno[3,2-d]pyrimidin-2-yl)pyrimidin-2-amine |
| 123 | 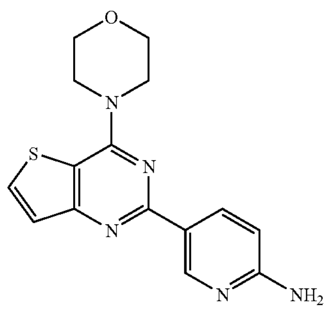 [SMILES: Nc1ccc(-c2nc(N3CCOCC3)c3sccc3n2)cn1] | 5-(4-morpholinothieno[3,2-d]pyrimidin-2-yl)pyridin-2-amine |
| 124 | 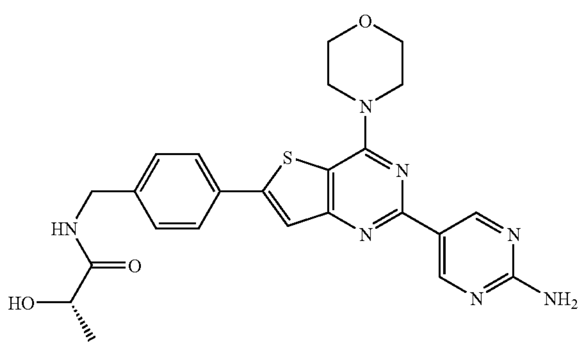 [SMILES: C[C@H](O)C(=O)NCc1ccc(-c2cc3nc(-c4cnc(N)nc4)nc(N4CCOCC4)c3s2)cc1] | (S)-N-((4-(2-(2-aminopyrimidin-5-yl)-4-morpholinothieno[3,2-d]pyrimidin-6-yl)phenyl)methyl)-2-hydroxypropanamide |
| 125 | 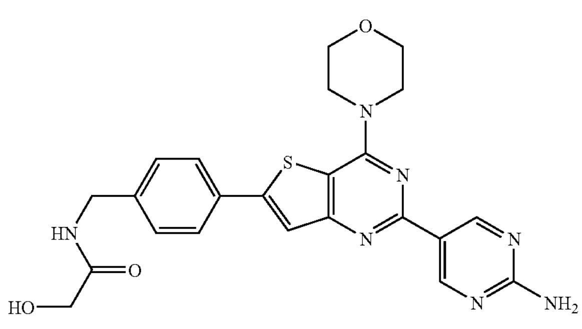 [SMILES: Nc1ncc(-c2nc(N3CCOCC3)c3sc(-c4ccc(CNC(=O)CO)cc4)cc3n2)cn1] | N-((4-(2-(2-aminopyrimidin-5-yl)-4-morpholinothieno[3,2-d]pyrimidin-6-yl)phenyl)methyl)-2-hydroxyacetamide |

TABLE 1-continued

| Compound | Structure | Name |
|---|---|---|
| 126 | 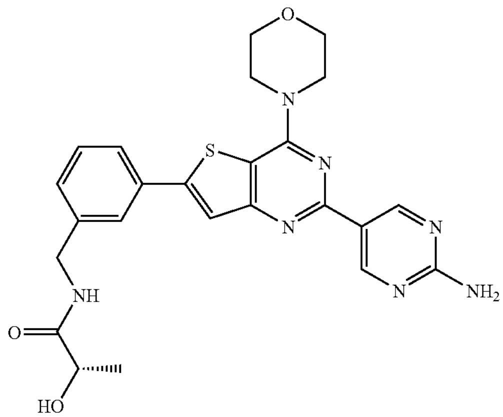 [SMILES: C[C@H](O)C(=O)NCc1cccc(-c2cc3nc(-c4cnc(N)nc4)nc(N4CCOCC4)c3s2)c1] | (2S)-N-((3-(2-(2-aminopyrimidin-5-yl)-4-morpholinothieno[3,2-d]pyrimidin-6-yl)phenyl)methyl)-2-hydroxypropanamaide |
| 127 | 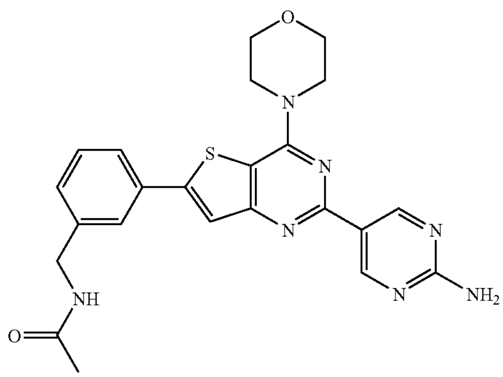 [SMILES: CC(=O)NCc1cccc(-c2cc3nc(-c4cnc(N)nc4)nc(N4CCOCC4)c3s2)c1] | N-((3-(2-(2-aminopyrimidin-5-yl)-4-morpholinothieno[3,2-d]pyrimidin-6-yl)phenyl)methyl)acetamide |
| 128 | 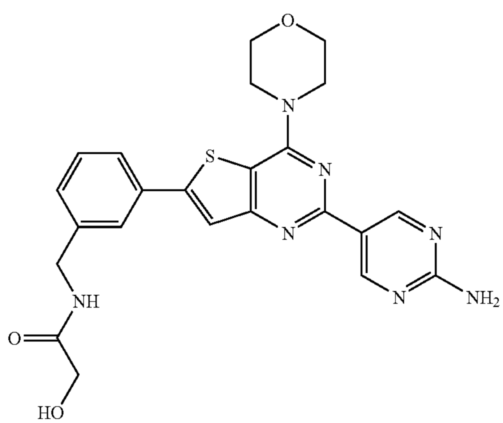 [SMILES: Nc1ncc(-c2nc(N3CCOCC3)c3sc(-c4cccc(CNC(=O)CO)c4)cc3n2)cn1] | N-((3-(2-(2-aminopyrimidin-5-yl)-4-morpholinothieno[3,2-d]pyrimidin-6-yl)phenyl)methyl)-2-hydroxyacetamide |
| 129 | 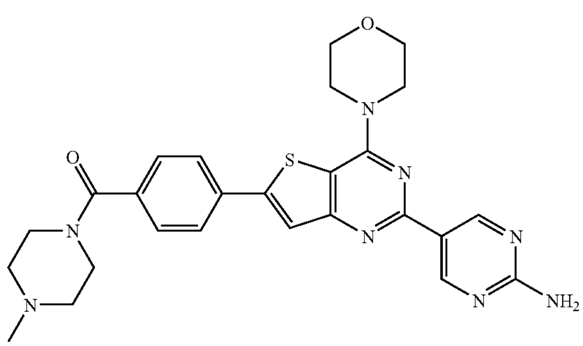 [SMILES: CN1CCN(C(=O)c2ccc(-c3cc4nc(-c5ccc(N)nc5)nc(N5CCOCC5)c4s3)cc2)CC1] | (4-(2-(2-aminopyrimidin-5-yl)-4-morpholinothieno[3,2-d]pyrimidin-6-yl)phenyl)(4-methylpiperiazin-1-yl)methanone |

TABLE 1-continued

| Compound | Structure | Name |
|---|---|---|
| 130 | 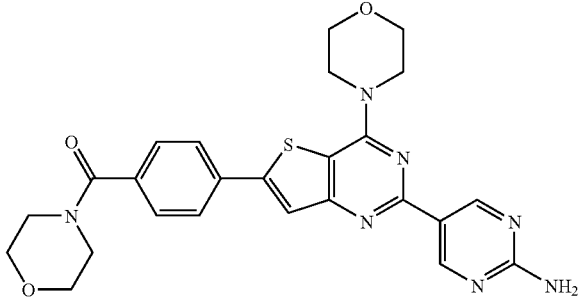 | (4-(2-(2-aminopyrimidin-5-yl)-4-morpholinothieno[3,2-d]pyrimidin-6-yl)phenyl)(morpholino)methanone |
| 131 | 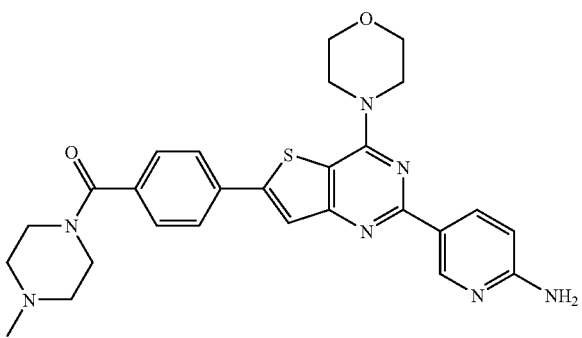 | (4-(2-(6-aminopyrimidin-3-yl)-4-morpholinothieno[3,2-d]pyrimidin-6-yl)phenyl)(4-methylpiperazin-1-yl)methanone |
| 132 | 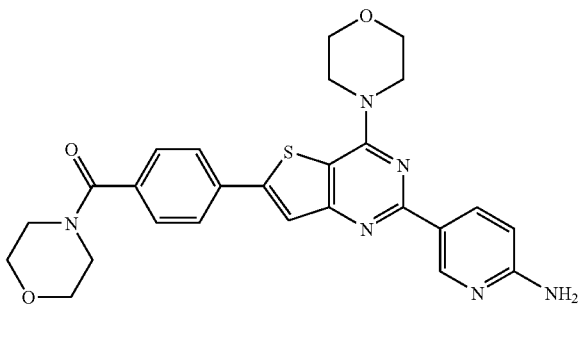 [SMILES: Nc1ccc(-c2nc(N3CCOCC3)c3sc(-c4ccc(C(=O)N5CCOCC5)cc4)cc3n2)cn1] | (4-(2-(6-aminopyridin-3-yl)-4-morpholinothieno[3,2-d]pyrimidin-6-yl)phenyl)(morpholino)methanone |
| 133 | 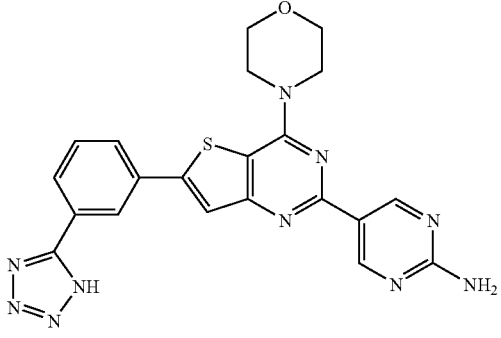 [SMILES: Nc1ncc(-c2nc(N3CCOCC3)c3sc(-c4cccc(-c5nnn[nH]5)c4)cc3n2)cn1] | 5-(6-(3-(1H-tetrazol-5-yl)phenyl)-4-morpholinothieno[3,2-d]pyrimidin-2-yl)pyrimidin-2-amine |

TABLE 1-continued

| Compound | Structure | Name |
|---|---|---|
| 134 | 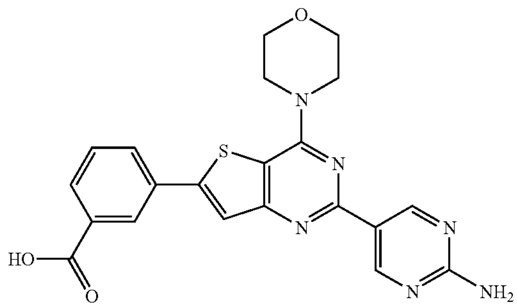 | 3-(2-(2-aminopyrimidin-5-yl)-4-morpholinothieno[3,2-d]pyrimidin-6-yl)benzoic acid |
| 135 | 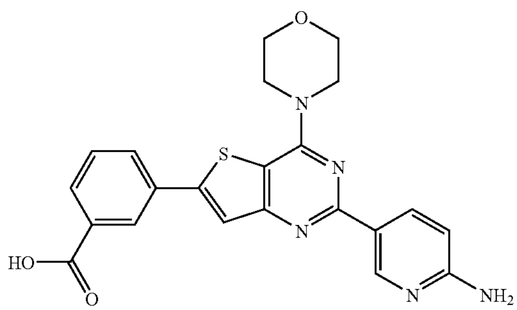 | 3-(2-(6-aminopyrimidin-3-yl)-4-morpholinothieno[3,2-d]pyrimidin-6-yl)benzoic acid |
| 136 | 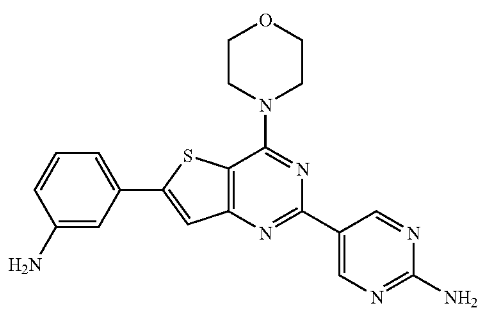 | 5-(6-(3-aminophenyl)-4-morpholinothieno[3,2-d]pyrimidin-2-yl)pyrimidin-2-amine |
| 137 | 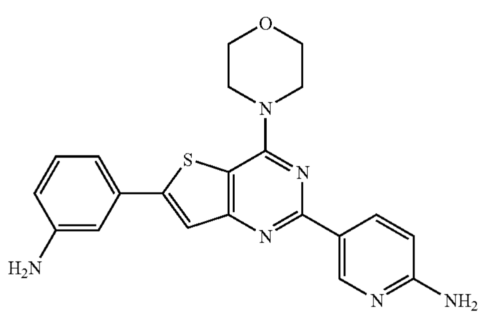 [SMILES: Nc1cccc(-c2cc3nc(-c4ccc(N)nc4)nc(N4CCOCC4)c3s2)c1] | 5-(6-(3-aminophenyl)-4-morpholinothieno[3,2-d]pyrimidin-2-yl)pyridin-2-amine |
| 138 | 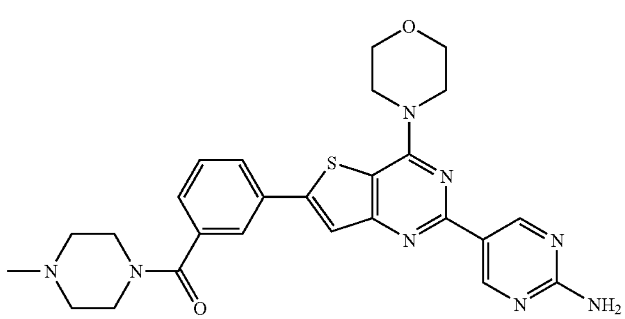 [SMILES: CN1CCN(C(=O)c2cccc(-c3cc4nc(-c5cnc(N)nc5)nc(N5CCOCC5)c4s3)c2)CC1] | (3-(2-(2-aminopyrimidin-5-yl)-4-morpholinothieno[3,2-d]pyrimidin-6-yl)phenyl)(4-methylpiperazin-1-yl)methanone |

TABLE 1-continued

| Compound | Structure | Name |
|---|---|---|
| 139 | 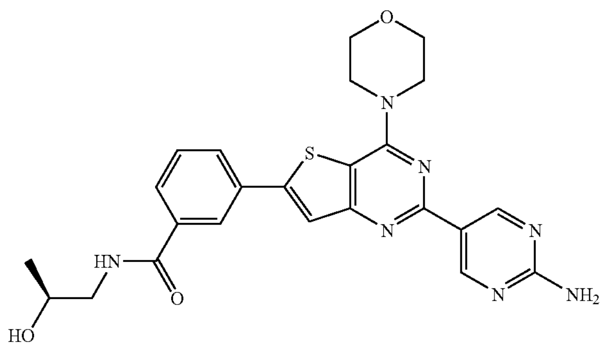 [SMILES: C[C@H](O)CNC(=O)c1cccc(-c2cc3nc(-c4cnc(N)nc4)nc(N4CCOCC4)c3s2)c1] | 3-(2-(2-aminopyrimidin-5-yl)-4-morpholinothieno[3,2-d]pyrimidin-6-yl)-N-((S)-2-hydroxypropyl)benzamide |
| 140 | 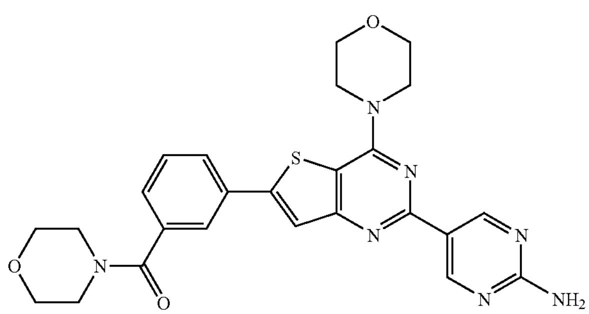 | (3-(2-(2-aminopyrimidin-5-yl)-4-morpholinothieno[3,2-d]pyrimidin-6-yl)phenyl)(morpholino)methanone |
| 141 | 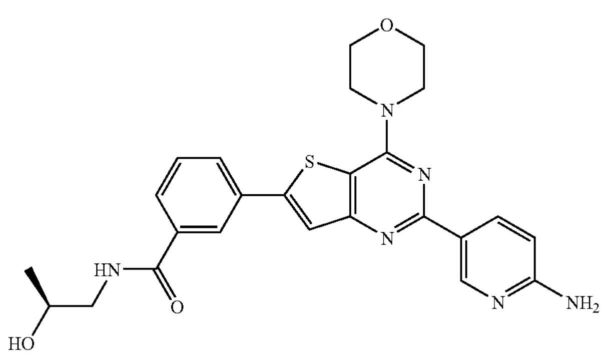 | 3-(2-(6-aminopyrimidin-3-yl)-4-morpholinothieno[3,2-d]pyrimidin-6-yl)-N-((S)-2-hydroxypropyl)benzamide |
| 142 | 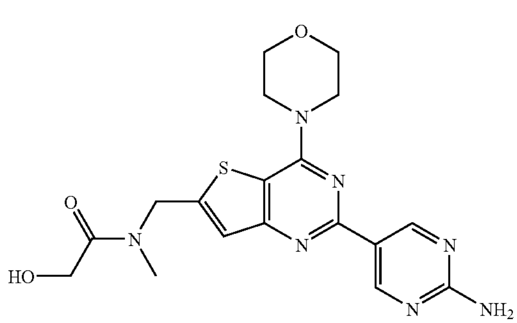 [SMILES: CN(Cc1cc2nc(-c3cnc(N)nc3)nc(N3CCOCC3)c2s1)C(=O)CO] | N-((2-(2-aminopyrimidin-5-yl)-4-morpholinothieno[3,2-d]pyrimidin-6-yl)methyl)-2-hydroxy-N-methylacetamide |

TABLE 1-continued

| Compound | Structure | Name |
|---|---|---|
| 143 | 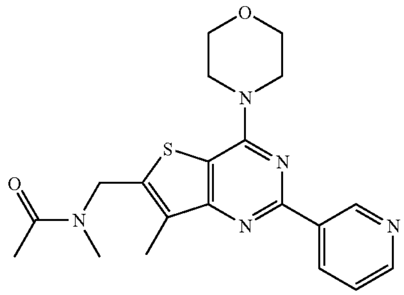 [SMILES: CC(=O)N(C)Cc1sc2c(N3CCOCC3)nc(-c3cccnc3)nc2c1C] | N-methyl-N-((7-methyl-4-morpholino-2-(pyridin-3-yl)thieno[3,2-d]pyrimidin-6-yl)thienyl)acetamide |
| 144 | 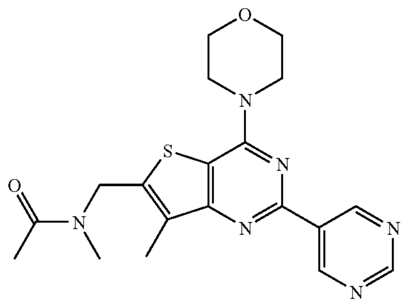 [SMILES: CC(=O)N(C)Cc1sc2c(N3CCOCC3)nc(-c3cncnc3)nc2c1C] | N-methyl-N-((7-methyl-4-morpholino-2-(pyrimidin-5-yl)thieno[3,2-d]pyrimidin-6-yl)methyl)acetamide |
| 145 | 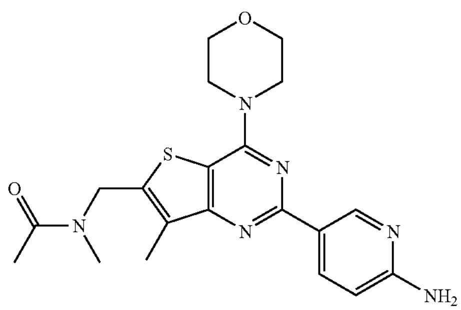 | N-((2-(6-aminopyridin-3-yl)-7-methyl-4-morpholinothieno[3,2-d]pyrimidin-6-yl)methyl)-N-methylacetamide |
| 146 | 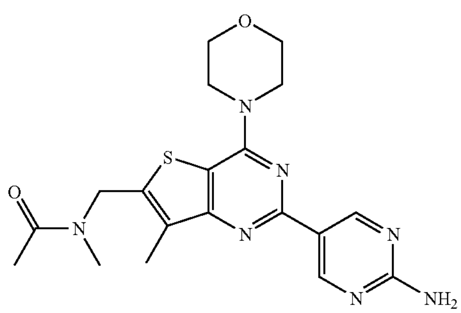 [SMILES: CC(=O)N(C)Cc1sc2c(N3CCOCC3)nc(-c3cnc(N)nc3)nc2c1C] | N-((2-(2-aminpyrimidin-5-yl)-7-methyl-4-morpholinothieno[3,2-d]pyrimidin-6-yl)methyl)-N-methylacetamide |
| 147 | 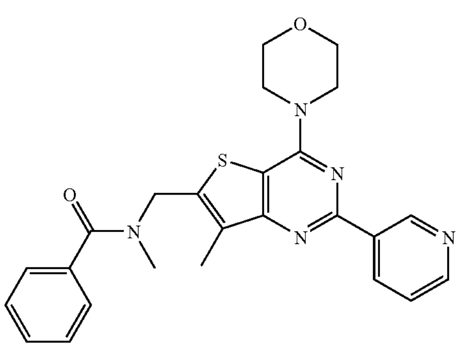 | N-methyl-N-((7-methyl-4-morpholino-2-(pyridin-3-yl)thieno[3,2-d]pyrimidin-6-yl)methyl)benzamide |

TABLE 1-continued

| Compound | Structure | Name |
|---|---|---|
| 148 | 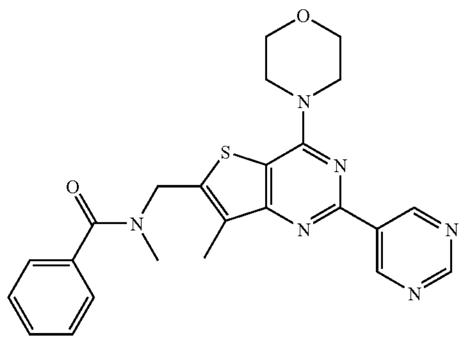 [SMILES: Cc1c(CN(C)C(=O)c2ccccc2)sc2c(N3CCOCC3)nc(-c3cccnc3)nc12] | N-methyl-N-((7-methyl-4-morpholino-2-(pyrimidin-5-yl)thieno[3,2-d]pyrimidin-6-yl)methyl)benzamide |
| 149 | 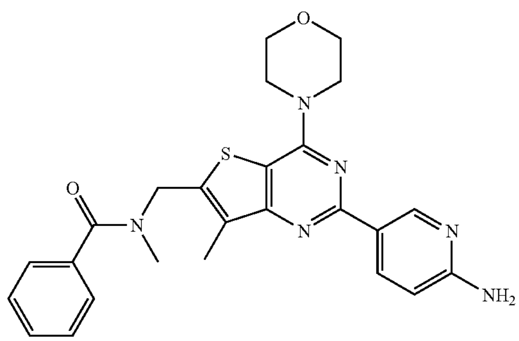 [SMILES: Cc1c(CN(C)C(=O)c2ccccc2)sc2c(N3CCOCC3)nc(-c3ccc(N)nc3)nc12] | N-((2-(6-aminopyridin-3-yl)-7-methyl-4-morpholinothieno[3,2-d]pyrimidin-6-yl)methyl)-N-methylbenzamide |
| 150 | 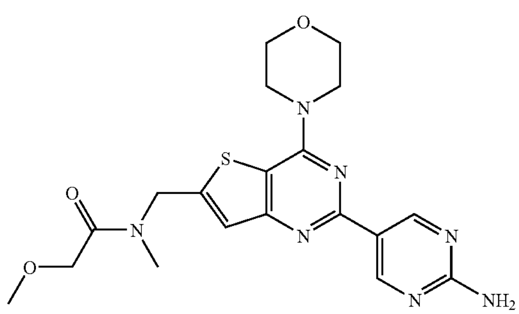 | N-((2-(2-aminopyrimidin-5-yl)-4-morpholinothieno[3,2-d]pyrimidin-6-yl)methyl)-2-methoxy-N-methylacetamide |
| 151 | 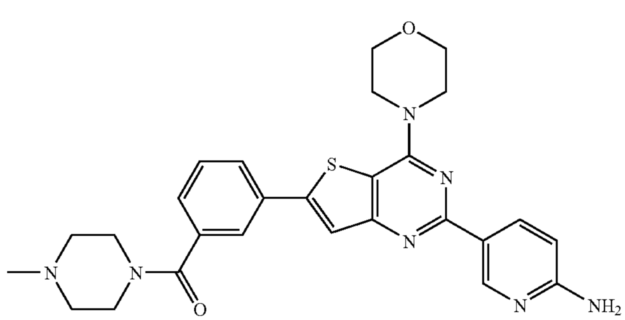 | (3-(2-(6-aminopyridin-3-yl)-4-morpholinothieno[3,2-d]pyrimidin-6-yl)phenyl)(4-methylpiperazin-1-yl)methanone |

TABLE 1-continued

| Compound | Structure | Name |
|---|---|---|
| 152 | 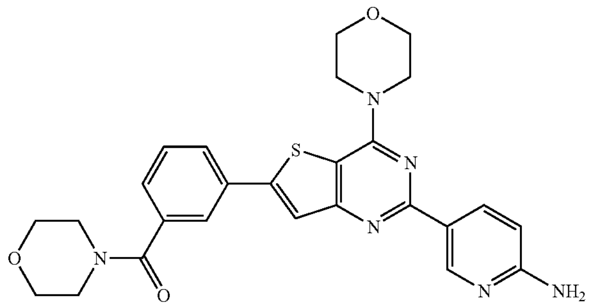 [SMILES: Nc1ccc(-c2nc(N3CCOCC3)c3sc(-c4cccc(C(=O)N5CCOCC5)c4)cc3n2)cn1] | (3-(2-(6-aminopyridin-3-yl)-4-morpholinothieno[3,2-d]pyrimidin-6-yl)phenyl)(morpholino)methanone |
| 153 | 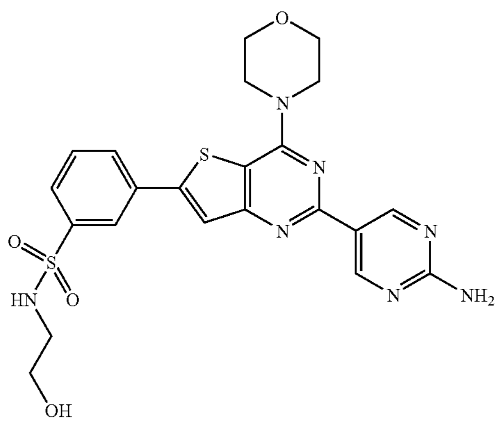 [SMILES: Nc1ncc(-c2nc(N3CCOCC3)c3sc(-c4cccc(S(=O)(=O)NCCO)c4)cc3n2)cn1] | 5-(4-morpholino-6-(3-N-2-hydroxyethylaminosulfonyl)phenyl-thieno[3,2-d]pyrimidin-2-yl)pyrimidin-2-amine |
| 154 | 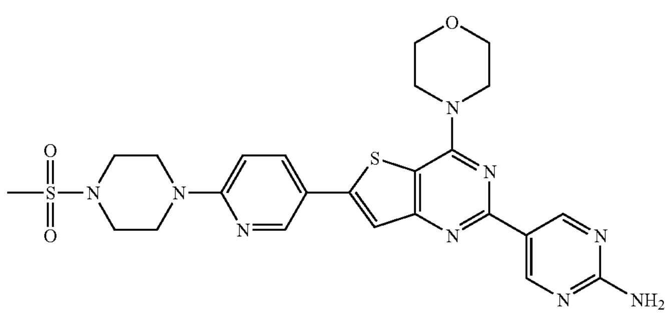 [SMILES: CS(=O)(=O)N1CCN(c2ccc(-c3cc4nc(-c5cnc(N)nc5)nc(N5CCOCC5)c4s3)cn2)CC1] | 5-(4-morpholino-6-(6-(4-methylsulfonylpiperazin-1-yl)pyridin-3-yl)thieno[3,2-d]pyrimidin-2-yl)pyrimidin-2-amine |
| 155 | 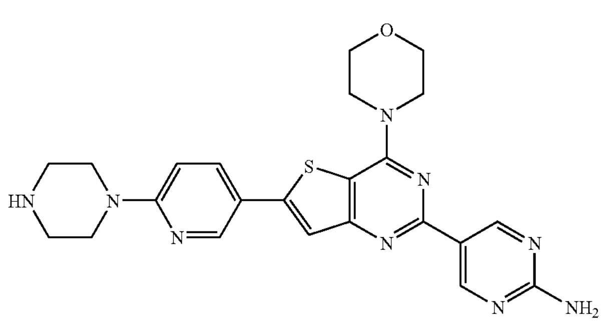 [SMILES: Nc1ncc(-c2nc(N3CCOCC3)c3sc(-c4ccc(N5CCNCC5)nc4)cc3n2)cn1] | 5-(4-morpholino-6-(6-piperazin-1-yl)pyridin-3-yl)thieno[3,2-d]pyrim,idin-2-yl)pyrimidin-2-amine |

TABLE 1-continued

| Compound | Structure | Name |
|---|---|---|
| 156 | 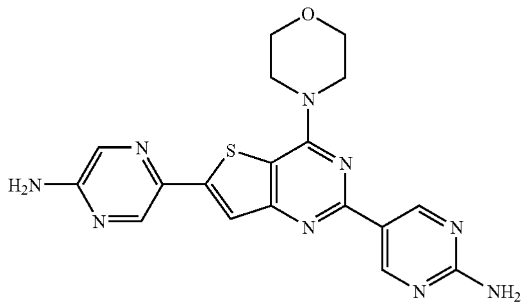 | 5-(2-(2-aminopyrimidin-5-yl)-4-morpholinothieno[3,2-d]pyrimidin-6-yl)pyrazin-2-amine |
| 157 | 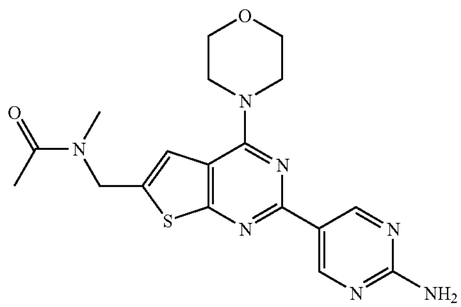 [SMILES: CC(=O)N(C)Cc1cc2c(N3CCOCC3)nc(-c3cnc(N)nc3)nc2s1] | N-((2-(2-aminopyrimidin-5-yl)-4-morpholinothieno[2,3-d]pyrimidin-6-yl)methyl)-N-methylacetamide |
| 158 | 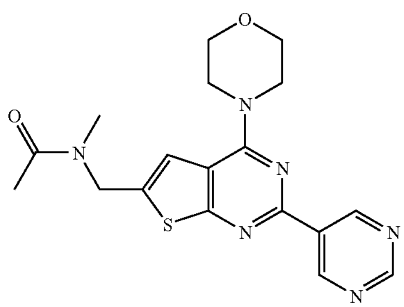 [SMILES: CC(=O)N(C)Cc1cc2c(N3CCOCC3)nc(-c3cncnc3)nc2s1] | N-methyl-N-((4-morpholino-2-(pyrimidin-5-yl)thieno[2,3-d]pyrimidin-6-yl)methyl)acetamide |
| 159 | 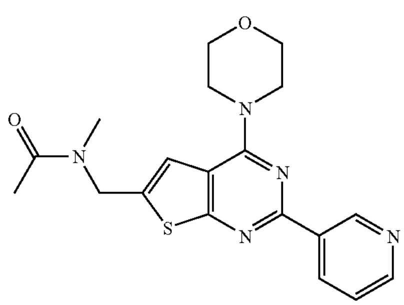 [SMILES: CC(=O)N(C)Cc1cc2c(N3CCOCC3)nc(-c3cccnc3)nc2s1] | N-methyl-N-((4-morpholino-2-(pyridin-3-yl)thieno[2,3-d]pyrimidin-6-yl)methyl)acetamide |
| 160 | 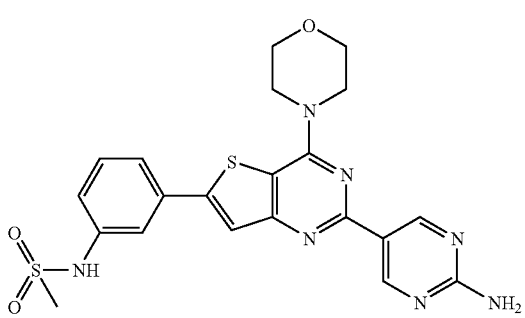 [SMILES: CS(=O)(=O)Nc1cccc(-c2cc3nc(-c4cnc(N)nc4)nc(N4CCOCC4)c3s2)c1] | 5-(6-(3-methylsulfonylaminophenyl)-4-morpholinothieno[3,2-d]pyrimidin-2-yl)pyrimidin-2-amine |

TABLE 1-continued

| Compound | Structure | Name |
|---|---|---|
| 161 | 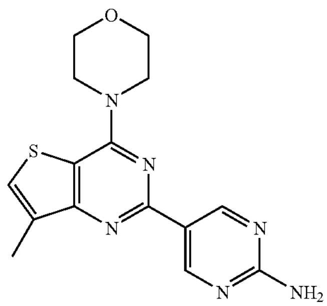 [SMILES: Cc1csc2c(N3CCOCC3)nc(-c3cnc(N)nc3)nc12] | 5-(7-methyl-4-morpholinothieno[3,2-d]pyrimidin-2-yl)pyrimidin-2-amine |
| 162 | 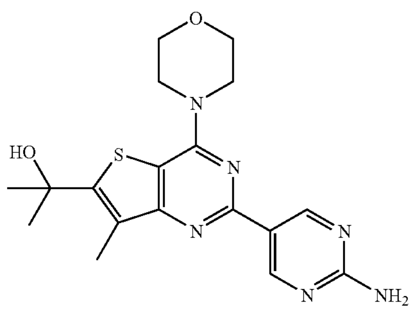 [SMILES: Cc1c(C(C)(C)O)sc2c(N3CCOCC3)nc(-c3cnc(N)nc3)nc12] | 2-(2-(2-aminopyrimidin-5-yl)-7-methyl-4-morpholinothieno[3,2-d]pyrimidin-6-yl)propan-2-ol |
| 163 | 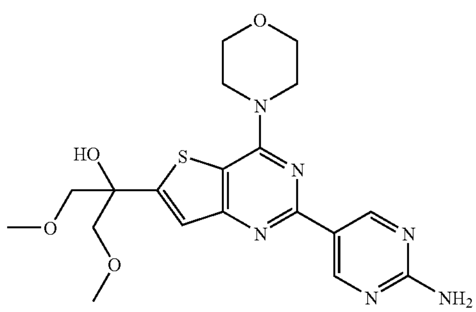 [SMILES: COCC(O)(COC)c1cc2nc(-c3cnc(N)nc3)nc(N3CCOCC3)c2s1] | 2-(2-(2-aminopyrimidin-5-yl)-4-morpholinothieno[3,2-d]pyrimidin-6-yl)-1,3-dimethoxypropan-2-ol |
| 164 | 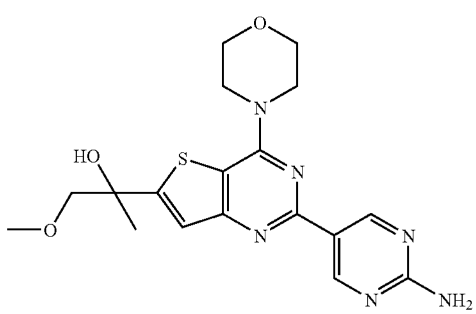 [SMILES: COCC(C)(O)c1cc2nc(-c3cnc(N)nc3)nc(N3CCOCC3)c2s1] | 2-(2-(2-aminopyrimidin-5-yl)-4-morpholinothieno[3,2-d]pyrimidin-6-yl)-1-methoxypropan-2-ol |
| 165 | 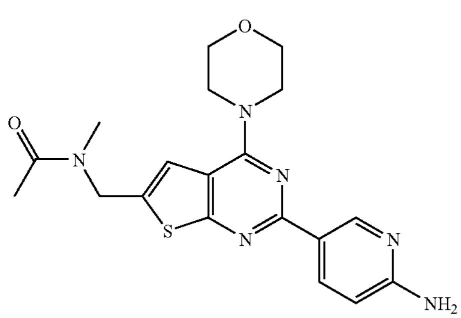 [SMILES: CC(=O)N(C)Cc1cc2c(N3CCOCC3)nc(-c3ccc(N)nc3)nc2s1] | N-((2-(6-aminopyridin-3-yl)-4-morpholinothieno[2,3-d]pyrimidin-6-yl)methyl)-N-methylacetamide |

TABLE 1-continued

| Compound | Structure | Name |
|---|---|---|
| 166 | 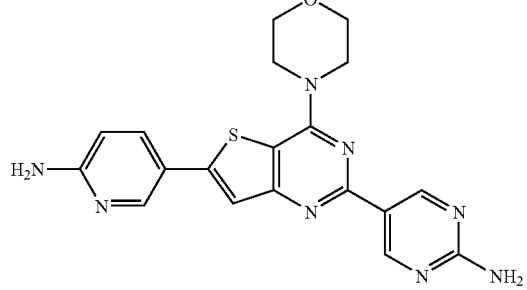 | 5-(6-(6-aminopyridin-3-yl)-4-morpholinothieno[3,2-d]pyrimidin-2-yl)pyrimidin-2-amine |
| 167 | 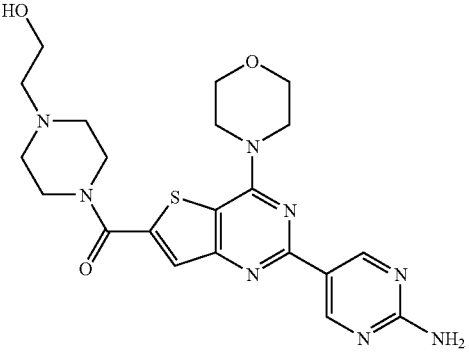 [SMILES: Nc1ncc(-c2nc(N3CCOCC3)c3sc(C(=O)N4CCN(CCO)CC4)cc3n2)cn1] | (2-(2-aminopyrimidin-5-yl)-4-morpholinothieno[3,2-d]pyrimidin-6-yl)(4-(2-hydroxyethyl)piperazin-1-yl)methanone |
| 168 | 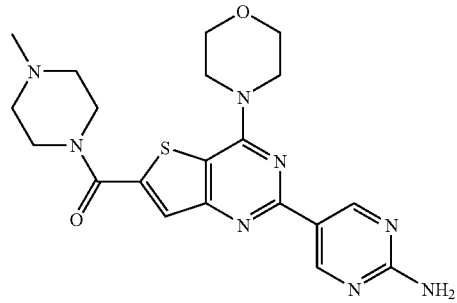 | (2-(2-aminopyrimidin-5-yl)-4-morpholinothieno[3,2-d]pyrimidin-6-yl)(4-methylpiperazin-1-yl)methanone |
| 169 | 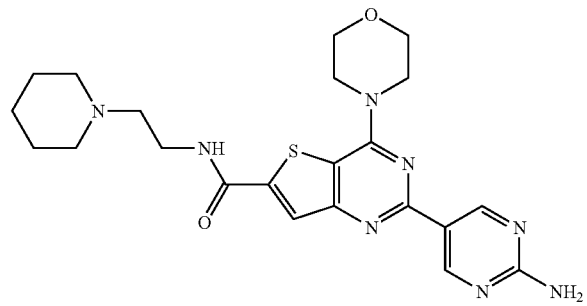 [SMILES: Nc1ncc(-c2nc(N3CCOCC3)c3sc(C(=O)NCCN4CCCCC4)cc3n2)cn1] | 2-(2-aminopyrimidin-5-yl)-4-morpholino-N-(2-(piperidin-1-yl)ethyl)thieno[3,2-d]pyrimidine-6-carboxamide |

TABLE 1-continued

| Compound | Structure | Name |
|---|---|---|
| 170 | 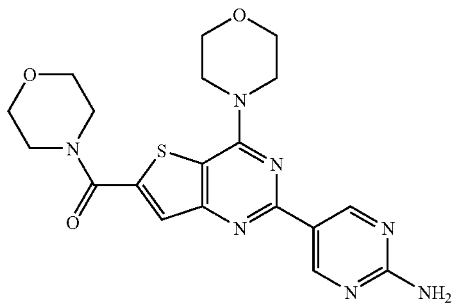 [SMILES: Nc1ncc(-c2nc(N3CCOCC3)c3sc(C(=O)N4CCOCC4)cc3n2)cn1] | (2-(2-aminopyrimidin-5-yl)-4-morpholinothieno[3,2-d]pyrimidin-6-yl)(morpholino)methanone |
| 171 | 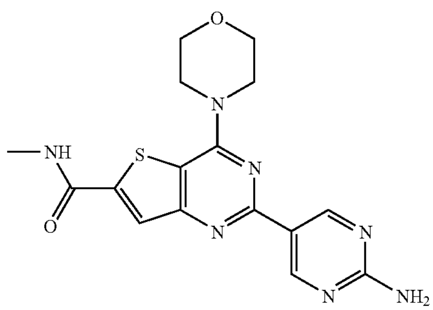 [SMILES: CNC(=O)c1cc2nc(-c3cnc(N)nc3)nc(N3CCOCC3)c2s1] | 2-(2-aminopyrimidin-5-yl)-N-methyl-4-morpholinothieno[3,2-d]pyrimidine-6-carboxamide |
| 172 | 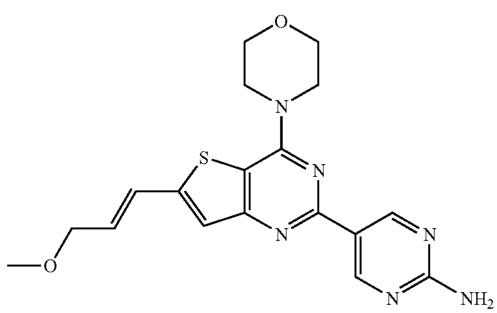 | 5-(6-((E)-3-methoxyprop-1-enyl)-4-morpholinothieno[3,2-d]pyrimidin-2-yl)pyrimidin-2-amine |
| 173 | 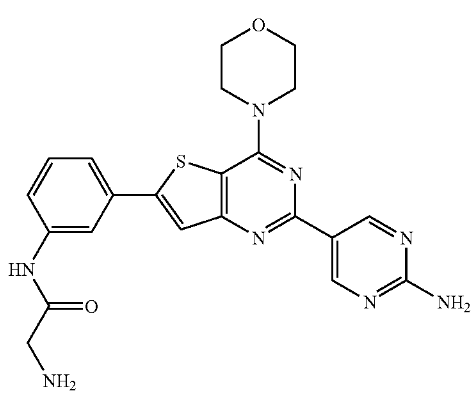 | 2-amino-N-(3-(2-(2-aminopyrimidin-5-yl)-4-morpholinothieno[3,2-d]pyrimidin-6-yl)phenyl)acetamide |

TABLE 1-continued

| Compound | Structure | Name |
|---|---|---|
| 174 | 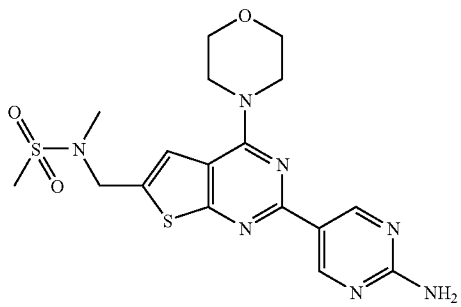 [SMILES: CN(Cc1cc2c(N3CCOCC3)nc(-c3cnc(N)nc3)nc2s1)S(C)(=O)=O] | 5-(6-((N-methyl,N-methylsulfonylamino)methyl)-4-morpholinothieno[2,3-d]pyrimidin-2-yl)pyrimidin-2-amine |
| 175 | 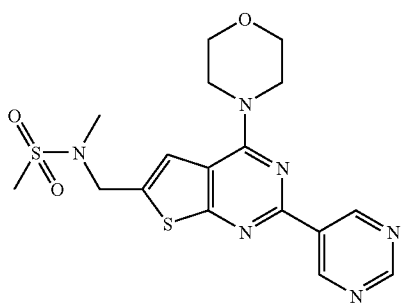 [SMILES: CN(Cc1cc2c(N3CCOCC3)nc(-c3cncnc3)nc2s1)S(C)(=O)=O] | N-methyl,N-methylsulfonyl(4-morpholino-2-(pyrimidin-5-yl)thieno[2,3-d]pyrimidin-6-yl)methanamine |
| 176 | 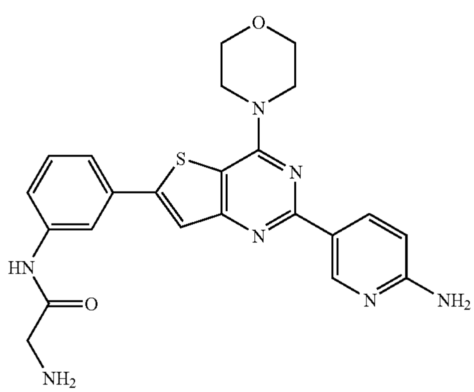 [SMILES: NCC(=O)Nc1cccc(-c2cc3nc(-c4ccc(N)nc4)nc(N4CCOCC4)c3s2)c1] | 2-amino-N-(3-(2-(6-aminopyridin-3-yl)-4-morpholinothieno[3,2-d]pyrimidin-6-yl)phenyl)acetamide |
| 177 | 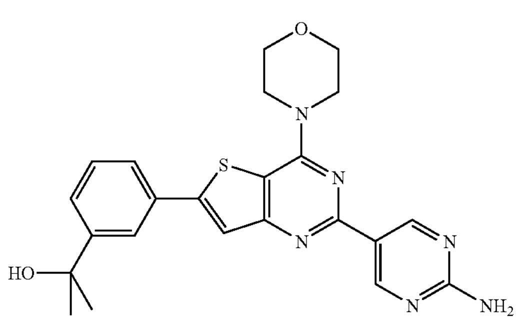 | 2-(3-(2-(2-aminopyrimidin-5-yl)-4-morpholinothieno[3,2-d]pyrimidin-6-yl)phenyl)propan-2-ol |

TABLE 1-continued

| Compound | Structure | Name |
|---|---|---|
| 178 | 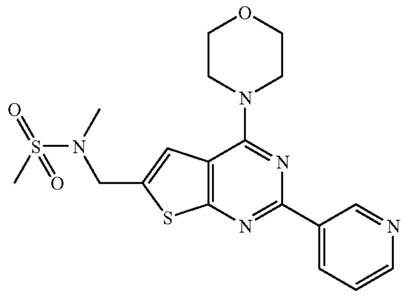 [SMILES: CN(Cc1cc2c(N3CCOCC3)nc(-c3cccnc3)nc2s1)S(C)(=O)=O] | N-methyl,N-methylsulfonyl(4-morpholino-2-(pyridin-3-yl)thieno[2,3-d]pyrimidin-6-yl)methanamine |
| 179 | 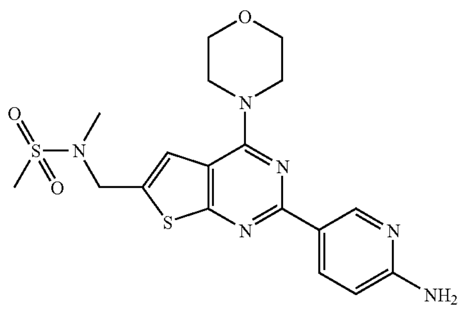 | 5-(6-((N-methyl,N-methylsulfonylamino)methyl)-4-morpholinothieno[2,3-d]pyrimidin-2-yl)pyridin-2-amine |
| 180 | 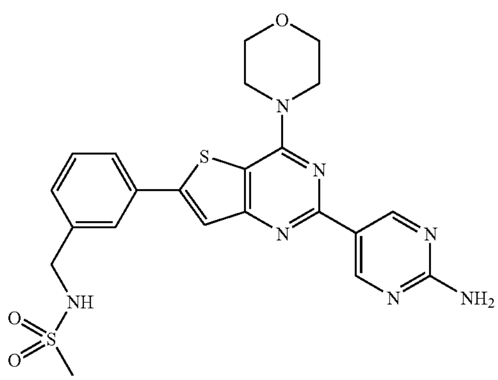 [SMILES: CS(=O)(=O)NCc1cccc(-c2cc3nc(-c4cnc(N)nc4)nc(N4CCOCC4)c3s2)c1] | 5-(6-(3-(N-methylsulfonylaminomethyl)phenyl)-4-morpholinothieno[3,2-d]pyrimidin-2-yl)pyrimidin-2-amine |
| 181 | 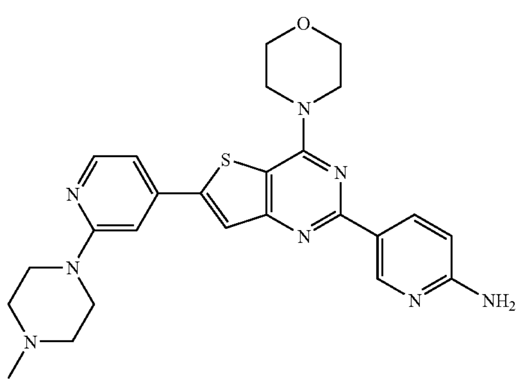 [SMILES: CN1CCN(c2cc(-c3cc4nc(-c5ccc(N)nc5)nc(N5CCOCC5)c4s3)ccn2)CC1] | 5-(6-(2-(4-methylpiperazin-1-yl)pyridin-4-yl)-4-morpholinothieno[3,2-d]pyrimidin-2-yl)pyridin-2-amine |

TABLE 1-continued

| Compound | Structure | Name |
|---|---|---|
| 182 | 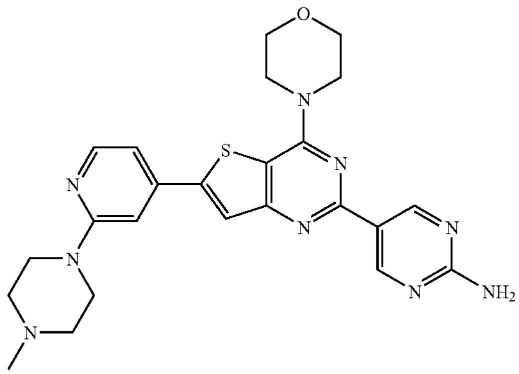 [SMILES: CN1CCN(c2cc(-c3cc4nc(-c5cnc(N)nc5)nc(N5CCOCC5)c4s3)ccn2)CC1] | 5-(6-(2-(4-methylpiperazin-1-yl)pyridin-4-yl)-4-morpholinothieno[3,2-d]pyrimidin-2-yl)pyrimidin-2-amine |
| 183 | 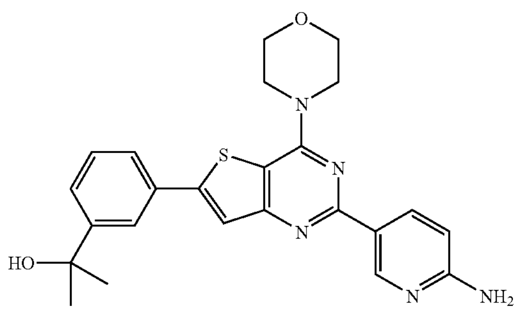 [SMILES: CC(C)(O)c1cccc(-c2cc3nc(-c4ccc(N)nc4)nc(N4CCOCC4)c3s2)c1] | 2-(3-(2-(6-aminopyridin-3-yl)-4-morpholinothieno[3,2-d]pyrimidin-6-yl)phenyl)propan-2-ol |
| 184 | 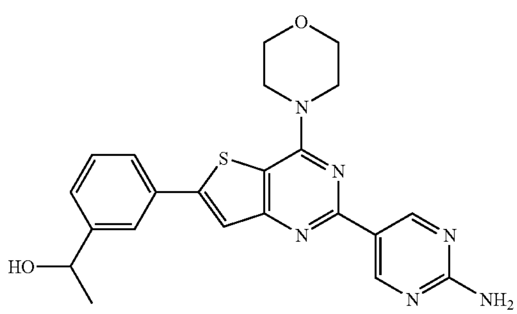 [SMILES: CC(O)c1cccc(-c2cc3nc(-c4cnc(N)nc4)nc(N4CCOCC4)c3s2)c1] | 1-(3-(2-(2-aminopyrimidin-5-yl)-4-morpholinothieno[3,2-d]pyrimidin-6-yl)phenyl)ethanol |
| 185 | 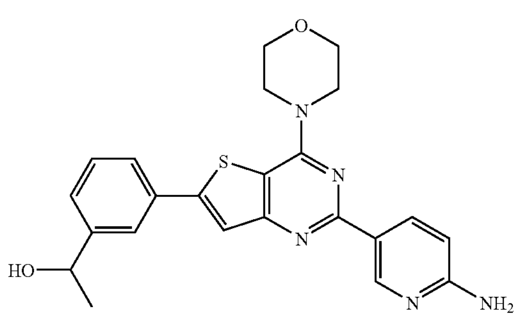 | 1-(3-(2-(6-aminopyridin-3-yl)-4-morpholinothieno[3,2-d]pyrimidin-6-yl)phenyl)ethanol |

TABLE 1-continued

| Compound | Structure | Name |
|---|---|---|
| 186 | 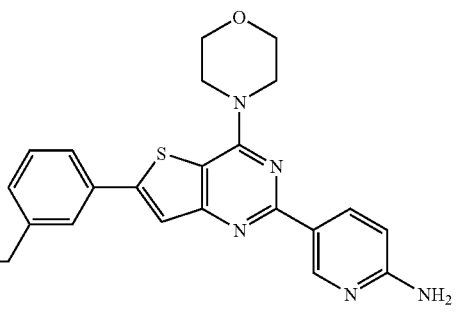 | 3-(3-(2-(6-aminopyridin-3-yl)-4-morpholinothieno[3,2-d]pyrimidin-6-yl)phenyl)propan-1-ol |
| 187 | 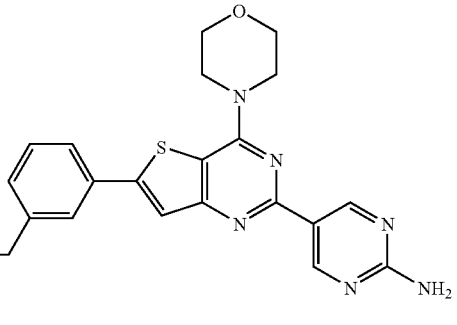 | 3-(3-(2-(2-aminopyrimidin-5-yl)-4-morpholinothieno[3,2-d]pyrimidin-6-yl)phenyl)propan-1-ol |
| 188 | 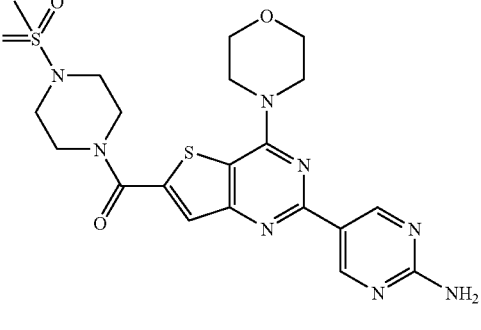 | (2-(2-aminopyrimidin-5-yl)-4-morpholinothieno[3,2-d]pyrimidin-6-yl)(N-4-methylsulfonylpiperazin-1-yl)methanone |
| 189 | 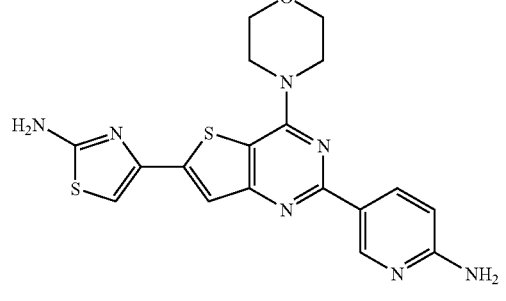 | 5-(6-(2-aminothiazol-4-yl)-4-morpholinothieno[3,2-d]pyrimidin-2-yl)pyridin-2-amine |
| 190 | 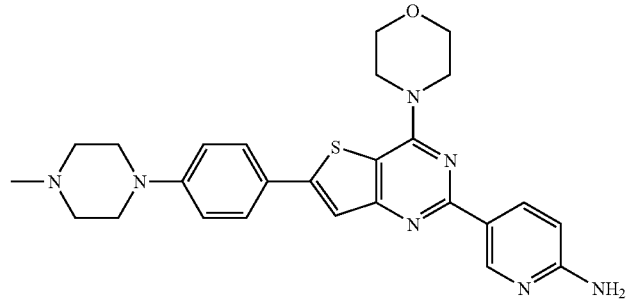 [SMILES: CN1CCN(c2ccc(-c3cc4nc(-c5ccc(N)nc5)nc(N5CCOCC5)c4s3)cc2)CC1] | 5-(6-(4-(4-methylpiperazin-1-yl)phenyl)-4-morpholinothieno[3,2-d]pyrimidin-2-yl)pyridin-2-amine |

TABLE 1-continued

| Compound | Structure | Name |
|---|---|---|
| 191 | 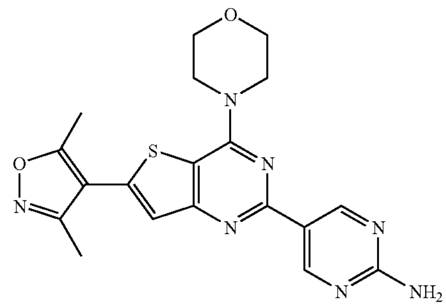 [SMILES: Cc1noc(C)c1-c1cc2nc(-c3cnc(N)nc3)nc(N3CCOCC3)c2s1] | 5-(6-(3,5-dimethylisoxazol-4-yl)-4-morpholinothieno[3,2-0d]pyrimidin-2-yl)pyrimidin-2-amine |
| 192 | 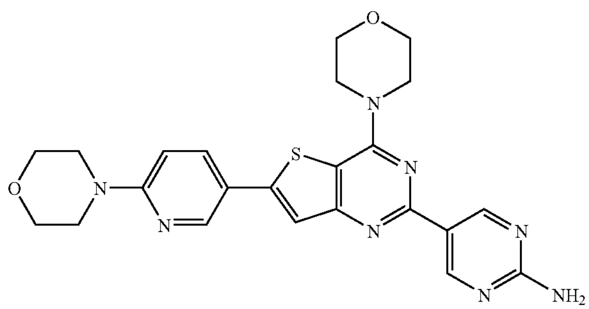 [SMILES: Nc1ncc(-c2nc(N3CCOCC3)c3sc(-c4ccc(N5CCOCC5)nc4)cc3n2)cn1] | 5-(4-morpholino-6-(6-morpholinopyridin-3-yl)thieno[3,2-d]pyrimidin-2-yl)pyrimidin-2-amine |
| 193 | 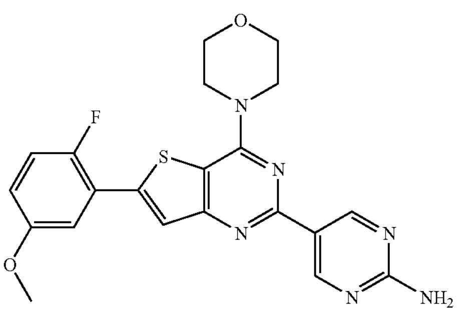 [SMILES: COc1ccc(F)c(-c2cc3nc(-c4cnc(N)nc4)nc(N4CCOCC4)c3s2)c1] | 5-(6-(2-fluoro-5-methoxyphenyl)-4-morpholinothieno[3,2-d]pyrimidin-2-yl)pyrimidin-2-amine |
| 194 | 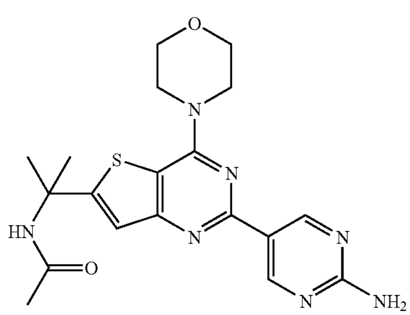 [SMILES: CC(=O)NC(C)(C)c1cc2nc(-c3cnc(N)nc3)nc(N3CCOCC3)c2s1] | N-(2-(2-(2-aminopyrimidin-5-yl)-4-morpholinothieno[3,2-d]pyrimidin-6-yl)propan-2-yl)acetamide |
| 195 | 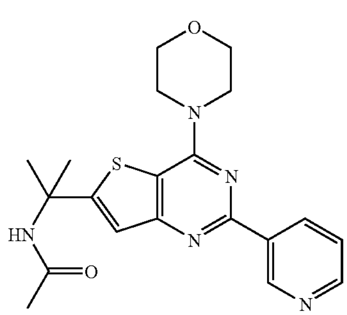 [SMILES: CC(=O)NC(C)(C)c1cc2nc(-c3cccnc3)nc(N3CCOCC3)c2s1] | N-(2-(4-morpholino-2-(pyridin-3-yl)thieno[3,2-d]pyrimidin-6-yl)propan-2-yl)acetamide |

TABLE 1-continued

| Compound | Structure | Name |
|---|---|---|
| 196 | 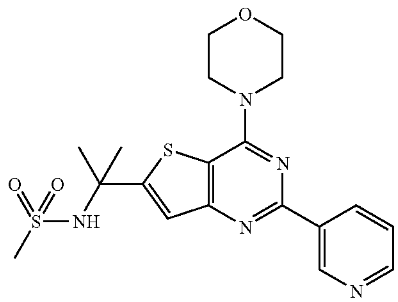 [SMILES: CC(C)(NS(C)(=O)=O)c1cc2nc(-c3cccnc3)nc(N3CCOCC3)c2s1] | 2-(4-morpholino-2-(pyridin-3-yl)thieno[3,2-d]pyrimidin-6-yl)propan-2-N-methylsulfonylamine |
| 197 | 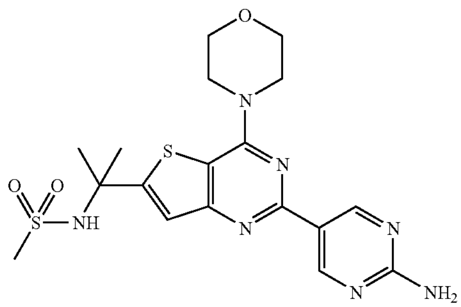 [SMILES: CC(C)(NS(C)(=O)=O)c1cc2nc(-c3cnc(N)nc3)nc(N3CCOCC3)c2s1] | 5-(6-(2-N-methylsulfonylaminopropan-2-yl)-4-morpholinothieno[3,2-d]pyrimidin-2-yl)pyrimidin-2-amine |
| 198 | 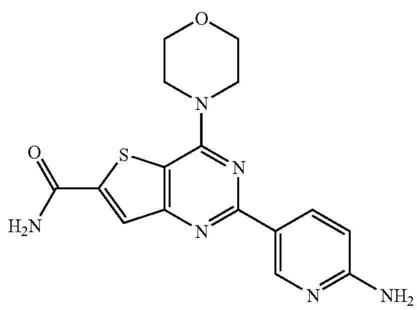 [SMILES: NC(=O)c1cc2nc(-c3ccc(N)nc3)nc(N3CCOCC3)c2s1] | 2-(6-aminopyridin-3-yl)-4-morpholinothieno[3,2-d]pyrimidine-6-carboxamide |
| 199 | 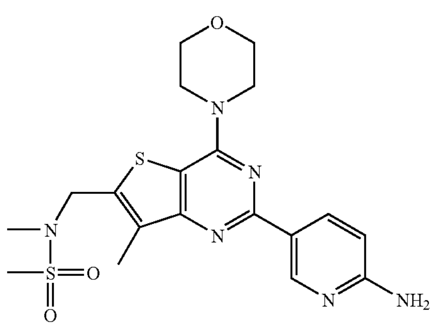 [SMILES: Cc1c(CN(C)S(C)(=O)=O)sc2c(N3CCOCC3)nc(-c3ccc(N)nc3)nc12] | 5-(7-methyl-6-((N-methyl,N-methylsulfonylamino)methyl)-4-morpholinothieno[3,2-d]pyrimidin-2-yl)pyridin-2-amine |
| 200 | 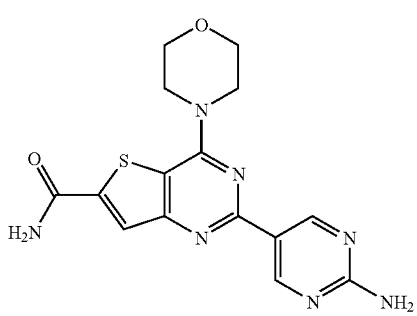 | 2-(2-aminopyrimidin-5-yl)-4-morpholinothieno[3,2-d]pyrimidine-6-carboxamide |

TABLE 1-continued
| Compound | Structure | Name |
|---|---|---|
| 201 | 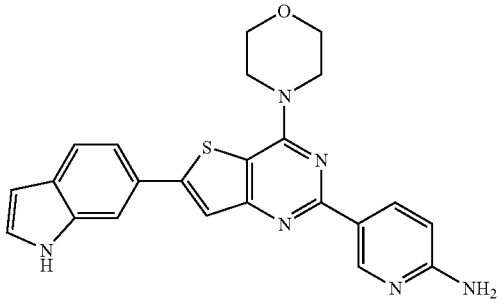 [SMILES: Nc1ccc(-c2nc(N3CCOCC3)c3sc(-c4ccc5cc[nH]c5c4)cc3n2)cn1] | 5-(6-(1H-indol-6-yl)-4-morpholinothieno[3,2-d]pyrimidin-2-yl)pyridin-2-amine |
| 202 | 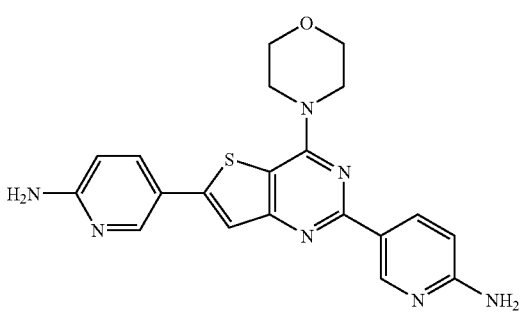 | 5-(2-(6-aminopyridin-3-yl)-4-morpholinothieno[3,2-d]pyrimidin-6-yl)pyridin-2-amine |
| 203 | 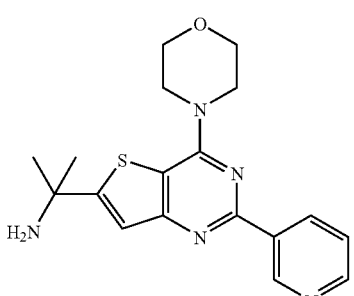 | 2-(4-morpholino-2-(pyridin-3-yl)theino[3,2-d]pyrimidin-6-yl)propan-2-amine |
| 204 | 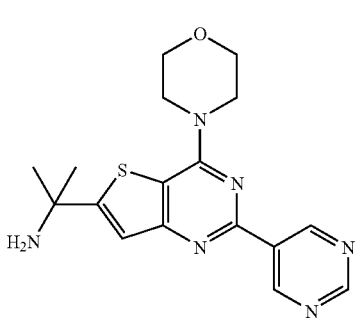 [SMILES: CC(C)(N)c1cc2nc(-c3cncnc3)nc(N3CCOCC3)c2s1] | 2-(4-morpholino-2-(pyrimidin-5-yl)thieno[3,2-d]pyrimidin-6-yl)propan-2-amine |
| 205 | 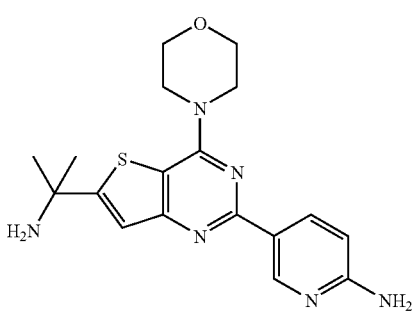 [SMILES: CC(C)(N)c1cc2nc(-c3ccc(N)nc3)nc(N3CCOCC3)c2s1] | 5-(6-(2-aminopropan-2-yl)-4-morpholinothieno[3,2-d]pyrimidin-2-yl)pyridin-2-amine |

TABLE 1-continued

| Compound | Structure | Name |
|---|---|---|
| 206 | 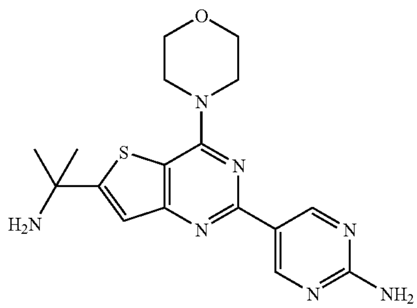 [SMILES: CC(C)(N)c1cc2nc(-c3cnc(N)nc3)nc(N3CCOCC3)c2s1] | 5-(6-(2-aminopropan-2-yl)-4-morpholinothieno[3,2-d]pyrimidin-2-yl)pyrimidin-2-amine |
| 207 | 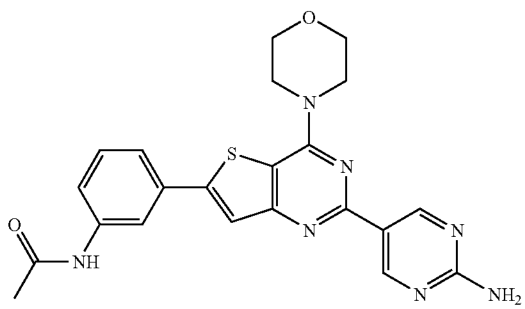 [SMILES: CC(=O)Nc1cccc(-c2cc3nc(-c4cnc(N)nc4)nc(N4CCOCC4)c3s2)c1] | N-(3-(2-(2-aminopyrimidin-5-yl)-4-morpholinothieno[3,2-d]pyrimidin-6-yl)phenyl)acetamide |
| 208 | 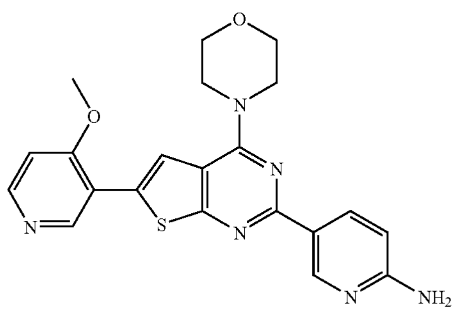 [SMILES: COc1ccncc1-c1cc2c(N3CCOCC3)nc(-c3ccc(N)nc3)nc2s1] | 5-(6-(4-methoxypyridin-3-yl)-4-morpholinothieno[2,3-d]pyrimidin-2-yl)pyridin-2-amine |
| 209 | 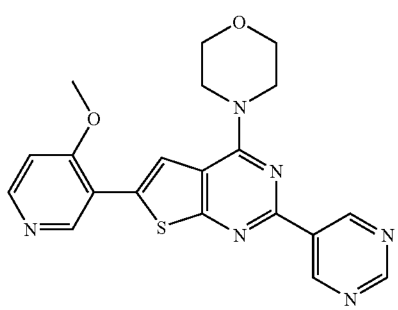 [SMILES: COc1ccncc1-c1cc2c(N3CCOCC3)nc(-c3cncnc3)nc2s1] | 6-(4-methoxypyridin-3-yl)-4-morpholino-2-(pyrimidin-5-yl)thieno[2,3-d]pyrumidine |
| 210 | 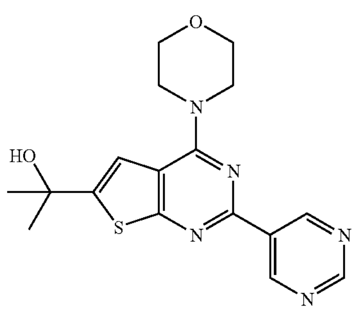 [SMILES: CC(C)(O)c1cc2c(N3CCOCC3)nc(-c3cncnc3)nc2s1] | 2-(4-morpholino-2-(pyrimidin-5-yl)thieno[2,3-d]pyrimidin-6-yl)propan-2-ol |

TABLE 1-continued

| Compound | Structure | Name |
| --- | --- | --- |
| 211 | 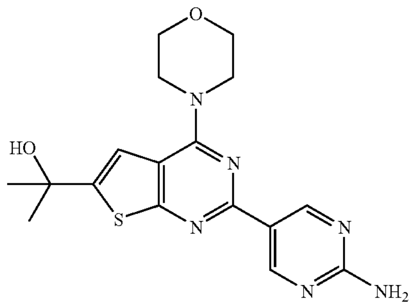 | 2-(2-(2-aminopyrimidin-5-yl)-4-morpholinothieno[2,3-d]pyrimidin-6-yl)propan-2-ol |
| 212 | 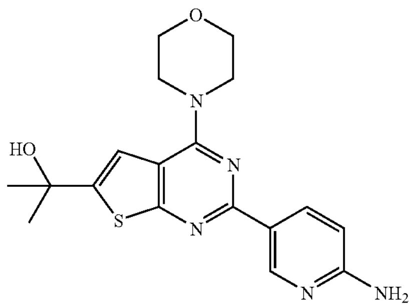 [SMILES: CC(C)(O)c1cc2c(N3CCOCC3)nc(-c3ccc(N)nc3)nc2s1] | 2-(2-(6-aminopyridin-3-yl)-4-morpholinothieno[2,3-d]pyrimidin-6-yl)propan-2-ol |
| 213 | 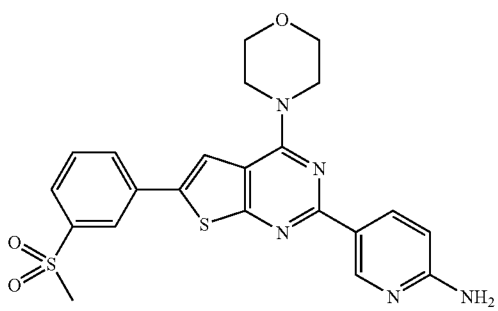 [SMILES: CS(=O)(=O)c1cccc(-c2cc3c(N4CCOCC4)nc(-c4cnc(N)nc4)nc3s2)c1] | 5-(6-(3-(methylsulfonyl)phenyl)-4-morpholinothieno[2,3-d]pyrimidin-2-yl)pyridin-2-amine |
| 214 | 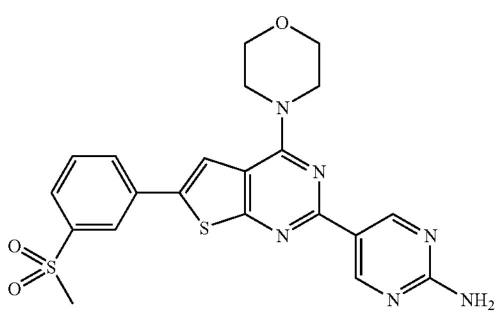 | 5-(6-(3-(methylsulfonyl)phenyl)-4-morpholinothieno[2,3-d]pyrimidin-2-yl)pyrimidin-2-amine |
| 215 | 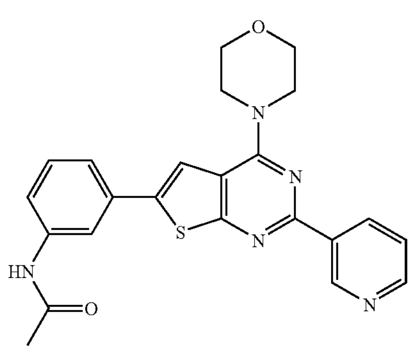 [SMILES: CC(=O)Nc1cccc(-c2cc3c(N4CCOCC4)nc(-c4cccnc4)nc3s2)c1] | N-(3-(4-morpholino-2-(pyridin-3-yl)thieno[2,3-d]pyrimidin-6-yl)phenyl)acetamide |

TABLE 1-continued

| Compound | Structure | Name |
|---|---|---|
| 216 | 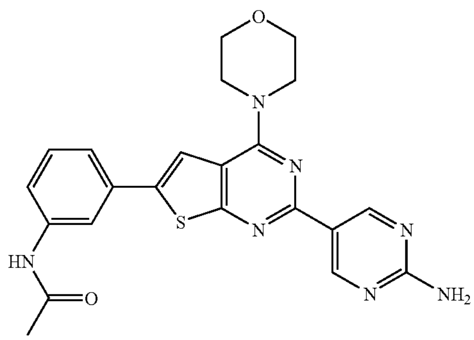 | N-(3-(2-(2-aminopyrimidin-5-yl)-4-morpholinothieno[2,3-d]pyrimidin-6-yl)phenyl)acetamide |
| 217 | 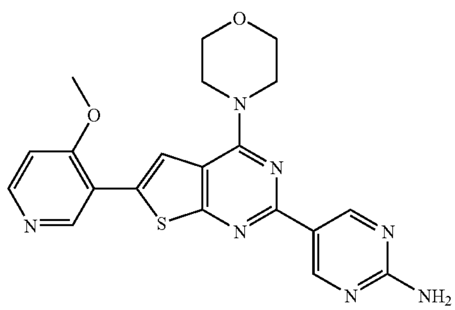 | 5-(6-(4-methoxypyridin-3-yl)-4-morpholinothieno[2,3-d]pyrimidin-2-yl)pyrimidin-2-amine |
| 218 | 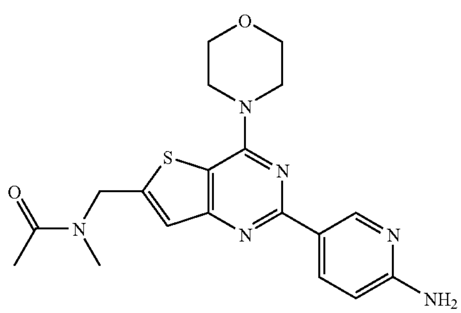 [SMILES: CC(=O)N(C)Cc1cc2nc(-c3ccc(N)nc3)nc(N3CCOCC3)c2s1] | N-((2-(6-aminopyridin-3-yl)-4-morpholinothieno[3,2-d]pyrimidin-6-yl)methyl)-N-methylacetamide |
| 219 | 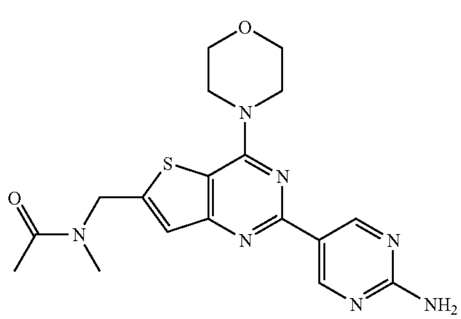 | N-((2-(2-aminopyrimidin-5-yl)-4-morpholinothieno[3,2-d]pyrimidin-6-yl)methyl)-N-methylacetamide |

TABLE 1-continued

| Compound | Structure | Name |
|---|---|---|
| 220 | 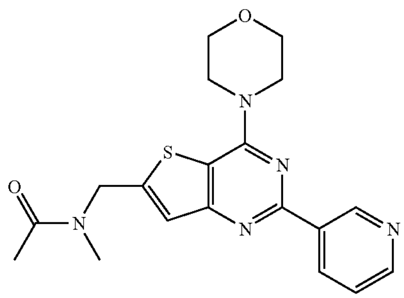 [SMILES: CC(=O)N(C)Cc1cc2nc(-c3cccnc3)nc(N3CCOCC3)c2s1] | N-methyl-N-((4-morpholino-2-(pyridin-3-yl)thieno[3,2-d]pyrimidin-6-yl)methyl)acetamide |
| 221 | 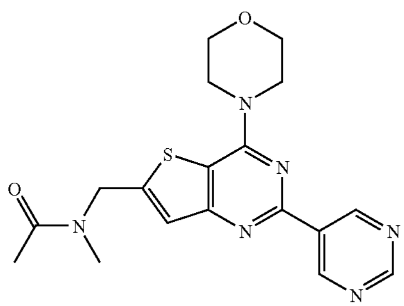 [SMILES: CC(=O)N(C)Cc1cc2nc(-c3cncnc3)nc(N3CCOCC3)c2s1] | N-methyl-N-((4-morpholino-2-(pyrimidin-5-yl)thieno[3,2-d]pyrimidin-6-yl)methyl)acetamide |
| 222 | 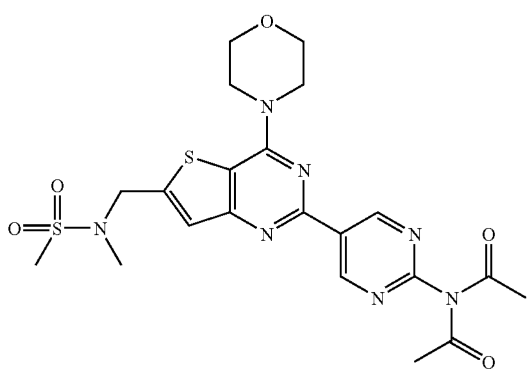 [SMILES: CC(=O)N(C(C)=O)c1ncc(-c2nc(N3CCOCC3)c3sc(CN(C)S(C)(=O)=O)cc3n2)cn1] | N-acetyl-N-(5-(6-((N-methyl,N-methylsulfonylamino)methyl)-4-morpholinothieno[3,2-d]pyrimidin-2-yl)pyrimidin-2-yl)acetamide |
| 223 | 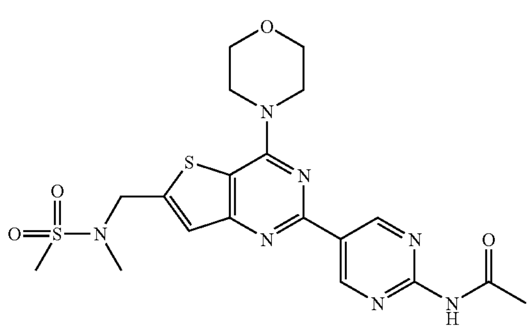 [SMILES: CC(=O)Nc1ncc(-c2nc(N3CCOCC3)c3sc(CN(C)S(C)(=O)=O)cc3n2)cn1] | N-(5-(6-((N-methyl,N-methylsulfonylamino)methyl)-4-morpholinothieno[3,2-d]pyrimidin-2-yl)pyrimidin-2-yl)acetamide |

TABLE 1-continued

| Compound | Structure | Name |
|---|---|---|
| 224 | 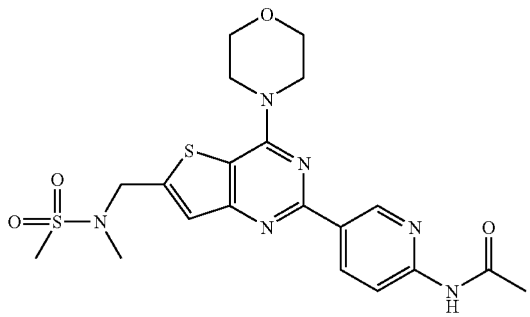 | N-(5-(6-((N-methyl,N-methylsulfonylamino)methyl)-4-morpholinothieno[3,2-d]pyrimidin-2-yl)pyridin-2-yl)acetamide |
| 225 | 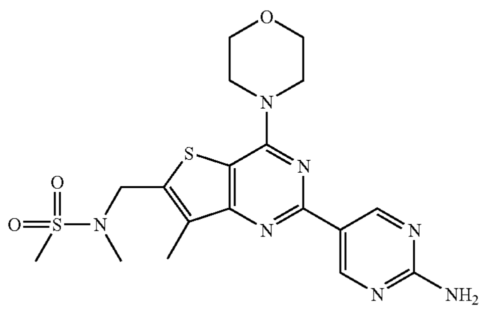 | 5-(7-methyl-6-((N-methyl,N-methylsulfonylamino)methyl)-4-morpholinothieno[3,2-d]pyrimidin-2-yl)pyrimidin-2-amine |
| 226 | 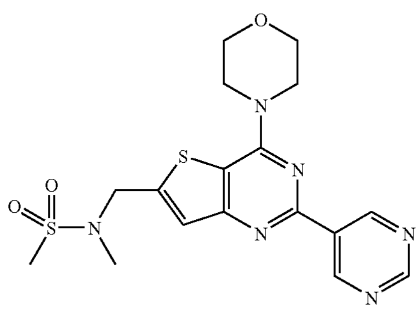 [SMILES: CN(Cc1cc2nc(-c3cncnc3)nc(N3CCOCC3)c2s1)S(C)(=O)=O] | N-methyl,N-methylsulfonyl(4-morpholino-2-(pyrimidin-5-yl)thieno[3,2-d]pyrimidin-6-yl)methanamine |
| 227 | 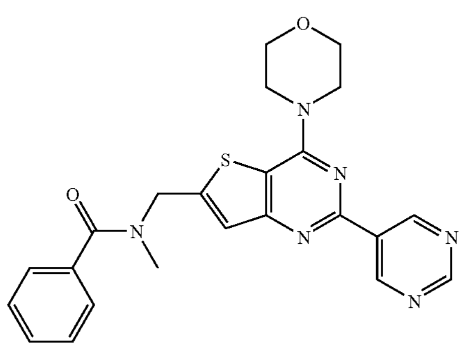 [SMILES: CN(Cc1cc2nc(-c3cncnc3)nc(N3CCOCC3)c2s1)C(=O)c1ccccc1] | N-methyl,N-((4-morpholino-2-(pyrimidin-5-yl)thieno[3,2-d]pyrimidin-6-yl)methyl)benzamide |
| 228 | 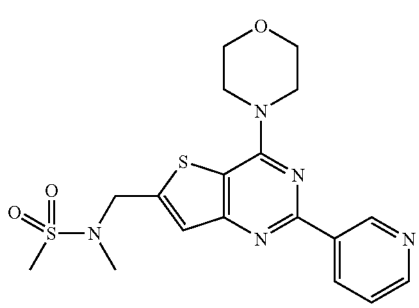 [SMILES: CN(Cc1cc2nc(-c3cccnc3)nc(N3CCOCC3)c2s1)S(C)(=O)=O] | N-methyl,N-methylsulfonyl(4-morpholino-2-(pyridin-3-yl)thieno[3,2-d]pyrimidin-6-yl)methanamine |

TABLE 1-continued

| Compound | Structure | Name |
|---|---|---|
| 229 | 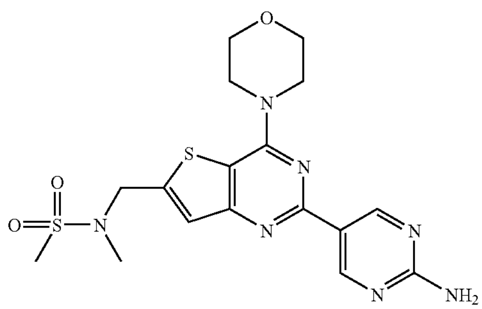 | 5-(6-((N-methyl,N-methylsulfonylamino)methyl)-4-morpholinothieno[3,2-d]pyrimidin-2-yl)pyrimidin-2-amine |
| 230 | 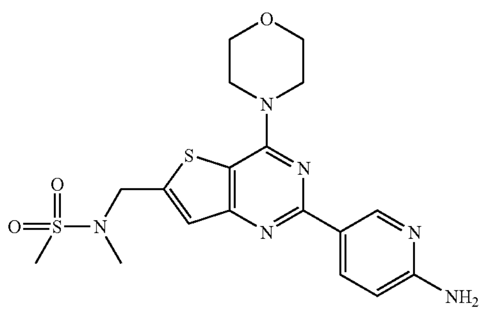 [SMILES: CN(Cc1cc2nc(-c3cnc(N)nc3)nc(N3CCOCC3)c2s1)S(C)(=O)=O] | 5-(6-((N-methyl,N-methylsulfonylamino)methyl)-4-morpholinothieno[3,2-d]pyrimidin-2-yl)pyridin-2-amine |
| 231 | 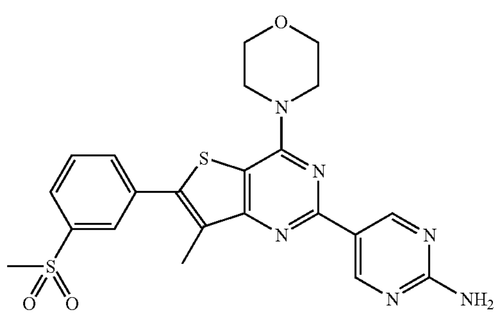 [SMILES: Cc1c(-c2cccc(S(C)(=O)=O)c2)sc2c(N3CCOCC3)nc(-c3cnc(N)nc3)nc12] | 5-(7-methyl-6-(3-(methylsulfonyl)phenyl)-4-morpholinothieno[3,2-d]pyrimidin-2-yl)pyrimidin-2-amine |
| 232 | 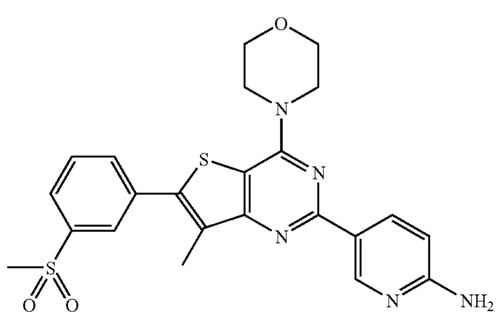 [SMILES: Cc1c(-c2cccc(S(C)(=O)=O)c2)sc2c(N3CCOCC3)nc(-c3ccc(N)nc3)nc12] | 5-(7-methyl-6-(3-(methylsulfonyl)phenyl)-4-morpholinothieno[3,2-d]pyrimidin-2-yl)pyridin-2-amine |
| 233 | 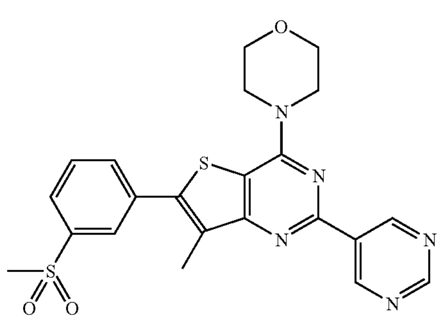 [SMILES: Cc1c(-c2cccc(S(C)(=O)=O)c2)sc2c(N3CCOCC3)nc(-c3cncnc3)nc12] | 7-methyl-6-(3-(methylsulfonyl)phenyl)-4-morpholino-2-(pyrimidin-5-yl)thieno[3,2-d]pyrimidine |

TABLE 1-continued

| Compound | Structure | Name |
|---|---|---|
| 234 | 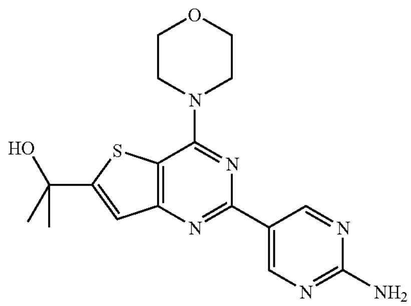 [SMILES: CC(C)(O)c1cc2nc(-c3cnc(N)nc3)nc(N3CCOCC3)c2s1] | 2-(2-(2-aminopyrimidin-5-yl)-4-morpholinothieno[3,2-d]pyrimidin-6-yl)propan-2-ol |
| 235 | 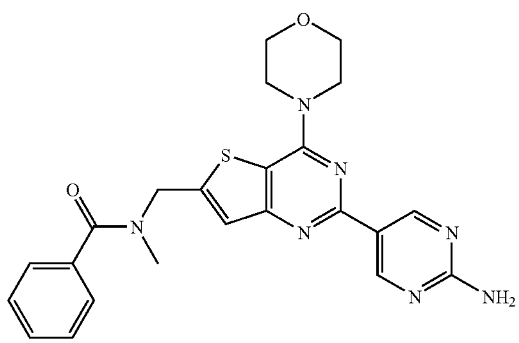 [SMILES: CN(Cc1cc2nc(-c3cnc(N)nc3)nc(N3CCOCC3)c2s1)C(=O)c1ccccc1] | N-((2-(2-aminopyrimidin-5-yl)-4-morpholinothieno[3,2-d]pyrimidin-6-yl)methyl)-N-methylbenzamide |
| 236 | 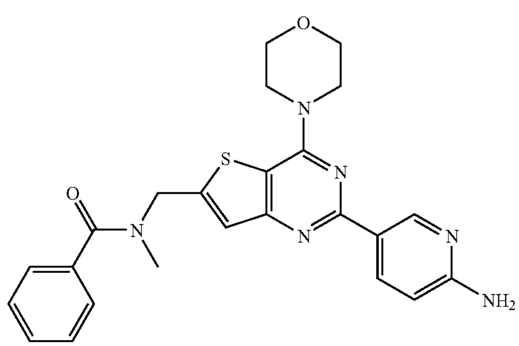 [SMILES: CN(Cc1cc2nc(-c3ccc(N)nc3)nc(N3CCOCC3)c2s1)C(=O)c1ccccc1] | N-((2-(6-aminopyridin-3-yl)-4-morpholinothieno[3,2-d]pyrimidin-6-yl)methyl)-N-methylbenzamide |
| 237 | 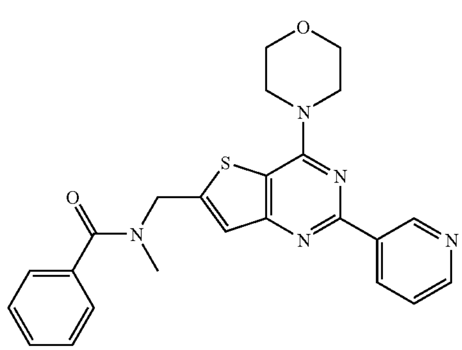 | N-methyl-N-((4-morpholin-2-(pyridin-3-yl)thieno[3,2-d]pyrimidin-6-yl)methyl)benzamide |

TABLE 1-continued

| Compound | Structure | Name |
|---|---|---|
| 238 | 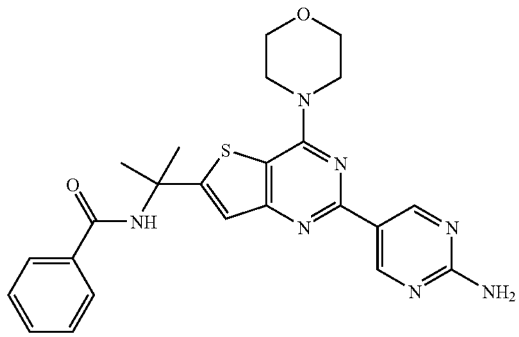 [SMILES: CC(C)(NC(=O)c1ccccc1)c1cc2nc(-c3cnc(N)nc3)nc(N3CCOCC3)c2s1] | N-(2-(2-(2-aminopyrimidin-5-yl)-4-morpholinothieno[3,2-d]pyrimidin-6-yl)propan-2-yl)benzamide |
| 239 | 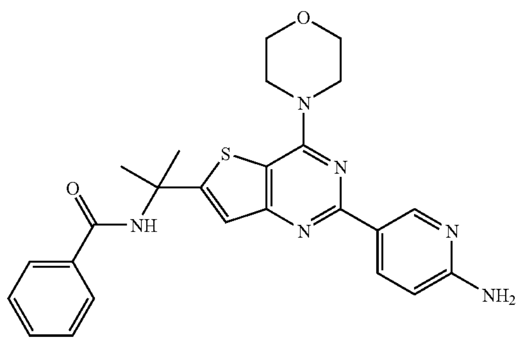 [SMILES: CC(C)(NC(=O)c1ccccc1)c1cc2nc(-c3ccc(N)nc3)nc(N3CCOCC3)c2s1] | N-(2-(2-(6-aminopyridin-3-yl)-4-morpholinothieno[3,2-d]pyrimidin-6-yl)propan-2-yl)benzamide |
| 240 | 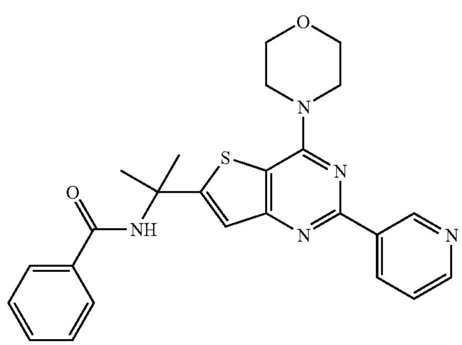 [SMILES: CC(C)(NC(=O)c1ccccc1)c1cc2nc(-c3cccnc3)nc(N3CCOCC3)c2s1] | N-(2-(4-morpholino-2-(pyridin-3-yl)thieno[3,2-d]pyrimidin-6-yl)propan-2-yl)benzamide |
| 241 | 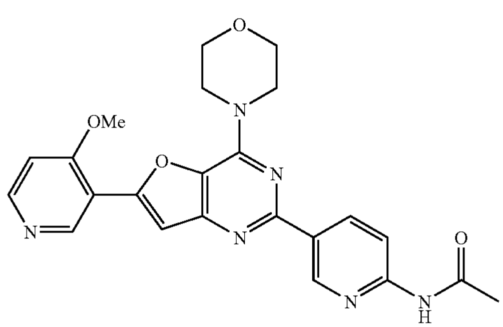 [SMILES: COc1ccncc1-c1cc2nc(-c3ccc(NC(C)=O)nc3)nc(N3CCOCC3)c2o1] | N-(5-(6-(4-methoxypyridin-3-yl)-4-morpholinofuro[3,2-d]pyrimidin-2-yl)pyridin-2-yl)acetamide |

TABLE 1-continued

| Compound | Structure | Name |
|---|---|---|
| 242 | 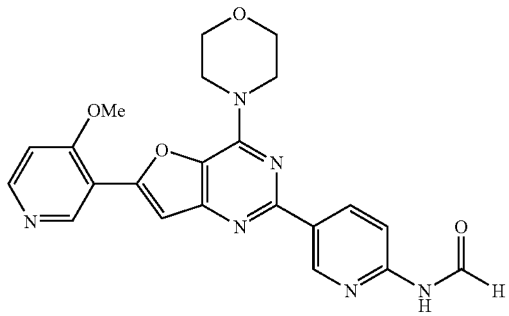 [SMILES: COc1ccncc1-c1cc2nc(-c3ccc(NC=O)nc3)nc(N3CCOCC3)c2o1] | N-(5-(6-(4-methoxypyridin-3-yl)-4-morpholinofuro[3,2-d]pyrimidin-2-yl)pyridin-2-yl)formamide |
| 243 | 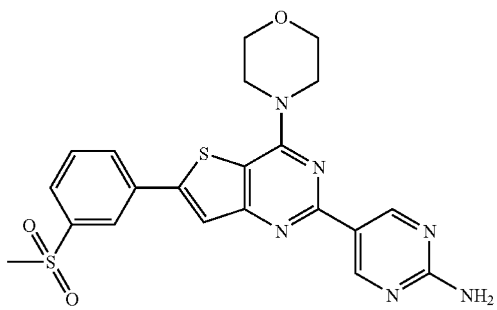 | 5-(6-(3-(methylsulfonyl)phenyl)-4-morpholinothieno[3,2-d]pyrimidin-2-yl)pyrimidin-2-amine |
| 244 | 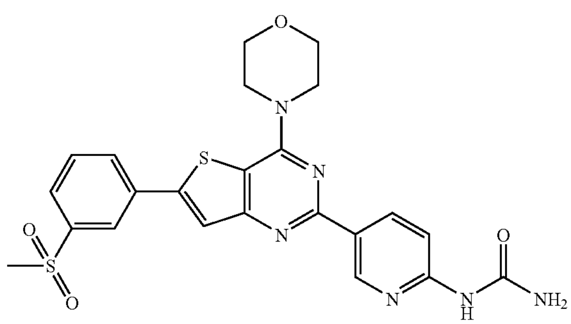 [SMILES: CS(=O)(=O)c1cccc(-c2cc3nc(-c4ccc(NC(N)=O)nc4)nc(N4CCOCC4)c3s2)c1] | 1-(5-(6-(3-(methylsulfonyl)phenyl)-4-morpholinothieno[3,2-d]pyrimidin-2-yl)pyridin-2-yl)urea |
| 245 | 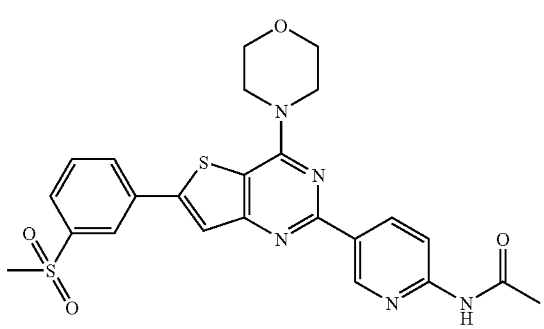 [SMILES: CC(=O)Nc1ccc(-c2nc(N3CCOCC3)c3sc(-c4cccc(S(C)(=O)=O)c4)cc3n2)cn1] | N-(5-(6-(3-(methylsulfonyl)phenyl)-4-morpholinothieno[3,2-d]pyriomidin-2-yl)pyridin-2-yl)acetamide |

TABLE 1-continued

| Compound | Structure | Name |
|---|---|---|
| 246 | 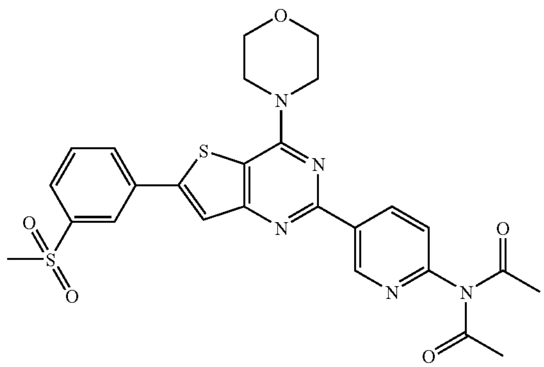 [SMILES: CC(=O)N(C(C)=O)c1ccc(-c2nc(N3CCOCC3)c3sc(-c4cccc(S(C)(=O)=O)c4)cc3n2)cn1] | N-acetyl-N-(5-(6-(3-(methylsulfonyl)phenyl)-4-morpholinothieno[3,2-d]pyrimidin-2-yl)pyridin-2-yl)acetamide |
| 247 | 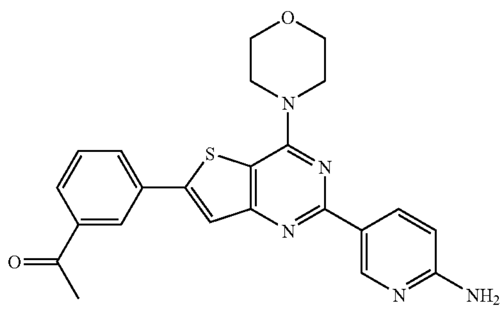 [SMILES: CC(=O)c1cccc(-c2cc3nc(-c4ccc(N)nc4)nc(N4CCOCC4)c3s2)c1] | 1-(3-(2-(6-aminopyridin-3-yl)-4-morpholinothieno[3,2-d]pyrimidin-6-yl)phenyl)ethanone |
| 248 | 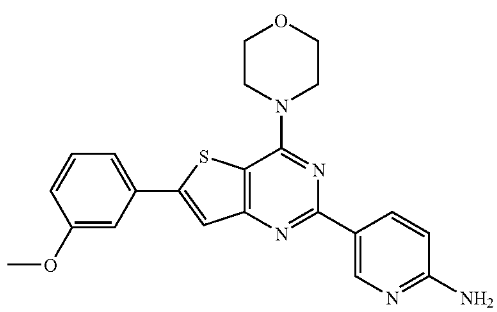 [SMILES: COc1cccc(-c2cc3nc(-c4ccc(N)nc4)nc(N4CCOCC4)c3s2)c1] | 5-(6-(3-methoxyphenyl)-4-morpholinothieno[3,2-d]pyrimidin-2-yl)pyridin-2-amine |
| 249 | 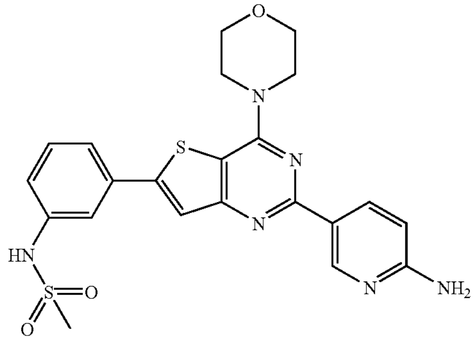 [SMILES: CS(=O)(=O)Nc1cccc(-c2cc3nc(-c4ccc(N)nc4)nc(N4CCOCC4)c3s2)c1] | 5-(6-(3-methylsulfonylaminophenyl)-4-morpholinothieno[3,2-d]pyrimidin-2-yl)pyridin-2-amine |

TABLE 1-continued

| Compound | Structure | Name |
|---|---|---|
| 250 | 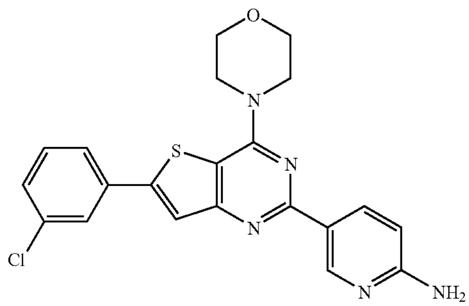 [SMILES: Nc1ccc(-c2nc(N3CCOCC3)c3sc(-c4cccc(Cl)c4)cc3n2)cn1] | 5-(6-(3-chlorophenyl)-4-morpholinothieno[3,2-d]pyrimidin-2-yl)pyridin-2-amine |
| 251 | 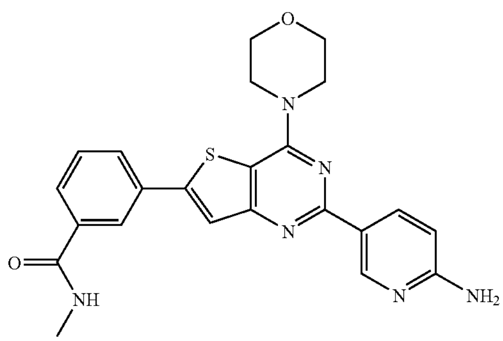 [SMILES: CNC(=O)c1cccc(-c2cc3nc(-c4ccc(N)nc4)nc(N4CCOCC4)c3s2)c1] | 3-(2-(6-aminopyridin-3-yl)-4-morpholinothieno[3,2-d]pyrimidin-6-yl)-N-methylbenzamide |
| 252 | 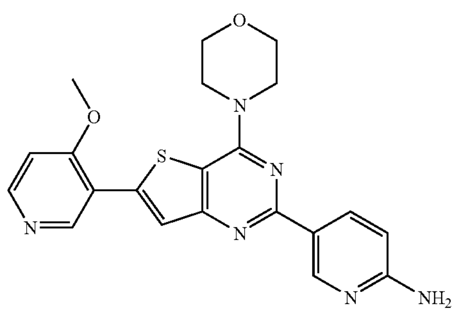 [SMILES: COc1ccncc1-c1cc2nc(-c3ccc(N)nc3)nc(N3CCOCC3)c2s1] | 5-(6-(4-methoxypyridin-3-yl)-4-morpholinothieno[3,2-d]pyrimidin-2-yl)pyridin-2-amine |
| 253 | 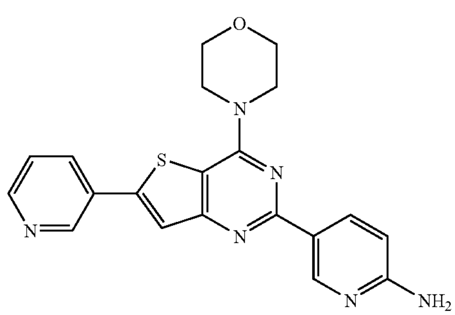 [SMILES: Nc1ccc(-c2nc(N3CCOCC3)c3sc(-c4cccnc4)cc3n2)cn1] | 5-(4-morpholino-6-(pyridin-3-yl)thieno[3,2-d]pyrimidin-2-yl)pyridin-2-amine |
| 254 | 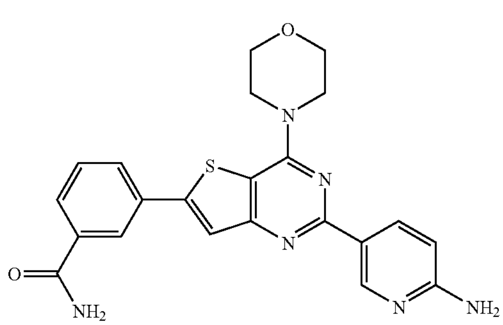 [SMILES: NC(=O)c1cccc(-c2cc3nc(-c4ccc(N)nc4)nc(N4CCOCC4)c3s2)c1] | 3-(2-(6-aminopyridin-3-yl)-4-morpholinothieno[3,2-d]pyrimidin-6-yl)benzamide |

TABLE 1-continued

| Compound | Structure | Name |
|---|---|---|
| 255 | 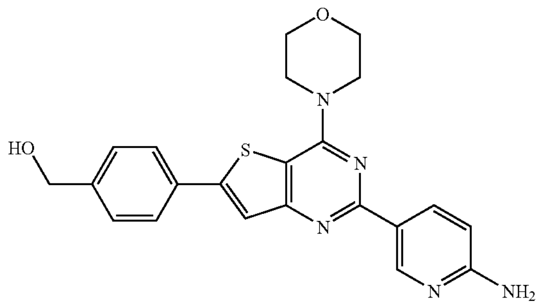 [SMILES: Nc1ccc(-c2nc(N3CCOCC3)c3sc(-c4ccc(CO)cc4)cc3n2)cn1] | (4-(2-(6-aminopyridin-3-yl)-4-morpholinothieno[3,2-d]pyrimidin-6-yl)phenyl)methanol |
| 256 | 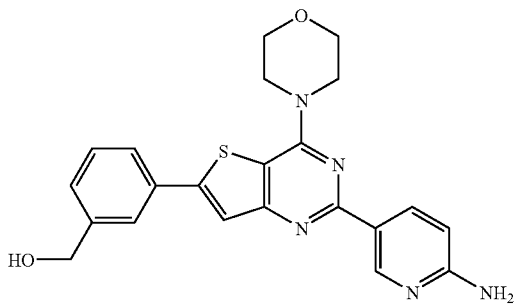 [SMILES: Nc1ccc(-c2nc(N3CCOCC3)c3sc(-c4cccc(CO)c4)cc3n2)cn1] | (3-(2-(6-aminopyridin-3-yl)-4-morpholinothieno[3,2-d]pyrimidin-6-yl)phenyl)methanol |
| 257 | 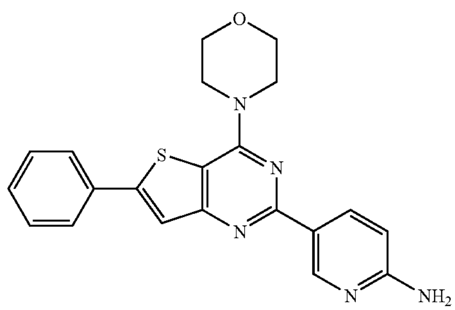 | 5-(4-morpholino-6-phenylthieno[3,2-d]pyrimidin-2-yl)pyridin-2-amine |
| 258 | 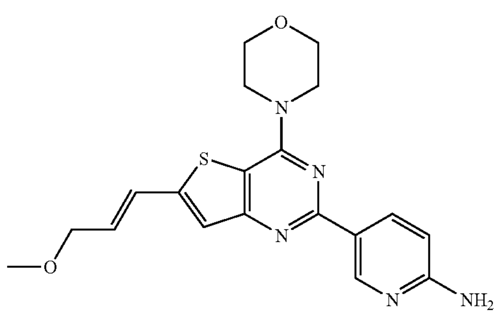 [SMILES: COC/C=C/c1cc2nc(-c3ccc(N)nc3)nc(N3CCOCC3)c2s1] | 5-(6-((E)-3-methoxyprop-1-enyl)-4-morpholinothieno[3,2-d]pyrimidin-2-yl)pyridin-2-amine |
| 259 | 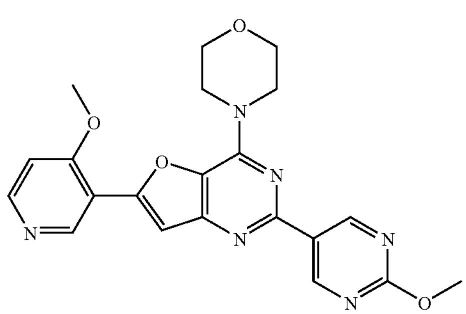 [SMILES: COc1ncc(-c2nc(N3CCOCC3)c3oc(-c4cnccc4OC)cc3n2)cn1] | 6-(4-methoxypyridin-3-yl)-2-(2-methoxypyrimidin-5-yl)-4-morpholinofuro[3,2-d]pyrimidine |

TABLE 1-continued

| Compound | Structure | Name |
|---|---|---|
| 260 | 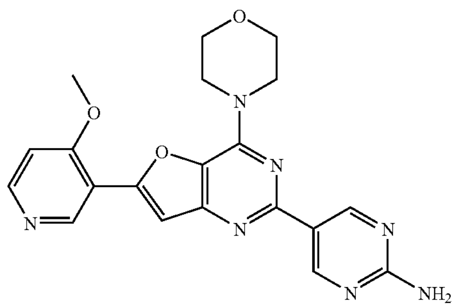 [SMILES: COc1ccncc1-c1cc2nc(-c3cnc(N)nc3)nc(N3CCOCC3)c2o1] | 5-(6-(4-methoxypyridin-3-yl)-4-morpholinofuro]3,2-d]pyrimidin-2-yl)pyrimidin-2-amine |
| 261 | 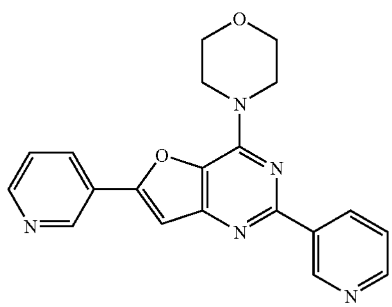 [SMILES: c1cncc(-c2nc(N3CCOCC3)c3oc(-c4cccnc4)cc3n2)c1] | 4-morpholino-2,6-di(pyridin-3-yl)furo[3,2-d]pyrimidine |
| 262 | 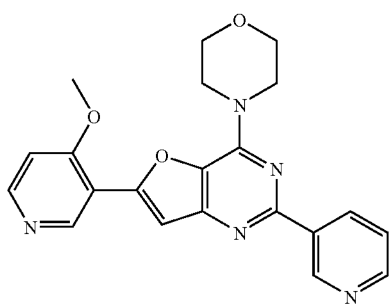 [SMILES: COc1ccncc1-c1cc2nc(-c3cccnc3)nc(N3CCOCC3)c2o1] | 6-(4-methoxypyridin-3-yl)-4-morpholino-2-(pyridin-3-yl)furo[3,2-d]pyrimidine |
| 263 | 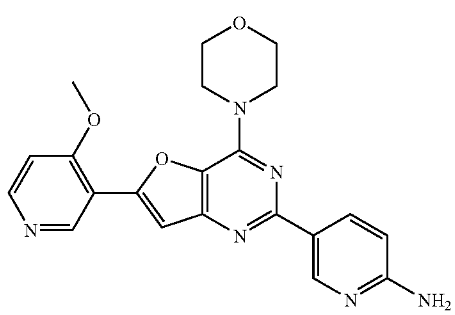 | 5-(6-(4-methoxypyridin-3-yl)-4-morpholinofuro[3,2-d]pyrimidin-2-yl)pyridin-2-amine |
| 264 | 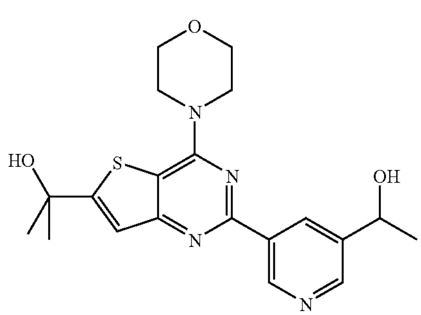 [SMILES: CC(O)c1cncc(-c2nc(N3CCOCC3)c3sc(C(C)(C)O)cc3n2)c1] | 2-(2-(5-(1-hydroxyethyl)pyridin-3-yl)-4-morpholinothieno[3,2-d]pyrimidin-6-yl)propan-2-ol |

TABLE 1-continued

| Compound | Structure | Name |
|---|---|---|
| 265 | 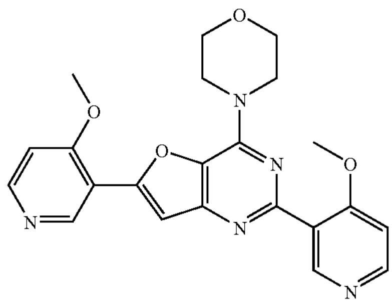 [SMILES: COc1ccncc1-c1nc(N2CCOCC2)c2oc(-c3cnccc3OC)cc2n1] | 2,6-bis(4-methoxypyridin-3-yl)-4-morpholinofuro[3,2-d]pyrimidine |
| 266 | 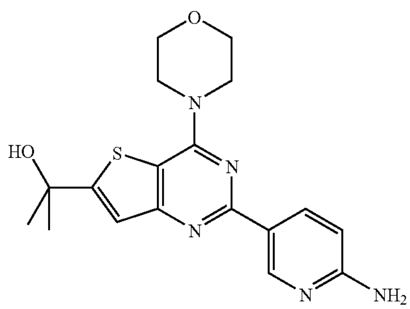 | 2-(2-(6-aminopyridin-3-yl)-4-morpholinothieno[3,2-d]pyrimidin-6-yl)propan-2-ol |
| 267 | 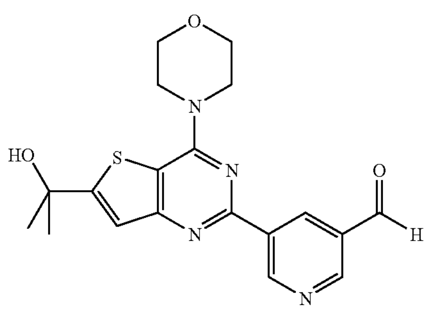 [SMILES: CC(C)(O)c1cc2nc(-c3cncc(C=O)c3)nc(N3CCOCC3)c2s1] | 5-(6-(2-hydroxypropan-2-yl)-4-morpholinothieno[3,2-d]pyrimidin-2-yl)pyridine-3-carbaldehyde |
| 268 | 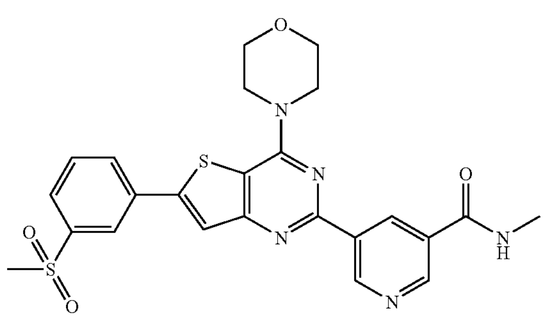 | N-methyl-5-(6-(3-(methylsulfonyl)phenyl)-4-morpholinothieno[3,2-d]pyrimidin-2-yl)pyridine-3-carboxamide |
| 269 | 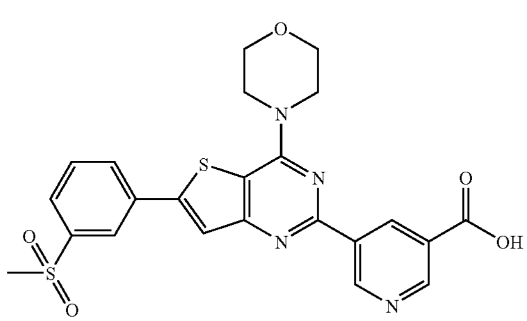 [SMILES: CS(=O)(=O)c1cccc(-c2cc3nc(-c4cncc(C(=O)O)c4)nc(N4CCOCC4)c3s2)c1] | 5-(6-(3-(mthylsulfonyl)phenyl)-4-morpholinothieno[3,2-d]pyrimidin-2-yl)pyridin-3-carboxylic acid |

TABLE 1-continued

| Compound | Structure | Name |
|---|---|---|
| 270 | 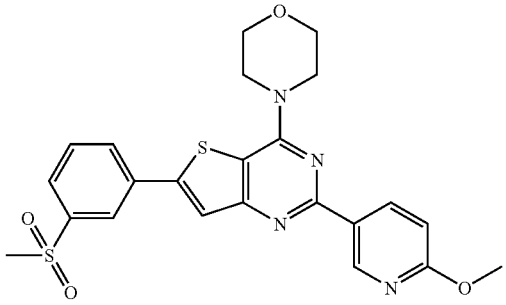 | 2-(2-methoxypyrimidin-5-yl)-6-(3-(methylsulfonyl)phenyl)-4-morpholinothieno[3,2-d]pyrimidine |
| 271 | 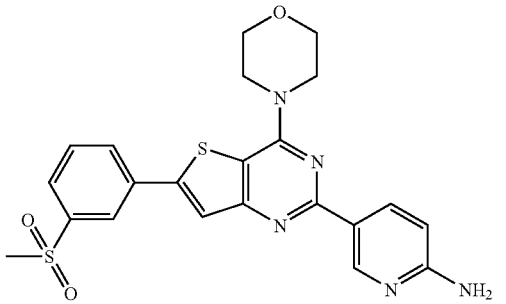 [SMILES: CS(=O)(=O)c1cccc(-c2cc3nc(-c4ccc(N)nc4)nc(N4CCOCC4)c3s2)c1] | 5-(6-(3-(methylsulfonyl)-phenyl)-4-morpholinothieno[3,2-d]pyrimidin-2-yl)pyridin-2-amine |
| 272 | 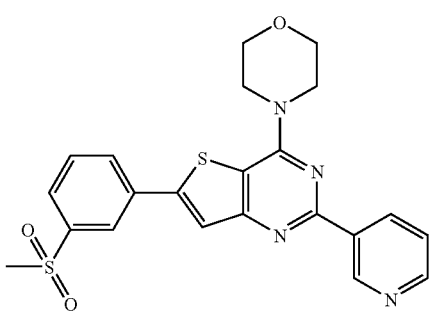 [SMILES: CS(=O)(=O)c1cccc(-c2cc3nc(-c4cccnc4)nc(N4CCOCC4)c3s2)c1] | 6-(3-((methylsulfonyl)phenyl)-4-morpholino-2-(pyridin-3-yl)thieno[3,2-d]pyrimidine |
| 273 | 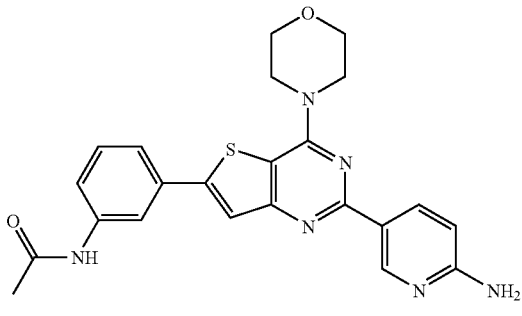 [SMILES: CC(=O)Nc1cccc(-c2cc3nc(-c4ccc(N)nc4)nc(N4CCOCC4)c3s2)c1] | N-(3-(2-(6-aminopyridin-3-yl)-4-morpholinothieno[3,2-d]pyrimidin-6-yl)phenyl)acetamide |
| 274 | 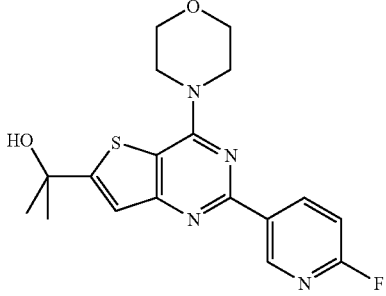 [SMILES: CC(C)(O)c1cc2nc(-c3ccc(F)nc3)nc(N3CCOCC3)c2s1] | 2-(2-(6-fluoropyridin-3-yl)-4-morpholinothieno[3,2-d]pyrimidin-6-yl)propan-2-ol |

TABLE 1-continued

| Compound | Structure | Name |
|---|---|---|
| 275 | 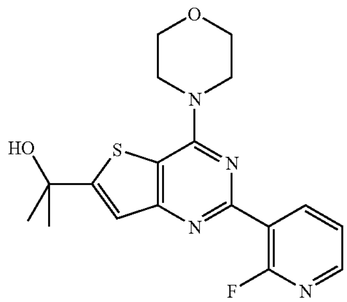 [SMILES: CC(C)(O)c1cc2nc(-c3cccnc3F)nc(N3CCOCC3)c2s1] | 2-(2-(2-fluoropyridin-3-yl)-4-morpholinothieno[3,2-d]pyrimidin-6-yl)propan-2-ol |
| 276 | 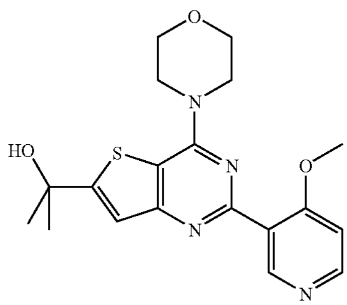 [SMILES: COc1ccncc1-c1nc(N2CCOCC2)c2sc(C(C)(C)O)cc2n1] | 2-(2-(4-methoxypyridin-3-yl)-4-morpholinothieno[3,2-d]pyrimidin-6-yl)propan-2-ol |
| 277 | 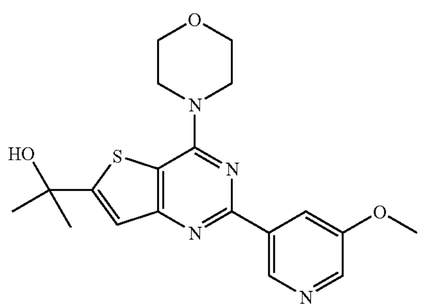 [SMILES: COc1cncc(-c2nc(N3CCOCC3)c3sc(C(C)(C)O)cc3n2)c1] | 2-(2-(5-methoxypyridin-3-yl)-4-morpholinothieno[3,2-d]pyrimidin-6-yl)propan-2-ol |
| 278 | 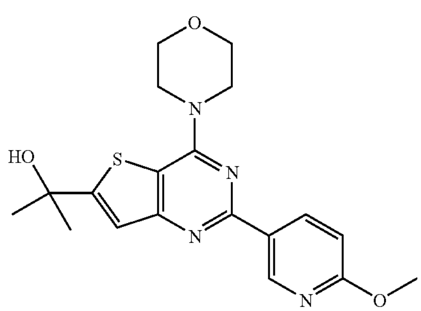 [SMILES: COc1ccc(-c2nc(N3CCOCC3)c3sc(C(C)(C)O)cc3n2)cn1] | 2-(2-(6-methoxypyridin-3-yl)-4-morpholinothieno[3,2-d]pyrimidin-6-yl)propan-2-ol |
| 279 | 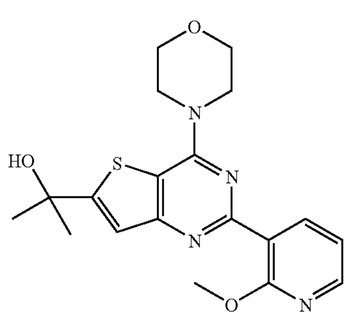 [SMILES: COc1ncccc1-c1nc(N2CCOCC2)c2sc(C(C)(C)O)cc2n1] | 2-(2-(2-methoxypyridin-3-yl)-4-morpholinothieno[3,2-d]pyrimidin-6-yl)propan-2-ol |

TABLE 1-continued

| Compound | Structure | Name |
|---|---|---|
| 280 | 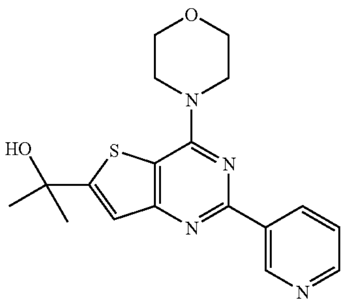 [SMILES: CC(C)(O)c1cc2nc(-c3cccnc3)nc(N3CCOCC3)c2s1] | 2-(4-morpholino-2-(pyridin-3-yl)thieno[3,2-d]pyrimidin-6-yl)propan-2-ol |
| 281 | 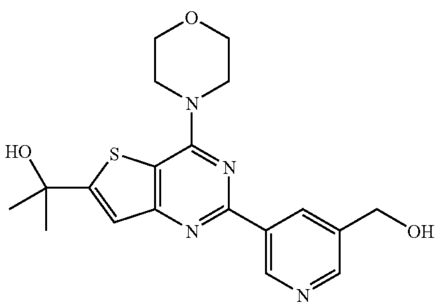 [SMILES: CC(C)(O)c1cc2nc(-c3cncc(CO)c3)nc(N3CCOCC3)c2s1] | 2-(2-(5-(hydroxymethyl)pyridin-3-yl)-4-morpholinothieno[3,2-d]pyrimidin-6-yl)propan-2-ol |
| 282 | 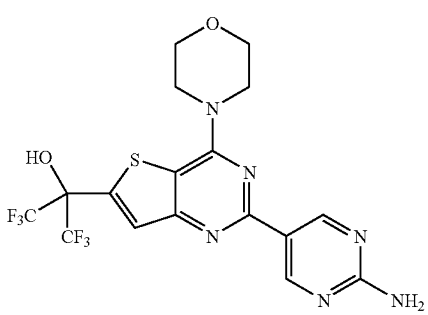 [SMILES: Nc1ncc(-c2nc(N3CCOCC3)c3sc(C(O)(C(F)(F)F)C(F)(F)F)cc3n2)cn1] | 2-(2-(2-aminopyrimidin-5-yl)-4-morpholinothieno[3,2-d]pyrimidin-6-yl)-1,1,1,3,3,3-hexafluoropropan-2-ol |
| 283 | 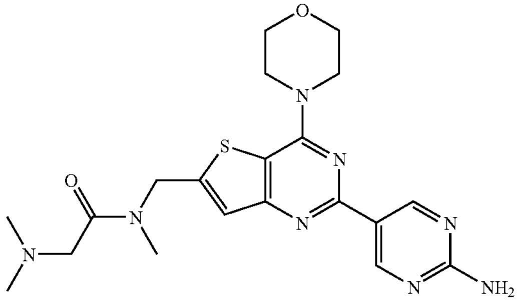 [SMILES: CN(C)CC(=O)N(C)Cc1cc2nc(-c3cnc(N)nc3)nc(N3CCOCC3)c2s1] | N-((2-(2-aminopyrimidin-5-yl)-4-morpholinothieno[3,2-d]pyrimidin-6-yl)methyl)-2-(dimethylamino)-N-methylacetamide |

TABLE 1-continued

| Compound | Structure | Name |
|---|---|---|
| 284 | 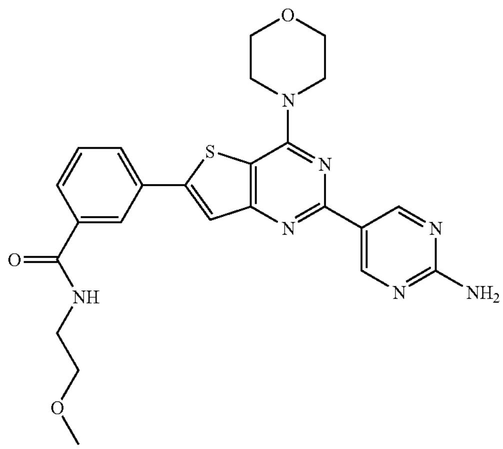 [SMILES: COCCNC(=O)c1cccc(-c2cc3nc(-c4cnc(N)nc4)nc(N4CCOCC4)c3s2)c1] | 3-(2-(2-aminopyrimidin-5-yl)-4-morpholinothieno[3,2-d]pyrimidin-6-yl)-N-(2-methoxyethyl)benzamide |
| 285 | 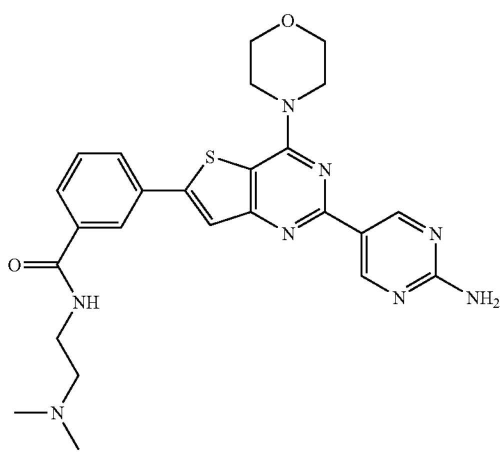 | 3-(2-(2-aminopyrimidin-5-yl)-4-morpholinothieno[3,2-d]pyrimidin-6-yl)-N-(2-(dimethylamino)ethyl)benzamide |
| 286 | 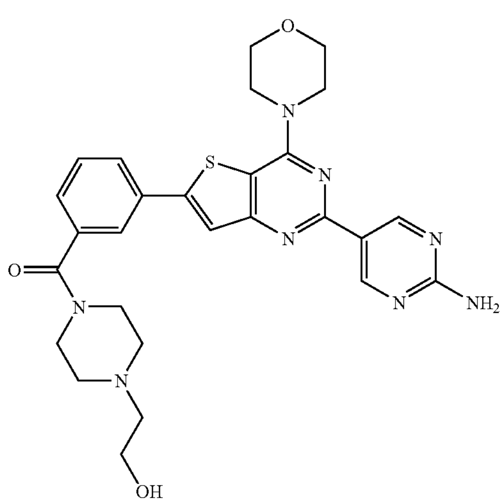 [SMILES: Nc1ncc(-c2nc(N3CCOCC3)c3sc(-c4cccc(C(=O)N5CCN(CCO)CC5)c4)cc3n2)cn1] | (3-(2-(2-aminopyrimidin-5-yl)-4-morpholinothieno[3,2-d]pyrimidin-6-yl)phenyl)(4-(2-hydroxyethyl)piperazin-1-yl)methanone |

TABLE 1-continued

| Compound | Structure | Name |
|---|---|---|
| 287 | 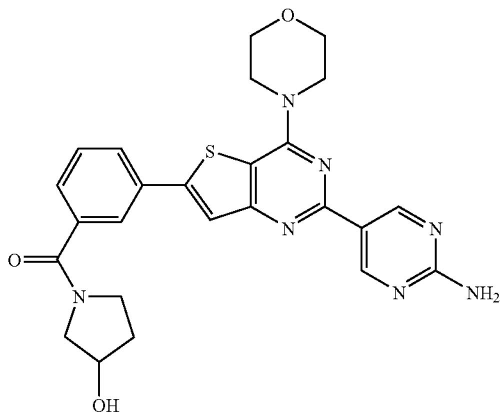 [SMILES: Nc1ncc(-c2nc(N3CCOCC3)c3sc(-c4cccc(C(=O)N5CCC(O)C5)c4)cc3n2)cn1] | (3-(2-(2-aminopyrimidin-5-yl)-4-morpholinothieno[3,2-d]pyrimidin-6-yl)phenyl)(3-hydroxypyrolidin-1-yl)methanone |
| 288 | 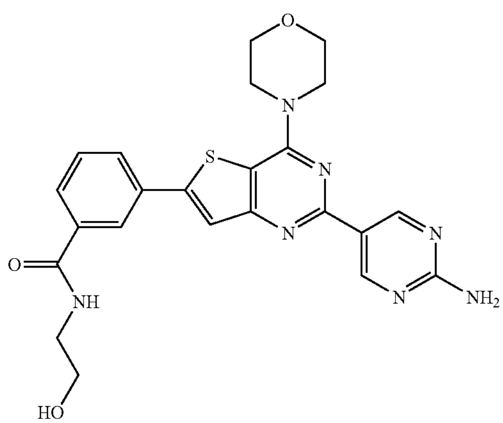 [SMILES: Nc1ncc(-c2nc(N3CCOCC3)c3sc(-c4cccc(C(=O)NCCO)c4)cc3n2)cn1] | 3-(2-(2-aminopyrimidin-5-yl)-4-morpholinothieno[3,2-d]pyrimidin-6-yl)-N-(2-hydroxyethyl)benzamide |
| 289 | 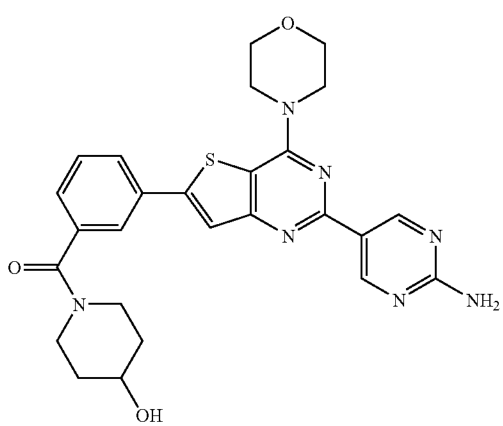 [SMILES: Nc1ncc(-c2nc(N3CCOCC3)c3sc(-c4cccc(C(=O)N5CCC(O)CC5)c4)cc3n2)cn1] | (3-(2-(2-aminopyrimidin-5-yl)-4-morpholinothieno[3,2-d]pyrimidin-6-yl)phenyl)(4-hydroxypiperidin-1-yl)methanone |
| 290 | 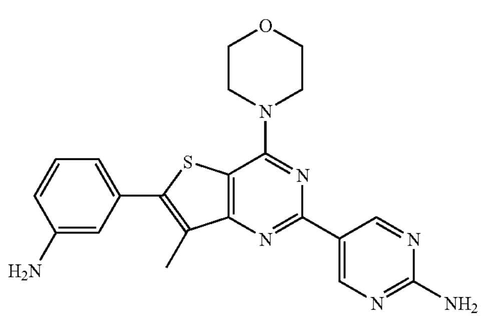 [SMILES: Cc1c(-c2cccc(N)c2)sc2c(N3CCOCC3)nc(-c3cnc(N)nc3)nc12] | 5-(6-(3-aminophenyl)-7-methyl-4-morpholinothieno[3,2-d]pyrimidin-2-yl)pyrimidin-2-amine |

TABLE 1-continued

| Compound | Structure | Name |
|---|---|---|
| 291 | 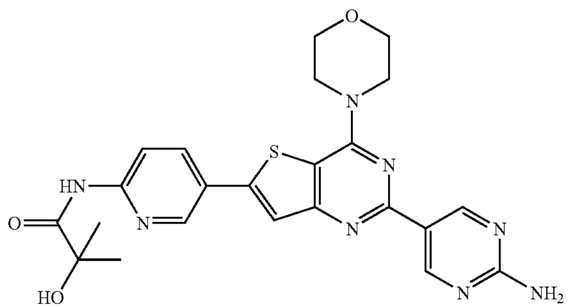 [SMILES: CC(C)(O)C(=O)Nc1ccc(-c2cc3nc(-c4cnc(N)nc4)nc(N4CCOCC4)c3s2)cn1] | N-(5-(2-(2-aminopyrimidin-5-yl)-4-morpholinothieno[3,2-d]pyrimidin-6-yl)pyridin-2-yl)-2-hydroxy-2-methylpropanamide |
| 292 | 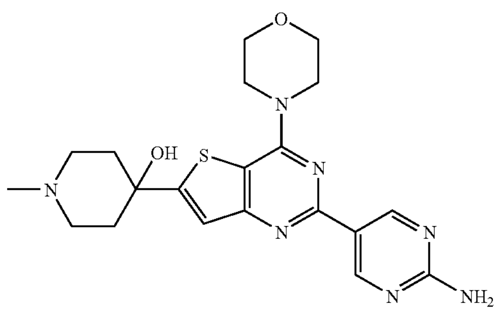 [SMILES: CN1CCC(O)(c2cc3nc(-c4cnc(N)nc4)nc(N4CCOCC4)c3s2)CC1] | 4-(2-(2-aminopyrimidin-5-yl)-4-morpholinothieno[3,2-d]pyrimidin-6-yl)-1-methylpiperidin-4-ol |
| 293 | 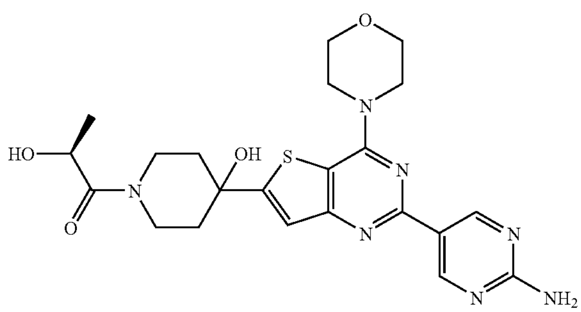 [SMILES: C[C@H](O)C(=O)N1CCC(O)(c2cc3nc(-c4cnc(N)nc4)nc(N4CCOCC4)c3s2)CC1] | (S)-1-(4-(2-(2-aminopyrimidin-5-yl)-4-morpholinothieno[3,2-d]pyrimidin-6-yl)-4-hydroxypiperidin-1-yl)-2-hydroxypropan-1-one |
| 294 | 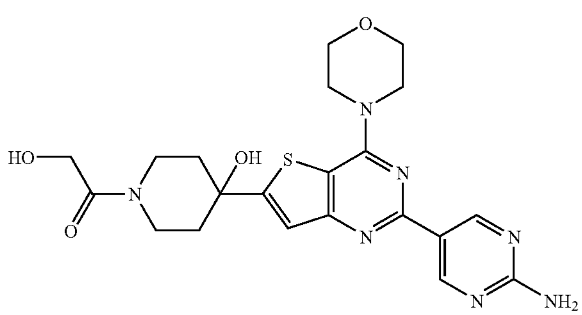 | 1-(4-(2-(2-aminopyrimidin-5-yl)-4-morpholinothieno[3,2-d]pyrimidin-6-yl)-4-hydroxypiperidin-1-yl)-2-hydroxyethanone |
| 295 | 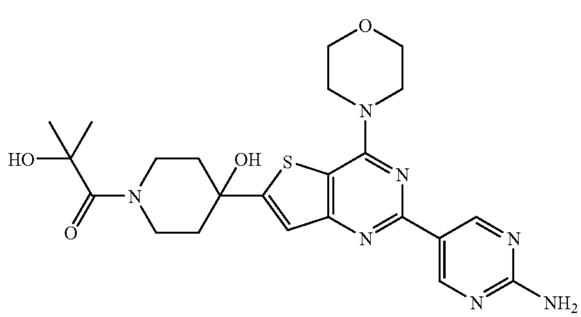 [SMILES: CC(C)(O)C(=O)N1CCC(O)(c2cc3nc(-c4cnc(N)nc4)nc(N4CCOCC4)c3s2)CC1] | 1-(4-(2-(2-aminopyrimidin-5-yl)-4-morpholinothieno[3,2-d]pyrimidin-6-yl)-4-hydroxypiperidin-1-yl)-2-hydroxy-2-methylpropan-1-one |

TABLE 1-continued

| Compound | Structure | Name |
|---|---|---|
| 296 | 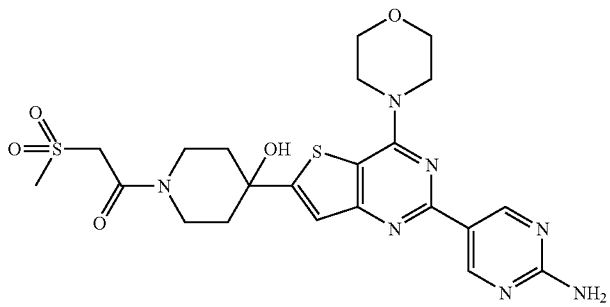 [SMILES: CS(=O)(=O)CC(=O)N1CCC(O)(c2cc3nc(-c4cnc(N)nc4)nc(N4CCOCC4)c3s2)CC1] | 1-(4-(2-(2-aminopyrimidin-5-yl)-4-morpholinothieno[3,2-d]pyrimidin-6-yl)-4-hydroxypiperidin-1-yl)-2-(methylsulfonyl)ethanone |
| 297 | 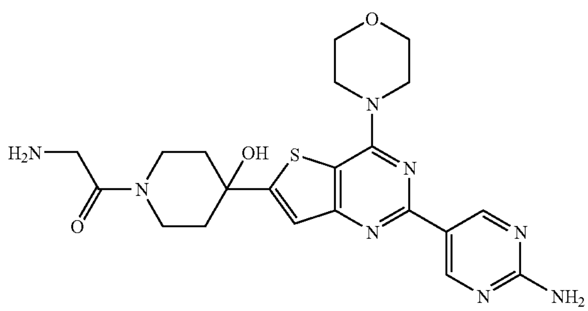 [SMILES: NCC(=O)N1CCC(O)(c2cc3nc(-c4cnc(N)nc4)nc(N4CCOCC4)c3s2)CC1] | 2-amino-1-(4-(2-(2-aminopyrimidin-5-yl)-4-morpholinothieno[3,2-d]pyrimidin-6-yl)-4-hydroxypiperidin-1-yl)ethanone |
| 298 | 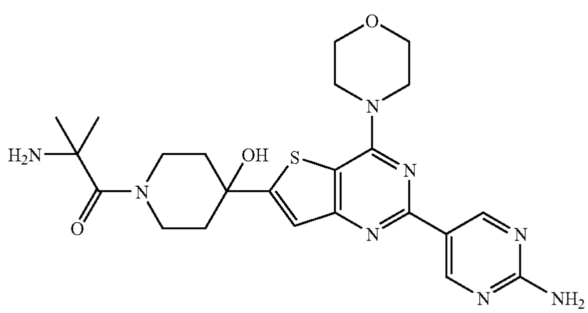 [SMILES: CC(C)(N)C(=O)N1CCC(O)(c2cc3nc(-c4cnc(N)nc4)nc(N4CCOCC4)c3s2)CC1] | 2-amino-1-(4-(2-(2-aminopyrimidin-5-yl)-4-morpholinthieno[3,2-d]pyrimidin-6-yl)-4-hydroxypiperidin-1-yl)-2-mthylpropan-1-one |
| 299 | 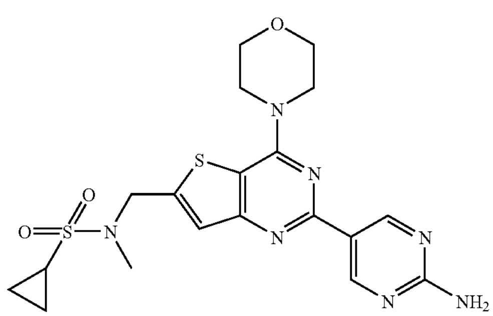 [SMILES: CN(Cc1cc2nc(-c3cnc(N)nc3)nc(N3CCOCC3)c2s1)S(=O)(=O)C1CC1] | 5-(6-((N-cyclopropylsulfonyl,N-methylamino)methyl)-4-morpholinothieno[3,2-d]pyrimidin-2-yl)pyrimidin-2-amine |
| 300 | 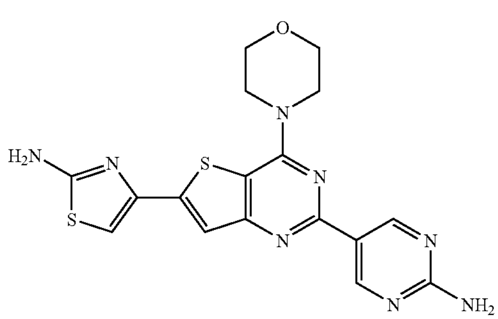 [SMILES: Nc1ncc(-c2nc(N3CCOCC3)c3sc(-c4csc(N)n4)cc3n2)cn1] | 5-(6-(2-aminothiazol-4-yl)-4-morpholinothieno[3,2-d]pyrimidin-2-yl)pyrimidin-2-amine |

TABLE 1-continued

| Compound | Structure | Name |
|---|---|---|
| 301 | 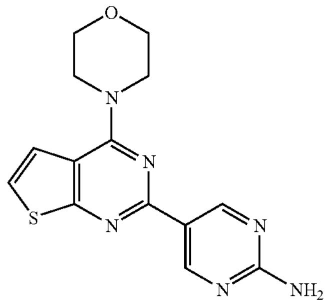 [SMILES: Nc1ncc(-c2nc(N3CCOCC3)c3ccsc3n2)cn1] | 5-(4-morpholinothieno[3,2-d]pyrimidin-2-yl)pyrimidin-2-amine |
| 302 | 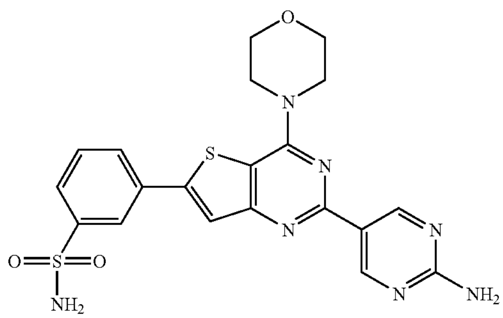 | 5-(4-morpholino-6-(3-aminosulfonyl)phenylthieno[3,2-d]pyrimidin-2-yl)pyrimidin-2-amine |
| 303 | 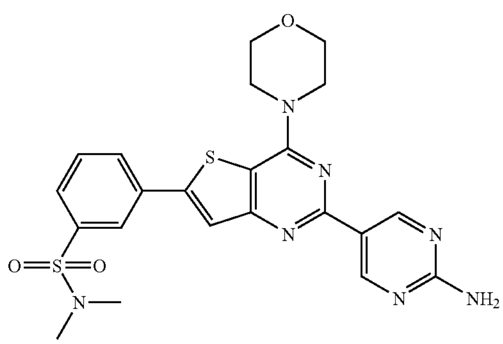 [SMILES: CN(C)S(=O)(=O)c1cccc(-c2cc3nc(-c4cnc(N)nc4)nc(N4CCOCC4)c3s2)c1] | 5-(4-morpholino-6-(3-dimethylaminosulfonyl)phenylthieno[3,2-d]pyrimidin-2-yl)pyrimidin-2-amine |
| 304 | 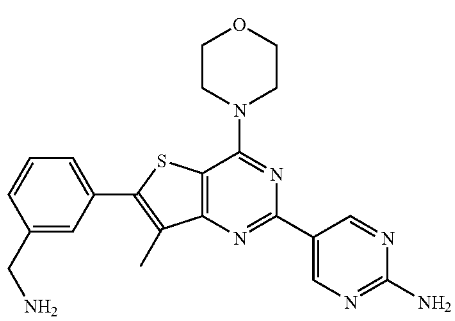 [SMILES: Cc1c(-c2cccc(CN)c2)sc2c(N3CCOCC3)nc(-c3cnc(N)nc3)nc12] | 5-(6-(3-(aminomethyl)phenyl)-7-methyl-4-morpholinothieno[3,2-d]pyrimidin-2-yl)pyrimidin-2-amine |

TABLE 1-continued

| Compound | Structure | Name |
|---|---|---|
| 305 | 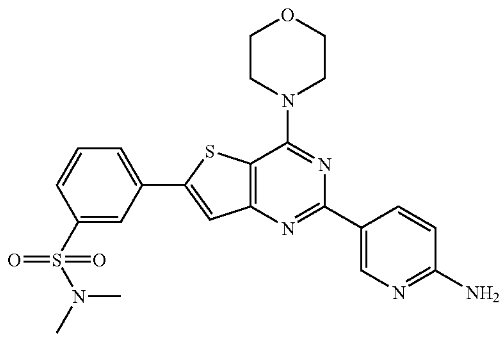 [SMILES: CN(C)S(=O)(=O)c1cccc(-c2cc3nc(-c4ccc(N)nc4)nc(N4CCOCC4)c3s2)c1] | 5-(4-morpholino-6-(3-dimethylaminosulfonyl)phenylthieno[3,2-d]pyrimidin-2-yl)pyridin-2-amine |
| 306 | 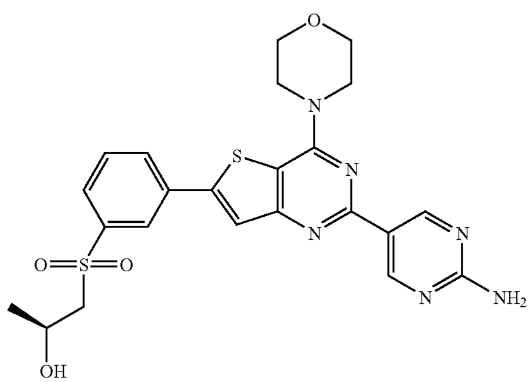 | (S)-1-(3-(2-(2-aminopyrimidin-5-yl)-4-morpholinothieno[3,2-d]pyrimidin-6-yl)phenylsulfonyl)propan-2-ol |
| 307 | 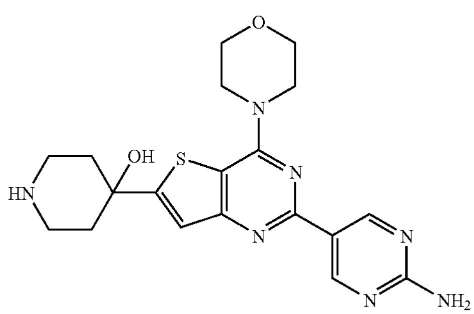 [SMILES: Nc1ncc(-c2nc(N3CCOCC3)c3sc(C4(O)CCNCC4)cc3n2)cn1] | 4-(2-(2-aminopyrimidin-5-yl)-4-morpholinothieno[3,2-d]pyrimidin-6-yl)piperidin-4-ol |
| 308 | 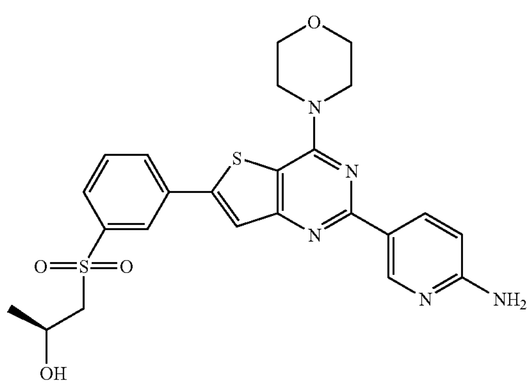 [SMILES: C[C@H](O)CS(=O)(=O)c1cccc(-c2cc3nc(-c4ccc(N)nc4)nc(N4CCOCC4)c3s2)c1] | (S)-1-(3-(2-(6-aminopyridin-3-yl)-4-morpholinothieno[3,2-d]pyrimidin-6-yl)phenylsulfonyl)propan-2-ol |

TABLE 1-continued

| Compound | Structure | Name |
|---|---|---|
| 309 | 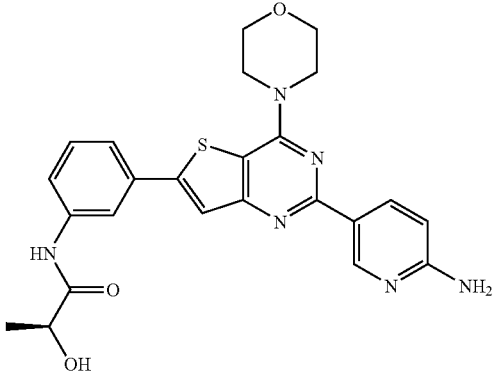 [SMILES: C[C@H](O)C(=O)Nc1cccc(-c2cc3nc(-c4ccc(N)nc4)nc(N4CCOCC4)c3s2)c1] | (2S)-N-(3-(2-(6-aminopyridin-3-yl)-4-morpholinothieno[3,2-d]pyrimidin-6-yl)phenyl)-2-hydroxypropanamide |
| 310 | 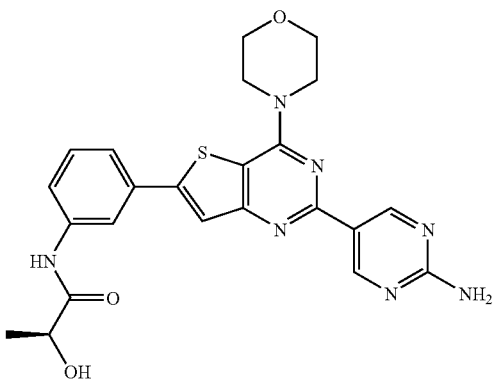 | (2S)-N-(3-(2-(2-aminopyrimidin-5-yl)-4-morpholinothieno[3,2-d]pyrimidin-6-yl)phenyl)-2-hydroxypropanamide |
| 311 | 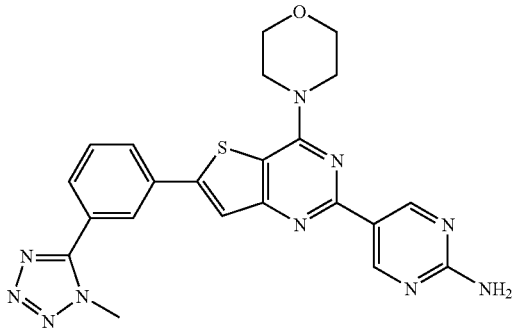 [SMILES: Cn1nnnc1-c1cccc(-c2cc3nc(-c4cnc(N)nc4)nc(N4CCOCC4)c3s2)c1] | 5-(6-(3-(1-methyl-1H-tetrazol-5-yl)phenyl)-4-morpholinothieno[3,2-d]pyrimidin-2-yl)pyrimidin-2-amine |
| 312 | 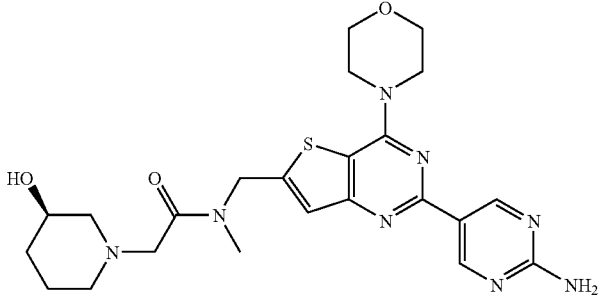 [SMILES: CN(Cc1cc2nc(-c3cnc(N)nc3)nc(N3CCOCC3)c2s1)C(=O)CN1CCC[C@@H](O)C1] | N-((2-(2-aminopyrimidin-5-yl)-4-morpholinothieno[3,2-d]pyrimidin-6-yl)methyl)-2-((R)-3-hydroxypiperidin-1-yl)-N-methylacetamide |

TABLE 1-continued

| Compound | Structure | Name |
|---|---|---|
| 313 | 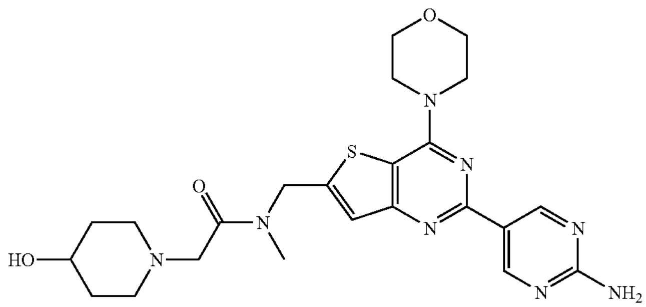 [SMILES: CN(Cc1cc2nc(-c3cnc(N)nc3)nc(N3CCOCC3)c2s1)C(=O)CN1CCC(O)CC1] | N-((2-(2-aminopyrimidin-5-yl)-4-morpholinothieno[3,2-d]pyrimidin-6-yl)methyl)-2-(4-hydroxypiperidin-1-yl)-N-methylacetamide |
| 314 | 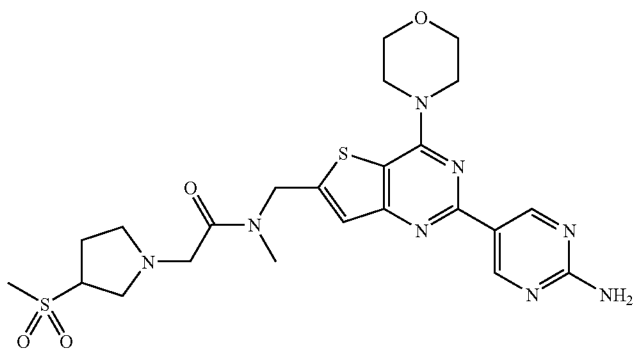 [SMILES: CN(Cc1cc2nc(-c3cnc(N)nc3)nc(N3CCOCC3)c2s1)C(=O)CN1CCC(S(C)(=O)=O)C1] | N-((2-(2-aminopyrimidin-5-yl)-4-morpholinothieno[3,2-d]pyrimidin-6-yl)methyl)-N-methyl-2-(3-(methylsulfonyl)pyrolidin-1-yl)acetamide |
| 315 | 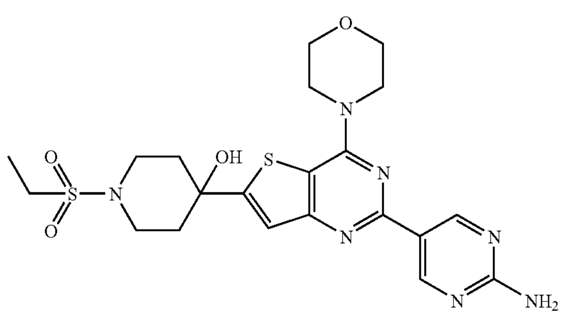 [SMILES: CCS(=O)(=O)N1CCC(O)(c2cc3nc(-c4cnc(N)nc4)nc(N4CCOCC4)c3s2)CC1] | 4-(2-(2-aminopyrimidin-5-yl)-4-morpholinothieno[3,2-d]pyrimidin-6-yl)-(4-N-ethylsulfonyl)piperidin-4-ol |
| 316 | 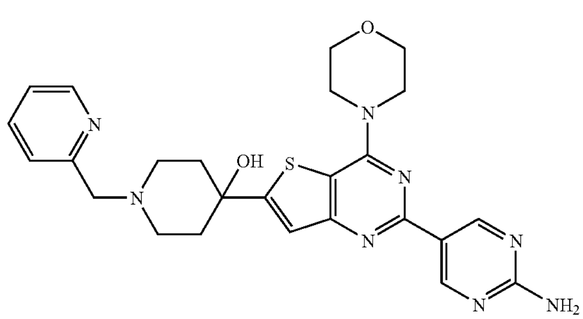 [SMILES: Nc1ncc(-c2nc(N3CCOCC3)c3sc(C4(O)CCN(Cc5ccccn5)CC4)cc3n2)cn1] | 4-(2-(2-aminopyrimidin-5-yl)-4-morpholinothieno[3,2-d]pyrimidin-6-yl)-1-((pyridin-2-yl)methyl)piperidin-4-ol |

TABLE 1-continued

| Compound | Structure | Name |
|---|---|---|
| 317 | 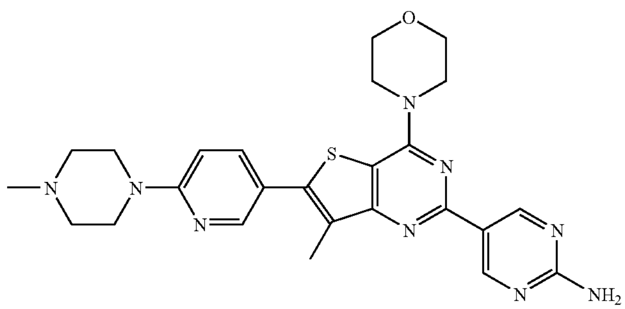 [SMILES: Cc1c(-c2ccc(N3CCN(C)CC3)nc2)sc2c(N3CCOCC3)nc(-c3cnc(N)nc3)nc12] | 5-(7-methyl-6-(6-(4-methylpiperazin-1-yl)pyridin-3-yl)-4-morpholinothieno[3,2-d]pyrimidin-2-yl)pyrimidin-2-amine |
| 318 | 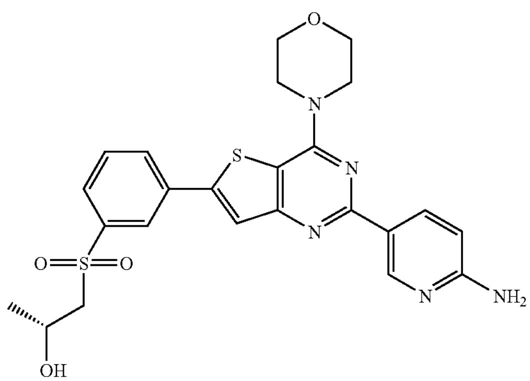 | (R)-1-(3-(2-(6-aminopyridin-3-yl)-4-morpholinothieno[3,2-d]pyrimidin-6-yl)phenylsulfonyl)propan-2-ol |
| 319 | 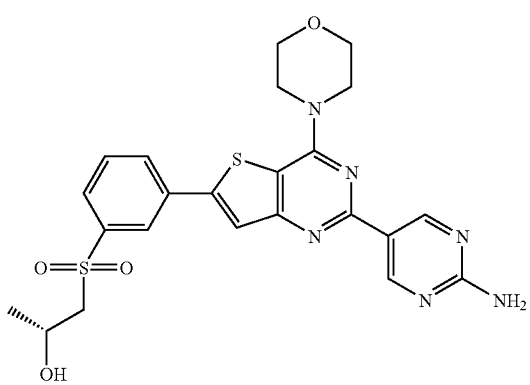 [SMILES: C[C@@H](O)CS(=O)(=O)c1cccc(-c2cc3nc(-c4cnc(N)nc4)nc(N4CCOCC4)c3s2)c1] | (R)-1-(3-(2-(2-aminopyrimidin-5-yl)-4-morpholinothieno[3,2-d]pyrimidin-6-yl)phenylsulfonyl)propan-2-ol |
| 320 | 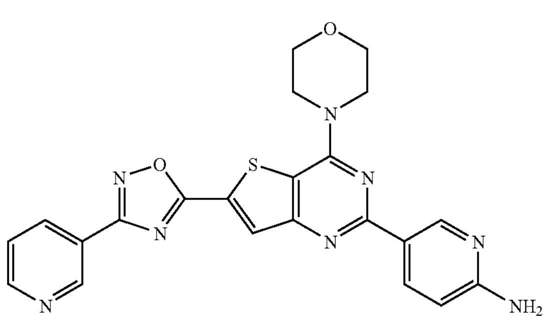 [SMILES: Nc1ccc(-c2nc(N3CCOCC3)c3sc(-c4nc(-c5cccnc5)no4)cc3n2)cn1] | 5-(4-morpholino-6-(3-(pyridin-3-yl)-1,2,4-oxadiazol-5-yl)thieno[3,2-d]pyrimidin-2-yl)pyridin-2-amine |

TABLE 1-continued

| Compound | Structure | Name |
|---|---|---|
| 321 | 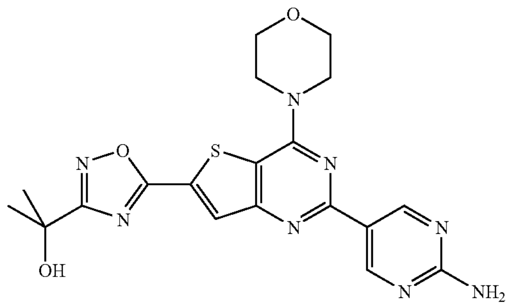 [SMILES: CC(C)(O)c1noc(-c2cc3nc(-c4cnc(N)nc4)nc(N4CCOCC4)c3s2)n1] | 2-(5-(2-(2-aminopyrimidin-5-yl)-4-morpholinothieno[3,2-d]pyrimidin-6-yl)-1,2,4-oxadiazol-3-yl)propan-2-ol |
| 322 | 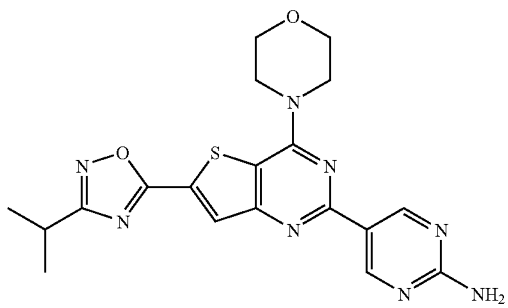 [SMILES: CC(C)c1noc(-c2cc3nc(-c4cnc(N)nc4)nc(N4CCOCC4)c3s2)n1] | 5-(6-(3-isopropyl-1,2,4-oxadiazol-5-yl)-4-morpholinothieno[3,2-d]pyrimidin-2-yl)pyrimidin-2-amine |
| 323 | 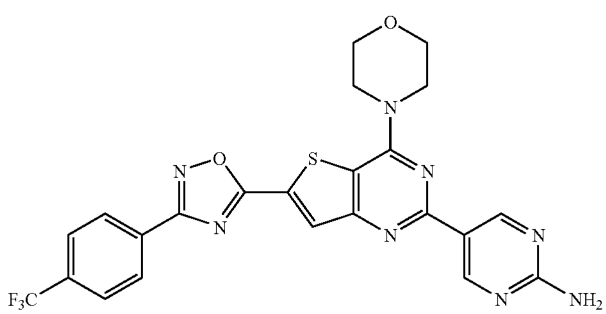 [SMILES: Nc1ncc(-c2nc(N3CCOCC3)c3sc(-c4nc(-c5ccc(C(F)(F)F)cc5)no4)cc3n2)cn1] | 5-(6-(3-(4-(trifluoromethyl)phenyl)-1,2,4-oxadiazol-5-yl)-4-morpholinothieno[3,2-d]pyrimidin-2-yl)pyrimidin-2-amine |
| 324 | 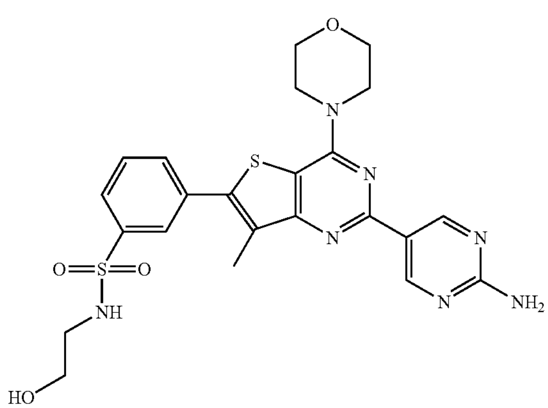 [SMILES: Cc1c(-c2cccc(S(=O)(=O)NCCO)c2)sc2c(N3CCOCC3)nc(-c3cnc(N)nc3)nc12] | 5-(7-methyl-4-morpholino-6-(3-(2-hydroxyethyl)aminosulfonyl)phenyl-thieno[3,2-d]pyrimidin-2-yl)pyrimidin-2-amine |

TABLE 1-continued

| Compound | Structure | Name |
|---|---|---|
| 325 | 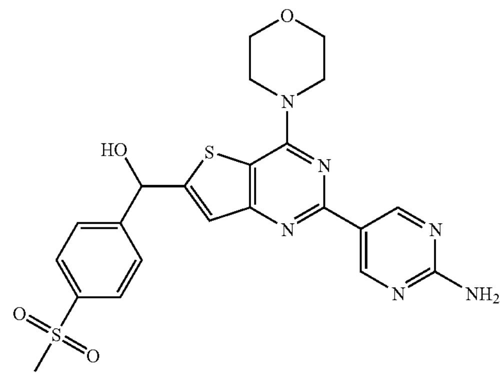 [SMILES: CS(=O)(=O)c1ccc(C(O)c2cc3nc(-c4cnc(N)nc4)nc(N4CCOCC4)c3s2)cc1] | (2-(2-aminopyrimidin-5-yl)-4-morpholinothieno[3,2-d]pyrimidin-6-yl)(4-(methylsulfonyl)phenyl)methanol |
| 326 | 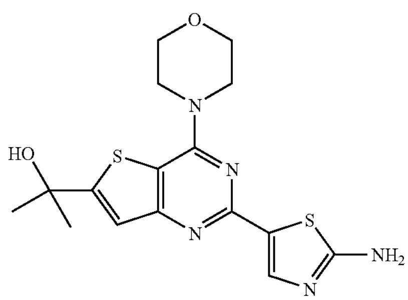 [SMILES: CC(C)(O)c1cc2nc(-c3cnc(N)s3)nc(N3CCOCC3)c2s1] | 2-(2-(2-aminothiazol-5-yl)-4-morpholinothieno[3,2-d]pyrimidin-6-yl)propan-2-ol |
| 327 | 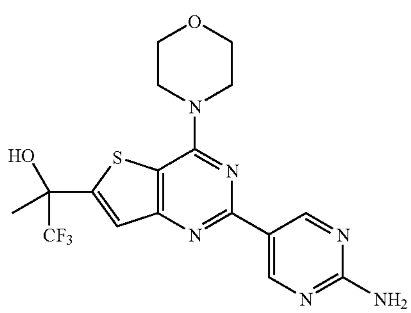 [SMILES: CC(O)(c1cc2nc(-c3cnc(N)nc3)nc(N3CCOCC3)c2s1)C(F)(F)F] | 2-(2-(2-aminopyrimidin-5-yl)-4-morpholinothieno[3,2-d]pyrimidin-6-yl)-1,1,1-trifluoropropan-2-ol |
| 328 | 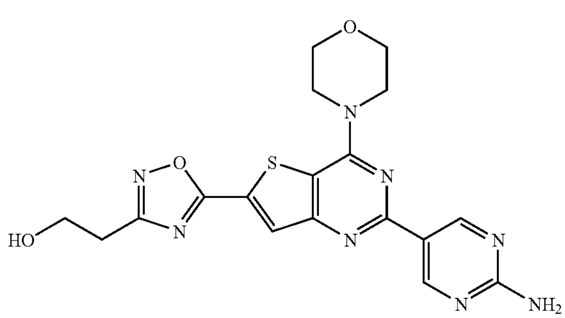 [SMILES: Nc1ncc(-c2nc(N3CCOCC3)c3sc(-c4nc(CCO)no4)cc3n2)cn1] | 2-(5-(2-(2-aminopyrimidin-5-yl)-4-morpholinothieno[3,2-d]pyrimidin-6-yl)-1,2,4-oxadiazol-3-yl)ethanol |

TABLE 1-continued

| Compound | Structure | Name |
|---|---|---|
| 329 | 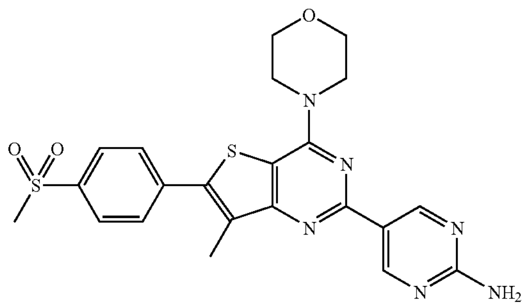 [SMILES: Cc1c(-c2ccc(S(C)(=O)=O)cc2)sc2c(N3CCOCC3)nc(-c3cnc(N)nc3)nc12] | 5-(7-methyl-6-(4-(methylsulfonyl)phenyl)-4-morpholinothieno[3,2-d]pyrimidin-2-yl)pyrimidin-2-amine |
| 330 | 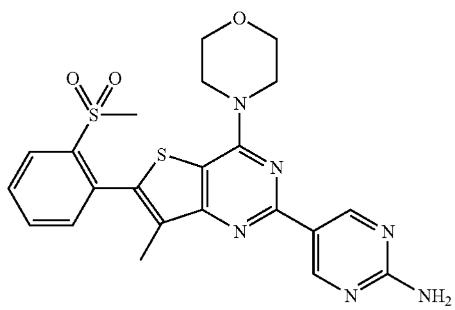 [SMILES: Cc1c(-c2ccccc2S(C)(=O)=O)sc2c(N3CCOCC3)nc(-c3cnc(N)nc3)nc12] | 5-(7-methyl-6-(2-(methylsulfonyl)phenyl)-4-morpholinothieno[3,2-d]pyrimidin-2-yl)pyrimidin-2-amine |
| 331 | 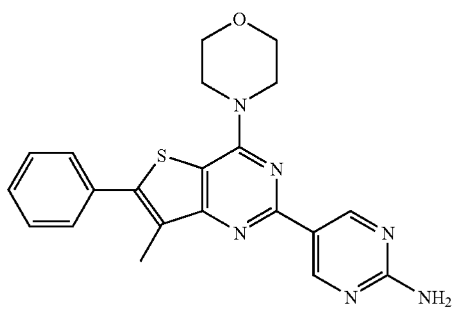 [SMILES: Cc1c(-c2ccccc2)sc2c(N3CCOCC3)nc(-c3cnc(N)nc3)nc12] | 5-(7-methyl-4-morpholino-6-phenylthieno[3,2-d]pyrimidin-2-yl)pyrimidin-2-amine |
| 332 | 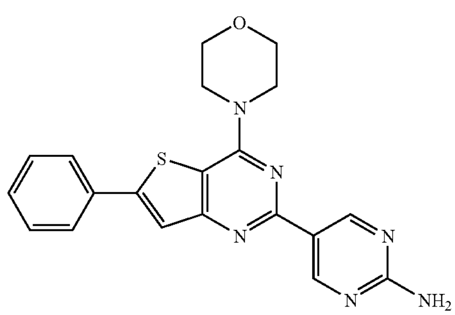 [SMILES: Nc1ncc(-c2nc(N3CCOCC3)c3sc(-c4ccccc4)cc3n2)cn1] | 5-(4-morpholino-6-phenylthieno[3,2-d]pyrimidin-2-yl)pyrimidin-2-amine |
| 333 | 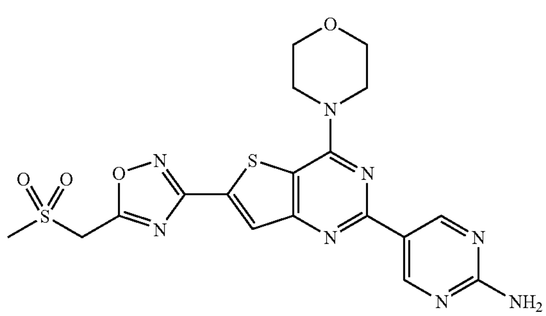 [SMILES: CS(=O)(=O)Cc1nc(-c2cc3nc(-c4cnc(N)nc4)nc(N4CCOCC4)c3s2)no1] | 5-(6-(5-((methylsulfonyl)methyl)-1,2,4-oxadiazol-3-yl)-4-morpholinothieno[3,2-d]pyrimidin-2-yl)pyrimidin-2-amine |

TABLE 1-continued

| Compound | Structure | Name |
|---|---|---|
| 334 | 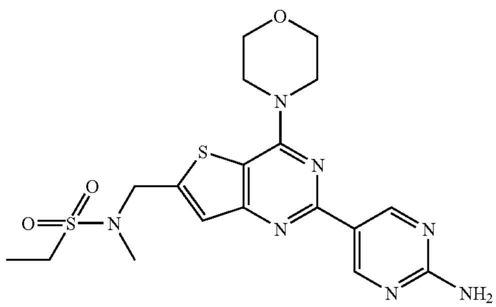 [SMILES: CCS(=O)(=O)N(C)Cc1cc2nc(-c3cnc(N)nc3)nc(N3CCOCC3)c2s1] | 5-(6-((N-ethylsulfony,N-methylamino)methyl)-4-morpholinothieno[3,2-d]pyrimidin-2-yl)pyrimidin-2-amine |
| 335 | 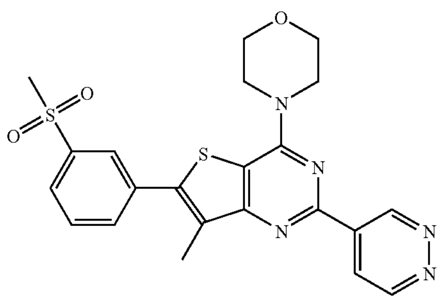 [SMILES: Cc1c(-c2cccc(S(C)(=O)=O)c2)sc2c(N3CCOCC3)nc(-c3ccnnc3)nc12] | 7-methyl-6-(3-(methylsulfonyl)phenyl)-4-morpholino-2-(pyridazin-4-yl)thieno[3,2-d]pyrimidine |
| 336 | 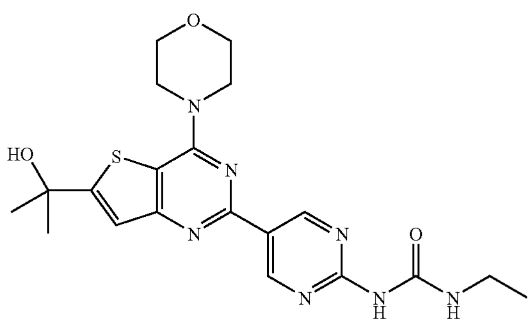 | 1-ethyl-3-(5-(6-(2-hydroxypropan-2-yl)-4-morpholinothieno[3,2-d]pyrimidin-2-yl)pyrimidin-2-yl)urea |
| 337 | 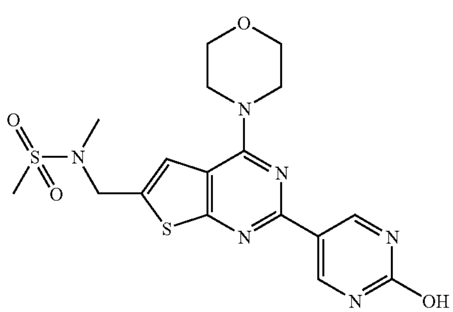 [SMILES: CN(Cc1cc2c(N3CCOCC3)nc(-c3cnc(O)nc3)nc2s1)S(C)(=O)=O] | 5-(6-((N-methylsulfonyl,N-methylamino)methyl)-4-morpholinothieno[2,3-d]pyrimidin-2-yl)pyrimidin-2-ol |
| 338 | 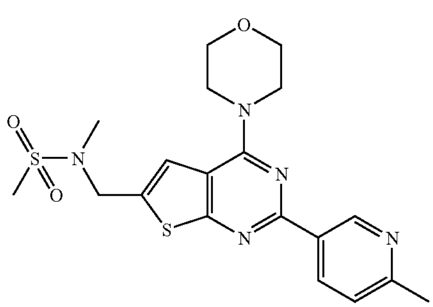 | N-methylsulfonyl,N-methyl(2-(6-methylpyridin-3-yl)-4-morpholinothieno[2,3-d]pyrimidin-6-yl)methanamine |

TABLE 1-continued

| Compound | Structure | Name |
|---|---|---|
| 339 | 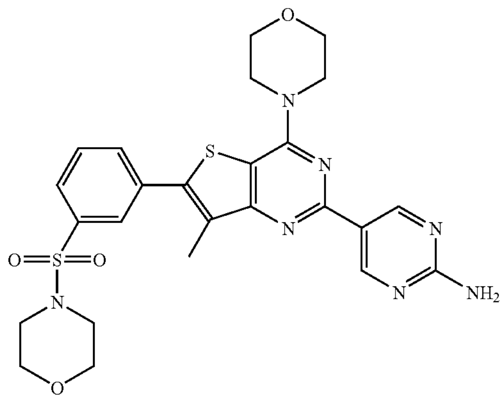 [SMILES: Cc1c(-c2cccc(S(=O)(=O)N3CCOCC3)c2)sc2c(N3CCOCC3)nc(-c3cnc(N)nc3)nc12] | 5-(7-methyl-4-morpholino-6-(3-morpholinosulfonyl)phenylthieno[3,2-d]pyrimidin-2-yl)pyrimidin-2-amine |
| 340 | 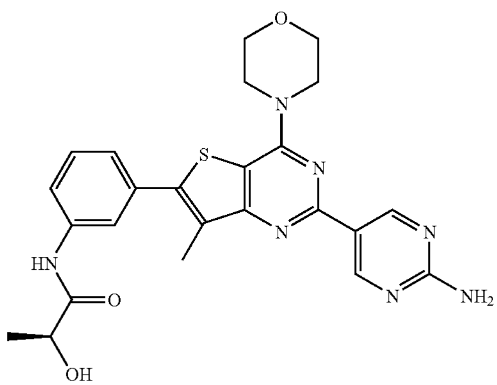 [SMILES: Cc1c(-c2cccc(NC(=O)[C@H](C)O)c2)sc2c(N3CCOCC3)nc(-c3cnc(N)nc3)nc12] | (2S)-N-(3-(2-(2-aminopyrimidin-5-yl)-7-methyl-4-morpholinothieno[3,2-d]pyrimidin-6-yl)phenyl)-2-hydroxypropanamide |
| 341 | 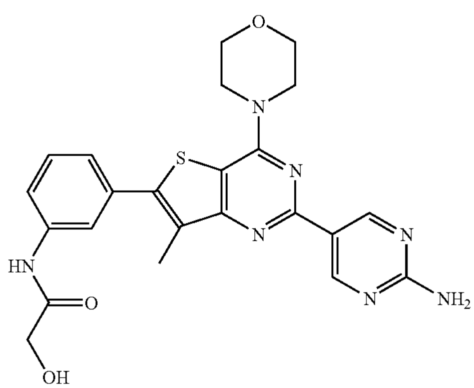 [SMILES: Cc1c(-c2cccc(NC(=O)CO)c2)sc2c(N3CCOCC3)nc(-c3cnc(N)nc3)nc12] | N-(3-(2-(2-aminopyrimidin-5-yl)-7-methyl-4-morpholinothieno[3,2-d]pyrimidin-6-yl)phenyl)-2-hydroxyacetamide |
| 342 | 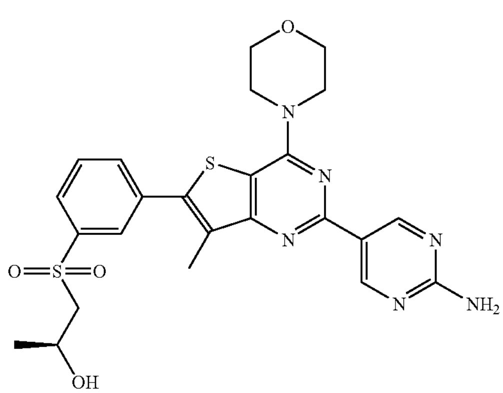 [SMILES: Cc1c(-c2cccc(S(=O)(=O)C[C@H](C)O)c2)sc2c(N3CCOCC3)nc(-c3cnc(N)nc3)nc12] | (S)-1-(3-(2-(2-aminopyrimidin-5-yl)-7-methyl-4-morpholinothieno[3,2-d]pyrimidin-6-yl)phenylsulfonyl)propan-2-ol |

TABLE 1-continued

| Compound | Structure | Name |
|---|---|---|
| 343 | 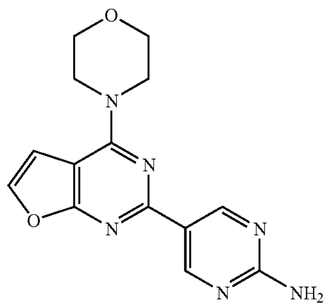 | 5-(4-morpholinofuro[2,3-d]pyrimidin-2-yl)pyrimidin-2-amine |
| 344 | 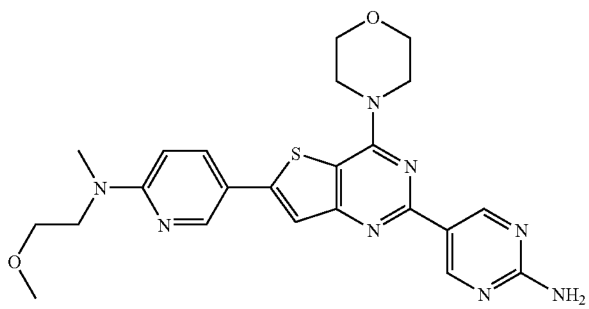 [SMILES: COCCN(C)c1ccc(-c2cc3nc(-c4cnc(N)nc4)nc(N4CCOCC4)c3s2)cn1] | 5-(6-(6-(N-(2-methoxyethyl)-N-methylamino)pyridin-3-yl)-4-morpholinothieno[3,2-d]pyrimidin-2-yl)pyrimidin-2-amine |
| 345 | 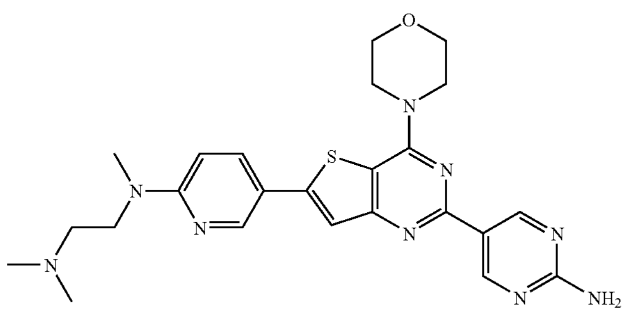 | 5-(6-(6-(N-(2-(dimethylamino)ethyl)-N-methylamino)pyridin-3-yl)-4-morpholinothieno[3,2-d]pyrimidin-2-yl)pyrimidin-2-amine |
| 346 | 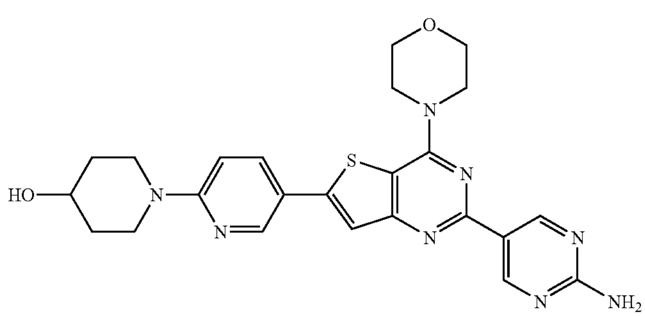 [SMILES: Nc1ncc(-c2nc(N3CCOCC3)c3sc(-c4ccc(N5CCC(O)CC5)nc4)cc3n2)cn1] | 1-(5-(2-(2-aminopyrimidin-5-yl)-4-morpholinothieno[3,2-d]pyrimidin-6-yl)pyridin-2-yl)piperidin-4-ol |
| 347 | 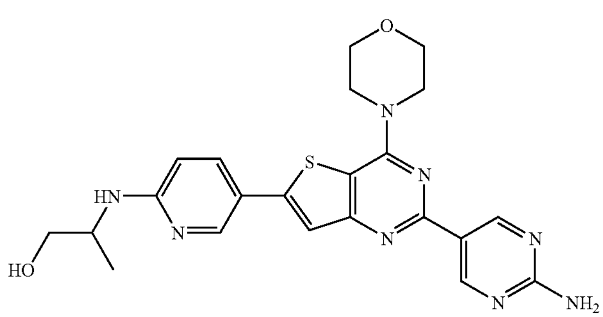 [SMILES: CC(CO)Nc1ccc(-c2cc3nc(-c4cnc(N)nc4)nc(N4CCOCC4)c3s2)cn1] | 2-(5-(2-(2-aminopyrimidin-5-yl)-4-morpholinothieno[3,2-d]pyrimidin-6-yl)pyridin-2-ylamino)propan-1-ol |

TABLE 1-continued

| Compound | Structure | Name |
|---|---|---|
| 348 | 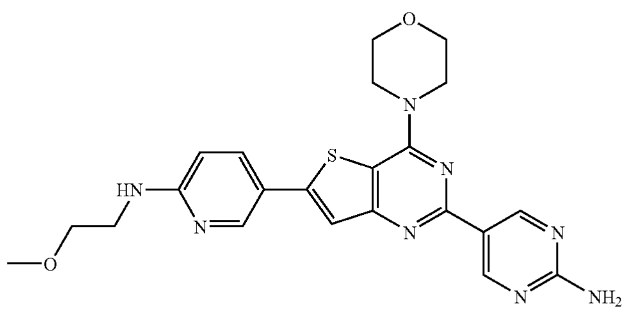 [SMILES: COCCNc1ccc(-c2cc3nc(-c4cnc(N)nc4)nc(N4CCOCC4)c3s2)cn1] | 5-(6-(6-(2-methoxyethylamino)pyridin-3-yl)-4-morpholinothieno[3,2-d]pyrimidin-2-yl)pyrimidin-2-amine |
| 349 | 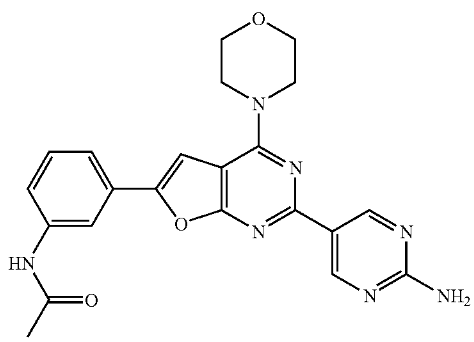 [SMILES: CC(=O)Nc1cccc(-c2cc3c(N4CCOCC4)nc(-c4cnc(N)nc4)nc3o2)c1] | N-(3-(2-(2-aminopyrimidin-5-yl)-4-morpholinofuro[2,3-d]pyrimidin-6-yl)phenyl)acetamide |
| 350 | 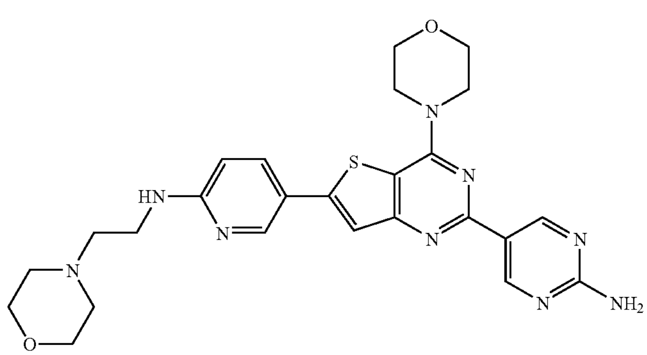 [SMILES: Nc1ncc(-c2nc(N3CCOCC3)c3sc(-c4ccc(NCCN5CCOCC5)nc4)cc3n2)cn1] | 5-(6-(6-(2-morpholinoethylamino)pyridin-3-yl)-4-morpholinothieno[3,2-d]pyrimidin-2-yl)pyrimidin-2-amine |
| 351 | 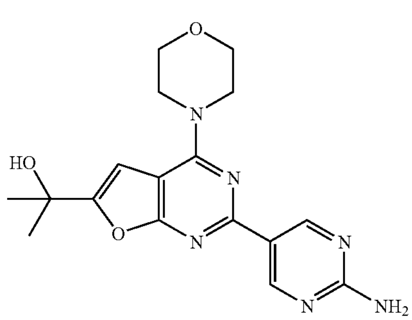 [SMILES: CC(C)(O)c1cc2c(N3CCOCC3)nc(-c3cnc(N)nc3)nc2o1] | 2-(2-(2-aminopyrimidin-5-yl)-4-morpholinofuro[2,3-d]pyrimidin-6-yl)propan-2-ol |

TABLE 1-continued

| Compound | Structure | Name |
|---|---|---|
| 352 | 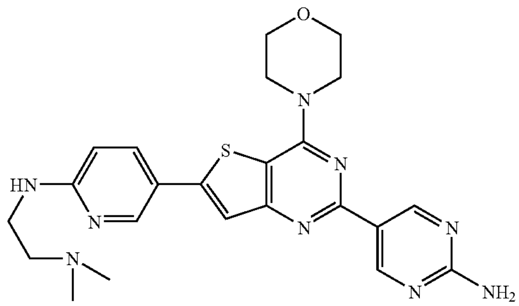 [SMILES: CN(C)CCNc1ccc(-c2cc3nc(-c4cnc(N)nc4)nc(N4CCOCC4)c3s2)cn1] | 5-(6-(6-(2-(dimethylamino)ethylamino)pyridin-3-yl)-4-morpholinothieno[3,2-d]pyrimidin-2-yl)pyrimidin-2-amine |
| 353 | 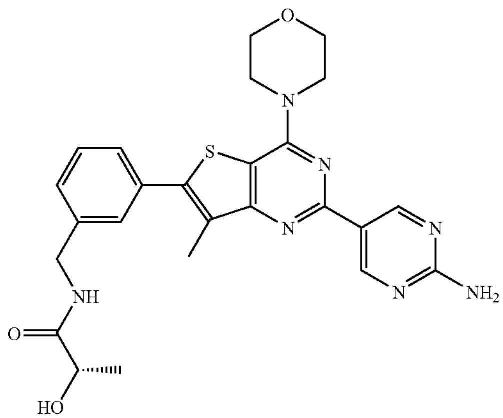 [SMILES: Cc1c(-c2cccc(CNC(=O)[C@H](C)O)c2)sc2c(N3CCOCC3)nc(-c3cnc(N)nc3)nc12] | (2S)-N-((3-(2-(2-aminopyrimidin-5-yl)-7-methyl-4-morpholinothieno[3,2-d]pyrimidin-6-yl)phenyl)methyl)-2-hydroxypropanamide |
| 354 | 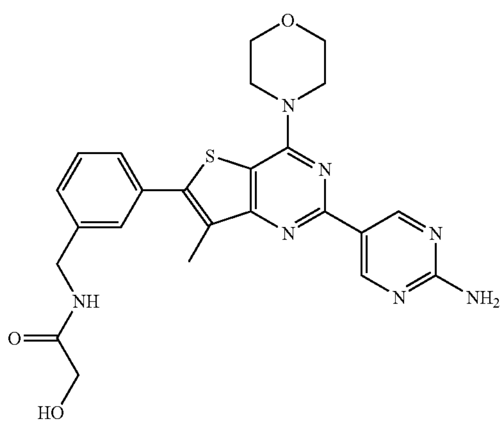 [SMILES: Cc1c(-c2cccc(CNC(=O)CO)c2)sc2c(N3CCOCC3)nc(-c3cnc(N)nc3)nc12] | N-((3-(2-(2-aminopyrimidin-5-yl)-7-methyl-4-morpholinothieno[3,2-d]pyrimidin-6-yl)phenyl)methyl)-2-hydroxyacetamide |
| 355 | 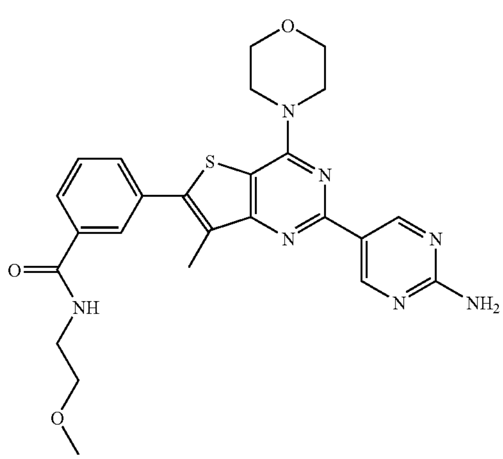 [SMILES: COCCNC(=O)c1cccc(-c2sc3c(N4CCOCC4)nc(-c4cnc(N)nc4)nc3c2C)c1] | 3-(2-(2-aminopyrimidin-5-yl)-7-methyl-4-morpholinothieno[3,2-d]pyrimidin-6-yl)-N-(2-methoxyethyl)benzamide |

TABLE 1-continued

| Compound | Structure | Name |
|---|---|---|
| 356 | 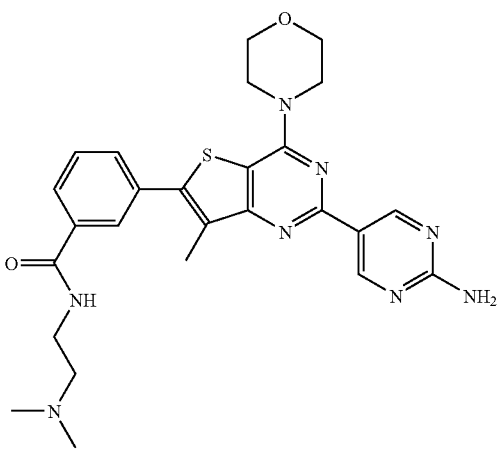 [SMILES: Cc1c(-c2cccc(C(=O)NCCN(C)C)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)-N-(2-(dimethylamino)ethyl)benzamide |
| 357 | 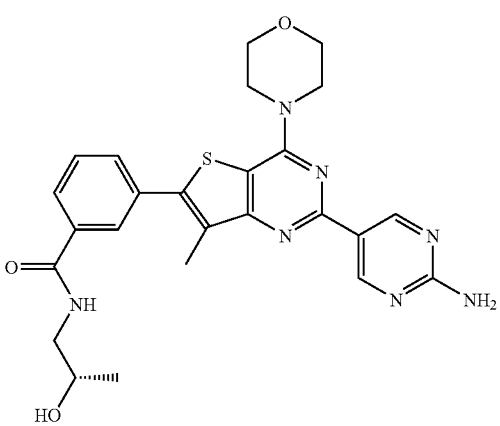 [SMILES: Cc1c(-c2cccc(C(=O)NC[C@H](C)O)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)-N-((S)-2-hydroxypropyl)benzamide |
| 358 | 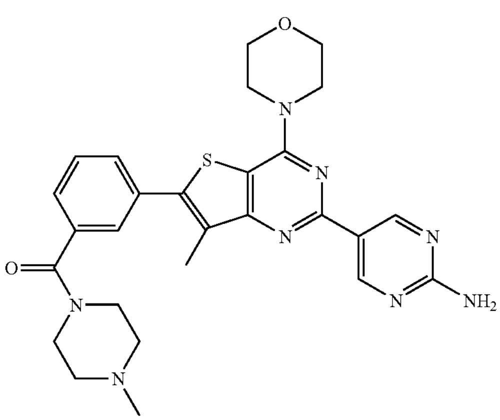 [SMILES: Cc1c(-c2cccc(C(=O)N3CCN(C)CC3)c2)sc2c(N3CCOCC3)nc(-c3cnc(N)nc3)nc12] | (3-(2-(2-aminopyrimidin-5-yl)-7-methyl-4-morpholinothieno[3,2-d]pyrimidin-6-yl)phenyl)(4-methylpiperazin-1-yl)methanone |

TABLE 1-continued

| Compound | Structure | Name |
|---|---|---|
| 359 | 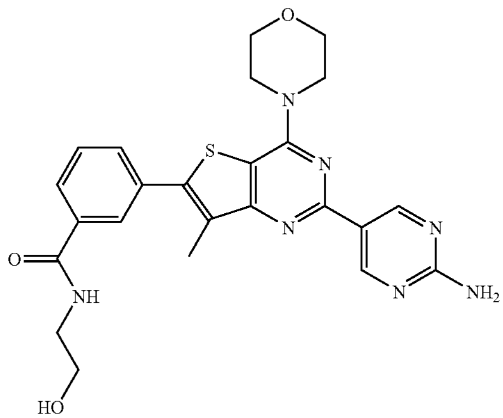 [SMILES: Cc1c(-c2cccc(C(=O)NCCO)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)-N-(2-hydroxyethyl)benzamide |
| 360 | 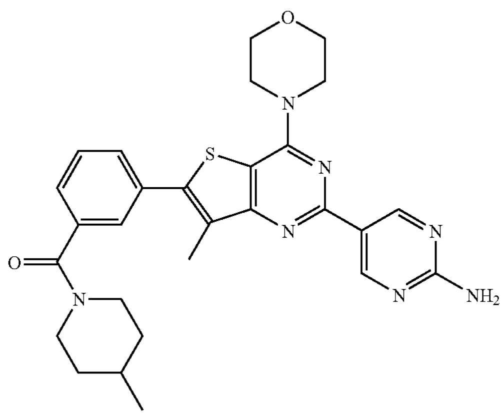 | (3-(2-(2-aminopyrimidin-5-yl)-7-methyl-4-morpholinothieno[3,2-d]pyrimidin-6-yl)phenyl)(4-hydroxypiperidin-1-yl)methanone |
| 361 | 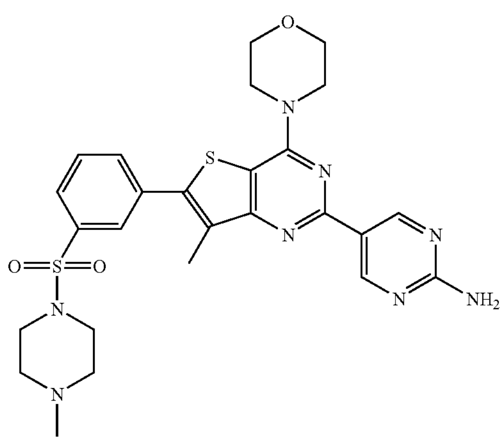 [SMILES: Cc1c(-c2cccc(S(=O)(=O)N3CCN(C)CC3)c2)sc2c(N3CCOCC3)nc(-c3cnc(N)nc3)nc12] | 5-(7-methyl-4-morpholino-6-(3-(4-methylpiperaziunylsulfonyl))phenyl-thieno[3,2-d]pyrimidin-2-yl)pyrimidin-2-amine |
| 362 | 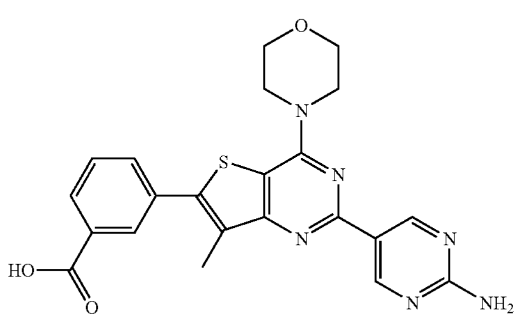 [SMILES: Cc1c(-c2cccc(C(=O)O)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)benzaoic acid |

TABLE 1-continued

| Compound | Structure | Name |
|---|---|---|
| 363 | 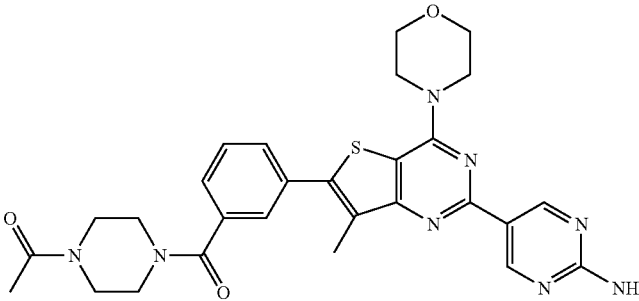 | (3-(2-(2-aminopyrimidin-5-yl)-7-methyl-4-morpholinothieno[3,2-d]pyrimidin-6-yl)phenyl)(4-acetylpiperazin-1-yl)methanone |
| 364 | 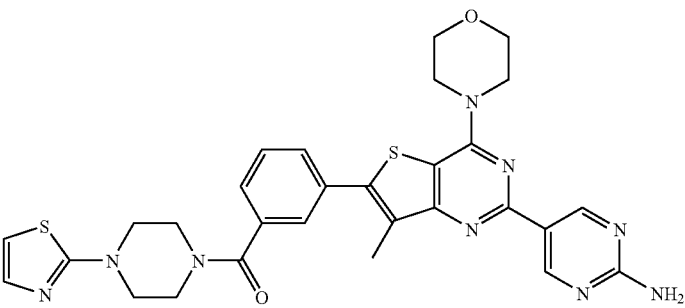 [SMILES: Cc1c(-c2cccc(C(=O)N3CCN(c4nccs4)CC3)c2)sc2c(N3CCOCC3)nc(-c3cnc(N)nc3)nc12] | (3-(2-(2-aminopyrimidin-5-yl)-7-methyl-4-morpholinothieno[3,2-d]pyrimidin-6-yl)phenyl)(4-(thiazol-2-yl)piperazin-1-yl)methanone |
| 365 | 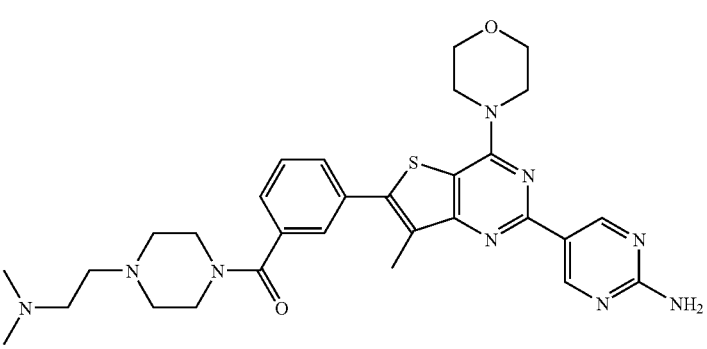 [SMILES: Cc1c(-c2cccc(C(=O)N3CCN(CCN(C)C)CC3)c2)sc2c(N3CCOCC3)nc(-c3cnc(N)nc3)nc12] | (3-(2-(2-aminopyrimidin-5-yl)-7-methyl-4-morpholinothieno[3,2-d]pyrimidin-6-yl)phenyl)(4-(2-(dimethylamino)ethyl)piperazin-1-yl)methanone |
| 366 | 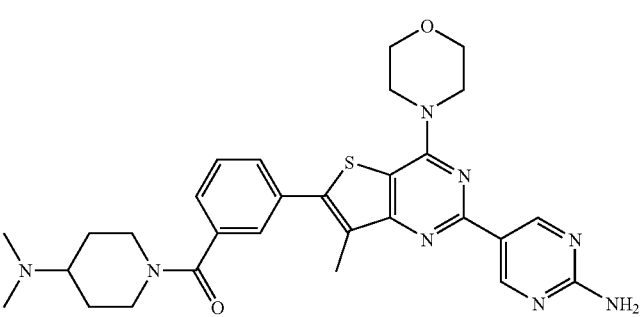 [SMILES: Cc1c(-c2cccc(C(=O)N3CCC(N(C)C)CC3)c2)sc2c(N3CCOCC3)nc(-c3cnc(N)nc3)nc12] | (3-(2-(2-aminopyrimidin-5-yl)-7-methyl-4-morpholinothieno[3,2-d]pyrimidin-6-yl)phenyl)(4-(dimethylamino)piperidin-1-yl)methanone |
| 367 | 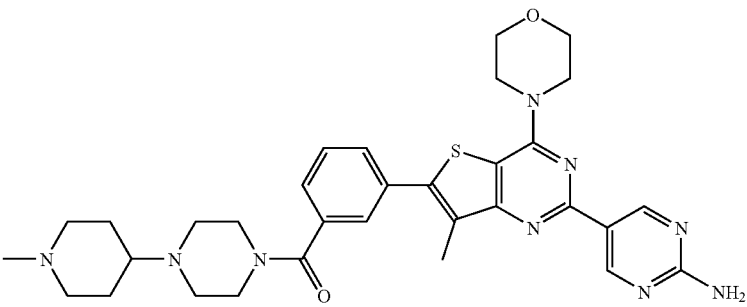 [SMILES: Cc1c(-c2cccc(C(=O)N3CCN(C4CCN(C)CC4)CC3)c2)sc2c(N3CCOCC3)nc(-c3cnc(N)nc3)nc12] | (3-(2-(2-aminopyrimidin-5-yl)-7-methyl-4-morpholinothieno[3,2-d]pyrimidin-6-yl)phenyl)(4-(1-methylpiperidin-4-yl)piperazin-1-yl)methanone |

TABLE 1-continued

| Compound | Structure | Name |
|---|---|---|
| 368 | 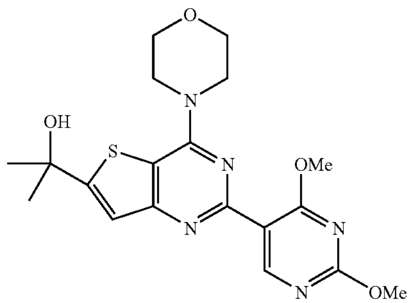 [SMILES: COc1ncc(-c2nc(N3CCOCC3)c3sc(C(C)(C)O)cc3n2)c(OC)n1] | 2-(2-(2,4-dimethoxypyrimidin-5-yl)-4-morpholinothieno[3,2-d]pyrimidin-6-yl)propan-2-ol |
| 369 | 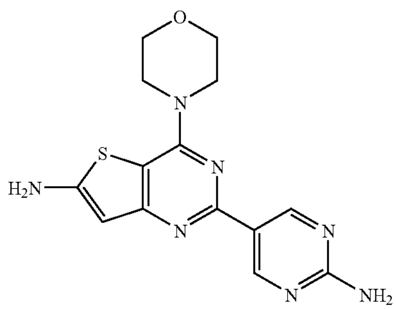 [SMILES: Nc1ncc(-c2nc(N3CCOCC3)c3sc(N)cc3n2)cn1] | 2-(2-aminopyrimidin-5-yl)-4-morpholinothieno[3,2-d]pyrimidin-6-amine |
| 370 | 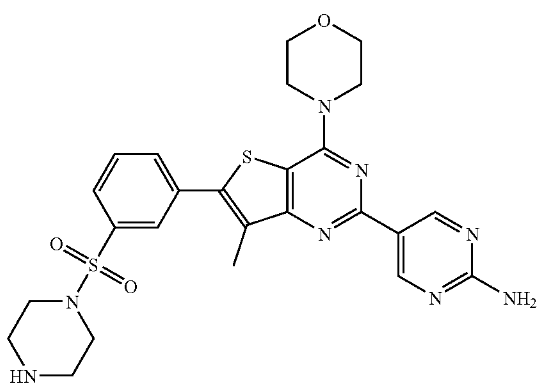 [SMILES: Cc1c(-c2cccc(S(=O)(=O)N3CCNCC3)c2)sc2c(N3CCOCC3)nc(-c3cnc(N)nc3)nc12] | 5-(7-methyl-4-morpholino-6-(3-piperazinylsulfonyl)phenylthieno[3,2-d]pyrimidin-2-yl)pyrimidin-2-amine |
| 371 | 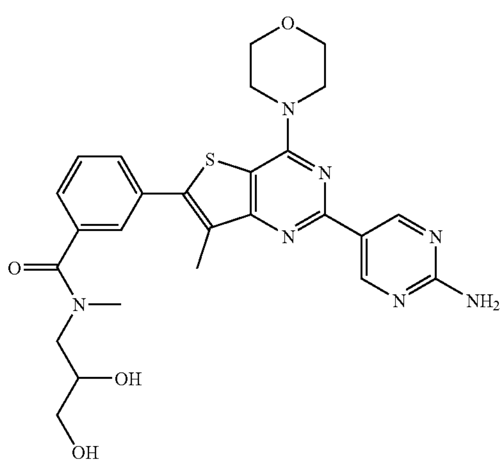 [SMILES: Cc1c(-c2cccc(C(=O)N(C)CC(O)CO)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)-N-(2,3-dihydroxypropyl)-N-methylbenzamide |

TABLE 1-continued

| Compound | Structure | Name |
|---|---|---|
| 372 | 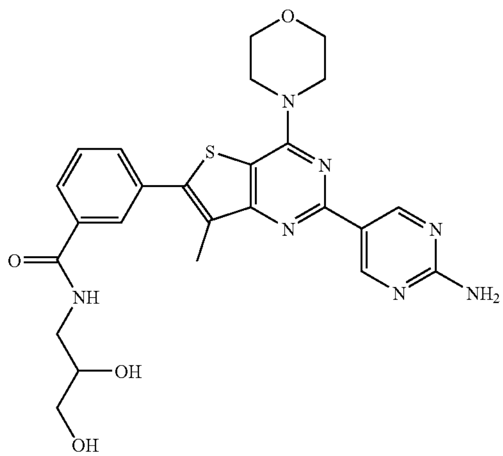 [SMILES: Cc1c(-c2cccc(C(=O)NCC(O)CO)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)-N-(2,3-dihydroxypropyl)benzamide |
| 373 | 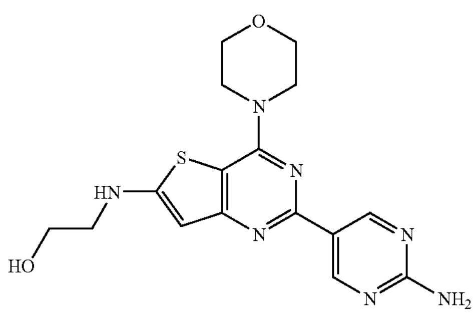 [SMILES: Nc1ncc(-c2nc(N3CCOCC3)c3sc(NCCO)cc3n2)cn1] | 2-(2-(2-aminopyrimidin-5-yl)-4-morpholinothieno[3,2-d]pyrimidin-6-ylamino)ethanol |
| 374 | 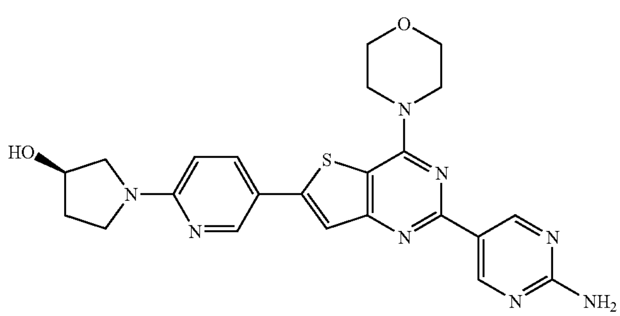 [SMILES: Nc1ncc(-c2nc(N3CCOCC3)c3sc(-c4ccc(N5CC[C@@H](O)C5)nc4)cc3n2)cn1] | (R)-1-(5-(2-(2-aminopyrimidin-5-yl)-4-morpholinothieno[3,2-d]pyrimidin-6-yl)pyridin-2-yl)pyrolidin-3-ol |
| 375 | 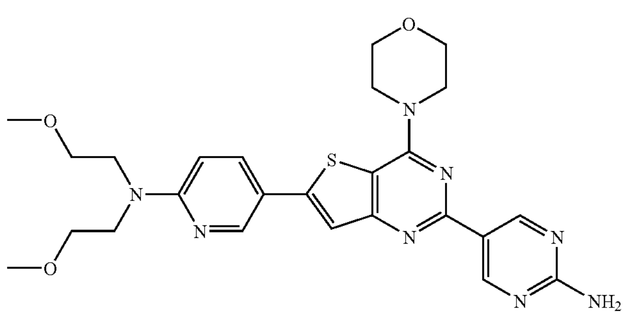 [SMILES: COCCN(CCOC)c1ccc(-c2cc3nc(-c4cnc(N)nc4)nc(N4CCOCC4)c3s2)cn1] | 5-(6-(6-(bis(2-methoxyethyl)amino)pyridin-3-yl)-4-morpholinothieno[3,2-d]pyrimidin-2-yl)pyrimidin-2-amine |

TABLE 1-continued

| Compound | Structure | Name |
|---|---|---|
| 376 | 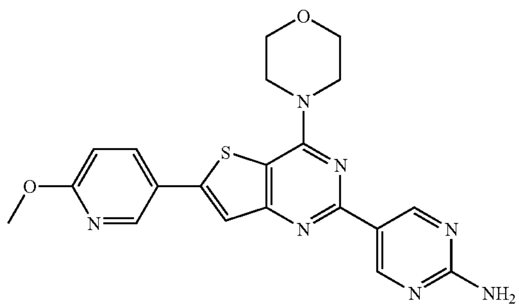 [SMILES: COc1ccc(-c2cc3nc(-c4cnc(N)nc4)nc(N4CCOCC4)c3s2)cn1] | 5-(6-(6-methoxypyridin-3-yl)-4-morpholinothieno[3,2-d]pyrimidin-2-yl)pyrimidin-2-amine |
| 377 | 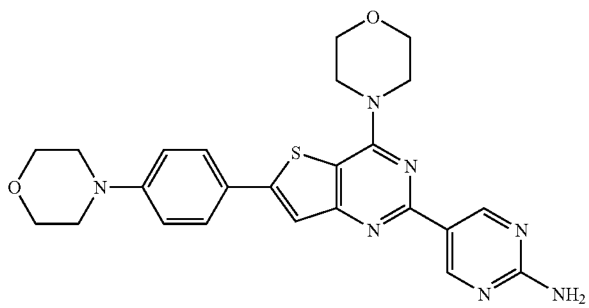 | 5-(4-morpholino-6-(4-morpholinophenyl)thieno[3,2-d]pyrimidin-2-yl)pyrimidin-2-amine |
| 378 | 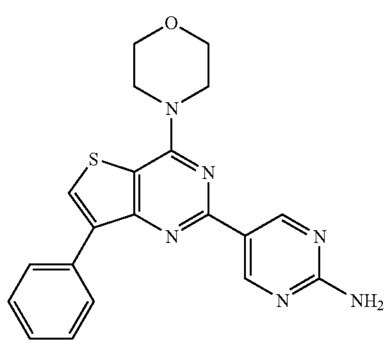 [SMILES: Nc1ncc(-c2nc(N3CCOCC3)c3scc(-c4ccccc4)c3n2)cn1] | 5-(4-morpholino-7-phenylthieno[3,2-d]pyrimidin-2-yl)pyrimidin-2-amine |
| 379 | 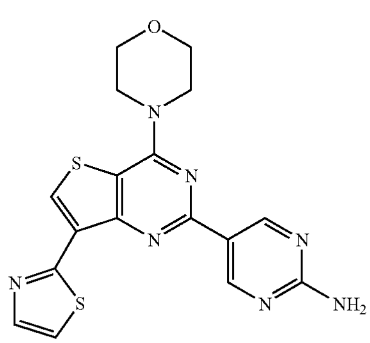 [SMILES: Nc1ncc(-c2nc(N3CCOCC3)c3scc(-c4nccs4)c3n2)cn1] | 5-(4-morpholino-7-(thiazol-2-yl)thieno[3,2-d]pyrimidin-2-yl)pyrimidin-2-amine |

TABLE 1-continued

| Compound | Structure | Name |
|---|---|---|
| 380 | 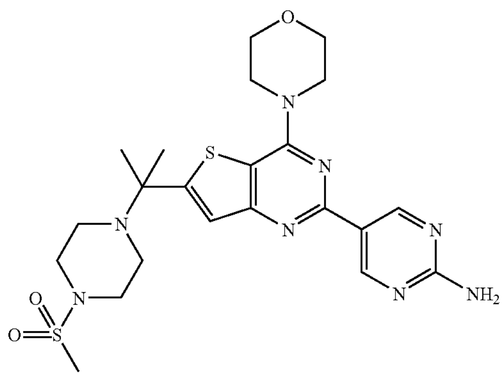 [SMILES: CC(C)(c1cc2nc(-c3cnc(N)nc3)nc(N3CCOCC3)c2s1)N1CCN(S(C)(=O)=O)CC1] | 5-(4-morpholino-6-(2-(4-N-methylsulfonylpiperazin-1-yl)propan-2-yl)thieno[3,2-d]pyrimidin-2-yl)pyrimidin-2-amine |
| 381 | 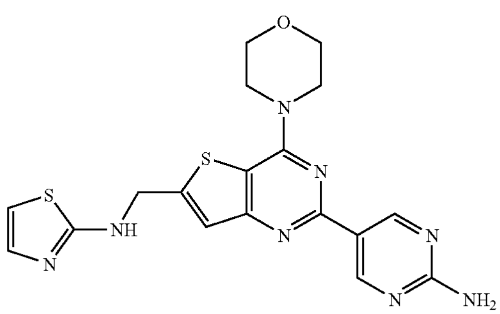 [SMILES: Nc1ncc(-c2nc(N3CCOCC3)c3sc(CNc4nccs4)cc3n2)cn1] | N-((2-(2-aminopyrimidin-5-yl)-4-morpholinothieno[3,2-d]pyrimidin-6-yl)methyl)thiazol-2-amine |
| 382 | | |
| 383 | | |
| 384 | 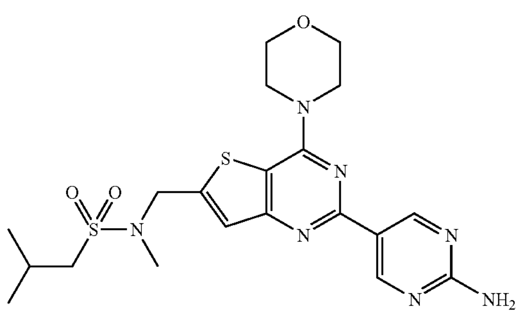 [SMILES: CC(C)CS(=O)(=O)N(C)Cc1cc2nc(-c3cnc(N)nc3)nc(N3CCOCC3)c2s1] | 5-(6-((N-issobutylsulfonyl,N-methylamino)methyl)-4-morpholinothieno[3,2-d]pyrimidin-2-yl)pyrimidin-2-amine |
| 385 | 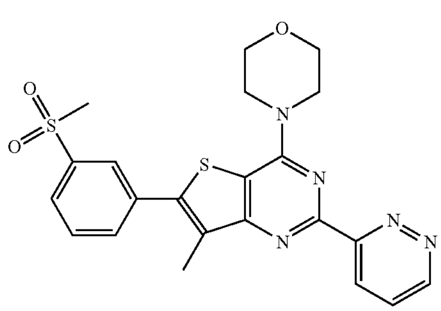 [SMILES: Cc1c(-c2cccc(S(C)(=O)=O)c2)sc2c(N3CCOCC3)nc(-c3cccnn3)nc12] | 7-methyl-6-(3-(methylsulfonyl)phenyl)-4-morpholino-2-(pyrazin-3-yl)thieno[3,2-d]pyrimidine |

TABLE 1-continued

| Compound | Structure | Name |
|---|---|---|
| 386 | 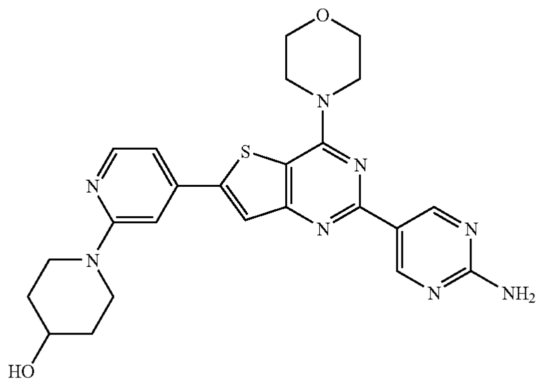 [SMILES: Nc1ncc(-c2nc(N3CCOCC3)c3sc(-c4ccnc(N5CCC(O)CC5)c4)cc3n2)cn1] | 1-(4-(2-(2-aminopyrimidin-5-yl)-4-morpholinothieno[3,2-d]pyrimidin-6-yl)pyridin-2-yl)piperidine-4-ol |
| 387 | 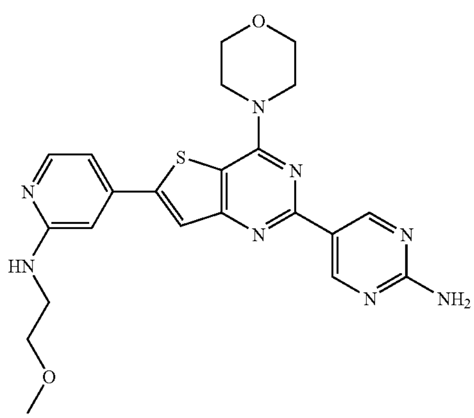 [SMILES: COCCNc1cc(-c2cc3nc(-c4cnc(N)nc4)nc(N4CCOCC4)c3s2)ccn1] | 5-(6-(2-(2-methoxyethylamino)pyridin-4-yl)-4-morpholinothieno[3,2-d]pyrimidin-2-yl)pyrimidin-2-amine |
| 388 | 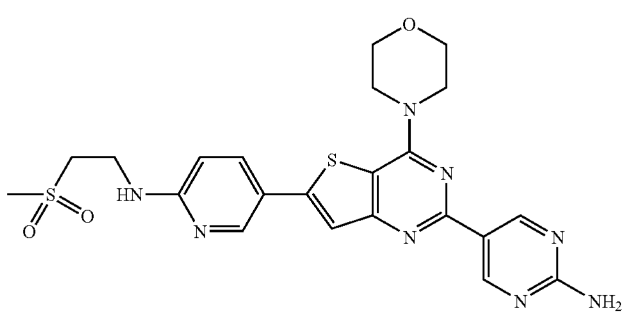 [SMILES: CS(=O)(=O)CCNc1ccc(-c2cc3nc(-c4cnc(N)nc4)nc(N4CCOCC4)c3s2)cn1] | 5-(6-(6-(2-(methylsulfonyl)ethylamino)pyridin-3-yl)-4-morpholinothieno[3,2-d]pyrimidin-2-yl)pyrimidin-2-amine |
| 389 | 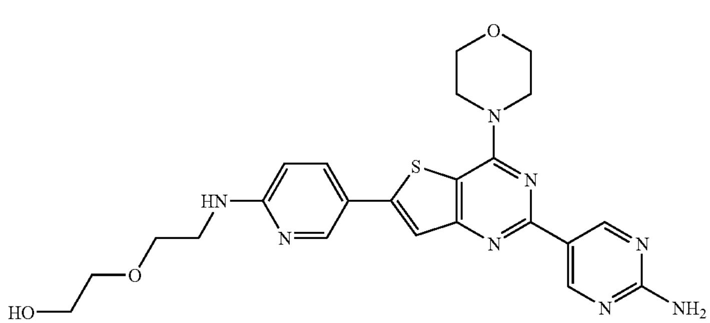 [SMILES: Nc1ncc(-c2nc(N3CCOCC3)c3sc(-c4ccc(NCCOCCO)nc4)cc3n2)cn1] | 5-(6-(6-(2-(2-hydroxyethyl)oxyethylamino)pyridin-3-yl)-4-morpholinothieno[3,2-d]pyrimidin-2-yl)pyrimidin-2-amine |

TABLE 1-continued

| Compound | Structure | Name |
|---|---|---|
| 390 | 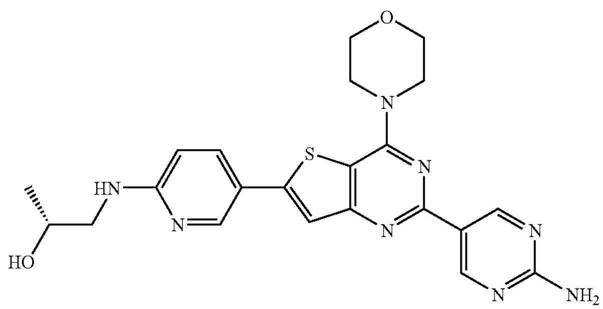 [SMILES: C[C@@H](O)CNc1ccc(-c2cc3nc(-c4cnc(N)nc4)nc(N4CCOCC4)c3s2)cn1] | (R)-1-(5-(2-(2-aminopyrimidin-5-yl)-4-morpholinothieno[3,2-d]pyrimidin-6-yl)pyridin-2-ylmaino)propan-2-ol |
| 391 | 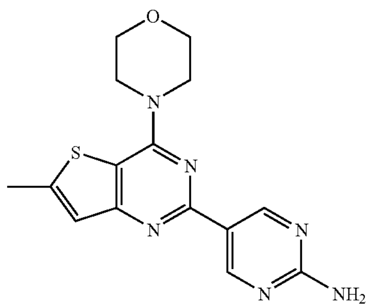 [SMILES: Cc1cc2nc(-c3cnc(N)nc3)nc(N3CCOCC3)c2s1] | 5-(6-mthyl-4-morpholinothieno[3,2-d]pyrimidin-2-yl)pyrimidin-2-amine |
| 392 | 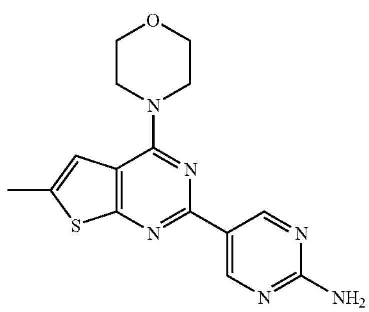 [SMILES: Cc1cc2c(N3CCOCC3)nc(-c3cnc(N)nc3)nc2s1] | 5-(6-methyl-4-morpholinothieno[2,3-d]pyrimidin-2-yl)pyrimidin-2-amine |
| 393 | 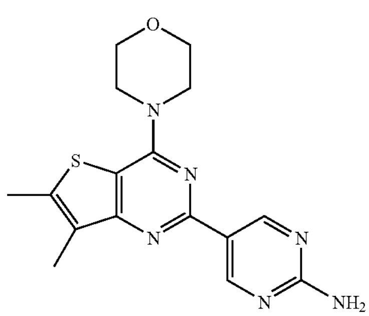 [SMILES: Cc1sc2c(N3CCOCC3)nc(-c3cnc(N)nc3)nc2c1C] | 5-(6,7-dimethyl-4-morpholinothieno[3,2-d]pyrimidin-2-yl)pyrimidin-2-amine |
| 394 | 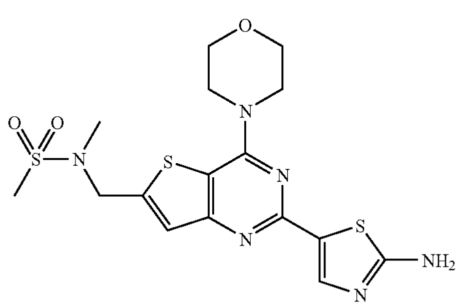 [SMILES: CN(Cc1cc2nc(-c3cnc(N)s3)nc(N3CCOCC3)c2s1)S(C)(=O)=O] | 5-(6-((N-methylsulfonyl,N-methylamino)methyl)-4-morpholinothieno[3,2-d]pyrimidin-2-yl)thiazol-2-amine |

TABLE 1-continued

| Compound | Structure | Name |
|---|---|---|
| 395 | 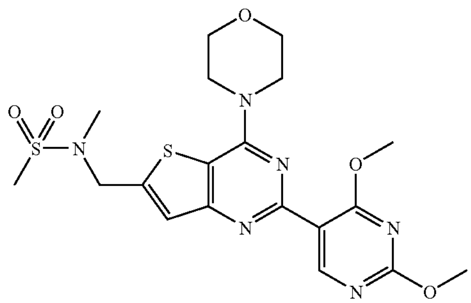 | (2-(2,4-dimethoxypyrimidin-5-yl)-4-morpholinothieno[3,2-d]pyrimidin-6-yl)-N-methyl,N-methylsulfonylmethanamine |
| 396 | 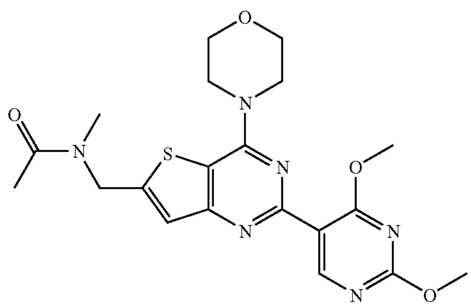 [SMILES: COc1ncc(-c2nc(N3CCOCC3)c3sc(CN(C)C(C)=O)cc3n2)c(OC)n1] | N-((2-(2,4-dimethoxypyrimidin-5-yl)-4-morpholinothieno[3,2-d]pyrimidin-6-yl)methyl)-N-methylacetamide |
| 397 | 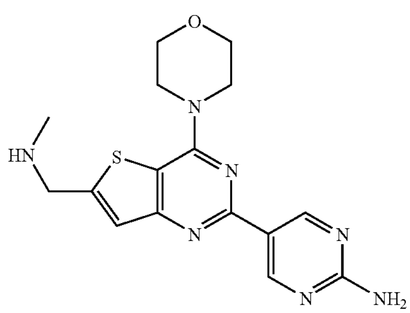 [SMILES: CNCc1cc2nc(-c3cnc(N)nc3)nc(N3CCOCC3)c2s1] | 5-(6-((methylamino)methyl)-4-morpholinothieno[3,2-d]pyrimidin-2-yl)pyrimidin-2-amine |

TABLE 2

| Example | Structure | Name |
|---|---|---|
| 398 | 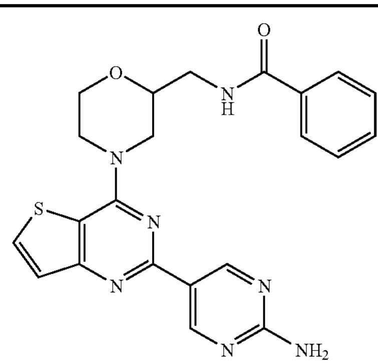 | N-((4-(2-(2-aminopyrimidin-5-yl)thieno[3,2-d]pyrimidin-4-yl)morpholin-2-yl)methyl)benzamide |

TABLE 2-continued

| Example | Structure | Name |
| --- | --- | --- |
| 399 | 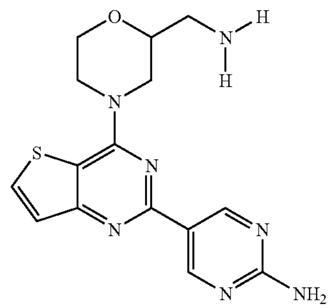 [SMILES: NCC1CN(c2nc(-c3cnc(N)nc3)nc3ccsc23)CCO1] | 5-(4-(2-(aminomethyl)morpholino)thieno[3,2-d]pyrimidin-2-yl)pyrimidin-2-amine |
| 400 | 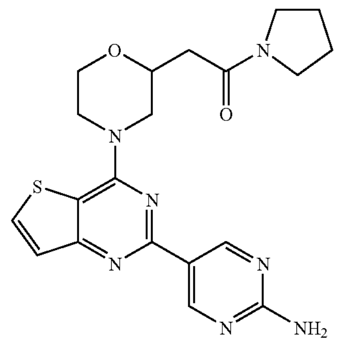 [SMILES: Nc1ncc(-c2nc(N3CCOC(CC(=O)N4CCCC4)C3)c3sccc3n2)cn1] | 2-(4-(2-(2-aminopyrimidin-5-yl)thieno[3,2-d]pyrimidin-4-yl)morpholin-2-yl)-1-(pyrrolidin-1-yl)ethanone |
| 401 | 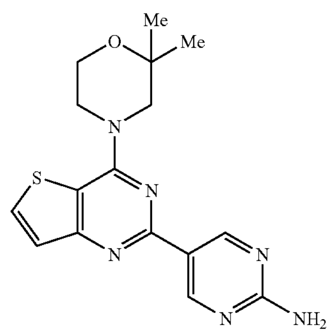 [SMILES: CC1(C)CN(c2nc(-c3cnc(N)nc3)nc3ccsc23)CCO1] | 5-(4-(2,2-dimethylmorpholino)thieno[3,2-d]pyrimidin-2-yl)pyrimidin-2-amine |
| 402 | 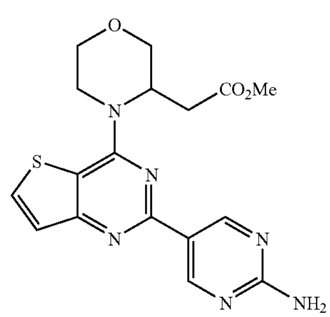 [SMILES: COC(=O)CC1COCCN1c1nc(-c2cnc(N)nc2)nc2ccsc12] | methyl 2-(4-(2-(2-aminopyrimidin-5-yl)thieno[3,2-d]pyrimidin-4-yl)morpholin-3-yl)acetate |
| 403 | 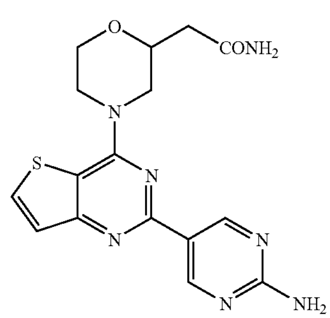 [SMILES: NC(=O)CC1CN(c2nc(-c3cnc(N)nc3)nc3ccsc23)CCO1] | 2-(4-(2-(2-aminopyrimidin-5-yl)thieno[3,2-d]pyrimidin-4-yl)morpholin-2-yl)acetamide |

TABLE 2-continued

| Example | Structure | Name |
|---|---|---|
| 404 | 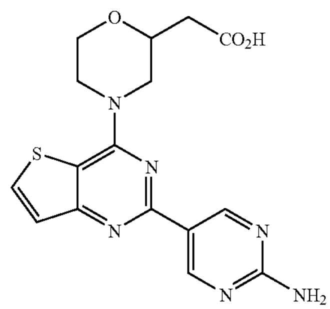 [SMILES: Nc1ncc(-c2nc(N3CCOC(CC(=O)O)C3)c3sccc3n2)cn1] | 2-(4-(2-(2-aminopyrimidin-5-yl)thieno[3,2-d]pyrimidin-4-yl)morpholin-2-yl)acetic acid |
| 405 | 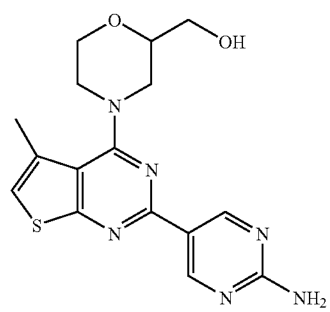 [SMILES: Cc1csc2nc(-c3cnc(N)nc3)nc(N3CCOC(CO)C3)c12] | (4-(2-(2-aminopyrimidin-5-yl)-5-methylthieno[2,3-d]pyrimidin-4-yl)morpholin-2-yl)methanol |
| 406 | 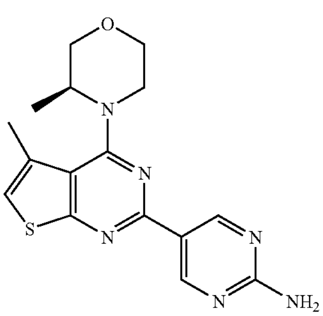 [SMILES: Cc1csc2nc(-c3cnc(N)nc3)nc(N3CCOC[C@@H]3C)c12] | (S)-5-(5-methyl-4-(3-methylmorpholino)thieno[2,3-d]pyrimidin-2-yl)pyrimidin-2-amine |
| 407 | 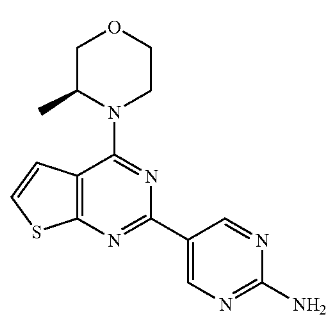 | (S)-5-(4-methylmorpholino)thieno[2,3-d]pyrimidin-2-yl)pyrimidin-2-amine |

TABLE 2-continued

| Example | Structure | Name |
|---|---|---|
| 408 | 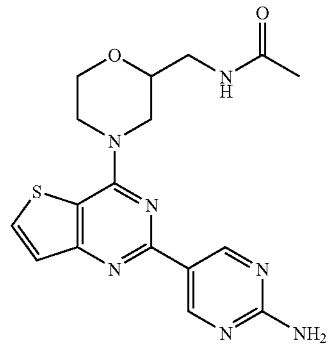 [SMILES: CC(=O)NCC1CN(c2nc(-c3cnc(N)nc3)nc3ccsc23)CCO1] | N-((4-(2-(2-aminopyrimidin-5-yl)thieno[3,2-d]pyrimidin-4-yl)morpholin-2-yl)methyl)acetamide |
| 409 | 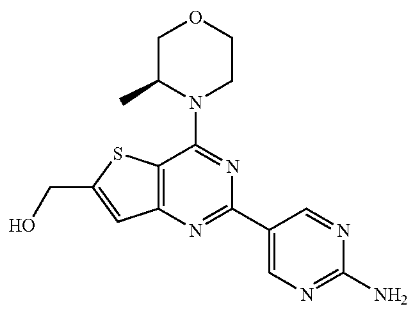 [SMILES: C[C@H]1COCCN1c1nc(-c2cnc(N)nc2)nc2cc(CO)sc12] | (S)-(2-(2-aminopyrimidin-5-yl)-4-(3-methylmorpholino)thieno[3,2-d]pyrimidin-6-yl)methanol |
| 410 | 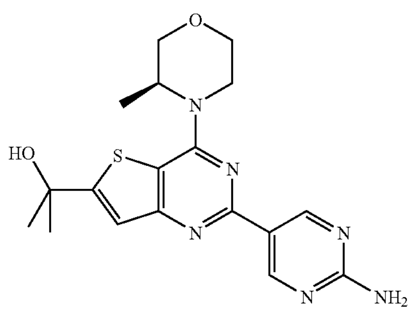 [SMILES: C[C@H]1COCCN1c1nc(-c2cnc(N)nc2)nc2cc(C(C)(C)O)sc12] | (S)-2-(2-(2-aminopyrimidin-5-yl)-4-(3-methylmorpholino)thieno[3,2-d]pyrimidin-6-yl)propan-2-ol |
| 411 | 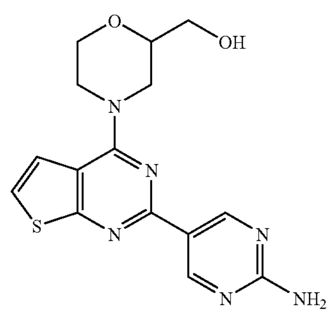 [SMILES: Nc1ncc(-c2nc(N3CCOC(CO)C3)c3ccsc3n2)cn1] | (4-(2-(2-aminopyrimidin-5-yl)thieno[2,3-d]pyrimidin-4-yl)morpholin-2-yl)methanol |
| 412 | 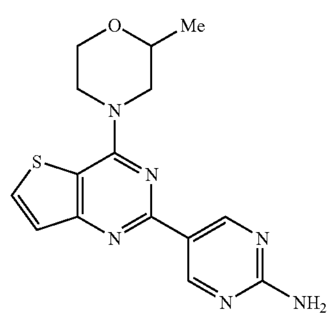 [SMILES: CC1CN(c2nc(-c3cnc(N)nc3)nc3ccsc23)CCO1] | 5-(4-(2-methylmorpholino)thieno[3,2-d]pyrimidin-2-yl)pyrimidin-2-amine |

TABLE 2-continued

| Example | Structure | Name |
| --- | --- | --- |
| 413 | 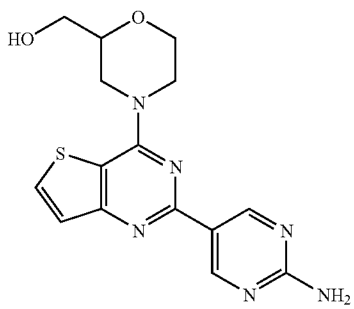 [SMILES: Nc1ncc(-c2nc(N3CCOC(CO)C3)c3sccc3n2)cn1] | (4-(2-(2-aminopyrimidin-5-yl)thieno[3,2-d]pyrimidin-4-yl)morpholin-2-yl)methanol |
| 414 | 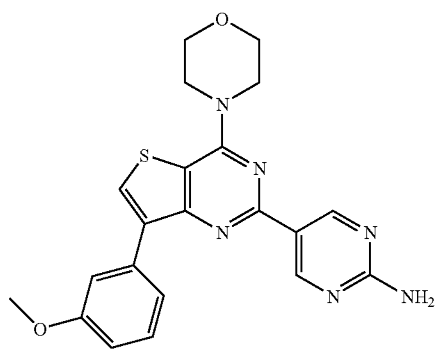 [SMILES: COc1cccc(-c2csc3c(N4CCOCC4)nc(-c4cnc(N)nc4)nc23)c1] | 5-(7-(3-methoxyphenyl)-4-morpholinothieno[3,2-d]pyrimidin-2-yl)pyrimidin-2-amine |
| 415 | 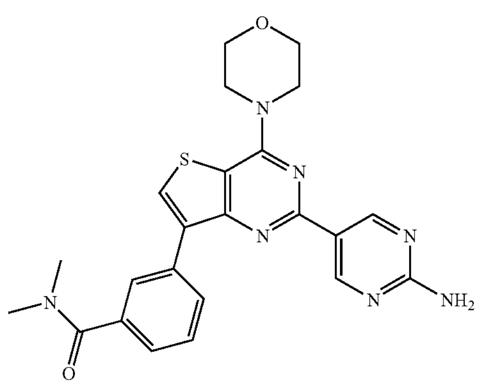 [SMILES: CN(C)C(=O)c1cccc(-c2csc3c(N4CCOCC4)nc(-c4cnc(N)nc4)nc23)c1] | 3-(2-(2-aminopyrimidin-5-yl)-4-morpholinothieno[3,2-d]pyrimidin-7-yl)-N,N-dimethylbenzamide |
| 416 | 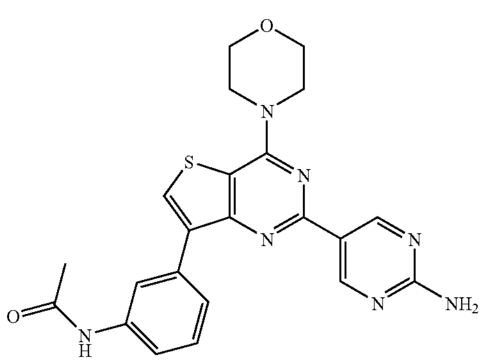 [SMILES: CC(=O)Nc1cccc(-c2csc3c(N4CCOCC4)nc(-c4cnc(N)nc4)nc23)c1] | N-(3-(2-(2-aminopyrimidin-5-yl)-4-morpholinothieno[3,2-d]pyrimidin-7-yl)phenyl)acetamide |

TABLE 2-continued

| Example | Structure | Name |
|---|---|---|
| 417 | 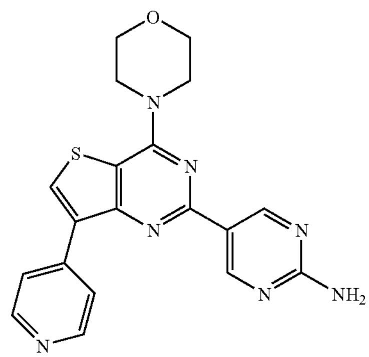 [SMILES: Nc1ncc(-c2nc(N3CCOCC3)c3scc(-c4ccncc4)c3n2)cn1] | 5-(4-morpholino-7-(pyridin-4-yl)thieno[3,2-d]pyrimidin-2-yl)pyrimidin-2-amine |
| 418 | 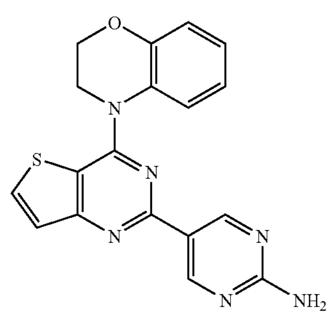 [SMILES: Nc1ncc(-c2nc(N3CCOc4ccccc43)c3sccc3n2)cn1] | 5-(4-(2H-benzo[b][1,4]oxazin-4(3H)-yl)thieno[3,2-d]pyrimidin-2-yl)pyrimidin-2-amine |
| 419 | 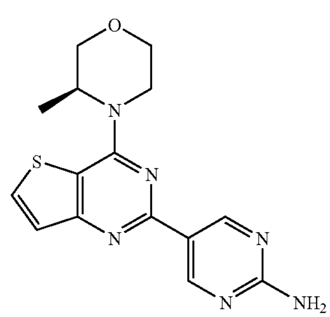 [SMILES: C[C@H]1COCCN1c1nc(-c2cnc(N)nc2)nc2ccsc12] | (S)-5-(4-(3-methylmorpholino)thieno[3,2-d]pyrimidin-2-yl)pyrimidin-2-amine |
| 420 | 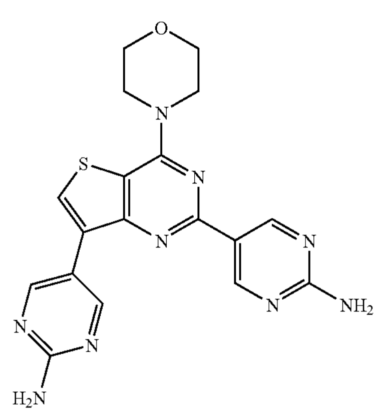 [SMILES: Nc1ncc(-c2nc(N3CCOCC3)c3scc(-c4cnc(N)nc4)c3n2)cn1] | 5,5'-(4-morpholinothieno[3,2-d]pyrimidine-2,7-diyl)dipyrimidin-2-amine |

TABLE 2-continued

| Example | Structure | Name |
| --- | --- | --- |
| 421 | 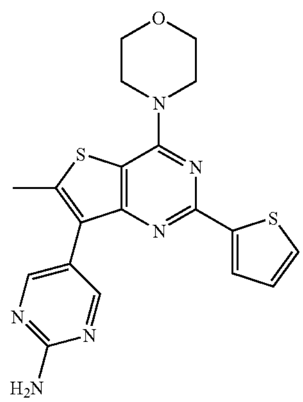 [SMILES: Cc1sc2c(N3CCOCC3)nc(-c3cccs3)nc2c1-c1cnc(N)nc1] | 5-(6-methyl-4-morpholino-2-(thiophen-2-yl)thieno[3,2-d]pyrimidin-7-yl)pyrimidin-2-amine |
| 422 | 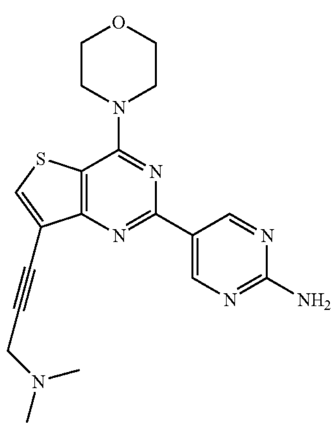 [SMILES: CN(C)CC#Cc1csc2c(N3CCOCC3)nc(-c3cnc(N)nc3)nc12] | 5-(7-(3-(dimethylamino)prop-1-ynyl)-4-morpholinothieno[3,2-d]pyrimidin-2-yl)pyrimidin-2-amine |
| 423 | 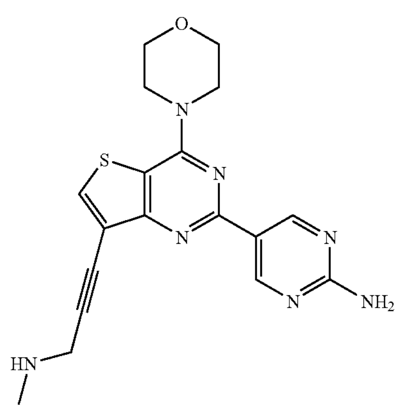 [SMILES: CNCC#Cc1csc2c(N3CCOCC3)nc(-c3cnc(N)nc3)nc12] | 5-(7-(3-(methylamino)prop-1-ynyl)-4-morpholinothieno[3,2-d]pyrimidin-2-yl)pyrimidin-2-amine |
| 424 | 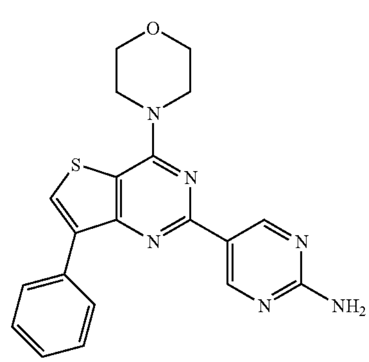 [SMILES: Nc1ncc(-c2nc(N3CCOCC3)c3scc(-c4ccccc4)c3n2)cn1] | 5-(4-morpholino-7-phenylthieno[3,2-d]pyrimidin-2-yl)pyrimidin-2-amine |

TABLE 2-continued

| Example | Structure | Name |
|---|---|---|
| 425 | 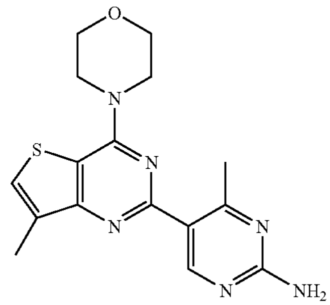 [SMILES: Cc1nc(N)ncc1-c1nc(N2CCOCC2)c2scc(C)c2n1] | 4-methyl-5-(7-methyl-4-morpholinothieno[3,2-d]pyrimidin-2-yl)pyrimidin-2-amine |
| 426 | 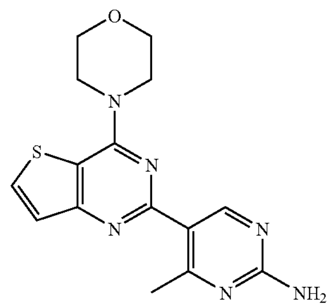 [SMILES: Cc1nc(N)ncc1-c1nc(N2CCOCC2)c2sccc2n1] | 4-methyl-5-(4-morpholinothieno[3,2-d]pyrimidin-2-yl)pyrimidin-2-amine |
| 427 | 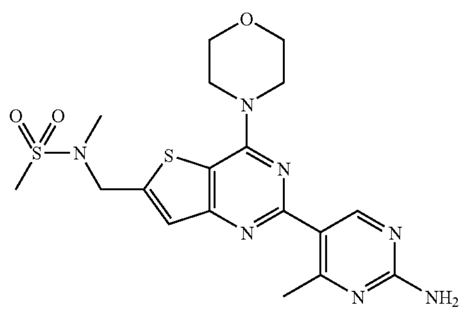 [SMILES: Cc1nc(N)ncc1-c1nc(N2CCOCC2)c2sc(CN(C)S(C)(=O)=O)cc2n1] | N-((2-(2-amino-4-methylpyrimidin-5-yl)-4-morpholinothieno[3,2-d]pyrimidin-6-yl)methyl)-N-methylmethanesulfonamide |
| 428 | 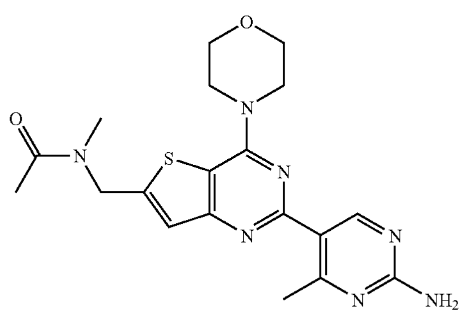 [SMILES: CC(=O)N(C)Cc1cc2nc(-c3cnc(N)nc3C)nc(N3CCOCC3)c2s1] | N-((2-(2-amino-4-methylpyrimidin-5-yl)-4-morpholinothieno[3,2-d]pyrimidin-6-yl)methyl)-N-methylacetamide |
| 429 | 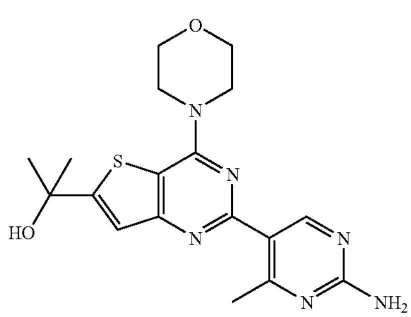 [SMILES: Cc1nc(N)ncc1-c1nc(N2CCOCC2)c2sc(C(C)(C)O)cc2n1] | 2-(2-(2-amino-4-methylpyrimidin-5-yl)-4-morpholinothieno[3,2-d]pyrimidin-6-yl)propan-2-ol |

TABLE 2-continued

| Example | Structure | Name |
|---|---|---|
| 430 | 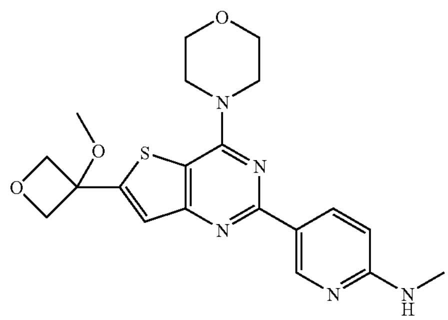 [SMILES: CNc1ccc(-c2nc(N3CCOCC3)c3sc(C4(OC)COC4)cc3n2)cn1] | 5-(6-(3-methoxyoxetan-3-yl)-4-morpholinothieno[3,2-d]pyrimidin-2-yl)-N-methylpyridin-2-amine |
| 431 | 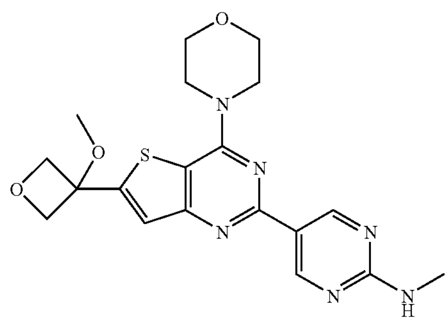 | 5-(6-(3-methoxyoxetan-3-yl)-4-morpholinothieno[3,2-d]pyrimidin-2-yl)-N-methylpyrimidin-2-amine |
| 432 | 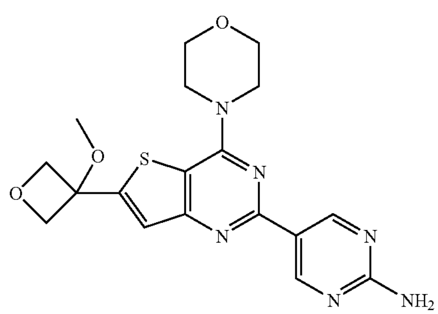 [SMILES: COC1(c2cc3nc(-c4cnc(N)nc4)nc(N4CCOCC4)c3s2)COC1] | 5-(6-(3-methoxyoxetan-3-yl)-4-morpholinothieno[3,2-d]pyrimidin-2-yl)pyrimidin-2-amine |
| 433 | 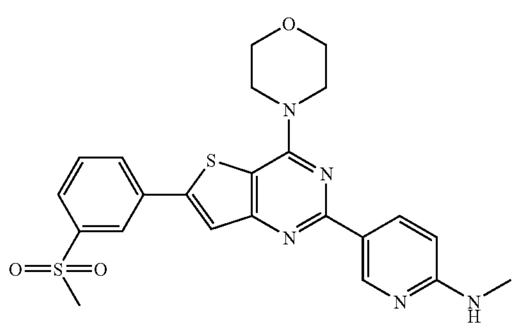 | N-methyl-5-(6-(3-(methylsulfonyl)phenyl)-4-morpholinothieno[3,2-d]pyrimidin-2-yl)pyridin-2-amine |
| 434 | 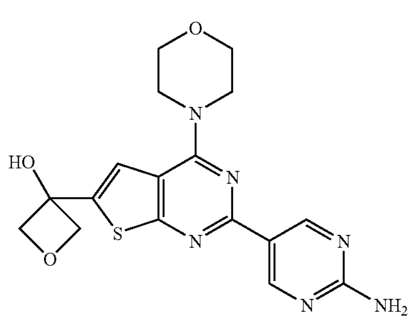 [SMILES: Nc1ncc(-c2nc(N3CCOCC3)c3cc(C4(O)COC4)sc3n2)cn1] | 3-(2-(2-aminopyrimidin-5-yl)-4-morpholinothieno[2,3-d]pyrimidin-6-yl)oxetan-3-ol |

TABLE 2-continued

| Example | Structure | Name |
|---|---|---|
| 435 | 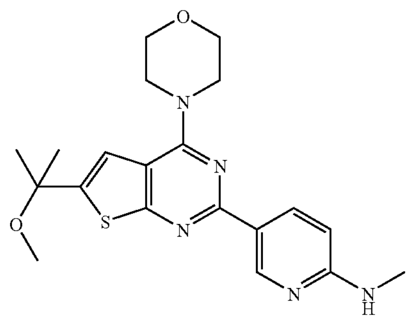 [SMILES: CNc1ccc(-c2nc(N3CCOCC3)c3cc(C(C)(C)OC)sc3n2)cn1] | 5-(6-(2-methoxypropan-2-yl)-4-morpholinothieno[2,3-d]pyrimidin-2-yl)-N-methylpyridin-2-amine |
| 436 | 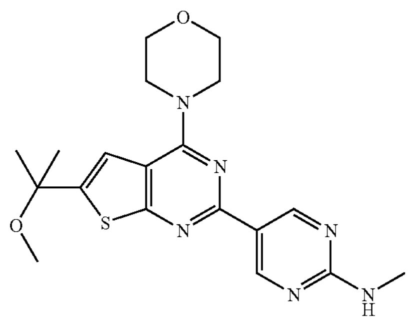 [SMILES: CNc1ncc(-c2nc(N3CCOCC3)c3cc(C(C)(C)OC)sc3n2)cn1] | 5-(6-(2-methoxypropan-2-yl)-4-morpholinothieno[2,3-d]pyrimidin-2-yl)-N-methylpyrimidin-2-amine |
| 437 | 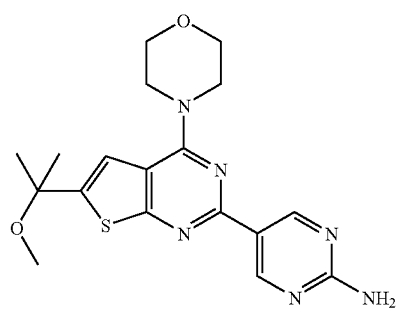 [SMILES: COC(C)(C)c1cc2c(N3CCOCC3)nc(-c3cnc(N)nc3)nc2s1] | 5-(6-(2-methoxypropan-2-yl)-4-morpholinothieno[2,3-d]pyrimidin-2-yl)pyrimidin-2-amine |
| 438 | 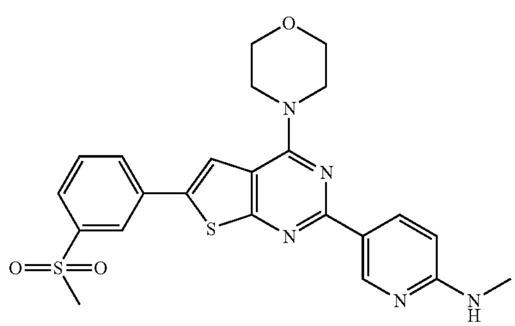 [SMILES: CNc1ccc(-c2nc(N3CCOCC3)c3cc(-c4cccc(S(C)(=O)=O)c4)sc3n2)cn1] | N-methyl-5-(6-(3-(methylsulfonyl)phenyl)-4-morpholinothieno[2,3-d]pyrimidin-2-yl)pyridin-2-amine |
| 439 | 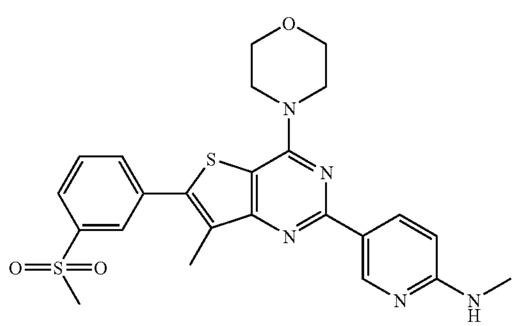 [SMILES: CNc1ccc(-c2nc(N3CCOCC3)c3sc(-c4cccc(S(C)(=O)=O)c4)c(C)c3n2)cn1] | N-methyl-5-(7-methyl-6-(3-(methylsulfonyl)phenyl)-4-morpholinothieno[3,2-d]pyrimidin-2-yl)pyridin-2-amine |

TABLE 2-continued

| Example | Structure | Name |
|---|---|---|
| 440 | 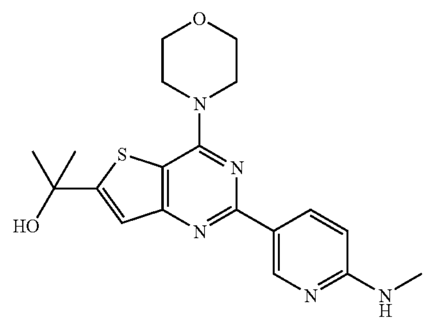 | 2-(2-(6-(methylamino)pyridin-3-yl)-4-morpholinothieno[3,2-d]pyrimidin-6-yl)propan-2-ol |
| 441 | 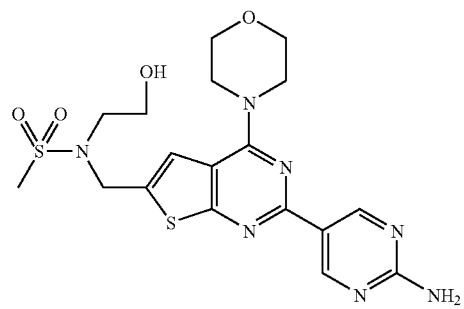 [SMILES: CS(=O)(=O)N(CCO)Cc1cc2c(N3CCOCC3)nc(-c3cnc(N)nc3)nc2s1] | N-((2-(2-aminopyrimidin-5-yl)-4-morpholinothieno[2,3-d]pyrimidin-6-yl)methyl)-N-(2-hydroxyethyl)methanesulfonamide |
| 442 | 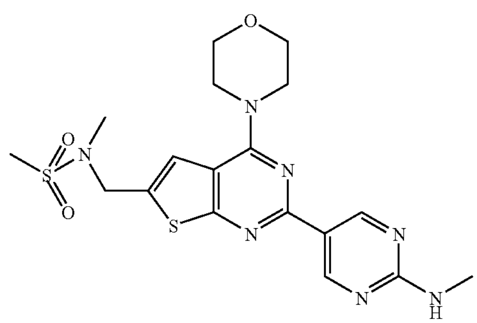 | N-methyl-N-((2-(2-(methylamino)pyrimidin-5-yl)-4-morpholinothieno[2,3-d]pyrimidin-6-yl)methyl)methanesulfonamide |
| 443 | 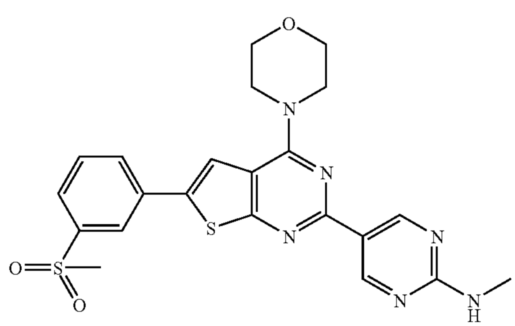 [SMILES: CNc1ncc(-c2nc(N3CCOCC3)c3cc(-c4cccc(S(C)(=O)=O)c4)sc3n2)cn1] | N-methyl-5-(6-(3-(methylsulfonyl)phenyl)-4-morpholinothieno[2,3-d]pyrimidin-2-yl)pyrimidin-2-amine |
| 444 | 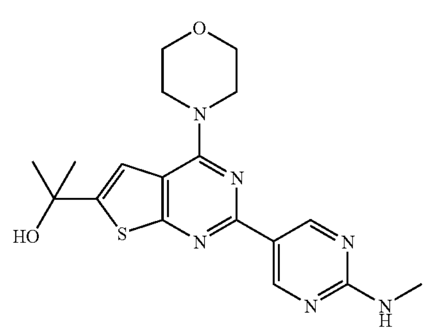 [SMILES: CNc1ncc(-c2nc(N3CCOCC3)c3cc(C(C)(C)O)sc3n2)cn1] | 2-(2-(2-(methylamino)pyrimidin-5-yl)-4-morpholinothieno[2,3-d]pyrimidin-6-yl)propan-2-ol |

TABLE 2-continued

| Example | Structure | Name |
|---|---|---|
| 445 | 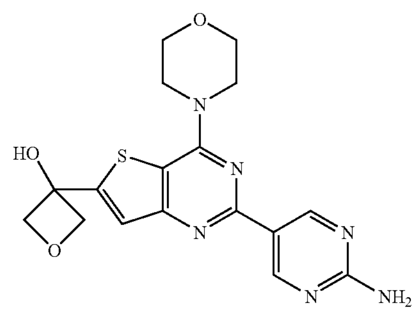 [SMILES: Nc1ncc(-c2nc(N3CCOCC3)c3sc(C4(O)COC4)cc3n2)cn1] | 3-(2-(2-aminopyrimidin-5-yl)-4-morpholinothieno[3,2-d]pyrimidin-6-yl)oxetan-3-ol |
| 446 | 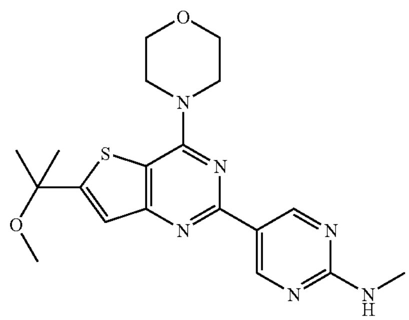 [SMILES: CNc1ncc(-c2nc(N3CCOCC3)c3sc(C(C)(C)OC)cc3n2)cn1] | 5-(6-(2-methoxypropan-2-yl)-4-morpholinothieno[3,2-d]pyrimidin-2-yl)-N-methylpyrimidin-2-amine |
| 447 | 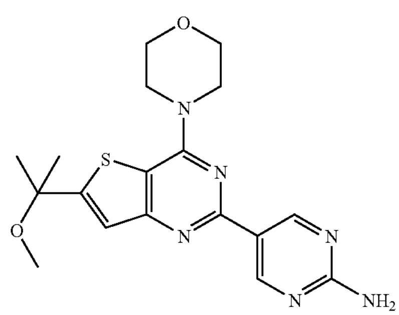 [SMILES: COC(C)(C)c1cc2nc(-c3cnc(N)nc3)nc(N3CCOCC3)c2s1] | 5-(6-(2-methoxypropan-2-yl)-4-morpholinothieno[3,2-d]pyrimidin-2-yl)pyrimidin-2-amine |
| 448 | 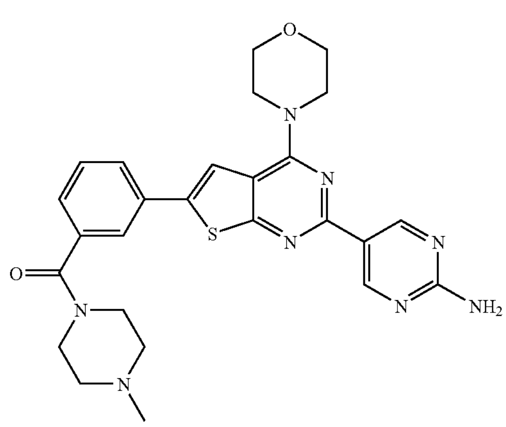 [SMILES: CN1CCN(C(=O)c2cccc(-c3cc4c(N5CCOCC5)nc(-c5cnc(N)nc5)nc4s3)c2)CC1] | (3-(2-(2-aminopyrimidin-5-yl)-4-morpholinothieno[2,3-d]pyrimidin-6-yl)phenyl)(4-methylpiperazin-1-yl)methanone |

TABLE 2-continued

| Example | Structure | Name |
|---|---|---|
| 449 | 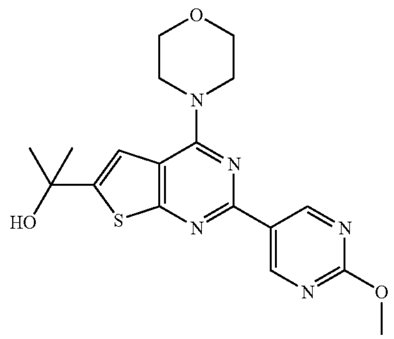 [SMILES: COc1ncc(-c2nc(N3CCOCC3)c3cc(C(C)(C)O)sc3n2)cn1] | 2-(2-(2-methoxypyrimidin-5-yl)-4-morpholinothieno[2,3-d]pyrimidin-6-yl)propan-2-ol |
| 450 | 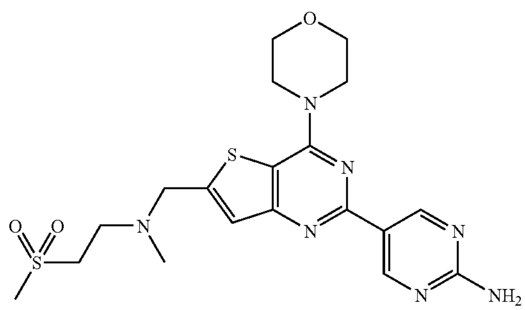 [SMILES: CN(CCS(C)(=O)=O)Cc1cc2nc(-c3cnc(N)nc3)nc(N3CCOCC3)c2s1] | 5-(6-((methyl(2-(methylsulfonyl)ethyl)amino)methyl)-4-morpholinothieno[3,2-d]pyrimidin-2-yl)pyrimidin-2-amine |
| 451 | 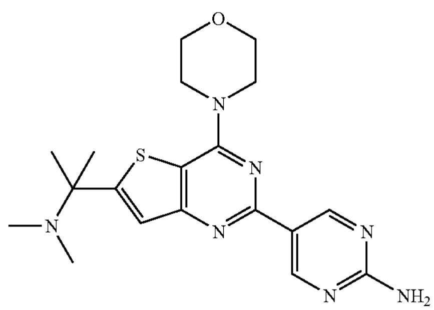 [SMILES: CN(C)C(C)(C)c1cc2nc(-c3cnc(N)nc3)nc(N3CCOCC3)c2s1] | 5-(6-(2-(dimethylamino)propan-2-yl)-4-morpholinothieno[3,2-d]pyrimidin-2-yl)pyrimidin-2-amine |
| 452 | 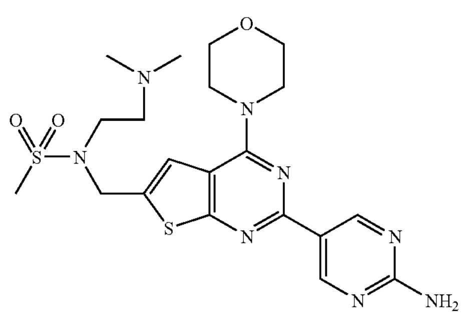 [SMILES: CN(C)CCN(Cc1cc2c(N3CCOCC3)nc(-c3cnc(N)nc3)nc2s1)S(C)(=O)=O] | N-((2-(2-aminopyrimidin-5-yl)-4-morpholinothieno[2,3-d]pyrimidin-6-yl)methyl)-N-(2-(dimethylamino)ethyl)methanesulfonamide |
| 453 | 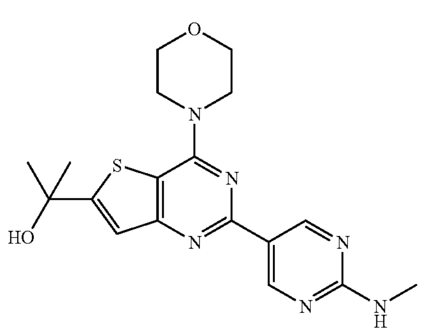 [SMILES: CNc1ncc(-c2nc(N3CCOCC3)c3sc(C(C)(C)O)cc3n2)cn1] | 2-(2-(2-(methylamino)pyrimidin-5-yl)-4-morpholinothieno[3,2-d]pyrimidin-6-yl)propan-2-ol |

TABLE 2-continued

| Example | Structure | Name |
|---|---|---|
| 454 | 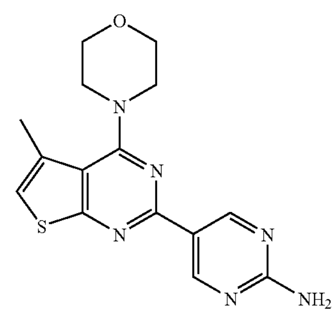 [SMILES: Cc1csc2nc(-c3cnc(N)nc3)nc(N3CCOCC3)c12] | 5-(5-methyl-4-morpholinothieno[2,3-d]pyrimidin-2-yl)pyrimidin-2-amine |
| 455 | 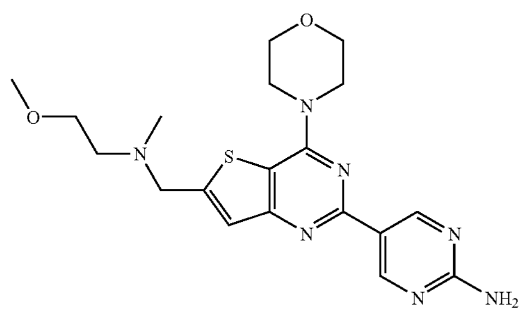 [SMILES: COCCN(C)Cc1cc2nc(-c3cnc(N)nc3)nc(N3CCOCC3)c2s1] | 5-(6-(((2-methoxyethyl)(methyl)amino)methyl)-4-morpholinothieno[3,2-d]pyrimidin-2-yl)pyrimidin-2-amine |
| 456 | 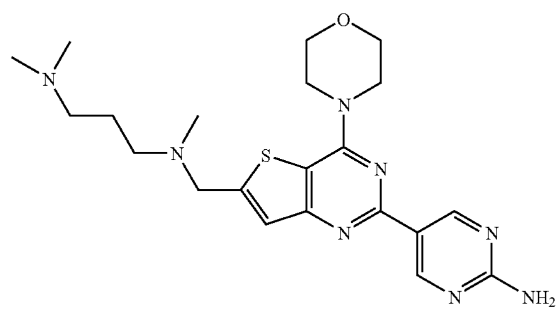 [SMILES: CN(C)CCCN(C)Cc1cc2nc(-c3cnc(N)nc3)nc(N3CCOCC3)c2s1] | N1-((2-(2-aminopyrimidin-5-yl)-4-morpholinothieno[3,2-d]pyrimidin-6-yl)methyl)-N1,N3,N3-trimethylpropane-1,3-diamine |
| 457 | 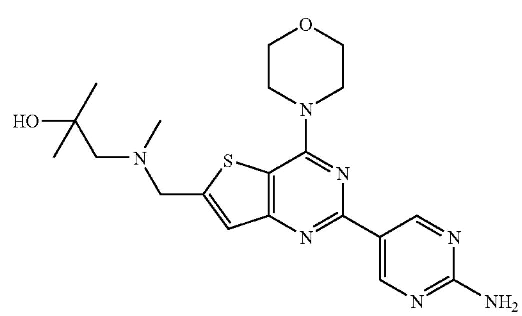 [SMILES: CN(Cc1cc2nc(-c3cnc(N)nc3)nc(N3CCOCC3)c2s1)CC(C)(C)O] | 1-(((2-(2-aminopyrimidin-6-yl)-4-morpholinothieno[3,2-d]pyrimidin-6-yl)methyl)(methyl)amino)-2-methylpropan-2-ol |
| 458 | 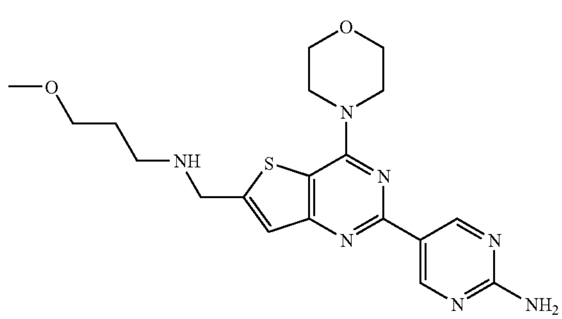 [SMILES: COCCCNCc1cc2nc(-c3cnc(N)nc3)nc(N3CCOCC3)c2s1] | 5-(6-((3-methoxypropylamino)methyl)-4-morpholinothieno[3,2-d]pyrimidin-2-yl)pyrimidin-2-amine |

TABLE 2-continued

| Example | Structure | Name |
|---|---|---|
| 459 | 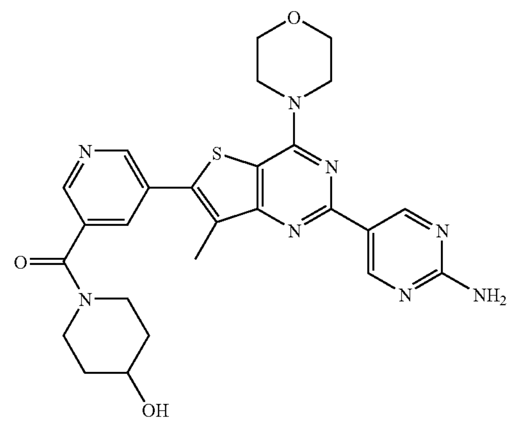 [SMILES: Cc1c(-c2cncc(C(=O)N3CCC(O)CC3)c2)sc2c(N3CCOCC3)nc(-c3cnc(N)nc3)nc12] | (5-(2-(2-aminopyrimidin-5-yl)-7-methyl-4-morpholinothieno[3,2-d]pyrimidin-6-yl)pyridin-3-yl)(4-hydroxypiperidin-1-yl)methanone |
| 460 | 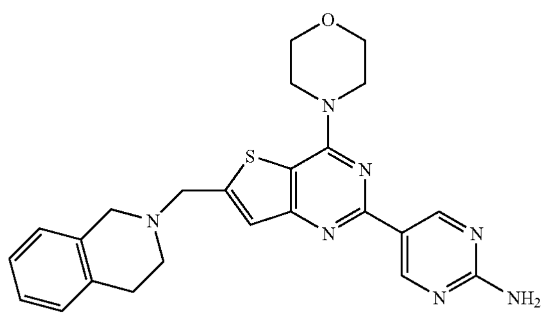 [SMILES: Nc1ncc(-c2nc(N3CCOCC3)c3sc(CN4CCc5ccccc5C4)cc3n2)cn1] | 5-(6-((3,4-dihydroisoquinolin-2(1H)-yl)methyl)-4-morpholinothieno[3,2-d]pyrimidin-2-yl)pyrimidin-2-amine |
| 461 | 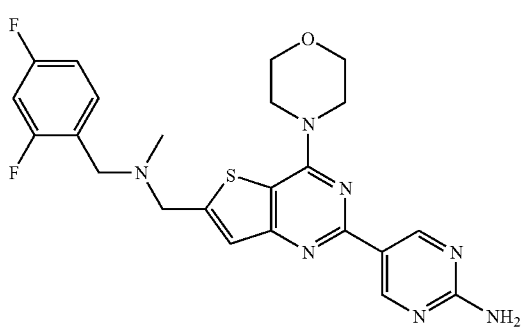 [SMILES: CN(Cc1cc2nc(-c3cnc(N)nc3)nc(N3CCOCC3)c2s1)Cc1ccc(F)cc1F] | 5-(6-(((2,4-difluorobenzyl)(methyl)amino)methyl)-4-morpholinothieno[3,2-d]pyrimidin-2-yl)pyrimidin-2-amine |
| 462 | 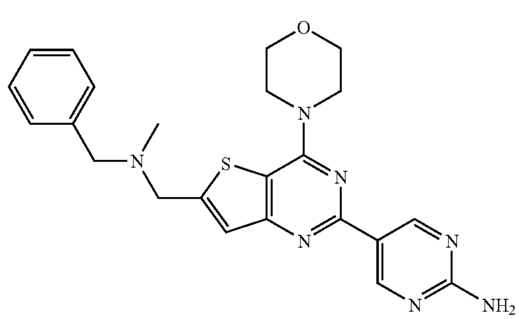 [SMILES: CN(Cc1ccccc1)Cc1cc2nc(-c3cnc(N)nc3)nc(N3CCOCC3)c2s1] | 5-(6-((benzyl(methyl)amino)methyl)-4-morpholinothieno[3,2-d]pyrimidin-2-yl)pyrimidin-2-amine |

TABLE 2-continued

| Example | Structure | Name |
|---|---|---|
| 463 | 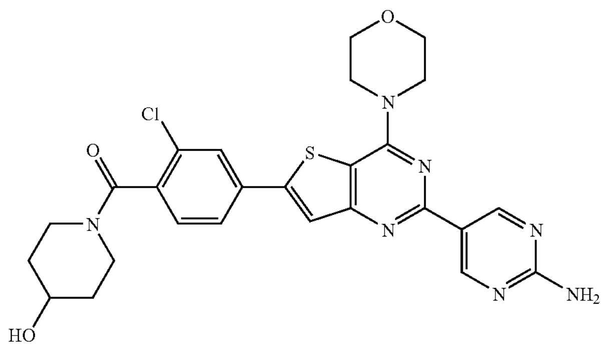 | (4-(2-(2-aminopyrimidin-5-yl)-4-morpholinothieno[3,2-d]pyrimidin-6-yl)-2-chlorophenyl)(4-hydroxypiperidin-1-yl)methanone |
| 464 | 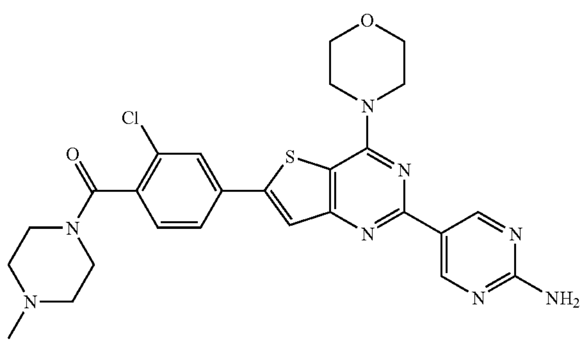 [SMILES: CN1CCN(C(=O)c2ccc(-c3cc4nc(-c5cnc(N)nc5)nc(N5CCOCC5)c4s3)cc2Cl)CC1] | (4-(2-(2-aminopyrimidin-5-yl)-4-morpholinothieno[3,2-d]pyrimidin-6-yl)-2-chlorophenyl)(4-methylpiperazin-1-yl)methanone |
| 465 | 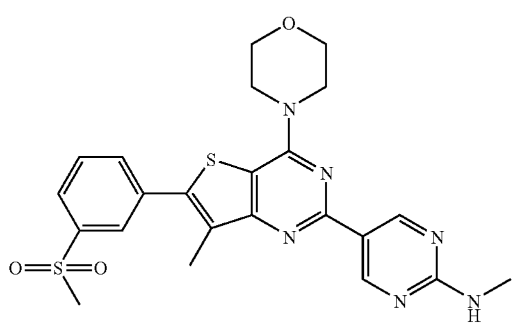 [SMILES: CNc1ncc(-c2nc(N3CCOCC3)c3sc(-c4cccc(S(C)(=O)=O)c4)c(C)c3n2)cn1] | N-methyl-5-(7-methyl-6-(3-(methylsulfonyl)phenyl)-4-morpholinothieno[3,2-d]pyrimidin-2-yl)pyrimidin-2-amine |
| 466 | 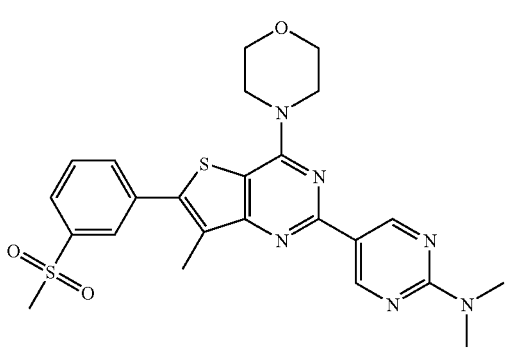 [SMILES: Cc1c(-c2cccc(S(C)(=O)=O)c2)sc2c(N3CCOCC3)nc(-c3cnc(N(C)C)nc3)nc12] | N,N-dimethyl-5-(7-methyl-6-(3-(methylsulfonyl)phenyl-4-morpholinothieno[3,2-d]pyrimidin-2-yl)pyrimidin-2-amine |

TABLE 2-continued

| Example | Structure | Name |
|---|---|---|
| 467 | 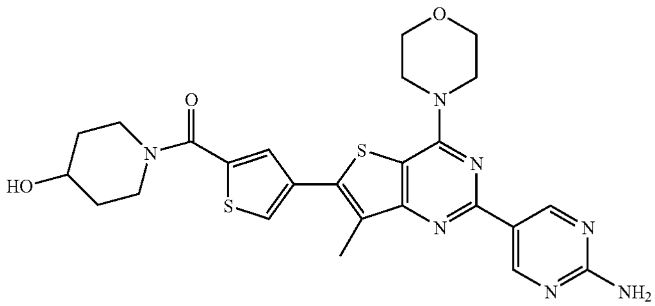 [SMILES: Cc1c(-c2csc(C(=O)N3CCC(O)CC3)c2)sc2c(N3CCOCC3)nc(-c3cnc(N)nc3)nc12] | (4-(2-(2-aminopyrimidin-5-yl)-7-methyl-4-morpholinothieno[3,2-d]pyrimidin-6-yl)thiophen-2-yl)(4-hydroxypiperidin-1-yl)methanone |
| 468 | 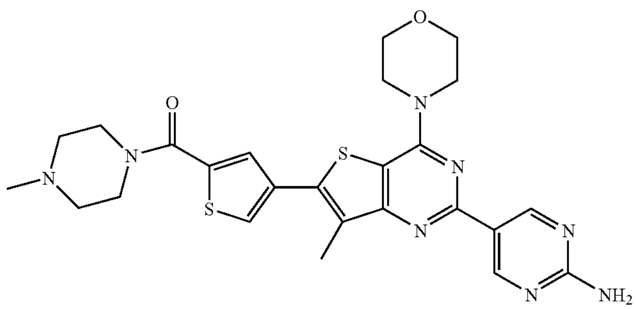 [SMILES: Cc1c(-c2csc(C(=O)N3CCN(C)CC3)c2)sc2c(N3CCOCC3)nc(-c3cnc(N)nc3)nc12] | (4-(2-(2-aminopyrimidin-5-yl)-7-methyl-4-morpholinothieno[3,2-d]pyrimidin-6-yl)thiophen-2-yl)(4-methylpiperazin-1-yl)methanone |
| 469 | 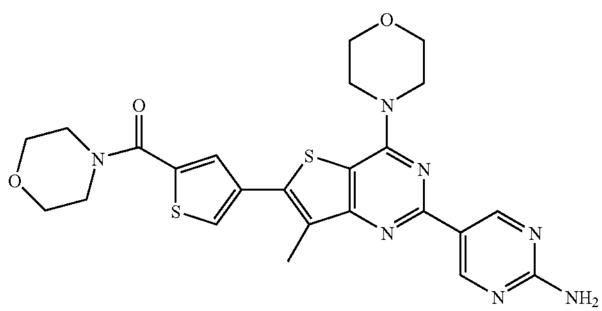 [SMILES: Cc1c(-c2csc(C(=O)N3CCOCC3)c2)sc2c(N3CCOCC3)nc(-c3cnc(N)nc3)nc12] | (4-(2-(2-aminopyrimidin-5-yl)-7-methyl-4-morpholinothieno[3,2-d]pyrimidin-6-yl)thiophen-2-yl)(morpholino)methanone |
| 470 | 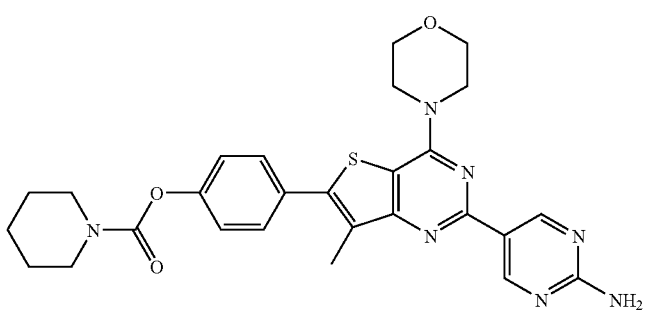 [SMILES: Cc1c(-c2ccc(OC(=O)N3CCCCC3)cc2)sc2c(N3CCOCC3)nc(-c3cnc(N)nc3)nc12] | 4-(2-(2-aminopyrimidin-5-yl)-7-methyl-4-morpholinothieno[3,2-d]pyrimidin-6-yl)phenyl piperidine-1-carboxylate |
| 471 | 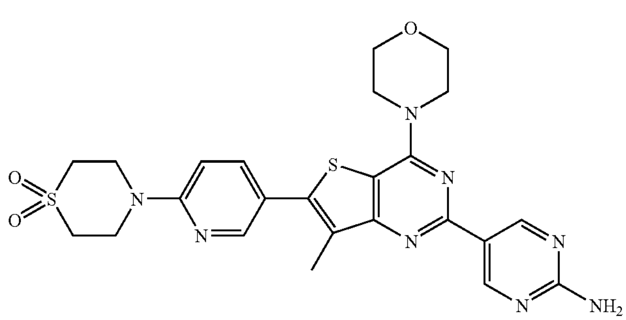 [SMILES: Cc1c(-c2ccc(N3CCS(=O)(=O)CC3)nc2)sc2c(N3CCOCC3)nc(-c3cnc(N)nc3)nc12] | 5-(7-methyl-4-morpholino-6-(6-(S,S-dioxo-thiomorpholino)pyridin-3-yl)thieno[3,2-d]pyrimidin-2-yl)pyrimidin-2-amine |

TABLE 2-continued

| Example | Structure | Name |
|---|---|---|
| 472 | 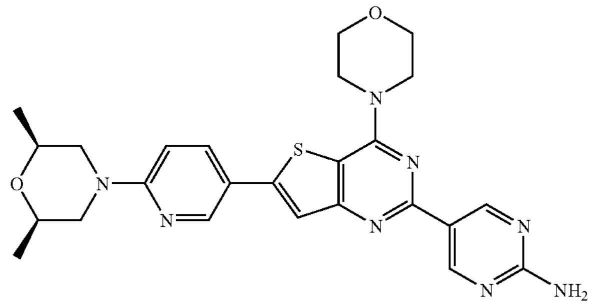 [SMILES: C[C@@H]1CN(c2ccc(-c3cc4nc(-c5cnc(N)nc5)nc(N5CCOCC5)c4s3)cn2)C[C@H](C)O1] | 5-(6-(6-((2S,6R)-2,6-dimethylmorpholino)pyridin-3-yl)-4-morpholinothieno[3,2-d]pyrimidin-2-yl)pyrimidin-2-amine |
| 473 | 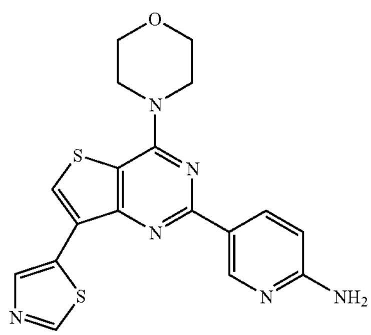 [SMILES: Nc1ccc(-c2nc(N3CCOCC3)c3scc(-c4cncs4)c3n2)cn1] | 5-(4-morpholino-7-(thiazol-5-yl)thieno[3,2-d]pyrimidin-2-yl)pyridin-2-amine |
| 474 | 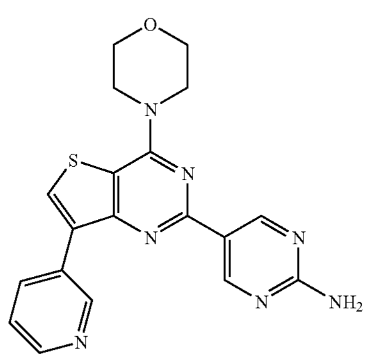 | 5-(4-morpholino-7-(pyridin-3-yl)thieno[3,2-d]pyrimidin-2-yl)pyrimidin-2-amine |
| 475 | 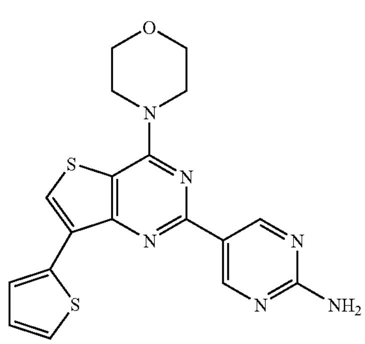 [SMILES: Nc1ncc(-c2nc(N3CCOCC3)c3scc(-c4cccs4)c3n2)cn1] | 5-(4-morpholino-7-(thiophen-2-yl)thieno[3,2-d]pyrimidin-2-yl)pyrimidin-2-amine |

TABLE 2-continued

| Example | Structure | Name |
|---|---|---|
| 476 | 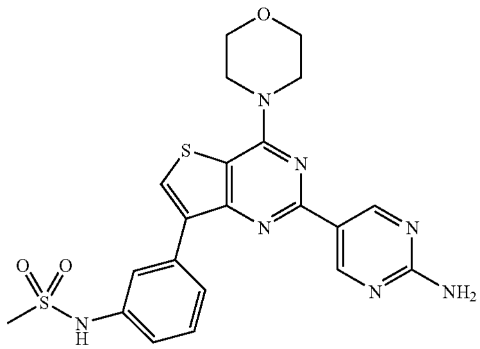 [SMILES: CS(=O)(=O)Nc1cccc(-c2csc3c(N4CCOCC4)nc(-c4cnc(N)nc4)nc23)c1] | N-(3-(2-(2-aminopyrimidin-5-yl)-4-morpholinothieno[3,2-d]pyrimidin-7-yl)phenyl)methanesulfonamide |
| 477 | 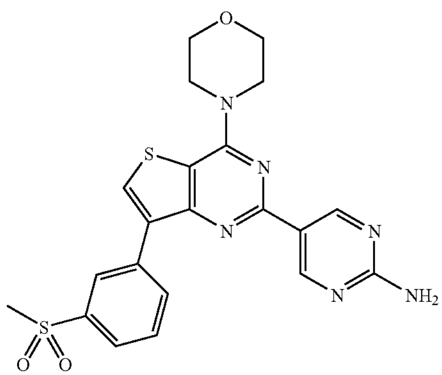 [SMILES: CS(=O)(=O)c1cccc(-c2csc3c(N4CCOCC4)nc(-c4cnc(N)nc4)nc23)c1] | 5-(7-(3-(methylsulfonyl)phenyl)-4-morpholinothieno[3,2-d]pyrimidin-2-yl)pyrimidin-2-amine |
| 478 | 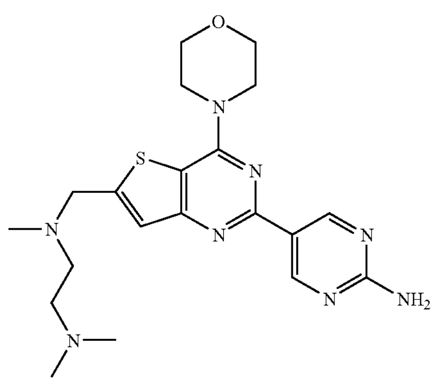 [SMILES: CN(C)CCN(C)Cc1cc2nc(-c3cnc(N)nc3)nc(N3CCOCC3)c2s1] | N1-((2-(2-aminopyrimidin-5-yl)-4-morpholinothieno[3,2-d]pyrimidin-6-yl)methyl)-N1,N2,N2-trimethylethane-1,2-diamine |
| 479 | 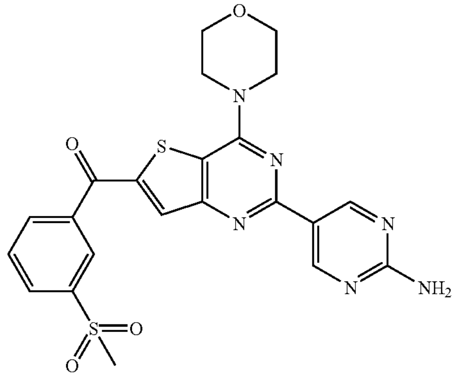 [SMILES: CS(=O)(=O)c1cccc(C(=O)c2cc3nc(-c4cnc(N)nc4)nc(N4CCOCC4)c3s2)c1] | (2-(2-aminopyrimidin-5-yl)-4-morpholinothieno[3,2-d]pyrimidin-6-yl)(3-(methylsulfonyl)phenyl)methanone |

TABLE 2-continued

| Example | Structure | Name |
|---|---|---|
| 480 | 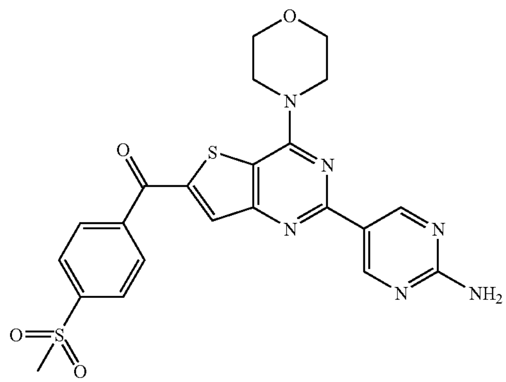 [SMILES: CS(=O)(=O)c1ccc(C(=O)c2cc3nc(-c4cnc(N)nc4)nc(N4CCOCC4)c3s2)cc1] | (2-(2-aminopyrimidin-5-yl)-4-morpholinothieno[3,2-d]pyrimidin-6-yl)(4-(methylsulfonyl)phenyl)methanone |
| 481 | 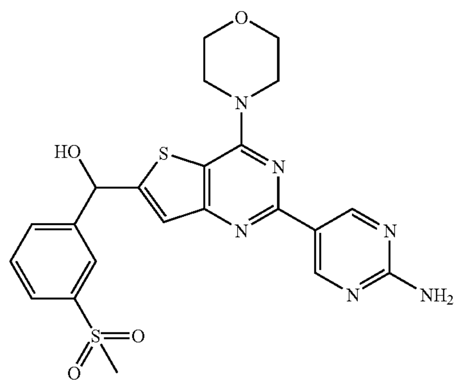 | (2-(2-aminopyrimidin-5-yl)-4-morpholinothieno[3,2-d]pyrimidin-6-yl)(3-(methylsulfonyl)phenyl)methanol |
| 482 | 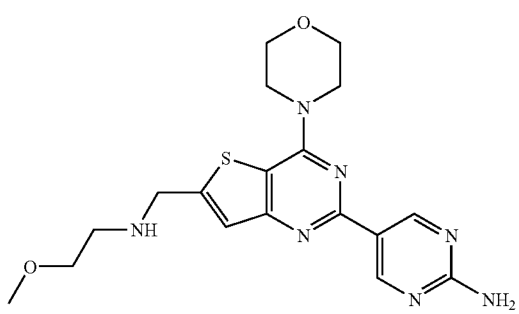 [SMILES: COCCNCc1cc2nc(-c3cnc(N)nc3)nc(N3CCOCC3)c2s1] | 5-(6-((2-methoxyethylamino)methyl)-4-morpholinothieno[3,2-d]pyrimidin-2-yl)pyrimidin-2-amine |
| 483 | 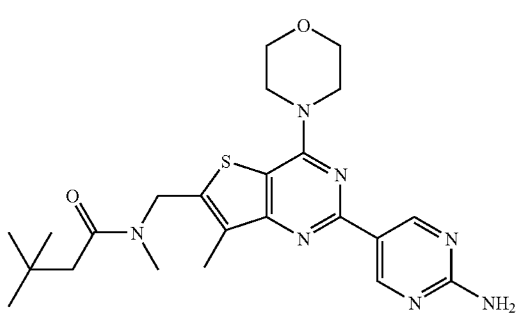 [SMILES: Cc1c(CN(C)C(=O)CC(C)(C)C)sc2c(N3CCOCC3)nc(-c3cnc(N)nc3)nc12] | N-((2-(2-aminopyrimidin-5-yl)-7-methyl-4-morpholinothieno[3,2-d]pyrimidin-6-yl)methyl)-N,3,3-trimethylbutanamide |

TABLE 2-continued

| Example | Structure | Name |
|---|---|---|
| 484 | 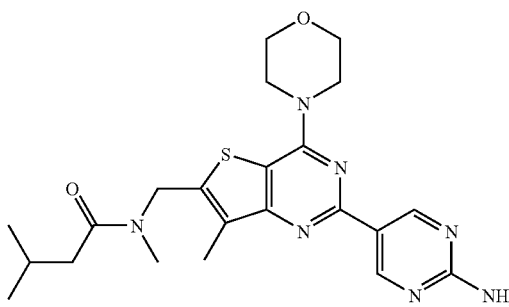 | N-((2-(2-aminopyrimidin-5-yl)-7-methyl-4-morpholinothieno[3,2-d]pyrimidin-6-yl)methyl)-N,3-dimethylbutanamide |
| 485 | 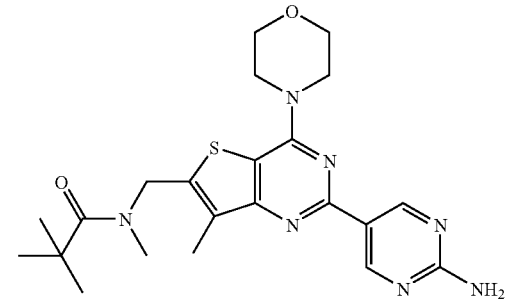 [SMILES: Cc1c(CN(C)C(=O)C(C)(C)C)sc2c(N3CCOCC3)nc(-c3cnc(N)nc3)nc12] | N-((2-(2-aminopyrimidin-5-yl)-7-methyl-4-morpholinothieno[3,2-d]pyrimidin-6-yl)methyl)-N-methylpivalamide |
| 486 | 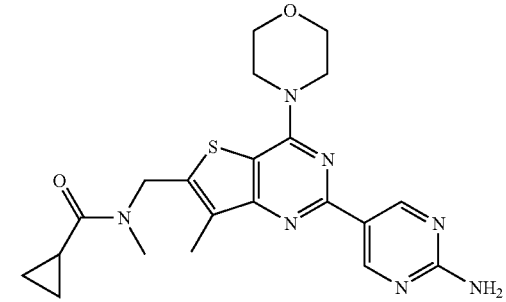 [SMILES: Cc1c(CN(C)C(=O)C2CC2)sc2c(N3CCOCC3)nc(-c3cnc(N)nc3)nc12] | N-((2-(2-aminopyrimidin-5-yl)-7-methyl-4-morpholinothieno[3,2-d]pyrimidin-6-yl)methyl)-N-methylcyclopropanecarboxamide |
| 487 | 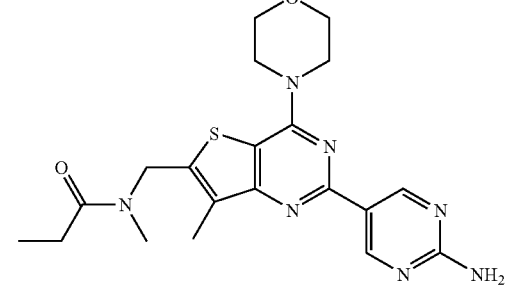 | N-((2-(2-aminopyrimidin-5-yl)-7-methyl-4-morpholinothieno[3,2-d]pyrimidin-6-yl)methyl)-N-methylpropionamide |
| 488 | 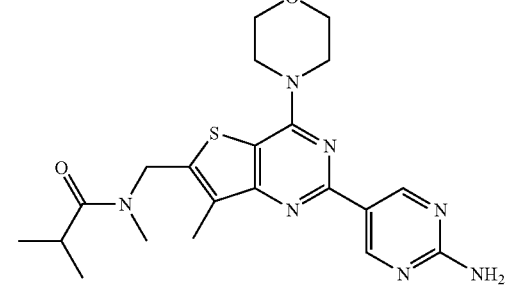 | N-((2-(2-aminopyrimidin-5-yl)-7-methyl-4-morpholinothieno[3,2-d]pyrimidin-6-yl)methyl)-N-methylisobutyramide |

TABLE 2-continued

| Example | Structure | Name |
|---|---|---|
| 489 | 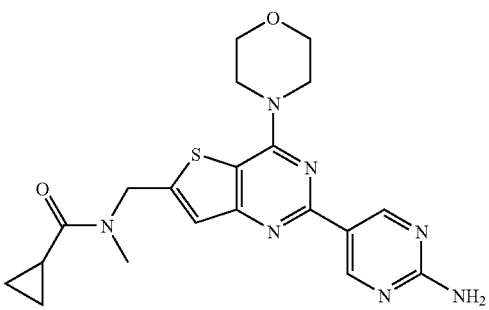 | N-((2-(2-aminopyrimidin-5-yl)-4-morpholinothieno[3,2-d]pyrimidin-6-yl)methyl)-N-methylcyclopropanecarboxamide |
| 490 | 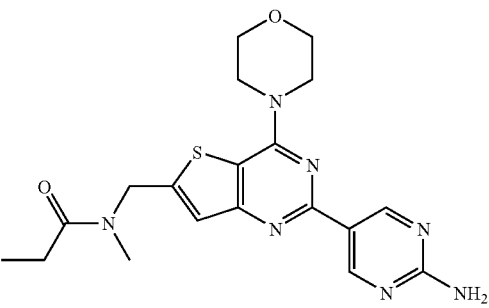 [SMILES: CCC(=O)N(C)Cc1sc2c(N3CCOCC3)nc(-c3cnc(N)nc3)nc2c1C] | N-((2-(2-aminopyrimidin-5-yl)-4-morpholinothieno[3,2-d]pyrimidin-6-yl)methyl)-N-methylpropionamide |
| 491 | 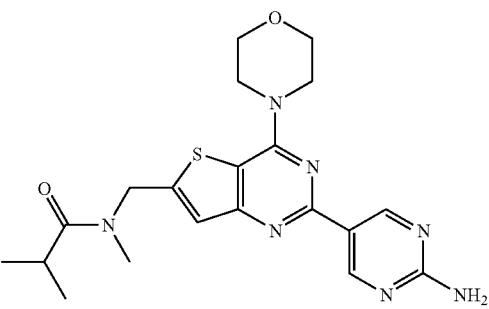 [SMILES: Cc1c(CN(C)C(=O)C(C)C)sc2c(N3CCOCC3)nc(-c3cnc(N)nc3)nc12] | N-((2-(2-aminopyrimidin-5-yl)-4-morpholinothieno[3,2-d]pyrimidin-6-yl)methyl)-N-methylisobutyramide |
| 492 | 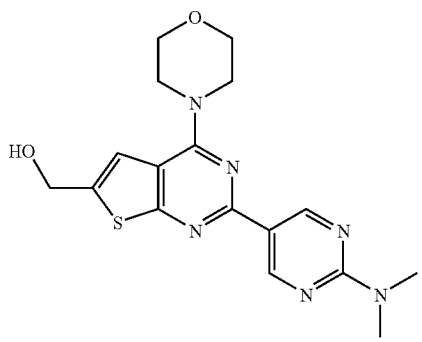 [SMILES: CN(C)c1ncc(-c2nc(N3CCOCC3)c3cc(CO)sc3n2)cn1] | (2-(2-(dimethylamino)pyrimidin-5-yl)-4-morpholinothieno[2,3-d]pyrimidin-6-yl)methanol |

TABLE 2-continued

| Example | Structure | Name |
|---|---|---|
| 493 | 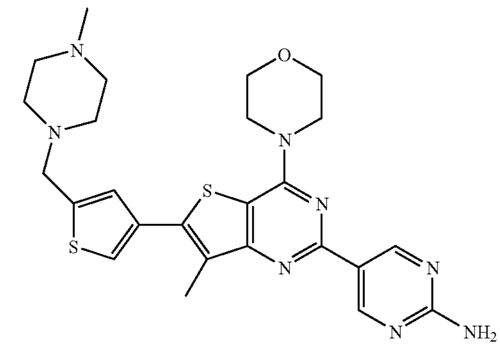 [SMILES: Cc1c(-c2csc(CN3CCN(C)CC3)c2)sc2c(N3CCOCC3)nc(-c3cnc(N)nc3)nc12] | 5-(7-methyl-6-(5-((4-methylpiperazin-1-yl)methyl)thiophen-3-yl)-4-morpholinothieno[3,2-d]pyrimidin-2-yl)pyrimidin-2-amine |
| 494 | 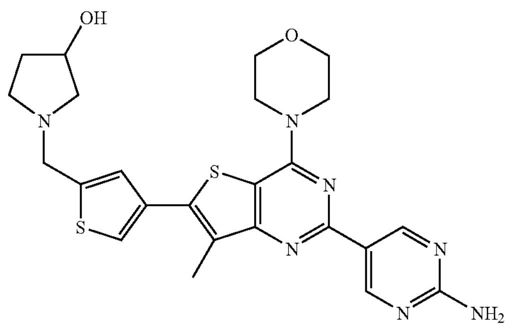 [SMILES: Cc1c(-c2csc(CN3CCC(O)C3)c2)sc2c(N3CCOCC3)nc(-c3cnc(N)nc3)nc12] | 1-((4-(2-(2-aminopyrimidin-5-yl)-7-methyl-4-morpholinothieno[3,2-d]pyrimidin-6-yl)thiophen-2-yl)methyl)pyrrolidin-3-ol |
| 495 | 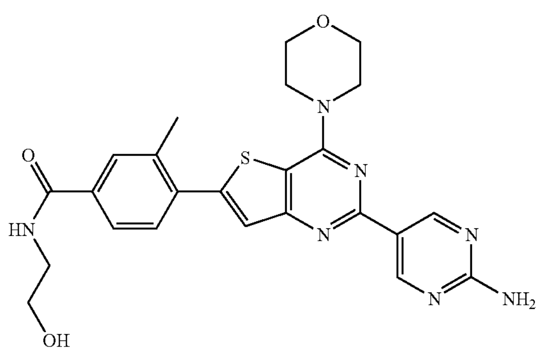 [SMILES: Cc1cc(C(=O)NCCO)ccc1-c1cc2nc(-c3cnc(N)nc3)nc(N3CCOCC3)c2s1] | 4-(2-(2-aminopyrimidin-5-yl)-4-morpholinothieno[3,2-d]pyrimidin-6-yl)-N-(2-hydroxyethyl)-3-methylbenzamide |
| 496 | 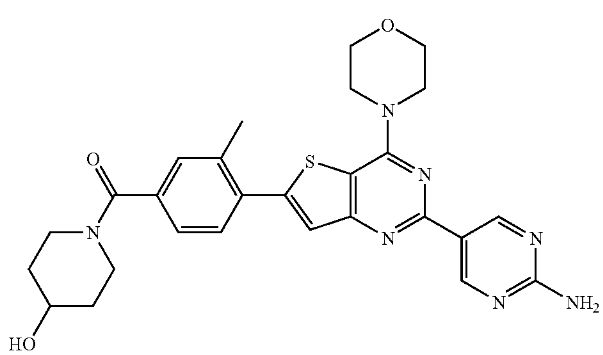 [SMILES: Cc1cc(C(=O)N2CCC(O)CC2)ccc1-c1cc2nc(-c3cnc(N)nc3)nc(N3CCOCC3)c2s1] | (4-(2-(2-aminopyrimidin-5-yl)-4-morpholinothieno[3,2-d]pyrimidin-6-yl)-3-methylphenyl)(4-hydroxypiperidin-1-yl)methanone |

TABLE 2-continued

| Example | Structure | Name |
|---|---|---|
| 497 | 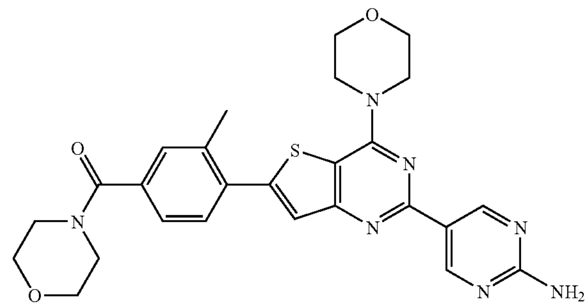 [SMILES: Cc1cc(C(=O)N2CCOCC2)ccc1-c1cc2nc(-c3cnc(N)nc3)nc(N3CCOCC3)c2s1] | (4-(2-(2-aminopyrimidin-5-yl)-4-morpholinothieno[3,2-d]pyrimidin-6-yl)-3-methylphenyl)(morpholino)methanone |
| 498 | 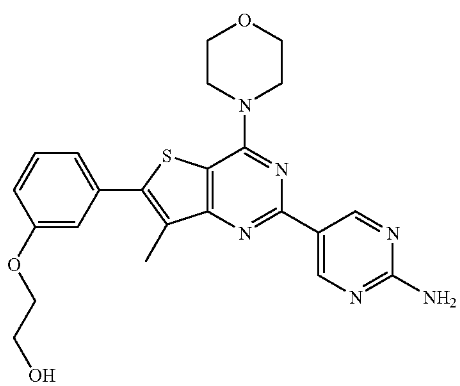 [SMILES: Cc1c(-c2cccc(OCCO)c2)sc2c(N3CCOCC3)nc(-c3cnc(N)nc3)nc12] | 2-(3-(2-(2-aminopyrimidin-5-yl)-7-methyl-4-morpholinothieno[3,2-d]pyrimidin-6-yl)phenoxy)ethanol |
| 499 | 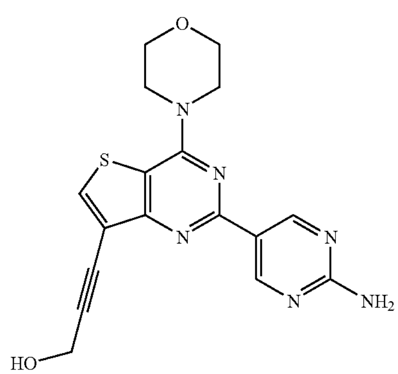 [SMILES: Nc1ncc(-c2nc(N3CCOCC3)c3scc(C#CCO)c3n2)cn1] | 3-(2-(2-aminopyrimidin-5-yl)-4-morpholinothieno[3,2-d]pyrimidin-7-yl)prop-2-yn-1-ol |
| 500 | 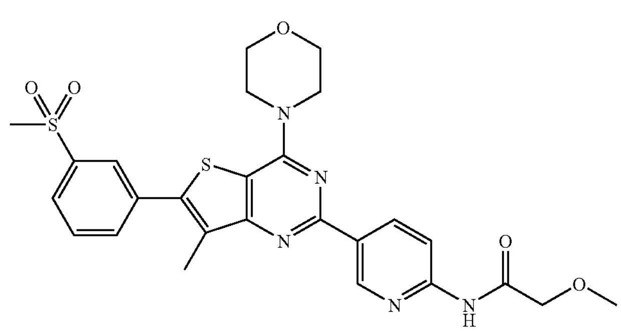 | 2-methoxy-N-(5-(7-methyl-6-(3-(methylsulfonyl)phenyl)-4-morpholinothieno[3,2-d]pyrimidin-2-yl)pyridin-2-yl)acetamide |

TABLE 2-continued

| Example | Structure | Name |
|---|---|---|
| 501 | 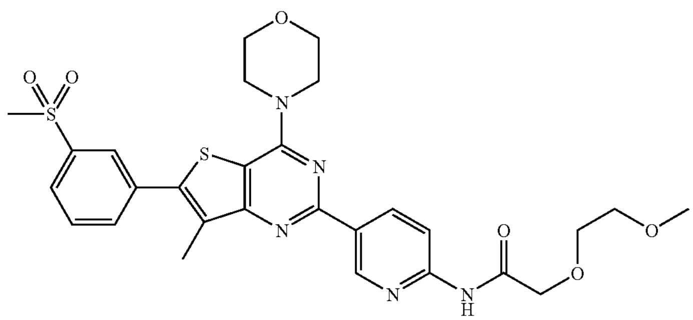 | 2-(2-methoxyethoxy)-N-(5-(7-methyl-6-(3-(methylsulfonyl)phenyl)-4-morpholinothieno[3,2-d]pyrimidin-2-yl)pyridin-2-yl)acetamide |
| 502 | 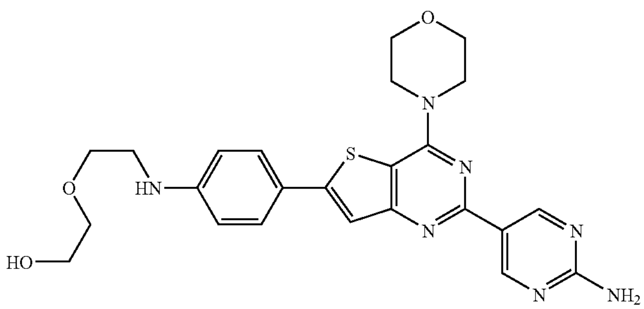 [SMILES: Nc1ncc(-c2nc(N3CCOCC3)c3sc(-c4ccc(NCCOCCO)cc4)cc3n2)cn1] | 2-(2-(4-(2-(2-aminopyrimidin-5-yl)-4-morpholinothieno[3,2-d]pyrimidin-6-yl)phenylamino)ethoxy)ethanol |
| 503 | 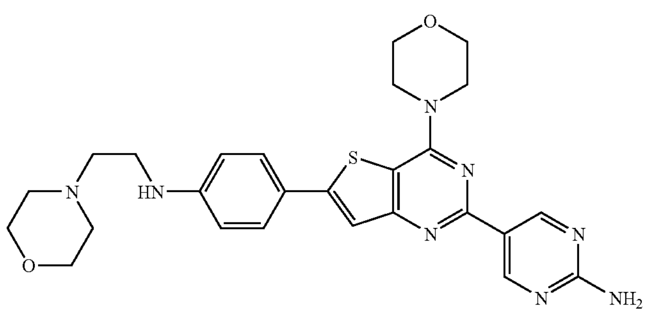 [SMILES: Nc1ncc(-c2nc(N3CCOCC3)c3sc(-c4ccc(NCCN5CCOCC5)cc4)cc3n2)cn1] | 5-(4-morpholino-6-(4-(2-morpholinoethylamino)phenyl)thieno[3,2-d]pyrimidin-2-yl)pyrimidin-2-amine |
| 504 | 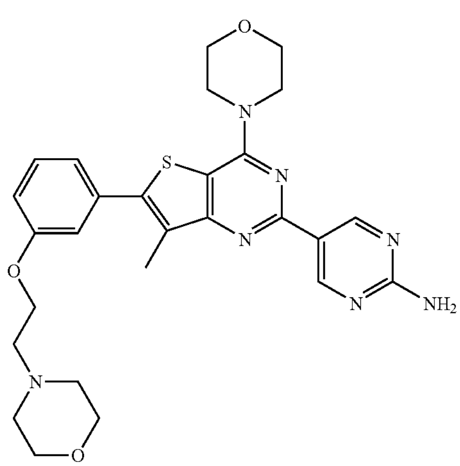 [SMILES: Cc1c(-c2cccc(OCCN3CCOCC3)c2)sc2c(N3CCOCC3)nc(-c3cnc(N)nc3)nc12] | 5-(7-methyl-4-morpholino-6-(3-(2-morpholinoethoxy)phenyl)thieno[3,2-d]pyrimidin-2-yl)pyrimidin-2-amine |

TABLE 2-continued

| Example | Structure | Name |
|---|---|---|
| 505 | 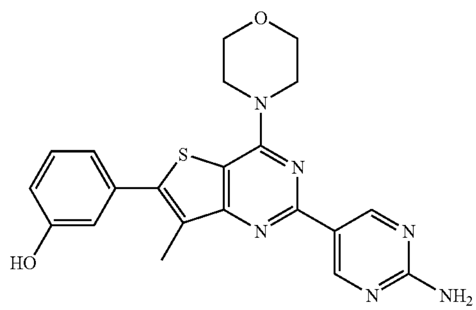 [SMILES: Cc1c(-c2cccc(O)c2)sc2c(N3CCOCC3)nc(-c3cnc(N)nc3)nc12] | 3-(2-(2-aminopyrimidin-5-yl)-7-methyl-4-morpholinothieno[3,2-d]pyrimidin-6-yl)phenol |
| 506 | 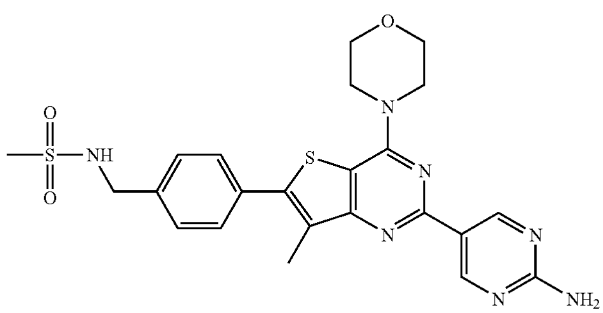 [SMILES: Cc1c(-c2ccc(CNS(C)(=O)=O)cc2)sc2c(N3CCOCC3)nc(-c3cnc(N)nc3)nc12] | N-(4-(2-(2-aminopyrimidin-5-yl)-7-methyl-4-morpholinothieno[3,2-d]pyrimidin-6-yl)benzyl)methanesulfonamide |
| 507 | 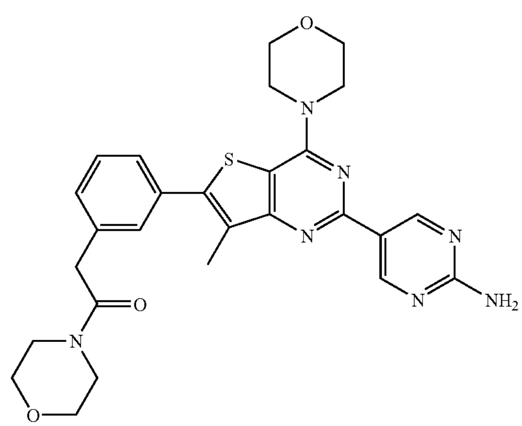 [SMILES: Cc1c(-c2cccc(CC(=O)N3CCOCC3)c2)sc2c(N3CCOCC3)nc(-c3cnc(N)nc3)nc12] | 2-(3-(2-(2-aminopyrimidin-5-yl)-7-methyl-4-morpholinothieno[3,2-d]pyrimidin-6-yl)phenyl)-1-morpholinoethanone |
| 508 | 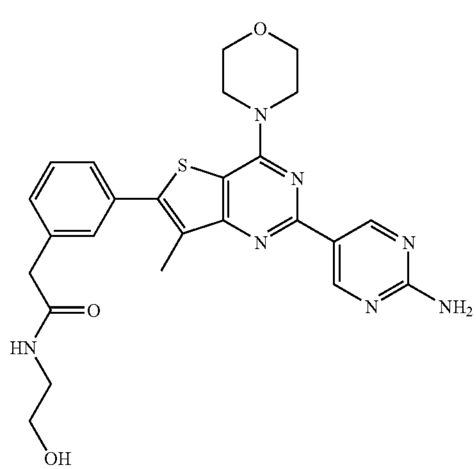 [SMILES: Cc1c(-c2cccc(CC(=O)NCCO)c2)sc2c(N3CCOCC3)nc(-c3cnc(N)nc3)nc12] | 2-(3-(2-(2-aminopyrimidin-5-yl)-7-methyl-4-morpholinothieno[3,2-d]pyrimidin-6-yl)phenyl)-N-(2-hydroxyethyl)acetamide |

TABLE 2-continued

| Example | Structure | Name |
|---|---|---|
| 509 | 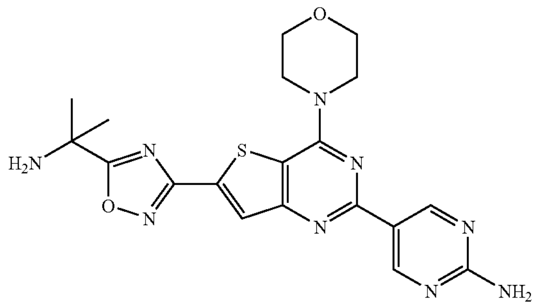 [SMILES: CC(C)(N)c1nc(-c2cc3nc(-c4cnc(N)nc4)nc(N4CCOCC4)c3s2)no1] | 5-(6-(5-(2-aminopropan-2-yl)-1,2,4-oxadiazol-3-yl)-4-morpholinothieno[3,2-d]pyrimidin-2-yl)pyrimidin-2-amine |
| 510 | 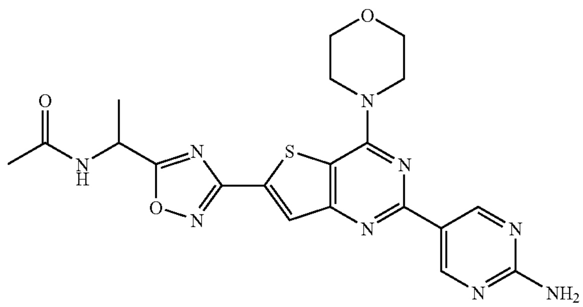 [SMILES: CC(=O)NC(C)c1nc(-c2cc3nc(-c4cnc(N)nc4)nc(N4CCOCC4)c3s2)no1] | N-(1-(3-(2-(2-aminopyrimidin-5-yl)-4-morpholinothieno[3,2-d]pyrimidin-6-yl)-1,2,4-oxadiazol-5-yl)ethyl)acetamide |
| 511 | 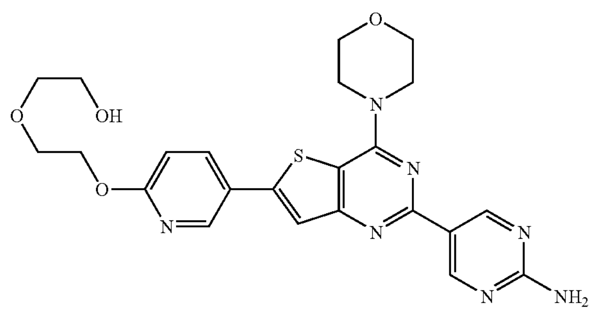 [SMILES: Nc1ncc(-c2nc(N3CCOCC3)c3sc(-c4ccc(OCCOCCO)nc4)cc3n2)cn1] | 2-(2-(5-(2-(2-aminopyrimidin-5-yl)-4-morpholinothieno[3,2-d]pyrimidin-6-yl)pyridin-2-yloxy)ethoxy)ethanol |
| 512 | 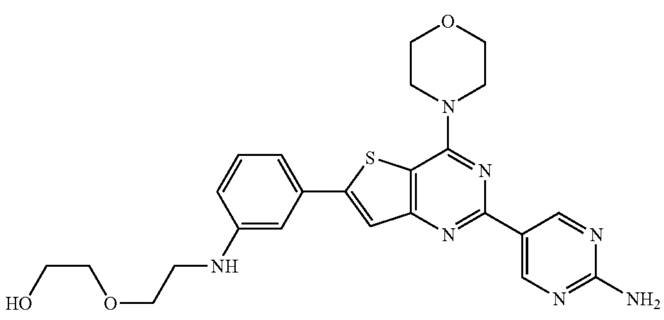 [SMILES: Nc1ncc(-c2nc(N3CCOCC3)c3sc(-c4cccc(NCCOCCO)c4)cc3n2)cn1] | 2-(2-(3-(2-(2-aminopyrimidin-5-yl)-4-morpholinothieno[3,2-d]pyrimidin-6-yl)phenylamino)ethoxy)ethanol |
| 513 | 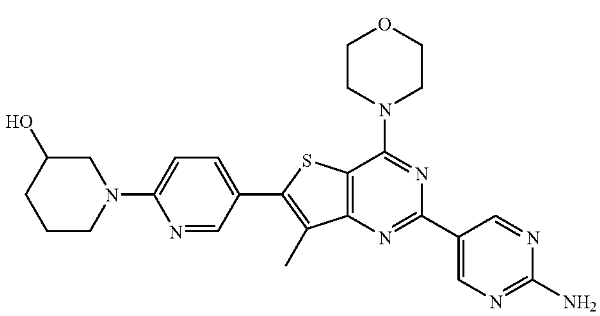 [SMILES: Cc1c(-c2ccc(N3CCCC(O)C3)nc2)sc2c(N3CCOCC3)nc(-c3cnc(N)nc3)nc12] | 1-(5-(2-(2-aminopyrimidin-5-yl)-7-methyl-4-morpholinothieno[3,2-d]pyrimidin-6-yl)pyridin-2-yl)piperidin-3-ol |

TABLE 2-continued

| Example | Structure | Name |
|---|---|---|
| 514 | 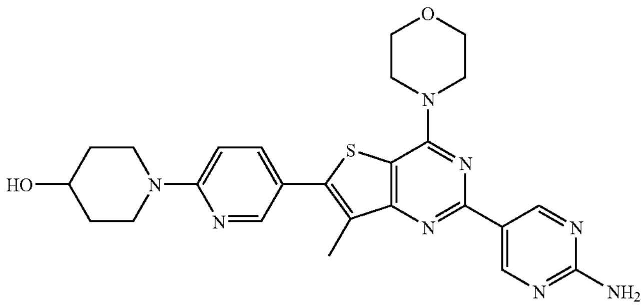 | 1-(5-(2-(2-aminopyrimidin-5-yl)-7-methyl-4-morpholinothieno[3,2-d]pyrimidin-6-yl)pyridin-2-yl)piperidin-4-ol |
| 515 | 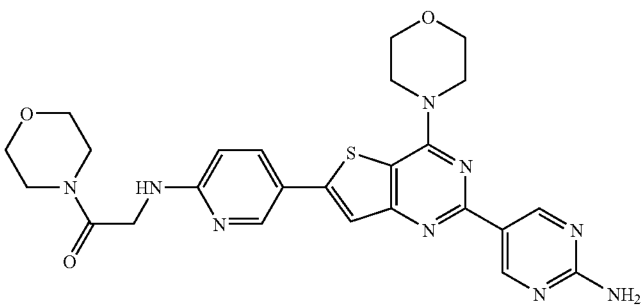 | 2-(5-(2-(2-aminopyrimidin-5-yl)-4-morpholinothieno[3,2-d]pyrimidin-6-yl)pyridin-2-ylamino)-1-morpholinoethanone |
| 516 | 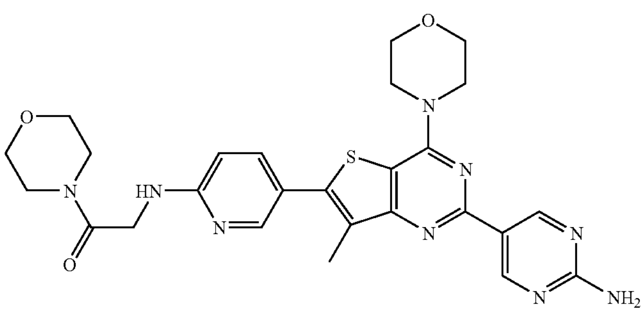 [SMILES: Cc1c(-c2ccc(NCC(=O)N3CCOCC3)nc2)sc2c(N3CCOCC3)nc(-c3cnc(N)nc3)nc12] | 2-(5-(2-(2-aminopyrimidin-5-yl)-7-methyl-4-morpholinothieno[3,2-d]pyrimidin-6-yl)pyridin-2-ylamino)-1-morpholinoethanone |
| 517 | 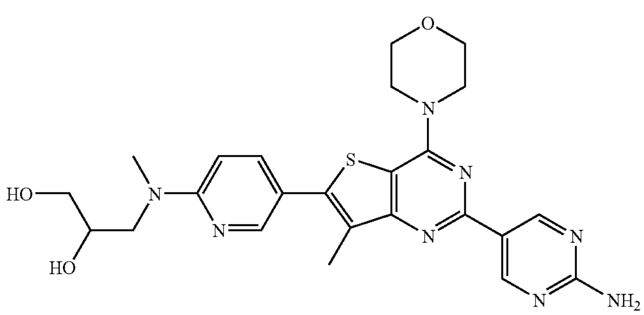 [SMILES: Cc1c(-c2ccc(N(C)CC(O)CO)nc2)sc2c(N3CCOCC3)nc(-c3cnc(N)nc3)nc12] | 3-((5-(2-(2-aminopyrimidin-5-yl)-7-methyl-4-morpholinothieno[3,2-d]pyrimidin-6-yl)pyridin-2-yl)(methyl)amino)propane-1,2-diol |
| 518 | 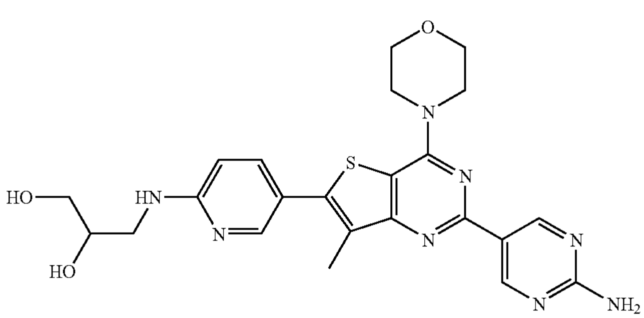 [SMILES: Cc1c(-c2ccc(NCC(O)CO)nc2)sc2c(N3CCOCC3)nc(-c3cnc(N)nc3)nc12] | 3-(5-(2-(2-aminopyrimidin-5-yl)-7-methyl-4-morpholinothieno[3,2-d]pyrimidin-6-yl)pyridin-2-ylamino)propane-1,2-diol |

TABLE 2-continued

| Example | Structure | Name |
|---|---|---|
| 519 | 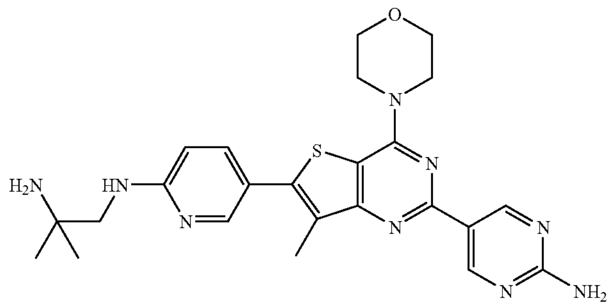 [SMILES: Cc1c(-c2ccc(NCC(C)(C)N)nc2)sc2c(N3CCOCC3)nc(-c3cnc(N)nc3)nc12] | N1-(5-(2-(2-aminopyrimidin-5-yl)-7-methyl-4-morpholinothieno[3,2-d]pyrimidin-6-yl)pyridin-2-yl)-2-methylpropane-1,2-diamine |
| 520 | 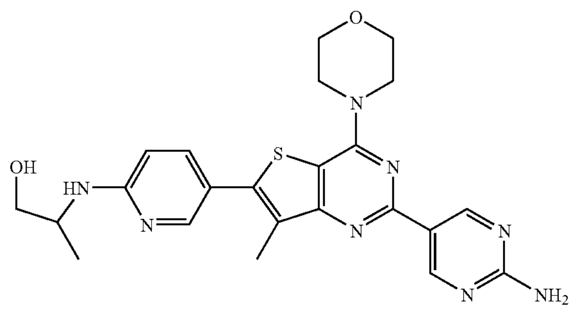 [SMILES: Cc1c(-c2ccc(NC(C)CO)nc2)sc2c(N3CCOCC3)nc(-c3cnc(N)nc3)nc12] | 2-(5-(2-(2-aminopyrimidin-5-yl)-7-methyl-4-morpholinothieno[3,2-d]pyrimidin-6-yl)pyridin-2-ylamino)propan-1-ol |
| 521 | 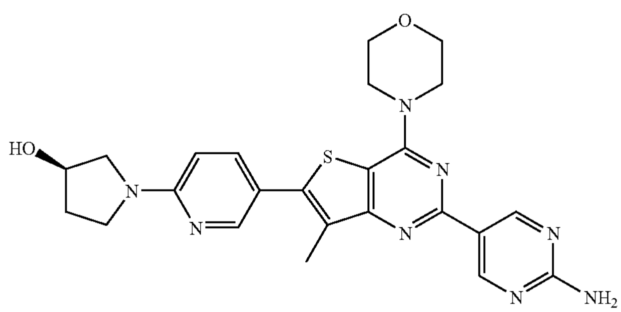 | (R)-1-(5-(2-(2-aminopyrimidin-5-yl)-7-methyl-4-morpholinothieno[3,2-d]pyrimidin-6-yl)pyridin-2-yl)pyrrolidin-3-ol |
| 522 | 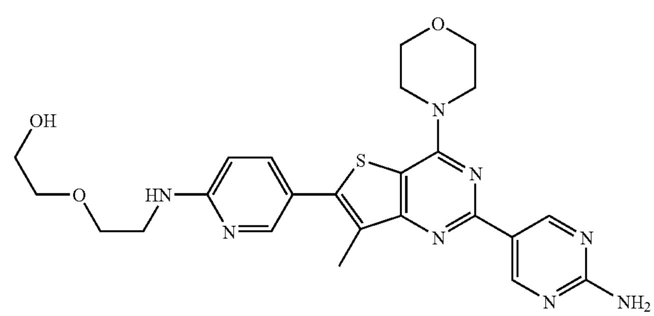 [SMILES: Cc1c(-c2ccc(NCCOCCO)nc2)sc2c(N3CCOCC3)nc(-c3cnc(N)nc3)nc12] | 2-(2-(5-(2-(2-aminopyrimidin-5-yl)-7-methyl-4-morpholinothieno[3,2-d]pyrimidin-6-yl)pyridin-2-ylamino)ethoxy)ethanol |
| 523 | 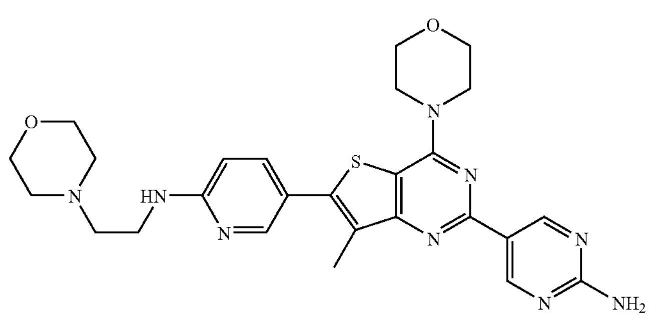 [SMILES: Cc1c(-c2ccc(NCCN3CCOCC3)nc2)sc2c(N3CCOCC3)nc(-c3cnc(N)nc3)nc12] | 5-(7-methyl-4-morpholino-6-(6-(2-morpholinoethylamino)pyridin-3-yl)thieno[3,2-d]pyrimidin-2-yl)pyrimidin-2-amine |

TABLE 2-continued
| Example | Structure | Name |
|---|---|---|
| 524 | 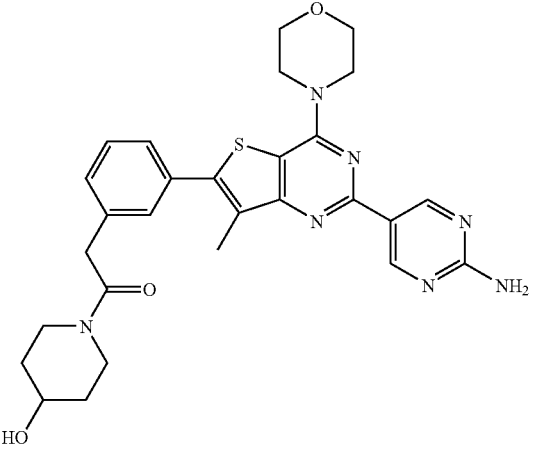 [SMILES: Cc1c(-c2cccc(CC(=O)N3CCC(O)CC3)c2)sc2c(N3CCOCC3)nc(-c3cnc(N)nc3)nc12] | 2-(3-(2-(2-aminopyrimidin-5-yl)-7-methyl-4-morpholinothieno[3,2-d]pyrimidin-6-yl)phenyl)-1-(4-hydroxypiperidin-1-yl)ethanone |
| 525 | 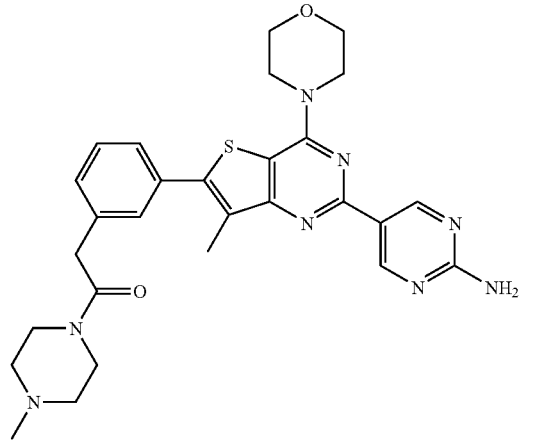 [SMILES: Cc1c(-c2cccc(CC(=O)N3CCN(C)CC3)c2)sc2c(N3CCOCC3)nc(-c3cnc(N)nc3)nc12] | 2-(3-(2-(2-aminopyrimidin-5-yl)-7-methyl-4-morpholinothieno[3,2-d]pyrimidin-6-yl)phenyl)-1-(4-methylpiperazin-1-yl)ethanone |
| 526 | 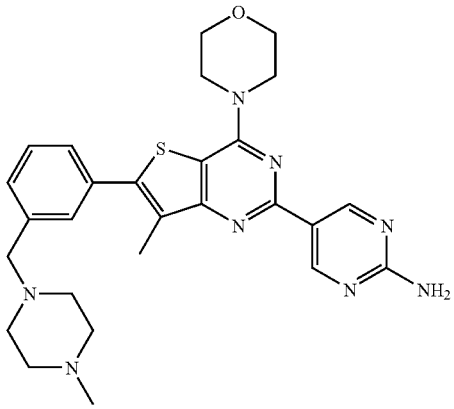 [SMILES: Cc1c(-c2cccc(CN3CCN(C)CC3)c2)sc2c(N3CCOCC3)nc(-c3cnc(N)nc3)nc12] | 5-(7-methyl-6-(3-((4-methylpiperazin-1-yl)methyl)phenyl)-4-morpholinothieno[3,2-d]pyrimidin-2-yl)pyrimidin-2-amine |

TABLE 2-continued

| Example | Structure | Name |
|---|---|---|
| 527 | 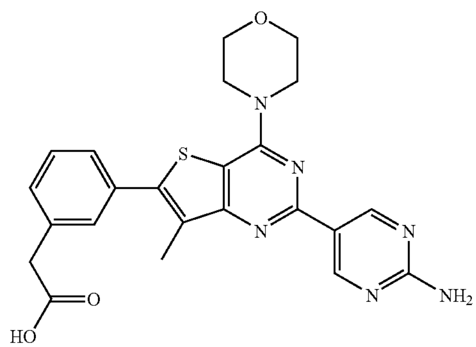 [SMILES: Cc1c(-c2cccc(CC(=O)O)c2)sc2c(N3CCOCC3)nc(-c3cnc(N)nc3)nc12] | 2-(3-(2-(2-aminopyrimidin-5-yl)-7-methyl-4-morpholinothieno[3,2-d]pyrimidin-6-yl)phenyl)acetic acid |
| 528 | 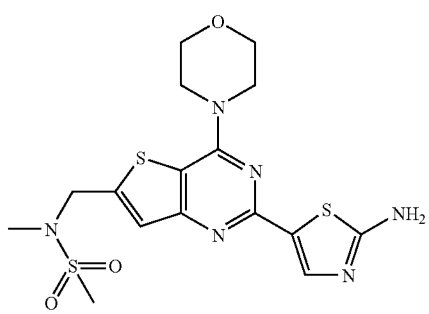 [SMILES: CN(Cc1cc2nc(-c3cnc(N)s3)nc(N3CCOCC3)c2s1)S(C)(=O)=O] | N-((2-(2-aminothiazol-5-yl)-4-morpholinothieno[3,2-d]pyrimidin-6-yl)methyl)-N-methylmethanesulfonamide |
| 529 | 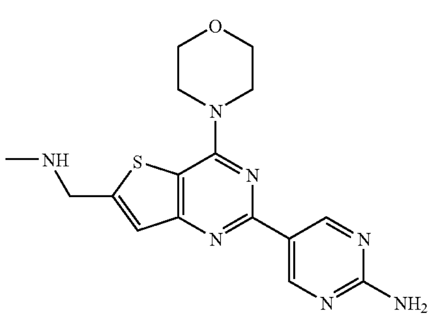 [SMILES: CNCc1cc2nc(-c3cnc(N)nc3)nc(N3CCOCC3)c2s1] | 5-(6-((methylamino)methyl)-4-morpholinothieno[3,2-d]pyrimidin-2-yl)pyrimidin-2-amine |
| 530 | 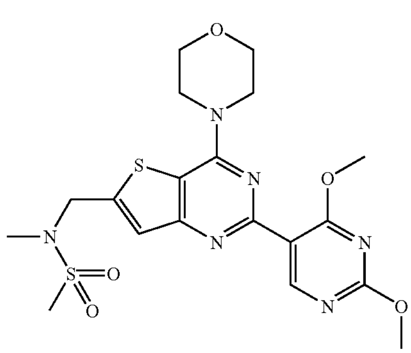 | N-((2-(2,4-dimethoxypyrimidin-5-yl)-4-morpholinothieno[3,2-d]pyrimidin-6-yl)methyl)-N-methylmethanesulfonamide |

TABLE 2-continued

| Example | Structure | Name |
|---|---|---|
| 531 | 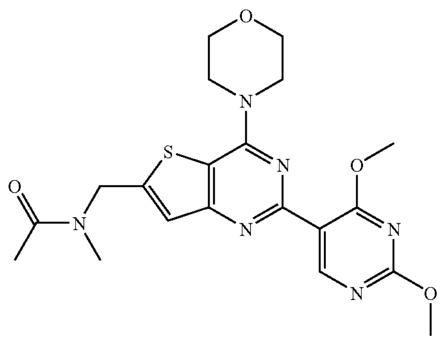 [SMILES: COc1ncc(-c2nc(N3CCOCC3)c3sc(CN(C)C(C)=O)cc3n2)c(OC)n1] | N-((2-(2,4-dimethoxypyrimidin-5-yl)-4-morpholinothieno[3,2-d]pyrimidin-6-yl)methyl)-N-methylacetamide |
| 532 | 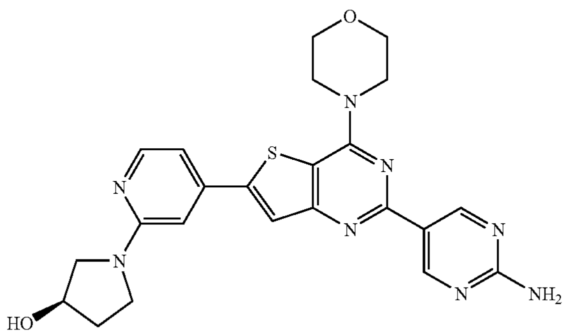 [SMILES: Nc1ncc(-c2nc(N3CCOCC3)c3sc(-c4ccnc(N5CC[C@@H](O)C5)c4)cc3n2)cn1] | (R)-1-(4-(2-(2-aminopyrimidin-5-yl)-4-morpholinothieno[3,2-d]pyrimidin-6-yl)pyridin-2-yl)pyrrolidin-3-ol |
| 533 | 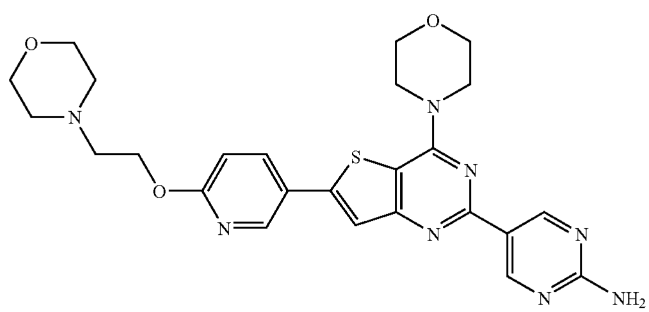 [SMILES: Nc1ncc(-c2nc(N3CCOCC3)c3sc(-c4ccc(OCCN5CCOCC5)nc4)cc3n2)cn1] | 5-(4-morpholino-6-(6-(2-morpholinoethoxy)pyridin-3-yl)thieno[3,2-d]pyrimidin-2-yl)pyrimidin-2-amine |
| 534 | 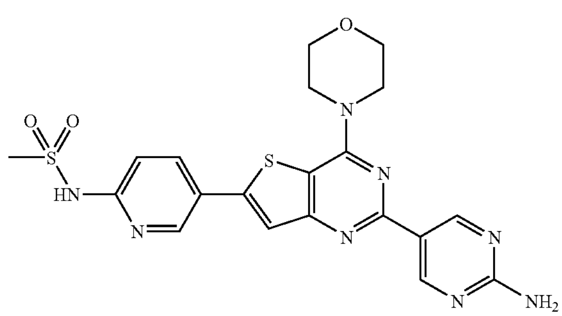 [SMILES: CS(=O)(=O)Nc1ccc(-c2cc3nc(-c4cnc(N)nc4)nc(N4CCOCC4)c3s2)cn1] | N-(5-(2-(2-aminopyrimidin-5-yl)-4-morpholinothieno[3,2-d]pyrimidin-6-yl)pyridin-2-yl)methanesulfonamide |
| 535 | 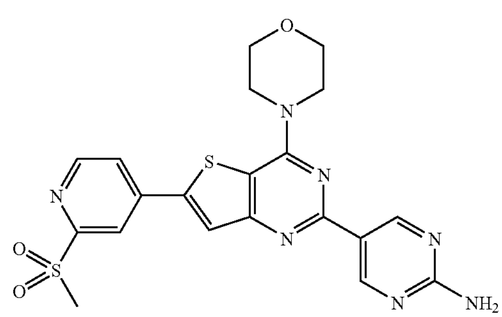 [SMILES: CS(=O)(=O)c1cc(-c2cc3nc(-c4cnc(N)nc4)nc(N4CCOCC4)c3s2)ccn1] | 5-(6-(2-(methylsulfonyl)pyridin-4-yl)-4-morpholinothieno[3,2-d]pyrimidin-2-yl)pyrimidin-2-amine |

TABLE 2-continued

| Example | Structure | Name |
| --- | --- | --- |
| 536 | 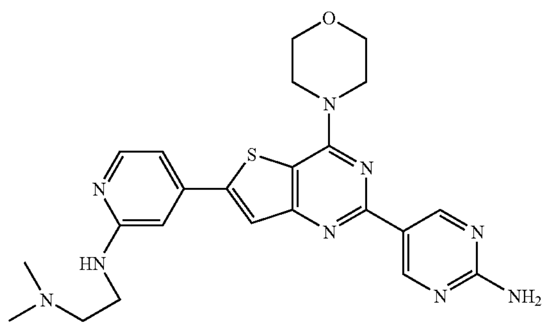 [SMILES: CN(C)CCNc1cc(-c2cc3nc(-c4cnc(N)nc4)nc(N4CCOCC4)c3s2)ccn1] | N1-(4-(2-(2-aminopyrimidin-5-yl)-4-morpholinothieno[3,2-d]pyrimidin-6-yl)pyridin-2-yl)-N2,N2-dimethylethane-1,2-diamine |
| 537 | 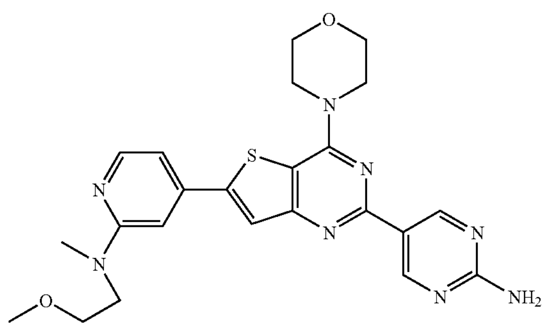 [SMILES: COCCN(C)c1cc(-c2cc3nc(-c4cnc(N)nc4)nc(N4CCOCC4)c3s2)ccn1] | 5-(6-(2-((2-methoxyethyl)(methyl)amino)pyridin-4-yl)-4-morpholinothieno[3,2-d]pyrimidin-2-yl)pyrimidin-2-amine |
| 538 | 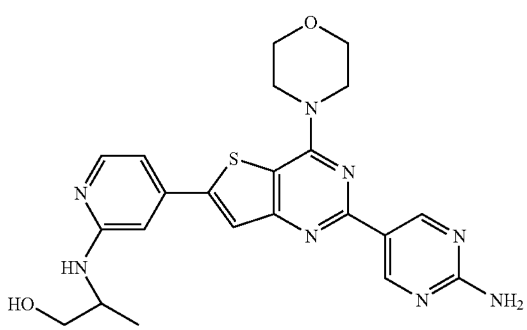 [SMILES: CC(CO)Nc1cc(-c2cc3nc(-c4cnc(N)nc4)nc(N4CCOCC4)c3s2)ccn1] | 2-(4-(2-(2-aminopyrimidin-5-yl)-4-morpholinothieno[3,2-d]pyrimidin-6-yl)pyridin-2-ylamino)propan-1-ol |
| 539 | 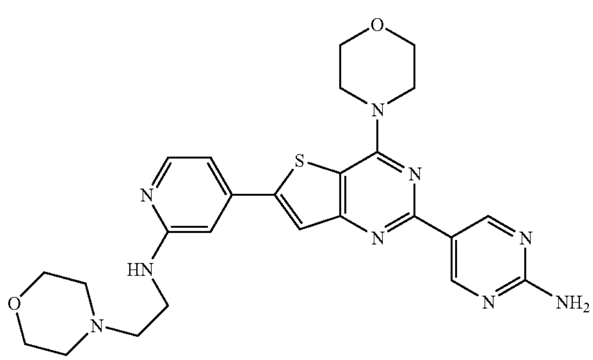 [SMILES: Nc1ncc(-c2nc(N3CCOCC3)c3sc(-c4ccnc(NCCN5CCOCC5)c4)cc3n2)cn1] | 5-(4-morpholino-6-(2-(2-morpholinoethylamino)pyridin-4-yl)thieno[3,2-d]pyrimidin-2-yl)pyrimidin-2-amine |

TABLE 2-continued

| Example | Structure | Name |
| --- | --- | --- |
| 540 | 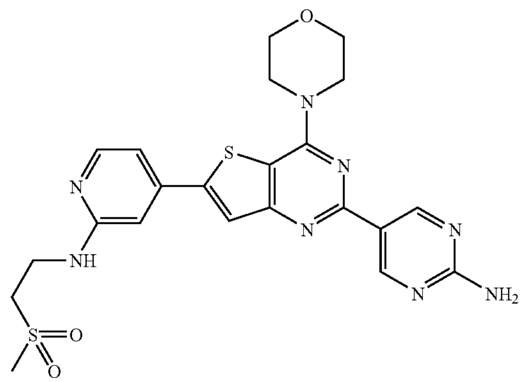 [SMILES: CS(=O)(=O)CCNc1cc(-c2cc3nc(-c4cnc(N)nc4)nc(N4CCOCC4)c3s2)ccn1] | 5-(6-(2-(2-(methylsulfonyl)ethylamino)pyridin-4-yl)-4-morpholinothieno[3,2-d]pyrimidin-2-yl)pyrimidin-2-amine |
| 541 | 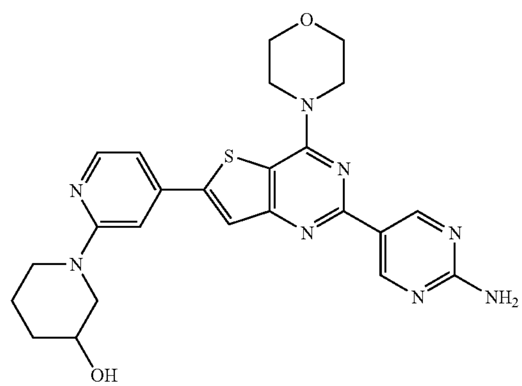 [SMILES: Nc1ncc(-c2nc(N3CCOCC3)c3sc(-c4ccnc(N5CCCC(O)C5)c4)cc3n2)cn1] | 1-(4-(2-(2-aminopyrimidin-5-yl)-4-morpholinothieno[3,2-d]pyrimidin-6-yl)pyridin-2-yl)piperidin-3-ol |
| 542 | 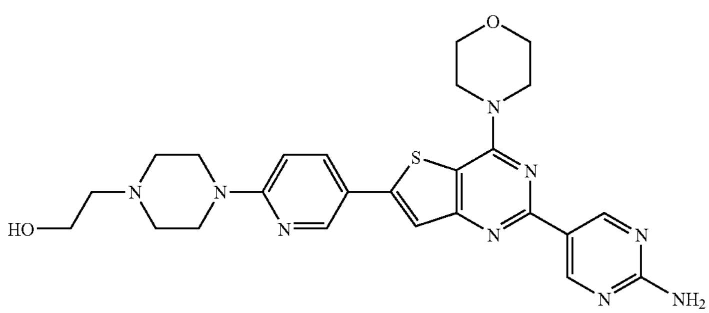 [SMILES: Nc1ncc(-c2nc(N3CCOCC3)c3sc(-c4ccc(N5CCN(CCO)CC5)nc4)cc3n2)cn1] | 2-(4-(5-(2-(2-aminopyrimidin-5-yl)-4-morpholinothieno[3,2-d]pyrimidin-6-yl)pyridin-2-yl)piperazin-1-yl)ethanol |
| 543 | 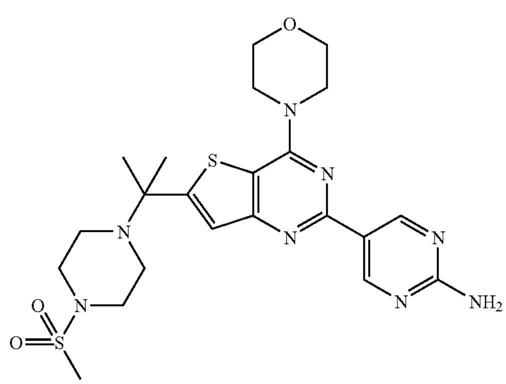 [SMILES: CC(C)(c1cc2nc(-c3cnc(N)nc3)nc(N3CCOCC3)c2s1)N1CCN(S(C)(=O)=O)CC1] | 5-(6-(2-(4-(methylsulfonyl)piperazin-1-yl)propan-2-yl)-4-morpholinothieno[3,2-d]pyrimidin-2-yl)pyrimidin-2-amine |

TABLE 2-continued

| Example | Structure | Name |
|---|---|---|
| 544 | 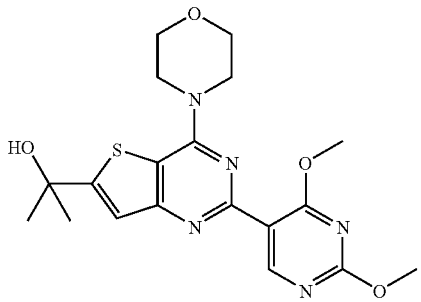 [SMILES: COc1ncc(-c2nc(N3CCOCC3)c3sc(C(C)(C)O)cc3n2)c(OC)n1] | 2-(2-(2,4-dimethoxypyrimidin-5-yl)-4-morpholinothieno[3,2-d]pyrimidin-6-yl)propan-2-ol |
| 545 | 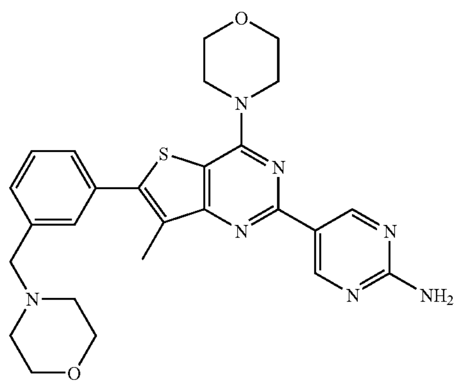 [SMILES: Cc1c(-c2cccc(CN3CCOCC3)c2)sc2c(N3CCOCC3)nc(-c3cnc(N)nc3)nc12] | 5-(7-methyl-4-morpholino-6-(3-(morpholinomethyl)phenyl)thieno[3,2-d]pyrimidin-2-yl)pyrimidin-2-amine |
| 546 | 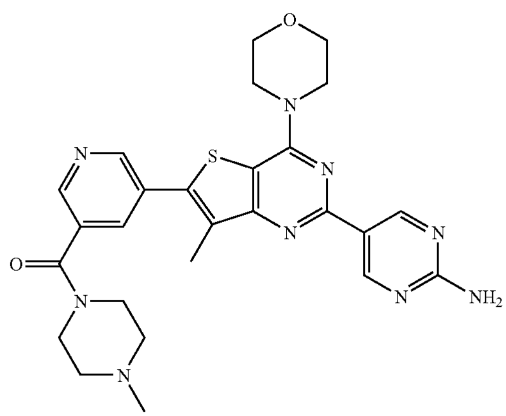 [SMILES: Cc1c(-c2cncc(C(=O)N3CCN(C)CC3)c2)sc2c(N3CCOCC3)nc(-c3cnc(N)nc3)nc12] | (5-(2-(2-aminopyrimidin-5-yl)-7-methyl-4-morpholinothieno[3,2-d]pyrimidin-6-yl)pyridin-3-yl)(4-methylpiperazin-1-yl)methanone |
| 547 | 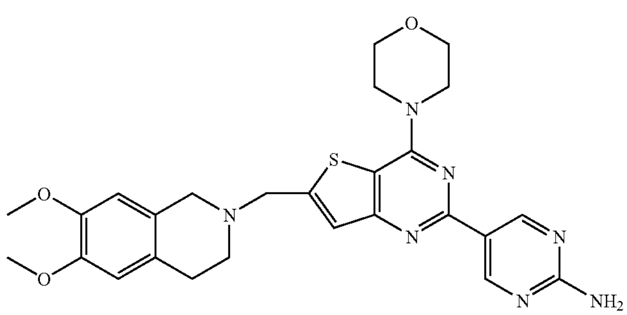 [SMILES: COc1cc2c(cc1OC)CN(Cc1cc3nc(-c4cnc(N)nc4)nc(N4CCOCC4)c3s1)CC2] | 5-(6-((3,4-dihydro-6,7-dimethoxyisoquinolin-2(1H)-yl)methyl)-4-morpholinothieno[3,2-d]pyrimidin-2-yl)pyrimidin-2-amine |

Administration of Compounds of Formula Ia-d

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula Ia-d compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula Ia-d Compounds

Compounds of the present invention are useful for treating diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula Ia-d, or a stereoisomer, geometric isomer, tautomer, solvate, metabolite, or pharmaceutically acceptable salt or prodrug thereof.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula Ia-d and a pharmaceutically acceptable carrier, adjuvant, or vehicle, wherein said compound of Formula Ia-d is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula Ia-d having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula Ia-d may be prepared. Suitable examples of sustained-release preparations include semipermeable matrices of solid hydrophobic polymers containing a compound of Formula Ia-d, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula Ia-d suitable for oral administration may be prepared as discrete units such as pills, capsules, cachets or tablets each containing a predetermined amount of a compound of Formula Ia-d.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula Ia-d intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula Ia-d compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula Ia-d may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formulas Ia-d may be employed alone or in combination with other therapeutic agents for the treatment of a disease or disorder described herein, such as a hyperproliferative disorder (e.g., cancer). In certain embodiments, a compound of Formula Ia-d is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula Ia-d such that they do not adversely affect each other. Such compounds are suitably present in combination in amounts that are effective for the purpose intended. In one embodiment, a composition of this invention comprises a compound of Formula Ia-d, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula Ia-d, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula Ia-d, or a stereoisomer, geometric isomer, tautomer, solvate, metabolite, or pharmaceutically acceptable salt or prodrug thereof, and the use of at least one other cancer treatment method. The amounts of the compound(s) of Formula Ia-d and the other pharmaceutically active chemotherapeutic agent(s) and the relative timings of administration will be selected in order to achieve the desired combined therapeutic effect.

Metabolites of Compounds of Formulas Ia-d

Also falling within the scope of this invention are the in vivo metabolic products of Formulas Ia-d described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formulas Ia-d, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Prodrugs of Formula Ia-d Compounds

In addition to compounds of Formulas Ia-d, the invention also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula Ia-d can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 *"Design and Application of Prodrugs,"* by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Articles of Manufacture

In another embodiment of the invention, an article of manufacture, or "kit", containing materials useful for the treatment of the diseases and disorders described above is provided. In one embodiment, the kit comprises a container comprising a compound of Formula Ia-d, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula Ia-d or a formulation thereof which is effective for treating the condition and may have a sterile access port (for example, the container may be an intravenous solution bag or a vial having a stopper pierceable by a hypodermic injection needle). At least one active agent in the composition is a compound of Formula Ia-d. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula Ia-d can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula Ia-d and, if present, the second pharmaceutical formulation. For example, if the kit comprises a first composition comprising a compound of Formula Ia-d and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula Ia-d, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula Ia-d contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula Ia-d and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures

General Procedure A Suzuki Coupling:

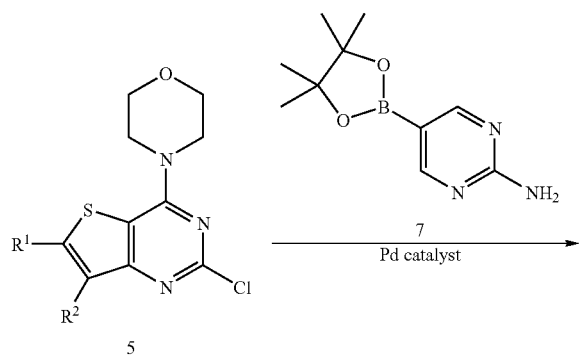

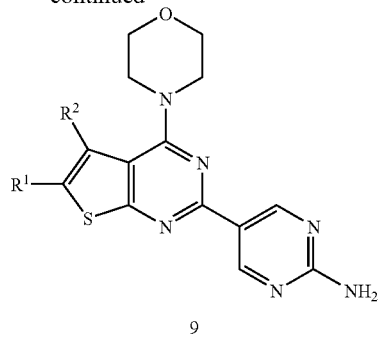

The Suzuki-type coupling reaction is useful to attach a monocyclic heteroaryl at the 2-position of the pyrimidine ring (see Scheme 4). Generally, substituted 2-chloro-4-morpholinothieno[3,2-d]pyrimidine 5 or substituted 2-chloro-4-morpholinothieno[2,3-d]pyrimidine 6 may be combined with 1.5 equivalents of 5-(4,4,5,5-tetramethyl-1,3,2-dioxaborolan-2-yl)pyrimidin-2-amine 7, and dissolved in 3 equivalents of sodium or potassium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the pinacol boronic ester indicated. Also alternatively, the nitrogen of the pyrimidin-2-amine may be protected, for example with a tetrahydropyranyl group. In some cases potassium acetate was used in place of sodium carbonate to adjust the pH of the aqueous layer. The reaction was then heated, for example to about 100-150° C. under pressure in a Biotage Optimizer microwave reactor (Biotage, Inc.) for 10 to 30 minutes. The contents are extracted with ethyl acetate, or another organic solvent. After evaporation of the organic layer the product, 8 or 9, may be purified on silica or by reverse phase HPLC.

General Procedure B-1 Amide Coupling:

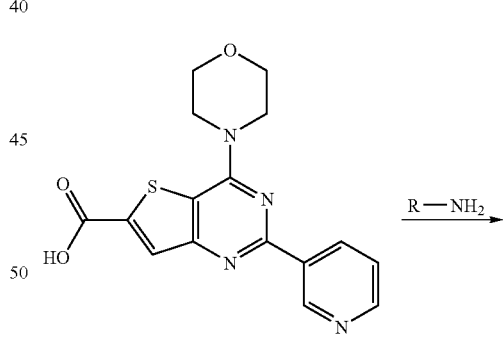

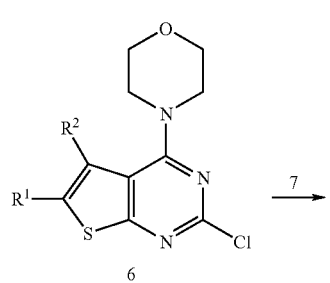

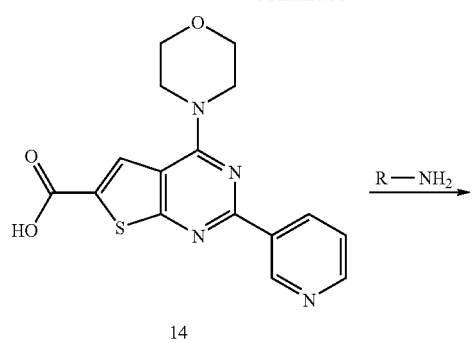

14

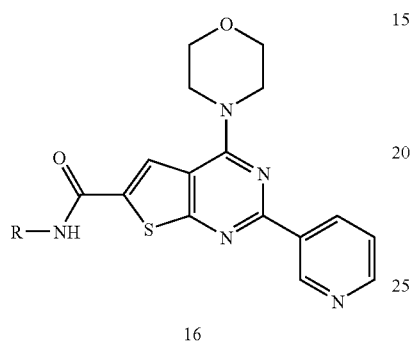

16

4-Morpholino-2-(pyridin-3-yl)thieno[3,2-d]pyrimidine-6-carboxylic acid 13 or 4-morpholino-2-(pyridin-3-yl)thieno[2,3-d]pyrimidine-6-carboxylic acid 14 is treated with 1.5 eq HATU, 3 eq of an alkylamine (R—NH$_2$) and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15 or 16.

General Procedure B-2 Amide Coupling:

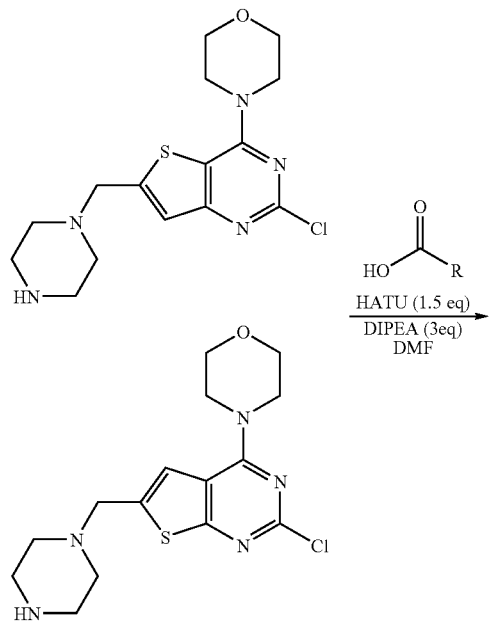

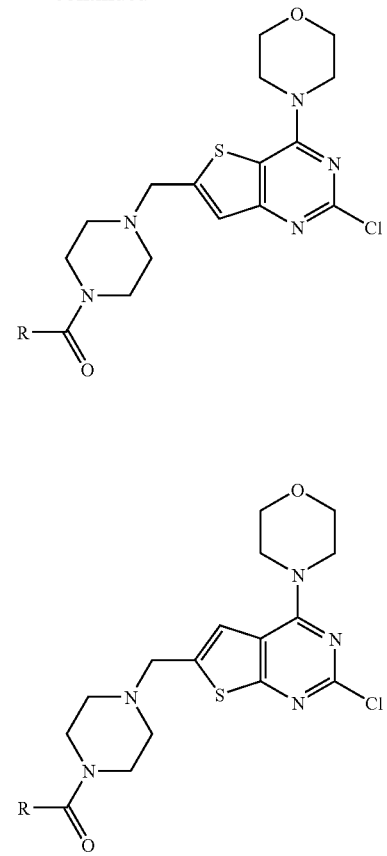

2-Chloro-4-morpholino-6-((piperazin-1-yl)methyl)thieno[3,2-d]pyrimidine or 2-chloro-4-morpholino-6-((piperazin-1-yl)methyl)thieno[2,3-d]pyrimidine is treated with 1.5 eq HATU, 3 eq of carboxylic acid (RCO$_2$H) and 3 eq of DIPEA in DMF to approximately 0.1 M concentration. The reaction is stirred until complete and extracted in ethyl acetate with saturated bicarbonate solution one time. The organic layer is dried, filtered and concentrated to yield the crude intermediate.

General Procedure B-3 Reductive Amination:

-continued

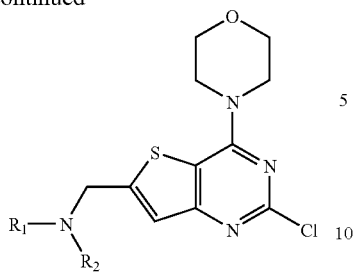

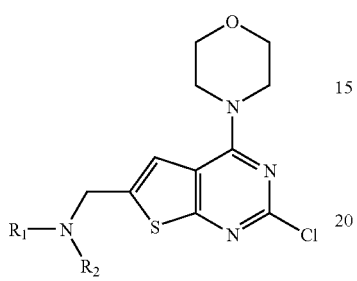

2-Chloro-4-morpholinothieno[3,2-d]pyrimidine-6-carbaldehyde 10 or 2-chloro-4-morpholinothieno[2,3-d]pyrimidine-6-carbaldehyde was dissolved to a 0.2 M concentration in dichloroethane. To this solution was added 1.5 to 2.0 equivalents of an amine ($R^1R^2NH$), 10 equivalents of trimethylorthoformate, and 1 equivalent of acetic acid. The mixture was allowed to stir for 2-6 hours prior to adding 1.5 equivalents of sodium triacetoxyborohydride. Following 12 to 16 hours of stirring the reaction was poured into saturated sodium bicarbonate and extracted several times with ethyl acetate. This intermediate was either purified on silica gel or used crude in the next reaction.

General Procedure B-4 Reductive Amination and Acylation:

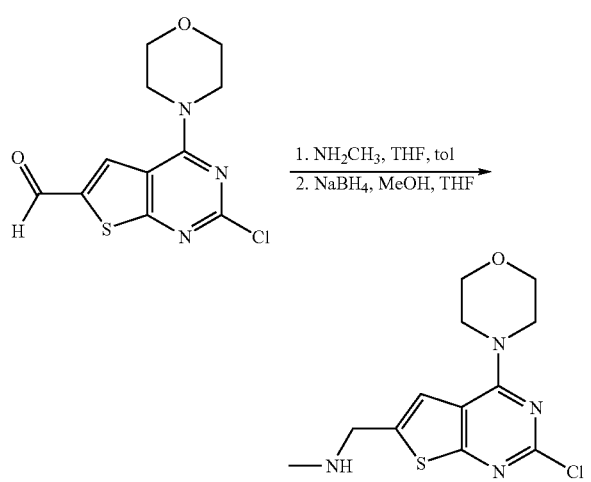

To 2-chloro-4-morpholinothieno[2,3-d]pyrimidine-6-carbaldehyde (2.0 g) in 50 mL toluene and 50 mL THF was added 20 mL of 40% methylamine in H₂O. The reaction mixture was stirred at room temperature under N₂ for 24 hours. The solvents were removed in vacuo and the residue was dissolved in 50 mL MeOH and 50 mL THF and the NaBH₄ added portion-wise. This reaction mixture was stirred at room temperature under N₂ for 24 hours and complete reaction was confirmed by LCMS. The solvents were removed in vacuo and the crude product purified by flash chromatography (EtOAc/EtOH) to give 1.12 g (2-chloro-4-morpholinothieno[2,3-d]pyrimidin-6-yl)-N-methylmethanamine (53% yield). MS (Q1) 300 (M+).

To a 0.25 to 0.40 M solution of (2-chloro-4-morpholinothieno[2,3-d]pyrimidin-6-yl)-N-methylmethanamine in DCM cooled to 0 C was added 1.5 eq. of TEA, followed by the drop wise addition of 1 to 1.5 eq. of an alkyl or aryl-acid chloride or sulfonylchloride, diluted in DCM. The reaction was stirred at ambient temperature and monitored for completeness by LC/MS. After completion, the reaction volume was increased with DCM, and dilute aqueous sodium bicarbonate was added to the solution. The organic and aqueous layers were separated. Finally the organic layer was washed with brine and dried (MgSO₄). The dried organic solution was concentrated in vacuo and purified by silica chromatography to give acylated compounds including N-((2-chloro-4-morpholinothieno[2,3-d]pyrimidin-6-yl)methyl)-N-methylacetamide (acetyl chloride, 68% yield, MS (Q1) 390.1 (M+), N-((2-chloro-4-morpholinothieno[2,3-d]pyrimidin-6-yl)methyl)-N-methylnicotinamide (nicotinyl chloride, 50% yield, MS (Q1) 404 (M+), and N-((2-chloro-4-morpholinothieno[2,3-d]pyrimidin-6-yl)methyl)-N-methylbenzamide (benzoyl chloride, 25% yield, MS (Q1) 403 (M+), or sulfonated compounds including (2-chloro-4-morpholinothieno[2,3-d]pyrimidin-6-yl)-N-methyl-N-(methylsulfono)methanamine (methanesulfonyl chloride, 56% yield, MS (Q1) 300 (M+).

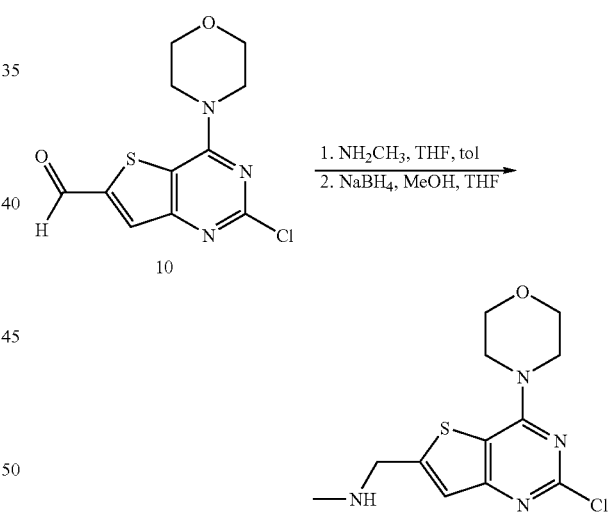

2-Chloro-4-morpholinothieno[3,2-d]pyrimidine-6-carbaldehyde 10 (2.0 g) was dissolved in 50 mL toluene and 50 mL THF followed by the addition of 20 mL of 40% methylamine in H₂O. The reaction mixture was stirred at room temperature under N₂ for 24 hours. The solvents were removed in vacuo and the residue was dissolved in 50 mL MeOH and 50 mL THF and the NaBH₄ added portion-wise. This reaction mixture was stirred at room temperature under N₂ for 24 hours and complete reaction was confirmed by LCMS. The solvents were removed in vacuo and the crude product purified by flash chromatography (EtOAc/EtOH) to give 1.12 g (2-chloro-4-morpholinothieno[3,2-d]pyrimidin-6-yl)-N-methylmethanamine (53% yield). MS (Q1) 300 (M+).

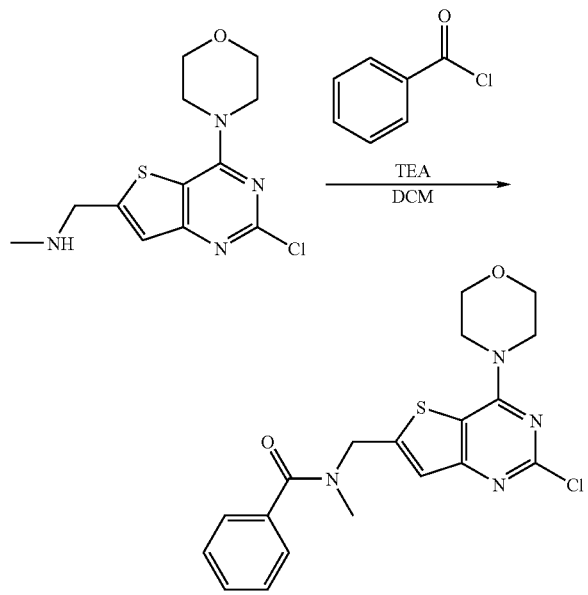

(2-Chloro-4-morpholinothieno[3,2-d]pyrimidin-6-yl)-N-methylmethanamine, was dissolved in 10 mL of dichloromethane and cooled to 0° C. under N₂ and 1.3 eq. triethylamine and 1.2 eq. benzoyl chloride was added. The reaction mixture was warmed to room temperature and stirred 24 hours at which time product formation was confirmed by LCMS. The reaction was diluted with 1 M HCl, extracted with dichloromethane, dried over MgSO₄, and concentrated in vacuo. This crude product was purified by flash chromatography (EtOAc/hexanes) to give 0.45 g N-((2-chloro-4-morpholinothieno[3,2-d]pyrimidin-6-yl)methyl)-N-methylbenzamide (67% yield). MS (Q1) 404 (M+).

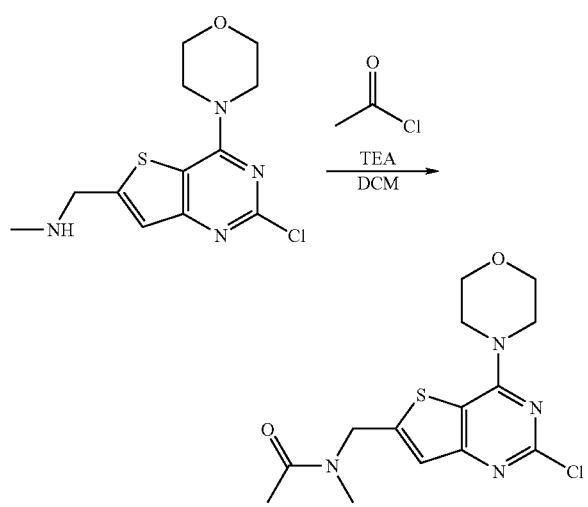

Alternatively, (2-chloro-4-morpholinothieno[3,2-d]pyrimidin-6-yl)-N-methylmethanamine was dissolved in 10 mL of dichloromethane and cooled to 0° C. under N₂ and 1.3 eq. triethylamine and 1.2 eq. acetyl chloride was added. This reaction mixture was allowed to warm to room temperature and stirred 24 hours at which time product formation was confirmed by LCMS. The reaction was concentrated in vacuo and purified by flash chromatography to give 0.61 g N-((2-chloro-4-morpholinothieno[3,2-d]pyrimidin-6-yl)methyl)-N-methylacetamide (64% yield). MS (Q1) 341 (M+).

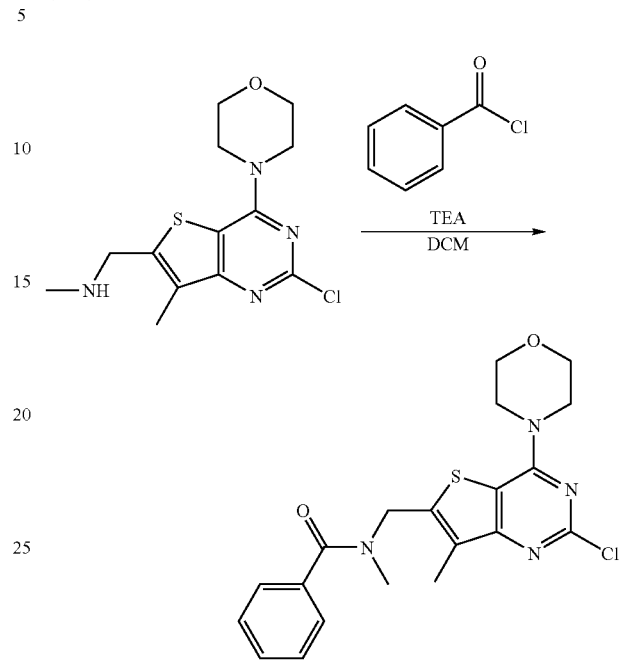

Alternatively, (2-chloro-7-methyl-4-morpholinothieno[3,2-d]pyrimidin-6-yl)-N-methylmethanamine (4.06 mmol) was dissolved in 10 mL of dichloromethane, cooled to 0° C. under N₂, and 1.3 eq. triethylamine and 1.2 eq. benzoyl chloride were added. The reaction mixture was allowed to warm to room temperature and stirred 24 hours at which time product formation was confirmed by LCMS. The reaction was concentrated in vacuo. The crude product was purified by flash chromatography (EtOAc/Hexanes) to give 1.69 g N-((2-chloro-7-methyl-4-morpholinothieno[3,2-d]pyrimidin-6-yl)methyl)-N-methylbenzamide (100% yield). MS (Q1) 419 (M+).

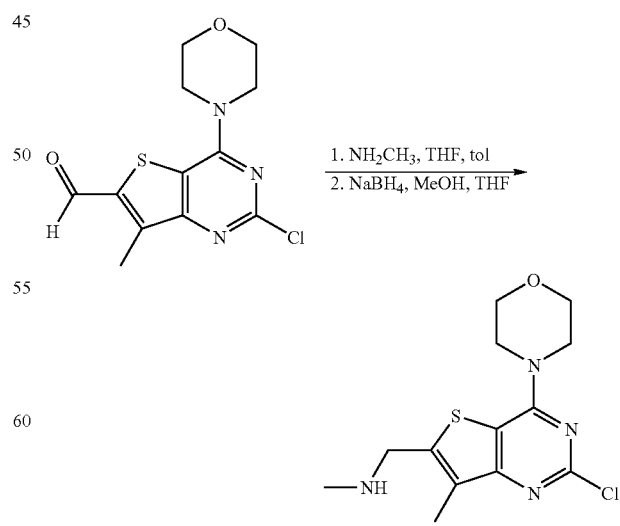

2-Chloro-7-methyl-4-morpholinothieno-[3,2-d]pyrimidine-6-carbaldehyde was dissolved in 20 mL toluene and 20 mL THF followed by the addition of 15 mL 40% methylamine in H$_2$O and the reaction was stirred for 24 hours. The reaction mixture was concentrated in vacuo and the residue dissolved in 30 mL MeOH and 30 mL THF followed by the addition of NaBH$_4$. The reaction was stirred at room temperature for at least 24 hours and product formation was confirmed by LCMS. The solvents were removed in vacuo and the crude product purified by flash chromatography to give 2.53 g of (2-chloro-7-methyl-4-morpholinothieno[3,2-d]pyrimidin-6-yl)-N-methylmethanamine. (70% yield) MS (Q1) 314 (M)+

General Procedure B-5 Carbinamine Formation:

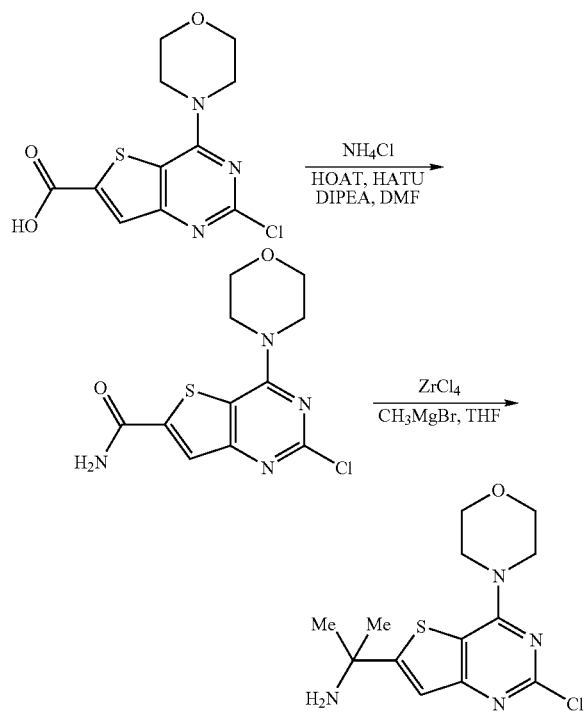

To a mixture of 4-morpholino-2-(pyridine-3-yl)thieno[3,2-d]pyrimidine-6-carboxylic acid (610 mg, 2.04 mmol), 1-hydroxy-7-azabenzotriazole (56 mg, 0.4 mmol), O-(7-azabenzotriazol-1-yl)-(N,N,N',N'-tetramethyluronium hexafluorophosphate (HATU; 1.2 g, 3.1 mmol), and N,N-diisopropylethylamine (1.4 mL, 8.1 mmol) in DMF (3 mL) was added ammonium chloride (330 mg, 6.1 mmol). The reaction mixture was stirred overnight at room temperature. The mixture was diluted with EtOAc, washed with saturated aqueous NaHCO$_3$ and brine. The aqueous layer was extracted with EtOAc. The combined organics were washed with saturated NaHCO$_3$ and brine then dried over MgSO$_4$, filtered and concentrated in vacuo. The residue was purified by silica gel chromatography (0-20% MeOH in CH$_2$Cl$_2$) to afford 2-chloro-4-morpholinothieno[3,2-d]pyrimidine-6-carboxamide (490 mg, 81% yield).

Zirconium (IV) chloride (780 mg, 3.3 mmol) was added to a mixture of 2-chloro-4-morpholinothieno[3,2-d]pyrimidine-6-carboxamide (400 mg, 1.3 mmol) in THF (8 mL) at −10° C. The reaction mixture was stirred for 1 h at −10° C. A solution of methylmagnesium bromide (2.7 mL, 3 M in Et$_2$O) was added dropwise. The resulting mixture was warmed to room temperature and stirred overnight. The reaction was quenched by the addition of water. The organic layer was separated and the aqueous layer was extracted with EtOAc. The aqueous solution was then basified with saturated NaHCO$_3$ and again extracted with EtOAc. The combined organic layers were dried over MgSO$_4$, filtered, and concentrated in vacuo. The crude mixture was purified by silica gel chromatography (0-15% MeOH in CH$_2$Cl$_2$) to afford 2-(2-chloro-4-morpholinothieno[3,2-d]pyrimidin-6-yl)propan-2-amine (220 mg, 53% yield).

General Procedure C-1 Sulfonamide Formation:

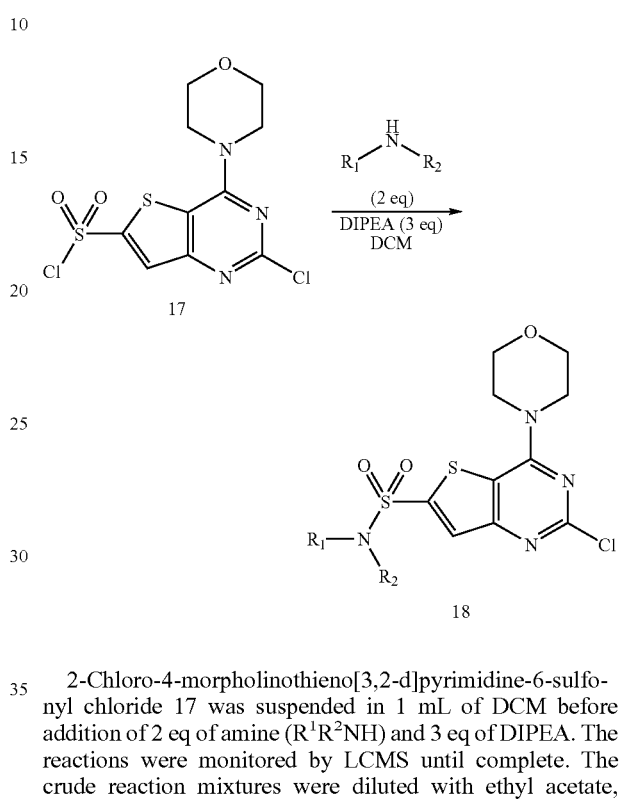

2-Chloro-4-morpholinothieno[3,2-d]pyrimidine-6-sulfonyl chloride 17 was suspended in 1 mL of DCM before addition of 2 eq of amine (R$^1$R$^2$NH) and 3 eq of DIPEA. The reactions were monitored by LCMS until complete. The crude reaction mixtures were diluted with ethyl acetate, extracted with saturated ammonium chloride and back-extracted once with ethyl acetate. The organic layers were combined and concentrated to dryness. The crude sulfonamide intermediates 18 were used directly in the subsequent Suzuki couplings.

General Procedure C-2 Sulfonamide Formation

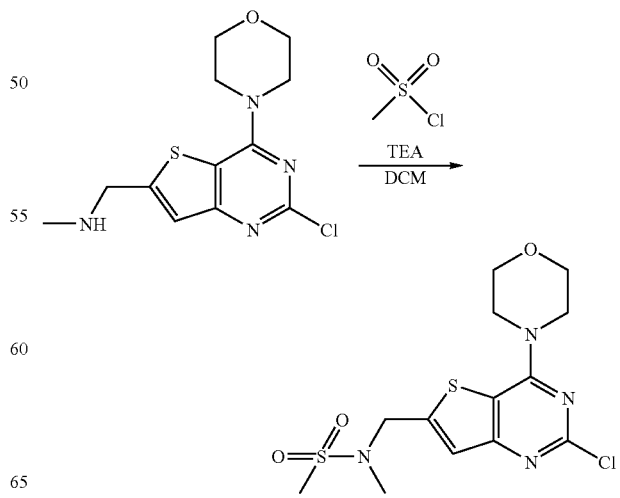

(2-Chloro-4-morpholinothieno[3,2-d]pyrimidin-6-yl)-N-methyl,N-methaneysulfonylmethanamine was synthesized when (2-chloro-4-morpholinothieno[3,2-d]pyrimidin-6-yl)-N-methylmethanamine (3.67 mmol) was dissolved in 10 mL of dichloromethane and cooled to 0° C. under $N_2$ and 1.3 eq. triethylamine and 1.2 eq. methanesulfonyl chloride was added. This reaction mixture was allowed to warm to room temperature and stirred 24 hours at which time product formation was confirmed by LCMS. The reaction was diluted with $H_2O$ and 1 M HCl, extracted with dichloromethane, dried over $MgSO_4$, and concentrated in vacuo. The crude product (2-chloro-4-morpholinothieno[3,2-d]pyrimidin-6-yl)-N-methyl,N-methanesulfonylmethanamine (1.38 g, 100% yield) was 97-100% pure by LCMS. MS (Q1) 377 (M)+

General Procedure D-1 Alcohol Synthesis

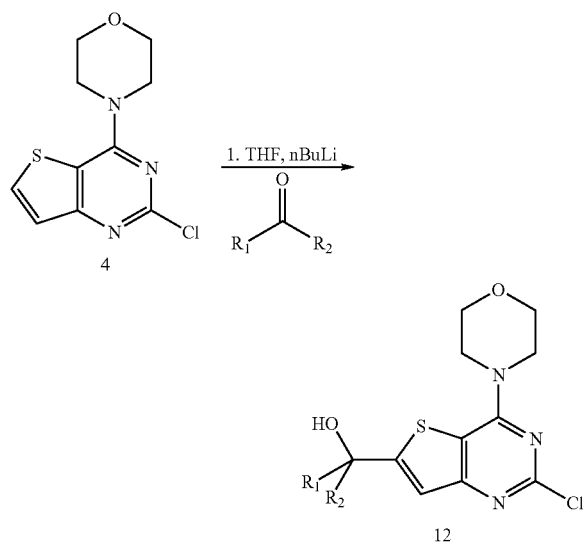

2-Chloro-4-morpholinothieno[3,2-d]pyrimidine 4 was suspended to a 0.2 molar concentration in THF and cooled to −50° C. in a dry ice/acetonitrile bath before adding 2 equivalents of 2.5 M nBuLi in hexanes. After 15 min 3.0 molar equivalents of a cyclic or acyclic ketone was added to the solution. The reaction continued to stir at −50° C. for 1 h and then in most cases was allowed to come to 0° C. When the reaction was complete by TLC or mass spec. it was quenched into a saturated ammonium chloride solution and extracted two times with EtOAc. The organic layer was concentrated and either used as a crude mixture, purified on silica, or the product 12 could be dissolved in a minimal amount of acetonitrile and filtered to remove remaining starting material 4.

General Procedure D-2 Aldehyde Synthesis

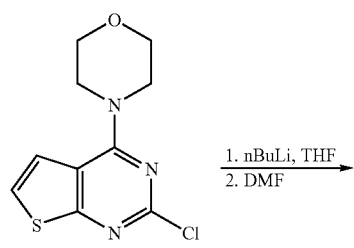

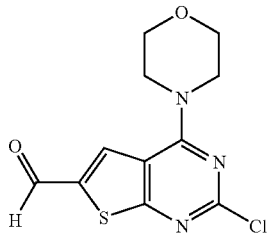

To a suspension of 2-chloro-4-morpholinothieno[2,3-d]pyrimidine (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 μL, 1.5 eq.) was added. The reaction mixture was stirred for 1 h at −78° C. and then warmed slowly to room temperature. After a further 2 h at room temperature the reaction mixture was poured onto ice/water yielding a yellow precipitate. This was collected by filtration and air-dried to yield 2-chloro-4-morpholinothieno[2,3-d]pyrimidine-6-carbaldehyde (1.50 g) MS (Q1) 284 (M+).

General Procedure D-3 2-Iodo Synthesis

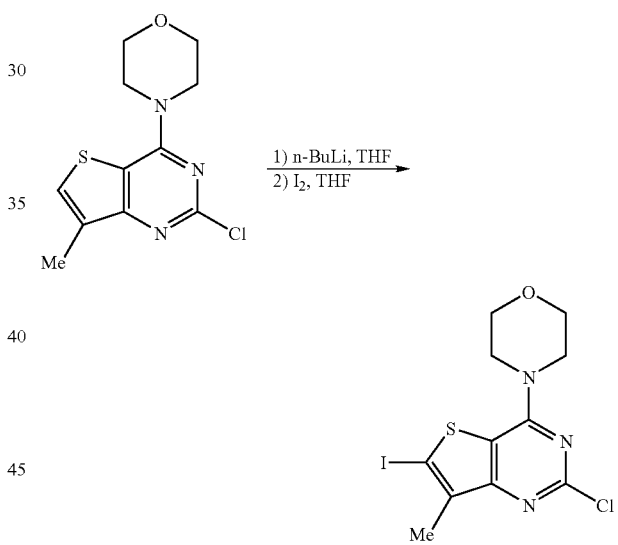

To a solution of 2-chloro-7-methyl-4-morpholinothieno[3,2-d]pyrimidine (3.0 g, 11.1 mmol; prepared according to the procedure for the synthesis of 2-Chloro-4-morpholin-4-yl-thieno[3,2-d]pyrimidine but commencing with 3-amino-4-methyl-thiophene-2-carboxylic acid ethyl ester) in THF (60 mL) at −78° C. was added n-BuLi (8.9 mL, 2.5 M in $Et_2O$). The resulting slurry was warmed to −40° C. and stirred 50 min. The reaction mixture was then cooled to −78° C. and a solution of 12 (5.6 g, 22.2 mmol) in THF (30 mL) was added. The solution was warmed to room temperature and stirred 5 h. The reaction was quenched by the addition of water. The organic layer was separated and the aqueous layer was extracted with $CH_2Cl_2$. The combined organics were washed with saturated aqueous $Na_2S_2O_3$, dried over $Na_2SO_4$, filtered, and concentrated in vacuo to provide 2-chloro-6-iodo-7-methyl-4-morpholinothieno[3,2-d]pyrimidine (3.8 g, 84% yield).

General Procedure E Removal of t-butoxycarbonyl (BOC) Group

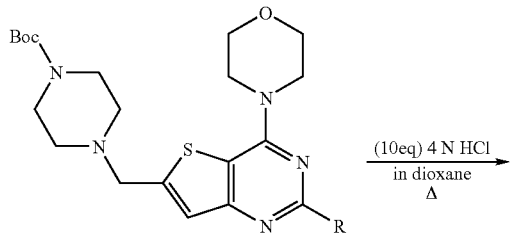

Ten or more equivalents of 4N HCl in Dioxane, with or without dichloromethane as a co-solvent, are added to the starting material (general scheme shown above but similar scaffolds also used). Heating up to 40° C. for several hours is occasionally required to remove the boc group. The reaction may be concentrated to dryness and used crude in subsequent reactions.

General Procedure F-1 Suzuki Coupling Reactions in One Pot

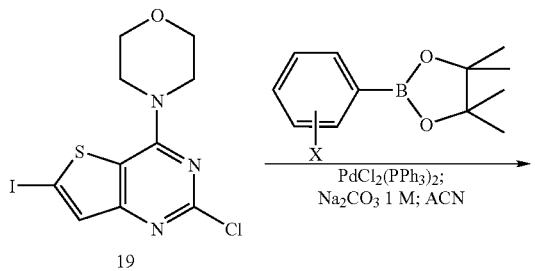

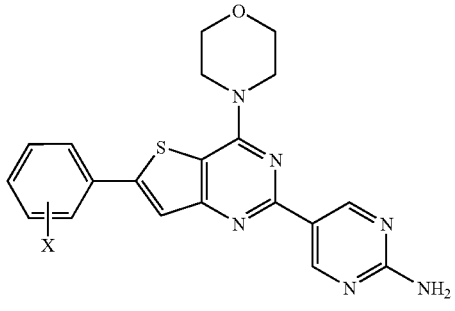

2-Chloro-6-iodo-4-morpholinothieno[3,2-d]pyrimidine 19, (example 12) (1 eq), optionally substituted phenylboronic acid or heterocycleboronic acid (1.1 eq) and bis(triphenylphosphine)palladium(II) dichloride (0.1 eq) in 1M Na$_2$CO$_3$ aqueous solution (3 eq) and an equal volume of acetonitrile was heated to 100° C. in a sealed microwave reactor for 10-40 min to give 84. Upon completion (purification was sometimes necessary), 5-(4,4,5,5-tetramethyl-1,3,2-dioxaborolan-2-yl)pyrimidin-2-amine (1.7 eq) (or other boronic acid/ester) and bis(triphenylphosphine)palladium(II) dichloride (0.1 eq) were added in the same pot. The reaction mixture was heated to 150° C. in a sealed microwave reactor for 10-15 min. The mixture was extracted with ethyl acetate (3×5 mL). The combined organic layers were concentrated to yield crude 85.

General Procedure F-2 Suzuki Coupling Reactions in One Pot

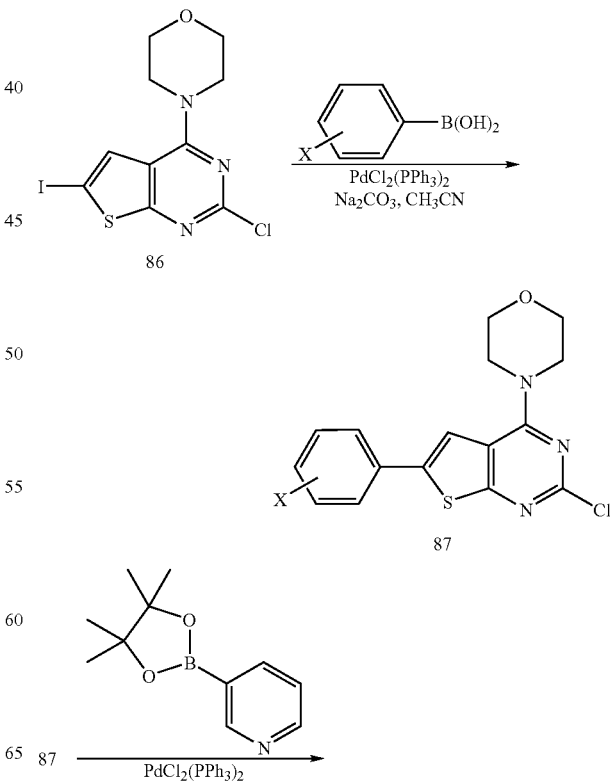

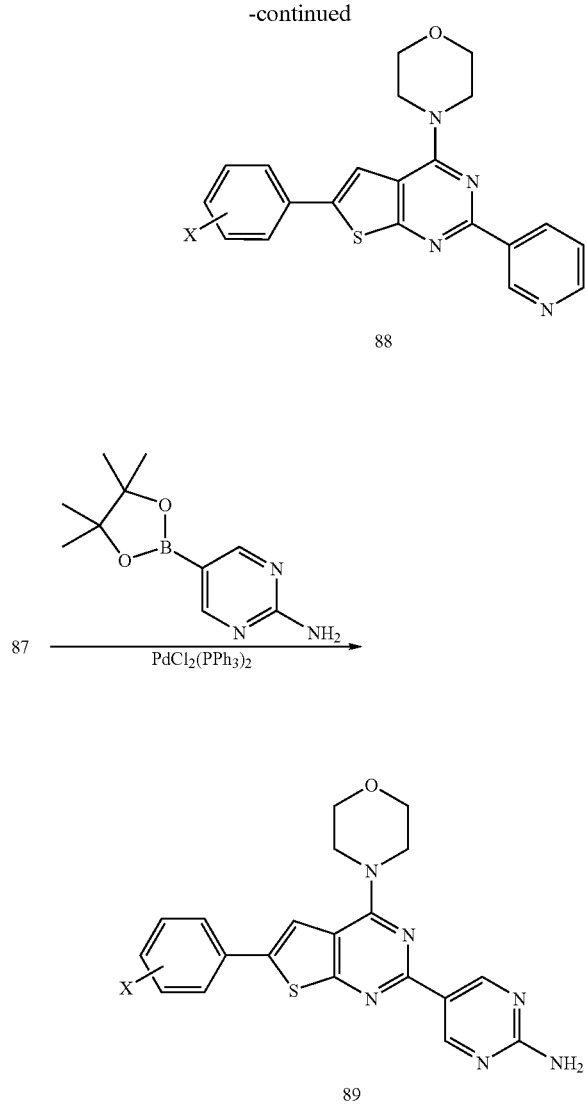

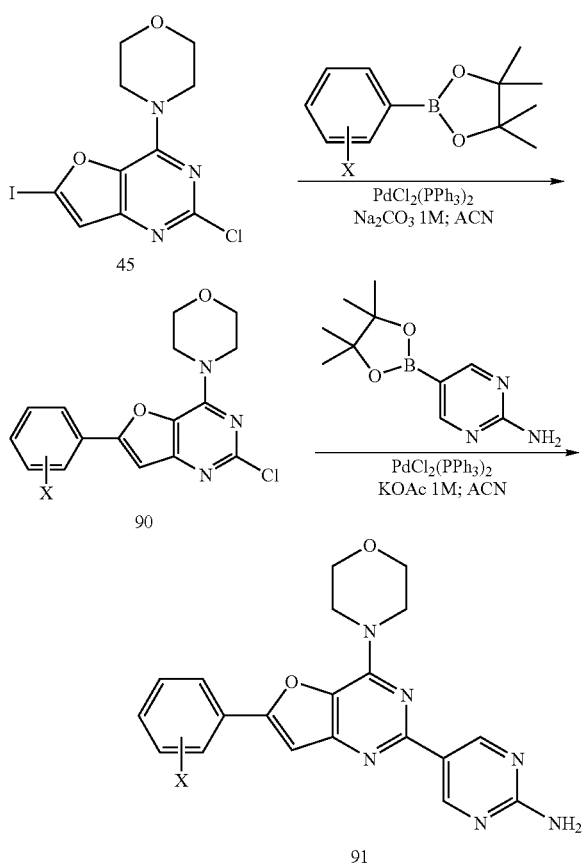

2-Chloro-6-iodo-4-morpholinothieno[3,2-d]pyrimidine 19 (1 eq), optionally substituted phenylboronic acid or heterocycleboronic acid (1.1 eq) and bis(triphenylphosphine)palladium(II) dichloride (0.1 eq) in 1M $Na_2CO_3$ aqueous solution (3 eq) and acetonitrile (3 eq) was heated to 100° C. in a sealed microwave reactor for 10-40 min to give 87. The optionally substituted phenylboronic acid or heterocycleboronic acid reagents may be pinacol boronates (4,4,5,5-tetramethyl-1,3,2-dioxaboro). Upon completion, 3-(4,4,5,5-tetramethyl-1,3,2-dioxaborolan-2-yl)pyridine (1.3 eq) and bis(triphenylphosphine)palladium(II) dichloride (0.1 eq) were added in the same pot to 87. The reaction mixture was heated to 150° C. in a sealed microwave reactor for 10-15 min. The mixture was extracted with ethyl acetate (3×5 mL). The combined organic layers were concentrated to yield crude 88. Alternatively, 5-(4,4,5,5-tetramethyl-1,3,2-dioxaborolan-2-yl)pyrimidin-2-amine (1.7 eq) (or other boronic acid/ester) and bis(triphenylphosphine)palladium(II) dichloride (0.1 eq) were added in the same pot. The reaction mixture was heated to 150° C. in a sealed microwave reactor for 10-15 min. The mixture was extracted with ethyl acetate (3×5 mL). The combined organic layers were concentrated to yield crude 89.

General Procedure F-3 Suzuki Coupling Reactions in One Pot

2-Chloro-6-iodo-4-morpholinofuro[3,2-d]pyrimidine 45 (Example 27) (1 eq), optionally substituted phenylboronic acid or heterocycleboronic acid (1.1 eq) and bis(triphenylphosphine)palladium(II) dichloride (0.1 eq) in 1M $Na_2CO_3$ aqueous solution (3 eq) and an equal volume of acetonitrile was heated to 100° C. in a sealed microwave reactor for 10-40 min to give 90. Upon completion (purification was sometime necessary), 5-(4,4,5,5-tetramethyl-1,3,2-dioxaborolan-2-yl)pyrimidin-2-amine (1.7 eq) (or other boronic acid/ester) and bis(triphenylphosphine)palladium(II) dichloride (0.1 eq) were added in the same pot. The reaction mixture was heated to 150° C. in a sealed microwave reactor for 10-15 min. The mixture was extracted with ethyl acetate (3×5 mL). The combined organic layers were concentrated to yield crude 91.

General Procedure G Amide Coupling Reaction

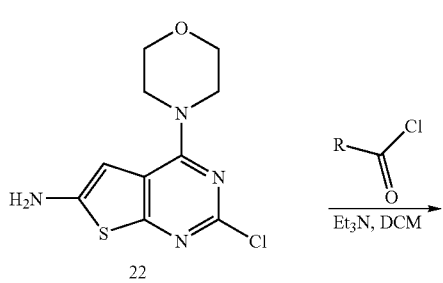

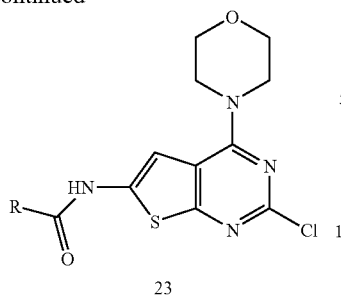

2-Chloro-4-morpholinothieno[3,2-d]pyrimidin-6-amine 22 (1 eq), acid chloride (1.5-2 eq) and triethylamine (2 eq) in dichloromethane was stirred. The reaction was monitored by LC/MS until complete. The mixture was evaporated to give the crude amide 23, which was directly used for the next step reaction without purification.

General Procedure H Amine Substitution on Fluoropyridine Followed by Suzuki Coupling Reaction.

4-(2-Chloro-6-(6-fluoropyridin-3-yl)thieno[3,2-d]pyrimidin-4-yl)morpholine 20 (1.0 eq), primary or secondary amine (4.0 eq) and diisopropylethylamine (2.0 eq) in N-methylpyrrolidine (~0.1M) was heated to 130-140° C. in a sealed microwave reactor for 10~40 min to give 21. Upon completion, N-methylpyrrolidine was concentrated under high vacuum and crude mixture was purified by flash chromatography to give intermediate 21, which was then treated with 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile was heated to 130-150° C. in a sealed microwave reactor for 7-20 min. The mixture was extracted with ethyl acetate (3×5 mL). The combined organic layers were concentrated to yield crude 22.

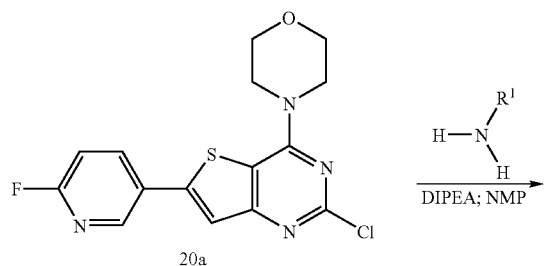

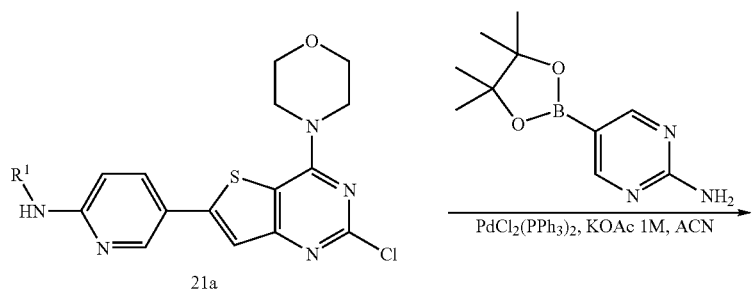

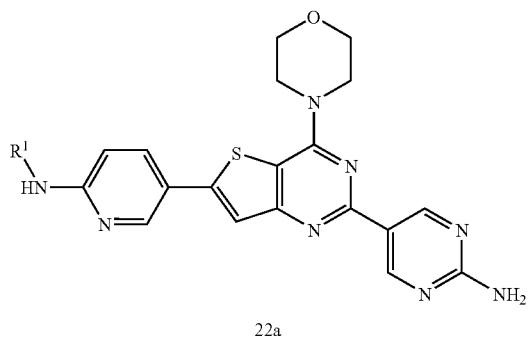

General Procedure I Amide Coupling Reaction for Benzenamine

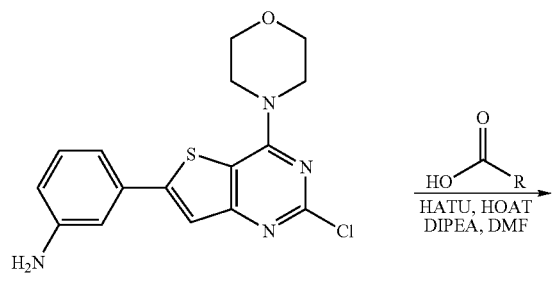

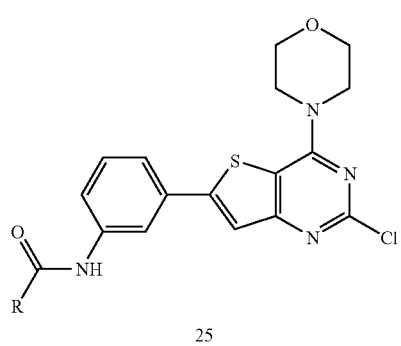

3-(2-Chloro-4-morpholinothieno[3,2-d]pyrimidin-6-yl) benzenamine 24 (1 eq), alkyl- or arylcarboxylic acid (1.5 eq), 1-hydroxy-7-azabenzotriazole (0.2 eq), O-(7-azabenzotriazol-1-yl)-(N,N,N',N'-tetramethyluronium hexafluorophosphate (HATU, 1.5 eq), and N,N-diisopropylethylamine (2.5 eq) in DMF was stirred at room temperature. The reaction was monitored by LC/MS until complete. The reaction mixture was diluted with ethyl acetate, washed with saturated sodium bicarbonate and brine. The organic layer was dried over $MgSO_4$, filtered and evaporated to yield amide product 25.

General Procedure J 6-Iodo Displacement and 2-Suzuki Coupling

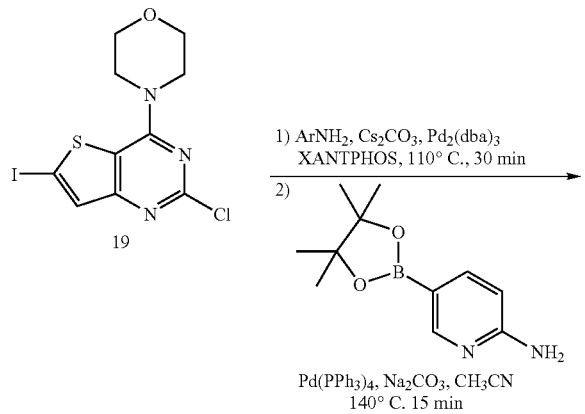

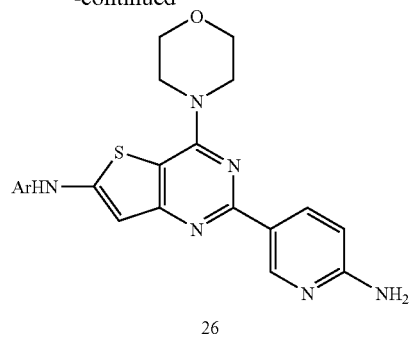

To a solution of 2-chloro-6-iodo-4-morpholinothieno[3,2-d]pyrimidine 19 (0.05 g, 0.13 mmol) in DMF (1.00 mL) was added the appropriate aniline (200 mol %), $Cs_2CO_3$ (50 mol %), $Pd_2(dba)_3$ (5 mol %), and XANTPHOS (10 mol %). The reaction was heated to 110° C. under pressure in a Biotage optimizer microwave reactor for 30 min. The resulting solution was concentrated in vacuo to give 26, after following General Procedure A.

General Procedure K 6-Aminoalkyl Acylation and 2-Suzuki Coupling

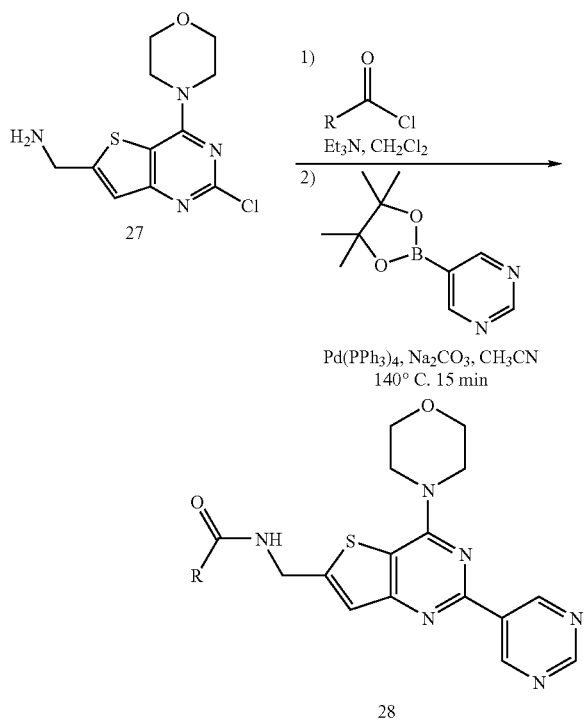

To a solution of 2-chloro-4-morpholinothieno[3,2-d]pyrimidin-6-yl)methanamine 27 (50 mg, 0.2 mmol) in $CH_2Cl_2$ (4 mL) was added $Et_3N$ (84 µL, 0.6 mmol) and the appropriate acid chloride or HCl salt thereof (0.3 mmol). The reaction stirred 18-48 hr at room temperature before being quenched with water. The aqueous layer was extracted with EtOAc. The combined organics were dried over $Na_2SO_4$ and concentrated in vacuo. The 2-chloro crude product was coupled with 5-(4,4,5,5-tetramethyl-1,3,2-dioxaborolan-2-yl)pyrimidine and tetrakis triphenylphosphine palladium catalyst according to General Procedure A to give 28 which was purified by reversed phase HPLC purification.

General Procedure L Amine Substitution on Fluoropyridine Followed by Suzuki Coupling Reaction.

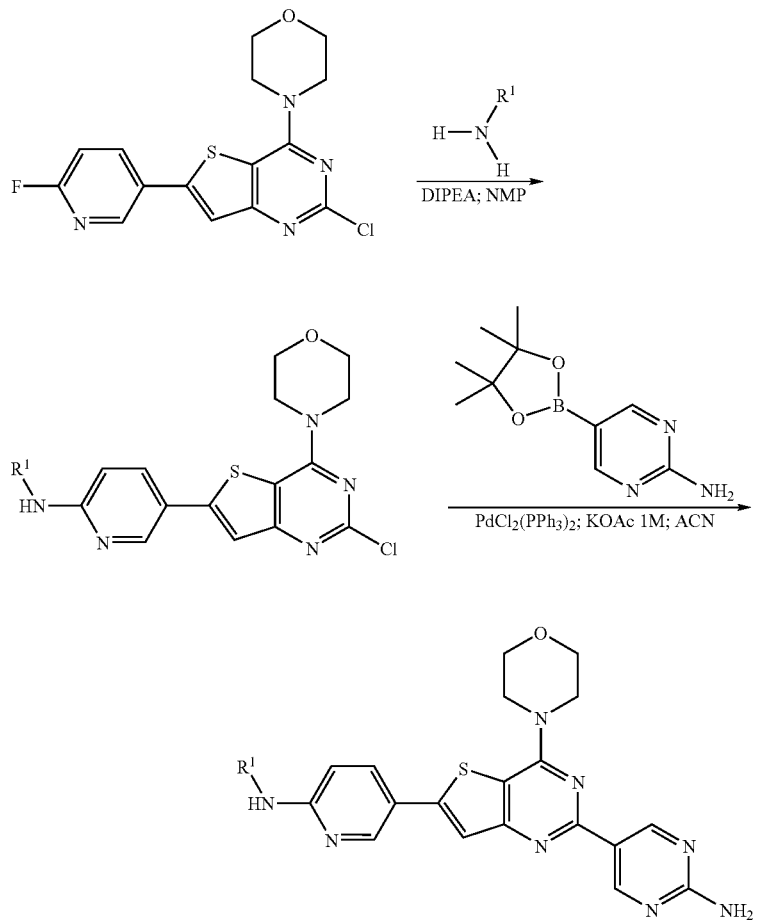

2-Chloro-6-(6-fluoropyridin-3-yl)-4-morpholinothieno[3,2-d]pyrimidine (1.0 eq), primary or secondary amine (4.0 eq) and diisopropylethylamine (2.0 eq) in N-methylpyrrolidine (~0.1M) were heated to 130-140° C. in a sealed microwave reactor for 10-40 min to give amine substituted product. Upon completion, N-methylpyrrolidine was concentrated under high vacuum and crude mixture was purified by flash chromatography to give purified amine substituted intermediate, which was then treated with 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile (3 eq) was heated to 130-150° C. in a sealed microwave reactor for 7-20 min. The mixture was extracted with ethyl acetate (3×5 mL). The combined organic layers were concentrated to yield crude pyrimidin-2-amine product.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2,4-Dichloro-thieno[3,2-d]pyrimidine 3

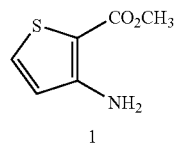 

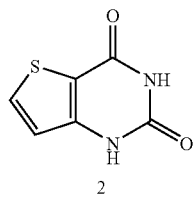  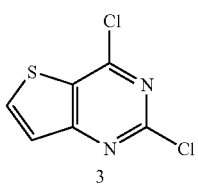

A mixture of methyl 3-amino-2-thiophenecarboxylate 1 (13.48 g, 85.85 mmol) and urea (29.75 g, 5 eq.) was heated at 190° C. for 2 hours. The hot reaction mixture was poured onto sodium hydroxide solution and any insoluble material was removed by filtration. The mixture was then acidified (HCl, 2N) to yield 1H-thieno[3,2-d]pyrimidine-2,4-dione 2 as a white precipitate, which was collected by filtration and air dried (9.49 g, 66%). $^1$H NMR 400 MHz, $d_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione 2 (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine 3 as a white solid (8.68 g, 75%). $^1$H NMR (400 MHz, CDCl$_3$) 7.56 (1H, d, J=5.5 Hz), 8.13 (1H, d, J=5.5 Hz).

Example 2

2-Chloro-4-morpholin-4-yl-thieno[3,2-d]pyrimidine 4

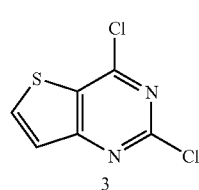 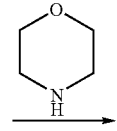

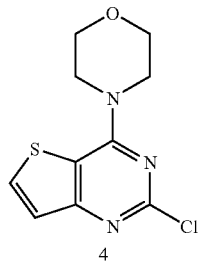

A mixture of 2,4-dichloro-thieno[3,2-d]pyrimidine 3, (8.68 g, 42.34 mmol), morpholine (8.11 mL, 2.2 eq.) and MeOH (150 mL) was stirred at room temperature for 1 h. The reaction mixture was then filtered, washed with water and MeOH, to yield 2-chloro-4-morpholin-4-yl-thieno[3,2-d]pyrimidine 4 as a white solid (11.04 g, 100%). $^1$H NMR (400 MHz, $d_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

Example 3

2-Chloro-4-morpholin-4-yl-thieno[3,2-d]pyrimidine-6-carbaldehyde 10

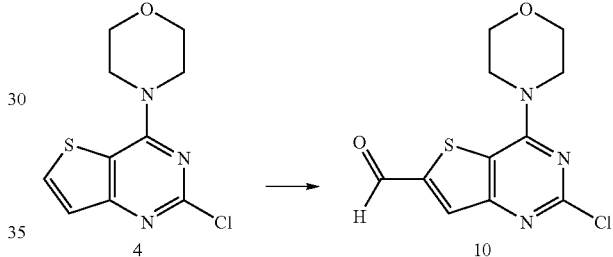

To a suspension of 2-chloro-4-morpholin-4-yl-thieno[3,2-d]pyrimidine 4 (1.75 g, 6.85 mmol) in dry THF (40 mL) at −78° C. was added a 2.5 M solution of n-butyllithium (nBuLi) in hexane (3.3 mL, 1.2 eq.). After stirring for 1 h, dry DMF (796 μL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield 2-chloro-4-morpholin-4-yl-thieno[3,2-d]pyrimidine-6-carbaldehyde 10 (1.50 g, 77%). $^1$H NMR (400 MHz, $d_6$-DMSO) 3.76 (4H, t, J=4.9), 3.95 (4H, t, J=4.9), 8.28 (1H, s), 10.20 (1H, s).

Example 8

(2-Chloro-4-morpholinothieno[3,2-d]pyrimidin-6-yl)methanol 29

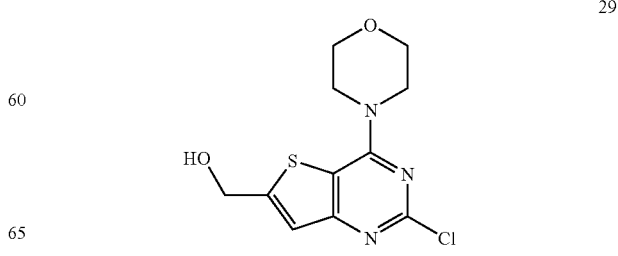

A solution of 2-chloro-4-morpholinothieno[3,2-d]pyrimidine-6-carbaldehyde 10 (Example 3, General Procedure B-3, 1.0 g, 3.5 mmol) in MeOH (30 mL) at 0° C. was treated with NaBH₄ (0.1 g, 3.5 mmol). The solution was allowed to warm to room temperature and stirred 15 min. The reaction mixture was quenched with a mixture of a saturated solution of sodium bicarbonate and water (1:1, v/v). The aqueous solution was extracted with EtOAc. The combined organic layers were dried over Na₂SO₄ and concentrated in vacuo. The crude material 29 required no further purification (0.9 g, 90%). MS (Q1) 286 (M)+

Example 9

6-(Bromomethyl)-2-chloro-4-morpholinothieno[3,2-d]pyrimidine 30

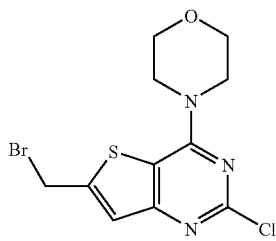

To a solution of (2-chloro-4-morpholinothieno[3,2-d]pyrimidin-6-yl)methanol 29 (100 mg, 0.4 mmol) in benzene (3.0 mL) at 0° C. was added PBr₃ (30 μL, 0.4 mmol). The reaction was heated at reflux for 1 hour. After cooling to room temperature the reaction was quenched by the addition of water. The aqueous layer was extracted with EtOAc. The combined organics were dried over Na₂SO₄ and concentrated in vacuo. The crude product 30 did not require further purification (115 mg, 94%). MS (Q1) 350 (M)+

Example 10

2-((2-Chloro-4-morpholinothieno[3,2-d]pyrimidin-6-yl)methyl)isoindoline-1,3-dione 31

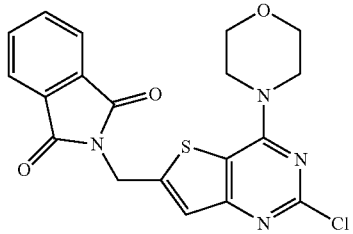

To a solution of 6-(bromomethyl)-2-chloro-4-morpholinothieno[3,2-d]pyrimidine 30 (0.3 g, 0.9 mmol) in DMF (10 mL) was added K₂CO₃ (0.2 g, 1.3 mmol), and phthalimide (0.1 g, 0.9 mmol). The resulting solution stirred 20 h at room temperature. The reaction was concentrated in vacuo and diluted with water (10 mL). The heterogeneous mixture was filtered to afford 2-((2-chloro-4-morpholinothieno[3,2-d]pyrimidin-6-yl)methyl)isoindoline-1,3-dione 31 (0.3 g, 75%). MS (Q1) 415 (M)+

Example 11

(2-Chloro-4-morpholinothieno[3,2-d]pyrimidin-6-yl)methanamine 27

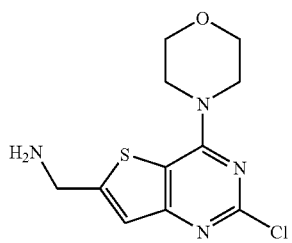

To a solution of 2-((2-chloro-4-morpholinothieno[3,2-d]pyrimidin-6-yl)methyl)isoindoline-1,3-dione 31 (100 mg, 0.24 mmol) in MeOH (7 mL) was added H₂NNH₂·H₂O (24 μL, 0.48 mmol). The reaction was heated at reflux for 1 h. After cooling to room temperature the reaction was quenched with water (10 mL) and extracted with EtOAc. The combined organics were dried over Na₂SO₄ and concentrated in vacuo to afford (2-chloro-4-morpholinothieno[3,2-d]pyrimidin-6-yl)methanamine 27 (0.05 g, 73%). MS (Q1) 285 (M)+

Example 12

2-Chloro-6-iodo-4-morpholinothieno[3,2-d]pyrimidine 19

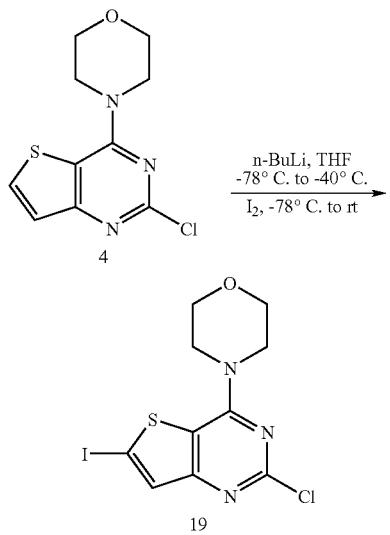

Following the procedures in U.S. Pat. No. 6,492,383, 2.5 M of n-Butylithium (9.4 mL, 22.48 mmol) in hexane solution was added to a mixture of 2-chloro-4-morpholinothieno[3,2-d]pyrimidine 4 (3.0 g, 11.74 mmol) in 60 mL of THF at −78° C. The reaction mixture was allowed to warm to −40° C. and stirred for 30 min. A solution of iodine (6.0 g, 23.48 mmol) in 10 mL of THF was added dropwise. After the addition was completed. The reaction mixture was brought to room temperature and stirred for 2 h. The mixture was quenched by diluting with dichloromethane and extracting with H₂O (2×100 mL). The organic layer was washed with Na₂S₂O₃ (2×100 mL), H₂O (2×100 mL), dried over MgSO₄, filtered and evaporated to afford 2-chloro-6-iodo-4-morpholinothieno[3,2-d]pyrimidine 19 (3.4 g, 75%).

Example 13

Tert-butyl furan-3-ylcarbamate 32

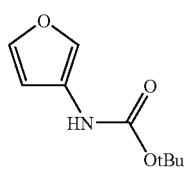

3-Furoic acid (5.60 g, 1.0 eq) was dissolved in tert-butanol (200 ml) and treated with triethylamine (10 ml, 1.4 eq) and diphenyl phosphoryl azide (12 ml, 1.1 eq). Mixture was heated at reflux for 18 h. Reaction mixture was cooled to room temperature, then concentrated to 50 ml and poured into saturated aq. NaHCO₃. Mixture was stirred at 0° C. for 2 h. Solid was collected by filtration and dried under high vacuum. The crude reaction mixture was purified by flash chromatography to yield tert-butyl furan-3-ylcarbamate 32 (6.95 g, 76%): ¹H NMR (CDCl₃, 400 MHz) δ 7.71 (bs, 1H), 7.27 (m, 1H), 6.27 (bs, 1H), 6.20 (bs, 1H), 1.50 (s, 9H); MS (Q1) 184 (M)⁺.

Example 14

Tert-butyl 2-(methoxycarbonyl)furan-3-ylcarbamate 33

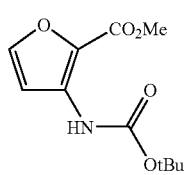

To a solution of tert-butyl furan-3-ylcarbamate 32 (1.7 g, 1.0 eq) in THF (50 ml) at −30° C. was added TMEDA (1.75 ml, 1.3 eq) followed by 1.6M solution of n-butyllithium (8.4 ml, 2.25 eq, 1.6M in hexanes). Reaction mixture was allowed to warm up to 0° C. and stirred for 1 h, before being cooled back to −30° C. Dimethyl carbonate (2.4 ml, 3.0 eq) was quickly added, before the reaction mixture was allowed to warm up to room temperature for 1 hr. Reaction mixture was quenched with 2M HCl, followed by addition of saturated aq. NaCl. Mixture was extracted with ethyl acetate. The combined organic extracts were dried with Na₂SO₄ and concentrated. The crude reaction mixture was purified by flash chromatography to yield tert-butyl 2-(methoxycarbonyl)furan-3-ylcarbamate 33 (1.14 g, 51%): MS (Q1) 242 (M)⁺.

Example 15

Methyl 3-aminofuran-2-carboxylate 34

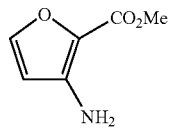

Tert-butyl 2-(methoxycarbonyl)furan-3-ylcarbamate 33 (1.14 g, 1.0 eq) was dissolved in dichloromethane (8 ml) and treated with trifluoroacetic acid (5 ml). Reaction mixture was stirred at room temperature for 3 h, and was then concentrated. Residue was dissolved in dichloromethane and washed with saturated aq. NaHCO₃. The organic layer was dried (Na₂SO₄) and concentrated Mixture was extracted with ethyl acetate. The combined organic extracts were dried with Na₂SO₄ and concentrated. The crude reaction mixture was purified by flash chromatography to yield methyl 3-aminofuran-2-carboxylate 34 (574 mg, 86%): MS (Q1) 142 (M)⁺.

Example 16

Ethyl 3-ureidofuran-2-carboxylate 35

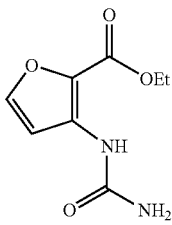

To a solution of methyl 3-aminofuran-2-carboxylate 34 (100 mg, 1.0 eq) in dichloromethane (3 ml) at −78° C. was added chlorosulfonyl isocyanate (0.09 ml, 1.4 eq) dropwise. The reaction was slowly warmed to room temperature and stirred for 40 minutes. Reaction was concentrated. To the residue was added 6N HCl (3.5 ml) and mixture was heated to 100° C. for 20 minutes. Reaction mixture was allowed to cool down to room temperature, and was neutralized with saturated aq. NaHCO₃. Solid was collected by filtration to yield ethyl 3-ureidofuran-2-carboxylate 35 (120 mg, 92%) as a beige solid which was used in the next reaction without further purification.

Example 17

Furo[3,2-d]pyrimidine-2,4-diol 36

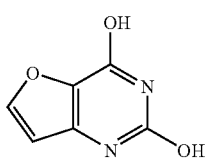

Ethyl 3-ureidofuran-2-carboxylate 35 (120 mg, 1.0 eq) was suspended in methanol (6 ml) and treated with 1.5 M NaOH (1.5 ml). Reaction mixture was heated to reflux for 90 minutes. Reaction mixture was allowed to cool down to room temperature, and was acidified with 6N HCl up to pH 3. Mixture was concentrated. Methanol was added to residue and solid was filtered and dried at 95° C. under high vacuum for 24 h to yield furo[3,2-d]pyrimidine-2,4-diol 36 (90 mg, 91%) which was used in the next reaction without further purification.

Example 18

2,4-Dichlorofuro[3,2-d]pyrimidine 37

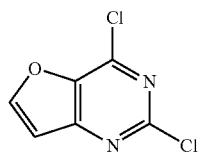

Furo[3,2-d]pyrimidine-2,4-diol 36 (39 mg, 1.0 eq) was dissolved in POCl₃ (1.8 ml). Mixture was cooled to −40° C. and N,N-diisopropylethylamine (0.45 ml) wad slowly added. Reaction mixture was then heated to reflux for 48 h, then cooled to room temperature Reaction mixture was poured into ice/water. Mixture was extracted with ethyl acetate. The combined organic layers were washed with saturated aq. NaHCO₃, dried (Na₂SO₄) and concentrated to yield 2,4-dichlorofuro[3,2-d]pyrimidine 37 (23 mg, 48%) which was used in the next reaction without further purification.

Example 19

2-Chloro-4-morpholinofuro[3,2-d]pyrimidine 38

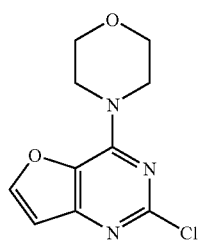

2,4-Dichlorofuro[3,2-d]pyrimidine 37 (23 mg, 1.0 eq) was suspended in methanol (1.7 ml) and treated with morpholine (0.09 ml, 4.0 eq). Reaction mixture was stirred at room temperature for 2 h, before being quenched with saturated aq. NaHCO₃. Mixture was extracted with dichloromethane. The combined organic layers were dried (Na₂SO₄) and concentrated to yield 2-chloro-4-morpholinofuro[3,2-d]pyrimidine 38 (14 mg, 48%) which was used in the next reaction without further purification.

Example 20

2-Chloro-4-morpholinofuro[3,2-d]pyrimidine-6-carbaldehyde 39

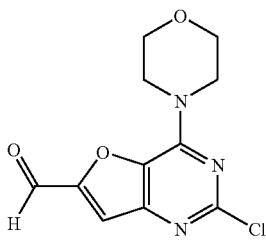

To a solution of 2-chloro-4-morpholinofuro[3,2-d]pyrimidine 38 (40 mg, 1.0 eq) dissolved in THF (1.7 ml) at −78° C. was added 1.6M solution of n-butyllithium (0.14 ml, 1.3 eq, 1.6M in hexanes). Reaction mixture was stirred at −78° C. for 30 minutes. DMF (0.05 ml, 4.0 eq) was added and reaction mixture was allowed to slowly warm up to room temperature and stirred for 90 minutes. Reaction mixture was quenched with water, and extracted with dichloromethane. The combined organic layers were dried (Na₂SO₄) and concentrated. The crude reaction mixture was purified by flash chromatography to yield 2-chloro-4-morpholinofuro[3,2-d]pyrimidine-6-carbaldehyde 39 (22 mg, 50%): $^1$H NMR (CDCl₃, 400 MHz) δ 9.92 (s, 1H), 7.48 (s, 1H), 4.12 (m, 4H), 3.86 (dd, 4H); MS (Q1) 268 (M)$^+$.

Example 23

Ethyl 5-phenyl-3-ureidofuran-2-carboxylate 41

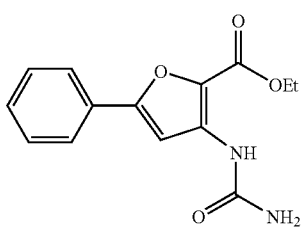

To a solution of 3-amino-5-phenyl-furan-2-carboxylate ester (116 mg, 1.0 eq) in dichloromethane (3 ml) at −78° C. was added chlorosulfonyl isocyanate (0.06 ml, 1.3 eq) dropwise (Redman, et al. (2000) J. Org. Lett. 2:2061-2063). The reaction was slowly warmed to room temperature and stirred for 40 minutes. The reaction was concentrated. To the residue was added 6N HCl (2.5 ml) and mixture was heated to 100° C. for 20 minutes. Reaction mixture was allowed to cool down to room temperature, and was neutralized with saturated aq. NaHCO₃. Solid was collected by filtration to yield 5-phenyl-3-ureidofuran-2-carboxylate 41 (130 mg, 95%) as a beige solid which was used in the next reaction without further purification.

Example 24

6-Phenylfuro[3,2-d]pyrimidine-2,4-diol 42

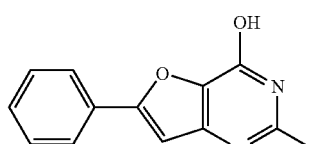

42

5-Phenyl-3-ureidofuran-2-carboxylate 41 (125 mg, 1.0 eq) was suspended in methanol (5 ml) and treated with 1.5 M NaOH (1 ml). Reaction mixture was heated to reflux for 90 minutes. Reaction mixture was allowed to cool down to room temperature, and was acidified with 6N HCl up to pH 3. Solid was filtered and dried at 95° C. under high vacuum for 24 h to yield 6-phenylfuro[3,2-d]pyrimidine-2,4-diol (79 mg, 76%) as a beige solid which was used in the next reaction without further purification.

Example 25

2,4-Dichloro-6-phenylfuro[3,2-d]pyrimidine 43

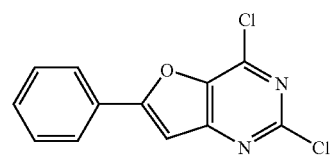

43

6-phenylfuro[3,2-d]pyrimidine-2,4-diol 42 (80 mg, 1.0 eq) was dissolved in $POCl_3$ (2.4 ml). Mixture was cooled to −40° C. and N,N-diisopropylethylamine (0.6 ml) was slowly added. Reaction mixture was heated to reflux for 48 h, then cooled to room temperature. The reaction mixture was poured into ice/water. Mixture was extracted with ethyl acetate. The combined organic layers were washed with saturated aq. $NaHCO_3$, dried ($Na_2SO_4$) and concentrated to yield 2,4-dichloro-6-phenylfuro[3,2-d]pyrimidine 43 (76 mg, 82%) which was used in the next reaction without further purification.

Example 26

2-Chloro-4-morpholino-6-phenylfuro[3,2-d]pyrimidine 44

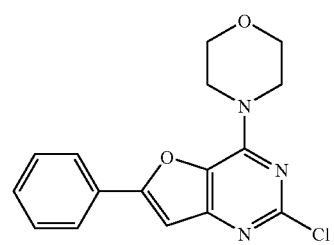

44

2,4-Dichloro-6-phenylfuro[3,2-d]pyrimidine 43 (165 mg, 1.0 eq) was suspended in methanol (4.2 ml) and treated with morpholine (0.22 ml, 4.0 eq). Reaction mixture was stirred at room temperature for 4 h. Solid was filtered to yield pure 2-chloro-4-morpholino-6-phenylfuro[3,2-d]pyrimidine 44 (163 mg, 83% yield) as a beige solid: $^1$H NMR ($CDCl_3$, 400 MHz) δ 7.80 (m, 2H), 7.51 (m, 3H), 6.99 (m, 1H), 4.10 (m, 4H), 3.89 (m, 1H); MS (Q1) 316 (M)$^+$.

Example 27

2-Chloro-6-iodo-4-morpholinofuro[3,2-d]pyrimidine 45

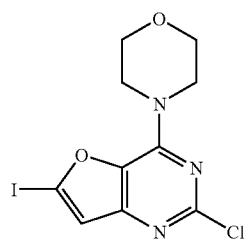

45

To a solution of 2-chloro-4-morpholinofuro[3,2-d]pyrimidine 38 (50 mg, 1.0 eq) dissolved in THF (2.1 ml) at −78° C. was added 1.6M solution of n-butyllithium (0.17 ml, 1.3 eq, 1.6M in hexanes). Reaction mixture was stirred at −78° C. for 30 minutes. A solution of iodine (159 mg, 3.0 eq) in THF (0.6 ml) was added and reaction mixture was allowed to slowly warm up to room temperature and stirred for 45 minutes. The reaction mixture was quenched with saturated aq. $Na_2S_2O_3$, and extracted with dichloromethane. The combined organic layers were dried ($Na_2SO_4$) and concentrated. The crude reaction mixture was purified by flash chromatography to yield 2-chloro-6-iodo-4-morpholinofuro[3,2-d]pyrimidine 45 (63 mg, 83%): MS (Q1) 366 (M)$^+$.

Example 28

2-(2-Chloro-4-morpholinofuro[3,2-d]pyrimidin-6-yl)propan-2-ol 46

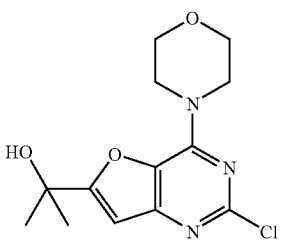

46

To a solution of 2-chloro-4-morpholinofuro[3,2-d]pyrimidine 38 (60 mg, 1.0 eq) dissolved in THF (2.5 ml) at −78° C. was added 1.6M solution of n-butyllithium (0.20 ml, 1.3 eq, 1.6M in hexanes). Reaction mixture was stirred at −78° C. for 30 minutes. Acetone (0.07 ml, 4.0 eq) was added and reaction mixture was allowed to warm up to −40° C. and stirred for 1 h. The crude reaction mixture was concentrated and purified by reverse phase HPLC to afford 2-(2-chloro-4-morpholinofuro[3,2-d]pyrimidin-6-yl)propan-2-ol 46. MS (Q1) 298 (M)⁺.

Example 29

4-(2-(2-aminopyrimidin-5-yl)-4-morpholinothieno[3,2-d]pyrimidin-6-yl)N-methylsulfonylpiperidin-4-ol 101

2-Chloro-4-morpholinothieno[3,2-d]pyrimidine 4 (3 g) was reacted with tert-butyl 4-oxopiperidine-1-carboxylate via General Procedure D-1 to give tert-butyl 4-(2-chloro-4-morpholinothieno[3,2-d]pyrimidin-6-yl)-4-hydroxypiperidine-1-carboxylate. Tert-butyl 4-(2-chloro-4-morpholinothieno[3,2-d]pyrimidin-6-yl)-4-hydroxypiperidine-1-carboxylate (1 g) was subjected to General Procedure E to give the HCl salt of 4-(2-chloro-4-morpholinothieno[3,2-d]pyrimidin-6-yl)piperidin-4-ol. The HCl salt of 4-(2-chloro-4-morpholinothieno[3,2-d]pyrimidin-6-yl)piperidin-4-ol (100 mg) was reacted with 120 μL of triethylamine and 66 μL of methanesulfonylchloride in 1 mL of dichloromethane. The reaction was stirred at room temperature until complete and then evaporated to dryness.

Crude 4-(2-chloro-4-morpholinothieno[3,2-d]pyrimidin-6-yl)-1-methylsulfonylpiperidin-4-ol (120 mg) was reacted with 80 mg of 5-(4,4,5,5-tetramethyl-1,3,2-dioxaborolan-2-yl)pyrimidin-2-amine via General Procedure A to give 12.5 mg of 4-(2-(2-aminopyrimidin-5-yl)-4-morpholinothieno[3,2-d]pyrimidin-6-yl)N-methylsulfonylpiperidin-4-ol 101. MS (Q1) 492.2 (M)+.

Example 30

N-((2-(2-aminopyrimidin-5-yl)-4-morpholinothieno[2,3-d]pyrimidin-6-yl)methyl)-N-methylbenzamide 102

A 5 L reaction vial equipped with a mechanical stirrer, internal temperature probe, and a nitrogen bubbler was charged with methyl 2-aminothiophene-3-carboxylate (95 g) and DCM (2.85 L) and cooled to −60 C chlorosulfonyl isocyanate (89.81 g) was added at a rate such that the internal temperature remained at −60 C to −55 C. After completion of addition the reaction was allowed to warm to ambient temperature. The reaction was monitored for complete consumption of starting material by LC/MS. The reaction mixture was concentrated to dryness in vacuo and the solid residue transferred back to the 5 l reaction vial by water (1.8 L). This mixture was heated at 75 C for one hour, then cooled to 30 C. Next, 10M aqueous NaOH (200 mL) was added and this mixture was heated at 85 C for 20 minutes before cooling to room temperature. The mixture was then acidified to pH=1 by the addition of conc. HCl. The mixture was then stirred for 18 hours at ambient temperature with a ppt forming. This solid material was collected by vacuum filtration and the filter cake washed with water (3×300 mL). The solid material was then dried in an vacuum oven at 55 C for 24 hours to afford thieno[2,3-d]pyrimidine-2,4(1H,3H)-dione as an off white solid (80.05 g, 78.8%) ¹H NMR (400 MHz, DMSO-d₆) δ 7.083 (d, J=5.6 Hz, 1H), δ 7.124 (d, J=5.6 Hz, 1H) LCMS (ESI pos) m/e 169 (M+1)

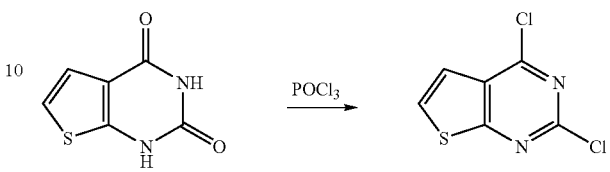

A 3 L reaction vial equipped with a mechanical stirrer, internal temperature probe, and a nitrogen bubbler was charged with 1H-thieno[3,2,-d]pyrimidine-2,4-dione (80 g). Next, N,N-dimethylaniline (42 g) and acetonitrile (400 mL) were added to the reaction flask and cooled to 10 C. Phosphorousoxychloride was added to the reaction mixture while maintaining am internal temperature of <25 C. After this addition the reaction mixture was heated to 80-85 C and stirred for 16 hours. An aliquot was taken from the reaction mixture and diluted with methanol/ACN and analyzed by LC/MS to confirm the consumption of starting material. The reaction was then cooled to 15 C and slowly transferred to a 5 L flask containing a mixture of ice and water (1.0 L). A solid was collected by vacuum filtration and the filter cake is washed with cold water (300 mL). The washed solid was dried in a vacuum oven at 40 C for 24 hours to afford 2,4-dichlorothieno[2,3-d]pyrimidine as an off white solid (91.43 g., 93.7%). ¹H NMR (400 MHz, DMSO-d₆) δ 7.619 (d, J=6.4 Hz, 1H), δ 8.155 (d, J=6.4 Hz, 1H) LCMS (ESI pos) m/e 205 (M+1).

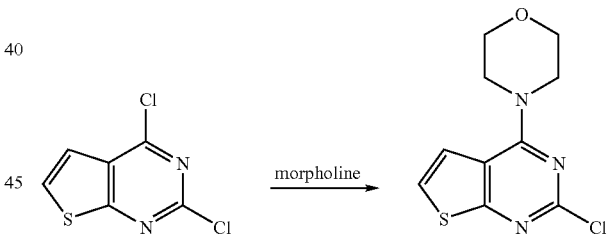

A 5 L reaction vial equipped with a mechanical stirrer, internal temperature probe, and a nitrogen bubbler was charged with 2,4-dichlorothieno[2,3-d]pyrimidine (91 g.) and methanol (1.5 L). Next, morpholine (85.1 g.) was added and the reaction mixture was stirred at ambient temperature for 1-2 hours. An aliquot was taken and diluted with DCM/ACN and analyzed by LC/MS to confirm consumption of the starting material. The reaction flask was then charged with water (3.0 L) at a rate that maintains an internal temperature below 25 C. A solid was collected by vacuum filtration and rinsed with water (500 mL). The washed solid was dried in a vacuum oven at 66 C for 24 hours to afford 2-chloro-4-morpholinothieno[2,3-d]pyrimidine as an off white solid (100.3 g., 88.4%). This intermediate may also be prepared by General Procedure D-2. ¹H NMR (400 MHz, DMSO-d₆) δ 3.736 (t, J=4.8 Hz, 4H), δ 3.897 (t, J=5.2 Hz, 4H), δ 7.658 (d, J=6.4 Hz, 1H), δ 7.682 (t, J=6.4 Hz, 4H). LCMS (ESI pos) m/e 257 (M+1

(2-Chloro-4-morpholinothieno[2,3-d]pyrimidine and 2-aminopyrimidine-5-boronic acid, pinacol ester were used in General Procedure A to produce 102 in 25% yield MS (Q1) 462 (M)

Example 31

N-((2-(2-aminopyrimidin-5-yl)-4-morpholinothieno[2,3-d]pyrimidin-6-yl)methyl)-N-methylnicotinamide 103

2-Chloro-4-morpholinothieno[2,3-d]pyrimidine (General Procedure D-2) and 2-aminopyrimidine-5-boronic acid, pinacol ester were used in General Procedure A to produce 103 in 25% yield MS (Q1) 463 (M)

Example 32

5-(6-(3-(N-methylsulfonylaminomethyl)phenyl)-7-methyl-4-morpholinothieno[3,2-d]pyrimidin-2-yl)pyrimidin-2-amine 104

2-Chloro-6-iodo-7-methyl-4-morpholinothieno[3,2-d]pyrimidine (70 mg) was coupled to 3-methanesulfonylaminomethylbenzeneboronic acid via General Procedure F-1. The product was purified by reverse phase HPLC to yield 51.6 mg of 104. MS (Q1) 512.2 (M)$^+$.

Example 33

5-(6-(3-N-methylsulfonylaminophenyl)-7-methyl-4-morpholinothieno[3,2-d]pyrimidin-2-yl)pyrimidin-2-amine 105

2-Chloro-6-iodo-7-methyl-4-morpholinothieno[3,2-d]pyrimidine (70 mg) was coupled to 3-methylsulfonylaminophenylboronic acid via General Procedure F-1. The product was purified by reverse phase HPLC to yield 37.5 mg of 5-(6-(3-N-methylsulfonylaminophenyl)-7-methyl-4-morpholinothieno[3,2-d]pyrimidin-2-yl)pyrimidin-2-amine 105. MS (Q1) 498.1 (M)$^+$.

Example 34

5-(6-(6-aminopyridin-3-yl)-7-methyl-4-morpholinothieno[3,2-d]pyrimidin-2-yl)pyrimidin-2-amine 106

2-Chloro-6-iodo-7-methyl-4-morpholinothieno[3,2-d]pyrimidine (70 mg) was coupled to 2-aminopyridine-5-boronic acid pinacol ester via General Procedure F-1. The product was purified by reverse phase HPLC to yield 35.8 mg of 5-(6-(6-aminopyridin-3-yl)-7-methyl-4-morpholinothieno[3,2-d]pyrimidin-2-yl)pyrimidin-2-amine 106. MS (Q1) 421.1 (M)$^+$.

Example 35

5-(6-(4-methoxypyridin-3-yl)-7-methyl-4-morpholinothieno[3,2-d]pyrimidin-2-yl)pyrimidin-2-amine 107

2-Chloro-6-iodo-7-methyl-4-morpholinothieno[3,2-d]pyrimidine (70 mg) was coupled to 4-methoxypyridine-3-boronic acid hydrate via General Procedure F-1. The product was purified by reverse phase HPLC to yield 27.6 mg of 5-(6-(4-methoxypyridin-3-yl)-7-methyl-4-morpholinothieno[3,2-d]pyrimidin-2-yl)pyrimidin-2-amine 107. MS (Q1) 436.1 (M)$^+$.

Example 36

5-(7-methyl-4-morpholino-6-(pyridin-3-yl)thieno[3,2-d]pyrimidin-2-yl)pyrimidin-2-amine 108

2-Chloro-6-iodo-7-methyl-4-morpholinothieno[3,2-d]pyrimidine (70 mg) was coupled to 3-pyridineboronic acid via General Procedure F-1. The product was purified by reverse phase HPLC to yield 10 mg of 5-(7-methyl-4-morpholino-6-(pyridin-3-yl)thieno[3,2-d]pyrimidin-2-yl)pyrimidin-2-amine 108. MS (Q1) 405 (M)$^+$.

Example 37

5-(6-(4-(aminomethyl)phenyl)-4-morpholinothieno[3,2-d]pyrimidin-2-yl)pyrimidin-2-amine 109

2-Chloro-6-iodo-4-morpholinothieno[3,2-d]pyrimidine 19 (Example 12) was reacted with 4-aminomethylphenylboronic acid hydrochloride via General Procedure A to give, after purification by flash chromatography, (4-(2-chloro-4-morpholinothieno[3,2-d]pyrimidin-6-yl)phenyl)methanamine, which was then reacted with 5-(4,4,5,5-tetramethyl-1,3,2-dioxaborolan-2-yl)pyrimidin-2-amine via General Procedure A again to give, after purification by reverse HPLC, 20 mg of 5-(6-(4-(aminomethyl)phenyl)-4-morpholinothieno[3,2-d]pyrimidin-2-yl)pyrimidin-2-amine 109. MS (Q1) 420 (M$^+$).

Example 38

5-(6-(3-(aminomethyl)phenyl)-4-morpholinothieno[3,2-d]pyrimidin-2-yl)pyrimidin-2-amine 110

2-Chloro-6-iodo-4-morpholinothieno[3,2-d]pyrimidine 19 (Example 12) was reacted with 3-aminomethylphenylboronic acid, pinacol ester via General Procedure A to give, after purification by flash chromatography, (3-(2-chloro-4-morpholinothieno[3,2-d]pyrimidin-6-yl)phenyl)methanamine, which was then reacted with 5-(4,4,5,5-tetramethyl-1,3,2-dioxaborolan-2-yl)pyrimidin-2-amine via General Procedure A again to give, after purification by reverse HPLC, 12 mg of 5-(6-(3-(aminomethyl)phenyl)-4-morpholinothieno[3,2-d]pyrimidin-2-yl)pyrimidin-2-amine 110. MS (Q1) 420 (M$^+$)

Example 39

5-(6-(4-amino-3-methoxyphenyl)-4-morpholinothieno[3,2-d]pyrimidin-2-yl)pyrimidin-2-amine 111

2-Chloro-6-iodo-4-morpholinothieno[3,2-d]pyrimidine 19 (Example 12) was reacted with 4-amino-3-methoxyphenylboronic acid, pinacol ester via General Procedure A to give 4-(2-chloro-4-morpholinothieno[3,2-d]pyrimidin-6-yl)-2-methoxybenzenamine, which was then reacted with 5-(4,4,5,5-tetramethyl-1,3,2-dioxaborolan-2-yl)pyrimidin-2-amine via General Procedure A again to give, after purification by reverse HPLC, 37 mg of 5-(6-(4-amino-3-methoxyphenyl)-4-morpholinothieno[3,2-d]pyrimidin-2-yl)pyrimidin-2-amine 111. MS (Q1) 436 (M$^+$).

Example 40

N-(2-(2-(2-aminopyrimidin-5-yl)-4-morpholinothieno[3,2-d]pyrimidin-6-yl)propan-2-yl)-3-methoxybenzamide 112

To a solution of amine 3 (150 mg, 0.5 mmol) in $CH_2Cl_2$ (10 mL) was added $Et_3N$ (230 µL, 1.6 mmol) and m-anisoyl chloride (160 mg, 0.9 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. A portion (0.2 mmol) of the resulting crude product was utilized in a Suzuki coupling using General Procedure A with 5-(4,4,5,5-tetramethyl-1,3,2-dioxaborolan-2-yl)pyrimidin-2-amine to provide 112 after reverse phase HPLC purification (9 mg). MS (Q1) 506 (M)+

Example 41

N-(2-(2-(2-aminopyrimidin-5-yl)-4-morpholinothieno[3,2-d]pyrimidin-6-yl)propan-2-yl)-4-methoxybenzamide 113

To a solution of amine 3 (150 mg, 0.5 mmol) in $CH_2Cl_2$ (10 mL) was added $Et_3N$ (230 µL, 1.6 mmol) and the HCl salt of p-anisoyl chloride (160 mg, 0.9 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. A portion (0.2 mmol) of the resulting crude was utilized in a Suzuki coupling using General Procedure A with 5-(4,4,5,5-tetramethyl-1,3,2-dioxaborolan-2-yl)pyrimidin-2-amine to provide 113 after reverse phase HPLC purification (14 mg). MS (Q1) 506 (M)+

Example 42

5-(6-(4-N-methylsulfonylaminophenyl)-4-morpholinothieno[3,2-d]pyrimidin-2-yl)pyrimidin-2-amine 114

2-Chloro-6-iodo-4-morpholinothieno[3,2-d]pyrimidine 19 (Example 12) was reacted with 4-(methanesulfonylamino)phenylboronic acid pinacol ester via General Procedure A to give 4-(2-chloro-4-morpholinothieno[3,2-d]pyrimidin-6-yl)-N-methanesulfonylbenzenamine, which was then reacted with 5-(4,4,5,5-tetramethyl-1,3,2-dioxaborolan-2-yl)pyrimidin-2-amine via General Procedure A again to give, after purification by reverse HPLC, 17 mg of 5-(6-(4-(methanesulfonylamino)phenyl)-4-morpholinothieno[3,2-d]pyrimidin-2-yl)pyrimidin-2-amine 114. MS (Q1) 484 ($M^+$).

Example 43

N-(2-(2-(2-aminopyrimidin-5-yl)-4-morpholinothieno[3,2-d]pyrimidin-6-yl)propan-2-yl)nicotinamide 115

To a solution of amine 3 (150 mg, 0.5 mmol) in $CH_2Cl_2$ (10 mL) was added $Et_3N$ (230 µL, 1.6 mmol) and nicotinoyl chloride (160 mg, 0.9 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. A portion (0.2 mmol) of the resulting crude product was utilized in a Suzuki coupling using General Procedure A with 5-(4,4,5,5-tetramethyl-1,3,2-dioxaborolan-2-yl)pyrimidin-2-amine to provide 115 after reverse phase HPLC purification (23 mg). MS (Q1) 477 (M)+

Example 44

N-(2-(4-morpholino-2-(pyrimidin-5-yl)thieno[3,2-d]pyrimidin-6-yl)propan-2-yl)benzamide 116

To a solution of amine 3 (290 mg, 0.9 mmol) in $CH_2Cl_2$ (20 mL) was added $Et_3N$ (450 µL, 3.2 mmol) and benzoyl chloride (230 µL, 1.8 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. A portion (0.2 mmol) of the resulting crude product was utilized in a Suzuki coupling using General Procedure A with pyrimidin-5-yl-5-boronic acid to provide 116 after reverse phase HPLC purification (75 mg). MS (Q1) 461 (M)+

Example 45

N-(2-(2-(6-methylpyridin-3-yl)-4-morpholinothieno[3,2-d]pyrimidin-6-yl)propan-2-yl)benzamide 117

To a solution of amine 3 (290 mg, 0.9 mmol) in $CH_2Cl_2$ (20 mL) was added $Et_3N$ (450 µL, 3.2 mmol) and benzoyl chloride (230 µL, 1.8 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. A portion (0.2 mmol) of the resulting crude product was utilized in a Suzuki coupling using General Procedure A with 2-methyl-5-(4,4,5,5-tetramethyl-1,3,2-dioxaborolan-2-yl)pyridine to provide G-39509 after reverse phase HPLC purification (79 mg). MS (Q1) 474 (M)+

Example 46

5-(4-morpholino-6-(3-morpholinosulfonyl)phenylthieno[3,2-d]pyrimidin-2-yl)pyrimidin-2-amine 118

2-Chloro-6-iodo-4-morpholinothieno[3,2-d]pyrimidine 19 from Example 12 (70 mg) was coupled to N-morpholinyl-3-boronobenzenesulfonamide via General Procedure F-1. The product was purified by reverse phase HPLC to yield 25.2 mg of 118. MS (Q1) 540 $(M)^+$.

Example 47

5-(4-morpholino-6-(3-morpholinosulfonyl)phenylthieno[3,2-d]pyrimidin-2-yl)pyridin-2-amine 119

2-Chloro-6-iodo-4-morpholinothieno[3,2-d]pyrimidine 19 from Example 12 (60 mg) was coupled to N-morpholinyl-3-boronobenzenesulfonamide via General Procedure F-1. The product was purified by reverse phase HPLC to yield 59.4 mg of 119. MS (Q1) 539.2 (M)+

Example 48

5-(4-morpholino-6-(3-(2-hydroxyethylamino)sulfonyl)phenylthieno[3,2-d]pyrimidin-2-yl)pyridin-2-amine 120

2-Chloro-6-iodo-4-morpholinothieno[3,2-d]pyrimidine 19 from Example 12 (60 mg) was coupled to N-(2-hydroxyethyl)-3-boronobenzenesulfonamide via General Procedure F-1. The product was purified by reverse phase HPLC to yield 59.4 mg of 120. MS (Q1) 513.2 (M)+.

Example 49

5-(4-morpholino-6-(3-aminosulfonyl)phenylthieno[3,2-d]pyrimidin-2-yl)pyridin-2-amine 121

2-Chloro-6-iodo-4-morpholinothieno[3,2-d]pyrimidine 19 from Example 12 (60 mg) was coupled to 3-boronobenzenesulfonamide via General Procedure F-1. The product was purified by reverse phase HPLC to yield 15.9 mg of 121. MS (Q1) 469.1 (M)+.

Example 50

5-(4-morpholinothieno[3,2-d]pyrimidin-2-yl)pyrimidin-2-amine 122

2-Chloro-6-iodo-4-morpholinothieno[3,2-d]pyrimidine 19 from Example 12 (70 mg) was coupled to 2-aminopyrimidine-5-boronic acid pinacol ester via General Procedure A. The product was purified by reverse phase HPLC to yield 47.2 mg of 122. MS (Q1) 315.9 (M)+.

Example 51

5-(4-morpholinothieno[3,2-d]pyrimidin-2-yl)pyridin-2-amine 123

2-Chloro-6-iodo-4-morpholinothieno[3,2-d]pyrimidine 19 from Example 12 (70 mg) was coupled to 2-aminopyridine-5-boronic acid pinacol ester via General Procedure A. The product was purified by reverse phase HPLC to yield 83 mg of 123. MS (Q1) 314 (M)+.

Example 52

(S)—N-((4-(2-(2-aminopyrimidin-5-yl)-4-morpholinothieno[3,2-d]pyrimidin-6-yl)phenyl)methyl)-2-hydroxypropanamide 124

(4-(2-Chloro-4-morpholinothieno[3,2-d]pyrimidin-6-yl)phenyl)methanamine (1.0 eq) was treated with 1.5 eq HATU, 3 eq of (L)-lactic acid and 3 eq of DIPEA in DMF at approximately 0.1 M concentration. The reaction is stirred until complete and extracted in ethylacetate with saturated bicarbonate solution one time. The organic layer is dried, filtered and concentrated to yield the crude intermediate which was purified by flash chromatography to yield (S)—N-((4-(2-chloro-4-morpholinothieno[3,2-d]pyrimidin-6-yl)phenyl)methyl)-2-hydroxypropanamide. This intermediate was reacted with 5-(4,4,5,5-tetramethyl-1,3,2-dioxaborolan-2-yl)pyrimidin-2-amine via General Procedure B to give, after purification by reverse HPLC, 4 mg of 124. MS (Q1) 492 (M+).

Example 53

N-((4-(2-(2-aminopyrimidin-5-yl)-4-morpholinothieno[3,2-d]pyrimidin-6-yl)phenyl)methyl)-2-hydroxyacetamide 125

(4-(2-Chloro-4-morpholinothieno[3,2-d]pyrimidin-6-yl)phenyl)methanamine (1.0 eq) is treated with 1.5 eq HATU, 3 eq of glycolic acid and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified by flash chromatography to yield N-((4-(2-chloro-4-morpholinothieno[3,2-d]pyrimidin-6-yl)phenyl)methyl)-2-hydroxyacetamide.

N-((4-(2-Chloro-4-morpholinothieno[3,2-d]pyrimidin-6-yl)phenyl)methyl)-2-hydroxyacetamide was reacted with 5-(4,4,5,5-tetramethyl-1,3,2-dioxaborolan-2-yl)pyrimidin-2-amine via General Procedure B to give, after purification by reverse HPLC, 18 mg of 125. MS (Q1) 478 (M+).

Example 54

(2S)—N-((3-(2-(2-aminopyrimidin-5-yl)-4-morpholinothieno[3,2-d]pyrimidin-6-yl)phenyl)methyl)-2-hydroxypropanamide 126

(3-(2-Chloro-4-morpholinothieno[3,2-d]pyrimidin-6-yl)phenyl)methanamine (1.0 eq) was treated with 1.5 eq HATU, 3 eq of (L)-lactic acid and 3 eq of DIPEA in DMF to approximately 0.1 M concentration. The reaction was stirred until complete and extracted in ethylacetate with saturated bicarbonate solution one time. The organic layer was dried, filtered and concentrated to yield the crude intermediate. This intermediate was purified by flash chromatography to yield (2S)—N-((3-(2-chloro-4-morpholinothieno[3,2-d]pyrimidin-6-yl)phenyl)methyl)-2-hydroxypropanamide.

(2S)—N-((3-(2-Chloro-4-morpholinothieno[3,2-d]pyrimidin-6-yl)phenyl)methyl)-2-hydroxypropanamide was reacted with 5-(4,4,5,5-tetramethyl-1,3,2-dioxaborolan-2-yl)pyrimidin-2-amine via General Procedure B to give, after purification by reverse HPLC, 44 mg of 126. MS (Q1) 492 (M+).

Example 55

N-((3-(2-(2-aminopyrimidin-5-yl)-4-morpholinothieno[3,2-d]pyrimidin-6-yl)phenyl)methyl)acetamide 127

(3-(2-Chloro-4-morpholinothieno[3,2-d]pyrimidin-6-yl)phenyl)methanamine (1.0 eq) is treated with 4.0 eq acetyl chloride, 2.0 eq of triethylamine in dichloromethane to approximately 0.1 M concentration. The reaction is stirred until complete. Water was added and the mixture was concentrated to yield the crude intermediate. This intermediate is purified by flash chromatography to yield N-((3-(2-chloro-4-morpholinothieno[3,2-d]pyrimidin-6-yl)phenyl)methyl)acetamide.

N-((3-(2-Chloro-4-morpholinothieno[3,2-d]pyrimidin-6-yl)phenyl)methyl)acetamide was reacted with 5-(4,4,5,5- tetramethyl-1,3,2-dioxaborolan-2-yl)pyrimidin-2-amine via General Procedure B to give, after purification by reverse HPLC, 48 mg of 127. MS (Q1) 462 (M+).

Example 56

N-((3-(2-(2-aminopyrimidin-5-yl)-4-morpholinothieno[3,2-d]pyrimidin-6-yl)phenyl)methyl)-2-hydroxyacetamide 128

(3-(2-Chloro-4-morpholinothieno[3,2-d]pyrimidin-6-yl)phenyl)methanamine (1.0 eq) is treated with 1.5 eq HATU, 3 eq of glycolic acid and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified by flash chromatography to yield N-((3-(2-chloro-4-morpholinothieno[3,2-d]pyrimidin-6-yl)phenyl)methyl)-2-hydroxyacetamide.

N-((3-(2-Chloro-4-morpholinothieno[3,2-d]pyrimidin-6-yl)phenyl)methyl)-2-hydroxyacetamide was reacted with 5-(4,4,5,5-tetramethyl-1,3,2-dioxaborolan-2-yl)pyrimidin-2-amine via General Procedure B to give, after purification by reverse HPLC, 55 mg of 128. MS (Q1) 478 (M$^+$).

Example 57

(4-(2-(2-aminopyrimidin-5-yl)-4-morpholinothieno[3,2-d]pyrimidin-6-yl)phenyl)(4-methylpiperazin-1-yl)methanone 129

2-Chloro-6-iodo-4-morpholinothieno[3,2-d]pyrimidine 19 from Example 12 (500 mg), 239 mg of 4-carboxyphenylboronic acid and 46 mg of Bis(triphenylphosphine)palladium(II) dichloride in 4 mL of 1M Na$_2$CO$_3$ aqueous solution and 4 mL of acetonitrile was heated to 100° C. in a sealed microwave reactor for 10 min. Upon completion, the reaction mixture was evaporated, and added H$_2$O (~30 mL), then acidified using 2N HCl to pH=2~3. The solid was filtered and washed with H$_2$O to yield 450 mg of 4-(2-chloro-4-morpholinothieno[3,2-d]pyrimidin-6-yl)benzoic acid.

4-(2-Chloro-4-morpholinothieno[3,2-d]pyrimidin-6-yl)benzoic acid (140 mg) was reacted with 1-methylpiperazine via General Procedure B to give 4-(2-chloro-4-morpholinothieno[3,2-d]pyrimidin-6-yl)phenyl)(4-methylpiperazin-1-yl)methanone. 80 mg of the crude 4-(2-chloro-4-morpholinothieno[3,2-d]pyrimidin-6-yl)phenyl)(4-methylpiperazin-1-yl)methanone was coupled to 2-aminopyrimidine-5-boronic acid pinacol ester via General Procedure A. The product was purified by reverse phase HPLC to yield 37.8 mg of 129. MS (Q1) 517 (M$^+$).

Example 58

(4-(2-(2-aminopyrimidin-5-yl)-4-morpholinothieno[3,2-d]pyrimidin-6-yl)phenyl)(morpholino)methanone 130

4-(2-Chloro-4-morpholinothieno[3,2-d]pyrimidin-6-yl)benzoic acid (140 mg) was reacted with morpholine via General Procedure B to give 4-(2-chloro-4-morpholinothieno[3,2-d]pyrimidin-6-yl)phenyl)morpholinomethanone. 80 mg of the crude 4-(2-chloro-4-morpholinothieno[3,2-d]pyrimidin-6-yl)phenyl)morpholinomethanone was coupled to 2-aminopyrimidine-5-boronic acid pinacol ester via General Procedure A. The product was purified by reverse phase HPLC to yield 2.8 mg of 130. MS (Q1) 504.2 (M)$^+$.

Example 59

(4-(2-(6-aminopyridin-3-yl)-4-morpholinothieno[3,2-d]pyrimidin-6-yl)phenyl)(4-methylpiperazin-1-yl)methanone 131

Crude 4-(2-chloro-4-morpholinothieno[3,2-d]pyrimidin-6-yl)phenyl)(4-methylpiperazin-1-yl)methanone (80 mg) was coupled to 2-aminopyridine-5-boronic acid pinacol ester via General Procedure A. The product was purified by reverse phase HPLC to yield 32.9 mg of 131. MS (Q1) 516 (M)$^+$.

Example 60

(4-(2-(6-aminopyridin-3-yl)-4-morpholinothieno[3,2-d]pyrimidin-6-yl)phenyl)(morpholino)methanone 132

Crude 4-(2-chloro-4-morpholinothieno[3,2-d]pyrimidin-6-yl)phenyl)morpholinomethanone (80 mg) was coupled to 2-aminopyridine-5-boronic acid pinacol ester via General Procedure A. The product was purified by reverse phase HPLC to yield 37.4 mg of 132. MS (Q1) 503.2 (M)$^+$.

Example 61

5-(6-(3-(1H-tetrazol-5-yl)phenyl)-4-morpholinothieno[3,2-d]pyrimidin-2-yl)pyrimidin-2-amine 133

2-Chloro-6-iodo-4-morpholinothieno[3,2-d]pyrimidine 19 from Example 12 was reacted with [3-(2H-Tetrazol-5-yl)phenyl]boronic acid via General Procedure A to give 6-(3-(1H-tetrazol-5-yl)phenyl)-2-chloro-4-morpholinothieno[3,2-d]pyrimidine, which was then reacted with 5-(4,4,5,5-tetramethyl-1,3,2-dioxaborolan-2-yl)pyrimidin-2-amine via General Procedure A again to give, after purification by reverse HPLC, 3 mg of 133. MS (Q1) 459 (M$^+$).

Example 62

3-(2-(2-aminopyrimidin-5-yl)-4-morpholinothieno[3,2-d]pyrimidin-6-yl)benzoic acid 134

2-Chloro-6-iodo-4-morpholinothieno[3,2-d]pyrimidine 19 from Example 12 (500 mg), 239 mg of 3-carboxyphenylboronic acid and 46 mg of Bis(triphenylphosphine)palladium(II) dichloride in 4 mL of 1M Na$_2$CO$_3$ aqueous solution and 4 mL of acetonitrile was heated to 100° C. in a sealed microwave reactor for 10 min (set up 2 reactions). Upon completion, the combined mixture was evaporated, and added H$_2$O (~30 mL), then acidified using 2N HCl to pH=2~3. The solid was filtered and washed with H$_2$O to yield 980 mg of 3-(2-chloro-4-morpholinothieno[3,2-d]pyrimidin-6-yl)benzoic acid.

3-(2-Chloro-4-morpholinothieno[3,2-d]pyrimidin-6-yl)benzoic acid (60 mg) was coupled to 2-aminopyrimidine-5-boronic acid pinacol ester via General Procedure A. The product was purified by reverse phase HPLC to yield 4.6 mg of 134. MS (Q1) 435 (M)$^+$.

Example 63

3-(2-(6-aminopyridin-3-yl)-4-morpholinothieno[3,2-d]pyrimidin-6-yl)benzoic acid 135

3-(2-Chloro-4-morpholinothieno[3,2-d]pyrimidin-6-yl) benzoic acid (60 mg) was coupled to 2-aminopyridine-5-boronic acid pinacol ester via General Procedure A. The product was purified by reverse phase HPLC to yield 14.9 mg of 135. MS (Q1) 434.1 (M)$^+$.

Example 64

5-(6-(3-aminophenyl)-4-morpholinothieno[3,2-d]pyrimidin-2-yl)pyrimidin-2-amine 136

2-Chloro-6-iodo-4-morpholinothieno[3,2-d]pyrimidine 19 from Example 12 (1 g), 446 mg of 3-aminophenylboronic acid and 92 mg of Bis(triphenylphosphine)palladium(II) dichloride in 5 mL of 1M Na$_2$CO$_3$ aqueous solution and 5 mL of acetonitrile was heated to 100° C. in a sealed microwave reactor for 15 min. The reaction mixture was filtered. The solid cake was washed with H$_2$O and dried to yield 900 mg of 3-(2-chloro-4-morpholinothieno[3,2-d]pyrimidin-6-yl)benzenamine.

3-(2-Chloro-4-morpholinothieno[3,2-d]pyrimidin-6-yl) benzenamine (60 mg) was coupled to 2-aminopyrimidine-5-boronic acid pinacol ester via General Procedure A. The product was purified by reverse phase HPLC to yield 19.7 mg of 136. MS (Q1) 406.1 (M)$^+$.

Example 65

5-(6-(3-aminophenyl)-4-morpholinothieno[3,2-d]pyrimidin-2-yl)pyridin-2-amine 137

3-(2-Chloro-4-morpholinothieno[3,2-d]pyrimidin-6-yl) benzenamine (60 mg) was coupled to 2-aminopyridine-5-boronic acid pinacol ester via General Procedure A. The product was purified by reverse phase HPLC to yield 47.6 mg of 137. MS (Q1) 405.1 (M)$^+$.

Example 66

(3-(2-(2-aminopyrimidin-5-yl)-4-morpholinothieno[3,2-d]pyrimidin-6-yl)phenyl)(4-methylpiperazin-1-yl)methanone 138

3-(2-Chloro-4-morpholinothieno[3,2-d]pyrimidin-6-yl) benzoic acid (150 mg) was reacted with 1-methylpiperazine via General Procedure B to give 130 mg of 3-(2-chloro-4-morpholinothieno[3,2-d]pyrimidin-6-yl)phenyl)(4-methylpiperazin-1-yl)methanone. Crude 3-(2-chloro-4-morpholinothieno[3,2-d]pyrimidin-6-yl)phenyl)(4-methylpiperazin-1-yl)methanone (60 mg) was coupled to 2-aminopyrimidine-5-boronic acid pinacol ester via General Procedure A. The product was purified by reverse phase HPLC to yield 38.5 mg of 138. MS (Q1) 517 (M)$^+$.

Example 67

3-(2-(2-aminopyrimidin-5-yl)-4-morpholinothieno[3,2-d]pyrimidin-6-yl)-N—((S)-2-hydroxypropyl)benzamide 139

3-(2-Chloro-4-morpholinothieno[3,2-d]pyrimidin-6-yl) benzoic acid (150 mg) was reacted with (S)-1-amino-2-propanol via General Procedure B to give 140 mg of 3-(2-chloro-4-morpholinothieno[3,2-d]pyrimidin-6-yl)-N—((S)-2-hydroxypropyl)benzamide. 60 mg of the crude 3-(2-chloro-4-morpholinothieno[3,2-d]pyrimidin-6-yl)-N—((S)-2-hydroxypropyl)benzamide was coupled to 2-aminopyrimidine-5-boronic acid pinacol ester via General Procedure A. The product was purified by reverse phase HPLC to yield 7.7 mg of 139. MS (Q1) 492.2 (M)$^+$.

Example 68

(3-(2-(2-aminopyrimidin-5-yl)-4-morpholinothieno[3,2-d]pyrimidin-6-yl)phenyl)(morpholino)methanone 140

3-(2-Chloro-4-morpholinothieno[3,2-d]pyrimidin-6-yl) benzoic acid (150 mg) was reacted with morpholine via General Procedure B to give 130 mg of 3-(2-chloro-4-morpholinothieno[3,2-d]pyrimidin-6-yl)phenyl)morpholinomethanone. 60 mg of the crude 3-(2-chloro-4-morpholinothieno[3,2-d]pyrimidin-6-yl)phenyl) morpholinomethanone was coupled to 2-aminopyrimidine-5-boronic acid pinacol ester via General Procedure A. The product was purified by reverse phase HPLC to yield 11.1 mg of 140. MS (Q1) 504.2 (M)$^+$.

Example 69

3-(2-(6-aminopyridin-3-yl)-4-morpholinothieno[3,2-d]pyrimidin-6-yl)-N—((S)-2-hydroxypropyl)benzamide 141

Crude 3-(2-chloro-4-morpholinothieno[3,2-d]pyrimidin-6-yl)-N—((S)-2-hydroxypropyl)benzamide (70 mg) was coupled to 2-aminopyridine-5-boronic acid pinacol ester via General Procedure A. The product was purified by reverse phase HPLC to yield 24.4 mg of 141. MS (Q1) 491.2 (M)$^+$.

Example 70

N-((2-(2-aminopyrimidin-5-yl)-4-morpholinothieno[3,2-d]pyrimidin-6-yl)methyl)-2-hydroxy-N-methylacetamide 142

(2-Chloro-4-morpholinothieno[3,2-d]pyrimidin-6-yl)-N-methylmethanamine, prepared from General Procedure B-4, (0.74 mM) was dissolved in 8 mL of dichloromethane and cooled to 0° C. under N$_2$ and 1.3 eq. triethylamine and 1.2 eq. acetoxyacetyl chloride was added. This reaction mixture was allowed to warm up to room temperature and stirred 24 hours at which time product formation was confirmed by LCMS. The reaction was concentrated in vacuo. This crude product was purified by flash chromatography (EtOAc/Hexanes) to give 0.234 g (N-((2-chloro-4-morpholinothieno[3,2-d]pyrimidin-6-yl)methyl)-N-methylcarbamoyl)methyl acetate (79% yield). MS (Q1) 400 (M)+

(N-((2-chloro-4-morpholinothieno[3,2-d]pyrimidin-6-yl)methyl)-N-methylcarbamoyl)methyl acetate (0.29 mM) and 5-(4,4,5,5-tetramethyl-1,3,2-dioxaborolan-2-yl)pyrimidin-2-amine were coupled using General Procedure A, followed by removal of the acetyl group by dissolving the Suzuki product in 2 mL THF, 2 mL MeOH, and 1M LiOH at 0° C. for 2.5 hours. The reaction was diluted with 1 M HCl and EtOAc. Product was in the aqueous layer. The water was removed on the genevac to give 142 (TFA salt) after reverse-phase HPLC purification. MS (Q1) 417 (M)+

Example 71

N-methyl-N-((7-methyl-4-morpholino-2-(pyridin-3-yl)thieno[3,2-d]pyrimidin-6-yl)methyl)acetamide 143

N-((2-Chloro-7-methyl-4-morpholinothieno[3,2-d]pyrimidin-6-yl)methyl)-N-methylacetamide (0.59 mmol) was reacted using General Procedure A to give 143 (TFA salt) in a 60% yield after reverse-phase HPLC purification. MS (Q1) 398 (M)

Example 72

N-methyl-N-((7-methyl-4-morpholino-2-(pyrimidin-5-yl)thieno[3,2-d]pyrimidin-6-yl)methyl)acetamide 144

N-((2-Chloro-7-methyl-4-morpholinothieno[3,2-d]pyrimidin-6-yl)methyl)-N-methylacetamide (0.59 mmol) was reacted using General Procedure A to give 144 (TFA salt) in a 25% yield after reverse-phase HPLC purification. MS (Q1) 399 (M)

Example 73

N-((2-(6-aminopyridin-3-yl)-7-methyl-4-morpholinothieno[3,2-d]pyrimidin-6-yl)methyl)-N-methylacetamide 145

N-((2-Chloro-7-methyl-4-morpholinothieno[3,2-d]pyrimidin-6-yl)methyl)-N-methylacetamide (0.59 mmol) was reacted using General Procedure A to give 145 (TFA salt) in a 44% yield after reverse-phase HPLC purification. MS (Q1) 413 (M)

Example 74

N-((2-(2-aminopyrimidin-5-yl)-7-methyl-4-morpholinothieno[3,2-d]pyrimidin-6-yl)methyl)-N-methylacetamide 146

(2-Chloro-7-methyl-4-morpholinothieno[3,2-d]pyrimidin-6-yl)-N-methylmethanamine was dissolved in 10 mL of dichloromethane and cooled to 0° C. under $N_2$ and 1.3 eq. triethylamine and 1.2 eq. acetyl chloride was added. This reaction mixture was allowed to warm to room temperature and stirred 24 hours at which time product formation was confirmed by LCMS. The reaction was concentrated in vacuo. The crude product was purified by flash chromatography (EtOAc/hexanes) to give 1.44 g N-((2-chloro-7-methyl-4-morpholinothieno[3,2-d]pyrimidin-6-yl)methyl)-N-methylacetamide (100% yield). MS (Q1) 355 (M)

N-((2-chloro-7-methyl-4-morpholinothieno[3,2-d]pyrimidin-6-yl)methyl)-N-methylacetamide (0.59 mmol) was reacted using General Procedure A to give 146 (TFA salt) in a 14% yield after reverse-phase HPLC purification. MS (Q1) 414 (M+).

Example 75

N-methyl-N-((7-methyl-4-morpholino-2-(pyridin-3-yl)thieno[3,2-d]pyrimidin-6-yl)methyl)benzamide 147

N-((2-Chloro-7-methyl-4-morpholinothieno[3,2-d]pyrimidin-6-yl)methyl)-N-methylbenzamide (0.49 mmol) was reacted using General Procedure A to give 147 (TFA salt) in a 14% yield after reverse-phase HPLC purification. MS (Q1) 460 (M+)

Example 76

N-methyl-N-((7-methyl-4-morpholino-2-(pyrimidin-5-yl)thieno[3,2-d]pyrimidin-6-yl)methyl)benzamide 148

N-((2-Chloro-7-methyl-4-morpholinothieno[3,2-d]pyrimidin-6-yl)methyl)-N-methylbenzamide (0.49 mmol) was reacted using General Procedure A to give 148 (TFA salt) in a 4% yield after reverse-phase HPLC purification. MS (Q1) 461 (M+)

Example 77

N-((2-(6-aminopyridin-3-yl)-7-methyl-4-morpholinothieno[3,2-d]pyrimidin-6-yl)methyl)-N-methylbenzamide 149

N-((2-chloro-7-methyl-4-morpholinothieno[3,2-d]pyrimidin-6-yl)methyl)-N-methylbenzamide (0.49 mmol) was reacted using General Procedure A to give 149 (TFA salt) in a 10% yield after reverse-phase HPLC purification. MS (Q1) 475 (M+)

Example 78

N-((2-(2-aminopyrimidin-5-yl)-4-morpholinothieno[3,2-d]pyrimidin-6-yl)methyl)-2-methoxy-N-methylacetamide 150

(2-Chloro-4-morpholinothieno[3,2-d]pyrimidin-6-yl)-N-methylmethanamine, prepared from General Procedure B-4, (0.74 mmol) was dissolved in 8 mL of dichloromethane and cooled to 0° C. under $N_2$ and 1.3 eq. triethylamine and 1.2 eq. methoxyacetyl chloride was added. This reaction mixture was allowed to warm to room temperature and stirred 24 hours at which time product formation was confirmed by LCMS. The reaction was concentrated in vacuo. This crude product was purified by flash chromatography (EtOAc/Hexanes) to give 0.27 g N-((2-chloro-4-morpholinothieno[3,2-d]pyrimidin-6-yl)methyl)-2-methoxy-N-methylacetamide (79% yield). MS (Q1) 371 (M)

N-((2-Chloro-4-morpholinothieno[3,2-d]pyrimidin-6-yl)methyl)-2-methoxy-N-methylacetamide (0.29 mmol) was reacted using General Procedure A to give 151 (TFA salt) in a 20% yield after reverse-phase HPLC purification. MS (Q1) 430 (M+)

Example 79

(3-(2-(6-aminopyridin-3-yl)-4-morpholinothieno[3,2-d]pyrimidin-6-yl)phenyl)(4-methylpiperazin-1-yl)methanone 151

3-(2-Chloro-4-morpholinothieno[3,2-d]pyrimidin-6-yl)phenyl)(4-methylpiperazin-1-yl)methanone (70 mg) was coupled to 2-aminopyridine-5-boronic acid pinacol ester via General Procedure A. The product was purified by reverse phase HPLC to yield 52.3 mg of 151. MS (Q1) 516 (M)+.

Example 80

(3-(2-(6-aminopyridin-3-yl)-4-morpholinothieno[3,2-d]pyrimidin-6-yl)phenyl)(morpholino)methanone 152

Crude 3-(2-chloro-4-morpholinothieno[3,2-d]pyrimidin-6-yl)phenyl)morpholinomethanone (70 mg) was coupled to 2-aminopyridine-5-boronic acid pinacol ester via General Procedure A. The product was purified by reverse phase HPLC to yield 37.6 mg of 152. MS (Q1) 503.2 (M)$^+$.

Example 81

5-(4-morpholino-6-(3-N-2-hydroxyethylaminosulfonyl)phenylthieno[3,2-d]pyrimidin-2-yl)pyrimidin-2-amine 153

2-Chloro-6-iodo-4-morpholinothieno[3,2-d]pyrimidine 19 from Example 12 (60 mg) was coupled to N-(2-hydroxyethyl)-3-boronobenzenesulfonamide via General Procedure F-1. The product was purified by reverse phase HPLC to yield 43.1 mg of 153. MS (Q1) 514.2 (M)$^+$.

Example 82

5-(4-morpholino-6-(6-(4-methylsulfonylpiperazin-1-yl)pyridin-3-yl)thieno[3,2-d]pyrimidin-2-yl)pyrimidin-2-amine 154

2-Chloro-4-morpholino-6-(6-(piperazin-1-yl)pyridin-3-yl)thieno[3,2-d]pyrimidin (1.0 eq) is treated with 8.0 eq methanesulfonylchloride, 5.0 eq of triethylamine in THF to approximately 0.1 M concentration. The reaction is stirred until complete and extracted in dichloromethane with saturated bicarbonate solution one time. The organic layer is dried, filtered and concentrated to yield the crude intermediate. This intermediate is purified by flash chromatography to yield 2-chloro-6-(6-(4-methanesulfonylpiperazin-1-yl)pyridin-3-yl)-4-morpholinothieno[3,2-d]pyrimidine.

2-Chloro-6-(6-(4-methanesulfonylpiperazin-1-yl)pyridin-3-yl)-4-morpholinothieno[3,2-d]pyrimidine was reacted with 5-(4,4,5,5-tetramethyl-1,3,2-dioxaborolan-2-yl)pyrimidin-2-amine via General Procedure B to give, after purification by reverse HPLC, N-((3-(2-(2-aminopyrimidin-5-yl)-4-morpholinothieno[3,2-d]pyrimidin-6-yl)phenyl)methyl)acetamide. MS (Q1) 554 (M+).

Example 83

5-(4-morpholino-6-(6-(piperazin-1-yl)pyridin-3-yl)thieno[3,2-d]pyrimidin-2-yl)pyrimidin-2-amine 155

2-Chloro-6-iodo-4-morpholinothieno[3,2-d]pyrimidine 19 from Example 12 was reacted with 6-(piperazin-1-yl)pyridine-3-boronic acid pinacol ester via General Procedure A to give, after purification by flash chromatography, 2-chloro-4-morpholino-6-(6-(piperazin-1-yl)pyridin-3-yl)thieno[3,2-d]pyrimidine, which was then reacted with 5-(4,4,5,5-tetramethyl-1,3,2-dioxaborolan-2-yl)pyrimidin-2-amine via General Procedure A again to give, after purification by reverse phase HPLC, 40 mg of 155. MS (Q1) 476 (M$^+$).

Example 84

5-(2-(2-aminopyrimidin-5-yl)-4-morpholinothieno[3,2-d]pyrimidin-6-yl)pyrazin-2-amine 156

2-Chloro-6-iodo-4-morpholinothieno[3,2-d]pyrimidine 19 from Example 12 was reacted with 5-(4,4,5,5-tetramethyl-1,3,2-dioxaborolan-2-yl)pyrazin-2-amine via General Procedure A to give, after purification by flash chromatography, 5-(2-chloro-4-morpholinothieno[3,2-d]pyrimidin-6-yl)pyrazin-2-amine, which was then reacted with 5-(4,4,5,5-tetramethyl-1,3,2-dioxaborolan-2-yl)pyrimidin-2-amine via General Procedure A again to give, after purification by reverse phase HPLC, 26 mg of 156. MS (Q1) 408 (M+).

Example 85

N-((2-(2-aminopyrimidin-5-yl)-4-morpholinothieno[2,3-d]pyrimidin-6-yl)methyl)-N-methylacetamide 157

2-Chloro-4-morpholinothieno[2,3-d]pyrimidine (General Procedure D-2) and 2-aminopyrimidine-5-boronic acid, pinacol ester were used in General Procedure A to produce 157 in 10% yield MS (Q1) 400 (M)

Example 86

N-methyl-N-((4-morpholino-2-(pyrimidin-5-yl)thieno[2,3-d]pyrimidin-6-yl)methyl)acetamide 158

2-Chloro-4-morpholinothieno[2,3-d]pyrimidine (General Procedure D-2) and pyrimidine-5-boronic acid were used in General Procedure A to produce 158 in 18% yield. MS (Q1) 385 (M+).

Example 87

N-methyl-N-((4-morpholino-2-(pyridin-3-yl)thieno[2,3-d]pyrimidin-6-yl)methyl)acetamide 159

2-Chloro-4-morpholinothieno[2,3-d]pyrimidine (General Procedure D-2) and 3-pyridinylboronic acid were used in General Procedure A to produce 159 in 22% yield MS (Q1) 384 (M+)

Example 88

5-(6-(3-methylsulfonylaminophenyl)-4-morpholinothieno[3,2-d]pyrimidin-2-yl)pyrimidin-2-amine 160

2-Chloro-6-iodo-4-morpholinothieno[3,2-d]pyrimidine 19 from Example 12 was reacted with 3-(methanesulfonylamino)phenylboronic acid via General Procedure A to give, after purification by flash chromatography, 3-(2-chloro-4-morpholinothieno[3,2-d]pyrimidin-6-yl)-N-methylsulfonylbenzenamine, which was then reacted with 5-(4,4,5,5-tetramethyl-1,3,2-dioxaborolan-2-yl)pyrimidin-2-amine via General Procedure A again to give, after purification by reverse phase HPLC, 10 mg of 160. MS (Q1) 484 (M+).

Example 89

5-(7-methyl-4-morpholinothieno[3,2-d]pyrimidin-2-yl)pyrimidin-2-amine 161

2-Chloro-7-methyl-4-morpholinothieno[3,2-d]pyrimidine (150 mg) was reacted with 5-(4,4,5,5-tetramethyl-1,3,

Example 90

2-(2-(2-aminopyrimidin-5-yl)-7-methyl-4-morpholinothieno[3,2-d]pyrimidin-6-yl)propan-2-ol 162

2-Chloro-7-methyl-4-morpholinothieno[3,2-d]pyrimidine (150 mg) was reacted with acetone via General Procedure D to give 2-(2-chloro-7-methyl-4-morpholinothieno[3,2-d]pyrimidin-6-yl)propan-2-ol, 180 mg of which was reacted with 160 mg of 5-(4,4,5,5-tetramethyl-1,3,2-dioxaborolan-2-yl)pyrimidin-2-amine via General Procedure A to give 55 mg of 162. MS (Q1) 387.2 (M)+

Example 91

2-(2-(2-aminopyrimidin-5-yl)-4-morpholinothieno[3,2-d]pyrimidin-6-yl)-1,3-dimethoxypropan-2-ol 163

2-Chloro-4-morpholinothieno[3,2-d]pyrimidine 4 (200 mg) was reacted with 1,3-dimethoxypropan-2-one via General Procedure D to give 2-(2-chloro-4-morpholinothieno[3,2-d]pyrimidin-6-yl)-1,3-dimethoxypropan-2-ol, of which 220 mg was reacted with 180 mg of 5-(4,4,5,5-tetramethyl-1,3,2-dioxaborolan-2-yl)pyrimidin-2-amine via General Procedure A to give 64.6 mg of 163. MS (Q1) 433.2 (M)+.

Example 92

2-(2-(2-aminopyrimidin-5-yl)-4-morpholinothieno[3,2-d]pyrimidin-6-yl)-1-methoxypropan-2-ol 164

2-Chloro-4-morpholinothieno[3,2-d]pyrimidine 4 (200 mg) was treated with 1-methoxypropan-2-one via General Procedure D to give 2-(2-chloro-4-morpholinothieno[3,2-d]pyrimidin-6-yl)-1-methoxypropan-2-ol, of which 220 mg was reacted with 180 mg of 5-(4,4,5,5-tetramethyl-1,3,2-dioxaborolan-2-yl)pyrimidin-2-amine via General Procedure A to give 11.5 mg of 164. MS (Q1) 403.2 (M+).

Example 93

N-((2-(6-aminopyridin-3-yl)-4-morpholinothieno[2,3-d]pyrimidin-6-yl)methyl)-N-methylacetamide 165

2-Chloro-4-morpholinothieno[2,3-d]pyrimidine (General Procedure D-2) and 2-aminopyridine-5-boronic acid, pinacol ester were used in General Procedure A to produce 165 in 23% yield MS (Q1) 394 (M+).

Example 94

5-(6-(6-aminopyridin-3-yl)-4-morpholinothieno[3,2-d]pyrimidin-2-yl)pyrimidin-2-amine 166

2-Chloro-6-iodo-4-morpholinothieno[3,2-d]pyrimidine 19 from Example 12 was reacted with 2-amino-5-(4,4,5,5-tetramethyl-1,3,2-dioxaborolan-2-yl)pyridine via General Procedure A to give, after purification by flash chromatography, 5-(2-chloro-4-morpholinothieno[3,2-d]pyrimidin-6-yl)pyridin-2-amine, which was then reacted with 5-(4,4,5,5-tetramethyl-1,3,2-dioxaborolan-2-yl)pyrimidin-2-amine via General Procedure A again to give, after purification by reverse phase HPLC, 16 mg of 166. MS (Q1) 407 (M+).

Example 95

(2-(2-aminopyrimidin-5-yl)-4-morpholinothieno[3,2-d]pyrimidin-6-yl)(4-(2-hydroxyethyl)piperazin-1-yl)methanone 167

2-Chloro-4-morpholinothieno[3,2-d]pyrimidine 4 (3.2 gm) was cooled to −78° C. in 32 mL of THF before adding 1.3 eq of a 2.5M solution of nBuLi in hexanes. The reaction was stirred at −78° C. for 30 minutes before warming to −40° C. for several minutes to allow for complete formation of the Lithium anion. The reaction was then re-cooled to −78° C. and carbon dioxide gas evolved from dry ice was bubbled in via cannula to the reaction solution for 1 hour. The reaction was then slowly warmed to 0° C. over 30 minutes and the THF was concentrated by rotovap. The reaction was then quenched with water and extracted with Ethyl Acetate to remove any 2-chloro-4-morpholinothieno[3,2-d]pyrimidine 4. The aqueous layer was then brought to pH of 2-3 by adding concentrated HCl. The resultant solid that crashed out of the aqueous layer was then collected by Buchner funnel, rinsed with water and dried overnight under vacuum to yield 3.56 g of 2-chloro-4-morpholinothieno[3,2-d]pyrimidine-6-carboxylic acid. 1 g of 2-chloro-4-morpholinothieno[3,2-d]pyrimidine-6-carboxylic acid was reacted with 1.03 g of 5-(4,4,5,5-tetramethyl-1,3,2-dioxaborolan-2-yl)pyrimidin-2-amine to give 2-(2-aminopyrimidin-5-yl)-4-morpholinothieno[3,2-d]pyrimidine-6-carboxylic acid.

2-(2-Aminopyrimidin-5-yl)-4-morpholinothieno[3,2-d]pyrimidine-6-carboxylic acid (100 mg) was reacted with 105 μL of 2-(piperazin-1-yl)ethanol via General Procedure B to give 18.7 mg of 167. MS (Q1) 471.2 (M+)

Example 96

(2-(2-aminopyrimidin-5-yl)-4-morpholinothieno[3,2-d]pyrimidin-6-yl)(4-methylpiperazin-1-yl)methanone 168

2-(2-Aminopyrimidin-5-yl)-4-morpholinothieno[3,2-d]pyrimidine-6-carboxylic acid (100 mg) was reacted with 85 μL of 1-methylpiperazine via General Procedure B to give 46 mg of 168. MS (Q1) 441.2 (M)+

Example 97

2-(2-aminopyrimidin-5-yl)-4-morpholino-N-(2-(piperidin-1-yl)ethyl)thieno[3,2-d]pyrimidine-6-carboxamide 169

2-(2-Aminopyrimidin-5-yl)-4-morpholinothieno[3,2-d]pyrimidine-6-carboxylic acid (100 mg) was reacted with 120 μL of 2-(piperidin-1-yl)ethanamine via General Procedure B to give 39.1 mg of 169. MS (Q1) 469.2 (M)+

Example 98

(2-(2-aminopyrimidin-5-yl)-4-morpholinothieno[3,2-d]pyrimidin-6-yl)(morpholino)methanone 170

2-(2-Aminopyrimidin-5-yl)-4-morpholinothieno[3,2-d]pyrimidine-6-carboxylic acid (100 mg) was reacted with 75 μL of morpholine via General Procedure B to give 12.9 mg of 170. MS (Q1) 428.2 (M)+

Example 99

2-(2-aminopyrimidin-5-yl)-N-methyl-4-morpholinothieno[3,2-d]pyrimidine-6-carboxamide 171

2-(2-Aminopyrimidin-5-yl)-4-morpholinothieno[3,2-d]pyrimidine-6-carboxylic acid (100 mg) was reacted with 57 mg of methylamine HCl via General Procedure B to give 171. MS (Q1) 372.1 (M)+

Example 100

5-(6-((E)-3-methoxyprop-1-enyl)-4-morpholinothieno[3,2-d]pyrimidin-2-yl)pyrimidin-2-amine 172

2-Chloro-6-iodo-4-morpholinothieno[3,2-d]pyrimidine 19 from Example 12 (300 mg), 171 mg of (E)-2-(3-methoxy-1-propen-1-yl)-4,4,5,5-tetramethyl-1,3,2-dioxaborolane and 28 mg of Bis(triphenylphosphine)palladium (II) dichloride in 2.4 mL of 1M $Na_2CO_3$ aqueous solution and 2.4 mL of acetonitrile was heated to 100° C. in a sealed microwave reactor for 10 min. The reaction mixture was evaporated. The crude product was purified by isco eluting with 5~100% EtOAc/Hexane to yield 2-chloro-6-((E)-3-methoxyprop-1-enyl)-4-morpholinothieno[3,2-d]pyrimidine (230 mg, 90%).

2-Chloro-6-((E)-3-methoxyprop-1-enyl)-4-morpholinothieno[3,2-d]pyrimidine (150 mg) was coupled to 2-aminopyrimidine-5-boronic acid pinacol ester via General Procedure A. The product was purified by reverse phase HPLC to yield 2.0 mg of 172. MS (Q1) 385.1 (M)$^+$.

Example 101

2-amino-N-(3-(2-(2-aminopyrimidin-5-yl)-4-morpholinothieno[3,2-d]pyrimidin-6-yl)phenyl)acetamide 173

3-(2-Chloro-4-morpholinothieno[3,2-d]pyrimidin-6-yl)benzenamine (200 mg) was reacted with Boc-glycine via General Procedure I to give 190 mg of tert-butyl (3-(2-chloro-4-morpholinothieno[3,2-d]pyrimidin-6-yl)phenylcarbamoyl)methylcarbamate. 100 mg of the crude tert-butyl (3-(2-chloro-4-morpholinothieno[3,2-d]pyrimidin-6-yl)phenylcarbamoyl)methylcarbamate was coupled to 2-aminopyrimidine-5-boronic acid pinacol ester via General Procedure A. Upon completion, added $H_2O$, and extracted with EtOAc (3×20 mL). The combined organic layers were dried over $MgSO_4$, filtered and evaporated to give 200 mg of tert-butyl (3-(2-(2-aminopyrimidin-5-yl)-4-morpholinothieno[3,2-d]pyrimidin-6-yl)phenylcarbamoyl)methylcarbamate.

A mixture of 110 mg of tert-butyl (3-(2-(2-aminopyrimidin-5-yl)-4-morpholinothieno[3,2-d]pyrimidin-6-yl)phenylcarbamoyl)methylcarbamate in 1.5 mL of trifluoroacetic acid and 1.5 mL of dichloromethane was stirred for 1 h at room temperature. The mixture was evaporated and the product was purified by reverse phase HPLC to yield 12.6 mg of 173. MS (Q1) 463.1 (M)$^+$.

Example 102

5-(6-((N-methyl,N-methylsulfonylamino)methyl)-4-morpholinothieno[2,3-d]pyrimidin-2-yl)pyrimidin-2-amine 174

2-Chloro-4-morpholinothieno[2,3-d]pyrimidine (General Procedure D-2) and 2-aminopyrimidine-5-boronic acid, pinacol ester were used in General Procedure A to produce 174 in 15% yield. MS (Q1) 436 (M+).

Example 103

N-methyl,N-methylsulfonyl(4-morpholino-2-(pyrimidin-5-yl)thieno[2,3-d]pyrimidin-6-yl)methanamine 175

2-Chloro-4-morpholinothieno[2,3-d]pyrimidine (General Procedure D-2) and pyrimidine-5-boronic acid were used in General Procedure A to produce 175 in 15% yield MS (Q1) 421 (M)

Example 104

2-amino-N-(3-(2-(6-aminopyridin-3-yl)-4-morpholinothieno[3,2-d]pyrimidin-6-yl)phenyl)acetamide 176

Crude tert-butyl (3-(2-chloro-4-morpholinothieno[3,2-d]pyrimidin-6-yl)phenylcarbamoyl)methylcarbamate (90 mg) was coupled to 2-aminopyridine-5-boronic acid pinacol ester via General Procedure A. Upon completion, water was added, and extracted with EtOAc (3×15 mL). The combined organic layers were dried over $MgSO_4$, filtered and evaporated to give tert-butyl (3-(2-(2-aminopyridin-5-yl)-4-morpholinothieno[3,2-d]pyrimidin-6-yl)phenylcarbamoyl)methylcarbamate.

A mixture of 100 mg of tert-butyl (3-(2-(2-aminopyridin-5-yl)-4-morpholinothieno[3,2-d]pyrimidin-6-yl)phenylcarbamoyl)methylcarbamate in 1.5 mL of trifluoroacetic acid and 1.5 mL of dichloromethane was stirred for 1 h at room temperature. The mixture was evaporated and the product was purified by reverse phase HPLC to yield 17.7 mg of 176. MS (Q1) 462.3 (M)$^+$.

Example 105

2-(3-(2-(2-aminopyrimidin-5-yl)-4-morpholinothieno[3,2-d]pyrimidin-6-yl)phenyl)propan-2-ol 177

2-Chloro-6-iodo-4-morpholinothieno[3,2-d]pyrimidine 19 from Example 12 (500 mg), 236 mg of 3-acetylbenezeneboronic acid and 46 mg of Bis(triphenylphosphine)palladium(II) dichloride in 4 mL of 1M $Na_2CO_3$ aqueous solution and 4 mL of acetonitrile was heated to 100° C. in a sealed microwave reactor for 10 min. The reaction mixture was evaporated. The crude product was purified by isco eluting with 0→40% EtOAc/Hexane to yield 1-(3-(2-chloro-4-morpholinothieno[3,2-d]pyrimidin-6-yl)phenyl)ethanone (440 mg, 90%).

Methyl magnesium bromide (980 μL, 3.0 M solution in diethyl ether) was added to a mixture of 220 mg of 1-(3-(2-chloro-4-morpholinothieno[3,2-d]pyrimidin-6-yl)phenyl)ethanone in 4 mL of THF at −50° C. The reaction mixture was allowed to warm to room temperature and stirred overnight. The reaction was quenched with saturated $NH_4Cl$ aqueous solution, extracted with EtOAc (3×20 mL). The combined organic layers were dried over $MgSO_4$, filtered and evaporated to give 220 mg of 2-(3-(2-chloro-4-morpholinothieno[3,2-d]pyrimidin-6-yl)phenyl)propan-2-ol.

2-(3-(2-Chloro-4-morpholinothieno[3,2-d]pyrimidin-6-yl)phenyl)propan-2-ol (60 mg) was coupled to 2-aminopyrimidine-5-boronic acid pinacol ester via General Procedure A. The product was purified by reverse phase HPLC to yield 22.2 mg of 177. MS (Q1) 449.3 (M)⁺.

Example 106

N-methyl,N-methylsulfonyl(4-morpholino-2-(pyridin-3-yl)thieno[2,3-d]pyrimidin-6-yl)methanamine 178

2-Chloro-4-morpholinothieno[2,3-d]pyrimidine (General Procedure D-2) and pyridine-3-boronic acid were used in General Procedure A to produce 178 in 10% yield MS (Q1) 420 (M).

Example 107

5-(6-((N-methyl,N-methylsulfonylamino)methyl)-4-morpholinothieno[2,3-d]pyrimidin-2-yl)pyridin-2-amine 179

2-Chloro-4-morpholinothieno[2,3-d]pyrimidine (General Procedure D-2) and 2-aminopyridine-5-boronic acid, pinacol ester were used in General Procedure A to produce 179 in 9% yield MS (Q1) 435 (M)

Example 108

5-(6-(3-(N-methylsulfonylaminomethyl)phenyl)-4-morpholinothieno[3,2-d]pyrimidin-2-yl)pyridin-2-amine 180

2-Chloro-6-iodo-4-morpholinothieno[3,2-d]pyrimidine 19 from Example 12 was reacted with 3-(methanesulfonylaminomethyl)phenylboronic acid via General Procedure A to give, after purification by flash chromatography, (3-(2-chloro-4-morpholinothieno[3,2-d]pyrimidin-6-yl)phenyl)-N-methylsulfonylmethanamine, which was then reacted with 5-(4,4,5,5-tetramethyl-1,3,2-dioxaborolan-2-yl)pyrimidin-2-amine via General Procedure A again to give, after purification by reverse phase HPLC, 180. MS (Q1) 498 (M+).

Example 109

5-(6-(2-(4-methylpiperazin-1-yl)pyridin-4-yl)-4-morpholinothieno[3,2-d]pyrimidin-2-yl)pyridin-2-amine 181

2-Chloro-6-iodo-4-morpholinothieno[3,2-d]pyrimidine 19 from Example 12 was reacted with 1-methyl-4-[4-(4,4,5,5-tetramethyl-1,3,2-dioxaborolan-2-yl)pyridin-2-yl]piperazine via General Procedure A to give, after purification by flash chromatography, 2-chloro-6-(2-(4-methylpiperazin-1-yl)pyridin-4-yl)-4-morpholinothieno[3,2-d]pyrimidine, which was then reacted with 2-amino-5-(4,4,5,5-tetramethyl-1,3,2-dioxaborolan-2-yl)pyridine via General Procedure A again to give, after purification by reverse phase HPLC, 18 mg of 181. MS (Q1) 489 (M⁺).

Example 110

5-(6-(2-(4-methylpiperazin-1-yl)pyridin-4-yl)-4-morpholinothieno[3,2-d]pyrimidin-2-yl)pyrimidin-2-amine 182

2-Chloro-6-iodo-4-morpholinothieno[3,2-d]pyrimidine 19 from Example 12 was reacted with 1-methyl-4-[4-(4,4,5,5-tetramethyl-1,3,2-dioxaborolan-2-yl)pyridin-2-yl]piperazine via General Procedure A to give, after purification by flash chromatography, 2-chloro-6-(2-(4-methylpiperazin-1-yl)pyridin-4-yl)-4-morpholinothieno[3,2-d]pyrimidine, which was then reacted with 5-(4,4,5,5-tetramethyl-1,3,2-dioxaborolan-2-yl)pyrimidin-2-amine via General Procedure A again to give, after purification by reverse phase HPLC, 3 mg of 182. MS (Q1) 490 (M⁺).

Example 111

2-(3-(2-(6-aminopyridin-3-yl)-4-morpholinothieno[3,2-d]pyrimidin-6-yl)phenyl)propan-2-ol 183

2-(3-(2-Chloro-4-morpholinothieno[3,2-d]pyrimidin-6-yl)phenyl)propan-2-ol (60 mg) was coupled to 2-aminopyridine-5-boronic acid pinacol ester via General Procedure A. The product was purified by reverse phase HPLC to yield 11.5 mg of 183. MS (Q1) 448 (M)⁺.

Example 112

1-(3-(2-(2-aminopyrimidin-5-yl)-4-morpholinothieno[3,2-d]pyrimidin-6-yl)phenyl)ethanol 184

Sodium borohydride (18 mg) was added to a mixture of 90 mg of 1-(3-(2-chloro-4-morpholinothieno[3,2-d]pyrimidin-6-yl)phenyl)ethanone in 3 ml of methanol. The reaction mixture was stirred for 2 h at room temperature. Upon completion, the reaction was quenched with H₂O, and extracted with DCM (3×20 mL). The combined organic layers were dried over MgSO₄, filtered and evaporated to give 1-(3-(2-chloro-4-morpholinothieno[3,2-d]pyrimidin-6-yl)phenyl)ethanol.

1-(3-(2-Chloro-4-morpholinothieno[3,2-d]pyrimidin-6-yl)phenyl)ethanol (83 mg) was coupled to 2-aminopyrimidine-5-boronic acid pinacol ester via General Procedure A. The product was purified by reverse phase HPLC to yield 23.3 mg of 184. MS (Q1) 435.3 (M)⁺.

Example 113

1-(3-(2-(6-aminopyridin-3-yl)-4-morpholinothieno[3,2-d]pyrimidin-6-yl)phenyl)ethanol 185

1-(3-(2-Chloro-4-morpholinothieno[3,2-d]pyrimidin-6-yl)phenyl)ethanol (55 mg) was coupled to 2-aminopyridine-5-boronic acid pinacol ester via General Procedure A. The product was purified by reverse phase HPLC to yield 26.6 mg of 185. MS (Q1) 434.1 (M)⁺.

Example 114

3-(3-(2-(6-aminopyridin-3-yl)-4-morpholinothieno[3,2-d]pyrimidin-6-yl)phenyl)propan-1-ol 186

2-Chloro-6-iodo-4-morpholinothieno[3,2-d]pyrimidine 19 from Example 12 (300 mg), 156 mg of 3-(3-hydroxypropyl)phenylboronic acid and 30 mg of bis(triphenylphosphine)palladium(II) dichloride in 3 mL of 1M Na₂CO₃ aqueous solution and 3 mL of acetonitrile was heated to 100° C. in a sealed microwave reactor for 10 min. The reaction mixture was evaporated. The crude product was purified by isco eluting with 5→100% EtOAc/Hexane to yield 3-(3-(2-chloro-4-morpholinothieno[3,2-d]pyrimidin-6-yl)phenyl)propan-1-ol (267 mg, 75%).

3-(3-(2-Chloro-4-morpholinothieno[3,2-d]pyrimidin-6-yl)phenyl)propan-1-ol (50 mg) was coupled to 2-aminopyridine-5-boronic acid pinacol ester via General Procedure A. The product was purified by reverse phase HPLC to yield 34.2 mg of 186. MS (Q1) 448.1 (M)+.

Example 115

3-(3-(2-(2-aminopyrimidin-5-yl)-4-morpholinothieno[3,2-d]pyrimidin-6-yl)phenyl)propan-1-ol 187

3-(3-(2-Chloro-4-morpholinothieno[3,2-d]pyrimidin-6-yl)phenyl)propan-1-ol (50 mg) was coupled to 2-aminopyrimidine-5-boronic acid pinacol ester via General Procedure A. The product was purified by reverse phase HPLC to yield 18 mg 187. MS (Q1) 449 (M)+.

Example 116

(2-(2-aminopyrimidin-5-yl)-4-morpholinothieno[3,2-d]pyrimidin-6-yl)(N-4-methylsulfonylpiperazin-1-yl)methanone 188

2-(2-Aminopyrimidin-5-yl)-4-morpholinothieno[3,2-d]pyrimidine-6-carboxylic acid (100 mg) was reacted with 65 mg of 1-methylsulfonylpiperazine via General Procedure B to give 19 mg of 188. MS (Q1) 505.2 (M)+.

Example 117

5-(6-(2-aminothiazol-4-yl)-4-morpholinothieno[3,2-d]pyrimidin-2-yl)pyridin-2-amine 189

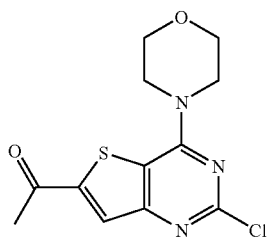 [SMILES: CC(=O)c1cc2nc(Cl)nc(N3CCOCC3)c2s1]

To a solution of 2-chloro-4-morpholinothieno[3,2-d]pyrimidine (4, Example 2) (1.0 eq) dissolved in THF (0.1M) at −78° C. was added a solution of n-butyllithium (1.3 eq, 1.6M in hexanes). Reaction mixture was stirred at −40° C. for 30 minutes. N,N-dimethylacetamide (4.0 eq) was added and reaction mixture was allowed to slowly warm up to 0° C. and stirred for 2 hours. Reaction mixture was poured in a cold solution of 0.25M HCl, and extracted with dichloromethane. The combined organic layers were dried (Na₂SO₄) and concentrated. The crude reaction mixture was purified by flash chromatography to yield 1-(2-chloro-4-morpholinothieno[3,2-d]pyrimidin-6-yl)ethanone.

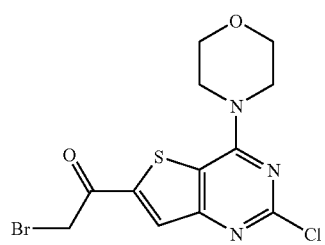 [SMILES: O=C(CBr)c1cc2nc(Cl)nc(N3CCOCC3)c2s1]

To a solution of 1-(2-chloro-4-morpholinothieno[3,2-d]pyrimidin-6-yl)ethanone (1.0 eq) dissolved in a mixture of CHCl₃, 33% wt HBr and acetic acid (1:1:1) at −0° C. was added a solution of Br₂ in CHCl₃ (1.05 eq). Reaction mixture was stirred at −0° C. until completed, then extracted in dichloromethane with saturated bicarbonate solution one time. The organic layer is dried, filtered and concentrated to yield the crude intermediate. This intermediate is purified by flash chromatography to yield 2-bromo-1-(2-chloro-4-morpholinothieno[3,2-d]pyrimidin-6-yl)ethanone.

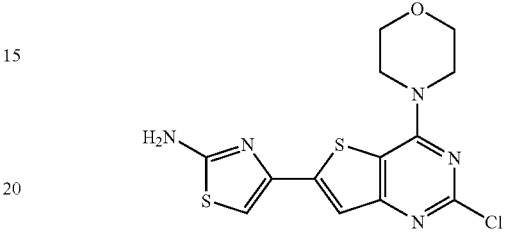

To a solution of 2-bromo-1-(2-chloro-4-morpholinothieno[3,2-d]pyrimidin-6-yl)ethanone (1.0 eq) dissolved in EtOH was added thiourea. Reaction mixture was heated at 70° C. until completed, then extracted in dichloromethane with saturated bicarbonate solution one time. The organic layer is dried, filtered and concentrated to yield the crude intermediate. This intermediate is purified by flash chromatography to yield 4-(2-chloro-4-morpholinothieno[3,2-d]pyrimidin-6-yl)thiazol-2-amine. MS (Q1) 413 (M+).

4-(2-Chloro-4-morpholinothieno[3,2-d]pyrimidin-6-yl)thiazol-2-amine was reacted with 2-amino-5-(4,4,5,5-tetramethyl-1,3,2-dioxaborolan-2-yl)pyridine via General Procedure B to give, after purification by reverse HPLC, 10 mg of 189. MS (Q1) 413 (M+).

Example 118

5-(6-(4-(4-methylpiperazin-1-yl)phenyl)-4-morpholinothieno[3,2-d]pyrimidin-2-yl)pyridin-2-amine 190

2-Chloro-6-iodo-4-morpholinothieno[3,2-d]pyrimidine 19 from Example 12 was reacted with 1-methyl-4-[4-(4,4,5,5-tetramethyl-1,3,2-dioxaborolan-2-yl)phenyl]piperazine via General Procedure A to give, after purification by flash chromatography, 2-chloro-6-(4-(4-methylpiperazin-1-yl)phenyl)-4-morpholinothieno[3,2-d]pyrimidine, which was then reacted with 5-(4,4,5,5-tetramethyl-1,3,2-dioxaborolan-2-yl)pyridin-2-amine via General Procedure A again to give, after purification by reverse phase HPLC, 36 mg of 190. MS (Q1) 489 (M+).

Example 119

5-(6-(3,5-dimethylisoxazol-4-yl)-4-morpholinothieno[3,2-d]pyrimidin-2-yl)pyrimidin-2-amine 191

2-Chloro-6-iodo-4-morpholinothieno[3,2-d]pyrimidine 19 from Example 12 was reacted with 3,5-dimethyl-4-(4,4,5,5-tetramethyl-1,3,2-dioxaborolane-2-yl)isoxazole via General Procedure A to give, after purification by flash chromatography, 2-chloro-6-(3,5-dimethylisoxazol-4-yl)-4-morpholinothieno[3,2-d]pyrimidine, which was then reacted with 5-(4,4,5,5-tetramethyl-1,3,2-dioxaborolan-2-yl)pyrimidin-2-amine via General Procedure A again to give, after purification by reverse phase HPLC, 6 mg of 191. MS (Q1) 411 (M+).

Example 120

5-(4-morpholino-6-(6-morpholinopyridin-3-yl)thieno [3,2-d]pyrimidin-2-yl)pyrimidin-2-amine 192

2-Chloro-6-iodo-4-morpholinothieno[3,2-d]pyrimidine 19 from Example 12 was reacted with 4-[5-(4,4,5,5-tetramethyl-1,3,2-dioxaborolan-2-yl)pyridin-2-yl]morpholine via General Procedure A to give, after purification by flash chromatography, 2-chloro-4-morpholino-6-(6-morpholinopyridin-3-yl)thieno[3,2-d]pyrimidine, which was then reacted with 5-(4,4,5,5-tetramethyl-1,3,2-dioxaborolan-2-yl)pyrimidin-2-amine via General Procedure A again to give, after purification by reverse phase HPLC, 192. MS (Q1) 477 (M$^+$).

Example 121

5-(6-(2-fluoro-5-methoxyphenyl)-4-morpholinothieno[3,2-d]pyrimidin-2-yl)pyrimidin-2-amine 193

2-Chloro-6-iodo-4-morpholinothieno[3,2-d]pyrimidine 19 from Example 12 was reacted with 2-fluoro-5-methoxyphenylboronic acid via General Procedure A to give, after purification by flash chromatography, 2-chloro-6-(2-fluoro-5-methoxyphenyl)-4-morpholinothieno[3,2-d]pyrimidine, which was then reacted with 5-(4,4,5,5-tetramethyl-1,3,2-dioxaborolan-2-yl)pyrimidin-2-amine via General Procedure A again to give, after purification by reverse phase HPLC, 193. MS (Q1) 440 (M+).

Example 122

N-(2-(2-(2-aminopyrimidin-5-yl)-4-morpholinothieno[3,2-d]pyrimidin-6-yl)propan-2-yl)acetamide 194

To a solution of amine 3 (400 mg, 1.3 mmol) in $CH_2Cl_2$ (20 mL) was added $Et_3N$ (630 µL, 4.5 mmol) and acetyl chloride (180 µL, 2.6 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. The crude material was purified by silica gel chromatography (0-100% EtOAc in hexane). A portion (0.2 mmol) of the resulting pure product was coupled using General Procedure A with 5-(4,4,5,5-tetramethyl-1,3,2-dioxaborolan-2-yl)pyrimidin-2-amine to provide G-38951 after reverse phase HPLC purification (14 mg). MS (Q1) 414 (M)+

Example 123

N-(2-(4-morpholino-2-(pyridin-3-yl)thieno[3,2-d]pyrimidin-6-yl)propan-2-yl)acetamide 195

To a solution of amine 3 (400 mg, 1.3 mmol) in $CH_2Cl_2$ (20 mL) was added $Et_3N$ (630 µL, 4.5 mmol) and acetyl chloride (180 µL, 2.6 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. The crude material was purified by silica gel chromatography (0-100% EtOAc in hexane). A portion (0.2 mmol) of the resulting pure product was coupled using General Procedure A with 3-(4,4,5,5-tetramethyl-1,3,2-dioxaborolan-2-yl)pyridine to provide 195 after reverse phase HPLC purification (55 mg). MS (Q1) 398 (M)+

Example 124

2-(4-morpholino-2-(pyridin-3-yl)thieno[3,2-d]pyrimidin-6-yl)propan-2-N-methylsulfonylamine 196

To a solution of amine 3 (400 mg, 1.3 mmol) in $CH_2Cl_2$ (20 mL) was added $Et_3N$ (630 µL, 4.5 mmol) and methanesulfonyl chloride (200 µL, 2.6 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. The crude material was purified by silica gel chromatography (0-100% EtOAc in hexane). A portion (0.2 mmol) of the resulting pure product was coupled using General Procedure A with 3-(4,4,5,5-tetramethyl-1,3,2-dioxaborolan-2-yl)pyridine to provide 196 after reverse phase HPLC purification (25 mg). MS (Q1) 434 (M)+

Example 125

5-(6-(2-N-methylsulfonylaminopropan-2-yl)-4-morpholinothieno[3,2-d]pyrimidin-2-yl)pyrimidin-2-amine 197

To a solution of amine 3 (400 mg, 1.3 mmol) in $CH_2Cl_2$ (20 mL) was added $Et_3N$ (630 µL, 4.5 mmol) and methanesulfonyl chloride (200 µL, 2.6 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. The crude material was purified by silica gel chromatography (0-100% EtOAc in hexane). A portion (0.2 mmol) of the resulting pure product was coupled using General Procedure A with 5-(4,4,5,5-tetramethyl-1,3,2-dioxaborolan-2-yl)pyrimidin-2-amine to provide 197 after reverse phase HPLC purification (20 mg). MS (Q1) 450 (M)+

Example 126

2-(6-aminopyridin-3-yl)-4-morpholinothieno[3,2-d]pyrimidine-6-carboxamide 198

2-Chloro-4-morpholinothieno[3,2-d]pyrimidine-6-carboxamide, prepared from General Procedure B-5, (65 mg) was coupled following General Procedure A with 5-(4,4,5,5-tetramethyl-1,3,2-dioxaborolan-2-yl)pyridin-2-amine to provide 198 after reverse phase HPLC purification (7 mg). (Q1) 357 (M)+

Example 127

5-(7-methyl-6-((N-methyl,N-methylsulfonylamino)methyl)-4-morpholinothieno[3,2-d]pyrimidin-2-yl)pyridin-2-amine 199

To a solution of (2-chloro-7-methyl-4-morpholinothieno[3,2-d]pyrimidin-6-yl)-N-methylmethanamine from General Procedure B-4 (400 mg, 1.3 mmol) in $CH_2Cl_2$ (20 mL) was added $Et_3N$ (630 µL, 4.5 mmol) and methanesulfonyl chloride (200 µL, 2.6 mmol). The resulting mixture stirred at room temperature overnight. The reaction was quenched by the addition of saturated aqueous $NaHCO_3$. The organic layer was separated and the aqueous layer was extracted with EtOAc. The combined organic layers were dried over $Na_2SO_4$, filtered, and concentrated in vacuo. The crude material was purified by silica gel chromatography (0-100% EtOAc in hexane). A portion (0.2 mmol) of the resulting pure product was coupled using General Procedure A with 5-(4,4,5,5-tetramethyl-1,3,2-dioxaborolan-2-yl)pyridin-2-amine to provide 199 after reverse phase HPLC purification (53 mg). MS (Q1) 449 (M)+

Example 128

2-(2-aminopyrimidin-5-yl)-4-morpholinothieno[3,2-d]pyrimidine-6-carboxamide 200

2-Chloro-4-morpholinothieno[3,2-d]pyrimidine-6-carboxamide, prepared from General Procedure B-5, (65 mg) was coupled following General Procedure A with 5-(4,4,5,5-tetramethyl-1,3,2-dioxaborolan-2-yl)pyrimidin-2-amine to provide 200 after reverse phase HPLC purification (7 mg). (Q1) 358 (M)+

Example 129

5-(6-(1H-indol-6-yl)-4-morpholinothieno[3,2-d]pyrimidin-2-yl)pyridin-2-amine 201

2-Chloro-6-iodo-4-morpholinothieno[3,2-d]pyrimidine 19 from Example 12 was reacted with indole-6-boronic acid via General Procedure A to give, after purification by flash chromatography, 2-chloro-6-(1H-indol-6-yl)-4-morpholinothieno[3,2-d]pyrimidine, which was then reacted with 5-(4,4,5,5-tetramethyl-1,3,2-dioxaborolan-2-yl)pyridin-2-amine to give, after purification by reverse phase HPLC, 4 mg of 201. MS (Q1) 429 (M+).

Example 130

5-(2-(6-aminopyridin-3-yl)-4-morpholinothieno[3,2-d]pyrimidin-6-yl)pyridin-2-amine 202

2-Chloro-6-iodo-4-morpholinothieno[3,2-d]pyrimidine 19 from Example 12 was reacted with 5-(4,4,5,5-tetramethyl-1,3,2-dioxaborolan-2-yl)pyridin-2-amine via General Procedure A to give, after purification by flash chromatography, 5-(2-chloro-4-morpholinothieno[3,2-d]pyrimidin-6-yl)pyridin-2-amine, which was then reacted with 5-(4,4,5,5-tetramethyl-1,3,2-dioxaborolan-2-yl)pyridin-2-amine via General Procedure A again to give, after purification by reverse phase HPLC, 20 mg of 202. MS (Q1) 406 (M+).

Example 131

2-(4-morpholino-2-(pyridin-3-yl)thieno[3,2-d]pyrimidin-6-yl)propan-2-amine 203

2-(2-Chloro-4-morpholinothieno[3,2-d]pyrimidin-6-yl)propan-2-amine, from General Procedure B-5, (100 mg) was coupled following General Procedure A with 3-(4,4,5,5-tetramethyl-1,3,2-dioxaborolan-2-yl)pyridine to provide 203 after reverse phase HPLC purification (13 mg). MS (Q1) 356 (M)+

Example 132

2-(4-morpholino-2-(pyrimidin-5-yl)thieno[3,2-d]pyrimidin-6-yl)propan-2-amine 204

2-(2-Chloro-4-morpholinothieno[3,2-d]pyrimidin-6-yl)propan-2-amine, from General Procedure B-5, (100 mg) was coupled following General Procedure A with pyrimidin-5-yl-5-boronic acid to provide 204 after reverse phase HPLC purification (13 mg). MS (Q1) 357 (M)+

Example 133

5-(6-(2-aminopropan-2-yl)-4-morpholinothieno[3,2-d]pyrimidin-2-yl)pyridin-2-amine 205

2-(2-Chloro-4-morpholinothieno[3,2-d]pyrimidin-6-yl)propan-2-amine, from General Procedure B-5, (100 mg) was coupled following General Procedure A with 5-(4,4,5,5-tetramethyl-1,3,2-dioxaborolan-2-yl)pyridin-2-amine to provide 205 after reverse phase HPLC purification (20 mg). (Q1) 371 (M)+

Example 134

5-(6-(2-aminopropan-2-yl)-4-morpholinothieno[3,2-d]pyrimidin-2-yl)pyrimidin-2-amine 206

2-(2-Chloro-4-morpholinothieno[3,2-d]pyrimidin-6-yl)propan-2-amine, from General Procedure B-5, (100 mg) was coupled following General Procedure A with 5-(4,4,5,5-tetramethyl-1,3,2-dioxaborolan-2-yl)pyrimidin-2-amine to provide 206 after reverse phase HPLC purification (9 mg). (Q1) 372 (M)+

Example 135

N-(3-(2-(2-aminopyrimidin-5-yl)-4-morpholinothieno[3,2-d]pyrimidin-6-yl)phenyl)acetamide 207

2-Chloro-6-iodo-4-morpholinothieno[3,2-d]pyrimidine 19 from Example 12 (500 mg), 258 mg of 3-acetamidophenylboronic acid and 46 mg of Bis(triphenylphosphine)palladium(II) dichloride in 3 mL of 1M $Na_2CO_3$ aqueous solution and 3 mL of acetonitrile was heated to 100° C. in a sealed microwave reactor for 10 min. The reaction mixture was evaporated. The crude product was purified by isco eluting with 30~100% EtOAc/Hexane to yield N-(3-(2-chloro-4-morpholinothieno[3,2-d]pyrimidin-6-yl)phenyl)acetamide (403 mg, 80%).

N-(3-(2-Chloro-4-morpholinothieno[3,2-d]pyrimidin-6-yl)phenyl)acetamide (120 mg) was coupled to 2-aminopyrimidine-5-boronic acid pinacol ester via General Procedure A. The product was purified by reverse phase HPLC to yield 49.2 mg of 207. MS (Q1) 448.1 (M)+.

Example 136

5-(6-(4-methoxypyridin-3-yl)-4-morpholinothieno[2,3-d]pyrimidin-2-yl)pyridin-2-amine 208

2-Chloro-6-iodo-4-morpholinothieno[2,3-d]pyrimidine was reacted with 4-methoxy-3-pyridineboronic acid via General Procedure C to give, after purification by flash chromatography, 2-chloro-6-(4-methoxypyridin-3-yl)-4-morpholinothieno[2,3-d]pyrimidine, which was then reacted with 5-(4,4,5,5-tetramethyl-1,3,2-dioxaborolan-2-yl)pyridin-2-amine via General Procedure C again to give, after purification by reverse phase HPLC, 7 mg of 208. MS (Q1) 421 (M+).

Example 137

6-(4-methoxypyridin-3-yl)-4-morpholino-2-(pyrimidin-5-yl)thieno[2,3-d]pyrimidine 209

2-Chloro-6-iodo-4-morpholinothieno[2,3-d]pyrimidine was reacted with 4-methoxy-3-pyridineboronic acid via General Procedure C to give, after purification by flash chromatography, 2-chloro-6-(4-methoxypyridin-3-yl)-4-morpholinothieno[2,3-d]pyrimidine, which was then reacted with pyrimidin-5-yl-5-boronic acid via General Procedure C again to give, after purification by reverse phase HPLC, 6 mg of 209. MS (Q1) 407 (M+).

Example 138

2-(4-morpholino-2-(pyrimidin-5-yl)thieno[2,3-d]pyrimidin-6-yl)propan-2-ol 210

To a solution of 2-chloro-4-morpholinothieno[2,3-d]pyrimidine (General Procedure D-2, 1.0 eq) dissolved in THF (0.15M) at −78° C. was added solution of n-butyllithium (1.3 eq, 1.6M in hexanes). Reaction mixture was stirred at −78° C. for 30 minutes. Acetone (4.0 eq) was added and reaction mixture was allowed to warm up to −40° C. and stirred for 1 h. The crude reaction mixture was concentrated and purified by reverse phase HPLC to afford 2-(2-chloro-4-morpholinothieno[2,3-d]pyrimidin-6-yl)propan-2-ol. MS (Q1) 314 (M+).

2-(2-Chloro-4-morpholinothieno[2,3-d]pyrimidin-6-yl)propan-2-ol was reacted with pyrimidin-5-yl-5-boronic acid via General Procedure B to give, after purification by reverse HPLC, 83 mg of 210. MS (Q1) 358 (M+).

Example 139

2-(2-(2-aminopyrimidin-5-yl)-4-morpholinothieno[2,3-d]pyrimidin-6-yl)propan-2-ol 211

2-(2-Chloro-4-morpholinothieno[2,3-d]pyrimidin-6-yl)propan-2-ol was reacted with 5-(4,4,5,5-tetramethyl-1,3,2-dioxaborolan-2-yl)pyrimidin-2-amine via General Procedure B to give, after purification by reverse HPLC, 7 mg of 211. MS (Q1) 373 (M+).

Example 140

2-(2-(6-aminopyridin-3-yl)-4-morpholinothieno[2,3-d]pyrimidin-6-yl)propan-2-ol 212

2-(2-Chloro-4-morpholinothieno[2,3-d]pyrimidin-6-yl)propan-2-ol was reacted with 5-(4,4,5,5-tetramethyl-1,3,2-dioxaborolan-2-yl)pyridin-2-amine via General Procedure B to give, after purification by reverse HPLC, 17 mg of 212. MS (Q1) 372 (M+).

Example 141

5-(6-(3-(methylsulfonyl)phenyl)-4-morpholinothieno[2,3-d]pyrimidin-2-yl)pyridin-2-amine 213

2-Chloro-6-iodo-4-morpholinothieno[2,3-d]pyrimidine was reacted with 3-methylsulfonylphenylboronic acid via General Procedure C to give, after purification by flash chromatography, 2-chloro-6-(3-(methylsulfonyl)phenyl)-4-morpholinothieno[2,3-d]pyrimidine, which was then reacted with 5-(4,4,5,5-tetramethyl-1,3,2-dioxaborolan-2-yl)pyridin-2-amine via General Procedure C again to give, after purification by reverse phase HPLC, 62 mg of 213. MS (Q1) 468 (M+).

Example 142

5-(6-(3-(methylsulfonyl)phenyl)-4-morpholinothieno[2,3-d]pyrimidin-2-yl)pyrimidin-2-amine 214

2-Chloro-6-iodo-4-morpholinothieno[2,3-d]pyrimidine was reacted with 3-methylsulfonylphenylboronic acid via General Procedure C to give, after purification by flash chromatography, 2-chloro-6-(3-(methylsulfonyl)phenyl)-4-morpholinothieno[2,3-d]pyrimidine, which was then reacted with 5-(4,4,5,5-tetramethyl-1,3,2-dioxaborolan-2-yl)pyrimidin-2-amine via General Procedure C again to give, after purification by reverse phase HPLC, 214. MS (Q1) 469 (M+).

Example 143

N-(3-(4-morpholino-2-(pyridin-3-yl)thieno[2,3-d]pyrimidin-6-yl)phenyl)acetamide 215

2-Chloro-6-iodo-4-morpholinothieno[2,3-d]pyrimidine was reacted with 3-acetamidophenylboronic acid via General Procedure C to give, after purification by flash chromatography, N-(3-(2-chloro-4-morpholinothieno[2,3-d]pyrimidin-6-yl)phenyl)acetamide, which was then reacted with pyridine-3-boronic acid via General Procedure C again to give, after purification by reverse phase HPLC, 215. MS (Q1) 432 (M+).

Example 144

N-(3-(2-(2-aminopyrimidin-5-yl)-4-morpholinothieno[2,3-d]pyrimidin-6-yl)phenyl)acetamide 216

2-Chloro-6-iodo-4-morpholinothieno[2,3-d]pyrimidine was reacted with 3-acetamidophenylboronic acid via General Procedure C to give, after purification by flash chromatography, N-(3-(2-chloro-4-morpholinothieno[2,3-d]pyrimidin-6-yl)phenyl)acetamide, which was then reacted with 5-(4,4,5,5-tetramethyl-1,3,2-dioxaborolan-2-yl)pyrimidin-2-amine via General Procedure C again to give, after purification by reverse phase HPLC, 216. MS (Q1) 448 (M+).

Example 145

5-(6-(4-methoxypyridin-3-yl)-4-morpholinothieno[2,3-d]pyrimidin-2-yl)pyrimidin-2-amine 217

2-Chloro-6-iodo-4-morpholinothieno[2,3-d]pyrimidine was reacted with 4-methoxy-3-pyridineboronic acid via General Procedure C to give, after purification by flash chromatography, 2-chloro-6-(4-methoxypyridin-3-yl)-4-morpholinothieno[2,3-d]pyrimidine, which was then reacted with 5-(4,4,5,5-tetramethyl-1,3,2-dioxaborolan-2-yl)pyrimidin-2-amine via General Procedure C again to give, after purification by reverse phase HPLC, 28 mg of 217. MS (Q1) 422 (M+).

Example 146

N-((2-(6-aminopyridin-3-yl)-4-morpholinothieno[3,2-d]pyrimidin-6-yl)methyl)-N-methylacetamide 218

N-((2-Chloro-4-morpholinothieno[3,2-d]pyrimidin-6-yl)methyl)-N-methylacetamide (0.18 mmol) was reacted using General Procedure A to give 218 (TFA salt) in a 35% yield after reverse-phase HPLC purification. MS (Q1) 399 (M+).

Example 147

N-((2-(2-aminopyrimidin-5-yl)-4-morpholinothieno[3,2-d]pyrimidin-6-yl)methyl)-N-methylacetamide 219

N-((2-Chloro-4-morpholinothieno[3,2-d]pyrimidin-6-yl)methyl)-N-methylacetamide (0.18 mmol) was reacted using General Procedure A to give 219 (TFA salt) in a 7% yield after reverse-phase HPLC purification. MS (Q1) 400 (M+).

Example 148

N-methyl-N-((4-morpholino-2-(pyridin-3-yl)thieno[3,2-d]pyrimidin-6-yl)methyl)acetamide 220

N-((2-Chloro-4-morpholinothieno[3,2-d]pyrimidin-6-yl)methyl)-N-methylacetamide (0.18 mmol) was reacted using General Procedure A to give 220 (TFA salt) in a 35% yield after reverse-phase HPLC purification. MS (Q1) 384 (M+).

Example 149

N-methyl-N-((4-morpholino-2-(pyrimidin-5-yl)thieno[3,2-d]pyrimidin-6-yl)methyl)acetamide 221

N-((2-Chloro-4-morpholinothieno[3,2-d]pyrimidin-6-yl)methyl)-N-methylacetamide (0.18 mmol) was reacted using General Procedure A to give 221 (TFA salt) in a 30% yield after reverse-phase HPLC purification. MS (Q1) 385 (M+).

Example 150

N-acetyl-N-(5-(6-((N-methyl,N-methylsulfonylamino)methyl)-4-morpholinothieno[3,2-d]pyrimidin-2-yl)pyrimidin-2-yl)acetamide 222

(2-Chloro-4-morpholinothieno[3,2-d]pyrimidin-6-yl)-N-methyl,N-methanesulfonylmethanamine (General Procedure C-2, 0.18 mmol) was reacted using General Procedure A to give 222 (TFA salt) in a 4% yield after reverse-phase HPLC purification. MS (Q1) 520 (M)

Example 151

N-(5-(6-((N-methyl,N-methylsulfonylamino)methyl)-4-morpholinothieno[3,2-d]pyrimidin-2-yl)pyrimidin-2-yl)acetamide 223

(2-Chloro-4-morpholinothieno[3,2-d]pyrimidin-6-yl)-N-methyl,N-methanesulfonylmethanamine (General Procedure C-2, 0.18 mmol) was reacted using General Procedure A to give 223 (TFA salt) in a 3% yield after reverse-phase HPLC purification. MS (Q1) 478 (M+)

Example 152

N-(5-(6-((N-methyl,N-methylsulfonylamino)methyl)-4-morpholinothieno[3,2-d]pyrimidin-2-yl)pyridin-2-yl)acetamide 224

(2-Chloro-4-morpholinothieno[3,2-d]pyrimidin-6-yl)-N-methyl,N-methanesulfonylmethanamine (General Procedure C-2, 0.22 mmol) was reacted using General Procedure A to give 224 (TFA salt) in a 1% yield after reverse-phase HPLC purification. MS (Q1) 477 (M+)

Example 153

5-(7-methyl-6-((N-methyl,N-methylsulfonylamino)methyl)-4-morpholinothieno[3,2-d]pyrimidin-2-yl)pyrimidin-2-amine 225

(2-Chloro-4-morpholinothieno[3,2-d]pyrimidin-6-yl)-N-methyl,N-methanesulfonylmethanamine (General Procedure C-2, 0.18 mmol) was reacted using General Procedure A to give 225 (TFA salt) in a 1% yield after reverse-phase HPLC purification. MS (Q1) 450 (M+)

Example 154

N-methyl,N-methylsulfonyl(4-morpholino-2-(pyrimidin-5-yl)thieno[3,2-d]pyrimidin-6-yl)methanamine 226

(2-Chloro-4-morpholinothieno[3,2-d]pyrimidin-6-yl)-N-methyl,N-methanesulfonylmethanamine (General Procedure C-2, 0.17 mmol) was reacted using General Procedure A to give 226 (TFA salt) in a 21% yield after reverse-phase HPLC purification. MS (Q1) 421 (M+).

Example 155

N-methyl-N-((4-morpholino-2-(pyrimidin-5-yl)thieno[3,2-d]pyrimidin-6-yl)methyl)benzamide 227

N-((2-Chloro-4-morpholinothieno[3,2-d]pyrimidin-6-yl)methyl)-N-methylbenzamide (0.17 mmol) was reacted using General Procedure A to give 227 (TFA salt) in a 59% yield after reverse-phase HPLC purification. MS (Q1) 447 (M+)

Example 156

N-methyl,N-methylsulfonyl(4-morpholino-2-(pyridin-3-yl)thieno[3,2-d]pyrimidin-6-yl)methanamine 228

(2-Chloro-4-morpholinothieno[3,2-d]pyrimidin-6-yl)-N-methyl,N-methanesulfonylmethanamine (General Procedure C-2, 0.22 mmol) was reacted using General Procedure A to give 228 (TFA salt) in a 48% yield after reverse-phase HPLC purification. MS (Q1) 420 (M)

Example 157

5-(6-((N-methyl,N-methylsulfonylamino)methyl)-4-morpholinothieno[3,2-d]pyrimidin-2-yl)pyrimidin-2-amine 229

(2-Chloro-4-morpholinothieno[3,2-d]pyrimidin-6-yl)-N-methyl,N-methanesulfonylmethanamine (General Procedure C-2, 0.8 mmol) was reacted using General Procedure A to give 229 (TFA salt) in a 2% yield after reverse-phase HPLC purification. MS (Q1) 436 (M+)

Example 158

5-(6-((N-methyl,N-methylsulfonylamino)methyl)-4-morpholinothieno[3,2-d]pyrimidin-2-yl)pyridin-2-amine 230

(2-Chloro-4-morpholinothieno[3,2-d]pyrimidin-6-yl)-N-methyl,N-methanesulfonylmethanamine (General Procedure C-2, 0.8 mmol) was reacted using General Procedure A to give 230 (TFA salt) in an 8% yield after reverse-phase HPLC purification. MS (Q1) 435 (M+).

Example 159

5-(7-methyl-6-(3-(methylsulfonyl)phenyl)-4-morpholinothieno[3,2-d]pyrimidin-2-yl)pyrimidin-2-amine 231

2-Chloro-6-iodo-7-methyl-4-morpholinothieno[3,2-d]pyrimidine from General Procedure D-3 (0.6 g, 1.5 mmol), 3-(methylsulfonyl)phenylboronic acid (0.3 g, 1.5 mmol), and bis(triphenylphosphine)palladium(II) dichloride (50 mg, 80 µmol) in 1 M aqueous $Na_2CO_3$ (3 mL) and acetonitrile (3 mL) were heated to 100° C. in a sealed microwave reactor for 10 min. Upon completion, the organic layer was separated and the aqueous layer was extracted with $CH_2Cl_2$ and EtOAc. The combined organic layers were concentrated in vacuo. A portion of the crude material (0.375 mmol), 5-(4,4,5,5-tetramethyl-1,3,2-dioxaborolan-2-yl)pyrimidin-2-amine (170 mg, 0.75 mmol), 1 M aqueous $Na_2CO_3$ (1.5 mL), acetonitrile (1.5 mL), and bis(triphenylphosphine)palladium(II) dichloride (13 mg, 20 µmol) were heated to 150° C. in a sealed microwave reactor for 20 min. The mixture was extracted with EtOAc and $CH_2Cl_2$. The combined organics were concentrated to yield 231 after reverse phase HPLC purification (54 mg). MS (Q1) 483 (M)+

Example 160

5-(7-methyl-6-(3-(methylsulfonyl)phenyl)-4-morpholinothieno[3,2-d]pyrimidin-2-yl)pyridin-2-amine 232

2-Chloro-6-iodo-7-methyl-4-morpholinothieno[3,2-d]pyrimidine from General Procedure D-3 (0.6 g, 1.5 mmol), 3-(methylsulfonyl)phenylboronic acid (0.3 g, 1.5 mmol), and bis(triphenylphosphine)palladium(II) dichloride (50 mg, 80 µmol) in 1 M aqueous $Na_2CO_3$ (3 mL) and acetonitrile (3 mL) were heated to 100° C. in a sealed microwave reactor for 10 min. Upon completion, the organic layer was separated and the aqueous layer was extracted with $CH_2Cl_2$ and EtOAc. The combined organic layers were concentrated in vacuo. A portion of the crude material (0.375 mmol), 5-(4,4,5,5-tetramethyl-1,3,2-dioxaborolan-2-yl)pyridin-2-amine (170 mg, 0.75 mmol), 1 M aqueous $Na_2CO_3$ (1.5 mL), acetonitrile (1.5 mL), and bis(triphenylphosphine)palladium (II) dichloride (13 mg, 20 µmol) were heated to 150° C. in a sealed microwave reactor for 20 min. The mixture was extracted with EtOAc and $CH_2Cl_2$. The combined organics were concentrated to yield 232 after reverse phase HPLC purification (36 mg). MS (Q1) 483 (M)+

Example 161

7-methyl-6-(3-(methylsulfonyl)phenyl)-4-morpholino-2-(pyrimidin-5-yl)thieno[3,2-d]pyrimidine 233

2-Chloro-6-iodo-7-methyl-4-morpholinothieno[3,2-d]pyrimidine from General Procedure D-3 (0.6 g, 1.5 mmol), 3-(methylsulfonyl)phenylboronic acid (0.3 g, 1.5 mmol), and bis(triphenylphosphine)palladium(II) dichloride (50 mg, 80 µmol) in 1 M aqueous $Na_2CO_3$ (3 mL) and acetonitrile (3 mL) were heated to 100° C. in a sealed microwave reactor for 10 min. Upon completion, the organic layer was separated and the aqueous layer was extracted with $CH_2Cl_2$ and EtOAc. The combined organic layers were concentrated in vacuo. A portion of the crude material (0.375 mmol), pyrimidin-5-yl-5-boronic acid (90 mg, 0.75 mmol), 1 M aqueous $Na_2CO_3$ (1.5 mL), acetonitrile (1.5 mL), and bis(triphenylphosphine)palladium(II) dichloride (13 mg, 20 µmol) were heated to 150° C. in a sealed microwave reactor for 20 min. The mixture was extracted with EtOAc and $CH_2Cl_2$. The combined organics were concentrated to yield 233 after reverse phase HPLC purification (4 mg). MS (Q1) 468 (M)+

Example 162

2-(2-(2-aminopyrimidin-5-yl)-4-morpholinothieno[3,2-d]pyrimidin-6-yl)propan-2-ol 234

2-(2-Chloro-4-morpholinothieno[3,2-d]pyrimidin-6-yl)propan-2-ol (950 mg, Example 274, General Procedure D-1) was combined with 1 g of boronic ester according to General Procedure A using 9 mL of 1M sodium carbonate and 9 mL of acetonitrile for 15 min at 140° C. in a large microwave vial. After cooling to room temperature the reaction was evaporated, the solids washed with water and a small amount of 50/50 ethylacetate/ether, and then purified by silica gel chromatography (0% to 15% methanol in dichloromethane) to give 700 mg of 234. MS (Q1) 374 (M)

Example 163

N-((2-(2-aminopyrimidin-5-yl)-4-morpholinothieno[3,2-d]pyrimidin-6-yl)methyl)-N-methylbenzamide 235

N-((2-Chloro-4-morpholinothieno[3,2-d]pyrimidin-6-yl)methyl)-N-methylbenzamide (0.17 mmol) was reacted using General Procedure A to give 235 (TFA salt) in a 23% yield after reverse-phase HPLC purification. MS (Q1) 462 (M+)

Example 164

N-((2-(6-aminopyridin-3-yl)-4-morpholinothieno[3,2-d]pyrimidin-6-yl)methyl)-N-methylbenzamide 236

N-((2-Chloro-4-morpholinothieno[3,2-d]pyrimidin-6-yl)methyl)-N-methylbenzamide (0.17 mmol) was reacted using General Procedure A to give 236 (TFA salt) in a 61% yield after reverse-phase HPLC purification. MS (Q1) 461 (M+)

Example 165

N-methyl-N-((4-morpholino-2-(pyridin-3-yl)thieno[3,2-d]pyrimidin-6-yl)methyl)benzamide 237

N-((2-Chloro-4-morpholinothieno[3,2-d]pyrimidin-6-yl)methyl)-N-methylbenzamide (0.17 mmol) was reacted using General Procedure A to give 237 (TFA salt) in a 73% yield after reverse-phase HPLC purification. MS (Q1) 469 (M)+

Example 166

N-(2-(2-(2-aminopyrimidin-5-yl)-4-morpholinothieno[3,2-d]pyrimidin-6-yl)propan-2-yl)benzamide 238

To a solution of 2-(2-chloro-4-morpholinothieno[3,2-d]pyrimidin-6-yl)propan-2-amine, prepared by General Procedure B-5, (1.1 g, 3.5 mmol) in $CH_2Cl_2$ (50 mL) was added $Et_3N$ (0.6 mL, 4.9 mmol) and benzoyl chloride (0.6 mL, 4.2 mmol). The resulting mixture stirred at room temperature overnight. The reaction was diluted with 1 M HCl and extracted with DCM, dried over $MgSO_4$, and concentrated in vacuo. The crude material was purified by silica gel chromatography (0-50% EtOAc in hexane). A portion (0.29 mmol) of the crude material was utilized in a Suzuki coupling using General Procedure A with 5-(4,4,5,5-tetramethyl-1,3,2-dioxaborolan-2-yl)pyrimidin-2-amine to provide 238 after reverse phase HPLC purification (42 mg). MS (Q1) 476 (M)+

Example 167

N-(2-(2-(6-aminopyridin-3-yl)-4-morpholinothieno[3,2-d]pyrimidin-6-yl)propan-2-yl)benzamide 239

To a solution of 2-(2-chloro-4-morpholinothieno[3,2-d]pyrimidin-6-yl)propan-2-amine, prepared by General Procedure B-5, (210 mg, 0.67 mmol) in $CH_2Cl_2$ (5 mL) was added $Et_3N$ (120 µL, 0.87 mmol) and benzoyl chloride (88 µL, 0.8 mmol). The resulting mixture stirred at room temperature overnight. The reaction was diluted with 1 M HCl and extracted with DCM, dried over $MgSO_4$, and concentrated in vacuo. The crude was purified by flash chromatography (EtOAc/hexanes) to yield 117 mg of a product of which a portion (0.07 mmol) was utilized in a Suzuki coupling using General Procedure A with 5-(4,4,5,5-tetramethyl-1,3,2-dioxaborolan-2-yl)pyridin-2-amine to provide 239 after reverse phase HPLC purification (8.4 mg). MS (Q1) 475 (M)+

Example 168

N-(2-(4-morpholino-2-(pyridin-3-yl)thieno[3,2-d]pyrimidin-6-yl)propan-2-yl)benzamide 240

To a solution of 2-(2-chloro-4-morpholinothieno[3,2-d]pyrimidin-6-yl)propan-2-amine, prepared by General Procedure B-5, (1.1 g, 3.5 mmol) in $CH_2Cl_2$ (50 mL) was added $Et_3N$ (0.6 mL, 4.9 mmol) and benzoyl chloride (0.6 mL, 4.2 mmol). The resulting mixture stirred at room temperature overnight. The reaction was diluted with 1 M HCl and extracted with DCM, dried over $MgSO_4$, and concentrated in vacuo. The crude material was purified by silica gel chromatography (0-50% EtOAc in hexane). A portion (0.65 mmol) of the crude material was utilized in a Suzuki coupling using General Procedure A with 3-(4,4,5,5-tetramethyl-1,3,2-dioxaborolan-2-yl)pyridine to provide 240 after reverse phase HPLC purification (58 mg). MS (Q1) 460 (M)+

Example 169

N-(5-(6-(4-methoxypyridin-3-yl)-4-morpholinofuro[3,2-d]pyrimidin-2-yl)pyridin-2-yl)acetamide 241

5-(6-(4-Methoxypyridin-3-yl)-4-morpholinofuro[3,2-d]pyrimidin-2-yl)pyridin-2-amine (1.0 eq) is treated with 10 eq of pyridine in acetyl chloride (~0.1M) at 80° C. The reaction is stirred until complete. Water/methanol (1:1) were added and the mixture was concentrated to yield the crude intermediate. This intermediate was purified by reverse phase HPLC to yield 20 mg of 241. MS (Q1) 447 (M+).

Example 170

N-(5-(6-(4-methoxypyridin-3-yl)-4-morpholinofuro[3,2-d]pyrimidin-2-yl)pyridin-2-yl)formamide 242

To a solution of 5-(6-(4-methoxypyridin-3-yl)-4-morpholinofuro[3,2-d]pyrimidin-2-yl)pyridin-2-amine (1.0 eq) in formic acid 96% (0.07M) at 0° C. was added 60 eq of acetic anhydride. The reaction mixture was allowed to warm up to r.t. and stirred for 60 h. Water/methanol (1:1) were added and the mixture was concentrated to yield the crude intermediate. This intermediate was purified by reverse phase HPLC to yield 9 mg of 242. MS (Q1) 433 ($M^+$).

Example 171

5-(6-(3-(methylsulfonyl)phenyl)-4-morpholinothieno[3,2-d]pyrimidin-2-yl)pyrimidin-2-amine 243

2-Chloro-6-iodo-4-morpholinothieno[3,2-d]pyrimidine 19 from Example 12 (500 mg), 288 mg of 3-methylsulfonylphenylboronic acid and 46 mg of Bis(triphenylphosphine)palladium(II) dichloride in 3 mL of 1M $Na_2CO_3$ aqueous solution and 3 mL of acetonitrile was heated to 100° C. in a sealed microwave reactor for 10 min. The reaction mixture was evaporated. The crude product was purified by isco eluting with 20~80% EtOAc/Hexane to yield 2-chloro-6-(3-(methylsulfonyl)phenyl)-4-morpholinothieno[3,2-d]pyrimidine (430 mg, 80%)

2-Chloro-6-(3-(methylsulfonyl)phenyl)-4-morpholinothieno[3,2-d]pyrimidine (80 mg) was coupled to 2-aminopyrimidine-5-boronic acid pinacol ester via General Procedure A. The product was purified by reverse phase HPLC to yield 9.5 mg of 243. MS (Q1) 469 (M)$^+$.

Example 172

1-(5-(6-(3-(methylsulfonyl)phenyl)-4-morpholinothieno[3,2-d]pyrimidin-2-yl)pyridin-2-yl)urea 244

2-Chloro-6-(3-(methylsulfonyl)phenyl)-4-morpholinothieno[3,2-d]pyrimidine (250 mg) was coupled to 2-aminopyridine-5-boronic acid pinacol ester via General Procedure A. The reaction mixture was evaporated. The crude product was purified by flash chromatography, eluting with 0~15% MeOH/DCM to yield 5-(6-(3-(methylsulfonyl)phenyl)-4-morpholinothieno[3,2-d]pyrimidin-2-yl)pyridin-2-amine (214 mg, 75%).

Chlorosulfonyl isocyanate (54 µL) was added to a mixture of 58 mg of 5-(6-(3-(methylsulfonyl)phenyl)-4-morpholinothieno[3,2-d]pyrimidin-2-yl)pyridin-2-amine in 3 mL of acetonitrile at 0° C. The reaction mixture was allowed to warm to room temperature and stirred for 1 h. The mixture was evaporated, and added 2 mL of 2N HCl. The reaction mixture was heated to 80° C. for 20 min. Upon completion, the reaction mixture was concentrated. The product was purified by reverse phase HPLC to yield 35 mg of 244. MS (Q1) 511 (M)$^+$.

Example 173

N-(5-(6-(3-(methylsulfonyl)phenyl)-4-morpholinothieno[3,2-d]pyrimidin-2-yl)pyridin-2-yl)acetamide 245

A suspension of 35 mg of 5-6-(3-(methylsulfonyl)phenyl)-4-morpholinothieno[3,2-d]pyrimidin-2-yl)pyridin-2-amine and 8 μL of acetic anhydride and 1 mL of pyridine was heated to 80° C. for 2 h. Upon completion, the mixture was evaporated. The product was purified by reverse phase HPLC to yield 9.9 mg of 245. MS (Q1) 510.3 (M)$^+$.

Example 174

N-acetyl-N-(5-(6-(3-(methylsulfonyl)phenyl)-4-morpholinothieno[3,2-d]pyrimidin-2-yl)pyridin-2-yl)acetamide 246

A suspension of 40 mg of 5-6-(3-(methylsulfonyl)phenyl)-4-morpholinothieno[3,2-d]pyrimidin-2-yl)pyridin-2-amine and 2 mL of acetic anhydride and 600 μL of pyridine was heated to 80° C. for 2 h. Upon completion, the mixture was evaporated. The product was purified by reverse phase HPLC to yield 17.1 mg of 246. MS (Q1) 552.2 (M)$^+$.

Example 175

1-(3-(2-(6-aminopyridin-3-yl)-4-morpholinothieno[3,2-d]pyrimidin-6-yl)phenyl)ethanone 247

2-Chloro-6-iodo-4-morpholinothieno[3,2-d]pyrimidine 19 from Example 12 (50 mg) was coupled to 3-acetylphenylboronic acid via General Procedure F-1. The product was purified by reverse phase HPLC to yield 32.8 mg of 247. MS (Q1) 32.8 (M)$^+$.

Example 176

5-(6-(3-methoxyphenyl)-4-morpholinothieno[3,2-d]pyrimidin-2-yl)pyridin-2-amine 248

2-Chloro-6-iodo-4-morpholinothieno[3,2-d]pyrimidine 19 from Example 12 (50 mg) was coupled to 3-methoxyphenylboronic acid via General Procedure F-1. The product was purified by reverse phase HPLC to yield 21.4 mg of 248. MS (Q1) 420.1 (M)$^+$.

Example 177

5-(6-(3-methylsulfonylaminophenyl)-4-morpholinothieno[3,2-d]pyrimidin-2-yl)pyridin-2-amine 249

2-Chloro-6-iodo-4-morpholinothieno[3,2-d]pyrimidine 19 from Example 12 (50 mg) was coupled to 3-methylsulfonylaminophenylboronic acid via General Procedure F-1. The product was purified by reverse phase HPLC to yield 23.4 mg of 249. MS (Q1) 483.3 (M)$^+$.

Example 178

5-(6-(3-chlorophenyl)-4-morpholinothieno[3,2-d]pyrimidin-2-yl)pyridin-2-amine 250

2-Chloro-6-iodo-4-morpholinothieno[3,2-d]pyrimidine 19 from Example 12 (50 mg) was coupled to 3-chlorophenylboronic acid via General Procedure F-1. The product was purified by reverse phase HPLC to yield 21.1 mg of 250. MS (Q1) 424.3 (M)$^+$.

Example 179

3-(2-(6-aminopyridin-3-yl)-4-morpholinothieno[3,2-d]pyrimidin-6-yl)-N-methylbenzamide 251

2-Chloro-6-iodo-4-morpholinothieno[3,2-d]pyrimidine 19 from Example 12 (120 mg), 60 mg of 3-(N-methylaminocarbonyl)phenylboronic acid and 11 mg of Bis(triphenylphosphine)palladium(II) dichloride in 0.6 mL of 1M Na$_2$CO$_3$ aqueous solution and 0.6 mL of acetonitrile was heated to 100° C. in a sealed microwave reactor for 10 min. The reaction mixture was evaporated. The crude product was purified by isco eluting with 30~100% EtOAc/Hexane to yield 3-(2-chloro-4-morpholinothieno[3,2-d]pyrimidin-6-yl)-N-methylbenzamide (89 mg, 73%). 89 mg of 3-(2-chloro-4-morpholinothieno[3,2-d]pyrimidin-6-yl)-N-methylbenzamide was coupled to 2-aminopyridine-5-boronic acid pinacol ester via General Procedure A. The product was purified by reverse phase HPLC to yield 40.2 mg of 251. MS (Q1) 477.3 (M)$^+$.

Example 180

5-(6-(4-methoxypyridin-3-yl)-4-morpholinothieno[3,2-d]pyrimidin-2-yl)pyridin-2-amine 252

2-Chloro-6-iodo-4-morpholinothieno[3,2-d]pyrimidine 19 from Example 12 (60 mg) was coupled to 4-methoxypyridine-3-boronic acid via General Procedure F-1. The product was purified by reverse phase HPLC to yield 20.4 mg of 252. MS (Q1) 421.3 (M)$^+$.

Example 181

5-(4-morpholino-6-(pyridin-3-yl)thieno[3,2-d]pyrimidin-2-yl)pyridin-2-amine 253

2-Chloro-6-iodo-4-morpholinothieno[3,2-d]pyrimidine 19 from Example 12 (60 mg) was coupled to 3-pyridineboronic acid via General Procedure F-1. The product was purified by reverse phase HPLC to yield 12 mg of 253. MS (Q1) 391.4 (M)$^+$.

Example 182

3-(2-(6-aminopyridin-3-yl)-4-morpholinothieno[3,2-d]pyrimidin-6-yl)benzamide 254

2-Chloro-6-iodo-4-morpholinothieno[3,2-d]pyrimidine 19 from Example 12 (60 mg) was coupled to 3-carbamoylphenylboronic acid via General Procedure F-1. The product was purified by reverse phase HPLC to yield 12.4 mg of 254. MS (Q1) 433.3 (M)$^+$.

Example 183

(4-(2-(6-aminopyridin-3-yl)-4-morpholinothieno[3,2-d]pyrimidin-6-yl)phenyl)methanol 255

2-Chloro-6-iodo-4-morpholinothieno[3,2-d]pyrimidine 19 from Example 12 (60 mg) was coupled to 4-hydroxymethylphenylboronic acid via General Procedure F-1. The product was purified by reverse phase HPLC to yield 20.3 mg of 255. MS (Q1) 420.1 (M)$^+$.

Example 184

(3-(2-(6-aminopyridin-3-yl)-4-morpholinothieno[3,2-d]pyrimidin-6-yl)phenyl)methanol 256

2-Chloro-6-iodo-4-morpholinothieno[3,2-d]pyrimidine 19 from Example 12 (60 mg) was coupled to 3-hydroxymethylphenylboronic acid via General Procedure F-1. The product was purified by reverse phase HPLC to yield 30.7 mg of 256. MS (Q1) 420.1 (M)$^+$.

Example 185

5-(4-morpholino-6-phenylthieno[3,2-d]pyrimidin-2-yl)pyridin-2-amine 257

2-Chloro-6-iodo-4-morpholinothieno[3,2-d]pyrimidine 19 from Example 12 (60 mg) was coupled to phenylboronic acid via General Procedure F-1. The product was purified by reverse phase HPLC to yield 18.4 mg of 257. MS (Q1) 390.3 (M)$^+$.

Example 186

5-(6-((E)-3-methoxyprop-1-enyl)-4-morpholinothieno[3,2-d]pyrimidin-2-yl)pyridin-2-amine 258

2-Chloro-6-((E)-3-methoxyprop-1-enyl)-4-morpholinothieno[3,2-d]pyrimidine (40 mg) was coupled to 2-aminopyridine-5-boronic acid pinacol ester via General Procedure A. The product was purified by reverse phase HPLC to yield 25.6 mg of 258. MS (Q1) 384.2 (M)$^+$.

Example 187

6-(4-methoxypyridin-3-yl)-2-(2-methoxypyrimidin-5-yl)-4-morpholinofuro[3,2-d]pyrimidine 259

2-Chloro-6-iodo-4-morpholinofuro[3,2-d]pyrimidine was reacted with 4-methoxy-3-pyridineboronic acid via General Procedure D to give, after purification by flash chromatography, 2-chloro-6-(4-methoxypyridin-3-yl)-4-morpholinofuro[3,2-d]pyrimidine, which was then reacted with 2-methoxypyrimidine-5-boronic acid via General Procedure D again to give, after purification by reverse phase HPLC, 8 mg of 259. MS (Q1) 421 (M$^+$).

Example 188

5-(6-(4-methoxypyridin-3-yl)-4-morpholinofuro[3,2-d]pyrimidin-2-yl)pyrimidin-2-amine 260

2-Chloro-6-iodo-4-morpholinofuro[3,2-d]pyrimidine was reacted with 4-methoxy-3-pyridineboronic acid via General Procedure D to give, after purification by flash chromatography, 2-chloro-6-(4-methoxypyridin-3-yl)-4-morpholinofuro[3,2-d]pyrimidine, which was then reacted with 5-(4,4,5,5-tetramethyl-1,3,2-dioxaborolan-2-yl)pyrimidin-2-amine via General Procedure D again to give, after purification by reverse phase HPLC, 6 mg of 260. MS (Q1) 406 (M$^+$).

Example 189

4-morpholino-2,6-di(pyridin-3-yl)furo[3,2-d]pyrimidine 261

2-Chloro-6-iodo-4-morpholinofuro[3,2-d]pyrimidine was reacted with pyridine-3-boronic acid via General Procedure D to give, after purification by flash chromatography, 2-chloro-4-morpholino-6-(pyridin-3-yl)furo[3,2-d]pyrimidine, which was then reacted with pyridine-3-boronic acid via General Procedure D again to give, after purification by reverse phase HPLC, 261. MS (Q1) 360 (M$^+$).

Example 190

6-(4-methoxypyridin-3-yl)-4-morpholino-2-(pyridin-3-yl)furo[3,2-d]pyrimidine 262

2-Chloro-6-iodo-4-morpholinofuro[3,2-d]pyrimidine was reacted with 4-methoxy-3-pyridineboronic acid via General Procedure D to give, after purification by flash chromatography, 2-chloro-6-(4-methoxypyridin-3-yl)-4-morpholinofuro[3,2-d]pyrimidine, which was then reacted with pyridine-3-boronic acid via General Procedure D again to give, after purification by reverse phase HPLC, 15 mg of 262. MS (Q1) 390 (M$^+$).

Example 191

5-(6-(4-methoxypyridin-3-yl)-4-morpholinofuro[3,2-d]pyrimidin-2-yl)pyridin-2-amine 263

2-Chloro-6-iodo-4-morpholinofuro[3,2-d]pyrimidine was reacted with 4-methoxy-3-pyridineboronic acid via General Procedure D to give, after purification by flash chromatography, 2-chloro-6-(4-methoxypyridin-3-yl)-4-morpholinofuro[3,2-d]pyrimidine, which was then reacted with 5-(4,4,5,5-tetramethyl-1,3,2-dioxaborolan-2-yl)pyridin-2-amine via General Procedure D again to give, after purification by flash chromatography, 52 mg of 263. MS (Q1) 405 (M$^+$).

Example 192

2-(2-(5-(1-hydroxyethyl)pyridin-3-yl)-4-morpholinothieno[3,2-d]pyrimidin-6-yl)propan-2-ol 264

2-(2-Chloro-4-morpholinothieno[3,2-d]pyrimidin-6-yl)propan-2-ol (50 mg) prepared according to Example 274 and General Procedure D-1 was combined with 3-acetopyridine-5-boronic acid according to General Procedure A to give the pyridylketone. The ketone was reduced by dissolving 66% of the crude in 1 mL of DMF and adding 3 equivalents of Na(OAc)$_3$BH and 0.02 mL of acetic acid. After overnight stirring, the reaction was extracted with ethylacetate and brine and submitted to reversed phase HPLC purification to give 31 mg of 264. MS (Q1) 400 (M+)

Example 193

2,6-bis(4-methoxypyridin-3-yl)-4-morpholinofuro[3,2-d]pyrimidine 265

2-Chloro-6-iodo-4-morpholinofuro[3,2-d]pyrimidine was reacted with 4-methoxy-3-pyridineboronic acid via General Procedure D to give, after purification by flash chromatography, 2-chloro-6-(4-methoxypyridin-3-yl)-4-morpholinofuro[3,2-d]pyrimidine, which was then reacted with 4-methoxy-3-pyridineboronic acid via General Procedure D again to give, after purification by reverse phase HPLC, 265. MS (Q1) 420 (M+).

Example 194

2-(2-(6-aminopyridin-3-yl)-4-morpholinothieno[3,2-d]pyrimidin-6-yl)propan-2-ol 266

2-(2-Chloro-4-morpholinothieno[3,2-d]pyrimidin-6-yl)propan-2-ol (200 gm), prepared according to Example 274 and General Procedure D-1, was combined with 2-aminopyridine-5-boronic acid pinacol ester according to General Procedure A to yield 36 mg of 266 following reversed phase HPLC purification. MS (Q1) 372 (M)

Example 195

5-(6-(2-hydroxypropan-2-yl)-4-morpholinothieno[3,2-d]pyrimidin-2-yl)pyridine-3-carbaldehyde 267

2-(2-Chloro-4-morpholinothieno[3,2-d]pyrimidin-6-yl)propan-2-ol (150 mg), prepared according to Example 274 and General Procedure D-1, was combined with 3-formylpyridine-5-boronic acid according to General Procedure A to yield 12 mg of 267 following reversed phase HPLC purification. MS (Q1) 385 (M)

Example 196

N-methyl-5-(6-(3-(methylsulfonyl)phenyl)-4-morpholinothieno[3,2-d]pyrimidin-2-yl)pyridine-3-carboxamide 268

5-(6-(3-(Methylsulfonyl)phenyl)-4-morpholinothieno[3,2-d]pyrimidin-2-yl)pyridine-3-carboxylic acid (50 mg) was reacted with methylamine via General Procedure B. The product was purified by reverse phase HPLC to yield 22.2 mg of 268. MS (Q1) 510.1 (M)$^+$.

Example 197

5-(6-(3-(methylsulfonyl)phenyl)-4-morpholinothieno[3,2-d]pyrimidin-2-yl)pyridine-3-carboxylic acid 269

2-Chloro-6-(3-(methylsulfonyl)phenyl)-4-morpholinothieno[3,2-d]pyrimidine (250 mg), 203 mg of 3-(ethoxycarbonyl)pyridine-5-boronic acid pinacol ester and 21 mg of bis(triphenylphosphine)palladium(II) dichloride in 1.5 mL of 1M $Na_2CO_3$ aqueous solution and 1.5 mL of acetonitrile was heated to 150° C. in a sealed microwave reactor for 10 min. The reaction mixture was diluted with $H_2O$, extracted with EtOAc. The aqueous layer was acidified with 1N HCl to pH=2~3. The solid was filtered to give 300 mg of 269. MS (Q1) 497 (M)$^+$.

Example 198

2-(2-methoxypyrimidin-5-yl)-6-(3-(methylsulfonyl)phenyl)-4-morpholinothieno[3,2-d]pyrimidine 270

2-Chloro-6-(3-(methylsulfonyl)phenyl)-4-morpholinothieno[3,2-d]pyrimidine (50 mg) was coupled to 2-methoxypyrimidine-5-boronic acid via General Procedure A. The product was purified by reverse phase HPLC to yield 9 mg of 270. MS (Q1) 484.1 (M)$^+$.

Example 199

5-(6-(3-(methylsulfonyl)phenyl)-4-morpholinothieno[3,2-d]pyrimidin-2-yl)pyridin-2-amine 271

2-Chloro-6-(3-(methylsulfonyl)phenyl)-4-morpholinothieno[3,2-d]pyrimidine (50 mg) was coupled to 2-aminopyridine-5-boronic acid pinacol ester via General Procedure A. The product was purified by reverse phase HPLC to yield 18.1 mg of 271. MS (Q1) 468.1 (M)$^+$.

Example 200

6-(3-(methylsulfonyl)phenyl)-4-morpholino-2-(pyridin-3-yl)thieno[3,2-d]pyrimidine 272

2-Chloro-6-(3-(methylsulfonyl)phenyl)-4-morpholinothieno[3,2-d]pyrimidine (50 mg) was coupled to 3-pyridineboronic acid via General Procedure A. The product was purified by reverse phase HPLC to yield 17.1 mg of 272. MS (Q1) 453.2 (M)$^+$.

Example 201

N-(3-(2-(6-aminopyridin-3-yl)-4-morpholinothieno[3,2-d]pyrimidin-6-yl)phenyl)acetamide 273

N-(3-(2-Chloro-4-morpholinothieno[3,2-d]pyrimidin-6-yl)phenyl)acetamide (35 mg) was coupled to 2-aminopyridine-5-boronic acid pinacol ester via General Procedure A. The product was purified by reverse phase HPLC to yield 29.3 mg of 273. MS (Q1) 447.1 (M)$^+$.

Example 202

2-(2-(6-fluoropyridin-3-yl)-4-morpholinothieno[3,2-d]pyrimidin-6-yl)propan-2-ol 274

2-Chloro-4-morpholinothieno[3,2-d]pyrimidine 4 (Example 2, 8.0 g) was cooled to −50° C. in 80 mL of THF. Following General Procedure D-1, after the addition of 20 mL of 2.5 M nBuLi in hexanes, the reaction was stirred for 10 to 15 min. 4.5 mL of acetone was added and the reaction was allowed to stir for an additional 2 hours prior to quenching with methanol. The solvent was evaporated and the solid was washed with acetonitrile and filtered. The filtrate containing 75% product and 25% starting material was evaporated onto silica gel and placed on a silica column. The pure product was eluted using a 0% to 10% methanol gradient in dichloromethane to give 4 grams of 2-(2-chloro-4-morpholinothieno[3,2-d]pyrimidin-6-yl)propan-2-ol.

2-(2-Chloro-4-morpholinothieno[3,2-d]pyrimidin-6-yl)propan-2-ol (50 mg), prepared by General Procedure D-1, was combined with 2-fluoropyridine-5-boronic acid according to General Procedure A to yield 38 mg of 274 following reversed phase HPLC purification. MS (Q1) 375 (M+)

Example 203

2-(2-(2-fluoropyridin-3-yl)-4-morpholinothieno[3,2-d]pyrimidin-6-yl)propan-2-ol 275

2-(2-Chloro-4-morpholinothieno[3,2-d]pyrimidin-6-yl)propan-2-ol (50 mg), prepared following Example 274 and General Procedure D-1, was combined with 2-fluoropyridine-3-boronic acid according to General Procedure A to yield 42 mg of 275 following reversed phase HPLC purification. MS (Q1) 375 (M+).

Example 204

2-(2-(4-methoxypyridin-3-yl)-4-morpholinothieno[3,2-d]pyrimidin-6-yl)propan-2-ol 276

2-(2-Chloro-4-morpholinothieno[3,2-d]pyrimidin-6-yl)propan-2-ol (50 mg), prepared following Example 274 and General Procedure D-1, was combined with 4-methoxypyridine-3-boronic acid according to General Procedure A to yield 26 mg of 276 following reversed phase HPLC purification. MS (Q1) 387 (M+)

Example 205

2-(2-(5-methoxypyridin-3-yl)-4-morpholinothieno[3,2-d]pyrimidin-6-yl)propan-2-ol 277

2-(2-Chloro-4-morpholinothieno[3,2-d]pyrimidin-6-yl)propan-2-ol (50 mg), prepared following Example 274 and General Procedure D-1, was combined with 3-methoxypyridine-5-boronic acid pinacol ester according to General Procedure A to yield 49 mg of 277 following reversed phase HPLC purification. MS (Q1) 387 (M+)

Example 206

2-(2-(6-methoxypyridin-3-yl)-4-morpholinothieno[3,2-d]pyrimidin-6-yl)propan-2-ol 278

2-(2-Chloro-4-morpholinothieno[3,2-d]pyrimidin-6-yl)propan-2-ol (50 mg), prepared following Example 274 and General Procedure D-1, was combined with 2-methoxypyridine-5-boronic acid according to General Procedure A to yield 40 mg of 278 following reversed phase HPLC purification. MS (Q1) 387 (M+)

Example 207

2-(2-(2-methoxypyridin-3-yl)-4-morpholinothieno[3,2-d]pyrimidin-6-yl)propan-2-ol 279

2-(2-Chloro-4-morpholinothieno[3,2-d]pyrimidin-6-yl)propan-2-ol (50 mg), prepared following Example 274 and General Procedure D-1, was combined with 2-methoxypyridine-3-boronic acid according to General Procedure A to yield 21 mg of 279 following reversed phase HPLC purification. MS (Q1) 387 (M+).

Example 208

2-(4-morpholino-2-(pyridin-3-yl)thieno[3,2-d]pyrimidin-6-yl)propan-2-ol 280

2-(2-Chloro-4-morpholinothieno[3,2-d]pyrimidin-6-yl)propan-2-ol (50 mg), prepared following Example 274 and General Procedure D-1, was combined with pyridine-3-boronic acid according to General Procedure A to yield 36 mg of 280 following reversed phase HPLC purification. MS (Q1) 357 (M+).

Example 209

2-(2-(5-(hydroxymethyl)pyridin-3-yl)-4-morpholinothieno[3,2-d]pyrimidin-6-yl)propan-2-ol 281

5-(6-(2-Hydroxypropan-2-yl)-4-morpholinothieno[3,2-d]pyrimidin-2-yl)pyridine-3-carbaldehyde 267 (47 mg) was reduced in 0.5 mL of DMF with 2 equivalents of Na(OAc)$_3$BH. After overnight stirring, the reaction was extracted with ethylacetate and brine and submitted to reversed phase HPLC purification to give 281. MS (Q1) 387 (M+).

Example 210

2-(2-(2-aminopyrimidin-5-yl)-4-morpholinothieno[3,2-d]pyrimidin-6-yl)-1,1,1,3,3,3-hexafluoropropan-2-ol 282

2-Chloro-4-morpholinothieno[3,2-d]pyrimidine 4 (Example 2, 400 mg) was reacted with hexafluoroacetone following General Procedure D-1 to give the corresponding tertiary alcohol. 140 mg of the crude material was used in a palladium catalyzed cross coupling reaction following General Procedure A to give 16 mg of 282 after reversed phase HPLC purification. MS (Q1) 481 (M+)

Example 211

N-((2-(2-aminopyrimidin-5-yl)-4-morpholinothieno[3,2-d]pyrimidin-6-yl)methyl)-2-(dimethylamino)-N-methylacetamide 283

(2-Chloro-4-morpholinothieno[3,2-d]pyrimidin-6-yl)-N-methylmethanamine (1.07 mM), prepared from General Procedure B-4, was dissolved in 20 mL of dichloromethane and cooled to 0° C. under N$_2$ and 2.2 eq. triethylamine and 1.2 eq. dimethylaminoacetyl chloride-HCl were added. The reaction mixture was allowed to warm up to room temperature and stirred 72 hours at which time product formation was incomplete. An additional 1.5 eq. of dimethylaminoacetyl chloride-HCl was added and the reaction stirred for one hour and complete product formation was confirmed by LCMS. The reaction was concentrated in vacuo. The crude product was purified by flash chromatography (MeOH/DCM) to give 0.41 g N-((2-chloro-4-morpholinothieno[3,2-d]pyrimidin-6-yl)methyl)-2-(dimethylamino)-N-methylacetamide (100% yield). MS (Q1) 385 (M)+
N-((2-Chloro-4-morpholinothieno[3,2-d]pyrimidin-6-yl)methyl)-2-(dimethylamino)-N-methylacetamide (0.53 mM) and 5-(4,4,5,5-tetramethyl-1,3,2-dioxaborolan-2-yl)pyrimidin-2-amine were coupled using General Procedure A to give 283 (TFA salt) in 24% yield after reverse-phase HPLC purification. MS (Q1) 444 (M)+

Example 212

3-(2-(2-aminopyrimidin-5-yl)-4-morpholinothieno[3,2-d]pyrimidin-6-yl)-N-(2-methoxyethyl)benzamide 284

3-(2-(2-Aminopyrimidin-5-yl)-4-morpholinothieno[3,2-d]pyrimidin-6-yl)benzoic acid (55 mg) was reacted with 2-methoxyethylamine via General Procedure B. The product was purified by reverse phase HPLC to yield 20.3 mg of 284. MS (Q1) 492.1 (M)+.

Example 213

3-(2-(2-aminopyrimidin-5-yl)-4-morpholinothieno[3,2-d]pyrimidin-6-yl)-N-(2-(dimethylamino)ethyl) benzamide 285

3-(2-(2-Aminopyrimidin-5-yl)-4-morpholinothieno[3,2-d]pyrimidin-6-yl)benzoic acid (55 mg) was reacted with N,N-dimethylethylenediamine via General Procedure B. The product was purified by reverse phase HPLC to yield 14.7 mg of 285. MS (Q1) 505 (M)+.

Example 214

(3-(2-(2-aminopyrimidin-5-yl)-4-morpholinothieno[3,2-d]pyrimidin-6-yl)phenyl)(4-(2-hydroxyethyl)piperazin-1-yl)methanone 286

3-(2-(2-Aminopyrimidin-5-yl)-4-morpholinothieno[3,2-d]pyrimidin-6-yl)benzoic acid (55 mg) was reacted with 1-(2-hydroxyethyl)piperazine via General Procedure B. The product was purified by reverse phase HPLC to yield 21 mg of 286. MS (Q1) 547 (M)+.

Example 215

(3-(2-(2-aminopyrimidin-5-yl)-4-morpholinothieno[3,2-d]pyrimidin-6-yl)phenyl)(3-hydroxypyrrolidin-1-yl)methanone 287

3-(2-(2-Aminopyrimidin-5-yl)-4-morpholinothieno[3,2-d]pyrimidin-6-yl)benzoic acid (55 mg) was reacted with 3-pyrrolidinol via General Procedure B. The product was purified by reverse phase HPLC to yield 17.8 mg of 287. MS (Q1) 504.2 (M)+.

Example 216

3-(2-(2-aminopyrimidin-5-yl)-4-morpholinothieno[3,2-d]pyrimidin-6-yl)-N-(2-hydroxyethyl)benzamide 288

3-(2-(2-Aminopyrimidin-5-yl)-4-morpholinothieno[3,2-d]pyrimidin-6-yl)benzoic acid (55 mg) was reacted with ethanolamine via General Procedure B. The product was purified by reverse phase HPLC to yield 14.5 mg of 288. MS (Q1) 478.2 (M)+.

Example 217

(3-(2-(2-aminopyrimidin-5-yl)-4-morpholinothieno[3,2-d]pyrimidin-6-yl)phenyl)(4-hydroxypiperidin-1-yl)methanone 289

3-(2-Chloro-4-morpholinothieno[3,2-d]pyrimidin-6-yl)benzoic acid (490 mg) was coupled to 2-aminopyrimidine-5-boronic acid pinacol ester via General Procedure A. The mixture was filtered, and the solid was washed with $H_2O$ and dried on the pump to yield 560 mg of 3-(2-(2-aminopyrimidin-5-yl)-4-morpholinothieno[3,2-d]pyrimidin-6-yl)benzoic acid.
3-(2-(2-Aminopyrimidin-5-yl)-4-morpholinothieno[3,2-d]pyrimidin-6-yl)benzoic acid (55 mg) was reacted with 4-hydroxypiperidine via General Procedure B. The product was purified by reverse phase HPLC to yield 8.4 mg of 289. MS (Q1) 518.2 (M)+.

Example 218

5-(6-(3-aminophenyl)-7-methyl-4-morpholinothieno[3,2-d]pyrimidin-2-yl)pyrimidin-2-amine 290

2-Chloro-6-iodo-7-methyl-4-morpholinothieno[3,2-d]pyrimidine (50 mg) was coupled to 3-aminophenylboronic acid via General Procedure F-1. The product was purified by reverse phase HPLC to yield 40.1 mg of 290. MS (Q1) 420.1 (M)+.

Example 219

N-(5-(2-(2-aminopyrimidin-5-yl)-4-morpholinothieno[3,2-d]pyrimidin-6-yl)pyridin-2-yl)-2-hydroxy-2-methylpropanamide 291

5-(2-Chloro-4-morpholinothieno[3,2-d]pyrimidin-6-yl)pyridin-2-amine (1.0 eq) is treated sequentially with 1.3 eq of 2-(chlorocarbonyl)propan-2-yl acetate, 1.5 eq of triethylamine in THF (~0.1M) at r.t. The reaction is stirred until complete. Methanol was added and the mixture was concentrated to yield the crude intermediate. This intermediate was purified by flash chromatography to yield 101 mg of 2-(5-(2-chloro-4-morpholinothieno[3,2-d]pyrimidin-6-yl)pyridin-2-ylcarbamoyl)propan-2-yl acetate. MS (Q1) 476 (M+).

2-(5-(2-Chloro-4-morpholinothieno[3,2-d]pyrimidin-6-yl)pyridin-2-ylcarbamoyl)propan-2-yl acetate (1.0 eq) was reacted with 5-(4,4,5,5-tetramethyl-1,3,2-dioxaborolan-2-yl)pyridin-2-amine via General Procedure A to give the crude intermediate, which was then dissolved in THF/water (1:1) and treated with 1M LiOH from 0° C. to room temperature (r.t.). Reaction mixture was stirred at r.t. for 2.5 h, before being quenched with 2M HCl. Mixture was extracted with ethyl acetate. The combined organic layers were dried ($Na_2SO_4$) and concentrated to give, after purification by reverse phase HPLC, 9 mg of 291. MS (Q1) 492 (M+)

Example 220

4-(2-(2-aminopyrimidin-5-yl)-4-morpholinothieno[3,2-d]pyrimidin-6-yl)-1-methylpiperidin-4-ol 292

The HCl salt of 4-(2-chloro-4-morpholinothieno[3,2-d]pyrimidin-6-yl)piperidin-4-ol (100 mg) was reacted with 50 mg of paraformaldehyde and 120 mg of sodium triacetoxyborohydride in 1 mL of DMF overnight at room temperature. The reaction was filtered and evaporated to dryness to give 4-(2-chloro-4-morpholinothieno[3,2-d]pyrimidin-6-yl)-1-methylpiperidin-4-ol. This crude intermediate was reacted with 80 mg of 5-(4,4,5,5-tetramethyl-1,3,2-dioxaborolan-2-yl)pyrimidin-2-amine via General Procedure A to give 24.2 mg of 292. MS (Q1) 428.2 (M)+

Example 221

(S)-1-(4-(2-(2-aminopyrimidin-5-yl)-4-morpholinothieno[3,2-d]pyrimidin-6-yl)-4-hydroxypiperidin-1-yl)-2-hydroxypropan-1-one 293

Tert-butyl 4-(2-chloro-4-morpholinothieno[3,2-d]pyrimidin-6-yl)-4-hydroxypiperidine-1-carboxylate (750 mg) was reacted with 5-(4,4,5,5-tetramethyl-1,3,2-dioxaborolan-2-yl)pyrimidin-2-amine via General Procedure A to give tert-butyl 4-(2-(2-aminopyrimidin-5-yl)-4-morpholinothieno[3,2-d]pyrimidin-6-yl)-4-hydroxypiperidine-1-carboxylate.
690 mg of tert-butyl 4-(2-(2-aminopyrimidin-5-yl)-4-morpholinothieno[3,2-d]pyrimidin-6-yl)-4-hydroxypiperidine-1-carboxylate was subjected to Procedure E to give the HCl salt of 4-(2-(2-aminopyrimidin-5-yl)-4-morpholinothieno[3,2-d]pyrimidin-6-yl)piperidin-4-ol.

The crude HCl salt of 4-(2-(2-aminopyrimidin-5-yl)-4-morpholinothieno[3,2-d]pyrimidin-6-yl)piperidin-4-ol (92 mg) was reacted with 60 mg lactic acid via General Procedure B to give 58.9 mg of 293. MS (Q1) 486.2 (M)+.

Example 222

1-(4-(2-(2-aminopyrimidin-5-yl)-4-morpholinothieno[3,2-d]pyrimidin-6-yl)-4-hydroxypiperidin-1-yl)-2-hydroxyethanone 294

The crude HCl salt of 4-(2-(2-aminopyrimidin-5-yl)-4-morpholinothieno[3,2-d]pyrimidin-6-yl)piperidin-4-ol (92 mg) was reacted with 50 mg glycolic acid via General Procedure B to give 50.5 mg of 294. MS (Q1) 472.2 (M)+.

Example 223

1-(4-(2-(2-aminopyrimidin-5-yl)-4-morpholinothieno[3,2-d]pyrimidin-6-yl)-4-hydroxypiperidin-1-yl)-2-hydroxy-2-methylpropan-1-one 295

The crude HCl salt of 4-(2-(2-aminopyrimidin-5-yl)-4-morpholinothieno[3,2-d]pyrimidin-6-yl)piperidin-4-ol (92 mg) was reacted with 70 mg of 2-Hydroxyisobutyric Acid via General Procedure B to give 49.7 mg of 295. MS (Q1) 500.2 (M)+.

Example 224

1-(4-(2-(2-aminopyrimidin-5-yl)-4-morpholinothieno[3,2-d]pyrimidin-6-yl)-4-hydroxypiperidin-1-yl)-2-(methylsulfonyl)ethanone 296

The crude HCl salt of 4-(2-(2-aminopyrimidin-5-yl)-4-morpholinothieno[3,2-d]pyrimidin-6-yl)piperidin-4-ol (92 mg) was reacted with 92 mg of Methanesulphonylacetic Acid via General Procedure B followed by Boc group removal with TFA to give 59.1 mg of 296 after purification. MS (Q1) 534.2 (M)+.

Example 225

2-amino-1-(4-(2-(2-aminopyrimidin-5-yl)-4-morpholinothieno[3,2-d]pyrimidin-6-yl)-4-hydroxypiperidin-1-yl)ethanone 297

The crude HCl salt of 4-(2-(2-aminopyrimidin-5-yl)-4-morpholinothieno[3,2-d]pyrimidin-6-yl)piperidin-4-ol (92 mg) was reacted with 115 mg Boc-Glycine via General Procedure B followed by Boc group removal with TFA to give 62.9 mg of 297 after purification. MS (Q1) 471.2 (M)+

Example 226

2-amino-1-(4-(2-(2-aminopyrimidin-5-yl)-4-morpholinothieno[3,2-d]pyrimidin-6-yl)-4-hydroxypiperidin-1-yl)-2-methylpropan-1-one 298

The crude HCl salt of 4-(2-(2-aminopyrimidin-5-yl)-4-morpholinothieno[3,2-d]pyrimidin-6-yl)piperidin-4-ol (92 mg) was reacted with 135 mg of Boc-2-Aminoisobutyric Acid via General Procedure B followed by Boc group removal with TFA to give 74.7 mg of 298 after purification. MS (Q1) 499.3 (M)+

Example 227

5-(6-((N-cyclopropylsulfonyl,N-methylamino)methyl)-4-morpholinothieno[3,2-d]pyrimidin-2-yl)pyrimidin-2-amine 299

(2-Chloro-4-morpholinothieno[3,2-d]pyrimidin-6-yl)-N-methylmethanamine (1.04 mM), prepared via General Procedure B-4, was dissolved in 20 mL of dichloromethane and cooled to 0° C. under $N_2$ and 1.6 eq. triethylamine and 1.5 eq. of cyclopropane sulfonylchloride were added. The reaction mixture was allowed to warm up to room temperature and stirred 24 hours at which time product formation was incomplete. An additional 1.5 eq. of cyclopropane sulfonylchloride was added and the reaction stirred for 24 hours. Complete product formation was confirmed by LCMS. The reaction was concentrated in vacuo. The crude product was purified by flash chromatography (MeOH/DCM) to give 0.388 g (2-chloro-4-morpholinothieno[3,2-d]pyrimidin-6-yl)-(N-cyclopropylsulfonyl,N-methyl)methanamine (93% yield). MS (Q1) 404 (M+)

(2-Chloro-4-morpholinothieno[3,2-d]pyrimidin-6-yl)-(N-cyclopropylsulfonyl,N-methyl)methanamine (0.96 mM) and 5-(4,4,5,5-tetramethyl-1,3,2-dioxaborolan-2-yl)pyrimidin-2-amine using General Procedure A to give 299 (TFA salt) in 43% yield after reverse-phase HPLC purification. MS (Q1) 463 (M+)

Example 228

5-(6-(2-aminothiazol-4-yl)-4-morpholinothieno[3,2-d]pyrimidin-2-yl)pyrimidin-2-amine 300

4-(2-Chloro-4-morpholinothieno[3,2-d]pyrimidin-6-yl)thiazol-2-amine was reacted with 2-amino-5-(4,4,5,5-tetramethyl-1,3,2-dioxaborolan-2-yl)pyrimidine via General Procedure B to give, after purification by reverse HPLC, 11 mg of 300. MS (Q1) 413 (M+)

Example 229

5-(4-morpholinothieno[2,3-d]pyrimidin-2-yl)pyrimidin-2-amine 301

A reaction vial was charged with 2-chloro-4-morpholinothieno[2,3-d]pyrimidine (1.0 mmol) and reacted with 2-aminopyrimidine-5-boronic acid, pinacol ester using General Procedure A Suzuki Coupling to give 301 as the TFA salt in 94% yield after RP-HPLC purification. MS (Q1) 315.0 (M)+.

Example 230

5-(4-morpholino-6-(3-aminosulfonyl)phenylthieno[3,2-d]pyrimidin-2-yl)pyrimidin-2-amine 302

2-Chloro-6-iodo-4-morpholinothieno[3,2-d]pyrimidine 19 from Example 12 (70 mg) was coupled to 3-boronobenzenesulfonamide via General Procedure F-1. The product was purified by reverse phase HPLC to yield 3.7 mg of 302. MS (Q1) 470.1 (M)+.

Example 231

5-(4-morpholino-6-(3-dimethylaminosulfonyl)phenylthieno[3,2-d]pyrimidin-2-yl)pyrimidin-2-amine 303

2-Chloro-6-iodo-4-morpholinothieno[3,2-d]pyrimidine 19 from Example 12 (70 mg) was coupled to N,N-dimethyl-3-borobenzenesulfonamide via General Procedure F-1. The product was purified by reverse phase HPLC to yield 28.7 mg of 303. MS (Q1) 498.1 (M+).

Example 232

5-(6-(3-(aminomethyl)phenyl)-7-methyl-4-morpholinothieno[3,2-d]pyrimidin-2-yl)pyrimidin-2-amine 304

2-Chloro-6-iodo-7-methyl-4-morpholinothieno[3,2-d]pyrimidine (70 mg) was coupled to 3-aminomethylphenylboronic acid hydrochloride via General Procedure F-1. The product was purified by reverse phase HPLC to yield 46.7 mg of 304. MS (Q1) 434 (M)+.

Example 233

5-(4-morpholino-6-(3-dimethylaminosulfonyl)phenylthieno[3,2-d]pyrimidin-2-yl)pyridin-2-amine 305

2-Chloro-6-iodo-4-morpholinothieno[3,2-d]pyrimidine 19 from Example 12 (70 mg) was coupled to N,N-dimethyl-3-borobenzenesulfonamide via General Procedure F-1. The product was purified by reverse phase HPLC to yield 51.2 mg of 305. MS (Q1) 497.1 (M)+.

Example 234

(S)-1-(3-(2-(2-aminopyrimidin-5-yl)-4-morpholinothieno[3,2-d]pyrimidin-6-yl)phenylsulfonyl)propan-2-ol 306

(S)-1-(3-(2-Chloro-4-morpholinothieno[3,2-d]pyrimidin-6-yl)phenylsulfonyl)propan-2-ol (55 mg) was coupled to 2-aminopyrimidine-5-boronic acid pinacol ester via General Procedure A. The product was purified by reverse phase HPLC to yield 16 mg of 306. MS (Q1) 513.1 (M)+.

Example 235

4-(2-(2-aminopyrimidin-5-yl)-4-morpholinothieno[3,2-d]pyrimidin-6-yl)piperidin-4-ol 307

The HCl salt of 4-(2-chloro-4-morpholinothieno[3,2-d]pyrimidin-6-yl)piperidin-4-ol (100 mg) was reacted with 80 mg of 5-(4,4,5,5-tetramethyl-1,3,2-dioxaborolan-2-yl)pyrimidin-2-amine via General Procedure A to give 20 mg of 307. MS (Q1) 414.2 (M)+.

Example 236

(S)-1-(3-(2-(6-aminopyridin-3-yl)-4-morpholinothieno[3,2-d]pyrimidin-6-yl)phenylsulfonyl)propan-2-ol 308

S-(−)Propylene oxide (152 µL) was added to a mixture of 500 mg of 3-mercaptophenylboronic acid and aluminum oxide (~30 eq, neutral, activated, ~150 mesh) in diethyl ether at room temperature. The reaction was monitored by LC/MS until complete. The reaction mixture was evaporated, and then added 1N HCl. The resulting mixture was extracted with ethyl acetate (3×50 mL). The combined organic layers were dried over MgSO4, filtered and evaporated to give 3-(S)-2-hydroxypropylthiophenylboronic acid (414 mg, 90%). The crude product was directly used for next step reaction without purification.

2-Chloro-6-iodo-4-morpholinothieno[3,2-d]pyrimidine 19 from Example 12 (500 mg), 305 mg of 3-(S)-2-hydroxypropylthiophenylboronic acid and 46 mg of bis(triphenylphosphine)palladium(II) dichloride in 4 mL of 1M Na2CO3 aqueous solution and 4 mL of acetonitrile was heated to 100° C. in a sealed microwave reactor for 40 min. Upon completion, the reaction mixture was evaporated. The crude product was purified by isco eluting with 5~80% EtOAc/Hexane to yield 250 mg of (S)-1-(3-(2-chloro-4-morpholinothieno[3,2-d]pyrimidin-6-yl)phenylthio)propan-2-ol.

A solution of 728 mg of oxone in 10 mL H2O was added to a mixture of 250 mg of (S)-1-(3-(2-chloro-4-morpholinothieno[3,2-d]pyrimidin-6-yl)phenylthio)propan-2-ol in 20 mL of methanol. The reaction mixture was stirred overnight at room temperature. The mixture was filtered through celite and the filtrate was evaporated to afford 250 mg of (S)-1-(3-(2-chloro-4-morpholinothieno[3,2-d]pyrimidin-6-yl)phenylsulfonyl)propan-2-ol.

(S)-1-(3-(2-Chloro-4-morpholinothieno[3,2-d]pyrimidin-6-yl)phenylsulfonyl)propan-2-ol (55 mg) was coupled to 2-aminopyridine-5-boronic acid pinacol ester via General Procedure A. The product was purified by reverse phase HPLC to yield 14.5 mg of 308. MS (Q1) 512.0 (M)+.

Example 237

(2S)—N-(3-(2-(6-aminopyridin-3-yl)-4-morpholinothieno[3,2-d]pyrimidin-6-yl)phenyl)-2-hydroxypropanamide 309

Crude (2S)—N-(3-(2-chloro-4-morpholinothieno[3,2-d]pyrimidin-6-yl)phenyl)-2-hydroxypropanamide (100 mg) was coupled to 2-aminopyridine-5-boronic acid pinacol ester via General Procedure A. The product was purified by reverse phase HPLC to yield 45.9 mg of 309. MS (Q1) 477.2 (M)+.

Example 238

(2S)—N-(3-(2-(2-aminopyrimidin-5-yl)-4-morpholinothieno[3,2-d]pyrimidin-6-yl)phenyl)-2-hydroxypropanamide 310

2-Chloro-6-iodo-4-morpholinothieno[3,2-a]pyrimidine 19 from Example 12 (1 gm), 446 mg of 3-aminophenylboronic acid and 92 mg of bis(triphenylphosphine)palladium (II) dichloride in 5 mL of 1M Na2CO3 aqueous solution and 5 mL of acetonitrile was heated to 100° C. in a sealed microwave reactor for 15 min. The reaction mixture was filtered. The solid cake was washed with H2O and dried to yield 900 mg of 3-(2-chloro-4-morpholinothieno[3,2-d]pyrimidin-6-yl)benzenamine.

3-(2-Chloro-4-morpholinothieno[3,2-d]pyrimidin-6-yl)benzenamine (200 mg) was reacted with L-lactic acid via General Procedure I to give 250 mg of (2S)—N-(3-(2-chloro-4-morpholinothieno[3,2-d]pyrimidin-6-yl)phenyl)-2-hydroxypropanamide. Crude (2S)—N-(3-(2-chloro-4-morpholinothieno[3,2-d]pyrimidin-6-yl)phenyl)-2-hydroxypropanamide (100 mg) was coupled to 2-aminopyrimidine-5-boronic acid pinacol ester via General Procedure A. The product was purified by reverse phase HPLC to yield 51 mg of 310. MS (Q1) 478.2 (M)⁺.

Example 239

5-(6-(3-(1-methyl-1H-tetrazol-5-yl)phenyl)-4-morpholinothieno[3,2-d]pyrimidin-2-yl)pyrimidin-2-amine 311

6-(3-(1H-Tetrazol-5-yl)phenyl)-2-chloro-4-morpholinothieno[3,2-d]pyrimidine (1.0 eq) was dissolved in DMF and treated with potassium carbonate (5.0 eq) and iodomethane (5.0 eq) at r.t. Reaction mixture was stirred at r.t. for 1 h, before being quenched with saturated aqueous solution of NaHCO₃. Mixture was extracted with dichloromethane. The combined organic layers were dried (Na₂SO₄) and concentrated to give, after purification by flash chromatography, 41 mg of 2-chloro-6-(3-(1-methyl-1H-tetrazol-5-yl)phenyl)-4-morpholinothieno[3,2-d]pyrimidine. MS (Q1) 414 (M⁺).

2-Chloro-6-(3-(1-methyl-1H-tetrazol-5-yl)phenyl)-4-morpholinothieno[3,2-d]pyrimidine was reacted with 5-(4,4,5,5-tetramethyl-1,3,2-dioxaborolan-2-yl)pyrimidin-2-amine via General Procedure B to give, after purification by reverse HPLC, 311. MS (Q1) 473 (M⁺).

Example 240

N-((2-(2-aminopyrimidin-5-yl)-4-morpholinothieno[3,2-d]pyrimidin-6-yl)methyl)-2-((R)-3-hydroxypiperidin-1-yl)-N-methylacetamide 312

(2-Chloro-4-morpholinothieno[3,2-d]pyrimidin-6-yl)-N-methylmethanamine (4.02 mmol), prepared from General Procedure B-4, and bromoacetyl chloride (6.03 mmol) were dissolved in 20 mL THF and cooled to 0° under N₂. DMAP (2.01 mmol) was added in 20 mL THF and the reaction was stirred at 0° for four hours at which time the reaction was complete by LCMS. The reaction was quenched with water, extracted with dichloromethane, dried over MgSO₄, and concentrated in vacuo to give 2-bromo-N-((2-chloro-4-morpholinothieno[3,2-d]pyrimidin-6-yl)methyl)-N-methylacetamide, used immediately without further purification.

Crude 2-bromo-N-((2-chloro-4-morpholinothieno[3,2-d]pyrimidin-6-yl)methyl)-N-methylacetamide was dissolved in 5 mL 1,4-dioxane followed by the addition of Et₃N (1.5 mmol) and (R)-3-hydroxypiperidine hydrochloride (2.2 mmol) and stirred for 72 hours at room temp. Complete reaction was confirmed by LCMS and the solvent removed in vacuo to give 430 mg of N-((2-chloro-4-morpholinothieno[3,2-d]pyrimidin-6-yl)methyl)-2-((R)-3-hydroxypiperidin-1-yl)-N-methylacetamide in 98% yield.

N-((2-chloro-4-morpholinothieno[3,2-d]pyrimidin-6-yl)methyl)-2-((R)-3-hydroxypiperidin-1-yl)-N-methylacetamide (0.98 mmol) was converted, using General Procedure A to give 312 in a 36% yield after reverse-phase HPLC purification. MS (Q1) 500 (M)+

Example 241

N-((2-(2-aminopyrimidin-5-yl)-4-morpholinothieno[3,2-d]pyrimidin-6-yl)methyl)-2-(4-hydroxypiperidin-1-yl)-N-methylacetamide 313

2-Bromo-N-((2-chloro-4-morpholinothieno[3,2-d]pyrimidin-6-yl)methyl)-N-methylacetamide, from Example 240, (1.0 mmol), was dissolved in 1,4-dioxane (5 mL) followed by the addition of Et₃N (1.5 mmol) and 4-hydroxypiperidine (2.2 mmol) and stirred for 72 hours at room temp. Complete reaction was confirmed by LCMS and the solvent removed in vacuo to give 380 mg of N-((2-chloro-4-morpholinothieno[3,2-d]pyrimidin-6-yl)methyl)-2-(4-hydroxypiperidin-1-yl)-N-methylacetamide in 86% yield.

N-((2-chloro-4-morpholinothieno[3,2-d]pyrimidin-6-yl)methyl)-2-(4-hydroxypiperidin-1-yl)-N-methylacetamide (0.86 mmol) was converted using General Procedure A to 313 in 59% yield after reverse-phase HPLC purification. MS (Q1) 500 (M)+.

Example 242

N-((2-(2-aminopyrimidin-5-yl)-4-morpholinothieno[3,2-d]pyrimidin-6-yl)methyl)-N-methyl-2-(3-(methylsulfonyl)pyrrolidin-1-yl)acetamide 314

2-Bromo-N-((2-chloro-4-morpholinothieno[3,2-d]pyrimidin-6-yl)methyl)-N-methylacetamide, from Example 240, (1.0 mmol), was dissolved in 1,4-dioxane (5 mL) followed by the addition of Et₃N (1.5 mmol) and 3-(methanesulfonyl)pyrrolidine (2.2 mmol) and stirred for 72 hours at room temp. Complete reaction was confirmed by LCMS and the solvent removed in vacuo to give 330 mg of N-((2-chloro-4-morpholinothieno[3,2-d]pyrimidin-6-yl)methyl)-N-methyl-2-(3-(methylsulfonyl)pyrrolidin-1-yl)acetamide in 68% yield.

N-((2-Chloro-4-morpholinothieno[3,2-d]pyrimidin-6-yl)methyl)-N-methyl-2-(3-(methylsulfonyl)pyrrolidin-1-yl)acetamide (0.61 mmol) was converted using General Procedure A to 314 in 55% yield after reverse-phase HPLC purification. MS (Q1) 548 (M)⁺.

Example 243

4-(2-(2-aminopyrimidin-5-yl)-4-morpholinothieno[3,2-d]pyrimidin-6-yl)-(4-N-ethylsulfonyl)piperidin-4-ol 315

The HCl salt of 4-(2-chloro-4-morpholinothieno[3,2-d]pyrimidin-6-yl)piperidin-4-ol (150 mg) was reacted with 120 µL of triethylamine and 60 µL of ethanesulfonylchloride in 1 mL of dichloromethane. The reaction was stirred at room temperature until complete and then evaporated to dryness.

Crude 4-(2-chloro-4-morpholinothieno[3,2-d]pyrimidin-6-yl)-1-ethylsulfonylpiperidin-4-ol (188 mg) was reacted with 130 mg of 5-(4,4,5,5-tetramethyl-1,3,2-dioxaborolan-2-yl)pyrimidin-2-amine via General Procedure A to give 10.3 mg of 315. MS (Q1) 506.2 (M)+

Example 244

4-(2-(2-aminopyrimidin-5-yl)-4-morpholinothieno[3,2-d]pyrimidin-6-yl)-1-((pyridin-2-yl)methyl)piperidin-4-ol 316

The HCl salt of 4-(2-chloro-4-morpholinothieno[3,2-d]pyrimidin-6-yl)piperidin-4-ol (150 mg) was reacted with 320 mg of 2-(bromomethyl)pyridine and 60 mg of potassium carbonate and excess triethylamine in 1 mL of DMF. The reaction was stirred at room temperature until complete, filtered to remove the excess carbonate and then evaporated to dryness.

Crude 4-(2-chloro-4-morpholinothieno[3,2-d]pyrimidin-6-yl)-1-((pyridin-2-yl)methyl)piperidin-4-ol (90 mg) was reacted with 65 mg of 5-(4,4,5,5-tetramethyl-1,3,2-dioxaborolan-2-yl)pyrimidin-2-amine via General Procedure A to give 51.3 mg of 316. MS (Q1) 505.2 (M)+

Example 245

5-(7-methyl-6-(6-(4-methylpiperazin-1-yl)pyridin-3-yl)-4-morpholinothieno[3,2-d]pyrimidin-2-yl)pyrimidin-2-amine 317

2-Chloro-6-iodo-7-methyl-4-morpholinothieno[3,2-d]pyrimidine (100 mg) was coupled to 2-(4-methylpiperazin-1-yl)pyridine-5-boronic acid via General Procedure F-1. The product was filtered and washed with H$_2$O and methanol to yield 67 mg of 317. MS (Q1) 445 (M)$^+$.

Example 246

(R)-1-(3-(2-(6-aminopyridin-3-yl)-4-morpholinothieno[3,2-d]pyrimidin-6-yl)phenylsulfonyl)propan-2-ol 318

(R)-1-(3-(2-Chloro-4-morpholinothieno[3,2-d]pyrimidin-6-yl)phenylsulfonyl)propan-2-ol (110 mg) was coupled to 2-aminopyridine-5-boronic acid pinacol ester via General Procedure A. The product was purified by reverse phase HPLC to yield 57 mg of 318. MS (Q1) 512.1 (M)$^+$.

Example 247

(R)-1-(3-(2-(2-aminopyrimidin-5-yl)-4-morpholinothieno[3,2-d]pyrimidin-6-yl)phenylsulfonyl)propan-2-ol 319

R-(+)Propylene oxide (607 μL) was added to a mixture of 2 g of 3-mercaptophenylboronic acid and aluminum oxide (~30 eq, neutral, activated, ~150 mesh) in 100 mL of diethyl ether at room temperature. The reaction was monitored by LC/MS until complete. The mixture was evaporated, and then added 1N HCl. The resulting mixture was extracted with ethyl acetate (3×150 mL). The combined organic layers were dried over MgSO$_4$, filtered and evaporated to give 3-(R)-2-hydroxypropylthiophenylboronic acid (1.3 g, 70%). The crude product was directly used for next step reaction without purification.

2-Chloro-6-iodo-4-morpholinothieno[3,2-d]pyrimidine 19 from Example 12 (500 mg), 305 mg of 3-(R)-2-hydroxypropylthiophenylboronic acid and 46 mg of bis(triphenylphosphine)palladium(II) dichloride in 4 mL of 1M Na$_2$CO$_3$ aqueous solution and 4 mL of acetonitrile was heated to 100° C. in a sealed microwave reactor for 40 min. Upon completion, the reaction mixture was evaporated. The crude product was purified by flash chromatography, eluting with 5~80% EtOAc/Hexane to yield 420 mg of (R)-1-(3-(2-chloro-4-morpholinothieno[3,2-d]pyrimidin-6-yl)phenylthio)propan-2-ol.

A solution of 1.17 g of oxone in 10 mL H$_2$O was added to a mixture of 400 mg of (R)-1-(3-(2-chloro-4-morpholinothieno[3,2-d]pyrimidin-6-yl)phenylthio)propan-2-ol in 30 mL of methanol. The reaction mixture was stirred overnight at room temperature. The mixture was filtered through celite and the filtrate was evaporated to afford 420 mg of (R)-1-(3-(2-Chloro-4-morpholinothieno[3,2-d]pyrimidin-6-yl)phenylsulfonyl)propan-2-ol.

(R)-1-(3-(2-Chloro-4-morpholinothieno[3,2-d]pyrimidin-6-yl)phenylsulfonyl)propan-2-ol (110 mg) was coupled to 2-aminopyrimidine-5-boronic acid pinacol ester via General Procedure A. The product was purified by reverse phase HPLC to yield 37.7 mg of 319. MS (Q1) 513.0 (M)$^+$.

Example 248

5-(4-morpholino-6-(3-(pyridin-3-yl)-1,2,4-oxadiazol-5-yl)thieno[3,2-d]pyrimidin-2-yl)pyridin-2-amine 320

A reaction vial was charged with 2-chloro-4-morpholinothieno[3,2-d]pyrimidine-6-carboxylic acid (2.3 mmol) and reacted with 2-aminopyrimidine-5-boronic acid, pinacol ester using General Procedure A Suzuki Coupling to give 2-(2-aminopyrimidin-5-yl)-4-morpholinothieno[3,2-d]pyrimidine-6-carboxylic acid in 97% yield after aqueous work up.

A microwave reaction vial was charged with 2-(2-aminopyrimidin-5-yl)-4-morpholinothieno[3,2-d]pyrimidine-6-carboxylic acid (0.28 mmol) in 1.5 ml of anhydrous DMF. Next, 1.5 eq. (0.4 mmol) of CDI was added portion-wise. This slurry was stirred at room temperature >1 hr. and then 1.1 eq. of N-hydroxynicotinamidine was stirred into solution. The reaction was monitored by LC/MS for appearance of the O-acyl intermediate. The reaction vial was then sealed and flash heated on Emrys Optimizer Microwave at 150 C for 10 min. The reaction mixture was diluted with EtOAc and water and the spent catalyst was removed by vacuum filtration. The organic/liquid was separated and the organic was dried (sodium sulfate) then conc. to a residue. The crude residue was purified by RP-HPLC to give 13 mg (10%) of 320 as a lypholized powder. MS (Q1) 460.1 (M)+.

Example 249

2-(5-(2-(2-aminopyrimidin-5-yl)-4-morpholinothieno[3,2-d]pyrimidin-6-yl)-1,2,4-oxadiazol-3-yl)propan-2-ol 321

A microwave reaction vial was charged with 2-(2-aminopyrimidin-5-yl)-4-morpholinothieno[3,2-d]pyrimidine-6-carboxylic acid in anhydrous DMF, following Example 248. Next, CDI was added portion-wise. This slurry was stirred at room temperature >1 hr. and then 1.1 eq. of N',2-dihydroxy-2-methylpropanamidine was stirred into solution. The reaction was monitored by LC/MS for appearance of the O-acyl intermediate. The reaction vial was then sealed and flash heated on Emrys Optimizer Microwave. The reaction mixture was diluted with EtOAc and water and the spent catalyst was removed by vacuum filtration. The organic/liquid was separated and the organic was dried (sodium sulfate) then conc. to a residue. The crude residue was purified by RP-HPLC to give 321 in 2% yield. MS (Q1) 441.0 (M)+.

Example 250

5-(6-(3-isopropyl-1,2,4-oxadiazol-5-yl)-4-morpholinothieno[3,2-d]pyrimidin-2-yl)pyrimidin-2-amine 322

A microwave reaction vial was charged with 2-(2-aminopyrimidin-5-yl)-4-morpholinothieno[3,2-d]pyrimidine-6-carboxylic acid in anhydrous DMF, following Example 248. Next, CDI was added portion-wise. This slurry was stirred at room temperature >1 hr. and then 1.1 eq. of N-hydroxyisobutylamidine was stirred into solution. The reaction was monitored by LC/MS for appearance of the O-acyl intermediate. The reaction vial was then sealed and flash heated on Emrys Optimizer Microwave. The reaction mixture was diluted with EtOAc and water and the spent catalyst was removed by vacuum filtration. The organic/liquid was separated and the organic was dried (sodium sulfate) then conc. to a residue. The crude residue was purified by RP-HPLC to give 322 in 8% yield. MS (Q1) 424.8 (M)+

Example 251

5-(6-(3-(4-(trifluoromethyl)phenyl)-1,2,4-oxadiazol-5-yl)-4-morpholinothieno[3,2-d]pyrimidin-2-yl)pyrimidin-2-amine 323

A microwave reaction vial was charged with 2-(2-aminopyrimidin-5-yl)-4-morpholinothieno[3,2-d]pyrimidine-6-carboxylic acid in anhydrous DMF, following Example 248. Next, CDI was added portion-wise. This slurry was stirred at room temperature >1 hr. and then 1.1 eq. of 4-(trifluoromethyl)-N'-hydroxybenzamidine was stirred into solution. The reaction was monitored by LC/MS for appearance of the O-acyl intermediate. The reaction vial was then sealed and flash heated on Emrys Optimizer Microwave. The reaction mixture was diluted with EtOAc and water and the spent catalyst was removed by vacuum filtration. The organic/liquid was separated and the organic was dried (sodium sulfate) then conc. to a residue. The crude residue was purified by RP-HPLC to give 323 in 6% yield. MS (Q1) 527.0 (M)+.

Example 252

5-(7-methyl-4-morpholino-6-(3-(2-hydroxyethyl)aminosulfonyl)phenylthieno[3,2-d]pyrimidin-2-yl)pyrimidin-2-amine 324

2-Chloro-6-iodo-7-methyl-4-morpholinothieno[3,2-d]pyrimidine (50 mg) was coupled to N-(2-hydroxyethyl)-3-boronobenzenesulfonamide via General Procedure F-1. The product was purified by reverse phase HPLC to yield 38.7 mg of 324. MS (Q1) 528.1 (M)+.

Example 253

(2-(2-aminopyrimidin-5-yl)-4-morpholinothieno[3,2-d]pyrimidin-6-yl)(4-(methylsulfonyl)phenyl)methanol 325

To a suspension of 2-chloro-4-morpholin-4-yl-thieno[3,2-d]pyrimidine 4 (2.74 g) in dry THF (40 mL) cooled to −78° C. was added nBuLi (2.5M solution in hexanes, 5.15 mL). After stirring for 1 hour, 4-methylmercaptobenzaldehyde (1.43 mL) was added. The reaction mixture stirred at −78° C. for 20 minutes and then gradually warmed to room temperature and stirred for 1 hour. The mixture was then poured onto water and the solid was collected by filtration and purified by recrystallisation from EtOAc/hexanes to give (2-chloro-4-morpholin-4-yl-thieno[3,2-d]pyrimidin-6-yl)-(4-methylsulfanyl-phenyl)-methanol (1.49 g).

To a solution of (2-chloro-4-morpholin-4-yl-thieno[3,2-d]pyrimidin-6-yl)-(4-methylsulfanyl-phenyl)-methanol (1.51 g) in dry dichloromethane (70 mL), cooled to 0° C., was added meta-chloroperbenzoic acid (mCPBA, 1.82 g). After stirring overnight, the reaction mixture was diluted with water and dichloromethane and sodium carbonate solution was added. A solid persisted which was collected by filtration to give (2-chloro-4-morpholin-4-yl-thieno[3,2-d]pyrimidin-6-yl)-(4-methanesulfonyl-phenyl)-methanol (0.70 g).

(2-Chloro-4-morpholin-4-yl-thieno[3,2-d]pyrimidin-6-yl)-(4-methanesulfonyl-phenyl)-methanol was reacted with 2-amino-pyrimidine-5-boronic acid pinacol ester in General Procedure A. Purification on silica and then using preparative HPLC gave 325. NMR (CDCl$_3$, 400 MHz) 3.00 (3H, s), 3.81-3.85 (4H, m), 3.88-3.92 (4H, m), 5.11 (2H, s, br.), 6.15 (1H, s), 7.62 (2H, d), 7.90 (2H, d), 9.11 (2H, s) MS: (ESI+): MH+ 499

Example 254

2-(2-(2-aminothiazol-5-yl)-4-morpholinothieno[3,2-d]pyrimidin-6-yl)propan-2-ol 326

To a suspension of 2-Chloro-4-morpholin-4-yl-thieno[3,2-d]pyrimidine (1.24 g) in dry THF (20 mL) cooled to −78° C. was added nBuLi (2.5M solution in hexanes, 2.32 mL). After stirring for 1 hour, acetone (0.53 mL) was added and the reaction mixture was warmed slowly to room temperature. After one hour the reaction mixture was poured onto water and the solid was collected by filtration. Purification on silica yielded 2-(2-chloro-4-morpholin-4-yl-thieno[3,2-d]pyrimidin-6-yl)-propan-2-ol (340 mg).

A suspension of 2-(2-Chloro-4-morpholin-4-yl-thieno[3,2-d]pyrimidin-6-yl)-propan-2-ol (109 mg, 0.35 mmol), (5-tributylstannyl-thiazol-2-yl)-carbamic acid tert-butyl ester (260 mg, 0.53 mmol), and Pd(PPh$_3$)$_4$ (23 mg, 0.02 mmol) in anhydrous DMA was heated in a microwave at 150° C. for 10 mins. The crude reaction was loaded onto a preconditioned SCX cartridge, washing the cartridge with methanol and dichloromethane before eluting with 7N ammonia in methanol to give crude material. This was purified by on silica using 10% methanol in ethyl acetate as the eluent to give 326 as an off-white solid (25 mg, 19%). NMR (DMSO, 400 MHz), 1.57 (6H, s), 3.74 (4H, t, J=5.2), 3.90 (4H, t, J=4.4), 5.80 (1H, s), 7.19 (1H, s), 7.29 (2H, s), 7.73 (1H, s). MS: (ESI+): MH+ 378

Example 255

2-(2-(2-aminopyrimidin-5-yl)-4-morpholinothieno[3,2-d]pyrimidin-6-yl)-1,1,1-trifluoropropan-2-ol 327

2-Chloro-4-morpholinothieno[3,2-d]pyrimidine 4 (Example 2, 400 mg) was reacted with 0.3 mL of 1,1,1-trifluoroacetone following General Procedure D-1 to give the corresponding tertiary alcohol. The crude material (140 mg) was used in a palladium catalyzed cross coupling reaction following General Procedure A to give 3 mg of 327 after reversed phase HPLC purification. MS (Q1) 427 (M+)

Example 256

2-(5-(2-(2-aminopyrimidin-5-yl)-4-morpholinothieno[3,2-d]pyrimidin-6-yl)-1,2,4-oxadiazol-3-yl)ethanol 328

A microwave reaction vial was charged with 2-(2-aminopyrimidin-5-yl)-4-morpholinothieno[3,2-d]pyrimidine-6-carboxylic acid in anhydrous DMF, following Example 248. Next, CDI was added portion-wise. This slurry was stirred at room temperature for more than 1 hr. and then 1.1 eq. of N',3-dihydroxypropanamidine was stirred into solution. The reaction was monitored by LC/MS for appearance of the O-acyl intermediate. The reaction vial was then sealed and flash heated on Emrys Optimizer Microwave. The reaction mixture was diluted with EtOAc and water and the spent catalyst was removed by vacuum filtration. The organic/liquid was separated and the organic was dried (sodium sulfate) then conc. to a residue. The crude residue was purified by RP-HPLC to give 328 in 2% yield. MS (Q1) 441.0 (M)+.

Example 257

5-(7-methyl-6-(4-(methylsulfonyl)phenyl)-4-morpholinothieno[3,2-d]pyrimidin-2-yl)pyrimidin-2-amine 329

Compound 329 was prepared and analyzed according to the General Procedures, and using the intermediates detailed herein. MS (Q1) 483 (M)+.

Example 258

5-(7-methyl-6-(2-(methylsulfonyl)phenyl)-4-morpholinothieno[3,2-d]pyrimidin-2-yl)pyrimidin-2-amine 330

Compound 330 was prepared and analyzed according to the General Procedures, and using the intermediates detailed herein. MS (Q1) 483 (M)+.

Example 259

5-(7-methyl-4-morpholino-6-phenylthieno[3,2-d]pyrimidin-2-yl)pyrimidin-2-amine 331

Compound 331 was prepared and analyzed according to the General Procedures, and using the intermediates detailed herein. MS (Q1) 405 (M)+.

Example 260

5-(4-morpholino-6-phenylthieno[3,2-d]pyrimidin-2-yl)pyrimidin-2-amine 332

Compound 332 was prepared and analyzed according to the General Procedures, and using the intermediates detailed herein. MS (Q1) 391 (M)+.

Example 261

5-(6-(5-((methylsulfonyl)methyl)-1,2,4-oxadiazol-3-yl)-4-morpholinothieno[3,2-d]pyrimidin-2-yl)pyrimidin-2-amine 333

To a solution of 2-chloro-6-iodo-4-morpholinothieno[3,2-d]pyrimidine 19 from Example 12 (1.0 g, 2.62 mmol) in 10 mL of anhydrous DMF was added 1.0 eq. of $Zn(CN)_2$ and 0.10 eq. of Pd tetrakistriphenylphosphine. The reaction was flash heated on the Emrys Optimizer at 150 C for 10 minutes. The reaction mixture was diluted with water and extracted with EtOAc, The organic layer was dried ($Na_2SO_4$) and concentrated to a solid residue. The crude material was plated onto silica and purified by chromatography on silica eluting with a gradient of 1 to 10% MeOH in DCM to give 2-chloro-4-morpholinothieno[3,2-d]pyrimidine-6-carbonitrile in 60% yield. MS (Q1) 279.1, 281.2 (M)+

A slurry of 2-chloro-4-morpholinothieno[3,2-d]pyrimidine-6-carbonitrile (0.35 mmol) and 2 eq. of $H_2NOH$—HCl in 1.5 mL of DCM/EtOH (1/1) was heated at 60° C. for several minutes followed by the addition of 2.3 eq. of TEA. The reaction was monitored by LC/MS for disappearance of SM. After 4 hrs. the rxn was noted to be complete. The reaction mixture was cooled to room temperature and a ppt was collected by vacuum filtration. No further purification was done to obtain 2-chloro-N-hydroxy-4-morpholinothieno[3,2-d]pyrimidine-6-carboxamide in 80% yield. MS (Q1) 314.0, 316.1 (M)+

A reaction vial was charged with 2-chloro-N-hydroxy-4-morpholinothieno[3,2-d]pyrimidine-6-carboxamide (0.16 mmol) and 1.25 eq. of 2-aminopyrimidine-5-boronic acid, pinacol ester and reacted according to General Procedure A to give 2-(2-aminopyrimidine0-5-yl)-N-hydroxy-4-morpholinothieno[3,2-d]pyrimidine-6-carboxamidine as a ppt in 90% yield. MS (Q1) 359.1 (M)+

A solution of methanesulfonyl acetic acid (0.43 mmol) in 1.5 mL of anh. DMF was treated with 2.0 eq. of CDI for ~1 hr. Next, 1.0 eq. of 2-(2-aminopyrimidine0-5-yl)-N-hydroxy-4-morpholinothieno[3,2-d]pyrimidine-6-carboxamidine was added portion-wise as a solid. This reaction was stirred at room temperature for >1 hr. then flash heated on an Emrys Optimizer microwave at 150° C. for 10 minutes. The crude material was purified by RP-HPLC to give 333 in 17% yield. MS (Q1) 475.2 (M)+

Example 262

5-(6-((N-ethylsulfonyl,N-methylamino)methyl)-4-morpholinothieno[3,2-d]pyrimidin-2-yl)pyrimidin-2-amine 334

(2-Chloro-4-morpholinothieno[3,2-d]pyrimidin-6-yl)-N-methylmethanamine (0.90 mM), prepared via General Procedure B-4, was dissolved in 20 mL of dichloromethane and cooled to 0° C. under $N_2$ and 1.3 eq. triethylamine and 1.2 eq. of ethanesulfonyl chloride were added. The reaction mixture was allowed to warm up to room temperature and stirred 27 hours at which time complete product formation was confirmed by LCMS. The reaction was diluted with 1 M HCl, extracted with dichloromethane, dried over $MgSO_4$, and concentrated in vacuo. This crude product was very clean by LCMS and therefore not further purified giving 0.35 g (2-chloro-4-morpholinothieno[3,2-d]pyrimidin-6-yl)-(N-ethylsulfonyl,N-methyl)methanamine (100% yield). MS (Q1) 392 (M+)

(2-Chloro-4-morpholinothieno[3,2-d]pyrimidin-6-yl)-(N-ethylsulfonyl,N-methyl)methanamine (0.90 mM) and 5-(4,4,5,5-tetramethyl-1,3,2-dioxaborolan-2-yl)pyrimidin-2-amine were coupled using General Procedure A to give 334 (TFA salt) in 71% yield after reverse-phase HPLC purification. MS (Q1) 463 (M+)

Example 263

7-methyl-6-(3-(methylsulfonyl)phenyl)-4-morpholino-2-(pyridazin-4-yl)thieno[3,2-d]pyrimidine 335

2-Chloro-7-methyl-6-(3-(methylsulfonyl)phenyl)-4-morpholinothieno[3,2-d]pyrimidine (0.22 mmol), 4-(tributylstannyl)pyridazine (0.33 mmol), and bis(triphenylphosphine)palladium(II) dichloride (0.022 mmol) were placed in a microwave vial. The reaction mixture was heated to 150° C. in a sealed microwave reactor for 30 min. The reaction mixture was diluted with HCL and the major side product extracted off with EtOAc. The aqueous layer was basified with 10% w/w KOH and the product was extracted with EtOAc, dried over MgSO$_4$, and the solvent removed in vacuo to give 335 after reverse phase HPLC purification (65 mg). MS (Q1) 469 (M)+

Example 264

1-ethyl-3-(5-(6-(2-hydroxypropan-2-yl)-4-morpholinothieno[3,2-d]pyrimidin-2-yl)pyrimidin-2-yl)urea 336

Compound 336 was prepared and analyzed according to the General Procedures, and using the intermediates detailed herein.

Example 265

5-(6-((N-methylsulfonyl,N-methylamino)methyl)-4-morpholinothieno[2,3-d]pyrimidin-2-yl)pyrimidin-2-ol 337

2-Chloro-4-morpholinothieno[2,3-d]pyrimidine and 2-methoxypyrimidin-5-yl-5-boronic acid were used in General Procedure A Suzuki Coupling to produce 337 in 11% yield MS (Q1) 437.0 (M).

Example 266

N-methylsulfonyl,N-methyl(2-(6-methylpyridin-3-yl)-4-morpholinothieno[2,3-d]pyrimidin-6-yl)methanamine 338

(2-Chloro-4-morpholinothieno[2,3-d]pyrimidine and 6-methylpyridin-3-yl-3-boronic acid were used in General Procedure A Suzuki Coupling to produce 338 in 10% yield MS (Q1) 434.1 (M).

Example 267

5-(7-methyl-4-morpholino-6-(3-morpholinosulfonyl)phenylthieno[3,2-d]pyrimidin-2-yl)pyrimidin-2-amine 339

Compound 339 was prepared and analyzed according to the General Procedures and using the intermediates detailed herein.

Example 268

(2S)—N-(3-(2-(2-aminopyrimidin-5-yl)-7-methyl-4-morpholinothieno[3,2-d]pyrimidin-6-yl)phenyl)-2-hydroxypropanamide 340

2-Chloro-6-iodo-7-methyl-4-morpholinothieno[3,2-d]pyrimidine (500 mg), 190 mg of 3-aminophenylboronic acid and 44 mg of Bis(triphenylphosphine)palladium(II) dichloride in 3.8 mL of 1M Na$_2$CO$_3$ aqueous solution and 3.8 mL of acetonitrile was heated to 80° C. in a sealed microwave reactor for 10 min. The reaction mixture was filtered. The solid cake was washed with H$_2$O and dried to yield 450 mg of 3-(2-chloro-7-methyl-4-morpholinothieno[3,2-d]pyrimidin-6-yl)benzenamine.

3-(2-Chloro-7-methyl-4-morpholinothieno[3,2-d]pyrimidin-6-yl)benzenamine (100 mg) was reacted with L-lactic acid via General Procedure I to give (2S)—N-(3-(2-chloro-7-methyl-4-morpholinothieno[3,2-d]pyrimidin-6-yl)phenyl)-2-hydroxypropanamide.

Crude (2S)—N-(3-(2-chloro-7-methyl-4-morpholinothieno[3,2-d]pyrimidin-6-yl)phenyl)-2-hydroxypropanamide (198 mg) was coupled to 2-aminopyrimidine-5-boronic acid pinacol ester via General Procedure A. The product was purified by reverse phase HPLC to yield 52.8 mg of 340. MS (Q1) 492.1 (M)$^+$.

Example 269

N-(3-(2-(2-aminopyrimidin-5-yl)-7-methyl-4-morpholinothieno[3,2-d]pyrimidin-6-yl)phenyl)-2-hydroxyacetamide 341

3-(2-Chloro-7-methyl-4-morpholinothieno[3,2-d]pyrimidin-6-yl)benzenamine (100 mg) was reacted with glycolic acid via General Procedure I to give N-(3-(2-chloro-7-methyl-4-morpholinothieno[3,2-d]pyrimidin-6-yl)phenyl)-2-hydroxyacetamide.

Crude N-(3-(2-chloro-7-methyl-4-morpholinothieno[3,2-d]pyrimidin-6-yl)phenyl)-2-hydroxyacetamide (120 mg) was coupled to 2-aminopyrimidine-5-boronic acid pinacol ester via General Procedure A. The product was purified by reverse phase HPLC to yield 20.6 mg of 341. MS (Q1) 478.1 (M)$^+$.

Example 270

(S)-1-(3-(2-(2-aminopyrimidin-5-yl)-7-methyl-4-morpholinothieno[3,2-d]pyrimidin-6-yl)phenylsulfonyl)propan-2-ol 342

2-Chloro-6-iodo-7-methyl-4-morpholinothieno[3,2-d]pyrimidine (400 mg), 236 mg of 3-(S)-2-hydroxypropylthiophenylboronic acid and 35 mg of bis(triphenylphosphine)palladium(II) dichloride in 3 mL of 1M Na$_2$CO$_3$ aqueous solution and 3 mL of acetonitrile was heated to 100° C. in a sealed microwave reactor for 50 min. Upon completion, the reaction mixture was evaporated. The crude product was purified by chromatography (Isco Inc.) eluting with 5~80% EtOAc/Hexane to yield 397 mg of (S)-1-(3-(2-chloro-7-methyl-4-morpholinothieno[3,2-d]pyrimidin-6-yl)phenylthio)propan-2-ol.

A solution of 1.1 g of oxone in 10 mL H$_2$O was added to a mixture of 397 mg of (S)-1-(3-(2-chloro-7-methyl-4-morpholinothieno[3,2-d]pyrimidin-6-yl)phenylthio)propan-2-ol in 15 mL of methanol and 5 mL of DCM. The reaction mixture was stirred for 4 h at room temperature. The mixture was filtered through celite and the filtrate was evaporated to afford 420 mg of (S)-1-(3-(2-chloro-7-methyl-4-morpholinothieno[3,2-d]pyrimidin-6-yl)phenylsulfonyl)propan-2-ol.

(S)-1-(3-(2-Chloro-7-methyl-4-morpholinothieno[3,2-d]pyrimidin-6-yl)phenylsulfonyl)propan-2-ol (180 mg) was coupled to 2-aminopyrimidine-5-boronic acid pinacol ester via General Procedure A. The product was purified by reverse phase HPLC to yield 94.9 mg of 342. MS (Q1) 527.1 (M)$^+$.

Example 271

5-(4-morpholinofuro[2,3-d]pyrimidin-2-yl)pyrimidin-2-amine 343

Furo[2,3-d]pyrimidine-2,4-diol (1.0 eq) was suspended in POCl$_3$ (55.0 eq) and diisopropylethylamine (10.0 eq) was added at −30° C. Reaction mixture was stirred at reflux for 72 h. Reaction mixture was poured in ice/water, then 28% wt NH₄OH was added until pH 7. Mixture was extracted with dichloromethane. The combined organic layers were dried (Na₂SO₄) and concentrated to yield 2,4-dichlorofuro[2,3-d] pyrimidine, which was used in the next reaction without further purification. MS (Q1) 189 (M⁺).

2,4-Dichlorofuro[2,3-d]pyrimidine (1.0 eq) was suspended in methanol (~0.2 M) and treated with morpholine (4.0 eq). Reaction mixture was stirred at r.t. for 1 h, before being quenched with saturated aq. NaHCO₃. Mixture was extracted with dichloromethane. The combined organic layers were dried (Na₂SO₄) and concentrated to give the crude product, which was purified by flash chromatography, to yield 2-chloro-4-morpholinofuro[2,3-d]pyrimidine which was used in the next reaction without further purification. S (Q1) 240 (M⁺).

2-Chloro-4-morpholinofuro[2,3-d]pyrimidine (1 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile (3 eq) was heated to 140° C. in a sealed microwave reactor for 10 min. Upon completion, the reaction mixture was concentrated and crude mixture was purified by reverse phase HPLC to yield 26 mg of 343. MS (Q1) 299 (M)⁺

Example 272

5-(6-(6-(N-(2-methoxyethyl)-N-methylamino)pyridin-3-yl)-4-morpholinothieno[3,2-d]pyrimidin-2-yl)pyrimidin-2-amine 344

2-Chloro-6-iodo-4-morpholinothieno[3,2-d]pyrimidine was reacted with 2-fluoro-5-pyridineboronic acid via General Procedure A to give, after purification by flash chromatography, 2-chloro-6-(6-fluoropyridin-3-yl)-4-morpholinothieno[3,2-d]pyrimidine. MS (Q1) 351 (M⁺).

2-Chloro-6-(6-fluoropyridin-3-yl)-4-morpholinothieno[3,2-d]pyrimidine was reacted with N-(2-methoxyethyl)methylamine via General Procedure L to give, after purification by flash chromatography, 6-(6-(N-(2-methoxyethyl)-N-methylamino)pyridin-3-yl)-2-chloro-N-(2-methoxyethyl) thieno[3,2-d]pyrimidin-4-amine, which was then reacted with 5-(4,4,5,5-tetramethyl-1,3,2-dioxaborolan-2-yl)pyrimidin-2-amine to give, after purification by reverse HPLC, 25 mg of 344. MS (Q1) 479 (M⁺).

Example 273

5-(6-(6-(N-(2-(dimethylamino)ethyl)-N-methylamino)pyridin-3-yl)-4-morpholinothieno[3,2-d]pyrimidin-2-yl)pyrimidin-2-amine 345

2-Chloro-6-(6-fluoropyridin-3-yl)-4-morpholinothieno[3,2-d]pyrimidine was reacted with N,N,N'-trimethylethylenediamine via General Procedure L to give, after purification by flash chromatography, 5-(2-chloro-4-morpholinothieno[3,2-d]pyrimidin-6-yl)-N-(2-(dimethylamino)ethyl)-N-methylpyridin-2-amine, which was then reacted with 5-(4,4,5,5-tetramethyl-1,3,2-dioxaborolan-2-yl)pyrimidin-2-amine to give, after purification by reverse HPLC, 35 mg of 345. MS (Q1) 492 (M⁺)

Example 274

1-(5-(2-(2-aminopyrimidin-5-yl)-4-morpholinothieno[3,2-d]pyrimidin-6-yl)pyridin-2-yl)piperidin-4-ol 346

2-Chloro-6-(6-fluoropyridin-3-yl)-4-morpholinothieno[3,2-d]pyrimidine was reacted with 4-hydroxypiperidine via General Procedure L to give, after purification by flash chromatography, 1-(5-(2-chloro-4-morpholinothieno[3,2-d]pyrimidin-6-yl)pyridin-2-yl)piperidin-4-ol, which was then reacted with 5-(4,4,5,5-tetramethyl-1,3,2-dioxaborolan-2-yl)pyrimidin-2-amine via General Procedure F again to give, after purification by reverse HPLC, 2 mg of 346. MS (Q1) 491 (M⁺)

Example 275

2-(5-(2-(2-aminopyrimidin-5-yl)-4-morpholinothieno[3,2-d]pyrimidin-6-yl)pyridin-2-ylamino)propan-1-ol 347

2-Chloro-6-(6-fluoropyridin-3-yl)-4-morpholinothieno[3,2-d]pyrimidine was reacted with DL-2-amino-1-propanol via General Procedure L to give, after purification by flash chromatography, 2-(5-(2-chloro-4-morpholinothieno[3,2-d]pyrimidin-6-yl)pyridin-2-ylamino)propan-1-ol, which was then reacted with 5-(4,4,5,5-tetramethyl-1,3,2-dioxaborolan-2-yl)pyrimidin-2-amine to give, after purification by reverse HPLC, 48 mg of 347. MS (Q1) 465 (M⁺).

Example 276

5-(6-(6-(2-methoxyethylamino)pyridin-3-yl)-4-morpholinothieno[3,2-d]pyrimidin-2-yl)pyrimidin-2-amine 348

2-Chloro-6-(6-fluoropyridin-3-yl)-4-morpholinothieno[3,2-d]pyrimidine was reacted with 2-methoxyethylamine via General Procedure L to give, after purification by flash chromatography, 5-(2-chloro-4-morpholinothieno[3,2-d]pyrimidin-6-yl)-N-(2-methoxyethyl)pyridin-2-amine, which was then reacted with 5-(4,4,5,5-tetramethyl-1,3,2-dioxaborolan-2-yl)pyrimidin-2-amine to give, after purification by reverse HPLC, 12 mg of 348. MS (Q1) 465 (M Example 277

N-(3-(2-(2-aminopyrimidin-5-yl)-4-morpholinofuro[2,3-d]pyrimidin-6-yl)phenyl)acetamide 349

To a solution of 2-chloro-4-morpholinofuro[2,3-d]pyrimidine (1.0 eq) dissolved in THF (0.15M) at −78° C. was added solution of n-butyllithium (1.3 eq, 1.6M in hexanes). Reaction mixture was stirred at −78° C. for 30 minutes. A solution of iodine (3.0 eq) was added and reaction mixture was allowed to warm up to r.t. The reaction is stirred until complete and extracted in dichloromethane with saturated Na₂S₂O₃. The organic layer is dried, filtered and concentrated to yield the crude intermediate. This intermediate is purified by flash chromatography to yield 2-chloro-6-iodo-4-morpholinofuro[2,3-d]pyrimidine. MS (Q1) 366 (M)⁺.

2-Chloro-6-iodo-4-morpholinothieno[2,3-d]pyrimidine (1 eq), 3-acetamidophenylboronic acid (1.1 eq) and bis (triphenylphosphine)palladium(II) dichloride (0.1 eq) in 1M Na₂CO₃ aqueous solution (3 eq) and an equal volume of acetonitrile was heated to 100° C. in a sealed microwave reactor for 30 min. Upon completion, 5-(4,4,5,5-tetramethyl-1,3,2-dioxaborolan-2-yl)pyrimidin-2-amine (1.7 eq) and bis(triphenylphosphine)palladium(II) dichloride (0.1 eq) were added in the same pot. The reaction mixture was heated to 140° C. in a sealed microwave reactor for 10 min. Upon completion, the reaction mixture was concentrated and crude mixture was purified by reverse phase HPLC to yield 10 mg of 349. MS (Q1) 432 (M)$^+$ Example 278

5-(6-(6-(2-morpholinoethylamino)pyridin-3-yl)-4-morpholinothieno[3,2-d]pyrimidin-2-yl)pyrimidin-2-amine 350

2-Chloro-6-(6-fluoropyridin-3-yl)-4-morpholinothieno[3,2-d]pyrimidine was reacted with 4-(2-aminoethyl)morpholine via General Procedure L to give, after purification by flash chromatography, 5-(2-chloro-4-morpholinothieno[3,2-d]pyrimidin-6-yl)-N-(2-morpholinoethyl)pyridin-2-amine, which was then reacted with 5-(4,4,5,5-tetramethyl-1,3,2-dioxaborolan-2-yl)pyrimidin-2-amine to give, after purification by reverse HPLC, 59 mg of 350. MS (Q1) 520 (M$^+$).

Example 279

2-(2-(2-aminopyrimidin-5-yl)-4-morpholinofuro[2,3-d]pyrimidin-6-yl)propan-2-ol 351

To a solution of 2-chloro-4-morpholinofuro[2,3-d]pyrimidine (1.0 eq) dissolved in THF (0.15M) at −78° C. was added solution of n-butyllithium (1.3 eq, 1.6M in hexanes). Reaction mixture was stirred at −78° C. for 30 minutes. Acetone (4.0 eq) was added and reaction mixture was allowed to warm up to −40° C. and stirred for 1 h. The crude reaction mixture was concentrated and purified by flash chromatography to afford 2-(2-chloro-4-morpholinofuro[2,3-d]pyrimidin-6-yl)propan-2-ol. MS (Q1) 297 (M)$^+$.

2-(2-Chloro-4-morpholinofuro[2,3-d]pyrimidin-6-yl)propan-2-ol (1 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile (3 eq) was heated to 140° C. in a sealed microwave reactor for 12 min. Upon completion, the reaction mixture was concentrated and crude mixture was purified by reverse phase HPLC to yield 20 mg of 351. MS (Q1) 356 (M)$^+$.

Example 280

5-(6-(6-(2-(dimethylamino)ethylamino)pyridin-3-yl)-4-morpholinothieno[3,2-d]pyrimidin-2-yl)pyrimidin-2-amine 352

2-Chloro-6-(6-fluoropyridin-3-yl)-4-morpholinothieno[3,2-d]pyrimidine was reacted with N,N-dimethylethylenediamine via General Procedure L to give, after purification by flash chromatography, 5-(2-chloro-4-morpholinothieno[3,2-d]pyrimidin-6-yl)-N-(2-(dimethylamino)ethyl)pyridin-2-amine, which was then reacted with 5-(4,4,5,5-tetramethyl-1,3,2-dioxaborolan-2-yl)pyrimidin-2-amine to give, after purification by reverse HPLC, 352. MS (Q1) 478 (M$^+$).

Example 281

(2S)—N-((3-(2-(2-aminopyrimidin-5-yl)-7-methyl-4-morpholinothieno[3,2-d]pyrimidin-6-yl)phenyl)methyl)-2-hydroxypropanamide 353

2-Chloro-6-iodo-7-methyl-4-morpholinothieno[3,2-d]pyrimidine (500 mg), 260 mg of 3-aminoethylphenylboronic acid hydrochloride and 44 mg of bis(triphenylphosphine)palladium(II) dichloride in 4 mL of 1M Na$_2$CO$_3$ aqueous solution and 4 mL of acetonitrile was heated to 90° C. in a sealed microwave reactor for 30 min. The reaction mixture was diluted with EtOAc, washed with brine. The organic layer was dried over MgSO$_4$, filtered and evaporated to give 450 mg of 3-(2-chloro-7-methyl-4-morpholinothieno[3,2-d]pyrimidin-6-yl)phenyl)methaneamine.

3-(2-Chloro-7-methyl-4-morpholinothieno[3,2-d]pyrimidin-6-yl)phenyl)methaneamine (140 mg) was reacted with L-lactic acid via General Procedure I to give (2S)—N-((3-(2-chloro-7-methyl-4-morpholinothieno[3,2-d]pyrimidin-6-yl)phenyl)methyl)-2-hydroxypropanamide.

Crude (2S)—N-((3-(2-chloro-7-methyl-4-morpholinothieno[3,2-d]pyrimidin-6-yl)phenyl)methyl)-2-hydroxypropanamide (90 mg) was coupled to 2-aminopyrimidine-5-boronic acid pinacol ester via General Procedure A. The product was purified by reverse phase HPLC to yield 27.1 mg of 353. MS (Q1) 506.2 (M)$^+$.

Example 282

N-((3-(2-(2-aminopyrimidin-5-yl)-7-methyl-4-morpholinothieno[3,2-d]pyrimidin-6-yl)phenyl)methyl)-2-hydroxyacetamide 354

3-(2-Chloro-7-methyl-4-morpholinothieno[3,2-d]pyrimidin-6-yl)methaneamine (140 mg) was reacted with glycolic acid via General Procedure I to give N-((3-(2-chloro-7-methyl-4-morpholinothieno[3,2-d]pyrimidin-6-yl)phenyl)methyl)-2-hydroxyacetamide.

Crude N-((3-(2-chloro-7-methyl-4-morpholinothieno[3,2-d]pyrimidin-6-yl)phenyl)methyl)-2-hydroxyacetamide (130 mg) was coupled to 2-aminopyrimidine-5-boronic acid pinacol ester via General Procedure A. The product was purified by reverse phase HPLC to yield 15.1 mg of 354. MS (Q1) 492.1 (M)$^+$.

Example 283

3-(2-(2-aminopyrimidin-5-yl)-7-methyl-4-morpholinothieno[3,2-d]pyrimidin-6-yl)-N-(2-methoxyethyl)benzamide 355

3-(2-(2-Aminopyrimidin-5-yl)-7-methyl-4-morpholinothieno[3,2-d]pyrimidin-6-yl)benzoic acid (70 mg) was reacted with 2-methoxyethylamine via General Procedure B. The product was purified by reverse phase HPLC to yield 11.6 mg of 355. MS (Q1) 506.1 (M)$^+$.

Example 284

3-(2-(2-aminopyrimidin-5-yl)-7-methyl-4-morpholinothieno[3,2-d]pyrimidin-6-yl)-N-(2-(dimethylamino)ethyl)benzamide 356

3-(2-(2-Aminopyrimidin-5-yl)-7-methyl-4-morpholinothieno[3,2-d]pyrimidin-6-yl)benzoic acid (70 mg) was reacted with N,N-dimethylethylenediamine via General Procedure B. The product was purified by reverse phase HPLC to yield 22.9 mg of 356. MS (Q1) 519.0 (M)$^+$.

Example 285

3-(2-(2-aminopyrimidin-5-yl)-7-methyl-4-morpholinothieno[3,2-d]pyrimidin-6-yl)-N—((S)-2-hydroxypropyl)benzamide 357

3-(2-(2-Aminopyrimidin-5-yl)-7-methyl-4-morpholinothieno[3,2-d]pyrimidin-6-yl)benzoic acid (70 mg) was reacted with (S)-(+)-1-amino-2-propanol via General Procedure B. The product was purified by reverse phase HPLC to yield 17 mg of 357. MS (Q1) 506.1 (M)+.

Example 286

(3-(2-(2-aminopyrimidin-5-yl)-7-methyl-4-morpholinothieno[3,2-d]pyrimidin-6-yl)phenyl)(4-methylpiperazin-1-yl)methanone 358

3-(2-(2-Aminopyrimidin-5-yl)-7-methyl-4-morpholinothieno[3,2-d]pyrimidin-6-yl)benzoic acid (70 mg) was reacted with 1-methylpiperizine via according to General Procedure B. The product was purified by reverse phase HPLC to yield 35.9 mg of 358. MS (Q1) 531.1 (M)+.

Example 287

3-(2-(2-aminopyrimidin-5-yl)-7-methyl-4-morpholinothieno[3,2-d]pyrimidin-6-yl)-N-(2-hydroxyethyl)benzamide 359

3-(2-(2-Aminopyrimidin-5-yl)-7-methyl-4-morpholinothieno[3,2-d]pyrimidin-6-yl)benzoic acid (70 mg) was reacted with ethanolamine according to General Procedure B. The product was purified by reverse phase HPLC to yield 13.6 mg of 359. MS (Q1) 492.1 (M)+.

Example 288

(3-(2-(2-aminopyrimidin-5-yl)-7-methyl-4-morpholinothieno[3,2-d]pyrimidin-6-yl)phenyl)(4-hydroxypiperidin-1-yl)methanone 360

3-(2-(2-Aminopyrimidin-5-yl)-7-methyl-4-morpholinothieno[3,2-d]pyrimidin-6-yl)benzoic acid (70 mg) was reacted with 4-hydroxypiperidine according to General Procedure B. The product was purified by reverse phase HPLC to yield 30.8 mg of 360. MS (Q1) 532.0 (M)+.

Example 289

5-(7-methyl-4-morpholino-6-(3-(4-methylpiperazinylsulfonyl))phenylthieno[3,2-d]pyrimidin-2-yl)pyrimidin-2-amine 361

3-Bromobenzenesulfonyl chloride (1 g) was added to a mixture of 357 mg of 1-methylpiperizine and 929 µL of N,N'-diisopropylethylamine in 5 mL of MeOH. The reaction mixture was stirred at room temperature. Upon completion, the reaction mixture was evaporated. The residue was diluted with ethyl acetate, washed with saturated NaHCO$_3$ and brine. The organic layer was dried over MgSO$_4$, filtered and evaporated to yield 850 mg of 1-bromo-3-(methylpiperizinesulfonyl)benzene.

1-Bromo-3-(methylpiperizinesulfonyl)benzene (250 mg), 229 mg of Bis(pinacolato)diboron, 230 mg of potassium acetate and 30 mg of PdCl$_2$(dppf) in 3 mL of toluene was heated to 80° C. for 2 h. The mixture was diluted with ethyl acetate, washed with saturated NaHCO$_3$ and brine. The organic layer was dried over MgSO$_4$, filtered and evaporated to yield 270 mg of 4,4,5,5-tetramethyl-2-(3-(methylpiperizinesulfonyl)phenyl)-1,3,2-dioxaborolane.

2-Chloro-6-iodo-7-methyl-4-morpholinothieno[3,2-d]pyrimidine (50 mg) was coupled to 4,4,5,5-tetramethyl-2-(3-(methylpiperizinesulfonyl)phenyl)-1,3,2-dioxaborolane via General Procedure F. The product was purified by reverse phase HPLC to yield 8.7 mg of 361. MS (Q1) 567.0 (M)+.

Example 290

3-(2-(2-aminopyrimidin-5-yl)-7-methyl-4-morpholinothieno[3,2-d]pyrimidin-6-yl)benzoic acid 362

2-Chloro-6-iodo-7-methyl-4-morpholinothieno[3,2-d]pyrimidine (350 mg), 161 mg of 3-carboxyphenylboronic acid and 46 mg of bis(triphenylphosphine)palladium(II) dichloride in 3 mL of 1M Na$_2$CO$_3$ aqueous solution and 3 mL of acetonitrile was heated to 80° C. in a sealed microwave reactor for 15 min. Upon completion, the reaction mixture was evaporated. The crude product was purified by isco eluting with 0~15% MeOH/DCM to yield 248 mg of 3-(2-chloro-7-methyl-4-morpholinothieno[3,2-d]pyrimidin-6-yl)benzoic acid.

3-(2-Chloro-7-methyl-4-morpholinothieno[3,2-d]pyrimidin-6-yl)benzoic acid (50 mg) was coupled to 2-aminopyrimidine-5-boronic acid pinacol ester via General Procedure A. 2 mL of water was added to the mixture. The resulting solid was filtered, and washed with water and DCM to yield 13 mg of 362. MS (Q1) 449.2 (M)+.

Example 291

(3-(2-(2-aminopyrimidin-5-yl)-7-methyl-4-morpholinothieno[3,2-d]pyrimidin-6-yl)phenyl)(4-acetylpiperazin-1-yl)methanone 363

2-Chloro-6-iodo-7-methyl-4-morpholinothieno[3,2-d]pyrimidine (500 mg) was coupled to 3-carboxyphenylboronic acid via General Procedure F. Water (4 mL) was added. The resulting solid was filtered, washed with H$_2$O and DCM. The product was dried to yield 560 mg of 3-(2-(2-aminopyrimidin-5-yl)-7-methyl-4-morpholinothieno[3,2-d]pyrimidin-6-yl)benzoic acid.

3-(2-(2-Aminopyrimidin-5-yl)-7-methyl-4-morpholinothieno[3,2-d]pyrimidin-6-yl)benzoic acid (60 mg) was reacted with 1-acetylpiperizine via General Procedure B. The product was purified by reverse phase HPLC to yield 34.9 mg of 363. MS (Q1) 559.2 (M)+.

Example 292

(3-(2-(2-aminopyrimidin-5-yl)-7-methyl-4-morpholinothieno[3,2-d]pyrimidin-6-yl)phenyl)(4-(thiazol-2-yl)piperazin-1-yl)methanone 364

3-(2-(2-Aminopyrimidin-5-yl)-7-methyl-4-morpholinothieno[3,2-d]pyrimidin-6-yl)benzoic acid (60 mg) was reacted with 1-thiazole-2-yl-piperizine via General Procedure B. The product was purified by reverse phase HPLC to yield 14.7 mg of 364. MS (Q1) 600.0 (M)+.

Example 293

(3-(2-(2-aminopyrimidin-5-yl)-7-methyl-4-morpholinothieno[3,2-d]pyrimidin-6-yl)phenyl)(4-(2-(dimethylamino)ethyl)piperazin-1-yl)methanone 365

3-(2-(2-Aminopyrimidin-5-yl)-7-methyl-4-morpholinothieno[3,2-d]pyrimidin-6-yl)benzoic acid (60 mg) was reacted with 1-(2-dimethylaminoethyl)piperizine via Gen-

Example 294

(3-(2-(2-aminopyrimidin-5-yl)-7-methyl-4-morpholinothieno[3,2-d]pyrimidin-6-yl)phenyl)(4-(dimethylamino)piperidin-1-yl)methanone 3-(2-(2-Aminopyrimidin-5-yl)-7-methyl-4-morpholinothieno[3,2-d]pyrimidin-6-yl)benzoic acid (60 mg) was reacted with 4-(dimethylamino)piperidine via General Procedure B. The product was purified by reverse phase HPLC to yield 38.3 mg of 366. MS (Q1) 559.0 (M)$^+$.

Example 295

(3-(2-(2-aminopyrimidin-5-yl)-7-methyl-4-morpholinothieno[3,2-d]pyrimidin-6-yl)phenyl)(4-(1-methyl-piperidin-4-yl)piperazin-1-yl)methanone 367

3-(2-(2-Aminopyrimidin-5-yl)-7-methyl-4-morpholinothieno[3,2-d]pyrimidin-6-yl)benzoic acid (60 mg) was reacted with 1-(1-methyl-4-piperidinyl)piperizine via General Procedure B. The product was purified by reverse phase HPLC to yield 5.7 mg of 367. MS (Q1) 614.0 (M)$^+$.

Example 296

2-(2-(2,4-dimethoxypyrimidin-5-yl)-4-morpholinothieno[3,2-d]pyrimidin-6-yl)propan-2-ol 368

To a suspension of 2-Chloro-4-morpholin-4-yl-thieno[3,2-d]pyrimidine (1.24 g) in dry THF (20 mL) cooled to −78° C. was added nBuLi (2.5M solution in hexanes, 2.32 mL). After stirring for 1 hour, acetone (0.53 mL) was added and the reaction mixture was warmed slowly to room temperature. After one hour the reaction mixture was poured onto water and the solid was collected by filtration. Purification on silica yielded 2-(2-chloro-4-morpholin-4-yl-thieno[3,2-d]pyrimidin-6-yl)-propan-2-ol (340 mg).

2-(2-Chloro-4-morpholin-4-yl-thieno[3,2-d]pyrimidin-6-yl)-propan-2-ol (125 mg, 0.40 mmol) was reacted with 2,4-dimethoxypyrimidine 5-boronic acid (103 mg, 0.56 mmol) via General Procedure A. Purification on silica and then using an SCX cartridge gave 368 as a white solid (53 mg, 32%). NMR (CDCl$_3$, 400 MHz), 8.86 (s, 1H); 7.23 (s, 1H); 3.99 (s, 3H); 3.97 (s, 3H); 3.96 (t, 4H, J=4.8 Hz); 3.79 (t, 4H, J=4.8 Hz); 1.67 (s, 6H) MS: (ESI+): MH+=418.16

Example 297

2-(2-aminopyrimidin-5-yl)-4-morpholinothieno[3,2-d]pyrimidin-6-amine 369

Tert-butyl 2-chloro-4-morpholinothieno[3,2-d]pyrimidin-6-ylcarbamate (30 mg) was coupled to 2-aminopyrimidine-5-boronic acid pinacol ester via General Procedure A. The product was purified by reverse phase HPLC to yield 6.0 mg of 369. MS (Q1) 330.0 (M)$^+$.

Example 298

5-(7-methyl-4-morpholino-6-(3-piperazinylsulfonyl)phenylthieno[3,2-d]pyrimidin-2-yl)pyrimidin-2-amine 370

3-Bromobenzenesulfonyl chloride (1 g) was added to a mixture of 663 mg of 1-Boc piperizine and 1 mL of N,N'-diisopropylethylamine in 5 mL of MeOH. The reaction mixture was stirred at room temperature. Upon completion, The solid was filtered and washed with MeOH to yield 1.2 g of 1-bromo-3-(tert-butylpiperizinesulfonyl)benzene.

1-Bromo-3-(tert-butylpiperizinesulfonyl)benzene (300 mg), 282 mg of Bis(pinacolato)diboron, 218 mg of potassium acetate and 30 mg of PdCl$_2$(dppf) in 3 mL of toluene was heated to 80° C. for 2 h. The mixture was diluted with ethyl acetate, then washed with saturated NaHCO$_3$ and brine. The organic layer was dried over MgSO$_4$, filtered and evaporated to yield 330 mg of 4,4,5,5-tetramethyl-2-(3-(tert-butylpiperizinesulfonyl)phenyl)-1,3,2-dioxaborolane.

2-Chloro-6-iodo-7-methyl-4-morpholinothieno[3,2-d]pyrimidine (50 mg) was coupled to 4,4,5,5-tetramethyl-2-(3-(tert-butylpiperizinesulfonyl)phenyl)-1,3,2-dioxaborolane via General Procedure F. Water (2 mL) was added and the resulting solid was filtered to yield tert-butyl 3-(2-(2-aminopyrimidin-5-yl)-7-methyl-4-morpholinothieno[3,2-d]pyrimidin-6-yl)phenylsulfonylpiperizine. A mixture of 80 mg of tert-butyl 3-(2-(2-aminopyrimidin-5-yl)-7-methyl-4-morpholinothieno[3,2-d]pyrimidin-6-yl)phenylsulfonylpiperizine in a solution of TFA/DCM (1.5 mL/1.5 mL) was stirred for 1 h at room temperature. The mixture was evaporated and the product was purified by reverse phase HPLC to yield 25.7 mg of 370. MS (Q1) 553.0 (M)$^+$.

Example 299

3-(2-(2-aminopyrimidin-5-yl)-7-methyl-4-morpholinothieno[3,2-d]pyrimidin-6-yl)-N-(2,3-dihydroxypropyl)-N-methylbenzamide 371

3-(2-(2-Aminopyrimidin-5-yl)-7-methyl-4-morpholinothieno[3,2-d]pyrimidin-6-yl)benzoic acid (70 mg) was reacted with 3-methylamino-1,2-propanediol via General Procedure B. The product was purified by reverse phase HPLC to yield 44.2 mg of 371. MS (Q1) 536.2 (M)$^+$.

Example 300

3-(2-(2-aminopyrimidin-5-yl)-7-methyl-4-morpholinothieno[3,2-d]pyrimidin-6-yl)-N-(2,3-dihydroxypropyl)benzamide 372

3-(2-(2-Aminopyrimidin-5-yl)-7-methyl-4-morpholinothieno[3,2-d]pyrimidin-6-yl)benzoic acid (70 mg) was reacted with 3-amino-1,2-propanediol via General Procedure B. The product was purified by reverse phase HPLC to yield 12.7 mg of 372. MS (Q1) 522.2 (M)$^+$.

Example 301

2-(2-(2-aminopyrimidin-5-yl)-4-morpholinothieno[3,2-d]pyrimidin-6-ylamino)ethanol 373

2-Chloro-6-iodo-4-morpholinothieno[3,2-d]pyrimidine (400 mg), 274 mg of 2-oxazolidinone, 667 mg of potassium phosphate tribasic, 40 mg of copper iodide, 27 µL of N,N-dimethylethylenediamine in 4 mL of 1,4-dioxane was heated to 120° C. for 50 min. The reaction mixture was diluted with ethyl acetate (~50 mL), washed with brine (~30 mL), dried over MgSO$_4$, filtered and evaporated to give a mixture of 3-(2-chloro-4-morpholinothieno[3,2-d]pyrimidin-6-yl)oxazolidin-2-one and 2-(2-chloro-4-morpholinothieno[3,2-d]pyrimidin-6-ylamino)ethanol.

The mixture of 3-(2-chloro-4-morpholinothieno[3,2-d]pyrimidin-6-yl)oxazolidin-2-one and 2-(2-chloro-4-morpholinothieno[3,2-d]pyrimidin-6-ylamino)ethanol (46 mg) was coupled to 2-aminopyrimidine-5-boronic acid pinacol ester via General Procedure A. The product was purified by reverse phase HPLC to yield 7.0 mg of 373. MS (Q1) 374.1 (M)+.

Example 302

(R)-1-(5-(2-(2-aminopyrimidin-5-yl)-4-morpholinothieno[3,2-d]pyrimidin-6-yl)pyridin-2-yl)pyrrolidin-3-ol 374

3-Bromobenzenesulfonyl chloride (1 g) was added to a mixture of 357 mg of 1-methylpiperizine and 929 µL of N,N'-diisopropylethylamine in 5 mL of MeOH. The reaction mixture was stirred at room temperature. Upon completion, the reaction mixture was evaporated. The residue was diluted with ethyl acetate, washed with saturated NaHCO$_3$ and brine. The organic layer was dried over MgSO$_4$, filtered and evaporated to yield 850 mg of 1-bromo-3-(methylpiperizinesulfonyl)benzene.

1-Bromo-3-(methylpiperizinesulfonyl)benzene (250 mg), 229 mg of Bis(pinacolato)diboron, 230 mg of potassium acetate and 30 mg of PdCl$_2$(dppf) in 3 mL of toluene was heated to 80° C. for 2 h. The mixture was diluted with ethyl acetate, washed with saturated NaHCO$_3$ and brine. The organic layer was dried over MgSO$_4$, filtered and evaporated to yield 270 mg of 4,4,5,5-tetramethyl-2-(3-(methylpiperizinesulfonyl)phenyl)-1,3,2-dioxaborolane.

2-Chloro-6-iodo-7-methyl-4-morpholinothieno[3,2-d]pyrimidine 50 mg was coupled to 4,4,5,5-tetramethyl-2-(3-(methylpiperizinesulfonyl)phenyl)-1,3,2-dioxaborolane via General Procedure F. The product was purified by reverse phase HPLC to yield 8.7 mg of 374. MS (Q1) 567.0 (M)+.

Example 303

5-(4-morpholino-7-phenylthieno[3,2-d]pyrimidin-2-yl)pyrimidin-2-amine 378

1H-Thieno[3,2-d]pyrimidine-2,4-dione (3 g, 18 mmol) was suspended in glacial acetic acid (90 ml) and heated to 80° C. before bromine (10.80 g, 3.23 ml, 63 mmol) was added dropwise. The reaction mixture was heated at 80° C. for a further 4 hours before pouring into water (~1 L) and the white precipitate collected and dried to yield 7-bromo-1H-thieno[3,2-d]pyrimidine-2,4-dione (3.92 g, 88%).

7-Bromo-1H-thieno[3,2-d]pyrimidine-2,4-dione (3.92 g, 15.87 mmol) was suspended in neat phosphorous oxychloride (50 ml) and refluxed overnight. The cooled reaction solution was poured into vigorously stirring ice-water before extracting into DCM. The organic layer was dried over MgSO$_4$, filtered and evaporated to give 7-bromo-2,4-dichloro-thieno[3,2-d]pyrimidine (4.11 g, 91%).

7-Bromo-2,4-dichloro-thieno[3,2-d]pyrimidine (4.10 g, 14.44 mmol) was suspended in methanol (100 ml), to this morpholine (3.15 ml, 36.10 mmol) was added and stirred at room temperature for 5 hours. Water was added to the solution and the resulting white precipitate filtered and dried (4.11 g, 85%) to yield 7-bromo-2-chloro-4-morpholin-4-yl-thieno[3,2-d]pyrimidine.

2-Chloro-4-morpholin-4-yl-7-phenyl-thieno[3,2-d]pyrimidine was made by reacting 7-bromo-2-chloro-4-morpholin-4-yl-thieno[3,2-d]pyrimidine and phenylboronic acid according to the General Procedure A. LCMS confirmed reaction at the bromine. MS: (ESI+): MH+ 332

2-chloro-4-morpholin-4-yl-7-phenyl-thieno[3,2-d]pyrimidine and 5-(4,4,5,5-tetramethyl-[1,3,2]dioxaborolan-2-yl)-pyrimidin-2-ylamine were reacted according to the General Procedure A to give 378. NMR (CDCl$_3$, 400 MHz), 3.84 (4H, t, J=4.4), 4.02 (4H, t, J=4.4), 5.12 (2H, s), 7.33 (1H, 7.2), 7.43 (2H, t, J=8.0), 7.77 (1H, s), 7.97 (2H, d, J=7.2), 9.27 (2H, s). MS: (ESI+): MH+ 391

Example 304

5-(4-morpholino-7-(thiazol-2-yl)thieno[3,2-d]pyrimidin-2-yl)pyrimidin-2-amine 379

A suspension of 7-bromo-2-chloro-4-morpholin-4-yl-thieno[3,2-d]pyrimidine (116 mg, 0.35 mmol), 5-tributylstannanyl thiazole (130 mg, 0.35 mmol), and Pd(PPh$_3$)$_4$ (20 mg, 0.017 mmol) in anhydrous DMA was heated in a microwave at 150° C. for 15 mins. The crude reaction was loaded onto a preconditioned SCX cartridge, washing the cartridge with methanol and dichloromethane before eluting with 7N ammonia in methanol to give crude material. This was purified by on silica using ethyl acetate as the eluent to give 2-chloro-4-morpholin-4-yl-7-thiazol-5-yl-thieno[3,2-d]pyrimidine as a white solid (93 mg, 80%). LCMS confirmed reaction at the bromine. MS: (ESI+): MH+ 339

2-Chloro-4-morpholin-4-yl-7-thiazol-5-yl-thieno[3,2-d]pyrimidine and 5-(4,4,5,5-tetramethyl-[1,3,2]dioxaborolan-2-yl)-pyrimidin-2-ylamine were reacted according to General Procedure A to give 379. NMR (DMSO, 400 MHz), 3.79 (4H, t, J=4.4), 4.01 (4H, t, J=4.4), 7.12 (2H, s), 8.69 (1H, s), 8.71 (2H, s), 9.13 (1H, s), 9.23 (2H, s). MS: (ESI+): MH+ 398

Example 305

5-(4-morpholino-6-(2-(4-N-methylsulfonylpiperazin-1-yl)propan-2-yl)thieno[3,2-d]pyrimidin-2-yl)pyrimidin-2-amine 380

To a solution of 2-chloro-4-morpholinothieno[3,2-d]pyrimidine 4 (5.0 g) in THF (100 mL) at −78° C. was added n-butyllithium (9.41 mL) according to General Procedure D-1. The reaction mixture was stirred at −78° C. for 1 h and then dry CO$_2$ was bubble through the mixture. The reaction was allowed to warm to room temperature over 16 h and then quenched with water (20 mL) and the solvent reduced in vacuo. The mixture was then diluted with saturated aqueous sodium hydrogencarbonate solution (30 mL) and washed with ethyl acetate (40 mL). The aqueous layer was acidified with 2 M aqueous hydrochloric acid and the product filtered and air dried to give 2-chloro-4-morpholin-4-yl-thieno[3,2-d]pyrimidine-6-carboxylic acid (4.21 g).

To a solution of 2-chloro-4-morpholin-4-yl-thieno[3,2-d]pyrimidine-6-carboxylic acid (1.85 g) in DMF (30 mL) was added 1,1-carbonyldiimidazole (2.00 g) and the reaction mixture was stirred at room temperature for 1 h. Triethylamine (2.58 mL) and 1-methanesulfonyl-piperazine hydrochloride salt (2.48 g) were then added and the reaction mixture stirred at room temperature for 16 h. The reaction was then quenched with water (20 mL) and the product filtered, washed with water and air dried to give (2-chloro-4-morpholin-4-yl-thieno[3,2-d]pyrimidin-6-yl)-(4-methanesulfonyl-piperazin-1-yl)-methanone (1.80 g).

To a solution of (2-chloro-4-morpholin-4-yl-thieno[3,2-d]pyrimidin-6-yl)-(4-methanesulfonyl-piperazin-1-yl)-methanone (1.80 g) in THF (40 mL) at −10° C. was added zirconium (IV) chloride (4.71 g). After stirring at −10° C. for 10 minutes, methylmagnesium bromide (8.09 mL of a 3 M solution) was added dropwise and the mixture allowed to warm to room temperature over 16 h. The mixture was then diluted with water (40 mL) and extracted into ethyl acetate (3×40 mL). The aqueous layer was basified with sodium carbonate and reextracted into ethyl acetate (2×20 mL). The combined organics were washed with brine (2×40 mL), dried (MgSO$_4$), reduced in vacuo and purified by column chromatography to give 2-chloro-6-[1-(4-methanesulfonyl-piperazin-1-yl)-1-methyl-ethyl]-4-morpholin-4-yl-thieno[3,2-d]pyrimidine.

2-Chloro-6-[1-(4-methanesulfonyl-piperazin-1-yl)-1-methyl-ethyl]-4-morpholin-4-yl-thieno[3,2-d]pyrimidine was reacted with 2-aminopyrimidine-5-boronic acid pinacol ester in General Procedure A. Purification on silica yielded 380. NMR: (CDCl$_3$) 1.45 (6H, s, Me), 2.62-2.65 (4H, m), 2.74 (3H, s, Me), 3.18-3.21 (4H, m), 3.80-3.83 (4H, m), 3.94-3.97 (4H, m), 5.13 (2H, s, NH), 7.18 (1H, s, Ar) and 9.20 (2H, m, Ar). MS: (ESI+): MH+ 519.23

Example 306

N-((2-(2-aminopyrimidin-5-yl)-4-morpholinothieno[3,2-d]pyrimidin-6-yl)methyl)thiazol-2-amine 381

A mixture of 2-chloro-4-morpholin-4-yl-thieno[3,2-d]pyrimidine-6-carbaldehyde, 10 from Example 3 (200 mg), 2-aminothiazole (71 mg) and ethanol (10 mL) was heated to reflux for 48 hours. The solvent was then removed in vacuo and the residue was dissolved in 1,2-dichloroethane (20 mL). To this was added sodium triacetoxyborohydride (221 mg) and the reaction mixture was stirred overnight. He reaction mixture was quenched with water, extracted into CHCl$_3$, dried (MgSO$_4$) and solvent removed in vacuo. The residue was purified using flash chromatography to yield (2-chloro-4-morpholin-4-yl-thieno[3,2-d]pyrimidin-6-ylmethyl)-thiazol-2-yl-amine.

(2-Chloro-4-morpholin-4-yl-thieno[3,2-d]pyrimidin-6-ylmethyl)-thiazol-2-yl-amine was reacted with 2-aminopyrimidine-5-boronic acid pinacol ester according to General Procedure A. Purification on silica yielded 381. NMR (DMSO): 3.27 (2H, s), 3.77-3.80 (4H, m), 3.90-3.94 (4H, m), 4.78 (2H, br), 6.70 (1H, d, J=3.6), 7.04-7.07 (3H, m), 7.35 (1H, s), 8.26 (1H, t), 9.11 (2H, s). MS (ESI+): MH+ 427.13 (55%)

Example 307

5-(6-((N-methylsulfonyl,N-methylamino)methyl)-4-morpholinothieno[3,2-d]pyrimidin-2-yl)thiazol-2-amine 394

(2-Chloro-4-morpholin-4-yl-thieno[3,2-d]pyrimidin-6-ylmethyl)-methylamine was made by treating 2-chloro-4-morpholin-4-yl-thieno[3,2-d]pyrimidine-6-carbaldehyde 10, from Example 3, and 40% methylamine in water according to the General Procedure B-4.

N-(2-Chloro-4-morpholin-4-yl-thieno[3,2-d]pyrimidin-6-ylmethyl)-N-methyl-methanesulfonamide was synthesized from (2-chloro-4-morpholin-4-yl-thieno[3,2-d]pyrimidin-6-ylmethyl)-methylamine and methanesulfonyl chloride with triethylamine in dichloromethane in an analogous manner to General Procedure C-2.

A suspension of N-(2-chloro-4-morpholin-4-yl-thieno[3,2-d]pyrimidin-6-ylmethyl)-N-methyl-methanesulfonamide (115 mg, 0.32 mmol), (5-tributylstannyl-thiazol-2-yl)-carbamic acid tert-butyl ester (233 mg, 0.47 mmol), and Pd(PPh$_3$)$_4$ (19 mg, 0.016 mmol) in anhydrous DMA was heated in a microwave at 150° C. for 15 mins. The crude reaction was loaded onto a preconditioned SCX cartridge, washing the cartridge with methanol and dichloromethane before eluting with 7N ammonia in methanol to give crude material. This was purified by on silica using 30% methanol in ethyl acetate as the eluent to give 394 as a white solid (17 mg, 12%). NMR (CDCl$_3$, 400 MHz), 2.83 (3H, s), 2.84 (3H, s), 3.79 (4H, t, J=4.4), 3.91 (4H, t, J=4.8), 4.54 (2H, s), 4.96 (2H, s), 7.22 (1H, s), 7.85 (1H, s). MS: (ESI+): MH+ 441

Example 308

(2-(2,4-dimethoxypyrimidin-5-yl)-4-morpholinothieno[3,2-d]pyrimidin-6-yl)-N-methyl,N-methylsulfonylmethanamine 395

N-(2-chloro-4-morpholin-4-yl-thieno[3,2-d]pyrimidin-6-ylmethyl)-N-methyl-methanesulfonamide and 2,4-dimethoxy-5-(4,4,5,5-tetramethyl-[1,3,2]dioxaborolan-2-yl)-pyrimidine were reacted according to the General Procedure A to give 395. NMR (CDCl$_3$, 400 MHz), 2.95 (3H, s), 2.96 (3H, s), 3.88 (4H, t, J=4.8), 4.04 (4H, t, J=5.2), 4.09 (3H, s), 4.12 (3H, s), 4.66 (2H, s), 7.42 (1H, s), 8.96 (1H, s). MS: (ESI+): MH+=481

Example 309

N-((2-(2,4-dimethoxypyrimidin-5-yl)-4-morpholinothieno[3,2-d]pyrimidin-6-yl)methyl)-N-methylacetamide 396

2-Chloro-4-morpholin-4-yl-thieno[3,2-d]pyrimidine-6-carbaldehyde 10 from Example 3, and 40% methylamine in water were reacted according to General Procedure B-4 to give (2-chloro-4-morpholin-4-yl-thieno[3,2-d]pyrimidin-6-ylmethyl)-methylamine.

(2-Chloro-4-morpholin-4-yl-thieno[3,2-d]pyrimidin-6-ylmethyl)-methylamine (190 mg, 0.64 mmol) was dissolved in 10 ml tetrahydrofuran and cooled to 0° C. under N$_2$ before adding triethylamine (180 ul, 1.3 mmol) and acetyl chloride (50 ul, 0.7 mmol). The reaction mixture was stirred 16 hrs at room temperature. The reaction was extracted into ethyl acetate, washed with water, the organic layer dried over MgSO$_4$, and concentrated in vacuo to give N-(2-chloro-4-morpholin-4-ylthieno[3,2-d]pyrimidin-6-ylmethyl)-N-methyl-acetamide (135 mg, 73%).

N-(2-Chloro-4-morpholin-4-ylthieno[3,2-d]pyrimidin-6-ylmethyl)-N-methyl-acetamide and 2,4-dimethoxy-5-(4,4,5,5-tetramethyl-[1,3,2]dioxaborolan-2-yl)-pyrimidine were reacted according to the General Procedure A to give 396. NMR (CDCl$_3$, 400 MHz), 2.10 (3H, s), 2.97 (3H, s), 3.77 (4H, t, J=4.4), 3.92 (4H, t, J=4.4), 3.99 (3H, s), 4.02 (3H, s), 4.74 (2H, s), 7.26 (1H, s), 8.71 (1H, s). MS: (ESI+): MH+ 445

Example 310

5-(6-((methylamino)methyl)-4-morpholinothieno[3,2-d]pyrimidin-2-yl)pyrimidin-2-amine 397

(2-Chloro-4-morpholin-4-yl-thieno[3,2-d]pyrimidin-6-ylmethyl)-methylamine and 5-(4,4,5,5-tetramethyl-[1,3,2]dioxaborolan-2-yl)-pyrimidin-2-ylamine were reacted according to the General Procedure A to give 397. NMR (CDCl$_3$, 400 MHz), 2.56 (3H, s), 3.89 (4H, t, J=5.2), 4.05

(4H, t, J=4.8), 4.11 (2H, d, J=0.8), 5.24 (2H, s), 7.29 (1H, s), 9.30 (2H, s). MS: (ESI+): MH+ 358

Example 311

N-((4-(2-(2-aminopyrimidin-5-yl)thieno[3,2-d]pyrimidin-4-yl)morpholin-2-yl)methyl)benzamide 398

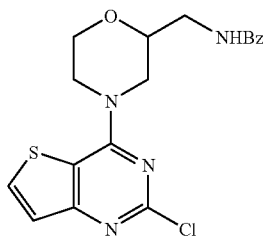

A solution of (4-(2-chlorothieno[3,2-d]pyrimidin-4-yl)morpholin-2-yl)methanamine from Example 312 (0.28 mmol) and Et$_3$N (0.10 mL) in CH$_2$Cl$_2$ (1.5 mL) at 0° C. was treated with benzoyl chloride (40 µM). After 10 min, the reaction mixture was warmed to room temperature, diluted with NaHCO$_3$ and extracted with CH$_2$Cl$_2$. The organics were concentrated to give crude N-((4-(2-chlorothieno[3,2-d]pyrimidin-4-yl)morpholin-2-yl)methyl)benzamide which was of suitable purity to use in further manipulations. MS (Q1) 389 (M)+

N-((4-(2-Chlorothieno[3,2-d]pyrimidin-4-yl)morpholin-2-yl)methyl)benzamide (ca. 0.28 mmol), 2-aminopyrimidine-5-boronic acid pinacol ester (82 mg), Pd(PPh$_3$)$_4$ (43 mg), MeCN (1.5 mL) and 1M KOAc in H$_2$O (1.5 mL) were irradiated at 130° C. for 20 min. The product was isolated by filtration and washed with H$_2$O. Purification by reverse-phase HPLC gave 398 (24 mg) MS (Q1) 448 (M)+

Example 312

5-(4-(2-(aminomethyl)morpholino)thieno[3,2-d]pyrimidin-2-yl)pyrimidin-2-amine 399

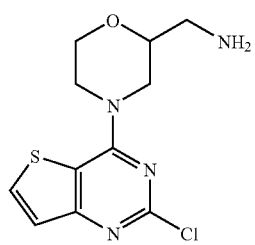 [SMILES: NCC1CN(c2nc(Cl)nc3ccsc23)CCO1]

A solution of (4-(2-chloro-5-methylthieno[2,3-d]pyrimidin-4-yl)morpholin-2-yl)methanol from Example 318 (500 mg, 1.75 mmol) and Et$_3$N (0.73 mL) in CH$_2$Cl$_2$ (10 mL) was treated with methanesulfonyl chloride (0.20 mL) at room temperature. After 10 min, the reaction mixture was diluted with sat. NaHCO$_3$ and extracted with CH$_2$Cl$_2$. The combined extracts were concentrated to obtain the crude mesylate. MS (Q1) 364 (M)+. A solution of the crude mesylate in 10 mL DMF and 2 mL DMSO was treated with NaN$_3$ (230 mg) and heated at 90° C. for 2.5 hr. After cooling to room temperature, the mixture was diluted with water and extracted with EtOAc. The combined extracts were washed with sat. brine and dried over Na$_2$SO$_4$. Concentration gave the crude azide. MS (Q1) 310 (M)+. The azide was dissolved in THF (10 mL) and the solution treated with water (0.1 mL) and PPh$_3$ (690 mg). The reaction mixture was heated at 60° C. for 2 hr. The cooled reaction mixture was concentrated, diluted with water and extracted with EtOAc. The combined extracts were concentrated and the residue obtained purified by silica-gel chromatography (2% MeOH, 2% TEA in CH$_2$Cl$_2$) to give (4-(2-chlorothieno[3,2-d]pyrimidin-4-yl)morpholin-2-yl)methanamine (158 mg, 32% over 3 steps). MS (Q1) 285 (M)+

(4-(2-Chlorothieno[3,2-d]pyrimidin-4-yl)morpholin-2-yl)methanamine (79 mg, 0.28 mmol), 2-aminopyrimidine-5-boronic acid pinacol ester (80 mg), Pd(PPh$_3$)$_4$ (32 mg), MeCN (1.5 mL) and 1M KOAc in H$_2$O (1.5 mL) were irradiated at 150° C. for 30 min. The mixture was diluted with H$_2$O and extracted with Et$_2$O. The aqueous layer was concentrated and dissolved in 1:1 THF:MeOH. The organic phase was concentrated to give a solid which was purified by reverse-phase HPLC to give 399 (18 mg) MS (Q1) 343 (M)+

Example 313

2-(4-(2-(2-aminopyrimidin-5-yl)thieno[3,2-d]pyrimidin-4-yl)morpholin-2-yl)-1-(pyrrolidin-1-yl)ethanone 400

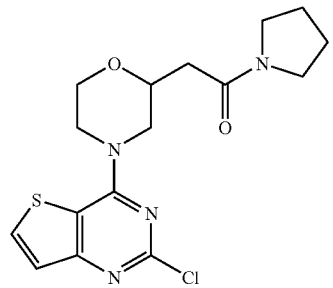 [SMILES: O=C(CC1CN(c2nc(Cl)nc3ccsc23)CCO1)N1CCCC1]

2-(4-(2-chlorothieno[3,2-d]pyrimidin-4-yl)morpholin-2-yl)acetic acid from Example 317 (0.35 mmol), HATU (200 mg, 0.52 mmol) and DIPEA (0.18 mL) in 3 mL DMF at room temperature was treated with pyrrolidine (45 µM). The reaction mixture was stirred at room temperature for 30 min, diluted with water and extracted with EtOAc. Crude 2-(4-(2-chlorothieno[3,2-d]pyrimidin-4-yl)morpholin-2-yl)-1-(pyrrolidin-1-yl)ethanone was used in subsequent reactions without purification. MS (Q1) 367 (M)+

2-(4-(2-Chlorothieno[3,2-d]pyrimidin-4-yl)morpholin-2-yl)-1-(pyrrolidin-1-yl)ethanone (ca. 0.35 mmol), 2-aminopyrimidine-5-boronic acid pinacol ester (85 mg), Pd(PPh$_3$)$_4$ (30 mg), MeCN (1.5 mL) and 1M KOAc in H$_2$O (1.5 mL) were irradiated at 150° C. for 30 min. The product was isolated by filtration and washed with H$_2$O to give 400 (21 mg) MS (Q1) 426 (M)+

Example 314

5-(4-(2,2-dimethylmorpholino)thieno[3,2-d]pyrimidin-2-yl)pyrimidin-2-amine 401

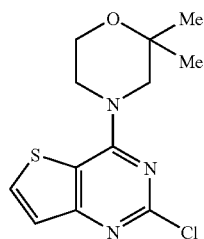 [SMILES: CC1(C)CN(c2nc(Cl)nc3ccsc23)CCO1]

2,2-Dimethylmorpholine.HCl (203 mg, 1.3 mmol, 1.1 eq), Et₃N (0.42 mL), and 2,4-dichlorothieno[2,3-d]pyrimidine (250 mg, 1.22 mmol) in 5 mL of MeOH at room temperature for 3 hr. Concentration to one third volume provided 4-(2-chlorothieno[3,2-d]pyrimidin-4-yl)-2,2-dimethylmorpholine as a solid that was collected by filtration. MS (Q1) 284 (M)+

4-(2-Chlorothieno[3,2-d]pyrimidin-4-yl)-2,2-dimethylmorpholine (115 mg, 0.40 mmol), 2-aminopyrimidine-5-boronic acid pinacol ester (107 mg), Pd(PPh₃)₄ (23 mg), MeCN (1 mL) and 1M KOAc in H₂O (1 mL) were irradiated at 150° C. for 30 min. The product was isolated by filtration and washed with H₂O. Purification by reverse-phase HPLC gave 401 (53 mg) MS (Q1) 342 (M)+

Example 315 methyl 2-(4-(2-(2-aminopyrimidin-5-yl)thieno[3,2-d]pyrimidin-4-yl)morpholin-3-yl)acetate 402

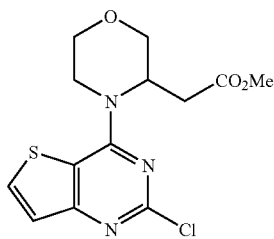 [SMILES: COC(=O)CC1COCCN1c1nc(Cl)nc2ccsc12]

Morpholine-3-acetic acid methyl ester (210 mg, 1.07 mmol, 1.1 eq), Et₃N (0.56 mL), and 2,4-dichlorothieno[2,3-d]pyrimidine (200 mg, 0.98 mmol) in 5 mL of MeOH at room temperature overnight. The mixture was concentrated to dryness, diluted with sat. NaHCO₃ and extracted with CH₂Cl₂. The combined extracts were concentrated to give methyl 2-(4-(2-chlorothieno[3,2-d]pyrimidin-4-yl)morpholin-3-yl)acetate which was pure enough to use in subsequent manipulations. MS (Q1) 328 (M)+

Methyl 2-(4-(2-chlorothieno[3,2-d]pyrimidin-4-yl)morpholin-3-yl)acetate (110 mg, 0.434 mmol), 2-aminopyrimidine-5-boronic acid pinacol ester (90 mg, 0.41 mmol), Pd(PPh₃)₄ (19 mg), MeCN (1.5 mL) and 1M KOAc in H₂O (1.5 mL) were irradiated at 130° C. for 30 min. The product was isolated by dilution with water and extraction by EtOAc. Purification by reverse-phase HPLC gave 402 (80 mg) MS (Q1) 386 (M)+

Example 316

2-(4-(2-(2-aminopyrimidin-5-yl)thieno[3,2-d]pyrimidin-4-yl)morpholin-2-yl)acetamide 403

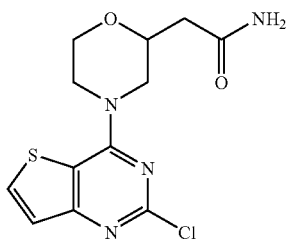 [SMILES: NC(=O)CC1CN(c2nc(Cl)nc3ccsc23)CCO1]

2-(4-(2-chlorothieno[3,2-d]pyrimidin-4-yl)morpholin-2-yl)acetic acid from Example 317 (0.48 mmol), HATU (274 mg, 0.72 mmol) and DIPEA (0.33 mL, 1.9 mmol) in 5 mL DMF at room temperature was treated with NH₄Cl (77 mg, 1.44 mmol). The reaction mixture was stirred at room temperature overnight, diluted with water and extracted with EtOAc. The combined extracts were concentrated and the residue obtained purified by silica-gel chromatography (1:1 hexanes:EtOAc) to give 2-(4-(2-chlorothieno[3,2-d]pyrimidin-4-yl)morpholin-2-yl)acetamide. MS (Q1) 314 (M)+

2-(4-(2-Chlorothieno[3,2-d]pyrimidin-4-yl)morpholin-2-yl)acetamide (ca. 0.48 mmol), 2-aminopyrimidine-5-boronic acid pinacol ester (116 mg, 0.53 mmol), Pd(PPh₃)₄ (28 mg), MeCN (1.5 mL) and 1M KOAc in H₂O (1.5 mL) were irradiated at 150° C. for 30 min. The product was isolated by filtration and washed with H₂O and purified by reverse-phase HPLC to give 403 (29 mg) MS (Q1) 371 (M)+.

Example 317

2-(4-(2-(2-aminopyrimidin-5-yl)thieno[3,2-d]pyrimidin-4-yl)morpholin-2-yl)acetic acid 404

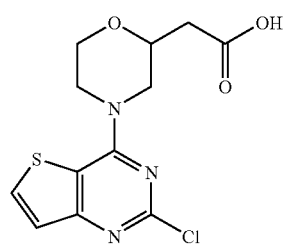 [SMILES: O=C(O)CC1CN(c2nc(Cl)nc3ccsc23)CCO1]

2-Morpholine acetic acid (156 mg, 1.07 mmol, 1.1 eq), Et₃N (0.54 mL, 4 eq), and 2,4-Dichlorothieno[2,3-d]pyrimidine (200 mg, 0.98 mmol) in 5 mL of MeOH at room temperature. Concentration to a third volume provided 2-(4-(2-chlorothieno[3,2-d]pyrimidin-4-yl)morpholin-2-yl)acetic acid as a solid, collected by filtration. MS (Q1) 314 (M)+

2-(4-(2-Chlorothieno[3,2-d]pyrimidin-4-yl)morpholin-2-yl)acetic acid (75 mg, 0.24 mmol), 2-aminopyrimidine-5-boronic acid pinacol ester (61 mg, 0.27 mmol), Pd(PPh₃)₄ (14 mg), MeCN (1 mL) and 1M KOAc in H₂O (1 mL) were irradiated at 150° C. for 30 min. The product was isolated by filtration and washed with H₂O. Purification by reverse-phase HPLC gave 404 (25 mg) MS (Q1) 372 (M)+

Example 318

(4-(2-(2-aminopyrimidin-5-yl)-5-methylthieno[2,3-d]pyrimidin-4-yl)morpholin-2-yl)methanol 405

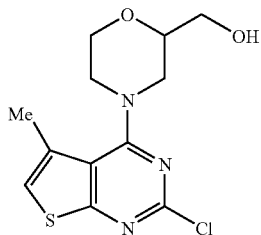 [SMILES: Cc1csc2nc(Cl)nc(N3CCOC(CO)C3)c12]

2-hydroxymethylmorpholine (253 mg, 2.2 mmol), Et$_3$N (0.5 mL), 2,4-dichloro-5-methyl-thieno[2,3-d]pyrimidine (400 mg, 1.8 mmol) in 5 mL of MeOH at room temperature for 1 h. The mixture was concentrated to dryness, diluted with sat. NaHCO$_3$ and extracted with CH$_2$Cl$_2$. The combined extracts were concentrated to give crude (4-(2-chloro-5-methylthieno[2,3-d]pyrimidin-4-yl)morpholin-2-yl)methanol. MS (Q1) 300 (M)+.

(4-(2-Chloro-5-methylthieno[2,3-d]pyrimidin-4-yl)morpholin-2-yl)methanol (71 mg, 0.24 mmol), 2-aminopyrimidine-5-boronic acid pinacol ester (64 mg, 0.28 mmol), Pd(PPh$_3$)$_4$ (14 mg), MeCN (1 mL) and 1M KOAc in H$_2$O (1 mL) were irradiated at 150° C. for 30 min. The product was isolated by filtration and washed with EtOAc and H$_2$O to give 405 (80 mg) MS (Q1) 358 (M)+

Example 319

(S)-5-(5-methyl-4-(3-methylmorpholino)thieno[2,3-d]pyrimidin-2-yl)pyrimidin-2-amine 406

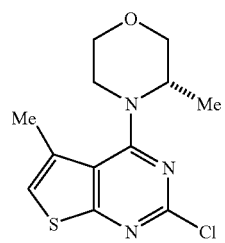 [SMILES: Cc1csc2nc(Cl)nc(N3CCOC[C@@H]3C)c12]

3-(S)-methylmorpholine (111 mg, 1.1 mmol), Et$_3$N (0.25 mL), 2,4-dichloro-5-methyl-thieno[2,3-d]pyrimidine (200 mg, 0.91 mmol) in 5 mL of MeOH at room temperature for 1 h. The mixture was concentrated to dryness, diluted with sat. NaHCO$_3$ and extracted with CH$_2$Cl$_2$. The combined extracts were concentrated to give crude (S)-4-(2-chloro-5-methylthieno[2,3-d]pyrimidin-4-yl)-3-methylmorpholine. MS (Q1) 284 (M)+

(S)-4-(2-Chloro-5-methylthieno[2,3-d]pyrimidin-4-yl)-3-methylmorpholine (45 mg, 0.16 mmol), 2-aminopyrimidine-5-boronic acid pinacol ester (42 mg), Pd(PPh$_3$)$_4$ (10 mg), MeCN (1 mL) and 1M KOAc in H$_2$O (1 mL) were irradiated at 150° C. for 30 min. The product was isolated by filtration and washed with EtOAc and H$_2$O to give 406 (30 mg) MS (Q1) 342 (M)+

Example 320

(S)-5-(4-(3-methylmorpholino)thieno[2,3-d]pyrimidin-2-yl)pyrimidin-2-amine 407

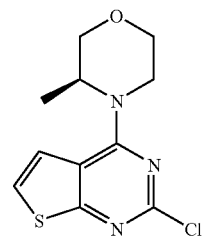 [SMILES: C[C@H]1COCCN1c1nc(Cl)nc2sccc12]

To a solution of 2,4-dichlorothieno[2,3-d]pyrimidine (0.5 g, 2.3 mmol) in methanol (20 mL) was added 3-(S)-methylmorpholine (5 mmol). The reaction stirred 2 h at room temperature then was concentrated in vacuo. The residue was diluted with water and filtered to yield (S)-4-(2-chlorothieno[2,3-d]pyrimidin-4-yl)-3-methylmorpholine (0.3 g). MS (Q1) 270 (M)+

(S)-4-(2-chlorothieno[2,3-d]pyrimidin-4-yl)-3-methylmorpholine (0.2 g) was utilized in a Suzuki coupling with (4,4,5,5-tetramethyl-1,3,2-dioxaborolan-2-yl)pyrimidin-2-amine according to General Procedure Suzuki to yield 407 (21 mg) after purification by reverse phase HPLC. MS (Q1) 329 (M)+

Example 321

N-((4-(2-(2-aminopyrimidin-5-yl)thieno[3,2-d]pyrimidin-4-yl)morpholin-2-yl)methyl)acetamide 408

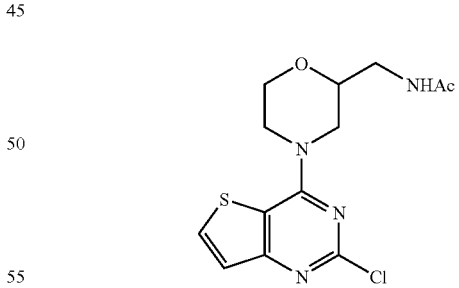

A solution of (4-(2-chlorothieno[3,2-d]pyrimidin-4-yl)morpholin-2-yl)methanamine from Example 312 (0.35 mmol) in CH$_2$Cl$_2$ (1 mL) and pyridine (3 mL) was treated with Ac$_2$O (0.17 mL). After 10 min, the reaction mixture was diluted with NaHCO$_3$ and extracted with CH$_2$Cl$_2$. The concentrated organics were flushed through a small column of silica-gel (CH$_2$Cl$_2$) to give N-((4-(2-chlorothieno[3,2-d]pyrimidin-4-yl)morpholin-2-yl)methyl)acetamide, used without purification. MS (Q1) 386 (M)+

N-((4-(2-Chlorothieno[3,2-d]pyrimidin-4-yl)morpholin-2-yl)methyl)acetamide (ca. 0.37 mmol), 2-aminopyrimidine-5-boronic acid pinacol ester (82 mg), Pd(PPh$_3$)$_4$ (43 mg), MeCN (1.5 mL) and 1M KOAc in H$_2$O (1.5 mL) were irradiated at 150° C. for 30 min. The product was isolated by filtration and washed with H$_2$O. Purification by reverse-phase HPLC gave 408. MS (Q1) 386 (M)+

Example 322

(S)-(2-(2-aminopyrimidin-5-yl)-4-(3-methylmorpholino)thieno[3,2-d]pyrimidin-6-yl)methanol 409

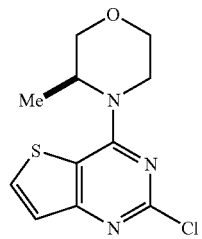 [SMILES: C[C@H]1COCCN1c1nc(Cl)nc2ccsc12]

3-(S)-Methylmorpholine (2.2 eq), 2,4-dichlorothieno[2,3-d]pyrimidine (400 mg, 1.95 mmol) in 5 mL of MeOH at room temperature for 3 hr. The mixture was concentrated to dryness, diluted with sat. NaHCO$_3$ and extracted with CH$_2$Cl$_2$. The combined extracts were concentrated and purified by silica-gel chromatography to give (S)-4-(2-chlorothieno[3,2-d]pyrimidin-4-yl)-3-methylmorpholine (286 mg, 54%). MS (Q1) 270 (M)+

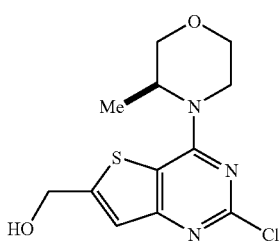 [SMILES: C[C@H]1COCCN1c1nc(Cl)nc2cc(CO)sc12]

(S)-4-(2-Chlorothieno[3,2-d]pyrimidin-4-yl)-3-methylmorpholine (670 mg, 2.48 mmol) in THF (20 mL) was treated with $^n$BuLi (1.48 mL, 2.5 M in hexanes, 3.7 mmol) then DMF (0.58 mL) to give the aldehyde (MS (Q1) 298 (M)+) which was reduced to (S)-(2-chloro-4-(3-methylmorpholino)thieno[3,2-d]pyrimidin-6-yl)methanol Crude (S)-(2-chloro-4-(3-methylmorpholino)thieno[3,2-d]pyrimidin-6-yl)methanol (ca. 25 mg), 2-aminopyrimidine-5-boronic acid pinacol ester (106 mg, 0.48 mmol), Pd(PPh$_3$)$_4$ (30 mg), MeCN (1.5 mL) and 1M KOAc in H$_2$O (1.5 mL) were irradiated at 140° C. for 30 min. The reaction mixture was diluted with CH$_2$Cl$_2$, and filtered. The filtrate was concentrated to give 409 (17 mg) purified by reverse phase HPLC. MS (Q1) 358 (M)+

Example 323

(S)-2-(2-(2-aminopyrimidin-5-yl)-4-(3-methylmorpholino)thieno[3,2-d]pyrimidin-6-yl)propan-2-ol 410

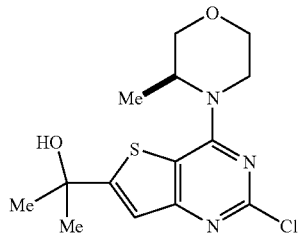 [SMILES: C[C@H]1COCCN1c1nc(Cl)nc2cc(C(C)(C)O)sc12]

(S)-4-(2-Chlorothieno[3,2-d]pyrimidin-4-yl)-3-methylmorpholine (150 mg, 0.56 mmol) in THF (6 mL) was treated with $^n$BuLi (0.40 mL, 2.5 M in hexanes, 1.0 mmol) then acetone (0.21 mL). (S)-2-(2-chloro-4-(3-methylmorpholino)thieno[3,2-d]pyrimidin-6-yl)propan-2-ol was purified by flash column chromatography (2:1 hexanes:EtOAc). MS (Q1) 328 (M)+.

(S)-2-(2-Chloro-4-(3-methylmorpholino)thieno[3,2-d]pyrimidin-6-yl)propan-2-ol (52 mg, 0.16 mmol), 2-aminopyrimidine-5-boronic acid pinacol ester (42 mg, 0.19 mmol), Pd(PPh$_3$)$_4$ (15 mg), MeCN (1 mL) and 1M KOAc in H$_2$O (1 mL) were irradiated at 140° C. for 30 min. The MeCN was removed by concentration and the mixture diluted with hexanes and water to precipitate the product which was isolated by filtration. Purification by reverse phase HPLC gave 410. (42 mg) MS (Q1) 387 (M)+

Example 324

(4-(2-(2-aminopyrimidin-5-yl)thieno[2,3-d]pyrimidin-4-yl)morpholin-2-yl)methanol 411

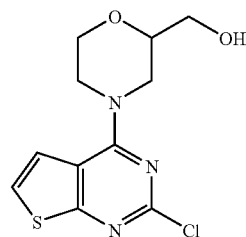 [SMILES: OCC1CN(c2nc(Cl)nc3sccc23)CCO1]

2-Hydroxymethylmorpholine (108 mg, 1.07 mmol, 1.1 eq), Et$_3$N (0.3 mL), 2,4-dichlorothieno[2,3-d]pyrimidine (200 mg, 0.98 mmol) in 5 mL of MeOH at room temperature for 1 h. The mixture was concentrated to dryness purified by silica-gel chromatography (5-20% MeOH in CH$_2$Cl$_2$ to give (4-(2-chlorothieno[2,3-d]pyrimidin-4-yl)morpholin-2-yl)methanol. MS (Q1) 286 (M)+

(4-(2-Chlorothieno[2,3-d]pyrimidin-4-yl)morpholin-2-yl)methanol was 2-aminopyrimidine-5-boronic acid pinacol ester, Pd(PPh$_3$)$_4$, MeCN and 1M KOAc in H$_2$O were irradiated at 140° C. for 30-60 min. The product was isolated by filtration and washed with H$_2$O. Purification by reverse-phase HPLC gave 411

Example 325

5-(4-(2-methylmorpholino)thieno[3,2-d]pyrimidin-2-yl)pyrimidin-2-amine 412

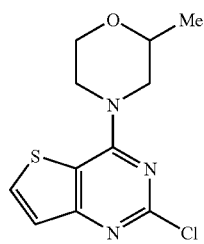 [SMILES: CC1CN(c2nc(Cl)nc3ccsc23)CCO1]

2-Methylmorpholine (135 mg, 1.34 mmol, 1.1 eq), Et$_3$N (0.34 mL, 3 eq), and 2,4-Dichlorothieno[2,3-d]pyrimidine (250 mg, 1.34 mmol) in 5 mL of MeOH at room temperature. Purification by silica-gel chromatography (10% MeOH in CH$_2$Cl$_2$) gave 4-(2-chlorothieno[3,2-d]pyrimidin-4-yl)-2-methylmorpholine (250 mg, 76% yield). MS (Q1) 270 (M)+

4-(2-Chlorothieno[3,2-d]pyrimidin-4-yl)-2-methylmorpholine (100 mg, 0.37 mmol), 2-aminopyrimidine-5-boronic acid pinacol ester (98 mg, 0.44 mmol), Pd(PPh$_3$)$_4$ (30 mg), MeCN (1.2 mL) and 1M KOAc in H$_2$O (1.2 mL) were irradiated at 140° C. for 30 min. The product was isolated by filtration and washed with H$_2$O. Purification by reverse-phase HPLC gave 412 (25 mg) MS (Q1) 328 (M)+.

Example 326

(4-(2-(2-aminopyrimidin-5-yl)thieno[3,2-d]pyrimidin-4-yl)morpholin-2-yl)methanol 413

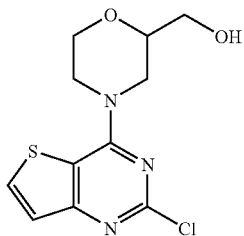 [SMILES: OCC1CN(c2nc(Cl)nc3ccsc23)CCO1]

2-Hydroxymethylmorpholine (126 mg, 1.07 mmol, 1.1 eq), Et$_3$N (0.3 mL), and 2,4-Dichlorothieno[2,3-d]pyrimidine (200 mg, 0.98 mmol) in 5 mL of MeOH at room temperature. Purification by silica-gel chromatography (5%-20% MeOH in CH$_2$Cl$_2$) gave (4-(2-chlorothieno[3,2-d]pyrimidin-4-yl)morpholin-2-yl)methanol. MS (Q1) 286 (M)+

(4-(2-Chlorothieno[3,2-d]pyrimidin-4-yl)morpholin-2-yl)methanol (95 mg, 0.33 mmol), 2-aminopyrimidine-5-boronic acid pinacol ester (88 mg, 0.39 mmol), Pd(PPh$_3$)$_4$ (38 mg), MeCN (1 mL) and 1M KOAc in H$_2$O (1 mL) were irradiated at 150° C. for 30 min. The product was isolated by filtration and washed with H$_2$O. Purification by reverse-phase HPLC gave 413 (25 mg) MS (Q1) 344 (M)+

Example 327

5-(7-(3-methoxyphenyl)-4-morpholinothieno[3,2-d]pyrimidin-2-yl)pyrimidin-2-amine 414

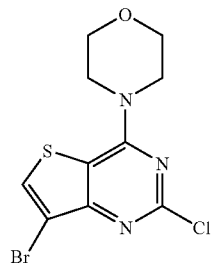 [SMILES: Clc1nc(N2CCOCC2)c2scc(Br)c2n1]

To a solution of thieno[3,2-d]pyrimidine-2,4(1H,3H)-dione (9 g, 54 mmol) in acetic acid (250 mL) at 80° C. was added bromine (10 mL) dropwise. The solution stirred at 80° C. for 4.5 h then was poured onto water. The resulting slurry was filtered to yield 7-bromothieno[3,2-d]pyrimidine-2,4 (1H,3H)-dione as a cream colored solid (5.5 g). To 7-bromothieno[3,2-d]pyrimidine-2,4(1H,3H)-dione (5.0 g) was added POCl$_3$ and the solution was heated at 110° C. for 72 h. After cooling to room temperature the solution was poured onto ice water and stirred for 20 min before filtering to yield 7-bromo-2,4-dichlorothieno[3,2-d]pyrimidine as a pale yellow solid (4 g). To a solution of 7-bromo-2,4-dichlorothieno[3,2-d]pyrimidine (4 g, 14 mmol) in methanol (65 mL) was added morpholine (3.1 mL, 36 mmol) and the reaction stirred 1 h at room temperature. The crude reaction mixture was concentrated in vacuo, diluted with water and filtered to yield 4-(7-bromo-2-chlorothieno[3,2-d]pyrimidin-4-yl)morpholine as a pale yellow solid (4 g). MS (Q1) 336 (M)+

A solution of 4-(7-bromo-2-chlorothieno[3,2-d]pyrimidin-4-yl)morpholine (210 mg, 0.6 mmol), 3-methoxyphenylboronic acid (0.6 mmol), and tetrakis(triphenylphosphine)palladium (72 mg) in 1.0 M aqueous sodium carbonate (2.5 mL) and acetonitrile (2.5 mL) was heated in a sealed microwave reactor at 100° C. for 15 min. After cooling, 5-(4,4,5,5-tetramethyl-1,3,2-dioxaborolan-2-yl)pyrimidin-2-amine (250 mg) was added and the reaction mixture was heated in a sealed microwave reactor at 150° C. for 12 min. The resulting mixture was concentrated in vacuo, the solid was rinsed with ethyl acetate, and the remaining solid was purified by reverse phase HPLC to afford 414 (64 mg). MS (Q1) 421 (M)+

Example 328

3-(2-(2-aminopyrimidin-5-yl)-4-morpholinothieno[3,2-d]pyrimidin-7-yl)-N,N-dimethylbenzamide 415

A solution of 4-(7-bromo-2-chlorothieno[3,2-d]pyrimidin-4-yl)morpholine (210 mg, 0.6 mmol), 3-carbamoylphenylboronic acid (0.6 mmol), and tetrakis(triphenylphosphine)palladium (72 mg) in 1.0 M aqueous sodium carbonate (2.5 mL) and acetonitrile (2.5 mL) was heated in a sealed microwave reactor at 100° C. for 15 min. After cooling, 5-(4,4,5,5-tetramethyl-1,3,2-dioxaborolan-2-yl)pyrimidin-2-amine (250 mg) was added and the reaction mixture was heated in a sealed microwave reactor at 150° C. for 12 min. The resulting mixture was concentrated in vacuo, the solid was rinsed with ethyl acetate, and the remaining solid was purified by reverse phase HPLC to afford 415 (32 mg). MS (Q1) 462 (M)+

Example 329

N-(3-(2-(2-aminopyrimidin-5-yl)-4-morpholinothieno[3,2-d]pyrimidin-7-yl)phenyl)acetamide 416

A solution of 4-(7-bromo-2-chlorothieno[3,2-d]pyrimidin-4-yl)morpholine (210 mg, 0.6 mmol), 3-acetamidophenylboronic acid (0.6 mmol), and tetrakis(triphenylphosphine)palladium (72 mg) in 1.0 M aqueous sodium carbonate (2.5 mL) and acetonitrile (2.5 mL) was heated in a sealed microwave reactor at 100° C. for 15 min. After cooling, 5-(4,4,5,5-tetramethyl-1,3,2-dioxaborolan-2-yl)pyrimidin-2-amine (250 mg) was added and the reaction mixture was heated in a sealed microwave reactor at 150° C. for 12 min. The resulting mixture was concentrated in vacuo, the solid was rinsed with ethyl acetate, and the remaining solid was purified by reverse phase HPLC to afford 416 (74 mg). MS (Q1) 448 (M)+

Example 330

5-(4-morpholino-7-(pyridin-4-yl)thieno[3,2-d]pyrimidin-2-yl)pyrimidin-2-amine 417

A solution of 4-(7-bromo-2-chlorothieno[3,2-d]pyrimidin-4-yl)morpholine (210 mg, 0.6 mmol), 4-pyridylboronic acid (0.6 mmol), and tetrakis(triphenylphosphine)palladium (72 mg) in 1.0 M aqueous sodium carbonate (2.5 mL) and acetonitrile (2.5 mL) was heated in a sealed microwave reactor at 100° C. for 15 min. After cooling, 5-(4,4,5,5-tetramethyl-1,3,2-dioxaborolan-2-yl)pyrimidin-2-amine (250 mg) was added and the reaction mixture was heated in a sealed microwave reactor at 150° C. for 12 min. The resulting mixture was concentrated in vacuo and the remaining solid was rinsed with ethyl acetate and the remaining solid was purified by reverse phase HPLC to afford 417 (16 mg). MS (Q1) 392 (M)+

Example 331

5-(4-(2H-benzo[b][1,4]oxazin-4(3H)-yl)thieno[3,2-d]pyrimidin-2-yl)pyrimidin-2-amine 418

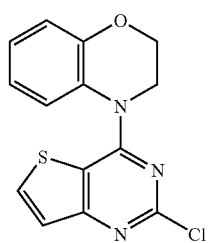 [SMILES: Clc1nc(N2CCOc3ccccc32)c2sccc2n1]

To a room temperature solution of 3,4-dihydro-2H-1,4-benzoxazine (218 mg, 1.61 mmol) in THF (3 mL) was added lithium hexamethyldisilamide (LHMDS, 1.9 mL, 1.0 M in THF, 1.9 mmol). After 5 min, the solution was cooled to −78° C. and treated with a solution of 2,4-dichlorothieno[2,3-d]pyrimidine (300 mg, 1.46 mmol) in THF (3 mL). The reaction mixture was allowed to slowly reach room temperature overnight. The mixture was diluted with water and the organics removed by concentration. The remaining was extracted with EtOAc and the combined organics washed with brine, dried over $Na_2SO_4$ and concentrated to give a residue that was purified by silica-gel chromatography (10%-40% EtOAc in hexanes) to give 4-(2-chlorothieno[3,2-d]pyrimidin-4-yl)-3,4-dihydro-2H-benzo[b][1,4]oxazine as a yellow solid (166 mg, 37%). MS (Q1) 304 (M)+

4-(2-Chlorothieno[3,2-d]pyrimidin-4-yl)-3,4-dihydro-2H-benzo[b][1,4]oxazine (122 mg, 0.40 mmol), 2-aminopyrimidine-5-boronic acid pinacol ester (107 mg), $Pd(PPh_3)_4$ (6 mg), MeCN (1.5 mL) and 1M KOAc in $H_2O$ (1.5 mL) were irradiated at 150° C. for 30 min. The product was isolated by filtration and washed with $H_2O$. Purification by reverse-phase HPLC gave 418 (7 mg) MS (Q1) 362 (M)+

Example 332

(S)-5-(4-(3-methylmorpholino)thieno[3,2-d]pyrimidin-2-yl)pyrimidin-2-amine 419

(S)-4-(2-Chlorothieno[3,2-d]pyrimidin-4-yl)-3-methylmorpholine (130 mg, 0.48 mmol), 2-aminopyrimidine-5-boronic acid pinacol ester (127 mg, 0.58 mmol), $Pd(PPh_3)_4$ (6 mg), MeCN (1.2 mL) and 1M KOAc in $H_2O$ (1.2 mL) were irradiated at 150° C. for 30 min. The MeCN was removed by concentration and the mixture diluted with hexanes and water to precipitate the product which was isolated by filtration. Purification by reverse phase HPLC gave 419 (119 mg). MS (Q1) 328 (M)+.

Example 333

5,5'-(4-morpholinothieno[3,2-d]pyrimidine-2,7-diyl)dipyrimidin-2-amine 420

A solution of 4-(7-bromo-2-chlorothieno[3,2-d]pyrimidin-4-yl)morpholine (210 mg, 0.6 mmol), (4,4,5,5-tetramethyl-1,3,2-dioxaborolan-2-yl)pyrimidin-2-amine (500 mg), and tetrakis(triphenylphosphine)palladium (72 mg) in 1.0 M aqueous sodium carbonate (2.5 mL) and acetonitrile (2.5 mL) was heated in a sealed microwave reactor at 150° C. for 30 min. The resulting mixture was concentrated in vacuo and the remaining solid was rinsed with ethyl acetate and then purified by reverse phase HPLC to afford 420 (24 mg). MS (Q1) 408 (M)+

Example 334

5-(6-methyl-4-morpholino-2-(thiophen-2-yl)thieno[3,2-d]pyrimidin-7-yl)pyrimidin-2-amine 421

To a suspension of 2-chloro-4-morpholin-4-yl-thieno[3,2-d]pyrimidine (955 mg, 3.7 mmol) in anhydrous THF (30 ml) at −78° C., n-butyllithium (2.5 M in hexanes, 1.8 ml, 4.5 mmol, 1.2 eq) was added and the reaction stirred at −78° C. for 1 hr. Iodomethane was then added and the reaction allowed to warm to room temperature overnight. Water carefully added before extracting into ethyl acetate (30 ml), washing with water (2×20 ml), and the organic layer dried over $MgSO_4$ and evaporated in vacuo to yield 2-chloro-6-methyl-4-morpholin-4-yl-thieno[3,2-d]pyrimidine.

2-Chloro-6-methyl-4-morpholin-4-yl-thieno[3,2-d]pyrimidine (640 mg, 2.4 mmol) was suspended in glacial acetic acid (10 ml), bromine added (430 ul, 8.3 mmol, 3.5 eq) and heated at 80° C. for 4 hrs. Reaction cooled and water added, solid sonicated, filtered and dried to give 2,7-dibromo-6- methyl-4-morpholin-4-yl-thieno[3,2-d]pyrimidine (600 mg, 63% yield). Product confirmed by M/z.

2,7-Dibromo-6-methyl-4-morpholin-4-yl-thieno[3,2-d]pyrimidine was reacted with 2-thiopheneboronic acid and according to General Procedure A to yield 7-bromo-6-methyl-4-morpholin-4-yl-2-thiophen-2-yl-thieno[3,2-d]pyrimidine. NOE confirmed position of the thiophene ring.

7-Bromo-6-methyl-4-morpholin-4-yl-2-thiophen-2-yl-thieno[3,2-d]pyrimidine was reacted with 5-(4,4,5,5-tetramethyl-[1,3,2]dioxaborolan-2-yl)-pyrimidin-2-ylamine according to General Procedure A. The resulting solid was triturated with diethylether and methanol to give 421 as a solid (18% yield). NMR (CDCl3, 400 MHz), 2.56 (3H, s), 3.82 (4H, t, J=4.8), 3.94 (4H, t, J=4.8), 5.05 (2H, s), 7.01-7.04 (1H, m), 7.36-7.38 (1H, m), 7.84-7.88 (1H, m), 8.54 (2H, s). MS: (ESI+): MH+=411

Example 335

5-(7-(3-(dimethylamino)prop-1-ynyl)-4-morpholinothieno[3,2-d]pyrimidin-2-yl)pyrimidin-2-amine 422

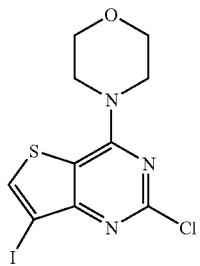

To a solution of thieno[3,2-d]pyrimidine-2,4(1H,3H)-dione (7 g, 42 mmol) in carbon tetrachloride (150 mL) was added bis(trifluoroacetoxy)iodobenzene (21.7 g, 50 mmol) and iodine (26 g, 100 mmol). The resulting solution stirred overnight then was concentrated in vacuo. The resulting solid was filtered and washed with water and diethyl ether to yield 7-iodothieno[3,2-d]pyrimidine-2,4(1H,3H)-dione as a pale yellow solid (6 g). To 7-iodothieno[3,2-d]pyrimidine-2,4(1H,3H)-dione (6 g) was added POCl₃ and the solution was heated at 110° C. overnight. After cooling to room temperature the solution was poured onto ice water and stirred for 20 min before filtering to yield 2,4-dichloro-7-iodothieno[3,2-d]pyrimidine as a pale yellow solid (5 g). To a solution of 2,4-dichloro-7-iodothieno[3,2-d]pyrimidine (5 g) in methanol (70 mL) was added morpholine (11 mL) and the reaction stirred 1 h at room temperature. The crude reaction mixture was concentrated in vacuo, diluted with water and filtered to yield 4-(2-chloro-7-iodothieno[3,2-d]pyrimidin-4-yl)morpholine as a pale yellow solid (3 g). MS (Q1) 382 (M)+

To a degassed solution of diisopropylamine (7 mL) containing 4-(2-chloro-7-iodothieno[3,2-d]pyrimidin-4-yl)morpholine (0.2 mmol) at 0° C. was added CuI (0.02 mmol), N,N-dimethylprop-2-yn-1-amine (0.24 mmol), and tetrakis(triphenylphosphine)palladium (0.04 mmol). The resulting solution was warmed to room temperature and stirred 2 h. The reaction mixture was concentrated in vacuo then dissolved in CH₂Cl₂ and washed with 1 M HCl and water. The organic layer was concentrated in vacuo. The crude intermediate was utilized in a Suzuki coupling with (4,4,5,5-tetramethyl-1,3,2-dioxaborolan-2-yl)pyrimidin-2-amine according to General Procedure Suzuki to yield 422 (8 mg) after purification by reverse phase HPLC. MS (Q1) 396 (M)+

Example 336

5-(7-(3-(methylamino)prop-1-ynyl)-4-morpholinothieno[3,2-d]pyrimidin-2-yl)pyrimidin-2-amine 423

To a degassed solution of diisopropyl amine (7 mL) containing 4-(2-chloro-7-iodothieno[3,2-d]pyrimidin-4-yl)morpholine (0.2 mmol) at 0° C. was added CuI (0.02 mmol), N-methylprop-2-yn-1-amine (0.24 mmol), and tetrakis(triphenylphosphine)palladium (0.04 mmol). The resulting solution was warmed to room temperature and stirred overnight. The reaction mixture was concentrated in vacuo then dissolved in CH₂Cl₂ and washed with 1 M HCl and water. The organic layer was concentrated in vacuo. The crude intermediate was utilized in a Suzuki coupling with (4,4,5,5-tetramethyl-1,3,2-dioxaborolan-2-yl)pyrimidin-2-amine according to General Procedure Suzuki to yield 423 (17 mg) after purification by reverse phase HPLC. MS (Q1) 382 (M)+

Example 337

5-(4-morpholino-7-phenylthieno[3,2-d]pyrimidin-2-yl)pyrimidin-2-amine 424

1H-Thieno[3,2-d]pyrimidine-2,4-dione (3 g, 18 mmol) was suspended in glacial acetic acid (90 ml) and heated to 80° C. before bromine (10.80 g, 3.23 ml, 63 mmol) was added dropwise. The reaction mixture was heated at 80° C. for a further 4 hours before pouring into water (~1 L) and the white precipitate collected and dried to yield 7-bromo-1H-thieno[3,2-d]pyrimidine-2,4-dione (3.92 g, 88%).

7-Bromo-1H-thieno[3,2-d]pyrimidine-2,4-dione (3.92 g, 15.87 mmol) was suspended in neat phosphorous oxychloride (50 ml) and refluxed overnight. The cooled reaction solution was poured into vigorously stirring ice-water before extracting into DCM. The organic layer was dried over MgSO₄, filtered and evaporated to give 7-bromo-2,4-dichloro-thieno[3,2-d]pyrimidine (4.11 g, 91%).

7-Bromo-2,4-dichloro-thieno[3,2-d]pyrimidine (4.10 g, 14.44 mmol) was suspended in methanol (100 ml), to this morpholine (3.15 ml, 36.10 mmol) was added and stirred at room temperature for 5 hours. Water was added to the solution and the resulting white precipitate filtered and dried (4.11 g, 85%) to yield 7-bromo-2-chloro-4-morpholin-4-yl-thieno[3,2-d]pyrimidine.

2-Chloro-4-morpholin-4-yl-7-phenyl-thieno[3,2-d]pyrimidine was made by reacting 7-bromo-2-chloro-4-morpholin-4-yl-thieno[3,2-d]pyrimidine and phenylboronic acid according to the General Procedure A. LCMS confirmed reaction at the bromine. MS: (ESI+): MH+=332

Reacting 2-chloro-4-morpholin-4-yl-7-phenyl-thieno[3,2-d]pyrimidine and 5-(4,4,5,5-tetramethyl-[1,3,2]dioxaborolan-2-yl)-pyrimidin-2-ylamine according to General Procedure A gave 424. NMR (CDCl₃, 400 MHz), 3.84 (4H, t, J=4.4), 4.02 (4H, t, J=4.4), 5.12 (2H, s), 7.33 (1H, 7.2), 7.43 (2H, t, J=8.0), 7.77 (1H, s), 7.97 (2H, d, J=7.2), 9.27 (2H, s). MS: (ESI+): MH+=391

Example 338

4-methyl-5-(7-methyl-4-morpholinothieno[3,2-d]pyrimidin-2-yl)pyrimidin-2-amine 425

2-Chloro-7-methyl-4-morpholin-4-yl-thieno[3,2-d]pyrimidine (80 mg) was coupled to 4-methyl-5-(4,4,5,5-tetramethyl-[1,3,2]dioxaborolan-2-yl)-pyrimidin-2-ylamine via General Procedure A to yield 79 mg of 425. MS (Q1) 343.1 (M)$^+$.

Example 339

4-methyl-5-(4-morpholinothieno[3,2-d]pyrimidin-2-yl)pyrimidin-2-amine 426

2-Chloro-4-morpholin-4-yl-thieno[3,2-d]pyrimidine (70 mg) was coupled to 4-Methyl-5-(4,4,5,5-tetramethyl-[1,3,2]dioxaborolan-2-yl)-pyrimidin-2-ylamine via General Procedure A to yield 51.2 mg of 426. MS (Q1) 329.1 (M)$^+$.

Example 340

N-((2-(2-amino-4-methylpyrimidin-5-yl)-4-morpholinothieno[3,2-d]pyrimidin-6-yl)methyl)-N-methylmethanesulfonamide 427

(2-Chloro-4-morpholin-4-yl-thieno[3,2-d]pyrimidin-6-ylmethyl)-methylamine and methanesulfonyl chloride with triethylamine in dichloromethane were reacted via General Procedure C-2 to give N-(2-Chloro-4-morpholin-4-yl-thieno[3,2-d]pyrimidin-6-ylmethyl)-N-methyl-methanesulfonamide.

N-(2-Chloro-4-morpholin-4-yl-thieno[3,2-d]pyrimidin-6-ylmethyl)-N-methyl-methanesulfonamide (74 mg) was coupled to 4-methyl-5-(4,4,5,5-tetramethyl-[1,3,2]dioxaborolan-2-yl)-pyrimidin-2-ylamine via General Procedure A to yield 18 mg of 427. MS (Q1) 450.2 (M)$^+$.

Example 341

N-((2-(2-amino-4-methylpyrimidin-5-yl)-4-morpholinothieno[3,2-d]pyrimidin-6-yl)methyl)-N-methylacetamide 428

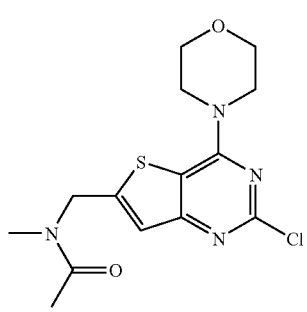 [SMILES: CC(=O)N(C)Cc1cc2nc(Cl)nc(N3CCOCC3)c2s1]

N-(2-Chloro-4-morpholin-4-yl-thieno[3,2-d]pyrimidin-6-ylmethyl)-N-methyl-acetamide (80 mg) was coupled to 4-methyl-5-(4,4,5,5-tetramethyl-[1,3,2]dioxaborolan-2-yl)-pyrimidin-2-ylamine via General Procedure A to yield 11 mg of 428. MS (Q1) 414.2 (M)$^+$.

Example 342

429

2-(2-Chloro-4-morpholin-4-yl-thieno[3,2-d]pyrimidin-6-yl)-propan-2-ol from Example 254 (80 mg) was coupled to 4-methyl-5-(4,4,5,5-tetramethyl-[1,3,2]dioxaborolan-2-yl)-pyrimidin-2-ylamine via General Procedure A to yield 15 mg of 429. MS (Q1) 387.2 (M)$^+$.

Example 343

5-(6-(3-methoxyoxetan-3-yl)-4-morpholinothieno[3,2-d]pyrimidin-2-yl)-N-methylpyridin-2-amine 430

4-(2-Chloro-6-(3-methoxyoxetan-3-yl)thieno[3,2-d]pyrimidin-4-yl)morpholine (74 mg) was reacted with 110 mg of tert-butyl methyl (5-(4,4,5,5-tetramethyl-1,3,2-dioxaborolan-2-yl)pyridin-2-yl)carbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 20.7 mg of 430. MS (Q1) 414.2 (M)+.

Example 344

5-(6-(3-methoxyoxetan-3-yl)-4-morpholinothieno[3,2-d]pyrimidin-2-yl)-N-methylpyrimidin-2-amine 431

4-(2-Chloro-6-(3-methoxyoxetan-3-yl)thieno[3,2-d]pyrimidin-4-yl)morpholine (74 mg) was reacted with 82 mg of tert-butyl methyl5-(4,4,5,5-tetramethyl-1,3,2-dioxaborolan-2-yl)pyrimidin-2-ylcarbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 18.5 mg of 431. MS (Q1) 415.2 (M)+

Example 345

5-(6-(3-methoxyoxetan-3-yl)-4-morpholinothieno[3,2-d]pyrimidin-2-yl)pyrimidin-2-amine 432

3-(2-Chloro-4-morpholinothieno[3,2-d]pyrimidin-6-yl)oxetan-3-ol (221 mg, 1 eq) in 5 mL DMF was cooled to 0° C. and added NaH (1.1 eq); the reaction was subsequently stirred for 10 minutes. Methyl iodide (1.5 eq) was added and the reaction mixture was stirred and monitored by LCMS/TLC until complete. Ethyl acetate was added and the reaction mixture was extracted with bicarbonate solution. The organic layer was dried, filtered and concentrated to give 221 mg crude 4-(2-chloro-6-(3-methoxyoxetan-3-yl)thieno[3,2-d]pyrimidin-4-yl)morpholine.

4-(2-Chloro-6-(3-methoxyoxetan-3-yl)thieno[3,2-d]pyrimidin-4-yl)morpholine (74 mg) was reacted with 72 mg of 5-(4,4,5,5-tetramethyl-1,3,2-dioxaborolan-2-yl)pyrimidin-2-amine via General Procedure A. The product was subsequently purified by reverse phase HPLC to give 16.9 mg of 432. MS (Q1) 401.2 (M)+

Example 346

N-methyl-5-(6-(3-(methylsulfonyl)phenyl)-4-morpholinothieno[3,2-d]pyrimidin-2-yl)pyridin-2-amine 433

2-Chloro-6-iodo-4-morpholin-4-yl-thieno[3,2-d]pyrimidine (500 mg) was reacted with 288 mg of 3-methylsulfonylphenylboronic acid via General Procedure A to yield 445 mg of 2-Chloro-6-(3-methanesulfonyl-phenyl)-4-morpholin-4-yl-thieno[3,2-d]pyrimidine.

2-Chloro-6-(3-methanesulfonyl-phenyl)-4-morpholin-4-yl-thieno[3,2-d]pyrimidine (90 mg) was reacted with 110 mg of N-Boc-aminomethylpyridine boronate ester via General Procedure A to yield 100 mg of {5-[6-(3-methanesulfonyl-phenyl)-4-morpholin-4-yl-thieno[3,2-d]pyrimidin-2-yl]-pyridin-2-yl}-methyl-carbamic acid tert-butyl ester. A mixture of 100 mg of {5-[6-(3-methanesulfonyl-phenyl)-4-morpholin-4-yl-thieno[3,2-d]pyrimidin-2-yl]-pyridin-2-yl}-methyl-carbamic acid tert-butyl ester in 1 mL of trifluoroacetic acid and 1 mL of DCM was stirred for 1 h. The reaction mixture was concentrated. The product was purified by reverse phase HPLC to yield 65.2 mg of 433. MS (Q1) 482.2 (M)$^+$.

Example 347

3-(2-(2-aminopyrimidin-5-yl)-4-morpholinothieno[2,3-d]pyrimidin-6-yl)oxetan-3-ol 434

4-(2,6-Dichlorothieno[2,3-d]pyrimidin-4-yl)morpholine (450 mg) was cooled to −50° C. in THF. 1.1 mL of a solution of 2.5M n-BuLi in THF was added dropwise to solution and stirred for 30 minutes at −50° C. 0.25 mL of oxetan-3-one was added via syringe and the reaction was stirred for one hour, slowly warming to 0° C. The reaction mixture was quenched with water then extracted with ethyl acetate. The product was purified by 12 g Isco column with 0-60% gradient over 30 mins. Clean fractions were collected and concentrated to get 180 mg 3-(2-chloro-4-morpholinothieno[2,3-d]pyrimidin-6-yl)oxetan-3-ol as yellow solid.

3-(2-Chloro-4-morpholinothieno[2,3-d]pyrimidin-6-yl)oxetan-3-ol (50 mg) was reacted with 47 mg 5-(4,4,5,5-tetramethyl-1,3,2-dioxaborolan-2-yl)pyrimidin-2-amine via General Procedure A. The product was subsequently purified by reverse phase HPLC to give 24.5 mg of 434. MS (Q1) 387.2 (M)+

Example 348

5-(6-(2-methoxypropan-2-yl)-4-morpholinothieno[2,3-d]pyrimidin-2-yl)-N-methylpyridine-2-amine 435

4-(2-Chloro-6-(2-methoxypropan-2-yl)thieno[2,3-d]pyrimidin-4-yl)morpholine (70 mg) was reacted with 110 mg tert-butyl methyl (5-(4,4,5,5-tetramethyl-1,3,2-dioxaborolan-2-yl)pyridin-2-yl)carbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 12.3 mg of 435. MS (Q1) 400.2 (M)+

Example 349

5-(6-(2-methoxypropan-2-yl)-4-morpholinothieno[2,3-d]pyrimidin-2-yl)-N-methylpyrimidin-2-amine 436

4-(2-Chloro-6-(2-methoxypropan-2-yl)thieno[2,3-d]pyrimidin-4-yl)morpholine (70 mg) was reacted with 81 mg tert-butyl methyl5-(4,4,5,5-tetramethyl-1,3,2-dioxaborolan-2-yl)pyrimidin-2-ylcarbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 29.4 mg of 436. MS (Q1) 401.2 (M)+

Example 350

5-(6-(2-methoxypropan-2-yl)-4-morpholinothieno[2,3-d]pyrimidin-2-yl)pyrimidin-2-amine 437

2-(2-Chloro-4-morpholinothieno[2,3-d]pyrimidin-6-yl)propan-2-ol (200 mg, 1 eq) in 5 mL DMF was cooled to 0° C. and added NaH (1.1 eq); the reaction was subsequently stirred for 10 minutes. Methyl iodide (1.5 eq) was added and the reaction mixture was stirred and monitored by LCMS/TLC until complete. Ethyl acetate was added and the reaction mixture was extracted with bicarbonate solution. The organic layer was dried, filtered and concentrated to give 200 mg crude 4-(2-chloro-6-(2-methoxypropan-2-yl)thieno[2,3-d]pyrimidin-4-yl)morpholine.

4-(2-Chloro-6-(2-methoxypropan-2-yl)thieno[2,3-d]pyrimidin-4-yl)morpholine (70 mg) was reacted with 71 mg 5-(4,4,5,5-tetramethyl-1,3,2-dioxaborolan-2-yl)pyrimidin-2-amine via General Procedure A. The product was subsequently purified by reverse phase HPLC to give 16 mg of 437. MS (Q1) 387.2 (M)+

Example 351

N-methyl-5-(6-(3-(methylsulfonyl)phenyl)-4-morpholinothieno[2,3-d]pyrimidin-2-yl)pyridin-2-amine 438

2-Chloro-6-iodo-4-morpholin-4-yl-thieno[2,3-d]pyrimidine (500 mg) was reacted with 288 mg of 3-methylsulfonylphenylboronic acid via General Procedure A to yield 500 mg of 2-Chloro-6-(3-methanesulfonyl-phenyl)-4-morpholin-4-yl-thieno[2,3-d]pyrimidine.

2-Chloro-6-(3-methanesulfonyl-phenyl)-4-morpholin-4-yl-thieno[2,3-d]pyrimidine (100 mg) was reacted with 98 mg of N-Boc-aminomethylpyridine boronate ester via General Procedure A to yield 110 mg of {5-[6-(3-Methanesulfonyl-phenyl)-4-morpholin-4-yl-thieno[2,3-d]pyrimidin-2-yl]-pyridin-2-yl}-methyl-carbamic acid tert-butyl ester.

A mixture of 110 mg of {5-[6-(3-Methanesulfonyl-phenyl)-4-morpholin-4-yl-thieno[2,3-d]pyrimidin-2-yl]-pyridin-2-yl}-methyl-carbamic acid tert-butyl ester in 1 mL of trifluoroacetic acid and 1 mL of DCM was stirred for 1 h. The reaction mixture was concentrated. The product was purified by reverse phase HPLC to yield 74 mg of 438. MS (Q1) 482.2 (M)$^+$.

Example 352

N-methyl-5-(7-methyl-6-(3-(methylsulfonyl)phenyl)-4-morpholinothieno[3,2-d]pyrimidin-2-yl)pyridin-2-amine 439

2-Chloro-6-iodo-7-methyl-4-morpholin-4-yl-thieno[3,2-d]pyrimidine (500 mg) was reacted with 290 mg of 3-methylsulfonylphenylboronic acid to yield 500 mg of 2-chloro-6-(3-methanesulfonyl-phenyl)-7-methyl-4-morpholin-4-yl-thieno[3,2-d]pyrimidine.

2-Chloro-6-(3-methanesulfonyl-phenyl)-7-methyl-4-morpholin-4-yl-thieno[3,2-d]pyrimidine (100 mg) was reacted with 98 mg of N-Boc-aminomethylpyridine boronate ester via General Procedure A to yield 100 mg of {5-[6-(3-methanesulfonyl-phenyl)-7-methyl-4-morpholin-4-yl-thieno[3,2-d]pyrimidin-2-yl]-pyridin-2-yl}-methyl-carbamic acid tert-butyl ester.

A mixture of 100 mg of {5-[6-(3-methanesulfonyl-phenyl)-7-methyl-4-morpholin-4-yl-thieno[3,2-d]pyrimidin-2-yl]-pyridin-2-yl}-methyl-carbamic acid tert-butyl ester in 1 mL of trifluoroacetic acid and 1 mL of DCM was stirred for 1 h. The reaction mixture was concentrated. The product was purified by reverse phase HPLC to yield 83 mg of 439. MS (Q1) 496.2 (M)+

Example 353

2-(2-(6-(methylamino)pyridin-3-yl)-4-morpholinothieno[3,2-d]pyrimidin-6-yl)propan-2-ol 440

2-(2-Chloro-4-morpholinothieno[3,2-d]pyrimidin-6-yl)propan-2-ol (75 mg) was reacted with 120 mg tert-butyl methyl(5-(4,4,5,5-tetramethyl-1,3,2-dioxaborolan-2-yl)pyridin-2-yl)carbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 62.3 mg of 440. MS (Q1) 386.2 (M)+

Example 354

N-((2-(2-aminopyrimidin-5-yl)-4-morpholinothieno[2,3-d]pyrimidin-6-yl)methyl)-N-(2-hydroxyethyl)methanesulfonamide 441

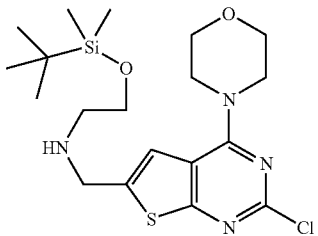 [SMILES: CC(C)(C)[Si](C)(C)OCCNCc1cc2c(N3CCOCC3)nc(Cl)nc2s1]

2-Chloro-4-morpholinothieno[2,3-d]pyrimidine-6-carbaldehyde, and 1-tert-butyldimethylsilyl 2-bromoethanol were reacted in General Procedure B-3 by reductive amination to give 2-(tert-butyldimethylsilyloxy)-N-((2-chloro-4-morpholinothieno[2,3-d]pyrimidin-6-yl)methyl)ethanamine which was sulfonated with methanesulfonyl chloride according to General Procedure C-2 to give N-(2-(tert-butyldimethylsilyloxy)ethyl)-N-((2-chloro-4-morpholinothieno[2,3-d]pyrimidin-6-yl)methyl)methanesulfonamide.

N-(2-(tert-Butyldimethylsilyloxy)ethyl)-N-((2-chloro-4-morpholinothieno[2,3-d]pyrimidin-6-yl)methyl)methanesulfonamide and 2-aminopyrimidine-5-boronic acid, pinacol ester were used in General procedure A by Suzuki coupling to produce 441 in 65% yield after RP-HPLC purification. MS (Q1) 466.2 (M)+, purity 100% by UV 254 nm, 1H NMR (DMSO)

Example 355

N-methyl-N-((2-(2-(methylamino)pyrimidin-5-yl)-4-morpholinothieno[2,3-d]pyrimidin-6-yl)methyl)methanesulfonamide 442

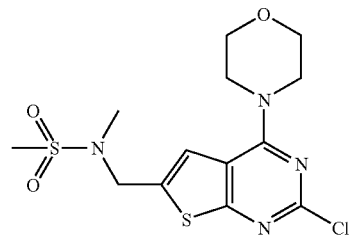 [SMILES: CN(Cc1cc2c(N3CCOCC3)nc(Cl)nc2s1)S(C)(=O)=O]

2-Chloro-4-morpholinothieno[2,3-d]pyrimidine-6-carbaldehyde and methylamine were reacted in General Procedure B-3 by reductive amination and sulfonated with methanesulfonyl chloride according to General Procedure C-2 to give N-((2-chloro-4-morpholinothieno[2,3-d]pyrimidin-6-yl)methyl)-N-methylmethanesulfonamide.

N-((2-chloro-4-morpholinothieno[2,3-d]pyrimidin-6-yl)methyl)-N-methylmethanesulfonamide and 2-N-methyl-aminopyridine 5-boronic acid were used in General procedure A Suzuki Coupling to produce 442 in 65% yield after RP-HPLC purification. MS (Q1) 450.2 (M)+, purity 100% by UV 254 nm, 1H NMR (DMSO).

Example 356

N-methyl-5-(6-(3-(methylsulfonyl)phenyl)-4-morpholinothieno[2,3-d]pyrimidin-2-yl)pyrimidin-2-amine 443

Methyl iodide (390 μL, 6.2 mmol) was added to a mixture of 2-(tert-butoxycarbonylamino)pyrimidine-5-boronic acid pinacol ester (1.0 g, 3 mmol) and cesium carbonate (2.0 g, 6.2 mmol) in N,N-Dimethylformamide (15 mL). The reaction mixture was stirred at room temperature for 1 h. Water (20 mL) was added. The mixture was neutralized to pH=7 using 1N HCl, then extracted with ethyl acetate (3×60 mL). The combined organic layers were dried over magnesium sulfate, filtered and evaporated to yield 560 mg of 2-(tert-butoxycarbonylamino)methylpyrimidine-5-boronic acid. 2-Chloro-6-(3-methanesulfonyl-phenyl)-4-morpholin-4-yl-thieno[2,3-d]pyrimidine (100 mg) was reacted with 100 mg of 2-(tert-butoxycarbonylamino)methylpyrimidine-5-boronic acid via General Procedure A. The product was purified by reverse phase HPLC to yield 39.7 mg of 443. MS (Q1) 483.2 (M)+

Example 357

2-(2-(2-(methylamino)pyrimidin-5-yl)-4-morpholinothieno[2,3-d]pyrimidin-6-yl)propan-2-ol 444

2-(2-Chloro-4-morpholinothieno[2,3-d]pyrimidin-6-yl)propan-2-ol (70 mg) was reacted with 73 mg tert-butyl methyl5-(4,4,5,5-tetramethyl-1,3,2-dioxaborolan-2-yl)pyrimidin-2-ylcarbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 20.6 mg of 444. MS (Q1) 387.3 (M)+.

Example 358

3-(2-(2-aminopyrimidin-5-yl)-4-morpholinothieno[3,2-d]pyrimidin-6-yl)oxetan-3-ol 445

Following the General Procedures herein, 445 was prepared. MS (Q1) 387.2 (M)+.

Example 359

5-(6-(2-Methoxypropan-2-yl)-4-morpholinothieno[3,2-d]pyrimidin-2-yl)-N-methylpyrimidin-2-amine 446

4-(2-Chloro-6-(2-methoxypropan-2-yl)thieno[3,2-d]pyrimidin-4-yl)morpholine (125 mg) was reacted with 125 mg tert-butyl methyl5-(4,4,5,5-tetramethyl-1,3,2-dioxaborolan-2-yl)pyrimidin-2-ylcarbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 104 mg of 446. MS (Q1) 401.2 (M)+

Example 360

5-(6-(2-Methoxypropan-2-yl)-4-morpholinothieno[3,2-d]pyrimidin-2-yl)pyrimidin-2-amine 447

2-(2-Chloro-4-morpholinothieno[3,2-d]pyrimidin-6-yl)propan-2-ol (250 mg, 1 eq) in 5 mL DMF was cooled to 0° C. and added NaH (1.1 eq); the reaction was subsequently stirred for 10 minutes. Methyl iodide (1.5 eq) was added and the reaction mixture was stirred and monitored by LCMS/TLC until complete. Ethyl acetate was added and the reaction mixture was extracted with bicarbonate sol'n. The organic layer was dried, filtered and concentrated to give 250 mg crude 4-(2-chloro-6-(2-methoxypropan-2-yl)thieno[3,2-d]pyrimidin-4-yl)morpholine.

4-(2-Chloro-6-(2-methoxypropan-2-yl)thieno[3,2-d]pyrimidin-4-yl)morpholine (125 mg) was then reacted with 110 mg 5-(4,4,5,5-tetramethyl-1,3,2-dioxaborolan-2-yl)pyrimidin-2-amine via General Procedure A. The product was subsequently purified by reverse phase HPLC to give 21.8 mg of 447. MS (Q1) 387.2 (M)+.

Example 361

(3-(2-(2-aminopyrimidin-5-yl)-4-morpholinothieno[2,3-d]pyrimidin-6-yl)phenyl)(4-methylpiperazin-1-yl)methanone 448

2-Chloro-6-iodo-4-morpholin-4-yl-thieno[2,3-d]pyrimidine (500 mg) was reacted with 240 mg of 3-methylsulfonylphenylboronic acid via General Procedure A to yield 490 mg of 3-(2-Chloro-4-morpholin-4-yl-thieno[2,3-d]pyrimidin-6-yl)-benzoic acid.

3-(2-Chloro-4-morpholin-4-yl-thieno[2,3-d]pyrimidin-6-yl)-benzoic acid (250 mg) was reacted with 1-methylpiperazine via General Procedure C to yield 300 mg of [3-(2-Chloro-4-morpholin-4-yl-thieno[2,3-d]pyrimidin-6-yl)-phenyl]-(4-methyl-piperazin-1-yl)-methanone.

[3-(2-Chloro-4-morpholin-4-yl-thieno[2,3-d]pyrimidin-6-yl)-phenyl]-(4-methyl-piperazin-1-yl)-methanone (150 mg) was coupled to 87 mg of 2-aminopyrimidine-5-boronic acid pinacol ester via General Procedure A. The product was purified by reverse phase HPLC to yield 38.8 mg of 448. MS (Q1) 517.3 (M)$^+$

Example 362

2-(2-(2-methoxypyrimidin-5-yl)-4-morpholinothieno[2,3-d]pyrimidin-6-yl)propan-2-ol 449

To 2-Chloro-4-morpholin-4-yl-thieno[2,3-d]pyrimidine (1.095 g) in dry THF (20 mL) cooled to −78° C. was added nBuLi (2.5M solution in hexanes, 2.06 mL). After 2 hours, acetone (0.47 mL) was added and the reaction mixture was slowly warmed to room temperature. The reaction mixture was then poured onto water and the resulting precipitate was collected by filtration to yield 2-(2-chloro-4-morpholin-4-yl-thieno[2,3-d]pyrimidin-6-yl)-propan-2-ol.

2-(2-Chloro-4-morpholin-4-yl-thieno[2,3-d]pyrimidin-6-yl)-propan-2-ol was reacted with 2-methoxy-5-pyrimidine boronic acid in General Procedure A. Purification on silica yielded 449. 400 MHz 1H NMR CDCl$_3$: 9.47 (s, 2H); 7.17 (s, 1H); 4.12 (s, 3H); 3.98 (t, 4H, J=4.3 Hz); 3.90 (t, 4H, J=4.3 Hz); 2.23 (s, 1H); 1.75 (s, 6H); LC-MS (m+1)=388.07

Example 363

5-(6-((methyl(2-(methylsulfonyl)ethyl)amino)methyl)-4-morpholinothieno[3,2-d]pyrimidin-2-yl)pyrimidin-2-amine 450

Reaction between 2-chloro-4-morpholin-4-yl-thieno[3,2-d]pyrimidine-6-carbaldehyde 10 and methylamine in MeOH with subsequent reduction with sodium borohydride yielded (2-chloro-4-morpholin-4-yl-thieno[3,2-d]pyrimidin-6-ylmethyl)-methylamine.

(2-Chloro-4-morpholin-4-yl-thieno[3,2-d]pyrimidin-6-ylmethyl)-methylamine was refluxed with methyl vinyl sulfone (1.1 equiv.) in MeOH for 4 hours to give (2-chloro-4-morpholin-4-yl-thieno[3,2-d]pyrimidin-6-ylmethyl)-(2-methanesulfonylethyl)-methylamine.

(2-Chloro-4-morpholin-4-yl-thieno[3,2-d]pyrimidin-6-ylmethyl)-(2-methanesulfonyl ethyl)-methylamine was reacted with 5-(4,4,5,5-tetramethyl-[1,3,2]dioxaborolan-2-yl)-pyridin-2-ylamine in General Procedure A. Purification on silica yielded 450. (CDCl$_3$): 2.39 (3H, s), 3.05 (3H, s), 3.09 (2H, t), 3.24 (2H, t), 3.89-3.92 (4H, m), 3.93 (2H, s), 4.03-4.07 (4H, m), 5.22 (2H, br, NH2), 7.31 (1H, s), 9.30 (2H, s). (ESI+): MH+ 464.09 (100%)

Example 364

5-(6-(2-(dimethylamino)propan-2-yl)-4-morpholinothieno[3,2-d]pyrimidin-2-yl)pyrimidin-2-amine 451

To a suspension of 2-chloro-4-morpholin-4-yl-thieno[3,2-d]pyrimidine (5.11 g) in dry THF cooled to −78° C. was added nBuLi (2.5 M solution in hexanes, 10.4 mL). After 45 minutes, carbon dioxide was bubbled through the solution, and the reaction mixture was then slowly warmed to room temperature. The reaction mixture was then reduced in vacuo and potassium carbonate solution added to the residue. Ethyl acetate was added and the mixture was filtered. The aqueous phase was then collected, acidified (HCl, 2N) to yield a pale precipitate which was collected by filtration. The solid was suspended in methanol and reduced in vacuo to yield 2-chloro-4-morpholin-4-yl-thieno[3,2-d]pyrimidine-6-carboxylic acid (4.07 g).

To 2-chloro-4-morpholin-4-yl-thieno[3,2-d]pyrimidine-6-carboxylic acid (760 mg) in dry DMF (5 mL) was added 1,1'-carbonyldiimidazole (824 mg). After 1 hour, dimethylamine hydrochloride (414 mg) and triethylamine (708 μL) was added. After 2 hours, the reaction mixture was diluted with ethyl acetate, washed with brine, dried (MgSO$_4$) and the solvent removed in vacuo. The residue was recrystallised from ethyl acetate/hexane to yield 2-chloro-4-morpholin-4-yl-thieno[3,2-d]pyrimidine-6-carboxylic acid dimethylamide (513 mg).

To 2-chloro-4-morpholin-4-yl-thieno[3,2-d]pyrimidine-6-carboxylic acid dimethylamide (513 mg) in dry tetrahydrofuran (20 mL) cooled to −10° C. was added zirconium chloride (732 mg). After stirring for 1 hour, methyl magnesium bromide (3.0 M solution in ether, 3.14 mL) was added dropwise. The reaction mixture was warmed slowly to room temperature. After 4 hours, the reaction mixture was poured onto cold sodium hydroxide solution, extracted into chloroform, dried (MgSO$_4$) and the solvent removed in vacuo. The residue was purified using flash chromatography to yield [1-(2-chloro-4-morpholin-4-yl-thieno[3,2-d]pyrimidin-6-yl)-1-methyl-ethyl]-dimethyl-amine (137 mg)

[1-(2-Chloro-4-morpholin-4-yl-thieno[3,2-d]pyrimidin-6-yl)-1-methyl-ethyl]-dimethyl-amine was reacted with 5-(4,4,5,5-tetramethyl-[1,3,2]dioxaborolan-2-yl)-pyridin-2-ylamine in General Procedure A. Purification on silica yielded 451. NMR (CDCl$_3$); 1.52 (6H, s), 2.33 (6H, s), 3.88-3.91 (4H, m), 4.05-4.09 (4H, m), 5.22 (2H, s, br.), 7.23 (1H, s), 9.30 (2H, s). MS (ESI+) m/z 400 (MH+, 100%)

Example 365

N-((2-(2-aminopyrimidin-5-yl)-4-morpholinothieno[2,3-d]pyrimidin-6-yl)methyl)-N-(2-(dimethylamino)ethyl)methanesulfonamide 452

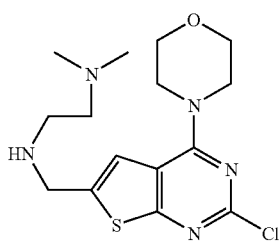 [SMILES: CN(C)CCNCc1cc2c(N3CCOCC3)nc(Cl)nc2s1]

2-Chloro-4-morpholinothieno[2,3-d]pyrimidine-6-carbaldehyde and N,N'-dimethylaminoethyleneamine were reacted according to General Procedure B-3 to produce intermediate N1-((2-chloro-4-morpholinothieno[2,3-d]pyrimidin-6-yl)methyl)-N2,N2-dimethylethane-1,2-diamine, which was sulfonylated to give N-((2-chloro-4-morpholinothieno[2,3-d]pyrimidin-6-yl)methyl)-N-(2-(dimethylamino)ethyl)methanesulfonamide.

N-((2-Chloro-4-morpholinothieno[2,3-d]pyrimidin-6-yl)methyl)-N-(2-(dimethylamino)ethyl)methanesulfonamide was reacted with 2-aminopyrimidine-5-boronic acid, pinacol ester according to General procedure A to produce 452 in 45% yield after RP-HPLC purification. MS (Q1) 493.2 (M)+, purity 95.46% by UV 254 nm, 1H NMR (DMSO)

Example 366

2-(2-(2-(Methylamino)pyrimidin-5-yl)-4-morpholinothieno[3,2-d]pyrimidin-6-yl)propan-2-ol 453

2-(2-Chloro-4-morpholinothieno[3,2-d]pyrimidin-6-yl)propan-2-ol (40 mg) was reacted with 51 mg of tert-butyl methyl5-(4,4,5,5-tetramethyl-1,3,2-dioxaborolan-2-yl)pyrimidin-2-ylcarbamate via General Procedure A. The crude intermediate was extracted with ethyl acetate and saturated sodium bicarbonate solution. The organic layer was concentrated to dryness then treated with TFA to remove the t-butoxycarbonyl group. The product was subsequently purified by reverse phase HPLC to give 28.8 mg of 453. MS (Q1) 387.2 (M)+.

Example 367

5-(5-methyl-4-morpholinothieno[2,3-d]pyrimidin-2-yl)pyrimidin-2-amine 454

2-Chloro-5-methyl-4-morpholin-4-yl-thieno[2,3-d]pyrimidine was reacted with 5-(4,4,5,5-tetramethyl-[1,3,2]dioxaborolan-2-yl)-pyridin-2-ylamine in General Procedure A. Purification on silica yielded 454. NMR (CDCl$_3$): 2.52 (3H, s), 3.52-3.55 (4H, m), 3.91-3.94 (4H, m), 5.26 (2H, s, br.), 6.99 (1H, s), 9.31 (2H, s). MS (ESI+) m/z 329 (MH+, 100%)

Example 368

5-(6-(((2-methoxyethyl)(methyl)amino)methyl)-4-morpholinothieno[3,2-d]pyrimidin-2-yl)pyrimidin-2-amine 455

Reaction between 2-chloro-4-morpholin-4-yl-thieno[3,2-d]pyrimidine-6-carbaldehyde 10 and N-(2-methoxyethyl) methylamine using standard reductive amination conditions yielded (2-chloro-4-morpholin-4-yl-thieno[3,2-d]pyrimidin-6-ylmethyl)-(2-methoxy-ethyl)-methyl-amine.

(2-Chloro-4-morpholin-4-yl-thieno[3,2-d]pyrimidin-6-ylmethyl)-(2-methoxy-ethyl)-methylamine was reacted with 5-(4,4,5,5-tetramethyl-[1,3,2]dioxaborolan-2-yl)-pyridin-2-ylamine via General Procedure A. Purification on silica yielded 455. NMR (CDCl$_3$): 2.42 (3H, s), 2.74 (2H, t), 3.39 (3H, s), 3.58 (2H, t), 3.87-3.91 (4H, m), 3.93 (2H, s), 4.03-4.06 (4H, m), 5.24 (2H, br), 7.28 (1H, s), 9.30 (2H, s). (ESI+): MH+ 516.14 (75%)

Example 369

N1-((2-(2-aminopyrimidin-5-yl)-4-morpholinothieno [3,2-d]pyrimidin-6-yl)methyl)-N1,N3,N3-trimethyl-propane-1,3-diamine 456

Reaction between 2-chloro-4-morpholin-4-yl-thieno[3,2-d]pyrimidine-6-carbaldehyde 10 and N,N,N'-trimethyl-1,3-propane-diamine using standard reductive amination conditions yielded N-(2-chloro-4-morpholin-4-yl-thieno[3,2-d]pyrimidin-6-ylmethyl)-N,N',N'trimethyl-propane-1,3-diamine.

N-(2-chloro-4-morpholin-4-yl-thieno[3,2-d]pyrimidin-6-ylmethyl)-N,N',N'trimethyl-propane-1,3-diamine with 5-(4,4,5,5-tetramethyl-[1,3,2]dioxaborolan-2-yl)-pyridin-2-ylamine in General Procedure A. Purification on silica yielded 456. NMR (CDCl3): 1.72-1.76 (2H, m), 2.25 (6H, s), 2.32-2.36 (2H, m), 2.36 (3H, s), 2.51-2.56 (2H, m), 3.84 (2H, s), 3.88-3.91 (4H, m), 4.03-4.06 (4H, m), 5.24 (2H, br), 7.27 (1H, s), 9.30 (2H, s) (ESI+): MH+ 443.21 (10%)

Example 370

1-(((2-(2-aminopyrimidin-5-yl)-4-morpholinothieno [3,2-d]pyrimidin-6-yl)methyl)(methyl)amino)-2-methylpropan-2-ol 457

Reaction between 2-chloro-4-morpholin-4-yl-thieno[3,2-d]pyrimidine-6-carbaldehyde 10 and sarcosine ethyl ester hydrochloride using standard reductive amination conditions yielded [(2-chloro-4-morpholin-4-yl-thieno[3,2-d]pyrimidin-6-ylmethyl)-methyl-amino]-acetic acid ethyl ester.

[(2-chloro-4-morpholin-4-yl-thieno[3,2-d]pyrimidin-6-ylmethyl)-methyl-amino]-acetic acid ethyl ester was reacted with methylmagnesium bromide (2.5 equiv.) in dry THF at room temperature to give 1-[(2-chloro-4-morpholin-4-yl-thieno[3,2-d]pyrimidin-6-ylmethyl)-methyl-amino]-2-methyl-propan-2-ol.

1-[(2-chloro-4-morpholin-4-yl-thieno[3,2-d]pyrimidin-6-ylmethyl)-methyl-amino]-2-methyl-propan-2-ol was reacted with 5-(4,4,5,5-tetramethyl-[1,3,2]dioxaborolan-2-yl)-pyridin-2-ylamine in General Procedure A. Purification on silica yielded 457. NMR (CDCl3): 1.27 (6H, s), 2.47 (3H, s), 2.58 (2H, s), 2.73 (1H, br. S), 3.89-3.93 (4H, m), 4.01 (2H, s), 4.03-4.06 (4H, m), 5.25 (2H, br), 7.29 (1H, s), 9.31 (2H, s). (ESI+): MH+ 430.19 (70%)

Example 371

5-(6-((3-methoxypropylamino)methyl)-4-morpholinothieno[3,2-d]pyrimidin-2-yl)pyrimidin-2-amine 458

Reaction between 2-chloro-4-morpholin-4-yl-thieno[3,2-d]pyrimidine-6-carbaldehyde 10 and 3-methoxypropylamine using the standard reductive amination conditions yielded (2-chloro-4-morpholin-4-yl-thieno[3,2-d]pyrimidin-6-ylmethyl)-(3-methoxy-propyl)-amine.

(2-Chloro-4-morpholin-4-yl-thieno[3,2-d]pyrimidin-6-ylmethyl)-(3-methoxy-propyl)-amine was reacted with 5-(4,4,5,5-tetramethyl-[1,3,2]dioxaborolan-2-yl)-pyridin-2-ylamine via General Procedure A. Purification on silica yielded 458. NMR (CDCl3): 1.82-1.90 (2H, m), 2.86 (2H, t), 3.36 (3H, s), 3.49-3.53 (2H, t), 3.87-3.91 (4H, m), 4.03-4.07 (4H, m), 4.16 (2H, s), 5.23 (2H, br, NH2), 7.31 (1H, s), 9.31 (2H, s). (ESI+): MH+ 416.16 (20%)

Example 372

(5-(2-(2-aminopyrimidin-5-yl)-7-methyl-4-morpholinothieno[3,2-d]pyrimidin-6-yl)pyridin-3-yl)(4-hydroxypiperidin-1-yl)methanone 459

5-[2-(2-Amino-pyrimidin-5-yl)-7-methyl-4-morpholin-4-yl-thieno[3,2-d]pyrimidin-6-yl]-nicotinic acid (60 mg) was reacted with 4-hydroxypiperazine via General Procedure C. The product was purified by reverse phase HPLC to yield 19.5 mg of 459. MS (Q1) 533.2 (M)+

Example 373

5-(6-((3,4-dihydroisoquinolin-2(1H)-yl)methyl)-4-morpholinothieno[3,2-d]pyrimidin-2-yl)pyrimidin-2-amine 460

Reaction between 2-chloro-4-morpholin-4-yl-thieno[3,2-d]pyrimidine-6-carbaldehyde 10 and 1,2,3,4-tetrahydroisoquinoline using standard reductive amination conditions yielded 2-(2-chloro-4-morpholin-4-yl-thieno[3,2-d]pyrimidin-6-ylmethyl)-1,2,3,4-tetrahydro-isoquinoline.

2-(2-Chloro-4-morpholin-4-yl-thieno[3,2-d]pyrimidin-6-ylmethyl)-1,2,3,4-tetrahydro-isoquinoline was reacted with 5-(4,4,5,5-tetramethyl-[1,3,2]dioxaborolan-2-yl)-pyridin-2-ylamine in General Procedure A. Purification on silica yielded 460. 400 Mz 1H NMR CDCl3: 9.21 (s, 2H); 7.31 (s, 1H); 7.11 (m, 3H); 6.98 (d, 1H, J=7.2 Hz); 4.00 (t, 4H+2H, J=4.7 Hz); 3.84 (t, 4H, J=4.8 Hz); 3.76 (s, 2H); 2.93 (t, 2H, J=5.6 Hz); 2.86 (t, 2H, J=5.5 Hz); LC-MS (m+1)=460.21

Example 374

5-(6-(((2,4-difluorobenzyl)(methyl)amino)methyl)-4-morpholinothieno[3,2-d]pyrimidin-2-yl)pyrimidin-2-amine 461

(2-Chloro-4-morpholin-4-yl-thieno[3,2-d]pyrimidin-6-ylmethyl)-methylamine was reacted with 2,4-difluorobenzaldehyde using standard reductive amination conditions. The resulting crude material was triturated with diethyl ether and methanol to give (2-chloro-4-morpholin-4-yl-thieno[3,2-d]pyrimidin-6-ylmethyl)(2,4-difluorobenzyl)methylamine as a solid (100% yield).

(2-Chloro-4-morpholin-4-yl-thieno[3,2-d]pyrimidin-6-ylmethyl)(2,4-difluoro-benzyl)methyl-amine was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 461 as a solid (100% yield). NMR (CDCL3, 400 MHz), 2.34 (3H, s), 3.70 (2H, s), 3.88 (2H, s), 3.91 (4H, t, J=4.8), 4.06 (4H, t, J=4.8), 5.25 (2H, s), 6.81-6.87 (1H, m), 6.89-6.94 (1H, m), 7.31 (1H, s), 7.42-7.48 (1H, m), 9.30 (2H, s). MS: (ESI+): MH+=484

Example 375

5-(6-((benzyl(methyl)amino)methyl)-4-morpholinothieno[3,2-d]pyrimidin-2-yl)pyrimidin-2-amine 462

(2-Chloro-4-morpholin-4-yl-thieno[3,2-d]pyrimidin-6-ylmethyl)-methylamine was reacted with benzaldehyde using standard reductive amination conditions. The resulting crude material was triturated with diethyl ether and methanol to give benzyl-(2-chloro-4-morpholin-4-yl-thieno[3,2-d]pyrimidin-6-ylmethyl)-methyl-amine as a solid (72% yield).

Benzyl-(2-chloro-4-morpholin-4-yl-thieno[3,2-d]pyrimidin-6-ylmethyl)-methyl-amine was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 462 as a solid (100% yield). NMR (CDCL3, 400 MHz), 2.34 (3H, s), 3.67 (2H, s), 3.85 (2H, s), 3.91 (4H, t, J=4.8), 4.07 (4H, t, J=4.8), 5.24 (2H, s), 7.28-7.32 (2H, m), 7.36-7.42 (4H, m), 9.30 (2H, s). MS: (ESI+): MH+=448

Example 376

(4-(2-(2-aminopyrimidin-5-yl)-4-morpholinothieno[3,2-d]pyrimidin-6-yl)-2-chlorophenyl)(4-hydroxypiperidin-1-yl)methanone 463

2-Chloro-6-iodo-4-morpholin-4-yl-thieno[3,2-d]pyrimidine (500 mg) was reacted with 309 mg of 3-chloro-4-methoxycarbonyl-phenylboronic acid, and then was coupled to 348 mg of 2-aminopyrimidine-5-boronic acid pinacol ester via General Procedure B to yield 550 mg of 4-[2-(2-Amino-pyrimidin-5-yl)-4-morpholin-4-yl-thieno[3,2-d]pyrimidin-6-yl]-benzoic acid.

4-[2-(2-Amino-pyrimidin-5-yl)-4-morpholin-4-yl-thieno[3,2-d]pyrimidin-6-yl]-benzoic acid (80 mg) was reacted with 4-hydroxypiperidine via General Procedure C. The product was purified by reverse phase HPLC to yield 18 mg of 463. MS (Q1) 552.2 (M)$^+$ Example 377

(4-(2-(2-aminopyrimidin-5-yl)-4-morpholinothieno[3,2-d]pyrimidin-6-yl)-2-chlorophenyl)(4-methylpiperazin-1-yl)methanone 464

4-[2-(2-Amino-pyrimidin-5-yl)-4-morpholin-4-yl-thieno[3,2-d]pyrimidin-6-yl]-benzoic acid (80 mg) was reacted with 1-methylpiperizine via General Procedure C. The product was purified by reverse phase HPLC to yield 20.1 mg of 464. MS (Q1) 551.2 (M)$^+$ Example 378

N-methyl-5-(7-methyl-6-(3-(methylsulfonyl)phenyl)-4-morpholinothieno[3,2-d]pyrimidin-2-yl)pyrimidin-2-amine 465

To a mixture of 5-[6-(3-methanesulfonyl-phenyl)-7-methyl-4-morpholin-4-yl-thieno[3,2-d]pyrimidin-2-yl]-pyrimidin-2-ylamine 231 (80 mg, 0.1 mmol) in N-methylpyrrolidinone (2 mL, 20 mmol) was added methyl iodide (11 uL, 0.18 mmol). The reaction mixture was stirred overnight at room temperature, then additional 0.5 equiv. methyl iodide was added and stirred until completion of the reaction. The reaction mixture was evaporated. The product was purified by reverse phase HPLC to yield 12.1 mg of 465. MS (Q1) 496.2 (M)$^+$ Example 379

N,N-dimethyl-5-(7-methyl-6-(3-(methylsulfonyl)phenyl)-4-morpholinothieno[3,2-d]pyrimidin-2-yl)pyrimidin-2-amine 466

2-Chloro-6-(3-methanesulfonyl-phenyl)-4-morpholin-4-yl-thieno[3,2-d]pyrimidine (50 mg) was reacted with 35 mg of 2,2-dimethylamino-pyrimidine-5-boronic acid pinacol ester via General Procedure A. The product was purified by reverse phase HPLC to yield 16.4 mg of 466. MS (Q1) 511.2 (M)$^+$ Example 380

(4-(2-(2-aminopyrimidin-5-yl)-7-methyl-4-morpholinothieno[3,2-d]pyrimidin-6-yl)thiophen-2-yl)(4-hydroxypiperidin-1-yl)methanone 467

2-Chloro-6-iodo-7-methyl-4-morpholin-4-yl-thieno[3,2-d]pyrimidine (500 mg) was reacted with 239 mg of 2-carboxythiophene-4-boronic acid. The product was coupled to 267 mg of 2-aminopyrimidine-5-boronic acid pinacol ester via General Procedure B to yield 460 mg of 4-[2-(2-aminopyrimidin-5-yl)-7-methyl-4-morpholin-4-yl-thieno[3,2-d]pyrimidin-6-yl]-thiophene-2-carboxylic acid.

4-[2-(2-Amino-pyrimidin-5-yl)-7-methyl-4-morpholin-4-yl-thieno[3,2-d]pyrimidin-6-yl]-thiophene-2-carboxylic acid (80 mg) was reacted with 4-hydroxypiperidine via General Procedure C. The product was purified by reverse phase HPLC to yield 30.4 mg of 467. MS (Q1) 538.2 (M)$^+$ Example 381

(4-(2-(2-aminopyrimidin-5-yl)-7-methyl-4-morpholinothieno[3,2-d]pyrimidin-6-yl)thiophen-2-yl)(4-methylpiperazin-1-yl)methanone 468

4-[2-(2-Amino-pyrimidin-5-yl)-7-methyl-4-morpholin-4-yl-thieno[3,2-d]pyrimidin-6-yl]-thiophene-2-carboxylic acid (80 mg) was reacted with 1-methylpiperazine via General Procedure C. The product was purified by reverse phase HPLC to yield 37 mg of 468. MS (Q1) 537.2 (M)$^+$.

Example 382

(4-(2-(2-aminopyrimidin-5-yl)-7-methyl-4-morpholinothieno[3,2-d]pyrimidin-6-yl)thiophen-2-yl)(morpholino)methanone 469

4-[2-(2-Amino-pyrimidin-5-yl)-7-methyl-4-morpholin-4-yl-thieno[3,2-d]pyrimidin-6-yl]-thiophene-2-carboxylic acid (80 mg) was reacted with morpholine via General Procedure C. The product was purified by reverse phase HPLC to yield 16.4 mg of 469. MS (Q1) 524.2 (M)$^+$ Example 383

4-(2-(2-aminopyrimidin-5-yl)-7-methyl-4-morpholinothieno[3,2-d]pyrimidin-6-yl)phenyl piperidine-1-carboxylate 470

2-Chloro-6-iodo-7-methyl-4-morpholin-4-yl-thieno[3,2-d]pyrimidine (100 mg) was reacted with 92 mg of 4-(piperidine-1-carbonyloxy)phenylboronic acid pinacol ester Upon completion, then was coupled to 62 mg of 2-aminopyrimidine-5-boronic acid pinacol ester via General Procedure B. The product was purified by reverse phase HPLC to yield 17.5 mg of 470. MS (Q1) 532.2 (M)+

Example 384

5-(7-methyl-4-morpholino-6-(6-(S,S-dioxo-thiomorpholino)pyridin-3-yl)thieno[3,2-d]pyrimidin-2-yl)pyrimidin-2-amine 471

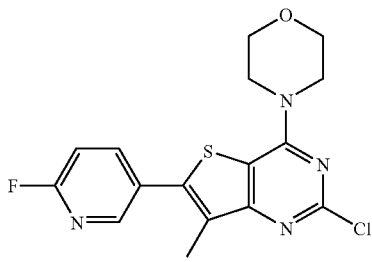 [SMILES: Cc1c(-c2ccc(F)nc2)sc2c(N3CCOCC3)nc(Cl)nc12]

2-Chloro-6-iodo-7-methyl-4-morpholinothieno[3,2-d]pyrimidine (1 eq), 2-fluoro-5-pyridineboronic acid (1.1 eq) and bis(triphenylphosphine)palladium(II) dichloride (0.1 eq) in 1M Na$_2$CO$_3$ aqueous solution (3 eq) and an equal volume of acetonitrile was heated to 100° C. in a sealed microwave reactor for 30 min. Reaction mixture was concentrated, then crude product was purified by flash chromatography to give intermediate 4-(2-chloro-6-(6-fluoropyridin-3-yl)-7-methyl-thieno[3,2-d]pyrimidin-4-yl)morpholine. MS (Q1) 365 (M+)

2-Chloro-6-(6-fluoropyridin-3-yl)-7-methyl-4-morpholinothieno[3,2-d]pyrimidine was reacted with thiomorpholine 1,1-dioxide via General Procedure G to give, after purification by flash chromatography, the corresponding intermediate, which was then submitted to General Procedure G again with 5-(4,4,5,5-tetramethyl-1,3,2-dioxaborolan-2-yl)pyrimidin-2-amine (1.7 eq) and bis(triphenylphosphine)palladium (II) dichloride (0.1 eq) in 1M KOAc aqueous solution (3 eq) and an equal volume of acetonitrile and heating to 130-150° C. in a sealed microwave reactor for 7-20 min. The mixture was extracted with ethyl acetate (3×5 mL). The combined organic layers were concentrated to yield after purification by reverse HPLC, 22 mg of 471. MS (Q1) 539 M+

Example 385

5-(6-(6-((2S,6R)-2,6-dimethylmorpholino)pyridin-3-yl)-4-morpholinothieno[3,2-d]pyrimidin-2-yl)pyrimidin-2-amine 472

4-(2-Chloro-6-(6-fluoropyridin-3-yl)thieno[3,2-d]pyrimidin-4-yl)morpholine was reacted with (2S,6R)-2,6-dimethylmorpholine via General Procedure H to give, after purification by flash chromatography, the corresponding intermediate, which was then reacted with 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile and heating to 130-150° C. in a sealed microwave reactor for 7-20 min. The mixture was extracted with ethyl acetate (3×5 mL). The combined organic layers were concentrated to yield after purification by reverse HPLC, 8 mg of 472. MS (Q1) 505 (M+)

Example 386

5-(4-morpholino-7-(thiazol-5-yl)thieno[3,2-d]pyrimidin-2-yl)pyridin-2-amine 473

1H-Thieno[3,2-d]pyrimidine-2,4-dione (3 g, 18 mmol) was suspended in glacial acetic acid (90 ml) and heated to 80° C. before bromine (10.80 g, 3.23 ml, 63 mmol) was added dropwise. The reaction mixture was heated at 80° C. for a further 4 hours before pouring into water (~1 L) and the white precipitate collected and dried to yield 7-bromo-1H-thieno[3,2-d]pyrimidine-2,4-dione (3.92 g, 88%).

7-Bromo-1H-thieno[3,2-d]pyrimidine-2,4-dione (3.92 g, 15.87 mmol) was suspended in neat phosphorous oxychloride (50 ml) and refluxed overnight. The cooled reaction solution was poured into vigorously stirring ice-water before extracting into DCM. The organic layer was dried over MgSO$_4$, filtered and evaporated to give 7-bromo-2,4-dichloro-thieno[3,2-d]pyrimidine (4.11 g, 91%).

7-Bromo-2,4-dichloro-thieno[3,2-d]pyrimidine (4.10 g, 14.44 mmol) was suspended in methanol (100 ml), to this morpholine (3.15 ml, 36.10 mmol) was added and stirred at room temperature for 5 hours. Water was added to the solution and the resulting white precipitate filtered and dried to yield 7-bromo-2-chloro-4-morpholin-4-yl-thieno[3,2-d]pyrimidine (4.11 g, 85%).

A suspension of 7-bromo-2-chloro-4-morpholin-4-yl-thieno[3,2-d]pyrimidine (116 mg, 0.35 mmol), 5-tributylstannanyl thiazole (130 mg, 0.35 mmol), and Pd(PPh$_3$)$_4$ (20 mg, 0.017 mmol) in anhydrous DMA was heated in a microwave at 150° C. for 15 mins. The crude reaction was loaded onto a preconditioned SCX cartridge, washing the cartridge with methanol and dichloromethane before eluting with 7N ammonia in methanol to give crude material. This was purified by on silica using ethyl acetate as the eluent to 2-chloro-4-morpholin-4-yl-7-thiazol-5-yl-thieno[3,2-d]pyrimidine as a white solid (93 mg, 80%). LCMS confirmed reaction at the bromine. MS: (ESI+): MH+=339

2-Chloro-4-morpholin-4-yl-7-thiazol-5-yl-thieno[3,2-d]pyrimidine was reacted with 5-(4,4,5,5-tetramethyl-[1,3,2]dioxaborolan-2-yl)-pyridin-2-ylamine according to procedure A. The resulting solid was purified by flash column chromatography using 5% methanol/ethyl acetate as the eluent to give 473 as a solid (39% yield). NMR (CDCl$_3$, 400 MHz), 3.84 (4H, t, J=5.2), 4.01 (4H, t, J=5.2), 4.66 (2H, br s), 6.54 (1H, d, J=8.4), 7.88 (1H, s), 8.52 (1H, dd, J=8.4, 2.0), 8.54 (1H, s), 8.80 (1H, s), 9.20 (1H, d, J=2.0). MS: (ESI+): MH+=397, M+MeCN=438

Example 387

5-(4-morpholino-7-(pyridin-3-yl)thieno[3,2-d]pyrimidin-2-yl)pyrimidin-2-amine 474

7-Bromo-2-chloro-4-morpholin-4-yl-thieno[3,2-d]pyrimidine was reacted with pyridine-3-boronic acid according to General Procedure A. The resulting solid was purified by flash column chromatography using 5% methanol/ethyl acetate as the eluent to give the 2-chloro-4-morpholin-4-yl-7-pyridin-3-yl-thieno[3,2-d]pyrimidine as a solid (39% yield).

2-Chloro-4-morpholin-4-yl-7-pyridin-3-yl-thieno[3,2-d]pyrimidine was reacted with 5-(4,4,5,5-tetramethyl-[1,3,2]dioxaborolan-2-yl)-pyrimidin-2-ylamine according to General Procedure A. The resulting solid was purified by flash column chromatography using 5% methanol/ethyl acetate as the eluent to give 474 as a solid (78% yield). NMR (CDCl3, 400 MHz), 3.94 (4H, t, J=5.2), 4.12 (4H, t, J=5.2), 5.23 (2H, s), 7.47-7.44 (1H, m), 7.95 (1H, s), 8.50-8.52 (1H, m), 8.65 (1H, dd, J=4.8, 1.6), 9.14 (1H, d, J=2), 9.34 (2H, s). MS: (ESI+): MH+=393, M+MeCN=433

Example 388

5-(4-morpholino-7-(thiophen-2-yl)thieno[3,2-d]pyrimidin-2-yl)pyrimidin-2-amine 475

7-Bromo-2-chloro-4-morpholin-4-yl-thieno[3,2-d]pyrimidine was reacted with 2-thiopheneboronic acid according to General Procedure A. The resulting solid was purified by flash column chromatography using 5% methanol/ethyl acetate as the eluent to give 2-chloro-4-morpholin-4-yl-7-thiophen-2-yl-thieno[3,2-d]pyrimidine as a solid (39% yield). M/z confirmed reaction at the bromo.

2-Chloro-4-morpholin-4-yl-7-thiophen-2-yl-thieno[3,2-d]pyrimidine was reacted with 5-(4,4,5,5-tetramethyl-[1,3,2]dioxaborolan-2-yl)-pyrimidin-2-ylamine according to General Procedure A. The resulting solid was purified by mass directed chromatography to give 475 as a solid (1% yield). NMR (CDCl3, 400 MHz), 3.93 (4H, t, J=5.2), 4.10 (4H, t, J=4.8), 5.25 (2H, br s), 7.17-7.19 (1H, m), 7.41-7.43 (1H, m), 7.89-7.91 (2H, m), 9.45 (2H, s). MS: (ESI+): MH+=397, M+MeCN=438

Example 389

N-(3-(2-(2-aminopyrimidin-5-yl)-4-morpholinothieno[3,2-d]pyrimidin-7-yl)phenyl)methanesulfonamide 476

7-Bromo-2-chloro-4-morpholin-4-yl-thieno[3,2-d]pyrimidine was reacted with N-[3-(4,4,5,5-tetramethyl-[1,3,2]dioxaborolan-2-yl)-phenyl]-methanesulfonamide according to General Procedure A to yield N-[3-(2-chloro-4-morpholin-4-yl-thieno[3,2-d]pyrimidin-7-yl)-phenyl]methanesulfonamide. M/z confirmed reaction at the bromo.

N-[3-(2-Chloro-4-morpholin-4-yl-thieno[3,2-d]pyrimidin-7-yl)-phenyl]methanesulfonamide was reacted with 5-(4,4,5,5-tetramethyl-[1,3,2]dioxaborolan-2-yl)-pyrimidin-2-ylamine according to General Procedure A. The resulting solid was purified by mass directed chromatography to give 476 as a solid (12% yield). NMR (CDCl3, 400 MHz), 3.07 (3H, s), 3.74-3.75 (4H, m), 3.78-3.79 (4H, m), 5.56 (2H, s), 7.33-7.34 (1H, m) 7.42-7.44 (1H, m), 7.65-7.67 (1H, m), 7.84 (1H, s), 8.20 (1H, s), 9.07 (2H, s). MS: (ESI+): MH+=484

Example 390

5-(7-(3-(methylsulfonyl)phenyl)-4-morpholinothieno[3,2-d]pyrimidin-2-yl)pyrimidin-2-amine 477

7-Bromo-2-chloro-4-morpholin-4-yl-thieno[3,2-d]pyrimidine was reacted with 2-(3-methanesulfonyl-phenyl)-4,4,5,5-tetramethyl-[1,3,2]dioxaborolane according to General Procedure A to yield 2-chloro-7-(3-methanesulfonyl-phenyl)-4-morpholin-4-yl-thieno[3,2-d]pyrimidine. M/z confirmed reaction at the bromo.

2-Chloro-7-(3-methanesulfonyl-phenyl)-4-morpholin-4-yl-thieno[3,2-d]pyrimidine was reacted with 5-(4,4,5,5-tetramethyl-[1,3,2]dioxaborolan-2-yl)-pyrimidin-2-ylamine according to General Procedure A. The resulting solid was purified by mass directed chromatography to give 477 as a solid (62% yield). NMR (CDCl$_3$, 400 MHz), 3.28 (3H, s), 3.82 (4H, t, J=4.4), 4.05 (4H, t, J=4.4), 7.11 (2H, s), 7.82 (1H, t, J=7.6), 7.94-7.96 (1H, m), 8.39-8.41 (1H, m), 8.75 (1H, s), 9.10 (1H, t, J=2.0), 9.22 (2H, s). MS: (ESI+): MH+=469, M+MeCN=510

Example 391

N1-((2-(2-aminopyrimidin-5-yl)-4-morpholinothieno[3,2-d]pyrimidin-6-yl)methyl)-N1,N2,N2-trimethylethane-1,2-diamine 478

Reaction between 2-chloro-4-morpholin-4-yl-thieno[3,2-d]pyrimidine-6-carbaldehyde 10 and N,N,N'-trimethylethylenediamine using standard reductive amination conditions yielded N-(2-chloro-4-morpholin-4-yl-thieno[3,2-d]pyrimidin-6-ylmethyl)-N,N',N'trimethyl-ethane-1,2-diamine.

N-(2-chloro-4-morpholin-4-yl-thieno[3,2-d]pyrimidin-6-ylmethyl)-N,N',N'trimethyl-ethane-1,2-diamine reacted with 5-(4,4,5,5-tetramethyl-[1,3,2]dioxaborolan-2-yl)-pyridin-2-ylamine via General Procedure A. Purification on silica yielded 478. (CDCl3): 1.92 (6H, s), 2.05 (3H, s), 2.13-2.18 (2H, m), 2.26-2.31 (2H, m), 3.53-3.56 (4H, m), 3.56 (2H, s), 3.69-3.72 (4H, m), 4.88 (2H, br, NH20, 6.96 (1H, s), 8.96 (2H, s) (ESI+): MH+ 429.2 (15%)

Example 392

(2-(2-aminopyrimidin-5-yl)-4-morpholinothieno[3,2-d]pyrimidin-6-yl)(3-(methylsulfonyl)phenyl)methanone 479

To a solution of 3-(methylthio)benzoic acid (2.00 g) in DMF (30 mL) was added carbonyldiimidazole (3.87 g). After stirring at room temperature for 1 h, triethylamine (3.31 mL) and N,O-dimethylhydroxylamine (3.48 g) were added and the reaction stirred at room temperature for 16 h. The reaction was quenched with water (40 mL) and extracted into ethylacetate (40 mL). The organic layer was washed with brine (3×40 mL), dried (MgSO$_4$), reduced in vacuo and purified on silica to give N-methoxy-N-methyl-3-methylsulfanyl-benzamide as a yellow oil.

To a solution of 2-chloro-4-morpholin-4-yl-thieno[3,2-d]pyrimidine (550 mg) in THF (10 mL) at −78° C. was added n-butyllithium (1.04 mL of a 2.5 m solution in hexanes). The mixture was stirred at −78° C. for 1 h and then N-methoxy-N-methyl-3-methylsulfanyl-benzamide (546 mg) was added. The reaction was allowed to cool to room temperature over 4 h and then quenched with water (20 mL). The product was extracted into ethyl acetate (3×30 mL) and the organics were washed with brine (40 mL), dried (MgSO$_4$), reduced in vacuo and purified on silica to give (2-chloro-4-morpholin-4-yl-thieno[3,2-d]pyrimidin-6-yl)-(3-methylsulfanyl-phenyl)-methanone as a white solid.

To a solution of (2-chloro-4-morpholin-4-yl-thieno[3,2-d]pyrimidin-6-yl)-(3-methylsulfanyl-phenyl)-methanone (450 mg) in dichloromethane (20 mL) at 0° C. was added m-chloroperoxybenzoic acid (498 mg) and the reaction was stirred at room temperature for 16 h. The reaction was quenched with aqueous sodium thiosulfate solution (30 mL) and extracted into dichloromethane (2×30 mL). The organic layers were washed with brine (2×20 mL), dried (MgSO$_4$), reduced in vacuo and purified on silica to yield (2-chloro-4-morpholin-4-yl-thieno[3,2-d]pyrimidin-6-yl)-(3-methanesulfonyl-phenyl)-methanone as an off-white solid.

(2-Chloro-4-morpholin-4-yl-thieno[3,2-d]pyrimidin-6-yl)-(3-methanesulfonyl-phenyl)-methanone was reacted with 2-aminopyrimidine-5-boronic acid via General Procedure A. Purification on silica yielded 479. NMR: (DMSO): 3.39 (3H, s, Me), 3.87-3.89 (4H, m), 4.08-4.10 (4H, m), 7.18 (2H, s, NH), 8.03 (1H, s, Ar), 8.22-8.24 (4H, m, Ar) and 9.18 (1H, s, Ar). MS: (ESI+): MH+ 497.07

Example 393

(2-(2-aminopyrimidin-5-yl)-4-morpholinothieno[3,2-d]pyrimidin-6-yl)(4-(methylsulfonyl)phenyl)methanone 480

To a solution of 2-chloro-4-morpholin-4-yl-thieno[3,2-d]pyrimidine (550 mg) in THF (10 mL) at −78° C. was added n-butyllithium (1.04 mL of a 2.5 M solution in hexanes). After stirring at −78° C. for 1 h, 4-(methylthio)benzaldehyde (0.34 mL) was added and the reaction was allowed to warm to room temperature for 16 h. The reaction mixture was then poured onto water and the solid filtered and air-dried to give (2-chloro-4-morpholin-4-yl-thieno[3,2-d]pyrimidin-6-yl)-(4-methylsulfanyl-phenyl)-methanol.

To a solution of (2-chloro-4-morpholin-4-yl-thieno[3,2-d]pyrimidin-6-yl)-(4-methylsulfanyl-phenyl)-methanol (450 mg) in dichloromethane (20 mL) at 0° C. was added m-chloroperoxybenzoic acid (498 mg) and the reaction was stirred at room temperature for 16 h. The reaction was quenched with aqueous sodium thiosulfate solution (30 mL) and extracted into dichloromethane (2×30 mL). The organic layers were washed with brine (2×20 mL), dried (MgSO$_4$), reduced in vacuo and purified on silica to yield (2-chloro-4-morpholin-4-yl-thieno[3,2-d]pyrimidin-6-yl)-(4-methanesulfonyl-phenyl)-methanol as an off-white solid.

To a solution of (2-chloro-4-morpholin-4-yl-thieno[3,2-d]pyrimidin-6-yl)-(4-methanesulfonyl-phenyl)-methanol (200 mg) in dichloromethane (10 mL) was added N-methylmorpholine oxide (160 mg) and freshly activated 4 Å molecular sieves. After stirring at room temperature for 20 min, TPAP (16 mg) was added and the reaction stirred at room temperature for 3 h. The mixture was filtered through Celite and the filtrate reduced in vacuo. Purification on silica yielded (2-chloro-4-morpholin-4-yl-thieno[3,2-d]pyrimidin-6-yl)-(4-methanesulfonyl-phenyl)-methanone.

(2-Chloro-4-morpholin-4-yl-thieno[3,2-d]pyrimidin-6-yl)-(4-methanesulfonyl-phenyl)-methanone was reacted with 2-aminopyrimidine-5-boronic acid in General Procedure A. Purification on silica yielded 480. NMR: (CDCl$_3$): 2.58-2.60 (4H, m), 2.73 (3H, s, Me), 3.20-3.23 (4H, m), 3.76 (2H, s), 3.82-3.85 (4H, m), 3.91-3.93 (4H, m), 7.10 (1H, s, Ar), 7.32-7.35 (1H, m, Ar), 7.36 (2H, t, J 6.5, Ar), 7.61-7.64 (2H, m, Ar), 8.81 (2H, dd, J 2.0 and 9.0, Ar) and 9.53 (1H, d, J 2.0, Ar). MS: (ESI+): MH+ 551.22

Example 394

(2-(2-aminopyrimidin-5-yl)-4-morpholinothieno[3,2-d]pyrimidin-6-yl)(3-(methylsulfonyl)phenyl)methanol 481

To a solution of [2-(2-amino-pyrimidin-5-yl)-4-morpholin-4-yl-thieno[3,2-d]pyrimidin-6-yl]-(3-methanesulfonyl-phenyl)-methanone 479 (50 mg) in methanol (6 mL) was added sodium borohydride (4 mg) and the reaction was stirred at room temperature for 2 h. The reaction was quenched with water (10 mL) and saturated aqueous sodium carbonate solution (10 mL) and the solid was filtered and air-dried to give 481. NMR: (CDCl$_3$): 3.10 (3H, s, Me), 3.15-3.17 (1H, m, CH), 3.87-3.90 (4H, m), 4.01-4.04 (4H, m), 5.24 (2H, s, NH), 6.27 (1H, s, OH), 7.27 (1H, s, Ar), 7.63 (1H, t, J 7.8, Ar), 7.79 (1H, d, J 7.8, Ar), 7.95 (1H, dt, J 7.8 and 1.5, Ar), 8.14 (1H, d, J 1.5, Ar) and 9.25 (2H, s, Ar). MS: (ESI+): MH+ 499.10

Example 395

5-(6-((2-methoxyethylamino)methyl)-4-morpholinothieno[3,2-d]pyrimidin-2-yl)pyrimidin-2-amine 482

Reaction between 2-chloro-4-morpholin-4-yl-thieno[3,2-d]pyrimidine-6-carbaldehyde 10 and 2-methoxyethylamine using standard reductive amination conditions yielded (2-chloro-4-morpholin-4-yl-thieno[3,2-d]pyrimidin-6-ylmethyl)-(2-methoxy-ethyl)-amine.

(2-Chloro-4-morpholin-4-yl-thieno[3,2-d]pyrimidin-6-ylmethyl)-(2-methoxy-ethyl)-amine was reacted with 5-(4,4,5,5-tetramethyl-[1,3,2]dioxaborolan-2-yl)-pyridin-2-ylamine in General Procedure A. Purification on silica yielded 482. NMR (CDCl$_3$): 2.90 (2H, t), 3.40 (3H, s), 3.56 (2H, t), 3.87-3.91 (4H, m), 4.03-4.07 (4H, m), 4.17 (2H, s), 5.12 (2H, br, NH2), 7.29 (1H, s), 9.30 (2H, s). (ESI+): MH+ 402.17 (10%)

Example 396

N-((2-(2-aminopyrimidin-5-yl)-7-methyl-4-morpholinothieno[3,2-d]pyrimidin-6-yl)methyl)-N,3,3-trimethylbutanamide 483

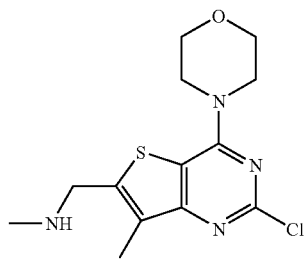 [SMILES: CNCc1sc2c(N3CCOCC3)nc(Cl)nc2c1C]

1-(2-Chloro-7-methyl-4-morpholinothieno[3,2-d]pyrimidin-6-yl)-N-methylmethanamine was reacted with t-butyl acetyl chloride via General procedure B-4 to give N-((2-chloro-7-methyl-4-morpholinothieno[3,2-d]pyrimidin-6-yl)methyl)-N,3,3-trimethylbutanamide, which was reacted with 5-(4,4,5,5-tetramethyl-1,3,2-dioxaborolan-2-yl)pyrimidin-2-amine as per General Procedure A to give 117.8 mg of 483 (25% yield over both steps).

Example 397

N-((2-(2-aminopyrimidin-5-yl)-7-methyl-4-morpholinothieno[3,2-d]pyrimidin-6-yl)methyl)-N,3-dimethylbutanamide 484

1-(2-Chloro-7-methyl-4-morpholinothieno[3,2-d]pyrimidin-6-yl)-N-methylmethanamine was reacted with isovaleryl chloride via General procedure B-4. The acylated butanamide intermediate was reacted with 5-(4,4,5,5-tetramethyl-1,3,2-dioxaborolan-2-yl)pyrimidin-2-amine as per General Procedure A to give 195.3 mg of 484 (38% yield over both steps).

Example 398

N-((2-(2-aminopyrimidin-5-yl)-7-methyl-4-morpholinothieno[3,2-d]pyrimidin-6-yl)methyl)-N-methylpivalamide 485

1-(2-Chloro-7-methyl-4-morpholinothieno[3,2-d]pyrimidin-6-yl)-N-methylmethanamine was reacted with pivaloyl chloride via General procedure B-4 to give the amide intermediate, followed by reaction with 5-(4,4,5,5-tetramethyl-1,3,2-dioxaborolan-2-yl)pyrimidin-2-amine as per General Procedure A to give 180 mg of 485 (35% yield over both steps).

Example 399

N-((2-(2-aminopyrimidin-5-yl)-7-methyl-4-morpholinothieno[3,2-d]pyrimidin-6-yl)methyl)-N-methylcyclopropanecarboxamide 486

1-(2-Chloro-7-methyl-4-morpholinothieno[3,2-d]pyrimidin-6-yl)-N-methylmethanamine was reacted with cyclopropane carbonyl chloride via General Procedure B-4 to give the cyclopropanamide intermediate, followed by reaction with 5-(4,4,5,5-tetramethyl-1,3,2-dioxaborolan-2-yl)pyrimidin-2-amine as per General Procedure A to give 89 mg of 486 (18% yield over both steps).

Example 400

N-((2-(2-aminopyrimidin-5-yl)-7-methyl-4-morpholinothieno[3,2-d]pyrimidin-6-yl)methyl)-N-methylpropionamide 487

1-(2-Chloro-7-methyl-4-morpholinothieno[3,2-d]pyrimidin-6-yl)-N-methylmethanamine was reacted with propionyl chloride via General procedure B-4 to give the propionamide intermediate, followed by reaction with 5-(4,4,5,5-tetramethyl-1,3,2-dioxaborolan-2-yl)pyrimidin-2-amine as per General Procedure A to give 108.8 mg of 487 (23% yield over both steps).

Example 401

N-((2-(2-aminopyrimidin-5-yl)-7-methyl-4-morpholinothieno[3,2-d]pyrimidin-6-yl)methyl)-N-methylisobutyramide 488

1-(2-Chloro-7-methyl-4-morpholinothieno[3,2-d]pyrimidin-6-yl)-N-methylmethanamine was reacted with isobutyryl chloride via General procedure B-4 to give the isobutyramide intermediate, followed by reaction with 5-(4,4,5,5-tetramethyl-1,3,2-dioxaborolan-2-yl)pyrimidin-2-amine as per General Procedure A to give 138.2 mg of 488 (28% yield over both steps).

Example 402

N-((2-(2-aminopyrimidin-5-yl)-4-morpholinothieno[3,2-d]pyrimidin-6-yl)methyl)-N-methylcyclopropanecarboxamide 489

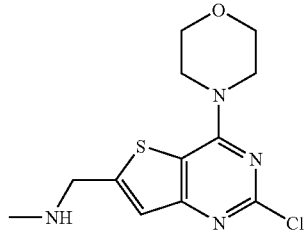 [SMILES: CNCc1cc2nc(Cl)nc(N3CCOCC3)c2s1]

1-(2-Chloro-4-morpholinothieno[3,2-d]pyrimidin-6-yl)-N-methylmethanamine was reacted with cyclopropane carbonyl chloride via General procedure B-4 to give the cyclopropylamide intermediate, followed by reaction with 5-(4,4,5,5-tetramethyl-1,3,2-dioxaborolan-2-yl)pyrimidin-2-amine as per General Procedure A to give 72 mg of 489 (25% yield over both steps).

Example 403

N-((2-(2-aminopyrimidin-5-yl)-4-morpholinothieno[3,2-d]pyrimidin-6-yl)methyl)-N-methylpropionamide 490

1-(2-Chloro-4-morpholinothieno[3,2-d]pyrimidin-6-yl)-N-methylmethanamine was reacted with propionyl chloride via General procedure B-4 to give the propionamide intermediate, followed by reaction with 5-(4,4,5,5-tetramethyl-1,3,2-dioxaborolan-2-yl)pyrimidin-2-amine as per General Procedure A to give 45.5 mg of 490 (16% yield over both steps).

Example 404

N-((2-(2-aminopyrimidin-5-yl)-4-morpholinothieno[3,2-d]pyrimidin-6-yl)methyl)-N-methylisobutyramide 491

1-(2-Chloro-4-morpholinothieno[3,2-d]pyrimidin-6-yl)-N-methylmethanamine was reacted with propionyl chloride via General procedure B-4 to give the isopropylamide intermediate, followed by reaction with 5-(4,4,5,5-tetramethyl-1,3,2-dioxaborolan-2-yl)pyrimidin-2-amine as per General Procedure A to give 24.7 mg of 491 (9% yield over both steps).

Example 405

(2-(2-(dimethylamino)pyrimidin-5-yl)-4-morpholinothieno[2,3-d]pyrimidin-6-yl)methanol 492

(2-Chloro-4-morpholinothieno[2,3-d]pyrimidin-6-yl)methanol (100 mg) was reacted with 71 mg of 2-(dimethylamino)pyrimidin-5-yl-5-boronic acid pinacol via General Procedure A and purified via reverse phase HPLC to give 492. MS (Q1) 373.2 (M)+.

Example 406

5-(7-methyl-6-(5-((4-methylpiperazin-1-yl)methyl)
thiophen-3-yl)-4-morpholinothieno[3,2-d]pyrimidin-
2-yl)pyrimidin-2-amine 493

2-Chloro-6-iodo-7-methyl-4-morpholin-4-yl-thieno[3,2-d]pyrimidine (500 mg) was reacted with 220 mg of 2-formyl thiophene-4-boronic acid via General Procedure A to yield 4-(2-Chloro-7-methyl-4-morpholin-4-yl-thieno[3,2-d]pyrimidin-6-yl)-thiophene-2-carbaldehyde (382 mg, 80%).

4-(2-Chloro-7-methyl-4-morpholin-4-yl-thieno[3,2-d]pyrimidin-6-yl)-thiophene-2-carbaldehyde (100 mg) was reacted with 1-methylpiperazine via General Procedure D to yield 2-Chloro-7-methyl-6-[5-(4-methyl-piperazin-1-ylmethyl)-thiophen-3-yl]-4-morpholin-4-yl-thieno[3,2-d]pyrimidine.

2-Chloro-7-methyl-6-[5-(4-methyl-piperazin-1-ylmethyl)-thiophen-3-yl]-4-morpholin-4-yl-thieno[3,2-d]pyrimidine (130 mg) was reacted with 74 mg of 2-aminopyrimidine-5-boronic acid pinacol ester via General Procedure A. The product was purified by reverse phase HPLC to yield 7.7 mg of 493. MS (Q1) 523.2 (M)$^+$

Example 407

1-((4-(2-(2-aminopyrimidin-5-yl)-7-methyl-4-morpholinothieno[3,2-d]pyrimidin-6-yl)thiophen-2-yl)methyl)pyrrolidin-3-ol 494

4-(2-Chloro-7-methyl-4-morpholin-4-yl-thieno[3,2-d]pyrimidin-6-yl)-thiophene-2-carbaldehyde (100 mg) was reacted with 3-pyrrolidinol via General Procedure D to yield 1-[4-(2-Chloro-7-methyl-4-morpholin-4-yl-thieno[3,2-d]pyrimidin-6-yl)-thiophen-2-ylmethyl]-pyrrolidin-3-ol.

1-[4-(2-Chloro-7-methyl-4-morpholin-4-yl-thieno[3,2-d]pyrimidin-6-yl)-thiophen-2-ylmethyl]-pyrrolidin-3-ol (120 mg) was reacted with 74 mg of 2-aminopyrimidine-5-boronic acid pinacol ester via General Procedure A. The product was purified by reverse phase HPLC to yield 33.3 mg of 494. MS (Q1) 510.2 (M)$^+$

Example 408

4-(2-(2-aminopyrimidin-5-yl)-4-morpholinothieno[3,2-d]pyrimidin-6-yl)-N-(2-hydroxyethyl)-3-methyl-benzamide 495

2-Chloro-6-iodo-4-morpholin-4-yl-thieno[3,2-d]pyrimidine (500 mg) was reacted with 398 mg of 3-methyl-4-(4,4,5,5-tetramethyl-[1,3,2]dioxaborolan-2-yl)-benzoic acid methyl ester via General Procedure A to yield 450 mg of 4-(2-Chloro-4-morpholin-4-yl-thieno[3,2-d]pyrimidin-6-yl)-3-methyl-benzoic acid methyl ester.

4-(2-Chloro-4-morpholin-4-yl-thieno[3,2-d]pyrimidin-6-yl)-3-methyl-benzoic acid methyl ester (450 mg) was reacted with 296 mg of 2-aminopyrimidine-5-boronic acid pinacol ester via General Procedure A to yield 370 mg of 4-[2-(2-Amino-pyrimidin-5-yl)-4-morpholin-4-yl-thieno[3,2-d]pyrimidin-6-yl]-3-methyl-benzoic acid.

4-[2-(2-Amino-pyrimidin-5-yl)-4-morpholin-4-yl-thieno[3,2-d]pyrimidin-6-yl]-3-methyl-benzoic acid (60 mg) was reacted with ethanolamine via General Procedure C. The product was purified by reverse phase HPLC to yield 17.9 mg of 495. MS (Q1) 492.2 (M)$^+$

Example 409

(4-(2-(2-aminopyrimidin-5-yl)-4-morpholinothieno[3,2-d]pyrimidin-6-yl)-3-methylphenyl)(4-hydroxypiperidin-1-yl)methanone 496

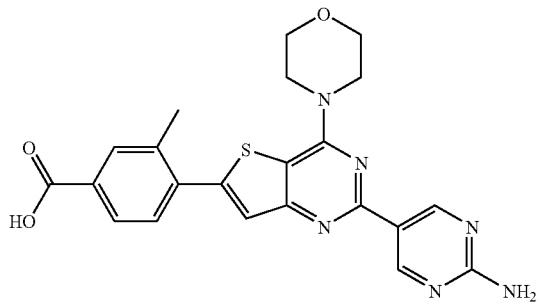 [SMILES: Cc1cc(C(=O)O)ccc1-c1cc2nc(-c3cnc(N)nc3)nc(N3CCOCC3)c2s1]

4-[2-(2-Amino-pyrimidin-5-yl)-4-morpholin-4-yl-thieno[3,2-d]pyrimidin-6-yl]-3-methyl-benzoic acid (60 mg) was reacted with 4-hydroxypiperidine via General Procedure C. The product was purified by reverse phase HPLC to yield 21.6 mg of 496. MS (Q1) 532.2 (M)$^+$

Example 410

(4-(2-(2-aminopyrimidin-5-yl)-4-morpholinothieno[3,2-d]pyrimidin-6-yl)-3-methylphenyl)(morpholino)methanone 497

4-[2-(2-Amino-pyrimidin-5-yl)-4-morpholin-4-yl-thieno[3,2-d]pyrimidin-6-yl]-3-methyl-benzoic acid (60 mg) was reacted with morpholine via General Procedure C. The product was purified by reverse phase HPLC to yield 24.8 mg of 497. MS (Q1) 518.2 (M)$^+$.

Example 411

2-(3-(2-(2-aminopyrimidin-5-yl)-7-methyl-4-morpholinothieno[3,2-d]pyrimidin-6-yl)phenoxy)ethanol 498

2-Chloro-6-iodo-7-methyl-4-morpholin-4-yl-thieno[3,2-d]pyrimidine (500 mg) was reacted with 192 mg of 3-hydroxybenazeneboronic acid via General Procedure A to yield 3-(2-chloro-7-methyl-4-morpholin-4-yl-thieno[3,2-d]pyrimidin-6-yl)-phenol (412 mg, 90%).

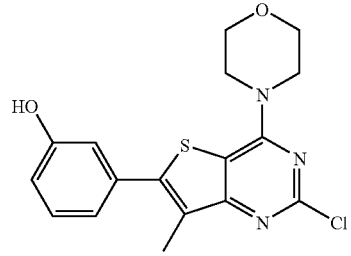 [SMILES: Cc1c(-c2cccc(O)c2)sc2c(N3CCOCC3)nc(Cl)nc12]

To a mixture of 3-(2-chloro-7-methyl-4-morpholin-4-yl-thieno[3,2-d]pyrimidin-6-yl)-phenol (80 mg, 0.22 mmol) and cesium carbonate (216 mg, 0.66 mmol) in DMF (1 mL) was added 2-chloroethanol (30 μL, 0.44 mmol). The reaction was heated to 60° C. overnight. The mixture was diluted with ethyl acetate, washed with water. The organic layer was dried over magnesium sulfate, filtered and evaporated to yield 90 mg of 2-[3-(2-chloro-7-methyl-4-morpholin-4-yl-thieno[3,2-d]pyrimidin-6-yl)-phenoxy]-ethanol.

2-[3-(2-Chloro-7-methyl-4-morpholin-4-yl-thieno[3,2-d] pyrimidin-6-yl)-phenoxy]-ethanol (90 mg) was reacted with 59 mg of 2-aminopyrimidine-5-boronic acid pinacol ester via General Procedure A. The product was purified by reverse phase HPLC to yield 33.4 mg of 498. MS (Q1) 465.2 (M)+

Example 412

3-(2-(2-aminopyrimidin-5-yl)-4-morpholinothieno[3,2-d]pyrimidin-7-yl)prop-2-yn-1-ol 499

A solution of toluene (0.6 mL) and diisopropyl amine (0.6 mL) containing 4-(2-chloro-7-iodothieno[3,2-d]pyrimidin-4-yl)morpholine (150 mg, 0.4 mmol), copper (I) iodide (4 mg), propargyl alcohol (3.2 mmol), and tetrakis(triphenylphosphine)palladium (15 mg) was heated in a sealed microwave reactor to 120° C. for 30 min. The resulting solution was concentrated in vacuo. The crude reaction material was utilized in a Suzuki coupling with (4,4,5,5-tetramethyl-1,3,2-dioxaborolan-2-yl)pyrimidin-2-amine according to General Procedure Suzuki to yield 499 (5 mg) after purification by reverse phase HPLC. MS (Q1) 369 (M)+

Example 413

2-methoxy-N-(5-(7-methyl-6-(3-(methylsulfonyl)phenyl)-4-morpholinothieno[3,2-d]pyrimidin-2-yl)pyridin-2-yl)acetamide 500

To a solution of 5-(7-methyl-6-(3-(methylsulfonyl)phenyl)-4-morpholinothieno[3,2-d]pyrimidin-2-yl)pyridin-2-amine 232 (50 mg, 0.1 mmol) in DMF (1 mL) and pyridine (1 mL) was added 2-methoxyacetyl chloride (2.0 mmol). The resulting reaction mixture has heated in a sealed microwave reactor at 200° C. for 15 min. The crude material was purified by reverse phase HPLC to afford 500 (14 mg). MS (Q1) 554 (M)+

Example 414

2-(2-methoxyethoxy)-N-(5-(7-methyl-6-(3-(methylsulfonyl)phenyl)-4-morpholinothieno[3,2-d]pyrimidin-2-yl)pyridin-2-yl)acetamide 501

To a solution of 5-(7-methyl-6-(3-(methylsulfonyl)phenyl)-4-morpholinothieno[3,2-d]pyrimidin-2-yl)pyridin-2-amine 232 (50 mg, 0.1 mmol) in DMF (1 mL) and pyridine (1 mL) was added 2-(methoxymethoxy)acetyl chloride (2.0 mmol). The resulting reaction mixture has heated in a sealed microwave reactor at 200° C. for 15 min. The crude material was purified by reverse phase HPLC to afford 501 (18 mg). MS (Q1) 598 (M)+

Example 415

2-(2-(4-(2-(2-aminopyrimidin-5-yl)-4-morpholinothieno[3,2-d]pyrimidin-6-yl)phenylamino)ethoxy)ethanol 502

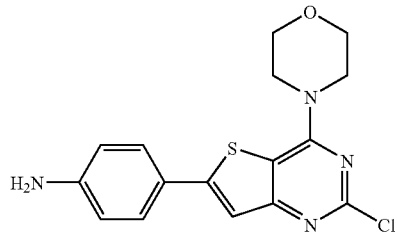 [SMILES: Nc1ccc(-c2cc3nc(Cl)nc(N4CCOCC4)c3s2)cc1]

2-Chloro-6-iodo-4-morpholinothieno[3,2-d]pyrimidine 19 from Example 12 (1 eq), 4-(4,4,5,5-tetramethyl-1,3,2-dioxaborolan-2-yl)aniline (1.1 eq) and bis(triphenylphosphine)palladium(II) dichloride (0.1 eq) in 1M Na$_2$CO$_3$ aqueous solution (3 eq) and an equal volume of acetonitrile was heated to 100° C. in a sealed microwave reactor for 30 min. Reaction mixture was concentrated, then crude product was purified by flash chromatography to give 4-(2-chloro-4-morpholinothieno[3,2-d]pyrimidin-6-yl)aniline. MS (Q1) 347 (M+)

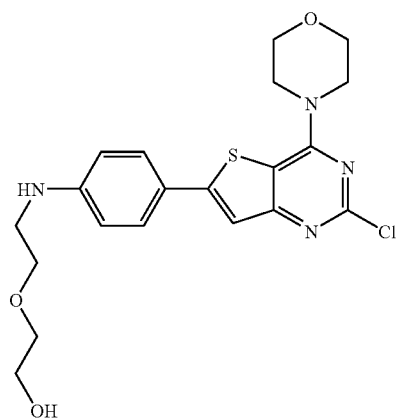 [SMILES: OCCOCCNc1ccc(-c2cc3nc(Cl)nc(N4CCOCC4)c3s2)cc1]

4-(2-Chloro-4-morpholinothieno[3,2-d]pyrimidin-6-yl) aniline (1.0 eq), 2-(2-chloroethoxy)ethanol (1.1 eq), potassium carbonate (1.1 eq) and potassium iodide (1.1 eq) in 0.25M acetonitrile was heated to 190° C. in a sealed microwave reactor for 15 min. Reaction mixture was diluted with dichloromethane, washed with sat. solution of sodium bicarbonate. The organic layer was dried over (MgSO$_4$) was concentrated, then crude product was purified by flash chromatography to give 2-(2-(4-(2-chloro-4-morpholinothieno[3,2-d]pyrimidin-6-yl)phenylamino)ethoxy)ethanol. MS (Q1) 435 (M+)

2-(2-(4-(2-Chloro-4-morpholinothieno[3,2-d]pyrimidin-6-yl)phenylamino)ethoxy)ethanol (1.0 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile was heated to 130° C. in a sealed microwave reactor for 10 min. The mixture was extracted with ethyl acetate (3×5 mL). The combined organic layers

Example 416

5-(4-morpholino-6-(4-(2-morpholinoethylamino)phenyl)thieno[3,2-d]pyrimidin-2-yl)pyrimidin-2-amine 503

4-(2-Chloro-4-morpholinothieno[3,2-d]pyrimidin-6-yl)aniline (1.0 eq), hydrochloride salt of 4-(2-chloroethyl)morpholine (1.0 eq), potassium carbonate (2.2 eq) and potassium iodide (1.1 eq) in 0.25M acetonitrile were heated to 190° C. in a sealed microwave reactor for 15 min. Reaction mixture was diluted with dichloromethane, washed with sat. solution of sodium bicarbonate. The organic layer was dried over (MgSO$_4$) was concentrated, then crude product was purified by flash chromatography to give 4-(2-chloro-4-morpholinothieno[3,2-d]pyrimidin-6-yl)-N-(2-morpholinoethyl)aniline. MS (Q1) 460 (M$^+$)

4-(2-Chloro-4-morpholinothieno[3,2-d]pyrimidin-6-yl)-N-(2-morpholinoethyl)aniline (1.0 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile was heated to 135° C. in a sealed microwave reactor for 10 min. The mixture was extracted with ethyl acetate (3×5 mL). The combined organic layers were concentrated to give, after purification by reverse HPLC, 9 mg of 503. MS (Q1) 519 (M$^+$)

Example 417

5-(7-methyl-4-morpholino-6-(3-(2-morpholinoethoxy)phenyl)thieno[3,2-d]pyrimidin-2-yl)pyrimidin-2-amine 504

To a mixture of 3-(2-chloro-7-methyl-4-morpholin-4-yl-thieno[3,2-d]pyrimidin-6-yl)-phenol (70 mg, 0.19 mmol) and cesium carbonate (252 mg, 0.77 mmol) in DMF (1 mL) was added 4-(2-chloroethyl)morpholine hydrochloride (72 mg, 0.39 mmol). The reaction was heated to 60° C. for 4 h. The mixture was diluted with ethyl acetate, washed with water. The organic layer was dried over magnesium sulfate, filtered and evaporated to yield 90 mg of 2-Chloro-7-methyl-4-morpholin-4-yl-6-[3-(2-morpholin-4-yl-ethoxy)-phenyl]-thieno[3,2-d]pyrimidine.

2-Chloro-7-methyl-4-morpholin-4-yl-6-[3-(2-morpholin-4-yl-ethoxy)-phenyl]-thieno[3,2-d]pyrimidine (90 mg) was reacted with 50 mg of 2-aminopyrimidine-5-boronic acid pinacol ester via General Procedure A. The product was purified by reverse phase HPLC to yield 53.7 mg of 504. MS (Q1) 534.2 (M)$^+$

Example 418

3-(2-(2-aminopyrimidin-5-yl)-7-methyl-4-morpholinothieno[3,2-d]pyrimidin-6-yl)phenol 505

3-(2-Chloro-7-methyl-4-morpholin-4-yl-thieno[3,2-d]pyrimidin-6-yl)-phenol (60 mg) was reacted with 44 mg of 2-aminopyrimidine-5-boronic acid pinacol ester via General Procedure A. The product was purified by reverse phase HPLC to yield 29 mg of 505. MS (Q1) 421.2 (M)$^+$

Example 419

N-(4-(2-(2-aminopyrimidin-5-yl)-7-methyl-4-morpholinothieno[3,2-d]pyrimidin-6-yl)benzyl)methanesulfonamide 506

2-Chloro-6-iodo-7-methyl-4-morpholinothieno[3,2-d]pyrimidine (100 mg) was reacted with 64 mg of 4-methanesulfonylaminomethyl phenyl boronic acid. The product was then coupled to 67 mg of 2-aminopyrimidine-5-boronic acid pinacol ester via General Procedure B. The product was purified by reverse phase HPLC to yield 5.2 mg of 506. MS (Q1) 512.2 (M)$^+$

Example 420

2-(3-(2-(2-aminopyrimidin-5-yl)-7-methyl-4-morpholinothieno[3,2-d]pyrimidin-6-yl)phenyl)-1-morpholinoethanone 507

2-(3-(2-(2-Aminopyrimidin-5-yl)-7-methyl-4-morpholinothieno[3,2-d]pyrimidin-6-yl)phenyl)acetic acid (70 mg) was reacted with morpholine via General Procedure C. The product was purified by reverse phase HPLC to yield 27.2 mg of 507. MS (Q1) 532.2 (M)$^+$

Example 421

2-(3-(2-(2-aminopyrimidin-5-yl)-7-methyl-4-morpholinothieno[3,2-d]pyrimidin-6-yl)phenyl)-N-(2-hydroxyethyl)acetamide 508

2-(3-(2-(2-Aminopyrimidin-5-yl)-7-methyl-4-morpholinothieno[3,2-d]pyrimidin-6-yl)phenyl)acetic acid (70 mg) was reacted with ethanolamine via General Procedure C. The product was purified by reverse phase HPLC to yield 18.4 mg of 508. MS (Q1) 506.2 (M)$^+$

Example 422

5-(6-(5-(2-aminopropan-2-yl)-1,2,4-oxadiazol-3-yl)-4-morpholinothieno[3,2-d]pyrimidin-2-yl)pyrimidin-2-amine 509

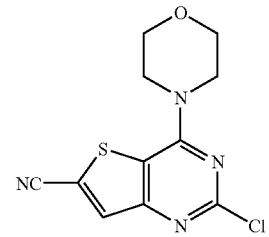

To a solution of 2-chloro-6-iodo-4-morpholinothieno[3,2-d]pyrimidine (1.0 g, 2.62 mmol) in 10 mL of anhydrous DMF was added 1.0 eq. of Zn(CN)$_2$ and 0.10 eq. of Pd tetrakistriphenylphosphine. The reaction was flash heated on the Emrys Optimizer at 150° C. for 10 minutes. The reaction mixture was diluted with water and extracted with EtOAc. The org. layer was dried (Na2SO4) and concentrated to a solid residue. The crude material was plated onto silica and purified by chromatography on silica eluting with a gradient of 1 to 10% MeOH in DCM to give 2-chloro-4-morpholinothieno[3,2-d]pyrimidine-6-carbonitrile in 60% yield. MS (Q1) 279.1, 281.2 (M)+

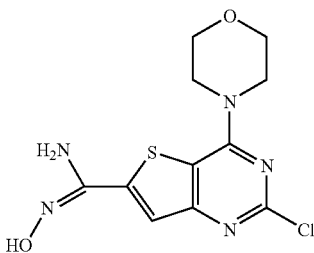 [SMILES: N/C(=N/O)c1cc2nc(Cl)nc(N3CCOCC3)c2s1]

A slurry of 2-chloro-4-morpholinothieno[3,2-d]pyrimidine-6-carbonitrile (0.35 mmol) and 2 eq. of H2NOH—HCl in 1.5 mL of DCM/EtOH (1/1) was heated at 60 C for several minutes followed by the addition of 2.3 eq. of TEA. The reaction was monitored by LC/MS for disappearance of starting material. After 4 hrs, the reaction was complete. The reaction mixture was cooled to room temperature and 2-chloro-N'-hydroxy-4-morpholinothieno[3,2-d]pyrimidine-6-carboximidamide was collected by vacuum filtration as a precipitate. No further purification was done. Yield=80%. MS (Q1) 314.0, 316.1 (M)+

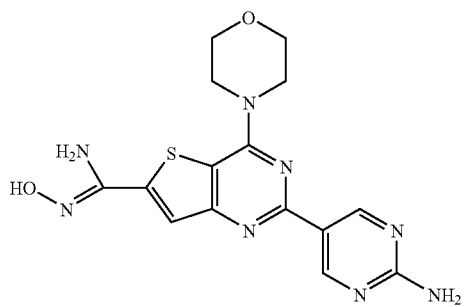 [SMILES: N/C(=N\O)c1cc2nc(-c3cnc(N)nc3)nc(N3CCOCC3)c2s1]

A reaction vial was charged with 2-chloro-N'-hydroxy-4-morpholinothieno[3,2-d]pyrimidine-6-carboximidamide (0.16 mmol) and 1.25 eq. of 2-aminopyrimidine-5-boronic acid, pinacol ester and reacted according to General Procedure A to give 2-(2-aminopyrimidin-5-yl)-N'-hydroxy-4-morpholinothieno[3,2-d]pyrimidine-6-carboximidamide as a precipitate in 90% yield. MS (Q1) 359.1 (M)+

A solution of Boc-aminoisobutyric acid (0.402 mmol) in 1.5 mL of anhydrous DMF was treated with 2.0 eq. of CDI for ~1 hr. Next, 1.0 eq. of 2-(2-aminopyrimidin-5-yl)-N'-hydroxy-4-morpholinothieno[3,2-d]pyrimidine-6-carboximidamide was added portion wise as a solid. This reaction was stirred at room temperature for more than 1 hr. then flash heated on an Emrys Optimizer microwave at 150° C. for 10 minutes to give the desired product. The amine was deprotected by treatment with TFA using standard conditions to give 509, isolated in 60% yield after RP-HPLC purification. MS (Q1) 440.2 (M)+, purity 92.97% by UV 254 nm, 1H NMR (DMSO)

Example 423

N-(1-(3-(2-(2-aminopyrimidin-5-yl)-4-morpholinothieno[3,2-d]pyrimidin-6-yl)-1,2,4-oxadiazol-5-yl)ethyl)acetamide 510

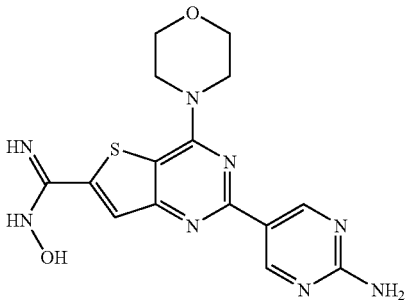 [SMILES: N=C(NO)c1cc2nc(-c3cnc(N)nc3)nc(N3CCOCC3)c2s1]

A solution of Boc-D,L-Ala-OH (0.80 mmol) in 3.0 mL of anh. DMF was treated with 2.0 eq. of CDI for ~1 hr. Next, 1.0 equiv. of 2-(2-aminopyrimidine-5-yl)-N-hydroxy-4-morpholinothieno[3,2-d]pyrimidine-6-carboxamidine was added portionwise as a solid. The reaction was stirred at room temperature for more than 1 hr, then flash heated on an Emrys Optimizer microwave at 150° C. for 10 minutes to give the N-Boc protected oxadiazole intermediate. The amine was deprotected by treatment with TFA using standard conditions and the free amine was converted to the acetamide via General Procedure B-4 to give 510, isolated in 68% yield after RP-HPLC purification. MS (Q1) 468.2 (M)+, 1H NMR (DMSO).

Example 424

2-(2-(5-(2-(2-aminopyrimidin-5-yl)-4-morpholinothieno[3,2-d]pyrimidin-6-yl)pyridin-2-yloxy)ethoxy)ethanol 511

To a solution of diethylene glycol (2.0 eq) in 0.5M tetrahydrofuran at 0° C. was added sodium hydride (60% in mineral oil, 2.2 eq). Reaction mixture was allowed to warm up at room temperature and stirred for 20 minutes. A slurry of 4-(2-chloro-6-(6-fluoropyridin-3-yl)thieno[3,2-d]pyrimidin-4-yl)morpholine (1.0 eq) in N,N-dimethylformamide (DMF) was added and the reaction mixture was stirred at room temperature for 15 minutes. The reaction mixture was diluted with dichloromethane, washed with water, the organic layer was dried over (MgSO4), and concentrated. The crude product was purified by flash chromatography to give 2-(2-(5-(2-chloro-4-morpholinothieno[3,2-d]pyrimidin-6-yl)pyridin-2-yloxy)ethoxy)ethanol. MS (Q1) 437 (M+)

2-(2-(5-(2-Chloro-4-morpholinothieno[3,2-d]pyrimidin-6-yl)pyridin-2-yloxy)ethoxy)ethanol (1.0 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M Na2CO3 aqueous solution (3 eq) and an equal volume of acetonitrile was heated to 130° C. in a sealed microwave reactor for 10 min. The mixture was extracted with ethyl acetate (3×5 mL). The combined organic layers were concentrated to give, after purification by reverse HPLC, 38 mg of 511. MS (Q1) 496 (M+)

Example 425

2-(2-(3-(2-(2-aminopyrimidin-5-yl)-4-morpholinothieno[3,2-d]pyrimidin-6-yl)phenylamino)ethoxy)ethanol 512

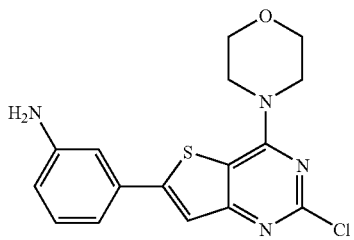 [SMILES: Nc1cccc(-c2cc3nc(Cl)nc(N4CCOCC4)c3s2)c1]

2-Chloro-6-iodo-4-morpholinothieno[3,2-d]pyrimidine 19 from Example 12 (1 eq), 3-(4,4,5,5-tetramethyl-1,3,2-dioxaborolan-2-yl)aniline (1.15 eq) and bis(triphenylphosphine)palladium(II) dichloride (0.1 eq) in 1M $Na_2CO_3$ aqueous solution (3 eq) and an equal volume of acetonitrile was heated to 100° C. in a sealed microwave reactor for 30 min. Reaction mixture was concentrated, then crude product was purified by flash chromatography to give 3-(2-chloro-4-morpholinothieno[3,2-d]pyrimidin-6-yl)aniline. MS (Q1) 347 ($M^+$)

3-(2-Chloro-4-morpholinothieno[3,2-d]pyrimidin-6-yl)aniline (1.0 eq), 2-(2-chloroethoxy)ethanol (1.1 eq), potassium carbonate (1.1 eq) and potassium iodide (1.1 eq) in 0.25M acetonitrile was heated to 170° C. in a sealed microwave reactor for 20 min. Reaction mixture was concentrated, then crude product was purified by flash chromatography to give 2-(2-(3-(2-chloro-4-morpholinothieno[3,2-d]pyrimidin-6-yl)phenylamino)ethoxy)ethanol. MS (Q1) 435 ($M^+$)

2-(2-(3-(2-Chloro-4-morpholinothieno[3,2-d]pyrimidin-6-yl)phenylamino)ethoxy)ethanol (1.0 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile was heated to 130° C. in a sealed microwave reactor for 10 min. The mixture was extracted with ethyl acetate (3×5 mL). The combined organic layers were concentrated to give, after purification by reverse HPLC, 32 mg of 512. MS (Q1) 494 ($M^+$)

Example 426

1-(5-(2-(2-aminopyrimidin-5-yl)-7-methyl-4-morpholinothieno[3,2-d]pyrimidin-6-yl)pyridin-2-yl)piperidin-3-ol 513

2-Chloro-6-(6-fluoropyridin-3-yl)-7-methyl-4-morpholinothieno[3,2-d]pyrimidine was reacted with piperidin-3-ol via General Procedure H to give, after purification by flash chromatography, the corresponding intermediate, which was then reacted with 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile and heating to 130-150° C. in a sealed microwave reactor for 7-20 min. The mixture was extracted with ethyl acetate (3×5 mL). The combined organic layers were concentrated to yield after purification by reverse HPLC, 59 mg of 513. MS (Q1) 505 ($M^+$)

Example 427

1-(5-(2-(2-aminopyrimidin-5-yl)-7-methyl-4-morpholinothieno[3,2-d]pyrimidin-6-yl)pyridin-2-yl)piperidin-4-ol 514

2-Chloro-6-(6-fluoropyridin-3-yl)-7-methyl-4-morpholinothieno[3,2-d]pyrimidine was reacted with piperidin-4-ol via General Procedure G to give, after purification by flash chromatography, the corresponding intermediate, which was then submitted to General Procedure G again to give, after purification by reverse HPLC, 68 mg of 514. MS (Q1) 505 ($M^+$)

Example 428

2-(5-(2-(2-aminopyrimidin-5-yl)-4-morpholinothieno[3,2-d]pyrimidin-6-yl)pyridin-2-ylamino)-1-morpholinoethanone 515

4-(2-Chloro-6-(6-fluoropyridin-3-yl)thieno[3,2-d]pyrimidin-4-yl)morpholine was reacted with hydrochloride salt of 2-amino-1-morpholino-1-ethanone via General Procedure H to give, after purification by flash chromatography, the corresponding intermediate, which was then submitted to General Procedure H again to give, after purification by reverse HPLC, 10 mg of 515. MS (Q1) 534 ($M^+$)

Example 429

2-(5-(2-(2-aminopyrimidin-5-yl)-7-methyl-4-morpholinothieno[3,2-d]pyrimidin-6-yl)pyridin-2-ylamino)-1-morpholinoethanone 516

2-Chloro-6-(6-fluoropyridin-3-yl)-7-methyl-4-morpholinothieno[3,2-d]pyrimidine was reacted with hydrochloride salt of 2-amino-1-morpholino-1-ethanone via General Procedure G to give, after purification by flash chromatography, the corresponding intermediate, which was then submitted to General Procedure G again to give, after purification by reverse HPLC, 11 mg of 516. MS (Q1) 548 ($M^+$)

Example 430

3-((5-(2-(2-aminopyrimidin-5-yl)-7-methyl-4-morpholinothieno[3,2-d]pyrimidin-6-yl)pyridin-2-yl)(methyl)amino)propane-1,2-diol 517

2-Chloro-6-(6-fluoropyridin-3-yl)-7-methyl-4-morpholinothieno[3,2-d]pyrimidine was reacted with 3-(methylamino)propane-1,2-diol via General Procedure G to give, after purification by flash chromatography, the corresponding intermediate, which was then submitted to General Procedure G again to give, after purification by reverse HPLC, 64 mg of 517. MS (Q1) 509 ($M^+$)

Example 431

3-(5-(2-(2-aminopyrimidin-5-yl)-7-methyl-4-morpholinothieno[3,2-d]pyrimidin-6-yl)pyridin-2-ylamino)propane-1,2-diol 518

2-Chloro-6-(6-fluoropyridin-3-yl)-7-methyl-4-morpholinothieno[3,2-d]pyrimidine was reacted with 3-aminopropane-1,2-diol via General Procedure G to give, after purification by flash chromatography, the corresponding intermediate, which was then submitted to General Procedure G again to give, after purification by reverse HPLC, 68 mg of 518. MS (Q1) 495 (M$^+$)

Example 432

N1-(5-(2-(2-aminopyrimidin-5-yl)-7-methyl-4-morpholinothieno[3,2-d]pyrimidin-6-yl)pyridin-2-yl)-2-methylpropane-1,2-diamine 519

2-Chloro-6-(6-fluoropyridin-3-yl)-7-methyl-4-morpholinothieno[3,2-d]pyrimidine was reacted with 2-methylpropane-1,2-diamine via General Procedure G to give, after purification by flash chromatography, the corresponding intermediate, which was then submitted to General Procedure G again to give, after purification by reverse HPLC, 52 mg of 519. MS (Q1) 492 (M$^+$)

Example 433

2-(5-(2-(2-aminopyrimidin-5-yl)-7-methyl-4-morpholinothieno[3,2-d]pyrimidin-6-yl)pyridin-2-ylamino)propan-1-ol 520

2-Chloro-6-(6-fluoropyridin-3-yl)-7-methyl-4-morpholinothieno[3,2-d]pyrimidine was reacted with 2-aminopropan-1-ol via General Procedure G to give, after purification by flash chromatography, the corresponding intermediate, which was then submitted to General Procedure G again to give, after purification by reverse HPLC, 69 mg of 520. MS (Q1) 479 (M$^+$)

Example 434

(R)-1-(5-(2-(2-aminopyrimidin-5-yl)-7-methyl-4-morpholinothieno[3,2-d]pyrimidin-6-yl)pyridin-2-yl)pyrrolidin-3-ol 521

2-Chloro-6-(6-fluoropyridin-3-yl)-7-methyl-4-morpholinothieno[3,2-d]pyrimidine was reacted with (R)-pyrrolidin-3-ol via General Procedure G to give, after purification by flash chromatography, the corresponding intermediate, which was then submitted to General Procedure G again to give, after purification by reverse HPLC, 35 mg of 521. MS (Q1) 491 (M$^+$)

Example 435

2-(2-(5-(2-(2-aminopyrimidin-5-yl)-7-methyl-4-morpholinothieno[3,2-d]pyrimidin-6-yl)pyridin-2-ylamino)ethoxy)ethanol 522

2-Chloro-6-(6-fluoropyridin-3-yl)-7-methyl-4-morpholinothieno[3,2-d]pyrimidine was reacted with 2-(2-aminoethoxy)ethanol via General Procedure G to give, after purification by flash chromatography, the corresponding intermediate, which was then submitted to General Procedure G again to give, after purification by reverse HPLC, 35 mg of 522. MS (Q1) 509 (M$^+$)

Example 436

5-(7-methyl-4-morpholino-6-(6-(2-morpholinoethylamino)pyridin-3-yl)thieno[3,2-d]pyrimidin-2-yl)pyrimidin-2-amine 523

2-Chloro-6-(6-fluoropyridin-3-yl)-7-methyl-4-morpholinothieno[3,2-d]pyrimidine was reacted with 2-morpholinoethanamine via General Procedure G to give, after purification by flash chromatography, the corresponding intermediate, which was then submitted to General Procedure G again to give, after purification by reverse HPLC, 92 mg of 523. MS (Q1) 534 (M$^+$)

Example 437

2-(3-(2-(2-aminopyrimidin-5-yl)-7-methyl-4-morpholinothieno[3,2-d]pyrimidin-6-yl)phenyl)-1-(4-hydroxypiperidin-1-yl)ethanone 524

2-(3-(2-(2-Aminopyrimidin-5-yl)-7-methyl-4-morpholinothieno[3,2-d]pyrimidin-6-yl)phenyl)acetic acid (60 mg) was reacted with 4-hydroxypiperidine via General Procedure C. The product was purified by reverse phase HPLC to yield 31.1 mg of 524. MS (Q1) 546.2 (M)$^+$ Example 438

2-(3-(2-(2-aminopyrimidin-5-yl)-7-methyl-4-morpholinothieno[3,2-d]pyrimidin-6-yl)phenyl)-1-(4-methylpiperazin-1-yl)ethanone 525

2-(3-(2-(2-Aminopyrimidin-5-yl)-7-methyl-4-morpholinothieno[3,2-d]pyrimidin-6-yl)phenyl)acetic acid (60 mg) was reacted with 1-methylpiperazine via General Procedure C. The product was purified by reverse phase HPLC to yield 34.6 mg of 525. MS (Q1) 545.2 (M)$^+$ Example 439

5-(7-methyl-6-(3-((4-methylpiperazin-1-yl)methyl)phenyl)-4-morpholinothieno[3,2-d]pyrimidin-2-yl)pyrimidin-2-amine 526

2-Chloro-6-iodo-7-methyl-4-morpholin-4-yl-thieno[3,2-d]pyrimidine (500 mg) was reacted with 210 mg of 3-formylphenylboronic acid via General Procedure A to yield 3-(2-Chloro-7-methyl-4-morpholin-4-yl-thieno[3,2-d]pyrimidin-6-yl)-benzaldehyde (430 mg, 83%).

To a mixture of 100 mg of 3-(2-Chloro-7-methyl-4-morpholin-4-yl-thieno[3,2-d]pyrimidin-6-yl)-benzaldehyde was treated with 29 mg of 1-methylpiperazine via General Procedure D to yield 120 mg of 2-Chloro-7-methyl-6-[3-(4-methyl-piperazin-1-ylmethyl)-phenyl]-4-morpholin-4-yl-thieno[3,2-d]pyrimidine.

2-Chloro-7-methyl-6-[3-(4-methyl-piperazin-1-ylmethyl)-phenyl]-4-morpholin-4-yl-thieno[3,2-d]pyrimidine (120 mg) was reacted with 70 mg of 2-aminopyrimidine-5-boronic acid pinacol ester via General Procedure A. The product was purified by reverse phase HPLC to yield 109 mg of 526. MS (Q1) 517.3 (M)$^+$ Example 440

2-(3-(2-(2-aminopyrimidin-5-yl)-7-methyl-4-morpholinothieno[3,2-d]pyrimidin-6-yl)phenyl)acetic acid 527

2-Chloro-6-iodo-7-methyl-4-morpholinothieno[3,2-d]pyrimidine (500 mg) was reacted with 360 mg of phenylacetic acid-3-boronic acid pinacol ester. Upon completion, then was coupled to 307 mg of 2-aminopyrimidine-5-boronic acid pinacol ester via General Procedure B to yield 527 (850 mg, 77%). MS (Q1) 563.2 (M)$^+$

Example 441

N-((2-(2-aminothiazol-5-yl)-4-morpholinothieno[3,2-d]pyrimidin-6-yl)methyl)-N-methylmethanesulfonamide 528

2-Chloro-4-morpholin-4-yl-thieno[3,2-d]pyrimidine-6-carbaldehyde 10 and 40% methylamine in water were reacted according to the standard reductive amination conditions to give (2-chloro-4-morpholin-4-yl-thieno[3,2-d]pyrimidin-6-ylmethyl)-methylamine which was treated with methanesulfonyl chloride and triethylamine in dichloromethane via General Procedure C-2 to give N-(2-Chloro-4-morpholin-4-yl-thieno[3,2-d]pyrimidin-6-ylmethyl)-N-methyl-methanesulfonamide.

A suspension of N-(2-chloro-4-morpholin-4-yl-thieno[3,2-d]pyrimidin-6-ylmethyl)-N-methyl-methanesulfonamide (115 mg, 0.32 mmol), (5-tributylstannyl-thiazol-2-yl)-carbamic acid tert-butyl ester (233 mg, 0.47 mmol), and Pd(PPh$_3$)$_4$ (19 mg, 0.016 mmol) in anhydrous DMA was heated in a microwave at 150° C. for 15 mins. The crude reaction mixture was loaded onto a preconditioned SCX cartridge, washing the cartridge with methanol and dichloromethane before eluting with 7N ammonia in methanol. The crude product was purified by silica using 30% methanol in ethyl acetate as the eluent to give 528 as a white solid (17 mg, 12%). NMR (CDCl$_3$, 400 MHz), 2.83 (3H, s), 2.84 (3H, s), 3.79 (4H, t, J=4.4), 3.91 (4H, t, J=4.8), 4.54 (2H, s), 4.96 (2H, s), 7.22 (1H, s), 7.85 (1H, s). MS: (ESI+): MH+=441

Example 442

5-(6-((methylamino)methyl)-4-morpholinothieno[3,2-d]pyrimidin-2-yl)pyrimidin-2-amine 529

(2-Chloro-4-morpholin-4-yl-thieno[3,2-d]pyrimidin-6-ylmethyl)-methylamine and 5-(4,4,5,5-tetramethyl-[1,3,2]dioxaborolan-2-yl)-pyrimidin-2-ylamine were reacted according to the General Procedure A to give 529. NMR (CDCl$_3$, 400 MHz), 2.56 (3H, s), 3.89 (4H, t, J=5.2), 4.05 (4H, t, J=4.8), 4.11 (2H, d, J=0.8), 5.24 (2H, s), 7.29 (1H, s), 9.30 (2H, s). MS: (ESI+): MH+=358

Example 443

N-((2-(2,4-dimethoxypyrimidin-5-yl)-4-morpholinothieno[3,2-d]pyrimidin-6-yl)methyl)-N-methylmethanesulfonamide 530

(2-Chloro-4-morpholin-4-yl-thieno[3,2-d]pyrimidin-6-ylmethyl)-methylamine and methanesulfonyl chloride with triethylamine in dichloromethane were reacted via General Procedure C-2 to give N-(2-chloro-4-morpholin-4-yl-thieno[3,2-d]pyrimidin-6-ylmethyl)-N-methyl-methanesulfonamide.

N-(2-Chloro-4-morpholin-4-yl-thieno[3,2-d]pyrimidin-6-ylmethyl)-N-methyl-methanesulfonamide and 2,4-dimethoxy-5-(4,4,5,5-tetramethyl-[1,3,2]dioxaborolan-2-yl)-pyrimidine were reacted according to General Procedure A to give 530. NMR (CDCl$_3$, 400 MHz), 2.95 (3H, s), 2.96 (3H, s), 3.88 (4H, t, J=4.8), 4.04 (4H, t, J=5.2), 4.09 (3H, s), 4.12 (3H, s), 4.66 (2H, s), 7.42 (1H, s), 8.96 (1H, s). MS: (ESI+): MH+=481

Example 444

N-((2-(2,4-dimethoxypyrimidin-5-yl)-4-morpholinothieno[3,2-d]pyrimidin-6-yl)methyl)-N-methylacetamide 531

2-chloro-4-morpholin-4-yl-thieno[3,2-d]pyrimidine-6-carbaldehyde (Intermediate 10) and 40% methylamine in water were reacted according to General Procedure B-4 to give (2-chloro-4-morpholin-4-yl-thieno[3,2-d]pyrimidin-6-ylmethyl)-methylamine.

(2-Chloro-4-morpholin-4-yl-thieno[3,2-d]pyrimidin-6-ylmethyl)-methylamine (190 mg, 0.64 mmol) was dissolved in 10 ml tetrahydrofuran and cooled to 0° C. under N$_2$ before adding triethylamine (180 ul, 1.3 mmol) and acetyl chloride (50 ul, 0.7 mmol). The reaction mixture was stirred 16 hrs at room temperature. The reaction was extracted into ethyl acetate washing with water, the organic layer dried over MgSO$_4$, and concentrated in vacuo to give N-(2-chloro-4-morpholin-4-ylthieno[3,2-d]pyrimidin-6-ylmethyl)-N-methyl-acetamide (135 mg, 73%).

N-(2-chloro-4-morpholin-4-ylthieno[3,2-d]pyrimidin-6-ylmethyl)-N-methyl-acetamide and 2,4-dimethoxy-5-(4,4,5,5-tetramethyl-[1,3,2]dioxaborolan-2-yl)-pyrimidine were reacted according to General Procedure A to give 431. NMR (CDCl$_3$, 400 MHz), 2.10 (3H, s), 2.97 (3H, s), 3.77 (4H, t, J=4.4), 3.92 (4H, t, J=4.4), 3.99 (3H, s), 4.02 (3H, s), 4.74 (2H, s), 7.26 (1H, s), 8.71 (1H, s). MS: (ESI+): MH+=445

Example 445

(R)-1-(4-(2-(2-aminopyrimidin-5-yl)-4-morpholinothieno[3,2-d]pyrimidin-6-yl)pyridin-2-yl)pyrrolidin-3-ol 532

5-(6-(2-Fluoropyridin-4-yl)-4-morpholinothieno[3,2-d]pyrimidin-2-yl)pyrimidin-2-amine was reacted with (R)-pyrrolidin-3-ol via General Procedure I to give, after purification by reverse HPLC, 32 mg of 532. MS (Q1) 477 (M$^+$)

Example 446

5-(4-morpholino-6-(6-(2-morpholinoethoxy)pyridin-3-yl)thieno[3,2-d]pyrimidin-2-yl)pyrimidin-2-amine 533

To a solution of diethylene glycol (2.0 eq) in 0.5M tetrahydrofuran at 0° C. was added sodium hydride (60% in mineral oil, 2.2 eq). Reaction mixture was allowed to warm up at room temperature and stirred for 20 minutes. A slurry of 4-(2-chloro-6-(6-fluoropyridin-3-yl)thieno[3,2-d]pyrimidin-4-yl)morpholine (1.0 eq) in N,N-dimethylformamide was added and reaction mixture was stirred at room temperature for 5 minutes, then at 50° C. for 5 minutes. Reaction mixture was diluted with dichloromethane, washed with water. The organic layer was dried over (MgSO$_4$) was concentrated, then crude product was purified by flash chromatography to give 4-(2-(5-(2-chloro-4-morpholinothieno[3,2-d]pyrimidin-6-yl)pyridin-2-yloxy)ethyl)morpholine. MS (Q1) 462 (M$^+$)

4-(2-(5-(2-chloro-4-morpholinothieno[3,2-d]pyrimidin-6-yl)pyridin-2-yloxy)ethyl)morpholine (1.0 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M Na$_2$CO$_3$ aqueous solution (3 eq) and an equal volume of acetonitrile was heated to 130° C. in a sealed microwave reactor for 10 min. The mixture was extracted with ethyl acetate (3×5 mL). The combined organic layers were concentrated to give, after purification by reverse HPLC, 7 mg of 533. MS (Q1) 521 (M$^+$)

Example 447

N-(5-(2-(2-aminopyrimidin-5-yl)-4-morpholinothieno[3,2-d]pyrimidin-6-yl)pyridin-2-yl)methanesulfonamide 534

2-Chloro-6-iodo-4-morpholinothieno[3,2-d]pyrimidine 19 from Example 12 (1 eq), 5-(4,4,5,5-tetramethyl-[1,3,2]dioxaborolan-2-yl)-pyridin-2-ylamine (1.15 eq) and bis(triphenylphosphine)palladium(II) dichloride (0.1 eq) in 1M Na$_2$CO$_3$ aqueous solution (3 eq) and an equal volume of acetonitrile was heated to 100° C. in a sealed microwave reactor for 30 min. Reaction mixture was concentrated, then crude product (1.0 eq) was dissolved in 0.2M pyridine and MsCl (5.0 eq) was added at room temperature. Reaction mixture was heated at 50° C. for 1 hour. Reaction mixture was diluted with dichloromethane, washed with sat. solution of sodium bicarbonate. The organic layer was dried over (MgSO$_4$) was concentrated, then crude product was purified by flash chromatography to give N-(5-(2-chloro-4-morpholinothieno[3,2-d]pyrimidin-6-yl)pyridin-2-yl)methanesulfonamide. MS (Q1) 426 (M$^+$)

N-(5-(2-chloro-4-morpholinothieno[3,2-d]pyrimidin-6-yl)pyridin-2-yl)methanesulfonamide (1.0 eq), 5-(4,4,5,5-tetramethyl-1,3,2-dioxaborolan-2-yl)pyrimidin-2-amine (1.0 eq) and bis(triphenylphosphine)palladium(II) dichloride (0.1 eq) in 1M Na$_2$CO$_3$ aqueous solution (3 eq) and an equal volume of acetonitrile was heated to 130° C. in a sealed microwave reactor for 10 min. The mixture was extracted with ethyl acetate (3×5 mL). The combined organic layers were concentrated to give, after purification by reverse HPLC, 2 mg of 534. MS (Q1) 485 (M$^+$)

Example 448

5-(6-(2-(methylsulfonyl)pyridin-4-yl)-4-morpholinothieno[3,2-d]pyrimidin-2-yl)pyrimidin-2-amine 535

5-(6-(2-Fluoropyridin-4-yl)-4-morpholinothieno[3,2-d]pyrimidin-2-yl)pyrimidin-2-amine (1.0 eq), sodium salt of sulfinic acid (5.0 eq) and diisopropylethylamine (5.0 eq) in N-methylpyrrolidine (~0.1M) was heated to 190° C. in a sealed microwave reactor for 30 minutes. Upon completion, N-methylpyrrolidine was concentrated under high vacuum to give, after purification by reverse HPLC, 29 mg of 535. MS (Q1) 470 (M$^+$)

Example 449

N1-(4-(2-(2-aminopyrimidin-5-yl)-4-morpholinothieno[3,2-d]pyrimidin-6-yl)pyridin-2-yl)-N2,N2-dimethylethane-1,2-diamine 536

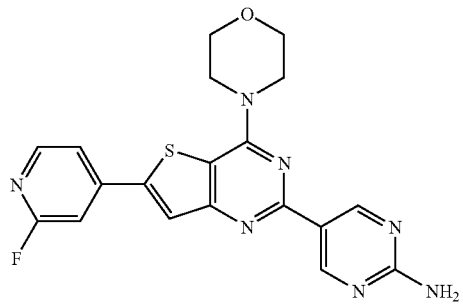 [SMILES: Nc1ncc(-c2nc(N3CCOCC3)c3sc(-c4ccnc(F)c4)cc3n2)cn1]

2-Chloro-6-iodo-4-morpholinothieno[3,2-d]pyrimidine 19 from Example 12 (1 eq), 2-fluoro-4-pyridineboronic acid (1.1 eq) and bis(triphenylphosphine)palladium(II) dichloride (0.1 eq) in 1M Na$_2$CO$_3$ aqueous solution (3 eq) and an equal volume of acetonitrile was heated to 100° C. in a sealed microwave reactor for 30 min. Reaction mixture was concentrated and crude mixture was purified by flash chromatography. The obtained intermediate (1.0 eq) was then treated with 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile was heated to 130-150° C. in a sealed microwave reactor for 7-20 min. The mixture was extracted with ethyl acetate (3×5 mL). The combined organic layers were concentrated in vacuo. Crude mixture was purified by flash chromatography to give 5-(6-(2-fluoropyridin-4-yl)-4-morpholinothieno[3,2-d]pyrimidin-2-yl)pyrimidin-2-amine. MS (Q1) 411 (M$^+$)

5-(6-(2-Fluoropyridin-4-yl)-4-morpholinothieno[3,2-d]pyrimidin-2-yl)pyrimidin-2-amine was reacted with N1,N1-dimethylethane-1,2-diamine via General Procedure I to give, after purification by reverse HPLC, 27 mg of 536. MS (Q1) 478 (M$^+$)

Example 450

5-(6-(2-((2-methoxyethyl)(methyl)amino)pyridin-4-yl)-4-morpholinothieno[3,2-d]pyrimidin-2-yl)pyrimidin-2-amine 537

5-(6-(2-Fluoropyridin-4-yl)-4-morpholinothieno[3,2-d]pyrimidin-2-yl)pyrimidin-2-amine was reacted with 2-methoxy-N-methylethanamine via General Procedure I to give, after purification by reverse HPLC, 71 mg of 537. MS (Q1) 479 (M$^+$)

Example 451

2-(4-(2-(2-aminopyrimidin-5-yl)-4-morpholinothieno[3,2-d]pyrimidin-6-yl)pyridin-2-ylamino)propan-1-ol 538

5-(6-(2-Fluoropyridin-4-yl)-4-morpholinothieno[3,2-d]pyrimidin-2-yl)pyrimidin-2-amine was reacted with 2-aminopropan-1-ol via General Procedure I to give, after purification by reverse HPLC, 24 mg of 538. MS (Q1) 465 (M+)

Example 452

5-(4-morpholino-6-(2-(2-morpholinoethylamino) pyridin-4-yl)thieno[3,2-d]pyrimidin-2-yl)pyrimidin-2-amine 539

5-(6-(2-Fluoropyridin-4-yl)-4-morpholinothieno[3,2-d] pyrimidin-2-yl)pyrimidin-2-amine was reacted with 2-morpholinoethanamine via General Procedure I to give, after purification by reverse HPLC, 15 mg of 539. MS (Q1) 520 (M+)

Example 453

5-(6-(2-(2-(methylsulfonyl)ethylamino)pyridin-4-yl)-4-morpholinothieno[3,2-d]pyrimidin-2-yl)pyrimidin-2-amine 540

5-(6-(2-Fluoropyridin-4-yl)-4-morpholinothieno[3,2-d] pyrimidin-2-yl)pyrimidin-2-amine was reacted with 2-aminoethylmethylsulfone via General Procedure I to give, after purification by reverse HPLC, 12 mg of 540. MS (Q1) 513 (M+)

Example 454

1-(4-(2-(2-aminopyrimidin-5-yl)-4-morpholinothieno[3,2-d]pyrimidin-6-yl)pyridin-2-yl)piperidin-3-ol 541

5-(6-(2-Fluoropyridin-4-yl)-4-morpholinothieno[3,2-d] pyrimidin-2-yl)pyrimidin-2-amine was reacted with 3-piperidinol via General Procedure I to give, after purification by reverse HPLC, 68 mg of 541. MS (Q1) 491 (M+)

Example 455

2-(4-(5-(2-(2-aminopyrimidin-5-yl)-4-morpholinothieno[3,2-d]pyrimidin-6-yl)pyridin-2-yl)piperazin-1-yl)ethanol 542

4-(2-Chloro-6-(6-fluoropyridin-3-yl)thieno[3,2-d]pyrimidin-4-yl)morpholine was reacted with 2-(piperazin-1-yl) ethanol via General Procedure H to give, after purification by flash chromatography, the corresponding intermediate, which was then submitted to General Procedure H again to give, after purification by reverse HPLC, 3 mg of 542. MS (Q1) 520 (M+)

Example 456

5-(6-(2-(4-(methylsulfonyl)piperazin-1-yl)propan-2-yl)-4-morpholinothieno[3,2-d]pyrimidin-2-yl)pyrimidin-2-amine 543

To a solution of 2-chloro-4-morpholin-4-yl-thieno[3,2-d] pyrimidine (5.0 g) in THF (100 mL) at −78° C. was added n-butyllithium (9.41 mL). The reaction mixture was stirred at −78° C. for 1 h and then dry $CO_2$ was bubble through the mixture. The reaction was allowed to warm to room temperature over 16 h and then quenched with water (20 mL) and the solvent reduced in vacuo. The mixture was then diluted with saturated aqueous sodium hydrogencarbonate solution (30 mL) and washed with ethyl acetate (40 mL). The aqueous layer was acidified with 2 M aqueous hydrochloric acid and the product filtered and air dried to give 2-chloro-4-morpholin-4-yl-thieno[3,2-d]pyrimidine-6-carboxylic acid (4.21 g).

To a solution of 2-chloro-4-morpholin-4-yl-thieno[3,2-d] pyrimidine-6-carboxylic acid (1.85 g) in DMF (30 mL) was added 1,1-carbonyldiimidazole (2.00 g) and the reaction mixture was stirred at room temperature for 1 h. Then, triethylamine (2.58 mL) and 1-methanesulfonyl-piperazine hydrochloride salt (2.48 g) were added and the reaction mixture stirred at room temperature for 16 h. The reaction was then quenched with water (20 mL) and the product filtered, washed with water and air dried to give (2-chloro-4-morpholin-4-yl-thieno[3,2-d]pyrimidin-6-yl)-(4-methanesulfonyl-piperazin-1-yl)-methanone (1.80 g).

To a solution of (2-chloro-4-morpholin-4-yl-thieno[3,2-d]pyrimidin-6-yl)-(4-methanesulfonyl-piperazin-1-yl)-methanone (1.80 g) in THF (40 mL) at −10° C. was added zirconium (IV) chloride (4.71 g). After stirring at −10° C. for 10 minutes, methylmagnesium bromide (8.09 mL of a 3 M solution) was added dropwise and the mixture allowed to warm to room temperature over 16 h. The mixture was then diluted with water (40 mL) and extracted into ethyl acetate (3×40 mL). The aqueous layer was made basic with sodium carbonate and reextracted into ethyl acetate (2×20 mL). The combined organics were washed with brine (2×40 mL), dried ($MgSO_4$), reduced in vacuo and purified by column chromatography to give 2-chloro-6-[1-(4-methanesulfonyl-piperazin-1-yl)-1-methyl-ethyl]-4-morpholin-4-yl-thieno[3,2-d]pyrimidine.

2-Chloro-6-[1-(4-methanesulfonyl-piperazin-1-yl)-1-methyl-ethyl]-4-morpholin-4-yl-thieno[3,2-d]pyrimidine was reacted with 2-aminopyrimidine-5-boronic acid pinacol ester in General Procedure A. Purification on silica yielded 543. NMR: ($CDCl_3$): 1.45 (6H, s, Me), 2.62-2.65 (4H, m), 2.74 (3H, s, Me), 3.18-3.21 (4H, m), 3.80-3.83 (4H, m), 3.94-3.97 (4H, m), 5.13 (2H, s, NH), 7.18 (1H, s, Ar) and 9.20 (2H, m, Ar). MS: (ESI+): MH+=519.23

Example 457

2-(2-(2,4-dimethoxypyrimidin-5-yl)-4-morpholinothieno[3,2-d]pyrimidin-6-yl)propan-2-ol 544

To a suspension of 2-chloro-4-morpholin-4-yl-thieno[3,2-d]pyrimidine (1.24 g) in dry THF (20 mL) cooled to −78° C. was added nBuLi (2.5M solution in hexanes, 2.32 mL). After stirring for 1 hour, acetone (0.53 mL) was added and the reaction mixture was warmed slowly to room temperature. After one hour the reaction mixture was poured onto water and the solid was collected by filtration. Purification on silica yielded 2-(2-chloro-4-morpholin-4-yl-thieno[3,2-d]pyrimidin-6-yl)-propan-2-ol (340 mg).

2-(2-Chloro-4-morpholin-4-yl-thieno[3,2-d]pyrimidin-6-yl)-propan-2-ol (125 mg, 0.40 mmol) was reacted with 2,4-dimethoxypyrimidine 5-boronic acid (103 mg, 0.56 mmol) in General Procedure A. Purification on silica and then using an SCX cartridge gave 544 as a white solid (53 mg, 32%) NMR (CDCl3, 400 MHz), 8.86 (s, 1H); 7.23 (s, 1H); 3.99 (s, 3H); 3.97 (s, 3H); 3.96 (t, 4H, J=4.8 Hz); 3.79 (t, 4H, J=4.8 Hz); 1.67 (s, 6H) MS: (ESI+): MH+=418.16

Example 458

5-(7-methyl-4-morpholino-6-(3-(morpholinomethyl) phenyl)thieno[3,2-d]pyrimidin-2-yl)pyrimidin-2-amine 545

2-Chloro-6-iodo-7-methyl-4-morpholinothieno[3,2-d]pyrimidine (70 mg) was reacted with 66 mg of 3-(4-morpholinomethyl)-phenylboronic acid pinacol ester. Upon completion, then was coupled to 47 mg of 2-aminopyrimidine-5-boronic acid pinacol ester via General Procedure B. The product was purified by reverse phase HPLC to yield 9.8 mg of 545. MS (Q1) 504.2 (M)$^+$

Example 459

(5-(2-(2-aminopyrimidin-5-yl)-7-methyl-4-morpholinothieno[3,2-d]pyrimidin-6-yl)pyridin-3-yl)(4-methylpiperazin-1-yl)methanone 546

2-Chloro-6-iodo-7-methyl-4-morpholinothieno[3,2-d]pyrimidine (500 mg) was reacted with 384 mg of 3-ethoxycarbonylpyridine-5-boronic acid pinacol ester. The product was then coupled to 306 mg of 2-aminopyrimidine-5-boronic acid pinacol ester via General Procedure B to yield 250 mg of 5-[2-(2-Amino-pyrimidin-5-yl)-7-methyl-4-morpholin-4-yl-thieno[3,2-d]pyrimidin-6-yl]-nicotinic acid.

5-[2-(2-Amino-pyrimidin-5-yl)-7-methyl-4-morpholin-4-yl-thieno[3,2-d]pyrimidin-6-yl]-nicotinic acid (60 mg) was reacted with 1-methylpiperazine via General Procedure C. The product was purified by reverse phase HPLC to yield 10.2 mg of 546. MS (Q1) 532.2 (M)$^+$

Example 460

5-(6-((3,4-dihydro-6,7-dimethoxyisoquinolin-2(1H)-yl)methyl)-4-morpholinothieno[3,2-d]pyrimidin-2-yl)pyrimidin-2-amine 547

6,7-Dimethoxy-1,2,3,4-tetrahydroisoquinoline hydrochloride (421 mg, 1.8 mmol) was reacted with 2-chloro-4-morpholinothieno[3,2-d]pyrimidine-6-carbaldehyde 10 from Example 3 (400 mg, 1.4 mmol) via General Procedure B-3. After quenching with saturated Na$_2$CO$_3$ solution and extraction into chloroform, the organics were washed with brine, dried (MgSO$_4$), and reduced in vacuo. Trituration with hot ethyl acetate gave 2-(2-chloro-4-morpholin-4-yl-thieno[3,2-d]pyrimidin-6-ylmethyl)-6,7-dimethoxy-1,2,3,4-tetrahydro-isoquinoline.

2-(2-Chloro-4-morpholin-4-yl-thieno[3,2-d]pyrimidin-6-ylmethyl)-6,7-dimethoxy-1,2,3,4-tetrahydro-isoquinoline (90 mg, 0.198 mmol) was reacted with 2-amino-pyrimidine-5-boronic acid pinacol ester (60.5 mg, 0.27 mmol) in General Procedure A. After extraction into 2M HCl, the mixture was washed with EtOAc then basified and the precipitate collected by filtration to give 547 (56 mg, 0.1 mmol). NMR (CDCl3, 400 MHz), 9.21 (s, 2H); 7.25 (s, 1H); 6.55 (s, 1H); 6.43 (s, 1H); 5.22 (s, 2H); 3.94 (t, 4H, J=4.56 Hz); 3.93 (s, 2H); 3.78 (t, 4H, J=4.72 Hz); 3.78 (s, 3H); 3.74 (s, 3H); 3.62 (s, 2H); 2.79 (s, 4H). MS: (ESI+): MH+ 520.27

Example 461 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$, 0.05% Chaps, and 1 mM DTT) to 10 mM PIP$_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume Proxiplates (PerkinElmer, Wellesley, Mass.) Fluorescence polarization values were plotted as a function of the protein concentration, and the EC$_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110alpha PI3K (final concentration) combined with PIP2 (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume proxi plates (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope).

Example 462

In Vitro Cell Proliferation Assay

Efficacy of Formula Ia-d compounds were measured by a cell proliferation assay employing the following protocol (Promega Corp. Technical Bulletin TB288; Mendoza et al (2002) Cancer Res. 62:5485-5488):
1. An aliquot of 100 μl of cell culture containing about 10$^4$ cells (PC3, Detroit562, or MDAMB361.1) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 463

Caco-2 Permeability

Caco-2 cells were seeded onto Millipore Multiscreen plates at $1\times10^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B–A) to investigate active transport. A permeability coefficient value, $P_{app}$, for each compound, a measure of the rate of permeation of the compound across the membrane, was calculated. Compounds were grouped into low ($P_{app}</=1.0\times10^6$ cm/s) or high ($P_{app}>/=1.0\times10^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B$>/=1.0$ indicated the occurrence of active cellular efflux. The had $P_{app}$ values$>/=1.0\times10^6$ cm/s.

Example 464

Hepatocyte Clearance

Suspensions of cryopreserved human hepatocytes were used. Incubations were performed at compound concentration of 1 mM or 3 μM at a cell density of $0.5\times10^6$ viable cells/mL. The final DMSO concentration in the incubation was 0.25%. Control incubations were also performed in the absence of cells to reveal any non-enzymatic degradation. Duplicate samples (50 μL) were removed from the incubation mixture at 0, 5, 10, 20, 40 and 60 minutes (control sample at 60 minutes only) and added to MeOH—containing internal standard (100 μL)—to terminate the reaction. Tolbutamide, 7-hydroxycoumarin, and testosterone were used as control compounds. Samples were centrifuged and the supernatants at each time point pooled for analysis by LC-MSMS. From a plot of in peak area ratio (parent compound peak area/internal standard peak area) against time, intrinsic clearance ($CL_{int}$) was calculated as follows: $CL_{int}$ (μl/min/million cells)=V×k, where k is the elimination rate constant, obtained from the gradient of in concentration plotted against time; V is a volume term derived from the incubation volume and is expressed as uL $10^6$ cells$^{-1}$.

On the basis of low (CL$</=4.6$ μL/min/$10^6$ cells), medium (CL$>/=4.6$; $</=25.2$ μl/min/$10^6$ cells) and high ($>/=25.2$ μl/min/$10^6$ cells) clearance, the compound of the invention was determined to have low hepatocyte clearance.

Example 465

Cytochrome P450 Inhibition

Certain compound of the invention was screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The compound displayed weak activity ($IC_{50}>/=5$ uM) against all isoforms of CYP450.

Example 466

Cytochrome P450 Induction

Freshly isolated human hepatocytes from a single donor were cultured for 48 h prior to addition of test compound at three concentrations and were incubated for 72 h. Probe substrates for CYP3A4 and CYP1A2 were added for 30 minutes and 1 h before the end of the incubation. At 72 h, cells and media were removed and the extent of metabolism of each probe substrate quantified by LC-MS/MS. The experiment was controlled by using inducers of the individual P450s incubated at one concentration in triplicate. The compound of the invention showed negligible effects on induction of cytochrome P450 enzymes.

Example 467

Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 h in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for the compound was calculated: highly protein bound compounds ($>/=90$% bound) had an Fu$</=0.1$. The compound of the invention had an Fu value$>/=0.1$.

Example 468 hERG Channel Blockage

The compound of the invention was evaluated for its ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with $3\times100$ μL of pre-incubation buffer (containing low [K$^+$]) at room temperature. Following the final aspiration, 50 μL of working stock (2×) compound was added to each well and incubated at room temperature for 10 minutes. 50 μL of stimulation buffer (containing high [K+]) was then added to each well giving the final test compound concentrations. Cell plates were then incubated at room temperature for a further 10 minutes. 80 μL of supernatant from each well was then transferred to equivalent wells of a 96-well plate and analysed via atomic emission spectroscopy. The compound was screened as 10 pt duplicate $IC_{50}$ curves, n=2, from a top concentration of 100 μM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:
1. A compound selected from
4-(2-(2-aminopyrimidin-5-yl)-4-morpholinothieno[3,2-d] pyrimidin-6-yl)N-methylsulfonylpiperidin-4-ol;
N-((2-(2-aminopyrimidin-5-yl)-4-morpholinothieno[2,3-d]pyrimidin-6-yl)methyl)-N-methylbenzamide;
N-((2-(2-aminopyrimidin-5-yl)-4-morpholinothieno[2,3-d]pyrimidin-6-yl)methyl)-N-methylnicotinamide;
5-(6-(3-(N-methylsulfonylaminomethyl)phenyl)-7-methyl-4-morpholinothieno[3,2-d]pyrimidin-2-yl)pyrimidin-2-amine;
5-(6-(3-N-methylsulfonylaminophenyl)-7-methyl-4-morpholinothieno[3,2-d]pyrimidin-2-yl)pyrimidin-2-amine;
5-(6-(6-aminopyridin-3-yl)-7-methyl-4-morpholinothieno[3,2-d]pyrimidin-2-yl)pyrimidin-2-amine;
5-(6-(4-methoxypyridin-3-yl)-7-methyl-4-morpholinothieno[3,2-d]pyrimidin-2-yl)pyrimidin-2-amine;
5-(7-methyl-4-morpholino-6-(pyridin-3-yl)thieno[3,2-d] pyrimidin-2-yl)pyrimidin-2-amine;
5-(6-(4-(aminomethyl)phenyl)-4-morpholinothieno[3,2-d]pyrimidin-2-yl)pyrimidin-2-amine;
5-(6-(3-(aminomethyl)phenyl)-4-morpholinothieno[3,2-d]pyrimidin-2-yl)pyrimidin-2-amine;
5-(6-(4-amino-3-methoxyphenyl)-4-morpholinothieno[3,2-d]pyrimidin-2-yl)pyrimidin-2-amine;
N-(2-(2-(2-aminopyrimidin-5-yl)-4-morpholinothieno[3,2-d]pyrimidin-6-yl)propan-2-yl)-3-methoxybenzamide;
N-(2-(2-(2-aminopyrimidin-5-yl)-4-morpholinothieno[3,2-d]pyrimidin-6-yl)propan-2-yl)-4-methoxybenzamide;
5-(6-(4-N-methylsulfonylaminophenyl)-4-morpholinothieno[3,2-d]pyrimidin-2-yl)pyrimidin-2-amine;
N-(2-(2-(2-aminopyrimidin-5-yl)-4-morpholinothieno[3,2-d]pyrimidin-6-yl)propan-2-yl)nicotinamide;
N-(2-(2-(6-methylpyridin-3-yl)-4-morpholinothieno[3,2-d]pyrimidin-6-yl)propan-2-yl)benzamide;
5-(4-morpholino-6-(3-morpholinosulfonyl)phenylthieno[3,2-d]pyrimidin-2-yl)pyrimidin-2-amine;
5-(4-morpholino-6-(3-morpholinosulfonyl)phenylthieno[3,2-d]pyrimidin-2-yl)pyridin-2-amine;
5-(4-morpholino-6-(3-(2-hydroxyethylamino)sulfonyl)phenylthieno[3,2-d]pyrimidin-2-yl)pyridin-2-amine;
5-(4-morpholino-6-(3-aminosulfonyl)phenylthieno[3,2-d]pyrimidin-2-yl)pyridin-2-amine;
(S)—N-((4-(2-(2-aminopyrimidin-5-yl)-4-morpholinothieno[3,2-d]pyrimidin-6-yl)phenyl)methyl)-2-hydroxypropanamide;
N-((4-(2-(2-aminopyrimidin-5-yl)-4-morpholinothieno[3,2-d]pyrimidin-6-yl)phenyl)methyl)-2-hydroxyacetamide;
(2S)—N-((3-(2-(2-aminopyrimidin-5-yl)-4-morpholinothieno[3,2-d]pyrimidin-6-yl)phenyl)methyl)-2-hydroxypropanamide;
N-((3-(2-(2-aminopyrimidin-5-yl)-4-morpholinothieno[3,2-d]pyrimidin-6-yl)phenyl)methyl)acetamide;
N-((3-(2-(2-aminopyrimidin-5-yl)-4-morpholinothieno[3,2-d]pyrimidin-6-yl)phenyl)methyl)-2-hydroxyacetamide;
(4-(2-(2-aminopyrimidin-5-yl)-4-morpholinothieno[3,2-d]pyrimidin-6-yl)phenyl)(4-methylpiperazin-1-yl)methanone;
(4-(2-(2-aminopyrimidin-5-yl)-4-morpholinothieno[3,2-d]pyrimidin-6-yl)phenyl)(morpholino)methanone;
(4-(2-(6-aminopyridin-3-yl)-4-morpholinothieno[3,2-d] pyrimidin-6-yl)phenyl)(4-methylpiperazin-1-yl)methanone;
(4-(2-(6-aminopyridin-3-yl)-4-morpholinothieno[3,2-d] pyrimidin-6-yl)phenyl)(morpholino)methanone;
5-(6-(3-(1H-tetrazol-5-yl)phenyl)-4-morpholinothieno[3,2-d]pyrimidin-2-yl)pyrimidin-2-amine;
3-(2-(2-aminopyrimidin-5-yl)-4-morpholinothieno[3,2-d] pyrimidin-6-yl)benzoic acid;
3-(2-(6-aminopyridin-3-yl)-4-morpholinothieno[3,2-d] pyrimidin-6-yl)benzoic acid;
5-(6-(3-aminophenyl)-4-morpholinothieno[3,2-d]pyrimidin-2-yl)pyrimidin-2-amine;
5-(6-(3-aminophenyl)-4-morpholinothieno[3,2-d]pyrimidin-2-yl)pyridin-2-amine;
(3-(2-(2-aminopyrimidin-5-yl)-4-morpholinothieno[3,2-d]pyrimidin-6-yl)phenyl)(4-methylpiperazin-1-yl)methanone;
3-(2-(2-aminopyrimidin-5-yl)-4-morpholinothieno[3,2-d] pyrimidin-6-yl)-N—((S)-2-hydroxypropyl)benzamide;
(3-(2-(2-aminopyrimidin-5-yl)-4-morpholinothieno[3,2-d]pyrimidin-6-yl)phenyl)(morpholino)methanone;
3-(2-(6-aminopyridin-3-yl)-4-morpholinothieno[3,2-d] pyrimidin-6-yl)-N—((S)-2-hydroxypropyl)benzamide;
N-((2-(6-aminopyridin-3-yl)-7-methyl-4-morpholinothieno[3,2-d]pyrimidin-6-yl)methyl)-N-methylacetamide;
N-((2-(2-aminopyrimidin-5-yl)-7-methyl-4-morpholinothieno[3,2-d]pyrimidin-6-yl)methyl)-N-methylacetamide;
N-((2-(6-aminopyridin-3-yl)-7-methyl-4-morpholinothieno[3,2-d]pyrimidin-6-yl)methyl)-N-methylbenzamide;
N-((2-(2-aminopyrimidin-5-yl)-4-morpholinothieno[3,2-d]pyrimidin-6-yl)methyl)-2-methoxy-N-methylacetamide;
(3-(2-(6-aminopyridin-3-yl)-4-morpholinothieno[3,2-d] pyrimidin-6-yl)phenyl)(4-methylpiperazin-1-yl)methanone;
(3-(2-(6-aminopyridin-3-yl)-4-morpholinothieno[3,2-d] pyrimidin-6-yl)phenyl)(morpholino)methanone;
5-(4-morpholino-6-(3-N-2-hydroxyethylaminosulfonyl) phenylthieno[3,2-d]pyrimidin-2-yl)pyrimidin-2-amine;
5-(4-morpholino-6-(6-(4-methylsulfonylpiperazin-1-yl) pyridin-3-yl)thieno[3,2-d]pyrimidin-2-yl)pyrimidin-2-amine;
5-(4-morpholino-6-(6-(piperazin-1-yl)pyridin-3-yl)thieno [3,2-d]pyrimidin-2-yl)pyrimidin-2-amine;
5-(2-(2-aminopyrimidin-5-yl)-4-morpholinothieno[3,2-d] pyrimidin-6-yl)pyrazin-2-amine;
N-((2-(2-aminopyrimidin-5-yl)-4-morpholinothieno[2,3-d]pyrimidin-6-yl)methyl)-N-methylacetamide;
5-(6-(3-methylsulfonylaminophenyl)-4-morpholinothieno[3,2-d]pyrimidin-2-yl)pyrimidin-2-amine;
2-(2-(2-aminopyrimidin-5-yl)-7-methyl-4-morpholinothieno[3,2-d]pyrimidin-6-yl)propan-2-ol;

2-(2-(2-aminopyrimidin-5-yl)-4-morpholinothieno[3,2-d]pyrimidin-6-yl)-1,3-dimethoxypropan-2-ol;
2-(2-(2-aminopyrimidin-5-yl)-4-morpholinothieno[3,2-d]pyrimidin-6-yl)-1-methoxypropan-2-ol;
N-((2-(6-aminopyridin-3-yl)-4-morpholinothieno[2,3-d]pyrimidin-6-yl)methyl)-N-methylacetamide;
5-(6-(6-aminopyridin-3-yl)-4-morpholinothieno[3,2-d]pyrimidin-2-yl)pyrimidin-2-amine;
(2-(2-aminopyrimidin-5-yl)-4-morpholinothieno[3,2-d]pyrimidin-6-yl)(4-(2-hydroxyethyl)piperazin-1-yl)methanone;
(2-(2-aminopyrimidin-5-yl)-4-morpholinothieno[3,2-d]pyrimidin-6-yl)(4-methylpiperazin-1-yl)methanone;
2-2-aminopyrimidin-5-yl)-4-morpholino-N-(2-(piperidin-1-yl)ethyl)thieno[3,2-d]pyrimidine-6-carboxamide;
(2-(2-aminopyrimidin-5-yl)-4-morpholinothieno[3,2-d]pyrimidin-6-yl)(morpholino)methanone;
2-(2-aminopyrimidin-5-yl)-N-methyl-4-morpholinothieno[3,2-d]pyrimidine-6-carboxamide;
5-(6-((E)-3-methoxyprop-1-enyl)-4-morpholinothieno[3,2-d]pyrimidin-2-yl)pyrimidin-2-amine;
2-amino-N-(3-(2-(2-aminopyrimidin-5-yl)-4-morpholinothieno[3,2-d]pyrimidin-6-yl)phenyl)acetamide;
5-(6-((N-methyl,N-methylsulfonylamino)methyl)-4-morpholinothieno[2,3-d]pyrimidin-2-yl)pyrimidin-2-amine;
2-amino-N-(3-(2-(6-aminopyridin-3-yl)-4-morpholinothieno[3,2-d]pyrimidin-6-yl)phenyl)acetamide;
2-(3-(2-(2-aminopyrimidin-5-yl)-4-morpholinothieno[3,2-d]pyrimidin-6-yl)phenyl)propan-2-ol;
5-(6-((N-methyl,N-methylsulfonylamino)methyl)-4-morpholinothieno[2,3-d]pyrimidin-2-yl)pyridin-2-amine;
5-6-(3-(N-methylsulfonylaminomethyl)phenyl)-4-morpholinothieno[3,2-d]pyrimidin-2-yl)pyrimidin-2-amine;
5-(6-(2-(4-methylpiperazin-1-yl)pyridin-4-yl)-4-morpholinothieno[3,2-d]pyrimidin-2-yl)pyridin-2-amine;
5-(6-(2-(4-methylpiperazin-1-yl)pyridin-4-yl)-4-morpholinothieno[3,2-d]pyrimidin-2-yl)pyrimidin-2-amine;
2-(3-(2-(6-aminopyridin-3-yl)-4-morpholinothieno[3,2-d]pyrimidin-6-yl)phenyl)propan-2-ol;
1-(3-(2-(2-aminopyrimidin-5-yl)-4-morpholinothieno[3,2-d]pyrimidin-6-yl)phenyl)ethanol;
1-(3-(2-(6-aminopyridin-3-yl)-4-morpholinothieno[3,2-d]pyrimidin-6-yl)phenyl)ethanol;
3-(3-(2-(6-aminopyridin-3-yl)-4-morpholinothieno[3,2-d]pyrimidin-6-yl)phenyl)propan-1-ol;
3-(3-(2-(2-aminopyrimidin-5-yl)-4-morpholinothieno[3,2-d]pyrimidin-6-yl)phenyl)propan-1-ol;
(2-(2-aminopyrimidin-5-yl)-4-morpholinothieno[3,2-d]pyrimidin-6-yl)(N-4-methylsulfonylpiperazin-1-yl)methanone;
5-(6-(2-aminothiazol-4-yl)-4-morpholinothieno[3,2-d]pyrimidin-2-yl)pyridin-2-amine;
5-(6-(4-(4-methylpiperazin-1-yl)phenyl)-4-morpholinothieno[3,2-d]pyrimidin-2-yl)pyridin-2-amine;
5-(6-(3,5-dimethylisoxazol-4-yl)-4-morpholinothieno[3,2-d]pyrimidin-2-yl)pyrimidin-2-amine;
5-(4-morpholino-6-(6-morpholinopyridin-3-yl)thieno[3,2-d]pyrimidin-2-yl)pyrimidin-2-amine;
5-(6-(2-fluoro-5-methoxyphenyl)-4-morpholinothieno[3,2-d]pyrimidin-2-yl)pyrimidin-2-amine;
N-(2-(2-(2-aminopyrimidin-5-yl)-4-morpholinothieno[3,2-d]pyrimidin-6-yl)propan-2-yl)acetamide;
5-(6-(2-N-methylsulfonylaminopropan-2-yl)-4-morpholinothieno[3,2-d]pyrimidin-2-yl)pyrimidin-2-amine;
2-(6-aminopyridin-3-yl)-4-morpholinothieno[3,2-d]pyrimidine-6-carboxamide;
5-(7-methyl-6-((N-methyl,N-methylsulfonylamino)methyl)-4-morpholinothieno[3,2-d]pyrimidin-2-yl)pyridin-2-amine;
2-(2-aminopyrimidin-5-yl)-4-morpholinothieno[3,2-d]pyrimidine-6-carboxamide;
5-(6-(1H-indol-6-yl)-4-morpholinothieno[3,2-d]pyrimidin-2-yl)pyridin-2-amine;
5-(2-(6-aminopyridin-3-yl)-4-morpholinothieno[3,2-d]pyrimidin-6-yl)pyridin-2-amine;
N-(3-(2-(2-aminopyrimidin-5-yl)-4-morpholinothieno[3,2-d]pyrimidin-6-yl)phenyl)acetamide;
5-(6-(4-methoxypyridin-3-yl)-4-morpholinothieno[2,3-d]pyrimidin-2-yl)pyridin-2-amine;
2-(2-(2-aminopyrimidin-5-yl)-4-morpholinothieno[2,3-d]pyrimidin-6-yl)propan-2-ol;
2-(2-(6-aminopyridin-3-yl)-4-morpholinothieno[2,3-d]pyrimidin-6-yl)propan-2-ol;
5-(6-(3-(methylsulfonyl)phenyl)-4-morpholinothieno[2,3-d]pyrimidin-2-yl)pyridin-2-amine;
5-(6-(3-(methylsulfonyl)phenyl)-4-morpholinothieno[2,3-d]pyrimidin-2-yl)pyrimidin-2-amine;
N-(3-(2-(2-aminopyrimidin-5-yl)-4-morpholinothieno[2,3-d]pyrimidin-6-yl)phenyl)acetamide;
5-(6-(4-methoxypyridin-3-yl)-4-morpholinothieno[2,3-d]pyrimidin-2-yl)pyrimidin-2-amine;
N-((2-(6-aminopyridin-3-yl)-4-morpholinothieno[3,2-d]pyrimidin-6-yl)methyl)-N-methylacetamide;
N-((2-(2-aminopyrimidin-5-yl)-4-morpholinothieno[3,2-d]pyrimidin-6-yl)methyl)-N-methylacetamide;
N-acetyl-N-(5-(6-((N-methyl,N-methylsulfonylamino)methyl)-4-morpholinothieno[3,2-d]pyrimidin-2-yl)pyrimidin-2-yl)acetamide;
N-(5-(6-N-methyl,N-methylsulfonylamino)methyl)-4-morpholinothieno[3,2-d]pyrimidin-2-yl)pyrimidin-2-yl)acetamide;
N-(5-(6-((N-methyl,N-methylsulfonylamino)methyl)-4-morpholinothieno[3,2-d]pyrimidin-2-yl)pyridin-2-yl)acetamide;
5-(7-methyl-6-((N-methyl,N-methylsulfonylamino)methyl)-4-morpholinothieno[3,2-d]pyrimidin-2-yl)pyrimidin-2-amine;
5-(6-((N-methyl,N-methylsulfonylamino)methyl)-4-morpholinothieno[3,2-d]pyrimidin-2-yl)pyrimidin-2-amine;
5-(6-((N-methyl,N-methylsulfonylamino)methyl)-4-morpholinothieno[3,2-d]pyrimidin-2-yl)pyridin-2-amine;
5-(7-methyl-6-(3-(methylsulfonyl)phenyl)-4-morpholinothieno[3,2-d]pyrimidin-2-yl)pyrimidin-2-amine;
5-(7-methyl-6-(3-(methylsulfonyl)phenyl)-4-morpholinothieno[3,2-d]pyrimidin-2-yl)pyridin-2-amine;
2-(2-(2-aminopyrimidin-5-yl)-4-morpholinothieno[3,2-d]pyrimidin-6-yl)propan-2-ol;
N-((2-(2-aminopyrimidin-5-yl)-4-morpholinothieno[3,2-d]pyrimidin-6-yl)methyl)-N-methylbenzamide;
N-((2-(6-aminopyridin-3-yl)-4-morpholinothieno[3,2-d]pyrimidin-6-yl)methyl-N-methylbenzamide;
N-(2-(2-(2-aminopyrimidin-5-yl)-4-morpholinothieno[3,2-d]pyrimidin-6-yl)propan-2-yl)benzamide;
N-(2-(2-(6-aminopyridin-3-yl)-4-morpholinothieno[3,2-d]pyrimidin-6-yl)propan-2-yl)benzamide;
N-(5-(6-(4-methoxypyridin-3-yl)-4-morpholinofuro[3,2-d]pyrimidin-2-yl)pyridin-2-yl)acetamide;

N-(5-(6-(4-methoxypyridin-3-yl)-4-morpholinofuro[3,2-d]pyrimidin-2-yl)pyridin-2-yl)formamide;
5-(6-(3-(methylsulfonyl)phenyl)-4-morpholinothieno[3,2-d]pyrimidin-2-yl)pyrimidin-2-amine;
1-(5-(6-(3-(methylsulfonyl)phenyl)-4-morpholinothieno[3,2-d]pyrimidin-2-yl)pyridin-2-yl)urea;
N-(5-(6-(3-(methylsulfonyl)phenyl)-4-morpholinothieno[3,2-d]pyrimidin-2-yl)pyridin-2-yl)acetamide;
N-acetyl-N-(5-(6-(3-(methylsulfonyl)phenyl)-4-morpholinothieno[3,2-d]pyrimidin-2-yl)pyridin-2-yl)acetamide;
1-(3-(2-(6-aminopyridin-3-yl)-4-morpholinothieno[3,2-d]pyrimidin-6-yl)phenyl)ethanone;
5-(6-(3-methoxyphenyl)-4-morpholinothieno[3,2-d]pyrimidin-2-yl)pyridin-2-amine;
5-(6-(3-methylsulfonylaminophenyl)-4-morpholinothieno[3,2-d]pyrimidin-2-yl)pyridin-2-amine;
5-(6-(3-chlorophenyl)-4-morpholinothieno[3,2-d]pyrimidin-2-yl)pyridin-2-amine;
3-(2-(6-aminopyridin-3-yl)-4-morpholinothieno[3,2-d]pyrimidin-6-yl)-N-methylbenzamide;
5-(6-(4-methoxypyridin-3-yl)-4-morpholinothieno[3,2-d]pyrimidin-2-yl)pyridin-2-amine;
5-(4-morpholino-6-(pyridin-3-yl)thieno[3,2-d]pyrimidin-2-yl)pyridin-2-amine;
3-(2-(6-aminopyridin-3-yl)-4-morpholinothieno[3,2-d]pyrimidin-6-yl)benzamide;
(4-(2-(6-aminopyridin-3-yl)-4-morpholinothieno[3,2-d]pyrimidin-6-yl)phenyl)methanol;
(3-(2-(6-aminopyridin-3-yl)-4-morpholinothieno[3,2-d]pyrimidin-6-yl)phenyl)methanol;
5-(4-morpholino-6-phenylthieno[3,2-d]pyrimidin-2-yl)pyridin-2-amine;
5-(6-((E)-3-methoxyprop-1-enyl)-4-morpholinothieno[3,2-d]pyrimidin-2-yl)pyridin-2-amine;
6-(4-methoxypyridin-3-yl)-2-(2-methoxypyrimidin-5-yl)-4-morpholinofuro[3,2-d]pyrimidine;
5-(6-(4-methoxypyridin-3-yl)-4-morpholinofuro[3,2-d]pyrimidin-2-yl)pyrimidin-2-amine;
5-(6-(4-methoxypyridin-3-yl)-4-morpholinofuro[3,2-d]pyrimidin-2-yl)pyridin-2-amine;
2,6-bis(4-methoxypyridin-3-yl)-4-morpholinofuro[3,2-d]pyrimidine;
2-(2-(6-aminopyridin-3-yl)-4-morpholinothieno[3,2-d]pyrimidin-6-yl)propan-2-ol;
5-(6-(2-hydroxypropan-2-yl)-4-morpholinothieno[3,2-d]pyrimidin-2-yl)pyridine-3-carbaldehyde;
N-methyl-5-(6-(3-(methylsulfonyl)phenyl)-4-morpholinothieno[3,2-d]pyrimidin-2-yl)pyridine-3-carboxamide;
5-(6-(3-(methylsulfonyl)phenyl)-4-morpholinothieno[3,2-d]pyrimidin-2-yl)pyridine-3-carboxylic acid;
2-(2-methoxypyrimidin-5-yl)-6-(3-(methylsulfonyl)phenyl)-4-morpholinothieno[3,2-d]pyrimidine;
5-(6-(3-(methylsulfonyl)phenyl)-4-morpholinothieno[3,2-d]pyrimidin-2-yl)pyridin-2-amine;
N-(3-(2-(6-aminopyridin-3-yl)-4-morpholinothieno[3,2-d]pyrimidin-6-yl)phenyl)acetamide;
2-(2-(6-fluoropyridin-3-yl)-4-morpholinothieno[3,2-d]pyrimidin-6-yl)propan-2-ol;
2-(2-(2-fluoropyridin-3-yl)-4-morpholinothieno[3,2-d]pyrimidin-6-yl)propan-2-ol;
2-(2-(4-methoxypyridin-3-yl)-4-morpholinothieno[3,2-d]pyrimidin-6-yl)propan-2-ol;
2-(2-(5-methoxypyridin-3-yl)-4-morpholinothieno[3,2-d]pyrimidin-6-yl)propan-2-ol;
2-(2-(6-methoxypyridin-3-yl)-4-morpholinothieno[3,2-d]pyrimidin-6-yl)propan-2-ol;
2-(2-(2-methoxypyridin-3-yl)-4-morpholinothieno[3,2-d]pyrimidin-6-yl)propan-2-ol;
2-(2-(5-(hydroxymethyl)pyridin-3-yl)-4-morpholinothieno[3,2-d]pyrimidin-6-yl)propan-2-ol;
2-(2-(2-aminopyrimidin-5-yl)-4-morpholinothieno[3,2-d]pyrimidin-6-yl)-1,1,1,3,3,3-hexafluoropropan-2-ol;
N-((2-(2-aminopyrimidin-5-yl)-4-morpholinothieno[3,2-d]pyrimidin-6-yl)methyl)-2-(dimethylamino)-N-methylacetamide;
3-(2-(2-aminopyrimidin-5-yl)-4-morpholinothieno[3,2-d]pyrimidin-6-yl)-N-(2-methoxyethyl)benzamide;
3-(2-(2-aminopyrimidin-5-yl)-4-morpholinothieno[3,2-d]pyrimidin-6-yl)-N-(2-(dimethylamino)ethyl)benzamide;
(3-(2-(2-aminopyrimidin-5-yl)-4-morpholinothieno[3,2-d]pyrimidin-6-yl)phenyl)(4-(2-hydroxyethyl)piperazin-1-yl)methanone;
(3-(2-(2-aminopyrimidin-5-yl)-4-morpholinothieno[3,2-d]pyrimidin-6-yl)phenyl)(3-hydroxypyrrolidin-1-yl)methanone;
3-(2-(2-aminopyrimidin-5-yl)-4-morpholinothieno[3,2-d]pyrimidin-6-yl)-N-(2-hydroxyethyl)benzamide;
(3-(2-(2-aminopyrimidin-5-yl)-4-morpholinothieno[3,2-d]pyrimidin-6-yl)phenyl)(4-hydroxypiperidin-1-yl)methanone;
5-(6-(3-aminophenyl)-7-methyl-4-morpholinothieno[3,2-d]pyrimidin-2-yl)pyridin-2-amine;
N-(5-(2-(2-aminopyrimidin-5-yl)-4-morpholinothieno[3,2-d]pyrimidin-6-yl)pyridin-2-yl)-2-hydroxy-2-methylpropanamide;
4-(2-(2-aminopyrimidin-5-yl)-4-morpholinothieno[3,2-d]pyrimidin-6-yl)-1-methylpiperidin-4-ol;
(S)-1-(4-(2-(2-aminopyrimidin-5-yl)-4-morpholinothieno[3,2-d]pyrimidin-6-yl)-4-hydroxypiperidin-1-yl)-2-hydroxypropan-1-one;
1-(4-(2-(2-aminopyrimidin-5-yl)-4-morpholinothieno[3,2-d]pyrimidin-6-yl)-4-hydroxypiperidin-1-yl)-2-hydroxyethanone;
1-(4-(2-(2-aminopyrimidin-5-yl)-4-morpholinothieno[3,2-d]pyrimidin-6-yl)-4-hydroxypiperidin-1-yl)-2-hydroxy-2-methylpropan-1-one;
1-(4-(2-(2-aminopyrimidin-5-yl)-4-morpholinothieno[3,2-d]pyrimidin-6-yl)-4-hydroxypiperidin-1-yl)-2-(methylsulfonyl)ethanone;
2-amino-1-(4-(2-(2-aminopyrimidin-5-yl)-4-morpholinothieno[3,2-d]pyrimidin-6-yl)-4-hydroxypiperidin-1-yl)ethanone;
2-amino-1-(4-(2-(2-aminopyrimidin-5-yl)-4-morpholinothieno[3,2-d]pyrimidin-6-yl)-4-hydroxypiperidin-1-yl)-2-methylpropan-1-one;
5-(6-((N-cyclopropylsulfonyl,N-methylamino)methyl)-4-morpholinothieno[3,2-d]pyrimidin-2-yl)pyrimidin-2-amine;
5-(6-(2-aminothiazol-4-yl)-4-morpholinothieno[3,2-d]pyrimidin-2-yl)pyrimidin-2-amine;
5-(4-morpholino-6-(3-aminosulfonyl)phenylthieno[3,2-d]pyrimidin-2-yl)pyrimidin-2-amine;
5-(4-morpholino-6-(3-dimethylaminosulfonyl)phenylthieno[3,2-d]pyrimidin-2-yl)pyrimidin-2-amine;
5-(6-(3-(aminomethyl)phenyl)-7-methyl-4-morpholinothieno[3,2-d]pyrimidin-2-yl)pyrimidin-2-amine;
5-(4-morpholino-6-(3-dimethylaminosulfonyl)phenylthieno[3,2-d]pyrimidin-2-yl)pyridin-2-amine;
(S)-1-(3-(2-(2-aminopyrimidin-5-yl)-4-morpholinothieno[3,2-d]pyrimidin-6-yl)phenylsulfonyl)propan-2-ol;

4-(2-(2-aminopyrimidin-5-yl)-4-morpholinothieno[3,2-d]pyrimidin-6-yl)piperidin-4-ol;

(S)-1-(3-(2-(6-aminopyridin-3-yl)-4-morpholinothieno[3,2-d]pyrimidin-6-yl)phenylsulfonyl)propan-2-ol;

(2S)—N-(3-(2-(6-aminopyridin-3-yl)-4-morpholinothieno[3,2-d]pyrimidin-6-yl)phenyl)-2-hydroxypropanamide;

(2S)—N-(3-(2-(2-aminopyrimidin-5-yl)-4-morpholinothieno[3,2-d]pyrimidin-6-yl)phenyl)-2-hydroxypropanamide;

5-(6-(3-(1-methyl-1H-tetrazol-5-yl)phenyl)-4-morpholinothieno[3,2-d]pyrimidin-2-yl)pyrimidin-2-amine;

N-((2-(2-aminopyrimidin-5-yl)-4-morpholinothieno[3,2-d]pyrimidin-6-yl)methyl)-2-((R)-3-hydroxypiperidin-1-yl)-N-methylacetamide;

N-((2-(2-aminopyrimidin-5-yl)-4-morpholinothieno[3,2-d]pyrimidin-6-yl)methyl)-2-(4-hydroxypiperidin-1-yl)-N-methylacetamide;

N-((2-(2-aminopyrimidin-5-yl)-4-morpholinothieno[3,2-d]pyrimidin-6-yl)methyl)-N-methyl-2-(3-(methylsulfonyl)pyrrolidin-1-yl)acetamide;

4-(2-(2-aminopyrimidin-5-yl)-4-morpholinothieno[3,2-d]pyrimidin-6-yl)-(4-N-ethylsulfonyl)piperidin-4-ol;

4-(2-(2-aminopyrimidin-5-yl)-4-morpholinothieno[3,2-d]pyrimidin-6-yl)-1-((pyridin-2-yl)methyl)piperidin-4-ol;

5-(7-methyl-6-(6-(4-methylpiperazin-1-yl)pyridin-3-yl)-4-morpholinothieno[3,2-d]pyrimidin-2-yl)pyrimidin-2-amine;

(R)-1-(3-(2-(6-aminopyridin-3-yl)-4-morpholinothieno[3,2-d]pyrimidin-6-yl)phenylsulfonyl)propan-2-ol;

(R)-1-(3-(2-(2-aminopyrimidin-5-yl)-4-morpholinothieno[3,2-d]pyrimidin-6-yl)phenylsulfonyl)propan-2-ol;

5-(4-morpholino-6-(3-(pyridin-3-yl)-1,2,4-oxadiazol-5-yl)thieno[3,2-d]pyrimidin-2-yl)pyridin-2-amine;

2-(5-(2-(2-aminopyrimidin-5-yl)-4-morpholinothieno[3,2-d]pyrimidin-6-yl)-1,2,4-oxadiazol-3-yl)propan-2-ol;

5-(6-(3-isopropyl-1,2,4-oxadiazol-5-yl)-4-morpholinothieno[3,2-d]pyrimidin-2-yl)pyrimidin-2-amine;

5-(6-(3-(4-(trifluoromethyl)phenyl)-1,2,4-oxadiazol-5-yl)-4-morpholinothieno[3,2-d]pyrimidin-2-yl)pyrimidin-2-amine;

5-(7-methyl-4-morpholino-6-(3-(2-hydroxyethyl)aminosulfonyl)phenylthieno[3,2-d]pyrimidin-2-yl)pyrimidin-2-amine;

(2-(2-aminopyrimidin-5-yl)-4-morpholinothieno[3,2-d]pyrimidin-6-yl)(4-(methylsulfonyl)phenyl)methanol;

2-(2-(2-aminopyrimidin-5-yl)-4-morpholinothieno[3,2-d]pyrimidin-6-yl)-1,1,1-trifluoropropan-2-ol;

2-(5-(2-(2-aminopyrimidin-5-yl)-4-morpholinothieno[3,2-d]pyrimidin-6-yl)-1,2,4-oxadiazol-3-yl)ethanol;

5-(7-methyl-6-(4-(methylsulfonyl)phenyl)-4-morpholinothieno[3,2-d]pyrimidin-2-yl)pyrimidin-2-amine;

5-(7-methyl-6-(2-(methylsulfonyl)phenyl)-4-morpholinothieno[3,2-d]pyrimidin-2-yl)pyrimidin-2-amine;

5-(7-methyl-4-morpholino-6-phenylthieno[3,2-d]pyrimidin-2-yl)pyrimidin-2-amine;

5-(4-morpholino-6-phenylthieno[3,2-d]pyrimidin-2-yl)pyrimidin-2-amine;

5-(6-(5-((methylsulfonyl)methyl)-1,2,4-oxadiazol-3-yl)-4-morpholinothieno[3,2-d]pyrimidin-2-yl)pyrimidin-2-amine;

5-(6-((N-ethylsulfonyl,N-methylamino)methyl)-4-morpholinothieno[3,2-d]pyrimidin-2-yl)pyrimidin-2-amine;

5-(6-((N-methylsulfonyl,N-methylamino)methyl)-4-morpholinothieno[2,3-d]pyrimidin-2-yl)pyrimidin-2-ol;

N-methylsulfonyl,N-methyl(2-(6-methylpyridin-3-yl)-4-morpholinothieno[2,3-d]pyrimidin-6-yl)methanamine;

5-(7-methyl-4-morpholino-6-(3-morpholinosulfonyl)phenylthieno[3,2-d]pyrimidin-2-yl)pyrimidin-2-amine;

(2S)—N-(3-(2-(2-aminopyrimidin-5-yl)-7-methyl-4-morpholinothieno[3,2-d]pyrimidin-6-yl)phenyl)-2-hydroxypropanamide;

N-(3-(2-(2-aminopyrimidin-5-yl)-7-methyl-4-morpholinothieno[3,2-d]pyrimidin-6-yl)phenyl)-2-hydroxyacetamide;

(S)-1-(3-(2-(2-aminopyrimidin-5-yl)-7-methyl-4-morpholinothieno[3,2-d]pyrimidin-6-yl)phenylsulfonyl)propan-2-ol;

5-(6-(6-(N-(2-methoxyethyl)-N-methylamino)pyridin-3-yl)-4-morpholinothieno[3,2-d]pyrimidin-2-yl)pyrimidin-2-amine;

5-(6-(6-(N-(2-(dimethylamino)ethyl)-N-methylamino)pyridin-3-yl)-4-morpholinothieno[3,2-d]pyrimidin-2-yl)pyrimidin-2-amine;

1-(5-(2-(2-aminopyrimidin-5-yl)-4-morpholinothieno[3,2-d]pyrimidin-6-yl)pyridin-2-yl)piperidin-4-ol;

2-(5-(2-(2-aminopyrimidin-5-yl)-4-morpholinothieno[3,2-d]pyrimidin-6-yl)pyridin-2-ylamino)propan-1-ol;

5-(6-(6-(2-methoxyethylamino)pyridin-3-yl)-4-morpholinothieno[3,2-d]pyrimidin-2-yl)pyrimidin-2-amine;

N-(3-(2-(2-aminopyrimidin-5-yl)-4-morpholinofuro[2,3-d]pyrimidin-6-yl)phenyl)acetamide;

5-(6-(6-(2-morpholinoethylamino)pyridin-3-yl)-4-morpholinothieno[3,2-d]pyrimidin-2-yl)pyrimidin-2-amine;

2-(2-(2-aminopyrimidin-5-yl)-4-morpholinofuro[2,3-d]pyrimidin-6-yl)propan-2-ol;

5-(6-(6-(2-(dimethylamino)ethylamino)pyridin-3-yl)-4-morpholinothieno[3,2-d]pyrimidin-2-yl)pyrimidin-2-amine;

(2S)—N-((3-(2-(2-aminopyrimidin-5-yl)-7-methyl-4-morpholinothieno[3,2-d]pyrimidin-6-yl)phenyl)methyl)-2-hydroxypropanamide;

N-((3-(2-(2-aminopyrimidin-5-yl)-7-methyl-4-morpholinothieno[3,2-d]pyrimidin-6-yl)phenyl)methyl)-2-hydroxyacetamide;

3-(2-(2-aminopyrimidin-5-yl)-7-methyl-4-morpholinothieno[3,2-d]pyrimidin-6-yl)-N-(2-methoxyethyl)benzamide;

3-(2-(2-aminopyrimidin-5-yl)-7-methyl-4-morpholinothieno[3,2-d]pyrimidin-6-yl)-N-(2-(dimethylamino)ethyl)benzamide;

3-(2-(2-aminopyrimidin-5-yl)-7-methyl-4-morpholinothieno[3,2-d]pyrimidin-6-yl)-N—((S)-2-hydroxypropyl)benzamide;

(3-(2-(2-aminopyrimidin-5-yl)-7-methyl-4-morpholinothieno[3,2-d]pyrimidin-6-yl)phenyl)(4-methylpiperazin-1-yl)methanone;

3-(2-(2-aminopyrimidin-5-yl)-7-methyl-4-morpholinothieno[3,2-d]pyrimidin-6-yl)-N-(2-hydroxyethyl)benzamide;

(3-(2-(2-aminopyrimidin-5-yl)-7-methyl-4-morpholinothieno[3,2-d]pyrimidin-6-yl)phenyl)(4-hydroxypiperidin-1-yl)methanone;

5-(7-methyl-4-morpholino-6-(3-(4-methylpiperazinylsulfonyl))phenylthieno[3,2-d]pyrimidin-2-yl)pyrimidin-2-amine;

3-(2-(2-aminopyrimidin-5-yl)-7-methyl-4-morpholinothieno[3,2-d]pyrimidin-6-yl)benzoic acid;

(3-(2-(2-aminopyrimidin-5-yl)-7-methyl-4-morpholinothieno[3,2-d]pyrimidin-6-yl)phenyl)(4-acetylpiperazin-1-yl)methanone;
(3-(2-(2-aminopyrimidin-5-yl)-7-methyl-4-morpholinothieno[3,2-d]pyrimidin-6-yl)phenyl)(4-(thiazol-2-yl)piperazin-1-yl)methanone;
(3-(2-(2-aminopyrimidin-5-yl)-7-methyl-4-morpholinothieno[3,2-d]pyrimidin-6-yl)phenyl)(4-(2-(dimethylamino)ethyl)piperazin-1-yl)methanone;
(3-(2-(2-aminopyrimidin-5-yl)-7-methyl-4-morpholinothieno[3,2-d]pyrimidin-6-yl)phenyl)(4-(dimethylamino)piperidin-1-yl)methanone;
(3-(2-(2-aminopyrimidin-5-yl)-7-methyl-4-morpholinothieno[3,2-d]pyrimidin-6-yl)phenyl)(4-(1-methylpiperidin-4-yl)piperazin-1-yl)methanone;
2-(2-(2,4-dimethoxypyrimidin-5-yl)-4-morpholinothieno[3,2-d]pyrimidin-6-yl)propan-2-ol;
2-(2-aminopyrimidin-5-yl)-4-morpholinothieno[3,2-d]pyrimidin-6-amine;
5-(7-methyl-4-morpholino-6-(3-piperazinylsulfonyl)phenylthieno[3,2-d]pyrimidin-2-yl)pyrimidin-2-amine;
3-(2-(2-aminopyrimidin-5-yl)-7-methyl-4-morpholinothieno[3,2-d]pyrimidin-6-yl)-N-(2,3-dihydroxypropyl)-N-methylbenzamide;
3-(2-(2-aminopyrimidin-5-yl)-7-methyl-4-morpholinothieno[3,2-d]pyrimidin-6-yl)-N-(2,3-dihydroxypropyl)benzamide;
2-(2-(2-aminopyrimidin-5-yl)-4-morpholinothieno[3,2-d]pyrimidin-6-ylamino)ethanol;
(R)-1-(5-(2-(2-aminopyrimidin-5-yl)-4-morpholinothieno[3,2-d]pyrimidin-6-yl)pyridin-2-yl)pyrrolidin-3-ol;
5-(6-(6-(bis(2-methoxyethyl)amino)pyridin-3-yl)-4-morpholinothieno[3,2-d]pyrimidin-2-yl)pyrimidin-2-amine;
5-(6-(6-methoxypyridin-3-yl)-4-morpholinothieno[3,2-d]pyrimidin-2-yl)pyrimidin-2-amine;
5-(4-morpholino-6-(4-morpholinophenyl)thieno[3,2-d]pyrimidin-2-yl)pyrimidin-2-amine;
5-(4-morpholino-6-(2-(4-N-methylsulfonylpiperazin-1-yl)propan-2-yl)thieno[3,2-d]pyrimidin-2-yl)pyrimidin-2-amine;
5-(4-morpholino-6-((thiazol-2-ylamino)methyl)thieno[3,2-d]pyrimidin-2-yl)pyrimidin-2-amine;
5-(6-((N-isobutylsulfonyl,N-methylamino)methyl)-4-morpholinothieno[3,2-d]pyrimidin-2-yl)pyrimidin-2-amine;
1-(4-(2-(2-aminopyrimidin-5-yl)-4-morpholinothieno[3,2-d]pyrimidin-6-yl)pyridin-2-yl)piperidin-4-ol;
5-(6-(2-(2-methoxyethylamino)pyridin-4-yl)-4-morpholinothieno[3,2-d]pyrimidin-2-yl)pyrimidin-2-amine;
5-(6-(6-(2-(methylsulfonyl)ethylamino)pyridin-3-yl)-4-morpholinothieno[3,2-d]pyrimidin-2-yl)pyrimidin-2-amine;
5-(6-(6-(2-(2-hydroxyethyl)oxyethylamino)pyridin-3-yl)-4-morpholinothieno[3,2-d]pyrimidin-2-yl)pyrimidin-2-amine;
(R)-1-(5-(2-(2-aminopyrimidin-5-yl)-4-morpholinothieno[3,2-d]pyrimidin-6-yl)pyridin-2-ylamino)propan-2-ol;
5-(6-methyl-4-morpholinothieno[3,2-d]pyrimidin-2-yl)pyrimidin-2-amine;
5-(6-methyl-4-morpholinothieno[2,3-d]pyrimidin-2-yl)pyrimidin-2-amine;
5-(6,7-dimethyl-4-morpholinothieno[3,2-d]pyrimidin-2-yl)pyrimidin-2-amine;
(2-(2,4-dimethoxypyrimidin-5-yl)-4-morpholinothieno[3,2-d]pyrimidin-6-yl)-N-methyl,N-methylsulfonylmethanamine; and
N-((2-(2,4-dimethoxypyrimidin-5-yl)-4-morpholinothieno[3,2-d]pyrimidin-6-yl)methyl)-N-methylacetamide;
and pharmaceutically acceptable salts thereof.

2. A compound selected from:
N-((2-(2-amino-4-methylpyrimidin-5-yl)-4-morpholinothieno[3,2-d]pyrimidin-6-yl)methyl)-N-methylmethanesulfonamide;
N-((2-(2-amino-4-methylpyrimidin-5-yl)-4-morpholinothieno[3,2-d]pyrimidin-6-yl)methyl)-N-methylacetamide;
2-(2-(2-amino-4-methylpyrimidin-5-yl)-4-morpholinothieno[3,2-d]pyrimidin-6-yl)propan-2-ol;
5-(6-(3-methoxyoxetan-3-yl)-4-morpholinothieno[3,2-d]pyrimidin-2-yl)-N-methylpyridin-2-amine;
5-(6-(3-methoxyoxetan-3-yl)-4-morpholinothieno[3,2-d]pyrimidin-2-yl)-N-methylpyrimidin-2-amine;
5-(6-(3-methoxyoxetan-3-yl)-4-morpholinothieno[3,2-d]pyrimidin-2-yl)pyrimidin-2-amine;
N-methyl-5-(6-(3-(methylsulfonyl)phenyl)-4-morpholinothieno[3,2-d]pyrimidin-2-yl)pyridin-2-amine;
3-(2-(2-aminopyrimidin-5-yl)-4-morpholinothieno[2,3-d]pyrimidin-6-yl)oxetan-3-ol;
5-(6-(2-methoxypropan-2-yl)-4-morpholinothieno[2,3-d]pyrimidin-2-yl)-N-methylpyridin-2-amine;
5-(6-(2-methoxypropan-2-yl)-4-morpholinothieno[2,3-d]pyrimidin-2-yl)-N-methylpyrimidin-2-amine;
5-(6-(2-methoxypropan-2-yl)-4-morpholinothieno[2,3-d]pyrimidin-2-yl)pyrimidin-2-amine;
N-methyl-5-(6-(3-(methylsulfonyl)phenyl)-4-morpholinothieno[2,3-d]pyrimidin-2-yl)pyridin-2-amine;
N-methyl-5-(7-methyl-6-(3-(methylsulfonyl)phenyl)-4-morpholinothieno[3,2-d]pyrimidin-2-yl)pyridin-2-amine;
2-(2-(6-(methylamino)pyridin-3-yl)-4-morpholinothieno[3,2-d]pyrimidin-6-yl)propan-2-ol;
N-((2-(2-aminopyrimidin-5-yl)-4-morpholinothieno[2,3-d]pyrimidin-6-yl)methyl)-N-(2-hydroxyethyl)methanesulfonamide;
N-methyl-N-((2-(2-(methylamino)pyrimidin-5-yl)-4-morpholinothieno[2,3-d]pyrimidin-6-yl)methyl)methanesulfonamide;
N-methyl-5-(6-(3-(methylsulfonyl)phenyl)-4-morpholinothieno[2,3-d]pyrimidin-2-yl)pyrimidin-2-amine;
2-(2-(2-(methylamino)pyrimidin-5-yl)-4-morpholinothieno[2,3-d]pyrimidin-6-yl)propan-2-ol;
3-(2-(2-aminopyrimidin-5-yl)-4-morpholinothieno[3,2-d]pyrimidin-6-yl)oxetan-3-ol;
5-(6-(2-methoxypropan-2-yl)-4-morpholinothieno[3,2-d]pyrimidin-2-yl)-N-methylpyrimidin-2-amine;
5-(6-(2-methoxypropan-2-yl)-4-morpholinothieno[3,2-d]pyrimidin-2-yl)pyrimidin-2-amine;
(3-(2-(2-aminopyrimidin-5-yl)-4-morpholinothieno[2,3-d]pyrimidin-6-yl)phenyl)(4-methylpiperazin-1-yl)methanone;
2-(2-(2-methoxypyrimidin-5-yl)-4-morpholinothieno[2,3-d]pyrimidin-6-yl)propan-2-ol;
N-((2-(2-aminopyrimidin-5-yl)-4-morpholinothieno[2,3-d]pyrimidin-6-yl)methyl)-N-(2-(dimethylamino)ethyl)methanesulfonamide;
2-(2-(2-(methylamino)pyrimidin-5-yl)-4-morpholinothieno[3,2-d]pyrimidin-6-yl)propan-2-ol;

(4-(2-(2-aminopyrimidin-5-yl)-4-morpholinothieno[3,2-d]pyrimidin-6-yl)-2-chlorophenyl)(4-hydroxypiperidin-1-yl)methanone;

(4-(2-(2-aminopyrimidin-5-yl)-4-morpholinothieno[3,2-d]pyrimidin-6-yl)-2-chlorophenyl)(4-methylpiperazin-1-yl)methanone;

N-methyl-5-(7-methyl-6-(3-(methylsulfonyl)phenyl)-4-morpholinothieno[3,2-d]pyrimidin-2-yl)pyrimidin-2-amine;

N,N-dimethyl-5-(7-methyl-6-(3-(methylsulfonyl)phenyl)-4-morpholinothieno[3,2-d]pyrimidin-2-yl)pyrimidin-2-amine;

(4-(2-(2-aminopyrimidin-5-yl)-7-methyl-4-morpholinothieno[3,2-d]pyrimidin-6-yl)thiophen-2-yl)(4-hydroxypiperidin-1-yl)methanone;

(4-(2-(2-aminopyrimidin-5-yl)-7-methyl-4-morpholinothieno[3,2-d]pyrimidin-6-yl)thiophen-2-yl)(4-methylpiperazin-1-yl)methanone;

(4-(2-(2-aminopyrimidin-5-yl)-7-methyl-4-morpholinothieno[3,2-d]pyrimidin-6-yl)thiophen-2-yl)(morpholino)methanone;

4-(2-(2-aminopyrimidin-5-yl)-7-methyl-4-morpholinothieno[3,2-d]pyrimidin-6-yl)phenyl piperidine-1-carboxylate;

5-(7-methyl-4-morpholino-6-(6-(S,S-dioxo-thiomorpholino)pyridin-3-yl)thieno[3,2-d]pyrimidin-2-yl)pyrimidin-2-amine;

5-(6-(6-((2S,6R)-2,6-dimethylmorpholino)pyridin-3-yl)-4-morpholinothieno[3,2-d]pyrimidin-2-yl)pyrimidin-2-amine;

(2-(2-aminopyrimidin-5-yl)-4-morpholinothieno[3,2-d]pyrimidin-6-yl)(3-(methylsulfonyl)phenyl)methanone;

(2-(2-aminopyrimidin-5-yl)-4-morpholinothieno[3,2-d]pyrimidin-6-yl)(4-(methylsulfonyl)phenyl)methanone;

(2-(2-aminopyrimidin-5-yl)-4-morpholinothieno[3,2-d]pyrimidin-6-yl)(3-(methylsulfonyl)phenyl)methanol;

N-((2-(2-aminopyrimidin-5-yl)-7-methyl-4-morpholinothieno[3,2-d]pyrimidin-6-yl)methyl)-N,3,3-trimethylbutanamide;

N-((2-(2-aminopyrimidin-5-yl)-7-methyl-4-morpholinothieno[3,2-d]pyrimidin-6-yl)methyl)-N,3-dimethylbutanamide;

N-((2-(2-aminopyrimidin-5-yl)-7-methyl-4-morpholinothieno[3,2-d]pyrimidin-6-yl)methyl)-N-methylpivalamide;

N-((2-(2-aminopyrimidin-5-yl)-7-methyl-4-morpholinothieno[3,2-d]pyrimidin-6-yl)methyl)-N-methylcyclopropanecarboxamide;

N-((2-(2-aminopyrimidin-5-yl)-7-methyl-4-morpholinothieno[3,2-d]pyrimidin-6-yl)methyl)-N-methylpropionamide;

N-((2-(2-aminopyrimidin-5-yl)-7-methyl-4-morpholinothieno[3,2-d]pyrimidin-6-yl)methyl)-N-methylisobutyramide;

N-((2-(2-aminopyrimidin-5-yl)-4-morpholinothieno[3,2-d]pyrimidin-6-yl)methyl)-N-methylcyclopropanecarboxamide;

N-((2-(2-aminopyrimidin-5-yl)-4-morpholinothieno[3,2-d]pyrimidin-6-yl)methyl)-N-methylpropionamide;

N-((2-(2-aminopyrimidin-5-yl)-4-morpholinothieno[3,2-d]pyrimidin-6-yl)methyl)-N-methylisobutyramide;

(2-(2-(dimethylamino)pyrimidin-5-yl)-4-morpholinothieno[2,3-d]pyrimidin-6-yl)methanol;

5-(7-methyl-6-(5-((4-methylpiperazin-1-yl)methyl)thiophen-3-yl)-4-morpholinothieno[3,2-d]pyrimidin-2-yl)pyrimidin-2-amine;

1-((4-(2-(2-aminopyrimidin-5-yl)-7-methyl-4-morpholinothieno[3,2-d]pyrimidin-6-yl)thiophen-2-yl)methyl)pyrrolidin-3-ol;

4-(2-(2-aminopyrimidin-5-yl)-4-morpholinothieno[3,2-d]pyrimidin-6-yl)-N-(2-hydroxyethyl)-3-methylbenzamide;

(4-(2-(2-aminopyrimidin-5-yl)-4-morpholinothieno[3,2-d]pyrimidin-6-yl)-3-methylphenyl)(4-hydroxypiperidin-1-yl)methanone;

(4-(2-(2-aminopyrimidin-5-yl)-4-morpholinothieno[3,2-d]pyrimidin-6-yl)-3-methylphenyl)(morpholino)methanone;

2-(3-(2-(2-aminopyrimidin-5-yl)-7-methyl-4-morpholinothieno[3,2-d]pyrimidin-6-yl)phenoxy)ethanol;

2-(2-(4-(2-(2-aminopyrimidin-5-yl)-4-morpholinothieno[3,2-d]pyrimidin-6-yl)phenylamino)ethoxy)ethanol;

5-(4-morpholino-6-(4-(2-morpholinoethylamino)phenyl)thieno[3,2-d]pyrimidin-2-yl)pyrimidin-2-amine;

5-(7-methyl-4-morpholino-6-(3-(2-morpholinoethoxy)phenyl)thieno[3,2-d]pyrimidin-2-yl)pyrimidin-2-amine;

3-(2-(2-aminopyrimidin-5-yl)-7-methyl-4-morpholinothieno[3,2-d]pyrimidin-6-yl)phenol;

N-(4-(2-(2-aminopyrimidin-5-yl)-7-methyl-4-morpholinothieno[3,2-d]pyrimidin-6-yl)benzyl)methanesulfonamide;

2-(3-(2-(2-aminopyrimidin-5-yl)-7-methyl-4-morpholinothieno[3,2-d]pyrimidin-6-yl)phenyl)-1-morpholinoethanone;

2-(3-(2-(2-aminopyrimidin-5-yl)-7-methyl-4-morpholinothieno[3,2-d]pyrimidin-6-yl)phenyl)-N-(2-hydroxyethyl)acetamide;

5-(6-(5-(2-aminopropan-2-yl)-1,2,4-oxadiazol-3-yl)-4-morpholinothieno[3,2-d]pyrimidin-2-yl)pyrimidin-2-amine;

N-(1-(3-(2-(2-aminopyrimidin-5-yl)-4-morpholinothieno[3,2-d]pyrimidin-6-yl)-1,2,4-oxadiazol-5-yl)ethyl)acetamide;

2-(2-(5-(2-(2-aminopyrimidin-5-yl)-4-morpholinothieno[3,2-d]pyrimidin-6-yl)pyridin-2-yloxy)ethoxy)ethanol;

2-(2-(3-(2-(2-aminopyrimidin-5-yl)-4-morpholinothieno[3,2-d]pyrimidin-6-yl)phenylamino)ethoxy)ethanol;

1-(5-(2-(2-aminopyrimidin-5-yl)-7-methyl-4-morpholinothieno[3,2-d]pyrimidin-6-yl)pyridin-2-yl)piperidin-3-ol;

1-(5-(2-(2-aminopyrimidin-5-yl)-7-methyl-4-morpholinothieno[3,2-d]pyrimidin-6-yl)pyridin-2-yl)piperidin-4-ol;

2-(5-(2-(2-aminopyrimidin-5-yl)-4-morpholinothieno[3,2-d]pyrimidin-6-yl)pyridin-2-ylamino)-1-morpholinoethanone;

2-(5-(2-(2-aminopyrimidin-5-yl)-7-methyl-4-morpholinothieno[3,2-d]pyrimidin-6-yl)pyridin-2-ylamino)-1-morpholinoethanone;

3-((5-(2-(2-aminopyrimidin-5-yl)-7-methyl-4-morpholinothieno[3,2-d]pyrimidin-6-yl)pyridin-2-yl)(methyl)amino)propane-1,2-diol;

3-(5-(2-(2-aminopyrimidin-5-yl)-7-methyl-4-morpholinothieno[3,2-d]pyrimidin-6-yl)pyridin-2-ylamino)propane-1,2-diol;

N1-(5-(2-(2-aminopyrimidin-5-yl)-7-methyl-4-morpholinothieno[3,2-d]pyrimidin-6-yl)pyridin-2-yl)-2-methylpropane-1,2-diamine;

2-(5-(2-(2-aminopyrimidin-5-yl)-7-methyl-4-morpholinothieno[3,2-d]pyrimidin-6-yl)pyridin-2-ylamino)propan-1-ol;

(R)-1-(5-(2-(2-aminopyrimidin-5-yl)-7-methyl-4-morpholinothieno[3,2-d]pyrimidin-6-yl)pyridin-2-yl)pyrrolidin-3-ol;
2-(2-(5-(2-(2-aminopyrimidin-5-yl)-7-methyl-4-morpholinothieno[3,2-d]pyrimidin-6-yl)pyridin-2-ylamino)ethoxy)ethanol;
5-(7-methyl-4-morpholino-6-(6-(2-morpholinoethylamino)pyridin-3-yl)thieno[3,2-d]pyrimidin-2-yl)pyrimidin-2-amine;
2-(3-(2-(2-aminopyrimidin-5-yl)-7-methyl-4-morpholinothieno[3,2-d]pyrimidin-6-yl)phenyl)-1-(4-hydroxypiperidin-1-yl)ethanone;
2-(3-(2-(2-aminopyrimidin-5-yl)-7-methyl-4-morpholinothieno[3,2-d]pyrimidin-6-yl)phenyl)-1-(4-methylpiperazin-1-yl)ethanone;
5-(7-methyl-6-(3-((4-methylpiperazin-1-yl)methyl)phenyl)-4-morpholinothieno[3,2-d]pyrimidin-2-yl)pyrimidin-2-amine;
2-(3-(2-(2-aminopyrimidin-5-yl)-7-methyl-4-morpholinothieno[3,2-d]pyrimidin-6-yl)phenyl)acetic acid;
N-((2-(2,4-dimethoxypyrimidin-5-yl)-4-morpholinothieno[3,2-d]pyrimidin-6-yl)methyl)-N-methylmethanesulfonamide;
N-((2-(2,4-dimethoxypyrimidin-5-yl)-4-morpholinothieno[3,2-d]pyrimidin-6-yl)methyl)-N-methylacetamide;
(R)-1-(4-(2-(2-aminopyrimidin-5-yl)-4-morpholinothieno[3,2-d]pyrimidin-6-yl)pyridin-2-yl)pyrrolidin-3-ol;
5-(4-morpholino-6-(6-(2-morpholinoethoxy)pyridin-3-yl)thieno[3,2-d]pyrimidin-2-yl)pyrimidin-2-amine;
N-(5-(2-(2-aminopyrimidin-5-yl)-4-morpholinothieno[3,2-d]pyrimidin-6-yl)pyridin-2-yl)methanesulfonamide;
5-(6-(2-(methylsulfonyl)pyridin-4-yl)-4-morpholinothieno[3,2-d]pyrimidin-2-yl)pyrimidin-2-amine;
N1-(4-(2-(2-aminopyrimidin-5-yl)-4-morpholinothieno[3,2-d]pyrimidin-6-yl)pyridin-2-yl)-N2,N2-dimethylethane-1,2-diamine;
5-(6-(2-((2-methoxyethyl)(methyl)amino)pyridin-4-yl)-4-morpholinothieno[3,2-d]pyrimidin-2-yl)pyrimidin-2-amine;
2-(4-(2-(2-aminopyrimidin-5-yl)-4-morpholinothieno[3,2-d]pyrimidin-6-yl)pyridin-2-ylamino)propan-1-ol;
5-(4-morpholino-6-(2-(2-morpholinoethylamino)pyridin-4-yl)thieno[3,2-d]pyrimidin-2-yl)pyrimidin-2-amine;
5-(6-(2-(2-(methylsulfonyl)ethylamino)pyridin-4-yl)-4-morpholinothieno[3,2-d]pyrimidin-2-yl)pyrimidin-2-amine;
1-(4-(2-(2-aminopyrimidin-5-yl)-4-morpholinothieno[3,2-d]pyrimidin-6-yl)pyridin-2-yl)piperidin-3-ol;
2-(4-(5-(2-(2-aminopyrimidin-5-yl)-4-morpholinothieno[3,2-d]pyrimidin-6-yl)pyridin-2-yl)piperazin-1-yl)ethanol;
2-(2-(2,4-dimethoxypyrimidin-5-yl)-4-morpholinothieno[3,2-d]pyrimidin-6-yl)propan-2-ol;
5-(7-methyl-4-morpholino-6-(3-(morpholinomethyl)phenyl)thieno[3,2-d]pyrimidin-2-yl)pyrimidin-2-amine;
(5-(2-(2-aminopyrimidin-5-yl)-7-methyl-4-morpholinothieno[3,2-d]pyrimidin-6-yl)pyridin-3-yl)(4-methylpiperazin-1-yl)methanone;
(5-(2-(2-aminopyrimidin-5-yl)-7-methyl-4-morpholinothieno[3,2-d]pyrimidin-6-yl)pyridin-3-yl)(4-hydroxypiperidin-1-yl)methanone; and
5-(6-((3,4-dihydro-6,7-dimethoxyisoquinolin-2(1H)-yl)methyl)-4-morpholinothieno[3,2-d]pyrimidin-2-yl)pyrimidin-2-amine;
and pharmaceutically acceptable salts thereof.

3. A pharmaceutical composition comprised of a compound of claim 1 and a pharmaceutically acceptable carrier.

4. The composition according to claim 3, further comprising a therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

5. A composition comprising a compound of claim 1 in an amount to detectably inhibit PI3 kinase activity and a pharmaceutically acceptable carrier, adjuvant, or vehicle.

* * * * *

UNITED STATES PATENT AND TRADEMARK OFFICE
CERTIFICATE OF CORRECTION

PATENT NO. : 9,487,533 B2  
APPLICATION NO. : 11/951189  
DATED : November 8, 2016  
INVENTOR(S) : Castanedo et al.

Page 1 of 1

It is certified that error appears in the above-identified patent and that said Letters Patent is hereby corrected as shown below:

In the Claims

Column 411, Line 15, Claim 1, delete "2-2-aminopyrimidin" and insert -- 2-(2-aminopyrimidin --;

Column 411, Line 35, Claim 1, delete "5-6-(3-" and insert -- 5-(6-(3- --;

Column 412, Line 38, Claim 1, delete "N-(5-(6-N-methyl" and insert -- N-(5-(6-((N-methyl --;

Column 412, Line 61, Claim 1, delete "methyl-N" and insert -- methyl)-N -- therefor.

Signed and Sealed this  
Eighteenth Day of April, 2017

Michelle K. Lee  
*Director of the United States Patent and Trademark Office*